US009695155B2

(12) United States Patent
Sharpe et al.

(10) Patent No.: US 9,695,155 B2
(45) Date of Patent: Jul. 4, 2017

(54) HERBICIDAL SUBSTITUTED PYRIMIDINYLOXY BENZENE COMPOUNDS

(71) Applicant: E. I. DU PONT DE NEMOURS AND COMPANY, Wilmington, DE (US)

(72) Inventors: Paula Louise Sharpe, Middletown, DE (US); Thomas Martin Stevenson, Newark, DE (US); Nicholas Ryan Deprez, Newark, DE (US); Ravisekhara P. Reddy, Secunderabad (IN); Srinivas Chittaboina, Bibipet (IN)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/101,095

(22) PCT Filed: Dec. 9, 2014

(86) PCT No.: PCT/US2014/069200
§ 371 (c)(1),
(2) Date: Jun. 2, 2016

(87) PCT Pub. No.: WO2015/089003
PCT Pub. Date: Jun. 18, 2015

(65) Prior Publication Data
US 2016/0340340 A1    Nov. 24, 2016

Related U.S. Application Data

(60) Provisional application No. 61/914,131, filed on Dec. 10, 2013.

(51) Int. Cl.
A01N 43/54     (2006.01)
A01N 43/50     (2006.01)
A01N 43/56     (2006.01)
A01N 43/647    (2006.01)
A01N 43/82     (2006.01)
C07D 403/12    (2006.01)
C07D 413/14    (2006.01)

(52) U.S. Cl.
CPC .......... C07D 403/12 (2013.01); A01N 43/54 (2013.01); A01N 43/56 (2013.01); A01N 43/647 (2013.01); A01N 43/82 (2013.01); C07D 413/14 (2013.01)

(58) Field of Classification Search
CPC ........ A01N 43/54; A01N 43/50; A01N 43/56; A01N 43/647; A01N 43/82; C07D 403/12; C07D 413/14
See application file for complete search history.

(56) References Cited

U.S. PATENT DOCUMENTS

2010/0022538 A1    1/2010 Boebel et al.

FOREIGN PATENT DOCUMENTS

| DE | 4438824 A1    | 10/1994 |
| JP | S61236766 A   | 10/1986 |
| JP | H4108777 A    | 4/1992  |
| JP | 10-251255 A   | 9/1998  |
| WO | 94/17059 A1   | 8/1994  |
| WO | 96/33994 A1   | 10/1996 |
| WO | 98/40379 A1   | 9/1998  |

OTHER PUBLICATIONS

Saito, Yoshihiro, et al., "Preparation of pyrimidine derivatives as herbicides", Database Accession No. 1992:545339, XP002735697, CAS-RN 143437-16-5.
Selby, et al., "N-azolyl Phenoxypyrimidine Herbicides: Novel Inhibitors of Carotenoid Biosysnthesis Part I", Water-Soluble Polyers: Synthesis, Solution Properties and Applications, vol. 800, Jan. 1, 2002, pp. 74-84, XP001120637, ISBN: 978-0-541-23408-9.
International Search Report of corresponding PCT/US2014/069200 mailed Mar. 3, 2015.

Primary Examiner — John Pak
Assistant Examiner — Nathan W Schlientz
(74) Attorney, Agent, or Firm — Linda D. Birch

(57) ABSTRACT

Disclosed are compounds of Formula 1, including all stereoisomers, N-oxides, and salts thereof, wherein each $Y^1$, $Y^2$, $Y^3$, $Y^4$, Z, $R^2$, m and $R^3$ are as defined in the disclosure.
Also disclosed are compositions containing a compound of Formula 1 and methods for controlling undesired vegetation comprising contacting the undesired vegetation or its environment with an effective amount of a compound or a composition of the invention.

14 Claims, No Drawings

HERBICIDAL SUBSTITUTED PYRIMIDINYLOXY BENZENE COMPOUNDS

FIELD OF THE INVENTION

This invention relates to certain substituted pyrimidinyloxy benzene compounds, their N-oxides, salts and compositions, and methods of their use for controlling undesirable vegetation.

BACKGROUND OF THE INVENTION

The control of undesired vegetation is extremely important in achieving high crop efficiency. Achievement of selective control of the growth of weeds especially in such useful crops as rice, soybean, sugar beet, maize, potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds that are more effective, less costly, less toxic, environmentally safer or have different sites of action.

JP 61236766 A discloses certain carbon-linked pyrimidinyloxy benzene derivatives as herbicides. The substituted pyrimidinyloxy benzene compounds of the present invention are not disclosed in this publication.

SUMMARY OF THE INVENTION

This invention is directed to compounds of Formula 1, including all stereoisomers, N-oxides, and salts thereof, agricultural compositions containing them and their use as herbicides

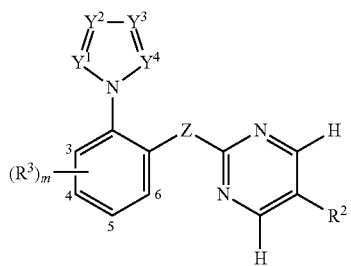

1 wherein
each $Y^1$, $Y^2$, $Y^3$ and $Y^4$ is independently N or $CR^1$, provided no more than 3 of $Y^1$, $Y^2$, $Y^3$ and $Y^4$ are N;
Z is O or S;
each $R^1$ is independently hydrogen, halogen, cyano, nitro, $SF_5$, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_8$ alkylaminocarbonyl, $C_3$-$C_{10}$ dialkylaminocarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $SO_nR^{1A}$, $Si(CH_3)_3$ or $B(-OC(R^{1B})_2C(R^{1B})_2O-)$; or a phenyl ring optionally substituted with up to 5 substituents independently selected from $R^{1C}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{1C}$ on carbon atom ring members and $R^{1D}$ on nitrogen atom ring members;

$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$, $C_1$-$C_4$ haloalkyl or $C_3$-$C_6$ cycloalkyl;

m is 0, 1, 2 or 3;

each $R^3$ is independently halogen, cyano, hydroxy, nitro, amino, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $Si(CH_3)_3$, $C≡CSi(CH_3)_3$, $C(=O)N(R^{3A})(R^{3B})$, $C(=NOR^{3C})H$, $C(=NR^{3D})H$, $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; or pyrimidinyloxy;

each n is independently 0, 1 or 2;

each $R^{1A}$, $R^{2A}$ and $R^{3E}$ is independently $C_1$-$C_4$ alkyl, $C_1$-$C_4$ haloalkyl, $C_1$-$C_4$ alkylamino or $C_2$-$C_6$ dialkylamino;

each $R^{1B}$ is independently H or $C_1$-$C_4$ alkyl;

each $R^{1C}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy;

each $R^{1D}$ is independently cyano, $C_1$-$C_6$ alkyl, $C_1$-$C_6$ haloalkyl, $C_1$-$C_6$ alkoxy or $C_2$-$C_6$ alkylcarbonyl;

each $R^{3A}$ is independently $C_1$-$C_4$ alkyl or $C_1$-$C_4$ haloalkyl;

each $R^{3B}$ is independently H, $C_1$-$C_4$ alkyl or $C_1$-$C_4$ haloalkyl;

each $R^{3C}$ is independently H or $C_1$-$C_4$ alkyl;

each $R^{3D}$ is independently H, amino, $C_1$-$C_4$ alkyl or $C_1$-$C_4$ alkylamino;

each $R^{3F}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy; and each $R^{3G}$ is independently cyano, $C_1$-$C_6$ alkyl, $C_1$-$C_6$ haloalkyl, $C_1$-$C_6$ alkoxy or $C_2$-$C_6$ alkylcarbonyl;

provided when i) $Y^1$ is N; $Y^2$ is CH; $Y^3$ is CBr; $Y^4$ is CH; and $R^2$ is Cl, then $R^3$ is other than 5-CF$_3$, 5-CN or 5-NO$_2$; ii) $Y^1$ is N; $Y^2$ is CH; $Y^3$ is CBr; $Y^4$ is CH; and $R^2$ is Br, then $R^3$ is other than 5-CF$_3$; and iii) $Y^1$ is N; $Y^2$ is CCH$_3$; $Y^3$ is CCl; $Y^4$ is CCl; and $R^2$ is Cl, then m is other than 0.

More particularly, this invention pertains to a compound of Formula 1 (including all stereoisomers), an N-oxide or a salt thereof. This invention also relates to a herbicidal composition comprising a compound of the invention (i.e. in a herbicidally effective amount) and at least one component selected from the group consisting of surfactants, solid diluents and liquid diluents. This invention further relates to a method for controlling the growth of undesired vegetation comprising contacting the vegetation or its environment with a herbicidally effective amount of a compound of the invention (e.g., as a composition described herein).

This invention also includes a herbicidal mixture comprising (a) a compound selected from Formula 1, N-oxides, and salts thereof, and (b) at least one additional active ingredient selected from (b1) through (b16); and salts of compounds of (b1) through (b16).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to herein, the term "seedling", used either alone or in a combination of words means a young plant developing from the embryo of a seed. As referred to herein, the term "broadleaf" used either alone or in words such as "broadleaf weed" means dicot or dicotyledon, a term used to describe a group of angiosperms characterized by embryos having two cotyledons.

As used herein, the term "alkylating agent" refers to a chemical compound in which a carbon-containing radical is bound through a carbon atom to a leaving group such as halide or sulfonate, which is displaceable by bonding of a nucleophile to said carbon atom. Unless otherwise indicated, the term "alkylating" does not limit the carbon-containing radical to alkyl; the carbon-containing radicals in alkylating agents include the variety of carbon-bound substituent radicals specified for $R^1$ and $R^3$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include CH$_3$OCH$_2$, CH$_3$OCH$_2$CH$_2$, CH$_3$CH$_2$OCH$_2$, CH$_3$CH$_2$CH$_2$CH$_2$OCH$_2$ and CH$_3$CH$_2$OCH$_2$CH$_2$. "Alkylthio" includes branched or straight-chain alkylthio moieties such as methylthio, ethylthio, and the different propylthio, butylthio, pentylthio and hexylthio isomers. "Alkylthioalkoxy" denotes alkylthio substitution on alkoxy. "Cyanoalkyl" denotes an alkyl group substituted with one cyano group. "Examples of" "cyanoalkyl" include NCCH$_2$, NCCH$_2$CH$_2$ and CH$_3$CH(CN)CH$_2$. "Cyanoalkoxy" denotes an alkoxy group substituted with one cyano group.

"Cycloalkyl" includes, for example, cyclopropyl, cyclobutyl, cyclopentyl and cyclohexyl. The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include F$_3$C, ClCH$_2$, CF$_3$CH$_2$ and CF$_3$CCl$_2$. The term "haloalkoxy" is defined analogously to the term "haloalkyl". Examples of "haloalkoxy" include CF$_3$O—, CCl$_3$CH$_2$O—, HCF$_2$CH$_2$CH$_2$O— and CF$_3$CH$_2$O—. "Alkylcarbonyl" denotes a straight-chain or branched alkyl moieties bonded to a C(=O) moiety. Examples of "alkylcarbonyl" include CH$_3$C(=O)—, CH$_3$CH$_2$CH$_2$C(=O)— and (CH$_3$)$_2$CHC(=O)—. Examples of "alkoxycarbonyl" include CH$_3$OC(=O)—, CH$_3$CH$_2$OC(=O)—, CH$_3$CH$_2$CH$_2$OC(=O)—, (CH$_3$)$_2$CHOC(=O)— and the different butoxy- or pentoxycarbonyl isomers.

The total number of carbon atoms in a substituent group is indicated by the "$C_i$-$C_j$" prefix where i and j are numbers from 1 to 6. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R^3)_m$, m is 0, 1, 2, 3 or 4. Further, when the subscript indicates a range, e.g. $(R)_{i-j}$, then the number of substituents may be selected from the integers between i and j inclusive. When a group contains a substituent which can be hydrogen, for example $R^{3B}$, $R^{3C}$ or $R^{3D}$ then when this substituent is taken as hydrogen, it is recognized that this is equivalent to said group being unsubstituted. When a variable group is shown to be optionally attached to a position, for example $(R^3)_m$ wherein m may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of Formula 1 (e.g., —$Y^1$=$Y^2$—$Y^3$=$Y^4$—) is heterocyclic. The term "ring member" refers to an atom or other moiety (e.g., $C(R^1)$, N) forming the backbone of a ring or ring system.

The term "optionally substituted" in connection with the heterocyclic rings refers to groups which are unsubstituted or have at least one non-hydrogen substituent that does not extinguish the biological activity possessed by the unsubstituted analog. As used herein, the following definitions shall apply unless otherwise indicated. The term "optionally substituted" is used interchangeably with the phrase "substituted or unsubstituted" or with the term "(un)substituted." Unless otherwise indicated, an optionally substituted group may have a substituent at each substitutable position of the group, and each substitution is independent of the other.

When —$Y^1$=$Y^2$—$Y^3$=$Y^4$— taken together with the nitrogen atom to which both ends are attached, it is a 5-membered nitrogen-containing heterocyclic ring, it is attached to the remainder of Formula 1 only though the indicated nitrogen ring atom.

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. Stereoisomers are isomers of identical constitution but differing in the arrangement of their atoms in space and include enantiomers, diastereomers, cis-trans isomers (also known as geometric isomers) and atropisomers. Atropisomers result from restricted rotation about single bonds where the rotational barrier is high enough to permit isolation of the isomeric species. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Preferably the compositions of this invention have at least a 50% enantiomeric excess; more preferably at least a 75% enantiomeric excess; still more preferably at least a 90% enantiomeric excess; and the most preferably at least a 94% enantiomeric excess of the more active isomer. Of particular note are enantiomerically pure embodiments of the more active isomer.

Compounds of Formula 1 can comprise additional chiral centers. For example, substituents and other molecular constituents such as $R^2$ and $R^3$ may themselves contain chiral centers. This invention comprises racemic mixtures as well as enriched and essentially pure stereoconfigurations at these additional chiral centers.

Compounds of Formula 1 typically exist in more than one form, and Formula 1 thus include all crystalline and non-crystalline forms of the compounds they represent. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound of Formula 1 can exhibit beneficial effects (e.g., suitability for preparation of useful formulations, improved biological performance) relative to another polymorph or a mixture of polymorphs of the same compound of Formula 1. Preparation and isolation of a particular polymorph of a compound of Formula 1 can be achieved by methods known to those skilled in the art including, for example, crystallization using selected solvents and temperatures. For a comprehensive discussion of polymorphism see R. Hilfiker, Ed., *Polymorphism in the Pharmaceutical Industry*, Wiley-VCH, Weinheim, 2006.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M.

Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of a compound of Formula 1 are useful for control of undesired vegetation (i.e. are agriculturally suitable). The salts of a compound of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides and agriculturally suitable salts thereof.

Embodiments of the present invention as described in the Summary of the Invention include the following (where Formula 1 as used in the following Embodiments includes N-oxides and salts thereof) and reference to "a compound of Formula 1" includes the definitions of substituents specified in the Summary of the Invention unless further defined in the Embodiments:

Embodiment 1

A compound of Formula 1 wherein —$Y^1$=$Y^2$—$Y^3$=$Y^4$— including the nitrogen to which $Y^1$ and $Y^4$ are both attached is selected from

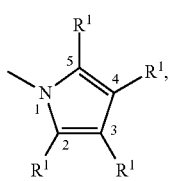
Q-1

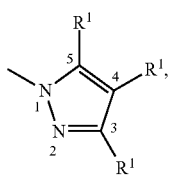
Q-2

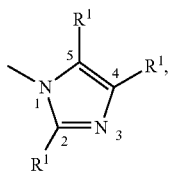
Q-3

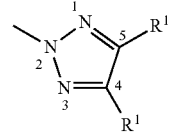
Q-4

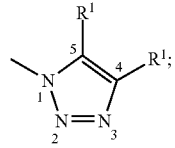
Q-5

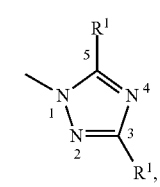
Q-6

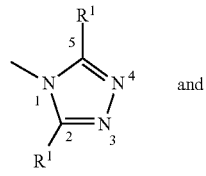
Q-7
and

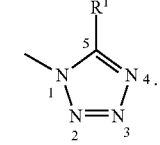
Q-8

Embodiment 2

A compound of Embodiment 1 wherein —$Y^1$=$Y^2$—$Y^3$=$Y^4$— including the nitrogen to which $Y^1$ and $Y^4$ are both attached is selected from Q-2, Q-3, Q-4 and Q-5.

Embodiment 3

A compound of Embodiment 2 wherein —$Y^1$=$Y^2$—$Y^3$=$Y^4$— including the nitrogen to which $Y^1$ and $Y^4$ are both attached is selected from Q-2 and Q-5.

Embodiment 4

A compound of Embodiment 3 wherein —$Y^1$=$Y^2$—$Y^3$=$Y^4$— including the nitrogen to which $Y^1$ and $Y^4$ are both attached is Q-2.

Embodiment 4a

A compound of Embodiment 4 wherein $R^1$ is hydrogen in the 3 and 5 positions and $R^1$ is other than hydrogen in the 4 position.

Embodiment 5

A compound of Embodiment 3 wherein —$Y^1$=$Y^2$—$Y^3$=$Y^4$— including the nitrogen to which $Y^1$ and $Y^4$ are both attached is Q-5.

Embodiment 5a

A compound of Embodiment 5 wherein $R^1$ is hydrogen in the 5 position and $R^1$ is other than hydrogen in the 4 position.

Embodiment 6

A compound of Formula 1 or any one of Embodiments 1 through 5a either alone or in combination, wherein Z is O.

Embodiment 7

A compound of Formula 1 or any one of Embodiments 1 through 6 either alone or in combination, wherein each $R^1$ is independently hydrogen, halogen, cyano, $SF_5$, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_6$ cyanoalkyl, $C_2$-$C_4$ alkylthioalkyl, $SO_nR^{1A}$, $Si(CH_3)_3$ or $B(—OC(R^{1B})_2C(R^{1B})_2O—)$.

Embodiment 8

A compound of Embodiment 7 wherein each $R^1$ is independently hydrogen, halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_4$ alkylthioalkyl or $SO_nR^{1A}$.

Embodiment 9

A compound of Embodiment 8 wherein each $R^1$ is independently hydrogen, halogen, cyano, $C_1$-$C_4$ alkyl, $C_1$-$C_4$ haloalkyl, $C_1$-$C_4$ alkoxy, $C_1$-$C_4$ haloalkoxy or $SO_nR^{1A}$.

Embodiment 10

A compound of Embodiment 9 wherein each $R^1$ is independently hydrogen, halogen, $C_1$-$C_4$ alkyl, $C_1$-$C_4$ haloalkyl or $C_1$-$C_4$ haloalkoxy.

Embodiment 11

A compound of Embodiment 10 wherein each $R^1$ is independently hydrogen, halogen, $C_1$-$C_4$ haloalkyl or $C_1$-$C_4$ haloalkoxy.

Embodiment 11a

A compound of Embodiment 11 wherein each $R^1$ is independently hydrogen, halogen or $C_1$-$C_4$ haloalkyl.

Embodiment 12

A compound of Formula 1 or any one of Embodiments 1 through 11a either alone or in combination, wherein $R^2$ is halogen, $C_1$-$C_4$ alkyl or $C_1$-$C_4$ haloalkyl.

Embodiment 13

A compound of Embodiment 12 wherein $R^2$ is halogen or $C_1$-$C_4$ alkyl.

Embodiment 14

A compound of Embodiment 13 wherein $R^2$ is halogen or $CH_3$.

Embodiment 15

A compound of Embodiment 14 wherein $R^2$ is halogen.

Embodiment 16

A compound of Embodiment 15 wherein $R^2$ is F, Cl or Br.

Embodiment 17

A compound of Formula 1 or any one of Embodiments 1 through 16 either alone or in combination, wherein m is 0, 1 or 2.

Embodiment 18

A compound of Embodiment 17 wherein m is 0 or 1.

Embodiment 19

A compound of Embodiment 18 wherein m is 1.

Embodiment 20

A compound of Embodiment 18 wherein m is 0 (i.e. the 3-, 4-, 5- and 6-positions are unsubstituted by $R^3$).

Embodiment 21

A compound of Formula 1 or any one of Embodiments 1 through 20 either alone or in combination, wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_6$ alkylcarbonyloxy, $C_2$-$C_6$ cyanoalkyl, $C(=O)N(R^{3A})(R^{3B})$, $C(=NOR^{3C})H$, $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 22

A compound of Embodiment 21 wherein each $R^3$ is independently halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl, $SO_nR^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members.

Embodiment 23

A compound of Embodiment 22 wherein each $R^3$ is independently halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl or $C_2$-$C_6$ haloalkoxyalkyl.

Embodiment 24

A compound of Embodiment 23 wherein each $R^3$ is independently halogen, cyano, $C_1$-$C_4$ alkyl or $C_1$-$C_4$ haloalkyl.

Embodiment 25

A compound of Embodiment 24 wherein each $R^3$ is independently halogen or cyano.

Embodiment 26

A compound of Formula 1 or any one of Embodiments 1 through 25 either alone or in combination, wherein each $R^3$ is attached to the remainder of Formula 1 at the 3-, 4- or 6-position.

Embodiment 27

A compound of Embodiment 26 wherein each $R^3$ is attached to the remainder of Formula 1 at the 3- or 4-position.

Embodiment 28

A compound of Embodiment 27 wherein $R^3$ is attached to the remainder of Formula 1 at the 3-position.

Embodiment 29

A compound of Formula 1 or any one of Embodiments 1 through 28 either alone or in combination, wherein each $R^{1A}$ is independently $C_1$-$C_4$ alkyl or $C_1$-$C_4$ haloalkyl.

Embodiment 30

A compound of Embodiment 29 wherein each $R^{1A}$ is independently $C_1$-$C_4$ haloalkyl.

Embodiment 31

A compound of Formula 1 or any one of Embodiments 1 through 30 either alone or in combination, wherein each $R^{3E}$ is independently $C_1$-$C_4$ alkyl.

Embodiment 32

A compound of Formula 1 or any one of Embodiments 1 through 31 either alone or in combination, wherein each $R^{3A}$ is independently $C_1$-$C_4$ alkyl.

Embodiment 33

A compound of Formula 1 or any one of Embodiments 1 through 32 either alone or in combination, wherein each $R^{3B}$ is independently H or $C_1$-$C_4$ alkyl.

Embodiment 34

A compound of Formula 1 or any one of Embodiments 1 through 33 either alone or in combination, wherein each $R^{3C}$ is independently H or $C_1$-$C_4$ alkyl.

Embodiment 35

A compound of Formula 1 or any one of Embodiments 1 through 34 either alone or in combination, wherein each $R^{3D}$ is independently H or $C_1$-$C_4$ alkyl.

Embodiment 36

A compound of Formula 1 or any one of Embodiments 1 through 35 either alone or in combination, wherein each n is independently 0 or 2.

Embodiment 37

A compound of Embodiment 36 wherein n is 2.

Embodiment 38

A compound of Embodiment 36 wherein n is 0.
Embodiments of the present invention as described in the Summary of the Invention also include the following:

Embodiment 1P

A compound of Formula 1 (including all stereoisomers), N-oxides, and salts thereof, agricultural compositions containing them and their use as herbicides as described in the Summary of the Invention.

Embodiment 2P

A compound of Embodiment 1 wherein each $Y^1$ and $Y^4$ is independently N or $CR^1$; and each $Y^2$ and $Y^3$ is $CR^1$; or each $Y^1$ and $Y^3$ is independently N or $CR^1$; and each $Y^2$ and $Y^4$ is $CR^1$.

Embodiment 3P

A compound of Embodiment 2 wherein $Y^1$ is N or $CR^1$; and each $Y^2$, $Y^3$ and $Y^4$ is $CR^1$.

Embodiment 4P

A compound of Embodiment 2 wherein $Y^3$ is N; and each $Y^1$, $Y^2$ and $Y^4$ is $CR^1$.

Embodiment 5P

A compound of Embodiment 3 wherein $Y^1$ is N; and each $Y^2$, $Y^3$ and $Y^4$ is $CR^1$.

Embodiment 6P

A compound of Embodiment 5 wherein $Y^1$ is N; and each $Y^2$ and $Y^4$ is CH; and $Y^3$ is $CR^1$.

Embodiment 7P

A compound of Embodiment 1 wherein —$Y^1$=$Y^2$—$Y^3$=$Y^4$— (including the nitrogen to which $Y^1$ and $Y^4$ are both attached) is selected from Q-1, Q-2, Q-3, Q-4, Q-5, Q-6, Q-7 and Q-8;

p is 0, 1, 2, 3 or 4;
q is 0, 1, 2 or 3;
r is 0, 1 or 2; and
s is 0 or 1.

Embodiment 8P

A compound of Embodiment 7 wherein —$Y^1$=$Y^2$—$Y^3$=$Y^4$— (including the nitrogen to which $Y^1$ and $Y^4$ are both attached) is selected from Q-2, Q-3 and Q-4; q is 0, 1 or 2; and r is 0 or 1.

Embodiment 9P

A compound of Embodiment 8 wherein —$Y^1$=$Y^2$—$Y^3$=$Y^4$— (including the nitrogen to which $Y^1$ and $Y^4$ are both attached) is selected from Q-2 and Q-3; and q is 1 or 2.

Embodiment 10P

A compound of Embodiment 9 wherein —$Y^1$=$Y^2$—$Y^3$=$Y^4$— (including the nitrogen to which $Y^1$ and $Y^4$ are both attached) is Q-2.

Embodiment 11P

A compound of Embodiment 10 wherein —$Y^1$=$Y^2$—$Y^3$=$Y^4$— (including the nitrogen to which $Y^1$ and $Y^4$ are both attached) is Q-2; and q is 1.

Embodiment 12P

A compound of any one of Embodiments 7 through 11 wherein each n is independently 0 or 2.

Embodiment 13P

A compound of Embodiment 12 wherein n is 2.

Embodiment 14P

A compound of Embodiment 12 wherein n is 0.

Embodiment 15P

A compound of any one of Embodiments 1 through 14 wherein Z is O.

Embodiment 16P

A compound of any one of Embodiments 1 through 15 wherein $R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy $C_2$-$C_4$ alkoxyalkyl, $C_2$-$C_4$ alkylthioalkyl or $SO_nR^{14}$.

Embodiment 17P

A compound of Embodiment 16 wherein $R^1$ is halogen, cyano, $C_1$-$C_4$ alkyl, $C_1$-$C_4$ alkoxy, $C_1$-$C_4$ haloalkyl or $SCF_3$.

Embodiment 18P

A compound of Embodiment 17 wherein $R^1$ is halogen, $C_1$-$C_4$ alkyl or $C_1$-$C_4$ haloalkyl.

Embodiment 19P

A compound of Embodiment 18 wherein $R^1$ is halogen or $C_1$-$C_4$ haloalkyl.

Embodiment 20P

A compound of any one of Embodiments 1 through 19 wherein $R^2$ is halogen, $C_1$-$C_4$ alkyl or $C_1$-$C_4$ haloalkyl.

Embodiment 21P

A compound of Embodiment 20 wherein $R^2$ is halogen or $C_1$-$C_4$ alkyl.

Embodiment 22P

A compound of Embodiment 21 wherein $R^2$ is halogen or $CH_3$.

Embodiment 23P

A compound of Embodiment 22 wherein $R^2$ is halogen.

Embodiment 24P

A compound of Embodiment 23 wherein $R^2$ is F, Cl or Br.

Embodiment 25P

A compound of any one of Embodiments 1 through 24 wherein m is 0, 1 or 2.

Embodiment 26P

A compound of Embodiment 25 wherein m is 0 or 1.

Embodiment 27P

A compound of Embodiment 26 wherein m is 1.

Embodiment 28P

A compound of any one of Embodiments 1 through 24 wherein m is 0 (i.e. the 3-, 4-, 5- and 6-positions are unsubstituted by $R^3$).

Embodiment 29P

A compound of any one of Embodiments 1 through 27 wherein each $R^3$ is independently halogen, cyano, hydroxy, nitro, amino, CHO, $C_1$-$C_4$ alkyl, $C_2$-$C_4$ alkenyl, $C_2$-$C_4$ alkynyl, $C(=O)N(R^{3A})(R^{3B})$, $C(=NOR^{3C})H$, $C(=N)(R^{3D})H$, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl.

Embodiment 30P

A compound of Embodiment 29 wherein each $R^3$ is independently halogen, cyano, amino, $C_1$-$C_4$ alkyl, $C_2$-$C_4$ alkenyl, $C_2$-$C_4$ alkynyl, $C_1$-$C_4$ alkoxy, $C_2$-$C_4$ alkoxycarbonyl, $C_2$-$C_4$ alkylcarbonyloxy, $C_2$-$C_4$ alkoxyalkyl or $C_1$-$C_4$ haloalkyl.

Embodiment 31P

A compound of Embodiment 30 wherein each $R^3$ is independently halogen, cyano, amino or $C_1$-$C_4$ alkyl.

Embodiment 32P

A compound of Embodiment 31 wherein each $R^3$ is independently cyano.

Embodiment 33P

A compound of any one of Embodiments 1 through 27 or 29 through 32 wherein each $R^3$ is attached to the remainder of Formula 1 at the 3-, 4- or 6-position.

Embodiment 34P

A compound of Embodiments 33 wherein each $R^3$ is attached to the remainder of Formula 1 at the 3- or 4-position.

Embodiment 35P

A compound of Embodiment 34 wherein $R^3$ is attached to the remainder of Formula 1 at the 3-position.

Embodiment 36P

A compound of any one of Embodiments 1 through 16 or 20 through 25 wherein $R^{1A}$ is $C_1$-$C_4$ alkyl or $C_1$-$C_4$ haloalkyl.

Embodiment 37P

A compound of Embodiment 36 wherein $R^{1A}$ is $C_1$-$C_4$ haloalkyl.

Embodiment 38P

A compound of any one of Embodiments 1 through 29 or 33 through 37 wherein $R^{3E}$ is $C_1$-$C_4$ alkyl.

Embodiment 39P

A compound of any one of Embodiments 1 through 38 wherein $R^{3A}$ is $C_1$-$C_4$ alkyl.

Embodiment 40P

A compound of any one of Embodiments 1 through 39 wherein $R^{3B}$ is H or $C_1$-$C_4$ alkyl.

Embodiment 41P

A compound of any one of Embodiments 1 through 40 wherein $R^{3C}$ is H or $C_1$-$C_4$ alkyl.

Embodiment 42P

A compound of any one of Embodiments 1 through 41 wherein $R^{3D}$ is H or $C_1$-$C_4$ alkyl.

Embodiments of this invention, including Embodiments 1-38 and 1P-42P above as well as any other embodiments described herein, can be combined in any manner, and the descriptions of variables in the embodiments pertain not only to the a compound of Formula 1 but also to the starting compounds and intermediate compounds useful for preparing the compounds of Formula 1. In addition, embodiments of this invention, including Embodiments 1-38 and 1P-42P above as well as any other embodiments described herein, and any combination thereof, pertain to the compositions and methods of the present invention.

Embodiment AAA

A compound of Formula 1 wherein
each $Y^1$, $Y^2$, $Y^3$ and $Y^4$ is independently N or $CR^1$, provided no more than 3 of $Y^1$, $Y^2$, $Y^3$ and $Y^4$ are N;
Z is O or S;
$R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy, $C_2$-$C_4$ alkoxyalkyl, $C_2$-$C_4$ alkylthioalkyl, $SO_nR^{1A}$, $C_3$-$C_6$ cycloalkyl, phenyl or pyridyl;

$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$ or $C_1$-$C_4$ haloalkyl;

m is 0, 1, 2 or 3;

each $R^3$ is independently halogen, cyano, hydroxy, nitro, amino, CHO, $C_1$-$C_4$ alkyl, $C_2$-$C_4$ alkenyl, $C_2$-$C_4$ alkynyl, $C(=O)N(R^{3A})(R^{3B})$, $C(=NOR^{3C})H$, $C(=N)(R^{3D})H$, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl; or phenyl optionally substituted with cyano, halogen or $C_1$-$C_4$ alkyl;

each n is independently 0, 1 or 2;

each $R^{1A}$, $R^{2A}$ and $R^{3E}$ is independently $C_1$-$C_4$ alkyl, $C_1$-$C_4$ haloalkyl, $C_1$-$C_4$ alkylamino or $C_2$-$C_6$ dialkylamino;

$R^{3A}$ is $C_1$-$C_4$ alkyl or $C_1$-$C_4$ haloalkyl;

$R^{3B}$ is H, $C_1$-$C_4$ alkyl or $C_1$-$C_4$ haloalkyl;

$R^{3C}$ is H or $C_1$-$C_4$ alkyl; and $R^{3D}$ is H or $C_1$-$C_4$ alkyl provided when i) $Y^1$ is N; $Y^2$ is CH; $Y^3$ is CBr; $Y^4$ is CH; and $R^2$ is Cl, then $R^3$ is other than 5-$CF_3$, 5-CN and 5-$NO_2$; ii) $Y^1$ is N; $Y^2$ is CH; $Y^3$ is CBr; $Y^4$ is CH; and $R^2$ is Br, then $R^3$ is other than 5-$CF_3$; and iii) $Y^1$ is N; $Y^2$ is $CCH_3$; $Y^3$ is CCl; $Y^4$ is CCl; and $R^2$ is Cl, then m is other than 0.

Embodiment AA

A compound of Embodiment A or a compound of Formula 1 as described in the Summary of the Invention wherein each $Y^1$, $Y^2$, $Y^3$ and $Y^4$ is independently N or $CR^1$, provided no more than 3 of $Y^1$, $Y^2$, $Y^3$ and $Y^4$ are N;

Z is O or S;

each $R^1$ is independently hydrogen, halogen, cyano, nitro, $SF_5$, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_8$ alkylaminocarbonyl, $C_3$-$C_{10}$ dialkylaminocarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $SO_nR^{1A}$, $Si(CH_3)_3$ or $B(—OC(R^{1B})_2C(R^{1B})_2O—)$; or a phenyl ring optionally substituted with up to 5 substituents independently selected from $R^{1C}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{1C}$ on carbon atom ring members and $R^{1D}$ on nitrogen atom ring members;

$R^2$ is halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$, $C_1$-$C_4$ haloalkyl or $C_3$-$C_6$ cycloalkyl;

m is 0, 1, 2 or 3;

each $R^3$ is independently halogen, cyano, hydroxy, nitro, amino, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $Si(CH_3)_3$, $C\equiv CSi(CH_3)_3$, $C(=O)N(R^{3A})(R^{3B})$, $C(=NOR^{3C})H$, $C(=NR^{3D})H$, $SO_nR^{3E}$; or a phenyl ring optionally substituted with up to 5 substituents independently selected from $R^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; or pyrimidinyloxy;

each n is independently 0, 1 or 2;

each $R^{1A}$, $R^{2A}$ and $R^{3E}$ is independently $C_1$-$C_4$ alkyl, $C_1$-$C_4$ haloalkyl, $C_1$-$C_4$ alkylamino or $C_2$-$C_6$ dialkylamino;

each $R^{1B}$ is independently H or $C_1$-$C_4$ alkyl;

each $R^{1C}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy;

each $R^{1D}$ is independently cyano, $C_1$-$C_6$ alkyl, $C_1$-$C_6$ haloalkyl, $C_1$-$C_6$ alkoxy or $C_2$-$C_6$ alkylcarbonyl;

each $R^{3A}$ is independently $C_1$-$C_4$ alkyl or $C_1$-$C_4$ haloalkyl;

each $R^{3B}$ is independently H, $C_1$-$C_4$ alkyl or $C_1$-$C_4$ haloalkyl;

each $R^{3C}$ is independently H or $C_1$-$C_4$ alkyl;

each $R^{3D}$ is independently H, amino, $C_1$-$C_4$ alkyl or $C_1$-$C_4$ alkylamino;

each $R^{3F}$ is independently hydroxy, halogen, cyano, nitro, $C_1$-$C_6$ alkyl, $C_1$-$C_6$ haloalkyl, $C_1$-$C_6$ alkoxy or $C_1$-$C_6$ haloalkoxy; and each $R^{3G}$ is independently cyano, $C_1$-$C_6$ alkyl, $C_1$-$C_6$ haloalkyl, $C_1$-$C_6$ alkoxy or $C_2$-$C_6$ alkylcarbonyl;

provided when i) $Y^1$ is N; $Y^2$ is CH; $Y^3$ is CBr; $Y^4$ is CH; and $R^2$ is Cl, then $R^3$ is other than 5-$CF_3$, 5-CN or 5-$NO_2$; ii) $Y^1$ is N; $Y^2$ is CH; $Y^3$ is CBr; $Y^4$ is CH; and $R^2$ is Br, then $R^3$ is other than 5-$CF_3$; and iii) $Y^1$ is N; $Y^2$ is $CCH_3$; $Y^3$ is CCl; $Y^4$ is CCl; and $R^2$ is Cl, then m is other than 0.

Embodiment A

A compound of Embodiment AA wherein
—$Y^1$=$Y^2$—$Y^3$=$Y^4$— including the nitrogen to which $Y^1$ and $Y^4$ are both attached is selected from

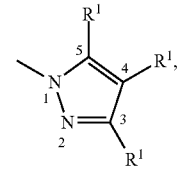

Q-2

-continued

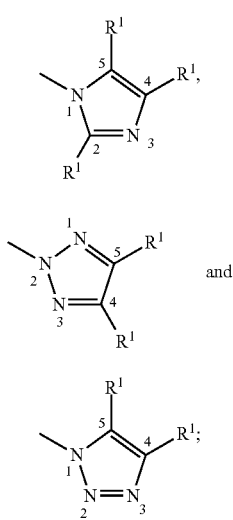

Z is O;
each R$^1$ is independently hydrogen, halogen, cyano, SF$_5$, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_2$-C$_6$ alkoxyalkyl, C$_2$-C$_6$ haloalkoxyalkyl, C$_2$-C$_6$ cyanoalkyl, C$_2$-C$_4$ alkylthioalkyl, SO$_n$R$^{1A}$, Si(CH$_3$)$_3$ or B(—OC(R$^{1B}$)$_2$C(R$^{1B}$)$_2$O—);
R$^2$ is halogen, C$_1$-C$_4$ alkyl or C$_1$-C$_4$ haloalkyl;
each R$^3$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_4$-C$_8$ alkylcycloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_3$-C$_6$ cycloalkoxy, C$_3$-C$_6$ halocycloalkoxy, C$_2$-C$_6$ alkoxyalkyl, C$_2$-C$_6$ haloalkoxyalkyl, C$_2$-C$_4$ alkylcarbonyloxy, C$_2$-C$_6$ cyanoalkyl, C(=O)N(R$^{3A}$)(R$^{3B}$), C(=NOR$^{3C}$)H, SO$_n$R$^{3E}$; or a phenyl ring optionally substituted with up to 5 substituents independently selected from R$^{3F}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{3F}$ on carbon atom ring members and R$^{3G}$ on nitrogen atom ring members; and
m is 0, 1 or 2.

Embodiment B

A compound of Embodiment A wherein
—Y$^1$=Y$^2$—Y$^3$=Y$^4$— including the nitrogen to which Y$^1$ and Y$^4$ are both attached is selected from Q-2 and Q-5.
each R$^1$ is independently hydrogen, halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_1$-C$_4$ alkoxy, C$_3$-C$_4$ alkenyloxy, C$_3$-C$_4$ alkynyloxy, C$_1$-C$_4$ haloalkoxy, C$_3$-C$_4$ haloalkenyloxy, C$_3$-C$_4$ haloalkynyloxy, C$_2$-C$_6$ alkoxyalkyl, C$_2$-C$_6$ haloalkoxyalkyl, C$_2$-C$_4$ alkylthioalkyl or SO$_n$R$^{1A}$;
R$^2$ is halogen or C$_1$-C$_4$ alkyl;
each R$^3$ is independently halogen, cyano, CHO, C$_1$-C$_4$ alkyl, C$_2$-C$_4$ alkenyl, C$_2$-C$_4$ alkynyl, C$_1$-C$_4$ haloalkyl, C$_2$-C$_4$ haloalkenyl, C$_2$-C$_4$ haloalkynyl, C$_3$-C$_6$ cycloalkyl, C$_3$-C$_6$ halocycloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_1$-C$_4$ haloalkoxy, C$_2$-C$_6$ alkoxyalkyl, C$_2$-C$_6$ haloalkoxyalkyl, C$_2$-C$_6$ cyanoalkyl, SO$_n$R$^{3E}$; or a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from R$^{3F}$ on carbon atom ring members and R$^{3G}$ on nitrogen atom ring members; and
m is 0 or 1.

Embodiment C

A compound of Embodiment B wherein
each R$^1$ is independently hydrogen, halogen, cyano, C$_1$-C$_4$ alkyl, C$_1$-C$_4$ haloalkyl, C$_1$-C$_4$ alkoxy, C$_1$-C$_4$ haloalkoxy or SO$_n$R$^{1A}$;
R$^2$ is halogen or CH$_3$;
each R$^3$ is independently halogen, cyano, C$_1$-C$_4$ alkyl, C$_2$-C$_4$ alkenyl, C$_2$-C$_4$ alkynyl, C$_1$-C$_4$ haloalkyl, C$_2$-C$_6$ alkylcarbonyl, C$_2$-C$_6$ haloalkylcarbonyl, C$_2$-C$_6$ alkoxycarbonyl, C$_1$-C$_4$ alkoxy, C$_1$-C$_4$ haloalkoxy, C$_2$-C$_6$ alkoxyalkyl or C$_2$-C$_6$ haloalkoxyalkyl; and
each R$^{1A}$ is independently C$_1$-C$_4$ alkyl or C$_1$-C$_4$ haloalkyl.

Embodiment D

A compound of Embodiment C wherein
—Y$^1$=Y$^2$—Y$^3$=Y$^4$— including the nitrogen to which Y$^1$ and Y$^4$ are both attached is Q-2;
each R$^1$ is independently hydrogen, halogen, C$_1$-C$_4$ haloalkyl or C$_1$-C$_4$ haloalkoxy; and
each R$^3$ is independently halogen, cyano, C$_1$-C$_4$ alkyl or C$_1$-C$_4$ haloalkyl.

Embodiment E

A compound of Embodiment C wherein
—Y$^1$=Y$^2$—Y$^3$=Y$^4$— including the nitrogen to which Y$^1$ and Y$^4$ are both attached is Q-5;
each R$^1$ is independently hydrogen, halogen, C$_1$-C$_4$ haloalkyl or C$_1$-C$_4$ haloalkoxy; and
each R$^3$ is independently halogen, cyano, C$_1$-C$_4$ alkyl or C$_1$-C$_4$ haloalkyl.

Specific embodiments include compounds of Formula 1 selected from the group consisting of:
5-chloro-2-[2-[3-(trifluoromethyl)-1H-pyrazol-1-yl]phenoxy]pyrimidine (Compound 2),
5-bromo-2-[2-(4-chloro-1H-pyrazol-1-yl)phenoxy]pyrimidine (Compound 5),
2-[2-(4-bromo-1H-pyrazol-1-yl)phenoxy]-5-chloropyrimidine (Compound 7),
2-[2-(4-bromo-1H-pyrazol-1-yl)phenoxy]-5-fluoropyrimidine (Compound 10),
5-bromo-2-[2-[4-(trifluoromethyl)-1H-pyrazol-1-yl]phenoxy]pyrimidine (Compound 18),
2-(4-bromo-1H-pyrazol-1-yl)-3-[(5-chloro-2-pyrimidinyl)oxy]benzonitrile (Compound 52), 2-[2-(4-bromo-2H-1,2,3-triazol-2-yl)phenoxy]-5-chloropyrimidine (Compound 54),
3[(5-chloro-2-pyrimidinyl)oxy]-2-[4-(trifluoromethyl)-1H-pyrazol-1-yl]benzonitrile (Compound 58),
3-[(5-bromo-2-pyrimidinyl)oxy]-2-[4-(trifluoromethyl)-1H-pyrazol-1-yl]benzonitrile (Compound 59),
5-chloro-2-[2-[4-(difluoromethyl)-1H-1,2,3-triazol-1-yl]-3-fluorophenoxy]pyrimidine (Compound 141),
5-chloro-2-[2-[4-(trifluoromethyl)-1H-1,2,3-triazol-1-yl]phenoxy]pyrimidine (Compound 166),
5-chloro-2-[2-[4-(difluoromethyl)-1H-1,2,3-triazol-1-yl]phenoxy]pyrimidine (Compound 147),
3-[(5-fluoro-2-pyrimidinyl)oxy]-2-[4-(trifluoromethyl)-1H-pyrazol-1-yl]benzonitrile (Compound 79),
2-[2-(4-bromo-1H-pyrazol-1-yl)-3-fluorophenoxy]-5-chloropyrimidine (Compound 178),
3-[(5-chloro-2-pyrimidinyl)oxy]-2-[4-(2,2,2-trifluoroethoxy)-1H-pyrazol-1-yl]benzonitrile (Compound 274),
5-chloro-2-[2-[4-(2,2,2-trifluoroethoxy)-1H-pyrazol-1-yl]phenoxy]pyrimidine (Compound 138),
2-[2-(4-bromo-1H-pyrazol-1-yl)-3-(difluoromethyl)phenoxy]-5-chloropyrimidine (Compound 194),
3-[(5-chloro-2-pyrimidinyl)oxy]-2-[4-(difluoromethyl)-1H-pyrazol-1-yl]benzonitrile (Compound 253),
3-[(5-chloro-2-pyrimidinyl)oxy]-2-[4-(trifluoromethyl)-1H-imidazol-1-yl]benzonitrile (Compound 252),
5-bromo-2-[2-[4-(difluoromethyl)-1H-1,2,3-triazol-1-yl]-3-fluorophenoxy]pyrimidine (Compound 305) and
5-chloro-2-[3-fluoro-2-[4-(trifluoromethyl)-1H-pyrazol-1-yl]phenoxy]pyrimidine.

Embodiments of the present invention as described in the Summary of the Invention also include the following:

Embodiment Ap

A compound of the Summary of the Invention wherein
each $Y^1$ and $Y^4$ is independently N or $CR^1$; and each $Y^2$ and $Y^3$ is $CR^1$; or
each $Y^1$ and $Y^3$ is independently N or $CR^1$; and each $Y^2$ and $Y^4$ is $CR^1$;
$R^1$ is halogen, cyano, CHO, $C_1$-$C_4$ alkyl, $C_2$-$C_4$ alkenyl, $C_2$-$C_4$ alkynyl, $C_1$-$C_4$ alkoxy, $C_3$-$C_4$ alkenyloxy, $C_3$-$C_4$ alkynyloxy, $C_1$-$C_4$ haloalkyl, $C_1$-$C_4$ haloalkoxy $C_2$-$C_4$ alkoxyalkyl, $C_2$-$C_4$ alkylthioalkyl or $SO_nR^{1A}$;
$R^2$ is halogen, $C_1$-$C_4$ alkyl or $C_1$-$C_4$ haloalkyl;
m is 0, 1 or 2;
each $R^3$ is independently halogen, cyano, hydroxy, nitro, amino, CHO, $C_1$-$C_4$ alkyl, $C_2$-$C_4$ alkenyl, $C_2$-$C_4$ alkynyl, C(=O)N($R^{3A}$)($R^{3B}$), C(=NO$R^{3C}$)H, C(=N)($R^{3D}$)H, $C_1$-$C_4$ alkoxy, $C_2$-$C_4$ cyanoalkoxy, $C_2$-$C_4$ alkylcarbonyl, $C_2$-$C_4$ alkoxycarbonyl, $C_2$-$C_4$ alkylcarbonyloxy, $C_2$-$C_4$ alkoxyalkyl, $C_1$-$C_4$ haloalkyl, $C_1$-$C_4$ haloalkoxy, $SO_nR^{3E}$ or $C_3$-$C_6$ cycloalkyl;
each $R^3$ is attached to the remainder of Formula 1 at the 3-, 4- or 6-position;
each n is independently 0 or 2;
$R^{1A}$ is $C_1$-$C_4$ alkyl or $C_1$-$C_4$ haloalkyl;
$R^{3E}$ is $C_1$-$C_4$ alkyl;
$R^{3A}$ is $C_1$-$C_4$ alkyl;
$R^{3B}$ is H or $C_1$-$C_4$ alkyl;
$R^{3C}$ is H or $C_1$-$C_4$ alkyl; and
$R^{3D}$ is H or $C_1$-$C_4$ alkyl.

Embodiment Bp

A compound of Embodiment A wherein
$Y^1$ is N or $CR^1$; and each $Y^2$, $Y^3$ and $Y^4$ is $CR^1$;
Z is O;
$R^1$ is halogen, cyano, $C_1$-$C_4$ alkyl, $C_1$-$C_4$ alkoxy, $C_1$-$C_4$ haloalkyl or $SCF_3$;
$R^2$ is halogen or $C_1$-$C_4$ alkyl;
m is 0 or 1;
each $R^3$ is independently halogen, cyano, amino, $C_1$-$C_4$ alkyl, $C_2$-$C_4$ alkenyl, $C_2$-$C_4$ alkynyl, $C_1$-$C_4$ alkoxy, $C_2$-$C_4$ alkoxycarbonyl, $C_2$-$C_4$ alkylcarbonyloxy, $C_2$-$C_4$ alkoxyalkyl or $C_1$-$C_4$ haloalkyl; and
each $R^3$ is attached to the remainder of Formula 1 at the 3- or 4-position.

Embodiment Cp

A compound of Embodiment B wherein
$Y^1$ is N; and each $Y^2$, $Y^3$ and $Y^4$ is $CR^1$;
$R^1$ is halogen, $C_1$-$C_4$ alkyl or $C_1$-$C_4$ haloalkyl;
$R^2$ is halogen or $CH_3$;
m is 1;
$R^3$ is independently halogen, cyano, amino or $C_1$-$C_4$ alkyl; and
$R^3$ is attached to the remainder of Formula 1 at the 3-position.

Embodiment Dp

A compound of Embodiment B wherein
$Y^1$ is N; and each $Y^2$ and $Y^4$ is CH; and $Y^3$ is $CR^1$;
$R^1$ is halogen or $C_1$-$C_4$ haloalkyl;
$R^2$ is halogen; and
m is 0.

Specific embodiments include compounds of Formula 1 selected from the group consisting of:
5-chloro-2-[2-[3-(trifluoromethyl)-1H-pyrazol-1-yl]phenoxy]pyrimidine Compound 2);
5-bromo-2-[2-(4-chloro-1H-pyrazol-1-yl)phenoxy]pyrimidine (Compound 5);
2-[2-(4-bromo-1H-pyrazol-1-yl)phenoxy]-5-chloropyrimidine Compound 7);
2-[2-(4-bromo-1H-pyrazol-1-yl)phenoxy]-5-fluoropyrimidine (Compound 10);
5-bromo-2-[2-[4-(trifluoromethyl)-1H-pyrazol-1-yl]phenoxy]pyrimidine (Compound 18);
2-(4-bromo-1H-pyrazol-1-yl)-3-[(5-chloro-2-pyrimidinyl)oxy]benzonitrile (Compound 52);
2-[2-(4-bromo-2H-1,2,3-triazol-2-yl)phenoxy]-5-chloropyrimidine (Compound 54);
3[(5-chloro-2-pyrimidinyl)oxy]-2-[4-(trifluoromethyl)-1H-pyrazol-1-yl]benzonitrile (Compound 58); and
3-[(5-bromo-2-pyrimidinyl)oxy]-2-[4-(trifluoromethyl)-1H-pyrazol-1-yl]benzonitrile (Compound 59).

This invention also relates to a method for controlling undesired vegetation comprising applying to the locus of the vegetation herbicidally effective amounts of the compounds of the invention (e.g., as a composition described herein). Of note as embodiments relating to methods of use are those involving the compounds of embodiments described above. Compounds of the invention are particularly useful for selective control of grass and broadleaf weeds in crops such as wheat, barley, maize, soybean, sunflower, cotton, oilseed rape and rice, and specialty crops such as sugarcane, citrus, fruit and nut crops.

Also noteworthy as embodiments are herbicidal compositions of the present invention comprising the compounds of embodiments described above.

This invention also includes a herbicidal mixture comprising (a) a compound selected from Formula 1, N-oxides, and salts thereof, and (b) at least one additional active ingredient selected from (b1) photosystem II inhibitors, (b2) acetohydroxy acid synthase (AHAS) inhibitors, (b3) acetyl-CoA carboxylase (ACCase) inhibitors, (b4) auxin mimics and (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solenesyltransererase (HST) inhibitors, (b14) cellulose biosynthesis inhibitors, (b15) other herbicides including mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, and (b16) herbicide safeners; and salts of compounds of (b1) through (b16).

"Photosystem II inhibitors" (b1) are chemical compounds that bind to the D-1 protein at the $Q_B$-binding niche and thus block electron transport from $Q_A$ to $Q_B$ in the chloroplast thylakoid membranes. The electrons blocked from passing through photosystem II are transferred through a series of reactions to form toxic compounds that disrupt cell membranes and cause chloroplast swelling, membrane leakage, and ultimately cellular destruction. The $Q_B$-binding niche has three different binding sites: binding site A binds the triazines such as atrazine, triazinones such as hexazinone, and uracils such as bromacil, binding site B binds the phenylureas such as diuron, and binding site C binds benzothiadiazoles such as bentazon, nitriles such as bromoxynil and phenyl-pyridazines such as pyridate. Examples of photosystem II inhibitors include ametryn, amicarbazone, atrazine, bentazon, bromacil, bromofenoxim, bromoxynil, chlorbromuron, chloridazon, chlorotoluron, chloroxuron, cumyluron, cyanazine, daimuron, desmedipham, desmetryn, dimefuron, dimethametryn, diuron, ethidimuron, fenuron, fluometuron, hexazinone, ioxynil, isoproturon, isouron, lenacil, linuron, metamitron, methabenzthiazuron, metobromuron, metoxuron, metribuzin, monolinuron, neburon, pentanochlor, phenmedipham, prometon, prometryn, propanil, propazine, pyridafol, pyridate, siduron, simazine, simetryn, tebuthiuron, terbacil, terbumeton, terbuthylazine, terbutryn and trietazine.

"AHAS inhibitors" (b2) are chemical compounds that inhibit acetohydroxy acid synthase (AHAS), also known as acetolactate synthase (ALS), and thus kill plants by inhibiting the production of the branched-chain aliphatic amino acids such as valine, leucine and isoleucine, which are required for DNA synthesis and cell growth. Examples of AHAS inhibitors include amidosulfuron, azimsulfuron, bensulfuron-methyl, bispyribac-sodium, cloransulam-methyl, chlorimuron-ethyl, chlorsulfuron, cinosulfuron, cyclosulfamuron, diclosulam, ethametsulfuron-methyl, ethoxysulfuron, flazasulfuron, florasulam, flucarbazone-sodium, flumetsulam, flupyrsulfuron-methyl, flupyrsulfuron-sodium, foramsulfuron, halosulfuron-methyl, imazamethabenz-methyl, imazamox, imazapic, imazapyr, imazaquin, imazethapyr, imazosulfuron, iodosulfuron-methyl (including sodium salt), iofensulfuron (2-iodo-N-[[(4-methoxy-6-methyl-1,3,5-triazin-2-yl)amino]carbonyl]benzenesulfonamide), mesosulfuron-methyl, metazosulfuron (3-chloro-4-(5,6-dihydro-5-methyl-1,4,2-dioxazin-3-yl)-N-[[(4,6-dimethoxy-2-pyrimidinyl)amino]carbonyl]-1-methyl-1H-pyrazole-5-sulfonamide), metosulam, metsulfuron-methyl, nicosulfuron, oxasulfuron, penoxsulam, primisulfuron-methyl, propoxycarbazone-sodium, propyrisulfuron (2-chloro-N-[[(4,6-dimethoxy-2-pyrimidinyl)amino]carbonyl]-6-propylimidazo[1,2-b]pyridazine-3-sulfonamide), prosulfuron, pyrazosulfuron-ethyl, pyribenzoxim, pyriftalid, pyriminobac-methyl, pyrithiobac-sodium, rimsulfuron, sulfometuron-methyl, sulfosulfuron, thiencarbazone, thifensulfuron-methyl, triafamone (N-[2-[(4,6-dimethoxy-1,3,5-triazin-2-yl)carbonyl]-6-fluorophenyl]-1,1-difluoro-N-methylmethanesulfonamide), triasulfuron, tribenuron-methyl, trifloxysulfuron (including sodium salt), triflusulfuron-methyl and tritosulfuron.

"ACCase inhibitors" (b3) are chemical compounds that inhibit the acetyl-CoA carboxylase enzyme, which is responsible for catalyzing an early step in lipid and fatty acid synthesis in plants. Lipids are essential components of cell membranes, and without them, new cells cannot be produced. The inhibition of acetyl CoA carboxylase and the subsequent lack of lipid production leads to losses in cell membrane integrity, especially in regions of active growth such as meristems. Eventually shoot and rhizome growth ceases, and shoot meristems and rhizome buds begin to die back. Examples of ACCase inhibitors include alloxydim, butroxydim, clethodim, clodinafop, cycloxydim, cyhalofop, diclofop, fenoxaprop, fluazifop, haloxyfop, pinoxaden, profoxydim, propaquizafop, quizalofop, sethoxydim, tepraloxydim and tralkoxydim, including resolved forms such as fenoxaprop-P, fluazifop-P, haloxyfop-P and quizalofop-P and ester forms such as clodinafop-propargyl, cyhalofop-butyl, diclofop-methyl and fenoxaprop-P-ethyl.

Auxin is a plant hormone that regulates growth in many plant tissues. "Auxin mimics" (b4) are chemical compounds mimicking the plant growth hormone auxin, thus causing uncontrolled and disorganized growth leading to plant death in susceptible species. Examples of auxin mimics include aminocyclopyrachlor (6-amino-5-chloro-2-cyclopropyl-4-pyrimidinecarboxylic acid) and its methyl and ethyl esters and its sodium and potassium salts, aminopyralid, benazolin-ethyl, chloramben, clacyfos, clomeprop, clopyralid, dicamba, 2,4-D, 2,4-DB, dichlorprop, fluroxypyr, halauxifen (4-amino-3-chloro-6-(4-chloro-2-fluoro-3-methoxyphenyl)-2-pyridinecarboxylic acid), halauxifen-methyl (methyl 4-amino-3-chloro-6-(4-chloro-2-fluoro-3-methoxyphenyl)-2-pyridinecarboxylate), MCPA, MCPB, mecoprop, picloram, quinclorac, quinmerac, 2,3,6-TBA, triclopyr, and methyl 4-amino-3-chloro-6-(4-chloro-2-fluoro-3-methoxyphenyl)-5-fluoro-2-pyridinecarboxylate.

"EPSP (5-enol-pyruvylshikimate-3-phosphate) synthase inhibitors" (b5) are chemical compounds that inhibit the enzyme, 5-enol-pyruvylshikimate-3-phosphate synthase, which is involved in the synthesis of aromatic amino acids such as tyrosine, tryptophan and phenylalanine. EPSP inhibitor herbicides are readily absorbed through plant foliage and translocated in the phloem to the growing points. Glyphosate is a relatively nonselective postemergence herbicide that belongs to this group. Glyphosate includes esters and salts such as ammonium, isopropylammonium, potassium, sodium (including sesquisodium) and trimesium (alternatively named sulfosate).

"Photosystem I electron diverters" (b6) are chemical compounds that accept electrons from Photosystem I, and after several cycles, generate hydroxyl radicals. These radicals are extremely reactive and readily destroy unsaturated lipids, including membrane fatty acids and chlorophyll. This destroys cell membrane integrity, so that cells and organelles "leak", leading to rapid leaf wilting and desiccation, and eventually to plant death. Examples of this second type of photosynthesis inhibitor include diquat and paraquat.

"PPO inhibitors" (b7) are chemical compounds that inhibit the enzyme protoporphyrinogen oxidase, quickly resulting in formation of highly reactive compounds in plants that rupture cell membranes, causing cell fluids to leak out. Examples of PPO inhibitors include acifluorfen-sodium, azafenidin, benzfendizone, bifenox, butafenacil, carfentrazone, carfentrazone-ethyl, chlomethoxyfen, cinidon-ethyl, fluazolate, flufenpyr-ethyl, flumiclorac-pentyl, flumioxazin, fluoroglycofen-ethyl, fluthiacet-methyl, fomesafen, halosafen, lactofen, oxadiargyl, oxadiazon, oxyfluorfen, pentoxazone, profluazol, pyraclonil, pyraflufen-ethyl, saflufenacil, sulfentrazone, thidiazimin, tiafenacil (methyl N-[2-[[2-chloro-5-[3,6-dihydro-3-methyl-2,6-dioxo-4-(trifluoromethyl)-1(2H)-pyrimidinyl]-4-fluorophenyl]thio]-1-oxopropyl]-β-alaninate) and 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione.

"GS (glutamine synthase) inhibitors" (b8) are chemical compounds that inhibit the activity of the glutamine synthetase enzyme, which plants use to convert ammonia into glutamine. Consequently, ammonia accumulates and glutamine levels decrease. Plant damage probably occurs due to the combined effects of ammonia toxicity and deficiency of amino acids required for other metabolic processes. The GS inhibitors include glufosinate and its esters and salts such as glufosinate-ammonium and other phosphinothricin derivatives, glufosinate-P ((2S)-2-amino-4-(hydroxymethylphosphinyl)butanoic acid) and bilanaphos.

"VLCFA (very long chain fatty acid) elongase inhibitors" (b9) are herbicides having a wide variety of chemical structures, which inhibit the elongase. Elongase is one of the enzymes located in or near chloroplasts which are involved in biosynthesis of VLCFAs. In plants, very-long-chain fatty acids are the main constituents of hydrophobic polymers that prevent desiccation at the leaf surface and provide stability to pollen grains. Such herbicides include acetochlor, alachlor, anilofos, butachlor, cafenstrole, dimethachlor, dimethenamid, diphenamid, fenoxasulfone (3-[[(2,5-dichloro-4-ethoxyphenyl)methyl]sulfonyl]-4,5-dihydro-5,5-dimethylisoxazole), fentrazamide, flufenacet, indanofan, mefenacet, metazachlor, metolachlor, naproanilide, napropamide, napropamide-M ((2R)—N,N-diethyl-2-(1-naphthalenyloxy)propanamide), pethoxamid, piperophos, pretilachlor, propachlor, propisochlor, pyroxasulfone, and thenylchlor, including resolved forms such as S-metolachlor and chloroacetamides and oxyacetamides.

"Auxin transport inhibitors" (b10) are chemical substances that inhibit auxin transport in plants, such as by binding with an auxin-carrier protein. Examples of auxin transport inhibitors include diflufenzopyr, naptalam (also known as N-(1-naphthyl)phthalamic acid and 2-[(1-naphthalenylamino)carbonyl]benzoic acid).

"PDS (phytoene desaturase inhibitors) (b11) are chemical compounds that inhibit carotenoid biosynthesis pathway at the phytoene desaturase step. Examples of PDS inhibitors include beflubutamid, diflufenican, fluridone, flurochloridone, flurtamone norflurzon and picolinafen.

"HPPD (4-hydroxyphenyl-pyruvate dioxygenase) inhibitors" (b12) are chemical substances that inhibit the biosynthesis of synthesis of 4-hydroxyphenyl-pyruvate dioxygenase. Examples of HPPD inhibitors include benzobicyclon, benzofenap, bicyclopyrone (4-hydroxy-3-[[2-[(2-methoxyethoxy)methyl]-6-(trifluoromethyl)-3-pyridinyl]carbonyl]bicyclo[3.2.1]oct-3-en-2-one), fenquinotrione (2-[[8-chloro-3,4-dihydro-4-(4-methoxyphenyl)-3-oxo-2-quinoxalinyl]carbonyl]-1,3-cyclohexanedione), isoxachlortole, isoxaflutole, mesotrione, pyrasulfotol, pyrazolynate, pyrazoxyfen, sulcotrione, tefuryltrione, tembotrione, topramezone, 5-chloro-3-[(2-hydroxy-6-oxo-1-cyclohexen-1-yl)carbonyl]-1-(4-methoxyphenyl)-2(1H)-quinoxalinone, 4-(2,6-diethyl-4-methylphenyl)-5-hydroxy-2,6-dimethyl-3(2H)-pyridazinone, 4-(4-fluorophenyl)-6-[(2-hydroxy-6-oxo-1-cyclohexen-1-yl)carbonyl]-2-methyl-1,2,4-triazine-3,5(2H,4H)-dione, 5-[(2-hydroxy-6-oxo-1-cyclohexen-1-yl)carbonyl]-2-(3-methoxyphenyl)-3-(3-methoxypropyl)-4(3H)-pyrimidinone, 2-methyl-N-(4-methyl-1,2,5-oxadiazol-3-yl)-3-(methylsulfinyl)-4-(trifluoromethyl)benzamide and 2-methyl-3-(methylsulfonyl)-N-(1-methyl-1H-tetrazol-5-yl)-4-(trifluoromethyl)benzamide.

HST (homogentisate solenesyltransererase) inhibitors (b13) disrupt a plant's ability to convert homogentisate to 2-methyl-6-solanyl-1,4-benzoquinone, thereby disrupting carotenoid biosynthesis. Examples of HST inhibitors include haloxydine, pyriclor, 3-(2-chloro-3,6-difluorophenyl)-4-hydroxy-1-methyl-1,5-naphthyridin-2(1H)-one, dichloro-4-pyridinyl)-5-(2,2-difluoroethyl)-8-hydroxy-pyrido[2,3-b]pyrazin-6(5H)-one and 4-(2,6-diethyl-4-methylphenyl)-5-hydroxy-2,6-dimethyl-3(2H)-pyridazinone.

HST inhibitors also include compounds of Formulae A and B.

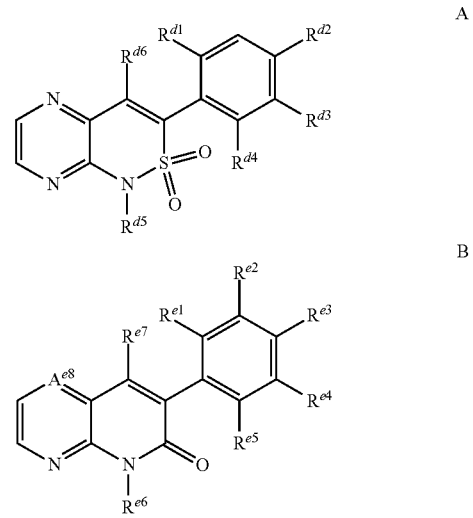

wherein $R^{d1}$ is H, Cl or $CF_3$; $R^{d2}$ is H, Cl or Br; $R^{d3}$ is H or Cl; $R^{d4}$ is H, Cl or $CF_3$; $R^{d5}$ is $CH_3$, $CH_2CH_3$ or $CH_2CHF_2$; and $R^{d6}$ is OH, or —OC(=O)-i-Pr; and $R^{e1}$ is H, F, Cl, $CH_3$ or $CH_2CH_3$; $R^{e2}$ is H or $CF_3$; $R^{e3}$ is H, $CH_3$ or $CH_2CH_3$; $R^{e4}$ is H, F or Br; $R^{e5}$ is Cl, $CH_3$, $CF_3$, $OCF_3$ or $CH_2CH_3$; $R^{e6}$ is H, $CH_3$, $CH_2CHF_2$ or C≡CH; $R^{e7}$ is OH, —OC(=O)Et, —OC(=O)-i-Pr or —OC(=O)-t-Bu; and $A^{e8}$ is N or CH.

Cellulose biosynthesis inhibitors (b14) inhibit the biosynthesis of cellulose in certain plants. They are most effective when using a pre-application or early post-application on young or rapidly growing plants. Examples of cellulose biosynthesis inhibitors include chlorthiamid, dichlobenil, flupoxam, indaziflam ($N^2$-[(1R,2S)-2,3-dihydro-2,6-dimethyl-1H-inden-1-yl]-6-(1-fluoroethyl)-1,3,5-triazine-2,4-diamine), isoxaben and triaziflam.

Other herbicides (b15) include herbicides that act through a variety of different modes of action such as mitotic disruptors (e.g., flamprop-M-methyl and flamprop-M-isopropyl) organic arsenicals (e.g., DSMA, and MSMA), 7,8-dihydropteroate synthase inhibitors, chloroplast isoprenoid synthesis inhibitors and cell-wall biosynthesis inhibitors. Other herbicides include those herbicides having unknown modes of action or do not fall into a specific category listed in (b1) through (b14) or act through a combination of modes of action listed above. Examples of other herbicides include aclonifen, asulam, amitrole, bromobutide, cinmethylin, clomazone, cumyluron, cyclopyrimorate (6-chloro-3-(2-cyclopropyl-6-methylphenoxy)-4-pyridazinyl 4-morpholinecarboxylate), daimuron, difenzoquat, etobenzanid, fluometuron, flurenol, fosamine, fosamine-ammonium, dazomet, dymron, ipfencarbazone (1-(2,4-dichlorophenyl)-N-(2,4-difluorophenyl)-1,5-dihydro-N-(1-methylethyl)-5-oxo-4H-1,2,4-triazole-4-carboxamide), metam, methyldymron, oleic acid, oxaziclomefone, pelargonic acid, pyributicarb and 5-[[(2,6-difluorophenyl)methoxy]methyl]-4,5-dihydro-5-methyl-3-(3-methyl-2-thienyl)isoxazole.

"Herbicide safeners" (b16) are substances added to a herbicide formulation to eliminate or reduce phytotoxic effects of the herbicide to certain crops. These compounds protect crops from injury by herbicides but typically do not prevent the herbicide from controlling undesired vegetation. Examples of herbicide safeners include but are not limited to benoxacor, cloquintocet-mexyl, cumyluron, cyometrinil, cyprosulfamide, daimuron, dichlormid, dicyclonon, dimepiperate, fenchlorazole-ethyl, fenclorim, flurazole, fluxofenim, furilazole, isoxadifen-ethyl, mefenpyr-diethyl, mephenate, methoxyphenone, naphthalic anhydride, oxabetrinil, N-(aminocarbonyl)-2-methylbenzenesulfonamide and N-(aminocarbonyl)-2-fluorobenzenesulfonamide, 1-bromo-4-[(chloromethyl)sulfonyl]benzene, 2-(dichloromethyl)-2-methyl-1,3-dioxolane (MG 191), 4-(dichloroacetyl)-1-oxa-4-azospiro[4.5]decane (MON 4660).

One or more of the following methods and variations as described in Schemes 1-14 can be used to prepare a compound of Formula 1. The definitions of $Y^1$, $Y^2$, $Y^3$ $Y^4$, $R^1$, $R^2$ and $R^3$ in the compounds of Formulae 1-14 below are as defined above in the Summary of the Invention unless otherwise noted. Compounds of Formulae 1A through 1H, 2A through 2L, 4A and 6A are various subsets of a compound of Formulae 1, 2, 4 and 6, and all substituents for Formulae 1, 2, 4 and 6 are as defined above for Formula 1 unless otherwise noted.

As shown in Scheme 1 a compound of Formula 1 can be prepared by nucleophilic substitution by heating a compound of Formula 2 in a suitable solvent, such as acetonitrile, tetrahydrofuran or N,N-dimethylformamide in the presence of a base such as potassium or cesium carbonate, with a compound of Formula 3, (where LG is halogen or $SO_2Me$). The reaction is typically conducted at temperatures ranging from 50 to 110° C.

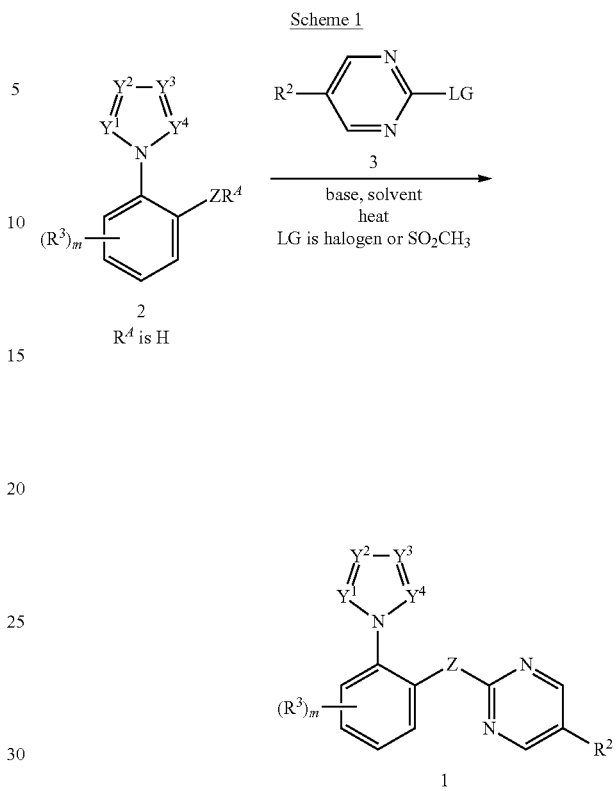

As shown in Scheme 2, a compound of Formula 2A (i.e. a compound of Formula 2 wherein Z is O; and $R^A$ is H or lower alkyl) can be prepared using a Buchwald copper(I) catalyzed carbon-nitrogen bond forming reaction in the presence of a ligand such as ethylene diamine or cyclohexane diamine by heating a compound of Formula 4 (wherein X is I or Br) in a suitable solvent, such as toluene, 1,4-dioxanes or N,N-dimethylformamide in the presence of a base such as potassium carbonate, cesium carbonate or tribasic potassium phosphate, with a compound of Formula 5. The reaction is typically conducted at about 110° C. as described for copper-catalyzed carbon-nitrogen bond formation methods using diamine ligands found in Surry and Buchwald, *Chemical Science* 2010, 1, 13-31. One skilled in the art can prepare a compound of Formula 5 by means found in *Comprehensive Heterocyclic Chemistry*, Part II, 1996, parts 2, 3 & 4, Pergamon Press, publisher, edited by Alan. R. Katritzky & Charles W. Reese and CHC, Part I, 1984 and series of *The Chemistry of Heterocyclic Compounds*, 1981, publisher John Wiley & sons and Interscience Publishers Inc, 1953.

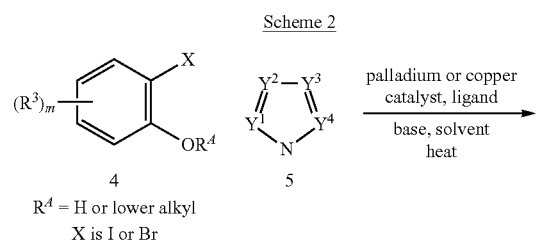

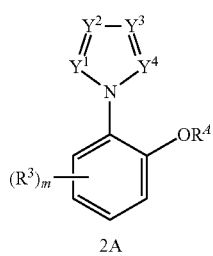

2A

Phosphine ligands can also be employed for palladium-catalyzed amination reactions to prepare a compound of Formula 2A. A review of suitable ligands, bases, solvents, catalysts and substrates for use with NH-containing heterocycles (i.e. a compound of Formula 5) can be found in Surry and Buchwald, *Chemical Science* 2011, 2, 27-50 and references cited therein. In particular, conditions for pyrazoles and imidazoles with aryl or heteroaryl halides using a palladium catalyst such as $Pd_2(dba)_3$, with ligands such as 2-di-t-butylphophino-2',4',6'-triisopropylbiphenyl (i.e. t-Bu-X-Phos) or 2-di-t-butylphophino-3,4,5,6-tetramethyl-2',4',6'-triisopropylbiphenyl (i.e. $Me_4$-t-Bu-X-Phos) with bases such as $Na^+{}^-O$-t-Bu or $K_3PO_4$ in solvents such as toluene or 1,4-dioxane at temperatures ranging from 60 to 105° C. are described. Alternative synthetic strategies can also be found in Sorokin, *Mini-Reviews in Organic Chemistry* 2008, 5, 323-330; Bellina and Rossi, *Advanced Synthesis & Catalysis* 2010, 352, 1223-1276, and Beletskaya and Cheprakov, *Organometallics* 2012, 31, 7753-7808.

As shown in Scheme 3, a compound of Formula 2B (i.e. a compound of Formula 2 wherein Z is O; and $R^A$ is H or lower alkyl) can also be prepared by direct nucleophilic displacement by heating a compound of Formula 4A, (i.e. a compound of Formula 4 wherein X is F or Cl; and $R^3$ is an electron withdrawing group) in a suitable solvent such as N,N-dimethylformamide, N,N-dimethylacetamide or N-methylpyrrolidinone and in the presence of a base such as potassium or cesium carbonate with a compound of Formula 5. The reaction is typically conducted at temperatures ranging from 120 to 160° C. but the transformation can be accomplished at higher or lower temperatures depending on the nature of the $R^3$ substituents.

Scheme 3

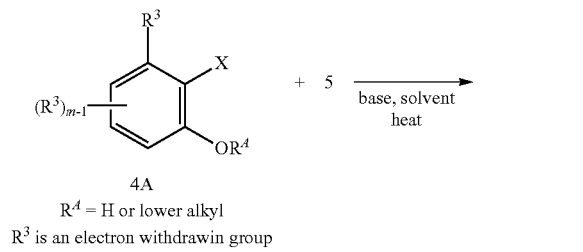

4A
$R^A$ = H or lower alkyl
$R^3$ is an electron withdrawin group

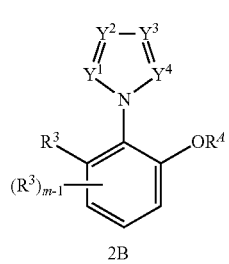

2B

As shown in Scheme 4, a compound of Formula 2C (i.e. a compound of Formula 2 where Z is O) can be prepared by deprotection of a compound of Formula 2D (i.e. a compound of Formula 2A wherein Z is O; and $R^A$ is $CH_3$ or $-C(=O)CH_3$) with a suitable deprotecting agent. Suitable methoxy (i.e. when $R^A$ is $CH_3$) deprotecting reagents such as $BBr_3$, $AlCl_3$ and HBr in acetic acid can be used in the presence of solvents such as toluene, dichloromethane and dichloroethane at a temperature of from −80 to 120° C. Suitable acetoxy (i.e. when $R^A$ is $-C(=O)CH_3$) deprotecting agents include potassium carbonate in methanol or ammonium acetate in aqueous methanol at room temperature can be used as discussed in Biswanath Das, *Tetrahedron* 2003, 59, 1049-1054 and methods cited therein. Alternatively, a compound of Formula 2D can be combined with Amberlyst 15© in methanol (as discussed in Biswanath Das, *Tet. Lett.* 2003, 44, 5465-5468) or combined with sodium acetate in ethanol (as discussed in T. Narender, et al. *Synthetic Communications* 2009, 39(11), 1949-1956. Other useful phenolic protecting groups suitable for use in preparing a compound of Formula 2C can be found in Greene, T. W.; Wuts, P. G. M. *Protective Groups in Organic Synthesis*, 4th ed.; Wiley: Hoboken, N.J., 1991).

Scheme 4

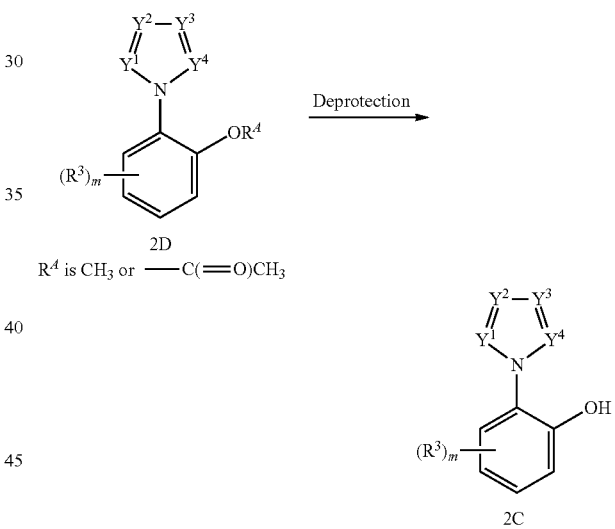

As shown in Scheme 5, a compound of Formula 1B, (i.e. a compound of Formula 1 where Z is O; and m is 1 at the 3-position) can be prepared by "C—H activation" of a compound of Formula 1A (a compound of Formula 1 wherein Z is O; and m is 0). For example, palladium(II) acetate along with either an N-halosuccinimide, $PhI(OAc)_2$, N-fluoropyridinium tetrafluoroborate, or a lower alkyl boronic acid can be used to introduce the $R^3$ variable as I, Br, Cl, —OAc, F, and lower alkyl substituents respectively. These methods are detailed in reviews of selective activation of C—H bonds in *Chemical Reviews* 2010, 110, 575-1211 and references cited therein. Methods for "C—H activation" can also be found in Wencel-Delord et al., *Nature Chemistry* 2013, 5, 369-375 and a series of reviews of "C—H activation" in *Accounts of Chemical Research* 2012, 45, 777-958 and references cited therein.

Scheme 5

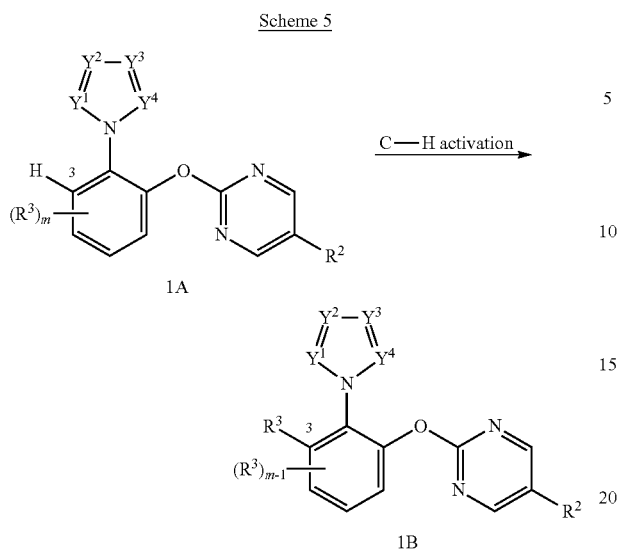

Chemistry based on "C—H activation" can also be used to prepare a compound of Formulae 2E (i.e. a compound of Formula 2 wherein Z is O; $R^4$ is —C(O)CH$_3$; and m is 1 at the 3-position) as shown in Scheme 6 utilizing palladium(II) acetate and (diacetoxyiodo)benzene as described above for Scheme 5. A compound of Formula 2E can subsequently be converted via methods disclosed in Schemes 1 and 4 to provide a compound of Formula 1.

Scheme 6

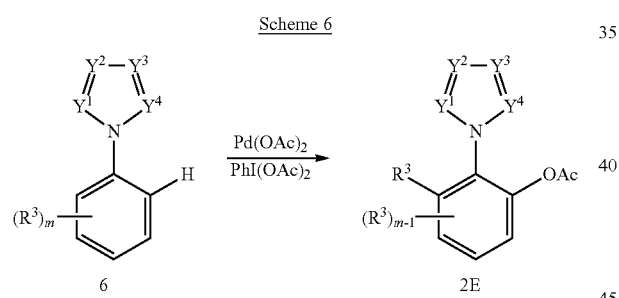

Similarly, chemistry based on "C—H activation" can be used to prepare a compound of Formulae 2F (i.e. a compound of Formula 2A wherein Z is S) as shown in Scheme 7. A compound of Formula 6 can first be converted to a compound of Formula 6A (i.e. a compound of Formula 6 wherein the ortho "H" is X; and X is Br or I) by utilizing a stepwise introduction of substituents using "C—H activation". Iodides and bromides of Formula 6A can then be further functionalized by copper mediated cross-coupling with thiourea as described in Qi, Junsheng, *Chin. J. Chem.* 2010, 28, 1441-1443 to provide the aryl thiol after acidic deprotection. Palladium catalyzed cross-coupling reactions of aryl halides can give protected thiols that can, in turn, be deprotected under either acidic conditions or basic conditions (e.g. cesium fluoride) to provide a compound of Formula 2F. These conditions are discussed in Organ, Michael G., *Angew. Chem. Int. Ed.* 2012, 51, 3314-3322 and the references cited therein. Also, relevant conditions can be found in Takashiro Itoh, *J. Org. Chem.* 2006, 71, 2203-2206. A compound of Formula 2F can then be converted via methods disclosed in Schemes 1 and 4 to provide a compound of Formula 1. Compounds of Formula 6 are commercially available or can be synthesized by methods described in Heterocycles 2007, 71, 1467-1502 and the references within. See also Lamberth, *Org. Prep. Proced. Internat.* 2002, 34, 98-102.

Scheme 7

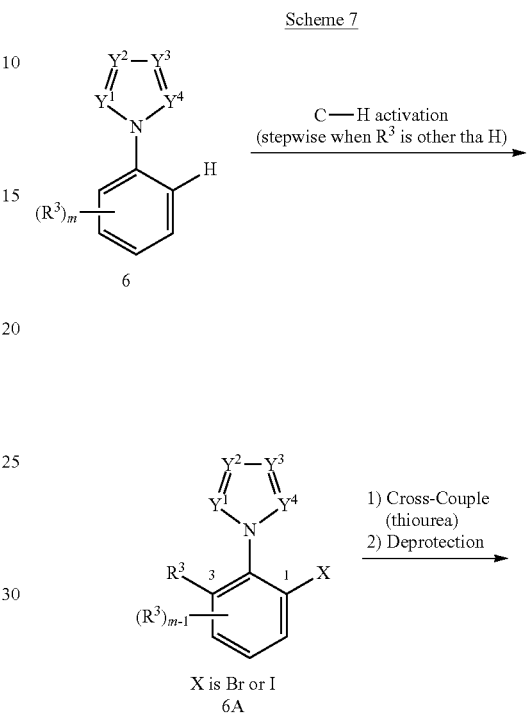

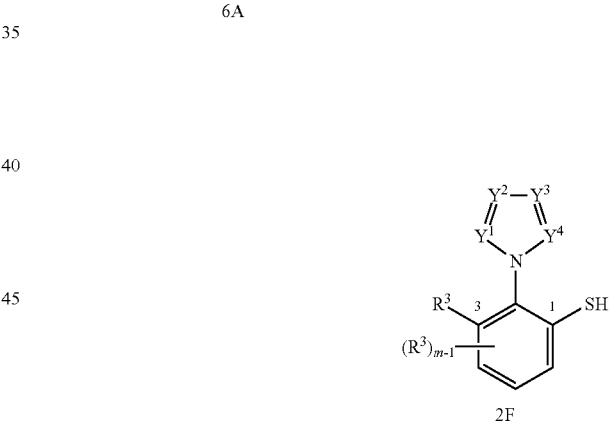

As shown in Scheme 8, functionalization of the —$Y^1$=$Y^2$—$Y^3$=$Y^4$— moiety (i.e the 5-membered heterocycle connected to the remainder of Formula 1 through a nitrogen atom) may also be accomplished by means of electrophilic substitution when any one (or all) of $Y^1$, $Y^2$, $Y^3$ and $Y^4$ is CH, to prepare a compound of Formula 1D (i.e. a compound of Formula 1 wherein Z is O; and any one (or all) of $R^1$ is other than H). Similarly, a compound of Formula 2H (a compound of Formula 2A wherein Z is O; and $R^4$ is CH$_3$ or —(C=O)CH$_3$). Reagents capable of electrophilic substitution such as N-halosuccinimides, sulfuryl halides and elemental halogens can be used in compatible solvents such as N,N-dimethylformamide or acetonitrile at temperatures from 20 to 120° C. to introduce substituents at reactive positions of the —$Y^1$=$Y^2$—$Y^3$=$Y^4$— moiety.

Scheme 8

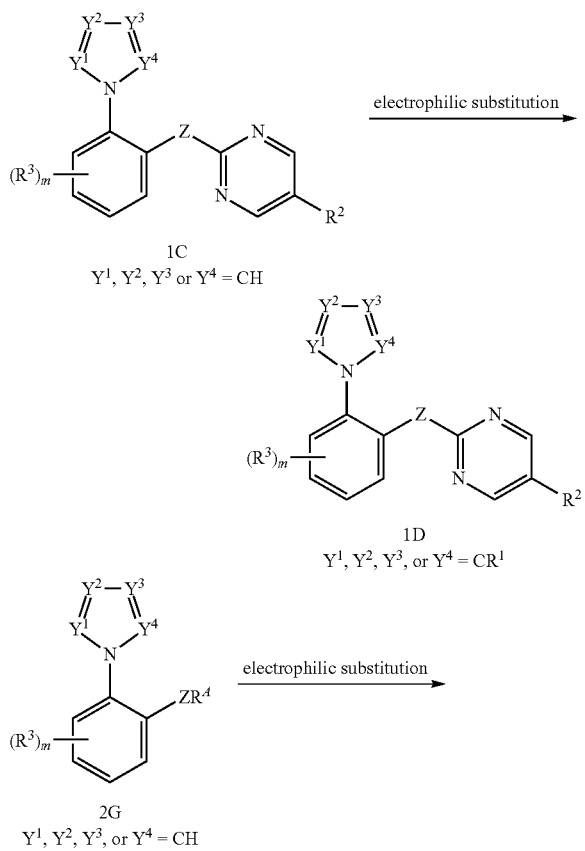

As shown in Scheme 9, functionalization of the —Y$^1$=Y$^2$—Y$^3$=Y$^4$— moiety (i.e the 5-membered heterocycle connected to the remainder of Formula 1 through nitrogen) may also be accomplished by means of suitable cross-coupling methods as described in V. Snieckus et al., *Angew. Chem. Int. Ed.* 2012, 51, 5062-5086 or *Accounts of Chemical Research* 2008, 41, 11, 1439-1564 and references cited therein. These methods involve selection of an appropriate catalyst and reagent system for converting the R$^1$ substituent (i.e. when any one of Y$^1$, Y$^2$, Y$^3$ and Y$^4$ is CR$^1$; and R$^1$ is halogen) utilizing cross-coupling methods to prepare compounds of Formula 1F (i.e. a compound of Formula 1 wherein Z is O; and R$^1$ is other then halogen) or 2J (wherein Z is O; and R$^A$ is a suitable protecting group such as CH$_3$ or —C(=O)CH$_3$). Reagents capable of electrophilic substitution such as N-halosuccinimides, sulfuryl halides and halogens can be used in compatible solvents such as N,N-dimethylformamide or acetonitrile at a temperature from 20 to 120° C. to introduce substituents in reactive positions of the —Y$^1$=Y$^2$—Y$^3$=Y$^4$— moiety. The CR$^1$ substituents on the —Y$^1$=Y$^2$—Y$^3$=Y$^4$— moiety may be introduced either before or after the coupling reaction used to form the N-heterocyclic bond discussed in Schemes 2 and 3. For palladium-catalyzed cross coupling reactions suitable for use with these types of heterocycles see Gribble and Li Eds., *Palladium in Heterocyclic Chemistry Volume* 1, Pergamon Press, 2000, Gribble and Li, Eds., *Palladium in Heterocyclic Chemistry Volume* 2, Pergamon Press, 2007 and deMeijere and Diederich Eds., *Metal-Catalyzed Cross-Coupling Reactions*, Second Edition, John Wiley and Sons, 2004.

Scheme 9

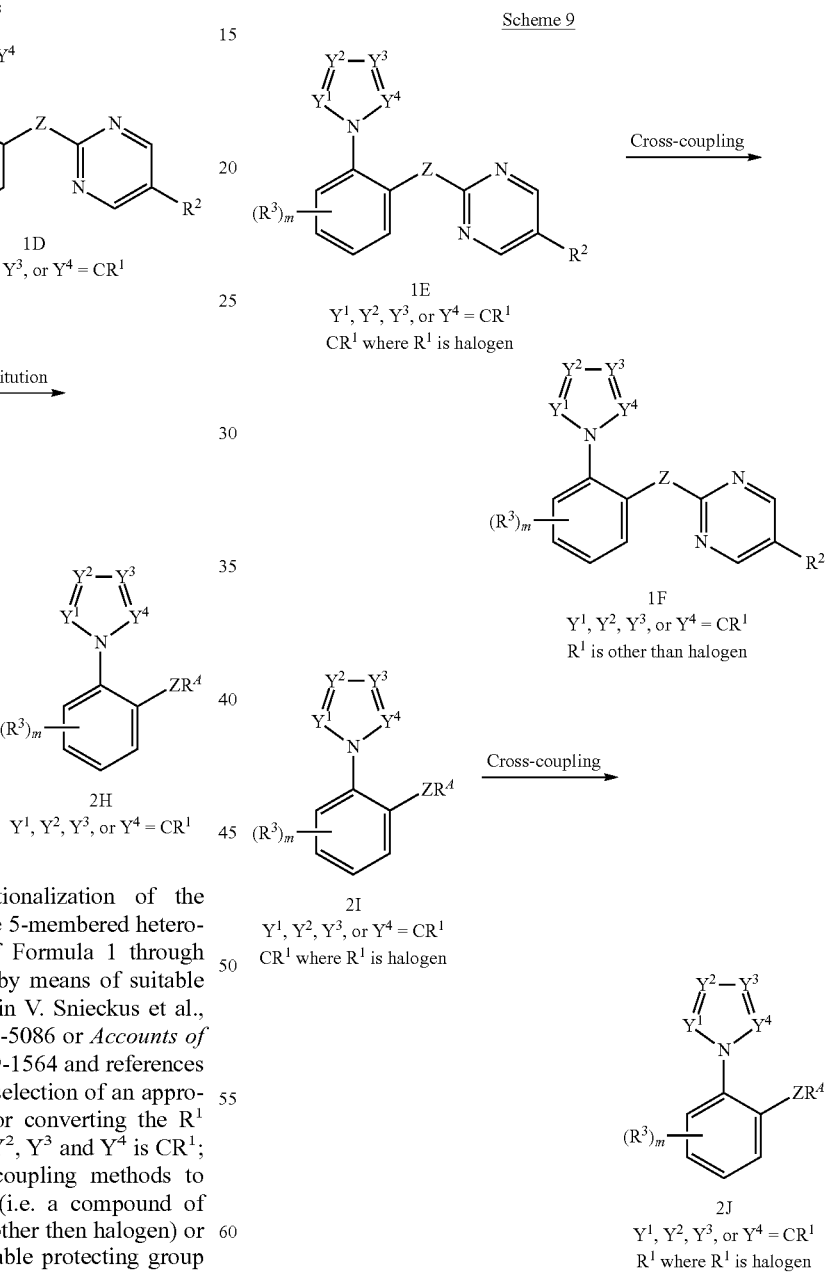

Products of Formula 2K (a compound of Formula 2 wherein Y$^1$ is N, Y$^2$ is CR$^1$, Y$^3$ is CR$^1$ and Y$^4$ is N) can be prepared by the methods shown in Scheme 10. Phenyl hydrazines of Formula 7 can be reacted with glyoxal in acetic acid followed by hydroxyl amine in ethanol to form arylhydrazone oxime intermediates of Formula 8. Reaction of a compound of Formula 8 in pyridine with a copper salt such as copper sulphate provides the 2-aryltriazole-1-oxide intermediates of Formula 9. Treatment of a compound of Formula 9 with trimethyloxonium tetrafluoroborate yields a 1-methoxy-2-phenyltriazolium salts that can react with $R^1$ nucleophiles (for example halides, cyanides or alkoxides) to produce a compound of Formula 2K, (i.e. a compound of Formula 2 wherein Z is O and $R^4$ is a suitable protecting group such as benzyl or $CH_3$). This route can also be used for substituted dicarbonyl compounds or their monooximes in place of glyoxal which result in compounds of Formula 9 where $R^1$ can be various alkyls after reduction of the N-oxide. For specific examples of this sequence with a variety of dicarbonyl compounds and nucleophiles, see M. Begtrup in *J. Chem. Society, Perkin Trans. 1* 1981, 503-513 and *Bull. Soc. Chim. Belg.* 1997, 106, 717-727.

intermediate S-aryl dimethylthiocarbamate of Formula 11. A one-pot deprotection of a compound of Formula 11 is readily achieved using 10% aqueous sodium hydroxide or methanolic potassium hydroxide to afford the corresponding aryl thiol. Subsequent reaction with a compound of Formula 3 at or slightly above room temperature provides the product 1G (i.e. a compound of Formula 1 wherein Z is S. Methods for the Newman-Kwart rearrangements are found in Lloyd-Jones, Guy C., *Synthesis* 2008, 661-689.

Scheme 10

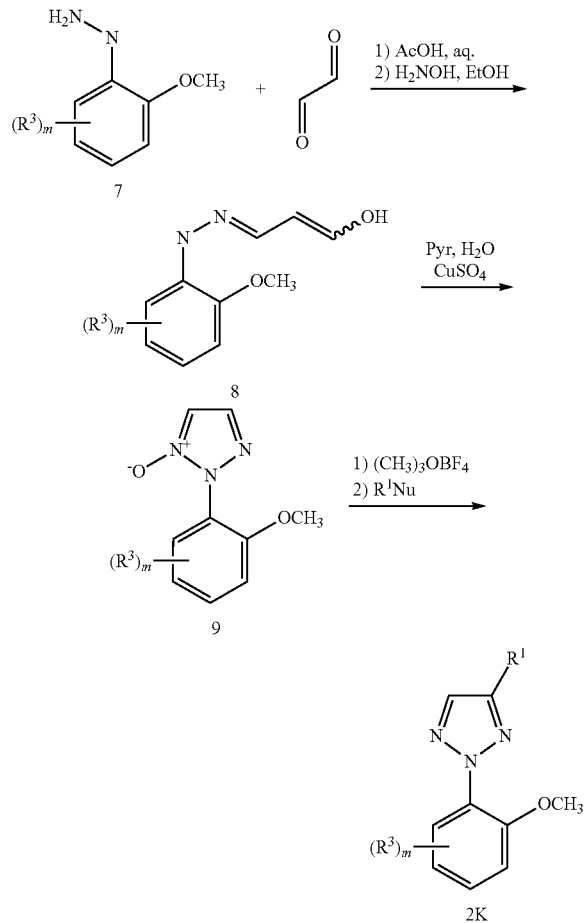

Scheme 11

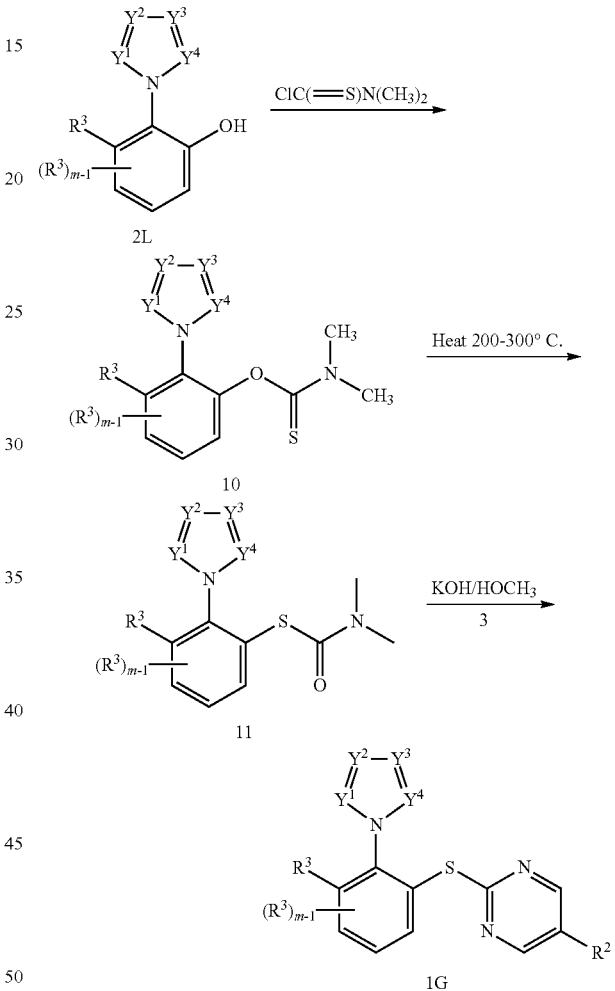

In Scheme 11, the phenol, 2L is reacted with N,N-dimethyl thiocarbamoyl chloride in N,N-dimethylformamide in the presence of a strong tertiary amine base such as 1,4-diazabicyclo[2.2.2]octane or N-methylmorpholine for acidic phenols (for less-acidic phenols, prior deprotonation with sodium hydride may be advantageous) to form the O-aryl N,N-dimethylthiocarbamate of Formula 10. Newman-Kwart rearrangement of a compound of Formula 10 at temperatures ranging from 200 to ~300° C. provides the As shown in Scheme 12 compounds of Formula 1H (compound of Formula 1 wherein $Y^1$ is N, $Y^2$ is N, $Y^3$ is $CR^1$ and $Y^4$ is $CR^1$) can be prepared by the coupling of an alkyne with an azide of Formula 12. This type of reaction is commonly referred to as 'click chemistry' and well known to those skilled in the art. A review of suitable conditions and catalysts for the coupling of alkynes with azides (i.e. a compound of Formula 12) can be found in Meldal and Tornoe in *Chemical Reviews* 2008, 108, 2952-3015 and references cited therein. Suitable conditions generally include a copper catalyst with ligands such as halides and ascorbate in a variety of organic solvents such as tert-butanol, methanol, dimethylsulfoxide, dimethyl formamide in addition to water. The regioselectivitiy of this coupling can be dependent upon the nature of $R^1$ however this can be controlled with the choice of reaction conditions such as metalating a terminal alkyne. Also note that the two R¹ groups on the alkyne need not be identical. For an example see Krasinski, Fokin, and Sharpless in *Organic Letters,* 2004, 6, 1237-1240.

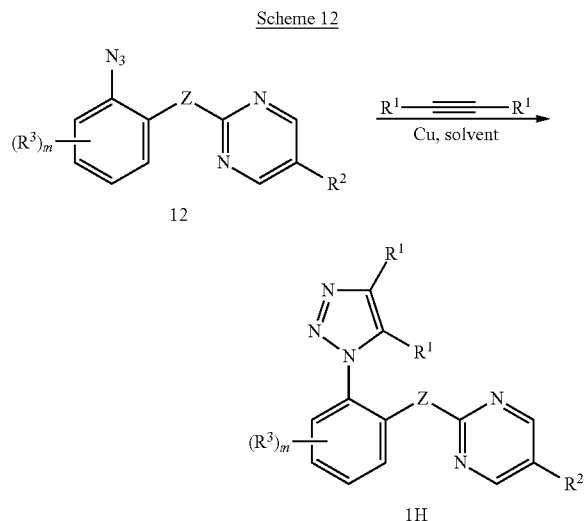

Scheme 12

As shown in Scheme 13, a compound of Formula 12 can be prepared using the same methods as described in Scheme 1.

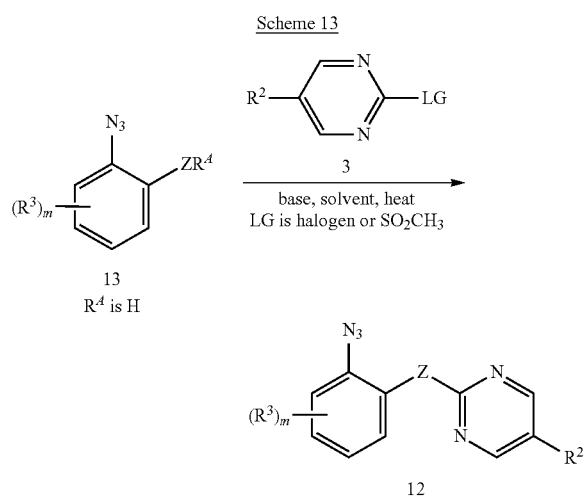

Scheme 13

As shown in Scheme 14 compounds of Formula 13 can be prepared by diazotisation of an amine of Formula 14 followed by substitution with azide using methods well known to those skilled in the art. Descriptions of how this transformation can be achieve are described in Wu, Zhao, Lan, Cao, Liu, Jinag, and Li in *The Journal of Organic Chemistry* 2012, 77, 4261-4270 or in Barral, Moorhouse, and Moses in *Organic Letters* 2007, 9, 1809-1811. Examples of suitable reagents for diazotization include sodium nitrite and tert-butyl nitrite, and suitable examples of azide sources include sodium azide and trimethylsilyl azide.

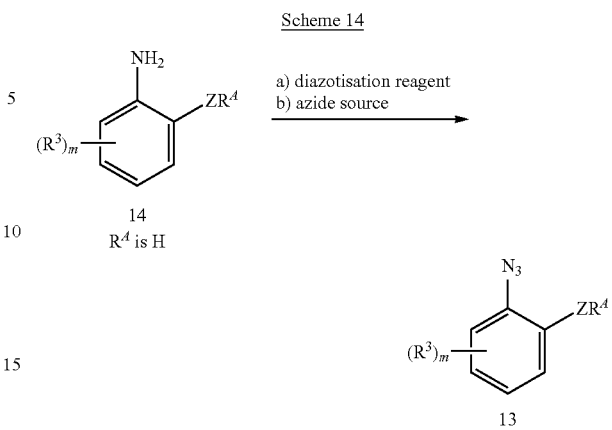

Scheme 14

It is recognized by one skilled in the art that various functional groups can be converted into others to provide different a compound of Formula 1. For a valuable resource that illustrates the interconversion of functional groups in a simple and straightforward fashion, see Larock, R. C., *Comprehensive Organic Transformations: A Guide to Functional Group Preparations,* 2nd Ed., Wiley-VCH, New York, 1999. For example, intermediates for the preparation of a compound of Formula 1 may contain aromatic nitro groups, which can be reduced to amino groups, and then be converted via reactions well known in the art such as the Sandmeyer reaction, to various halides, providing a compound of Formula 1. The above reactions can also in many cases be performed in alternate order It is recognized that some reagents and reaction conditions described above for preparing a compound of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 4th ed.; Wiley: Hoboken, N.J., 1991). One skilled in the art will recognize that, in some cases, after the introduction of a given reagent as it is depicted in any individual scheme, it may be necessary to perform additional routine synthetic steps not described in detail to complete the synthesis of a compound of Formula 1. One skilled in the art will also recognize that it may be necessary to perform a combination of the steps illustrated in the above schemes in an order other than that implied by the particular presented to prepare a compound of Formula 1.

One skilled in the art will also recognize that a compound of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. ¹H NMR spectra are reported in ppm downfield from tetramethylsilane in CDCl₃; "s" means singlet, "d" means doublet, "t" means triplet, "q" means quartet, "m" means multiplet, "dd" means doublet of doublets, "dt" means doublet of triplets, and "bs" means broad singlet.

Synthesis Example 1

Preparation of 5-chloro-2-[2-[3-(trifluoromethyl)-1H-pyrazol-1-yl]phenoxy]pyrimidine (Compound 2)

Step A: Preparation of 1-(2-methoxyphenyl)-3-(trifluoromethyl)-1H-pyrazole

2-Iodoanisole (1.43 g, 6.12 mmol) and 3-(trifluoromethyl)-1H-pyrazole (1.0 g, 7.4 mmol) were combined in 3 mL of p-dioxane under a nitrogen atmosphere. Powdered potassium carbonate (1.78 g, 12.9 mmol), copper(I) iodide (12 mg, 0.0612 mmol) and trans 1,2-diaminocyclohexane (70 mg, 0.61 mmol) were added and the resulting mixture was heated at reflux for 18 h. The reaction mixture was cooled and then diluted with de-ionized water and ethyl acetate and the layers separated. The aqueous layer was extracted with ethyl acetate (2×). The combined organic layers were washed with a saturated aqueous solution of EDTA, brine, then dried over MgSO4, filtered and concentrated to give 2.2 g of oil. Column chromatography through 40 g silica gel using a gradient of hexanes to 11% ethyl acetate in hexanes provided 0.25 g of the title compound as an oil.

¹H NMR δ 8.05 (s, 1H), 7.72 (d, 1H), 7.38 (t, 1H), 7.05-7.12 (m, 2H), 6.67 (s, 1H), 3.89 (s, 3H).

Step B: Preparation of 2-[3-(trifluoromethyl)-1H-pyrazol-1-yl]phenol 1-(2-Methoxyphenyl)-3-(trifluoromethyl)-1H-pyrazole (i.e. the product of Step A) (0.21 g, 0.87 mmol) was dissolved in 4.4 mL of dichloromethane under a nitrogen atmosphere. A solution of 1 M solution of boron tribromide in dichloromethane (0.96 mL, 0.96 mmol) was then added dropwise a room temperature. The resulting brown solution was stirred at room temperature for three hours. The solution was then poured into an ice and de-ionized water mixture. The mixture was diluted with dichloromethane and the aqueous layer separated. The aqueous layer was extracted with dichloromethane. The combined organic layers were washed with brine, dried over MgSO₄, filtered and concentrated to give 150 mg of the title compound as a solid.

¹H NMR δ 10.12 (bs, 1H), 8.04 (d, 1H), 7.40 (d, 1H), 7.28 (t, 1H), 7.15 (d, 1H), 6.97 (t, 1H), 6.78 (d, 1H).

Step C: Preparation of 5-chloro-2-[2-[3-(trifluoromethyl)-1H-pyrazol-1-yl]phenoxy]pyrimidine 2-[3-(Trifluoromethyl)-1H-pyrazol-1-yl]phenol (i.e. the product of Step B), (70 mg, 0.31 mmol) and 2,5-dichloropyrimidine (50 mg, 0.337 mmol) were combined in 2 mL of acetonitrile under a nitrogen atmosphere. Powdered potassium carbonate (128 mg, 0.920 mmol) was added and the resulting mixture was heated at reflux for 18 h. The reaction was cooled and diluted with de-ionized water and ethyl acetate. The aqueous layer was separated and extracted twice with ethyl acetate. The combined organic layers were washed with brine, dried over MgSO4, filtered and concentrated to give 100 mg of a solid. The solid was filtered from hexanes to give 23 mg of the title compound, a compound of the invention.

¹H NMR δ 8.39 (s, 2H), 7.93 (s, 1H), 7.81 (d, 1H), 7.48 (t, 1H), 7.42 (t, 1H), 7.35 (d, 1H), 6.58 (s, 1H).

Synthesis Example 2

Preparation of 5-chloro-2-[2-(1H-pyrazol-1-yl)phenoxy]pyrimidine (Compound 12)

Step A: Preparation of 2-(1H-pyrazol-1-yl)-phenol

2-Iodophenol (13.4 g, 60.9 mmol) and 1H-pyrazole (5.0 g, 74 mmol) were dissolved in 30 mL of p-dioxane and 30 mL of toluene under a nitrogen atmosphere. Powdered potassium carbonate (21.0 g, 152 mmol) was added and the reaction mixture was sparged with nitrogen for ten minutes. Copper(I) iodide (2.9 g, 15.22 mmol) and trans 1,2-diaminocyclohexane (3.66 mL, 30.4 mmol) were added sequentially, then the reaction mixture was heated at reflux for 18 h. The cooled reaction mixture was diluted with de-ionized water and ethyl acetate and saturated aqueous EDTA. The aqueous layer separated and extracted twice with ethyl acetate. The combined organic layers were washed twice with saturated aqueous EDTA solution, brine, then dried over MgSO4, filtered and concentrated to give 13 g of a brown solid. Chromatography through 120 gram of silica eluting with 10% ethyl acetate in hexanes provided 5.08 g of the title compound as a liquid.

¹H NMR δ 10.12 (s, 1H), 8.04 (d, 1H), 7.39 (d, 1H), 7.26 (t, 1H), 7.15 (d, 1H), 6.97 (t, 1H), 6.79 (d, 1H).

Step B: Preparation of 5-chloro-2-[2-(1H-pyrazol-1-yl)phenoxy]pyrimidine

The title compound was prepared in the same fashion as described in Example 1, Step C, using 2-(1H-pyrazol-1-yl)-phenol (5.08 g, 31.7 mmol) in place of 2-[3-(trifluoromethyl)-1H-pyrazol-1-yl]-phenol to give 7.88 g of the title compound, a compound of the invention, as a solid.

¹H NMR δ 8.37 (s, 2H), 7.90 (d, 1H), 7.82 (d, 1H), 7.58 (d, 1H), 7.43 (t, 2H), 7.32 (d, 1H), 6.31 (s, 1H).

Synthesis Example 3

Preparation of 2-[2-(4-bromo-1H-pyrazol-1-yl)phenoxy]-5-chloropyrimidine (Compound 7)

Step A: Preparation of 2-[2-(4-bromo-1H-pyrazol-1-yl)phenoxy]-5-chloropyrimidine To 5-chloro-2-[2-(1H-pyrazol-1-yl)phenoxy]pyrimidine (i.e. the product of Example 2, Step B) (7.88 g, 28.9 mmol) dissolved in 40 mL of N,N-dimethylformamide under a nitrogen atmosphere was added N-bromosuccinimide (5.66 g, 31.8 mmol). The resulting mixture was heated at 80° C. for 18 h. The cooled reaction mixture was diluted with de-ionized water and diethyl ether and the layers separated. The aqueous layer was extracted twice with diethyl ether. The combined organic layers were washed (3×) with de-ionized water, brine then concentrated to give 10.98 g of a solid. The solid was filtered from hexanes to give 8.92 g of the title compound, a compound of the invention.

¹H NMR δ 8.41 (s, 2H), 7.94 (s, 1H), 7.77 (d, 1H), 7.55 (s, 1H), 7.42 (m, 2H), 7.32 (d, 1H).

Synthesis Example 4

Preparation of 3-[(5-chloro-2-pyrimidinyl-oxy)]-2-[4-(trifluoromethyl)-1H-pyrazol-1-yl]-benzonitrile (Compound 58)

Step A: Preparation of 3-hydroxy-2-[4-(trifluoromethyl)-1H-pyrazol-1-yl]benzonitrile To a solution of 2-fluoro-3-hydroxybenzonitrile (0.92 g, 6.7 mmol) and 4-(trifluoromethyl)-1H-pyrazole (1.0 g, 7.3 mmol) dissolved in 14 mL of N,N-dimethylacetamide under a nitrogen atmosphere was added powdered potassium carbonate (2.78 g, 20.1 mmol). The resulting mixture was then heated at 153° C. for 18 h. The cooled reaction mixture was diluted with de-ionized water and ethyl acetate and the layers separated. The aqueous layer was extracted (4×) with ethyl acetate, and the combined organic layers were washed (3×) with de-ionized water followed by brine. The combined organic layers were dried over MgSO4, filtered and concentrated to give 1.58 g of an oil. Chromatography through 40 g of silica gel eluting with a gradient of 20 to 40% ethyl acetate in hexanes to give 1.37 g of a solid. The solid was filtered from hexanes to give 680 mg of the title compound.
¹H NMR δ 9.86 (bs, 1H), 8.64 (s, 1H), 8.07 (s, 1H), 7.40 (m, 2H), 7.37 (m, 1H).

Step B: Preparation of 3-[(5-chloro-2-pyrimidinyl)oxy]-2-[4-(trifluoromethyl)-1H-pyrazol-1-yl]benzonitrile To a stirred mixture of 3-hydroxy-2-[4-(trifluoromethyl)-1H-pyrazol-1-yl]benzonitrile (i.e. the product of Example 4, Step A) (0.15 g, 0.592 mmol) and 2,5-dichloropyrimidine (0.10 g, 0.65 mmol) in 1.5 mL of N,N-dimethylformamide under a nitrogen atmosphere was added powdered potassium carbonate (0.25 g, 1.77 mmol). The resulting mixture was heated to 100° C. for approximately 1 h. The cooled reaction mixture was diluted with de-ionized water and diethyl ether and the layers were separated. The aqueous layer was extracted twice with diethyl ether, combined and washed (3×) with de-ionized water followed by brine, then dried over sodium sulfate, filtered and concentrated to provide 0.23 g of oil which solidified on standing. The solid was filtered from hexanes and diethyl ether to yield 154 mg of the title compound, a compound of the invention.
¹H NMR δ 8.40 (s, 2H), 8.05 (s, 1H), 7.85 (s, 1H), 7.77 (d, 1H), 7.62-7.65 (m, 2H).

Synthesis Example 5

Preparation of 2-[2-(4-bromo-2H-1,2,3-triazol-2-yl)phenoxy]-5-chloropyrimidine (Compound 54)

Step A: Preparation of 1,2-ethanedione 1-[2-(2-methoxyphenyl)hydrazone]2-oxime

To a stirred solution of 40% glyoxal (8.06 mL, 70.2 mmol, 1.7 eq.) in water (275 mL) was added a solution of 2-methoxyphenylhydrazine hydrochloride (7.22 g, 41.3 mmol, 1.0 eq.) in 50% acetic acid (18 mL). The reaction was stirred at 23° C. for 2 h. A brown precipitate formed and was collected by filtration. The precipitate was dissolved in ethanol (82 mL) and 50% aq. hydroxylamine (5.06 mL, 82.6 mmol, 2.0 eq.) was added to the solution. The reaction mixture was stirred at 23° C. for 2 h, then concentrated in vaccuo to a volume of about 5 mL and then diluted with water. The mixture was extracted with ethyl acetate (3×50 mL) and the combined organic layers dried and concentrated in vaccuo to afford the crude title compound (4.40 g) which was used directly in the next step without further purification.

Step B: Preparation of 2-(2-methoxyphenyl)-2H-1,2,3-triazole 1-oxide

To a stirred solution of 1,2-ethanedione 1-[2-(2-methoxyphenyl)hydrazone]2-oxime (4.40 g, 22.8 mmol, 1.0 eq.) in pyridine (100 mL) was added a solution of CuSO4 5H2O (11.4 g, 45.5 mmol, 2.0 eq.) in water (55 mL). The reaction mixture was heated to reflux at 100° C. for 18 h. The reaction mixture was cooled to ambient temperature and acidified with concentrated hydrochloric acid until a green precipitate formed. The mixture was filtered through a plug of Celite® diatomaceaous filter aid. The aqueous layer was separated and extracted with ethyl acetate (2×50 mL). The combined organic layers were washed with aqueous 1 N hydrochloric acid and then with brine. The organic layer was dried and concentrated in vaccuo to afford the crude title compound (2.80 g) which required no further purification.
¹H NMR δ 7.74 (d, 1H), 7.55 (t, 1H), 7.46 (s, 1H), 7.43 (d, 1H), 7.15-7.06 (m, 2H), 3.85 (s, 3H).

Step C: Preparation of 4-bromo-2-(2-methoxyphenyl)-2H-1,2,3-triazole 3-oxide 2-(2-Methoxyphenyl)-2H-1,2,3-triazole 1-oxide (i.e. the product from Example 5, Step B) (0.500 g, 2.61 mmol, 1.0 eq.) dissolved in a 1:1 mixture of chloroform (5 mL) and water (5 mL) was cooled to 0° C. Sodium carbonate (0.387 g, 3.65 mmol, 1.4 eq.) was added, followed by the addition of bromine (0.336 mL, 6.52 mmol, 2.5 eq.). The reaction mixture was stirred at 23° C. for 48 h, then quenched with saturated aqueous sodium thiosulfate and extracted with dichloromethane (3×10 mL). The organic layers were combined, dried and concentrated in vaccuo. The crude residue was purified by chromatography on silica gel, eluting with ethyl acetate in hexanes, to afford the title compound (0.250 g).
¹H NMR δ 7.79 (s, 1H), 7.66-7.50 (m, 1H), 7.40 (dd, 1H), 7.14-7.05 (m, 2H), 3.84 (s, 3H).

Step D: Preparation of 4-bromo-2-(2-methoxyphenyl)-2H-1,2,3-triazole

A stirred mixture of 4-bromo-2-(2-methoxyphenyl)-2H-1,2,3-triazole 3-oxide (i.e. the product from Example 5, Step C) (0.250 g, 0.926 mmol, 1.0 eq.) and phosphorus trichloride (0.242 mL, 2.78 mmol, 3.0 eq.) was heated to reflux at 80° C. for 2 h, then cooled to 0° C. and diluted with dichloromethane (10 mL). Methanol (5 mL) was added dropwise, followed by the addition of water (15 mL). The aqueous layer was separated and extracted with dichloromethane (2×10 mL). The combined organic layers were dried and concentrated. The crude residue was purified by chromatography on silica gel, eluting with 0 to 30% ethyl acetate in hexanes, to afford the title compound (0.170 g) as a white solid.

$^1$H NMR δ 7.79 (s, 1H), 7.49 (d, 1H), 7.44 (t, 1H), 7.10-6.95 (m, 2H), 3.87 (s, 3H).

Step E: Preparation of
2-(4-bromo-2H-1,2,3-triazol-2-yl)phenol

To a solution of 4-bromo-2-(2-methoxyphenyl)-2H-1,2,3-triazole (i.e. the product of Example 5, Step D) (0.150 g, 0.590 mmol, 1.0 eq.) in dichloromethane at 0° C. was added a 1.0 M solution of boron tribromide in dichloromethane (2.95 mL, 2.95 mmol, 5.0 equiv). The reaction mixture was warmed to ambient temperature and stirred for 2 h. The reaction as cooled to 0° C. and slowly quenched with a saturated aqueous solution of sodium bicarbonate (5 mL). The biphasic mixture was stirred at room temperature for 1 h. The phases were separated and the aqueous layer was extracted with dichloromethane (2×10 mL). The combined organic layers were dried and concentrated in vacuo. The crude residue was purified by chromatography on silica gel, eluting with 0 to 30% ethyl acetate in hexanes, to afford the title compound (0.135 g) as a white solid.
$^1$H NMR δ 9.98 (s, 1H), 8.05 (dd, 1H), 7.81 (s, 1H), 7.30-7.23 (m, 1H), 7.14 (dd, 1H), 7.01-6.98 (m, 1H).

Step F: Preparation of 2-[2-(4-bromo-2H-1,2,3-triazol-2-yl)phenoxy]-5-chloropyrimidine To a solution of 2-(4-bromo-2H-1,2,3-triazol-2-yl)phenol (i.e. the product from Example 5, Step E) (0.115 g, 0.479 mmol, 1.0 eq.) in acetonitrile was added 2,5-dichloropyrimidine (71.4 mg, 0.479 mmol, 1.0 eq.) and potassium carbonate (79.4 mg, 5.75 mmol, 1.2 eq.). The reaction mixture was heated at 80° C. overnight. After cooling to room temperature, the reaction mixture was filtered through a plug of Celite® diatomaceaous filter aid and rinsed with ethyl acetate. The filtrate was concentrated onto Celite® diatomaceaous filter aid and purified by chromatography on silica gel, eluting with 0 to 25% ethyl acetate in hexanes, to afford the title compound (135 mg).
$^1$H NMR δ 8.43 (s, 2H), 7.93 (dd, 1H), 7.61 (s, 1H), 7.56-7.48 (m, 1H), 7.47-7.41 (m, 1H), 7.38 (dd, 1H).

Synthesis Example 6

Preparation of 5-chloro-2-[2-[4-(difluoromethyl)-1H-pyrazol-1-yl]phenoxy]pyrimidine (Compound 80)

Step A: Preparation of
1-phenyl-1H-pyrazole-4-carboxaldehyde

A solution of 1-phenylpyrazole (2.0 g, 13.87 mmoles) in TFA (17 mL) was stirred under a nitrogen atmosphere and treated with. hexamethylene tetramine (2.92 g, 20.81 mmoles). The reaction was refluxed overnight, and then cooled and poured into saturated sodium bicarbonate aqueous solution to adjust the pH to 7. The aqueous phase was extracted three times with ethyl acetate. The combined organic phases were washed with brine, dried over MgSO$_4$, filtered and concentrated to 2.78 g of crude oil. Flash column chromatography on silica gel with a 40 gram Isco MPLC column using 10-20% EtOAc-Hexanes gradient provided 0.72 g of the title compound.
$^1$H NMR δ 9.98 (s, 1H), 8.44 (s, 1H), 8.17 (s, 1H), 7.70 (m, 2H), 7.5 (m, 2H), 7.4 (m, 1H).

Step B: Preparation of
1-phenyl-4-(difluoromethyl)-1H-pyrazole

1-Phenyl-1H-pyrazole-4-carboxaldehyde (i.e. the product from Example 6, Step A), (529 mg, 3.07 mmoles) was heated neat in DeoxyFluor® (1.0 mL, 5.22 mmoles) at 80° C. under a nitrogen atmosphere overnight. The reaction mixture was cooled and then diluted with saturated sodium bicarbonate aqueous solution. The aqueous phase was extracted three times with dichloromethane. The combined organic phases were washed with brine, dried over MgSO$_4$, filtered and concentrated to 0.86 g of crude oil. Flash column chromatography on silica gel with a 12 gram Isco MPLC column using 10-20% EtOAc-Hexanes gradient provided 0.49 g of the title compound.
$^1$H NMR δ 8.09 (s, 1H), 7.85 (s, 1H), 7.68 (d, 2H), 7.49 (t, 2H), 7.35 (t, 1H), 6.79 (t, 1H).

Step C: Preparation of
2-[4-(difluoromethyl)-1H-pyrazol-1-yl]phenol
1-acetate

1-Phenyl-4-(difluoromethyl)-1H-pyrazole (i.e. the product from Example 6, Step B), (0.49 g, 2.52 mmoles) was stirred in 19 mL of acetic acid. The mixture was treated with iodobenzene diacetate (0.89 g, 2.78 mmoles) and palladium acetate (28 mg, 0.126 mmoles) and heated to 100° C. for three hours. The mixture was cooled and concentrated from toluene to give 0.68 grams of crude oil. Flash column chromatography on silica gel with a 12 gram Isco MPLC column using 20% EtOAc-Hexanes provided 0.41 g of the title compound.
$^1$H NMR δ 7.93 (s, 1H), 7.85 (s, 1H), 7.61 (d, 1H), 7.44 (t, 1H), 7.38 (t, 1H), 7.25 (d, 1H), 6.78 (t, 1H), 2.218 (s, 3H).

Step D: Preparation of
2-[4-(difluoromethyl)-1H-pyrazol-1-yl]phenol

2-[4-(Difluoromethyl)-1H-pyrazol-1-yl]phenol 1-acetate (i.e. the product from Example 6, Step C), (0.41 g, 1.626 mmoles) was dissolved in 13 mL of methanol under a nitrogen atmosphere. The mixture was treated with 3 mL of de-ionized water and then ammonium acetate (1.0 g, 13.0 mmoles). The mixture was stirred at room temperature overnight. The mixture was concentrated under vacuum and then partitioned between water and EtOAc. The phases were separated and the aqueous phase was extracted with EtOAc. The combined organic phases were washed with brine, dried over Na$_2$SO$_4$, filtered and concentrated to give 0.3 g solid. The crude product was treated with hexanes and filtered to yield 166 mg of the title compound.
$^1$H NMR δ 8.18 (s, 1H), 7.87 (s, 1H), 7.36 (d, 1H), 7.23 (t, 1H), 7.13 (d, 1H), 6.96 (t, 1H), 6.82 (t, 1H).

Step E: Preparation of 5-chloro-2-[2-[4-(difluoromethyl)-1H-pyrazol-1-yl]phenoxy]-pyrimidine The title compound was prepared in the same fashion as described in Example 1, Step C, using 2-[4-(difluoromethyl)-1H-pyrazol-1-yl]phenol (i.e. the product from Example 6, Step D), (161 mg, 0.766 mmoles) in place of 2-[3-(trifluoromethyl)-1H-pyrazol-1-yl]-phenol to give 170 mg of the title compound, a compound of the present invention, as a solid.
$^1$H NMR δ 8.40 (s, 2H), 8.08 (s, 1H), 7.80 (d, 1H), 7.72 (s, 1H), 7.41-7.50 (m, 2H), 7.33 (d, 1H), 6.67 (t, 1H).

Synthesis Example 7

Preparation of 3-(5-chloropyrimidin-2-yl)oxy-2-[4-(difluoromethyl)-1H-pyrazol-1-yl]benzonitrile (Compound 253)

Step A: Preparation of 5-chloro-2-[2-[4-(difluoromethyl)-1H-pyrazol-1-yl]-3-iodophenoxy]pyrimidine 5-Chloro-2-[2-[4-(difluoromethyl)-1H-pyrazol-1-yl]phenoxy]-pyrimidine (i.e. the product from Example 6, Step E), (285 mg, 0.883 mmoles) was dissolved in 6.3 mL of acetic acid. The mixture was treated with palladium acetate (10 mg, 0.044 mmoles) and N-iodosuccinimide (220 mg, 0.971 mmoles) and then heated at 100° C. for four hours. The mixture was cooled and then concentrated under vacuum from toluene. The resultant mixture was partitioned in saturated NaHCO$_3$ aqueous solution and EtOAc. The phases were separated and the aqueous phase was extracted with EtOAc. The combined organic phases were washed with saturated aqueous NaHCO$_3$, brine, dried over MgSO$_4$, filtered and concentrated to a crude oil. Flash column chromatography on silica gel with a 12 gram Isco MPLC column using 10 to 20% EtOAc-Hexanes gradient provided 0.46 g of the title compound.

$^1$H NMR δ 8.39 (s, 2H), 7.89 (d, 1H), 7.71 (s, 1H), 7.64 (s, 1H), 7.27-7.33 (m, 2H), 7.69 (t, 1H).

Step B: Preparation of 3-(5-chloropyrimidin-2-yl)oxy-2-[4-(difluoromethyl)-1H-pyrazol-1-yl]benzonitrile 5-Chloro-2-[2-[4-(difluoromethyl)-1H-pyrazol-1-yl]-3-iodophenoxy]pyrimidine (i.e. the product from Example 7, Step A), (0.23 g, 0.513 mmoles) was dissolved in 2.85 mL of N,N-dimethylacetamide. The mixture was treated with copper(I)cyanide (0.07 g, 0.770 mmoles) and heated at 130° C. overnight. The mixture was cooled and then diluted with EtOAc. The mixture was filtered thru a celite pad and rinsed with EtOAc. The filtrate was washed twice with saturated EDTA aqueous solution, once with brine, dried over MgSO$_4$, filtered and concentrated to 0.29 g crude oil. Flash column chromatography on silica gel with a 12 gram Isco MPLC column using Hexanes to 40% EtOAc-Hexanes gradient provided 0.13 g. The solid was triturated with hexanes and some Et$_2$O to give 56 mg of the title compound, a compound of the present invention, as a solid.

$^1$H NMR δ 8.39 (s, 2H), 7.94 (s, 1H), 7.78 (s, 1H), 7.76 (d, 1H), 7.61 (m, 2H), 6.68 (t, 1H).

Synthesis Example 8

Preparation of 3-[(5-chloro-2-pyrimidinyl)oxy]-2-[4-(trifluoromethylthio)-1-pyrazolyl]benzonitrile (Compound 134)

Step A: Preparation of 1-phenyl-4-(trifluoromethylthio)-1H-pyrazol-5-amine 1-pheny-1H-pyrazol-5-amine (5.0 g, 31.41 mmoles) was dissolved in 25 mL of dichloromethane under a nitrogen atmosphere. The mixture was cooled to 0° C. and treated with 2 mL of pyridine. Trifluoromethylsulfenyl chloride (3 mL) was condensed into a gas addition funnel before adding over 40 minutes at a temperature ≤5° C. An additional 1 mL of trifluoromethylsulfenyl chloride was added. The reaction mixture was allowed to warm to ambient temperature, diluted with dichloromethane, and washed twice with saturated NaHCO$_3$ aqueous solution., brine, dried over MgSO$_4$ and concentrated to give 8 grams of solid. The crude solid was treated with hexanes and filtered to give 6.98 g of the title solid.

$^1$H NMR δ 7.50-7.58 (m, 5H), 7.41 (t, 1H), 4.40 (bs, 2H).

Step B: Preparation of 1-phenyl-4-(trifluoromethylthio)-1H-pyrazole

1-Phenyl-4-(trifluoromethylthio)-1H-pyrazol-5-amine (i.e. the product from Example 8, Step A), (1.0 g, 3.86 mmoles) was dissolved in 19 mL of THF under a nitrogen atmosphere. The mixture was treated with isopentyl nitrite (1.036 mL, 7.71 mmoles) and then heated at 68° C. overnight. The reaction mixture was cooled and concentrated to 1.7 g of liquid. The mixture was taken up in hexanes and concentrated to 1.2 g of solid. The solid was taken up in hexanes and filtered off to give 218 mg of the title compound as a solid. The filtrate was concentrated for Flash column chromatography on silica gel with a 12 gram Isco MPLC column using Hexanes to give 0.8 g of the title compound as a solid.

$^1$H NMR δ 8.16 (s, 1H), 7.85 (s, 1H), 7.70 (d, 2H), 7.49 (t, 2H), 7.36 (t, 1H).

Step C: Preparation of 2-[4-(trifluoromethylthio)-1H-pyrazol-1-yl]phenol 1-acetate The title compound was prepared in the same fashion as described in Example 6, Step C, using 1-phenyl-4-(trifluoromethylthio)-1H-pyrazole (i.e. the product from Example 8, Step B) (0.21 g, 0.819 mmoles) in place of 1-phenyl-4-(difluoromethyl)-1H-pyrazole to give 0.43 g of the title compound.

$^1$H NMR δ 8.00 (s, 1H), 7.85 (s, 1H), 7.63 (d, 1H), 7.46 (t, 1H), 7.39 (t, 1H), 7.27 (d, 1H), 2.20 (s, 3H).

Step D: Preparation of 2-[4-(trifluoromethylthio)-1H-pyrazol-1-yl]phenol

The title compound was prepared in the same fashion as described in Example 6, Step D, using 2-[4-(trifluoromethylthio)-1H-pyrazol-1-yl]phenol 1-acetate (i.e. the product from Example 8, Step C) (0.21 g, 0.819 mmoles) in place of 2-[4-(Difluoromethyl)-1H-pyrazol-1-yl]phenol 1-acetate to give 0.10 g of the title compound, $^1$H NMR δ 8.22 (s, 1H), 7.89 (s, 1H), 7.37 (d, 1H), 7.25 (t, 1H), 7.14 (d, 1H), 6.96 (t, 1H).

Step E: Preparation of 5-chloro-2-[2-[4-(trifluoromethylthio)-1H-pyrazol-1-yl]phenoxy]pyrimidine The title compound was prepared in the same fashion as described in Example 1, Step C, using 2-[4-(trifluoromethylthio)-1H-pyrazol-1-yl]phenol (i.e. the product from Example 8, Step D) (0.4 g, 1.537 mmoles) in place of (2-[3-(trifluoromethyl)-1H-pyrazol-1-yl]-phenol), to give 114 mg of the title compound, $^1$H NMR δ 8.37 (s, 2H), 8.14 (s, 1H), 7.80 (d, 1H), 7.71 (s, 1H), 7.41-7.50 (2×t, 1H each), 7.35 (d, 1H).

Step F: Preparation of 5-chloro-2-[3-iodo-2-[4-(trifluoromethylthio)-1H-pyrazol-1-yl]phenoxy]pyrimidine The title compound was prepared in the same fashion as described in Example 7, Step A, using 5-chloro-2-[2-[4-

(trifluoromethylthio)-1H-pyrazol-1-yl]phenoxy]-pyrimidine (i.e. the product from Example 8, Step E) (0.29 g, 0.778 mmoles) in place of 5-Chloro-2-[2-[4-(difluoromethyl)-1H-pyrazol-1-yl]phenoxy]-pyrimidine, to give 270 mg of the title compound.

$^1$H NMR δ 8.38 (s, 2H), 7.91 (d, 1H), 7.72 (d, 2H),) 7.28-7.37 (m, 2H).

Step G: Preparation of 3-[(5-chloro-2-pyrimidinyl)oxy]-2-[4-(trifluoromethylthio)-1H-pyrazol-1-yl]benzonitrile The title compound was prepared in the same fashion as described in Example 7, Step B, using 5-chloro-2-[3-iodo-2-[4-(trifluoromethylthio)-1H-pyrazol-1-yl]phenoxy]-pyrimidine (i.e. the product from Example 8, Step F) (0.26 g, 0.521 mmoles) in place of 5-Chloro-2-[2-[4-(difluoromethyl)-1H-pyrazol-1-yl]-3-iodophenoxy]pyrimidine, to give 103 mg of the title compound, a compound of the present invention.

$^1$H NMR δ 8.36 (s, 2H), 8.01 (s, 1H), 7.78 (s&d, 2H), 7.63 (2×t, 2H).

Synthesis Example 9

Preparation of 3-[(5-chloro-2-pyrimidinyl)oxy]-2-[4-(trifluoromethylthio)-1H-pyrazol-1-yl]-benzonitrile (Compound 143)

5-Chloro-2-[2-[4-(trifluoromethylthio)-1H-pyrazol-1-yl]phenoxy]pyrimidine (i.e. the product from Example 8, Step E) (80 mg, 0.214 mmoles) was dissolved in acetone under a nitrogen atmosphere. The mixture was treated with water and Oxone® (0.20 g, 0.322 mmoles) and then stirred at room temperature overnight. The mixture was concentrated under vacuum and diluted with water and dichloromethane. The phases were separated and the aqueous phase was extracted twice with dichloromethane. The combined organic phases were washed 1× brine, dried over MgSO$_4$, and concentrated to 0.13 g crude oil. Flash column chromatography on silica gel with a 12 gram Isco MPLC column using Hexanes to 40% EtOAc-Hexanes gradient to give 50 mg of the title compound as a solid.

$^1$H NMR δ 8.43 (s, 1H), 8.40 (s, 2H), 8.01 (s, 1H), 7.82 (d, 1H), 7.53 (t, 1H), 7.46 (t, 1H), 7.37 (d, 1H).

Synthesis Example 10

Preparation of 5-chloro-2-[2-(4-cyclopropyl-1H-1,2,3-triazol-1-yl)phenoxy]pyrimidine (Compound 160)

Step A: Preparation of 2-azidophenol

To a solution of tert-butyl nitrite (4.91 ml, 41.2 mmol, 1.5 equiv) and 2-aminophenol (3.00 g, 27.5 mmol, 1.0 equiv) in acetonitrile (92 mL) at 0° C. was added azidotrimethylsilane (4.38 mL, 33.0 mmol, 1.2 equiv), dropwise. The reaction was removed from the ice bath and stirred at ambient temperature for 2 h. The reaction mixture was concentrated under vacuum onto Celite® and purified by column chromatography, eluting with 0 to 10% ethyl acetate in hexanes to afford the title product (3.55 g).

$^1$H NMR δ 7.11-7.03 (m, 2H), 6.97-6.90 (m, 2H), 5.35 (s, 1H).

Step B: Preparation of 5-chloro-2-(2-azidophenoxy)pyrimidine

To a solution of 2-azidophenol (i.e. the product from Example 10, Step A) (3.55 g, 26.2 mmol, 1.0 equiv) and 2,5-dichloropyrimidine (3.91 g, 26.2 mmol, 1.0 equiv) in acetonitrile (87 mL) was added powdered potassium carbonate (4.35 g, 31.4 mmol, 1.2 equiv). The reaction mixture was heated to 70° C. for 4 h. The mixture was cooled to ambient temperature and filtered through a small pad of Celite®. The filtrate was concentrated under vacuum and purified by column chromatography on silica gel, eluting with 0 to 30% ethyl acetate in hexanes to afford the title product (4.44 g).

$^1$H NMR δ 8.48 (s, 2H), 7.37-7.29 (m, 1H), 7.25-7.17 (m, 3H).

Step C: Preparation of 5-chloro-2-[2-(4-cyclopropyl-1H-1,2,3-triazol-1-yl)phenoxy]pyrimidine To a solution of 5-chloro-2-(2-azidophenoxy)pyrimidine (i.e. the product from Example 10, Step B) (0.437 g, 1.76 mmol, 1.0 equiv) and cyclopropylacetylene (0.179 mL, 2.12 mmol, 1.2 equiv) in tert-butanol (3 mL) and water (3 mL) was added CuSO$_4$.5H$_2$O (43.9 mg, 0.176 mmol, 0.1 equiv) and sodium L-ascorbate (34.9 mg, 0.176 mmol, 0.1 equiv). The reaction was stirred at ambient temperature for 18 h. The reaction mixture was filtered through a small pad of Celite®. The filtrate was concentrated under vacuum and purified by column chromatography on silica gel, eluting with 0 to 30% ethyl acetate in hexanes to afford the title compound, a compound of the present invention, as a solid (0.461 g).

$^1$H NMR δ 8.39 (s, 2H), 7.83 (dd, J=8.0, 1.7 Hz, 1H), 7.71 (s, 1H), 7.53-7.49 (m, 1H), 7.47-7.41 (m, 1H), 7.35 (dd, J=8.2, 1.4 Hz, 1H) 1.95-1.87 (m, 1H), 0.95-0.90 (m, 2H), 0.85-0.78 (m, 2H).

Synthesis Example 11

Preparation of 2-[3-[(5-chloro-2-pyrimidinyl)oxy]-2-[4-(trifluoromethyl)-1H-pyrazol-1-yl]phenyl]-1,3,4-oxadiazole (Compound 298)

Step A: Preparation of 3-hydroxy-2-[4-(trifluoromethyl)-1H-pyrazol-1-yl]benzoic acid A solution of 3-hydroxy-2-[4-(trifluoromethyl)-1H-pyrazol-1-yl]benzonitrile (i.e. the product from Example 4, Step A) (1.25 g, 4.94 mmol) in mixture of acetic acid (6 mL) and concentrated sulfuric acid (6 mL) was heated at 105° C. for 35 minutes. The reaction mixture was poured into 200 g of ice and water. The slurry was saturated with sodium chloride. After stirring at room temperature for 3 hr, the solid was collected by filtration, washed with water and dried under a stream of nitrogen under vacuum to give 0.9 g of the title compound as a tan solid.

$^1$H NMR (DMSO-d$_6$) δ 8.5 (s, 1H), 8.02 (s, 1H), 7.41 (t, 1H), 7.26 (d, 1H), 7.22 (d, 1H).

Step B: Preparation of 3-hydroxy-2-[4-(trifluoromethyl)-1H-pyrazol-1-yl]benzoic acid methyl ester To a solution of 3-hydroxy-2-[4-(trifluoromethyl)-1H-pyrazol-1-yl]benzoic acid (i.e. the product from Example 11, Step A) (670 mg, 2.45 mmol) in mixture of methanol (3 mL) and dichloromethane (3 mL) was slowly added a solution of trimethylsilyldiazomethane (2.4 mL of 2M solution in hexane). After stirring for a few minutes at room temperature, the solvent was evaporated off under a stream of nitrogen and the reaction mixture was purified by medium pressure liquid chromatography on 40 g of silica gel eluted with a gradient of 0-60% ethyl acetate in hexane to give 530 mg of the title compound as a solid.

$^1$H NMR δ 8.20 (bs, 1H), 8.00 (s, 1H), 7.88 (s, 1H), 7.45 (d, 1H), 7.37 (t, 1H), 7.25 (d, 1H).

Step C: Preparation of 3-hydroxy-2-[4-(trifluoromethyl)-1H-pyrazol-1-yl]benzo-hydrazide A solution of 3-hydroxy-2-[4-(trifluoromethyl)-1H-pyrazol-1-yl]benzoic acid methyl ester (i.e. the product from Example 11, Step B) (376 mg, 1.31 mmol) and hydrazine hydrate (1.5 ml) in ethanol (4 ml) was heated at 78° C. for 2.5 days. The reaction was diluted with 80 mL of ethyl acetate and washed with 40 mL of water. The ethyl acetate phase was filtered through a Varian Chem Elut celite tube and concentrated to a crude solid. This was triturated with dichloromethane, filtered, and collected to yield 240 mg of the title compound as a solid.

$^1$H NMR (DMSO-$d_6$) δ 10.4 (bs, 1H), 9.35 (s, 1H), 8.42 (s, 1H), 7.96 (s, 1H), 7.35 (t, 1H), 7.12 (d, 1H), 6.92 (d, 1H), 4.21 (bs, 2H).

Step D: Preparation of 2-[3-[(5-chloro-2-pyrimidinyl)oxy]-2-[4-(trifluoromethyl)-1H-pyrazol-1-yl]phenyl]-1,3,4-oxadiazole A solution of 3-hydroxy-2-[4-(trifluoromethyl)-1H-pyrazol-1-yl]benzo-hydrazide (i.e. the product from Example 11, Step C) (189 mg, 0.66 mmol), toluenesulfonic acid hydrate (22 mg) in triethylorthoformate (6 mL) was heated at 120° C. for 27 hr. The solvent was evaporated off under a stream of nitrogen and the crude reaction was purified by MPLC on 12 g of silica gel eluted with a gradient of 0-80% ethyl acetate in hexane to give 104 mg of the intermediate phenol, which treated with dichloropyrimidine (166 mg) and cesium carbonate (617 mg) in acetonitrile (5 ml) at 48 C for 18 hr. After evaporation, the crude reaction mixture was combined with an earlier batch (55 mg phenol intermediate, 80 mg dichloropyrimidine, 260 mg cesium carbonate) and purified by medium pressure liquid chromatography on 24 g silica gel eluted with 0-80% ethyl acetate in hexane to give 120 mg of the title compound, a compound of the present invention, as a solid.

$^1$H NMR δ 8.41 (s, 2H), 8.32 (s, 1H), 8.12 (s, 1H), 7.90 (s, 1H), 7.72 (m, 3H), 7.55 (d, 1H).

By the procedures described herein together with methods known in the art, the following compounds of Tables 1 to 1584 can be prepared. The following abbreviations are used in the Tables which follow: i means iso, c means cyclo, Me means methyl, Et means ethyl, Pr means propyl, Bu means butyl, i-Pr means isopropyl, c-Pr cyclopropyl, c-Bu means cyclobutyl, Ph means phenyl, $OCH_3$ means methoxy, OEt means ethoxy, —CN means cyano, —$NO_2$ means nitro, S(O)Me means methylsulfinyl, and $S(O)_2CH_3$ means methylsulfonyl.

TABLE 1

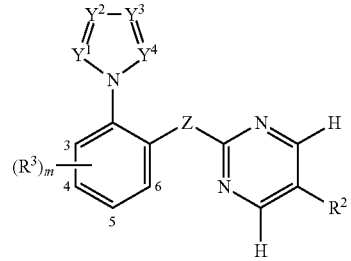

1

$R^2$ = Cl; Z = O; and $R^3$ = H (m = 0)

| $Y^1$, $Y^2$, $Y^3$ and $Y^4$ | $Y^1$, $Y^2$, $Y^3$ and $Y^4$ |
|---|---|
| $Y^1$ = CH, $Y^2$ = $CCF_3$, $Y^3$ = CH and $Y^4$ = CH | $Y^1$ = N, $Y^2$ = CBr, $Y^3$ = CBr and $Y^4$ = CH |
| $Y^1$ = $CCH_3$, $Y^2$ = CH, $Y^3$ = $CCH_3$ and $Y^4$ = CH | $Y^1$ = N, $Y^2$ = CH, $Y^3$ = CCHO and $Y^4$ = CH |
| $Y^1$ = CH, $Y^2$ = CBr, $Y^3$ = CBr and $Y^4$ = CH | $Y^1$ = N, $Y^2$ = CH, $Y^3$ = $CCH_2CF_3$ and $Y^4$ = CH |
| $Y^1$ = CH, $Y^2$ = $CCHF_2$, $Y^3$ = CH and $Y^4$ = CH | $Y^1$ = N, $Y^2$ = CH, $Y^3$ = C(i-Pr) and $Y^4$ = CH |
| $Y^1$ = CH, $Y^2$ = $CCF_3$, $Y^3$ = $CCF_3$ and $Y^4$ = CH | $Y^1$ = N, $Y^2$ = CH, $Y^3$ = C(CHC=CH) and $Y^4$ = CH |
| $Y^1$ = CH, $Y^2$ = CCl, $Y^3$ = CCl and $Y^4$ = CH | $Y^1$ = N, $Y^2$ = CH, $Y^3$ = $CSCHF_2$ and $Y^4$ = CH |
| $Y^1$ = CH, $Y^2$ = $CCH_3$, $Y^3$ = CH and $Y^4$ = CH | $Y^1$ = N, $Y^2$ = CH, $Y^3$ = $CSO_2CF_3$ and $Y^4$ = CH |
| $Y^1$ = CH, $Y^2$ = $CCH_3$, $Y^3$ = $CCH_3$ and $Y^4$ = CH | $Y^1$ = N, $Y^2$ = CH, $Y^3$ = $CCH_2SCH_3$ and $Y^4$ = CH |
| $Y^1$ = $CCF_3$, $Y^2$ = CH, $Y^3$ = $CCF_3$ and $Y^4$ = CH | $Y^1$ = N, $Y^2$ = CF, $Y^3$ = CH and $Y^4$ = CH |
| $Y^1$ = N, $Y^2$ = CH, $Y^3$ = CH and $Y^4$ = CH | $Y^1$ = N, $Y^2$ = CH, $Y^3$ = $CCH_3$ and $Y^4$ = CH |
| $Y^1$ = N, $Y^2$ = $CCF_3$, $Y^3$ = CH and $Y^4$ = CH | $Y^1$ = N, $Y^2$ = CH, $Y^3$ = CH and $Y^4$ = $CCF_3$ |
| $Y^1$ = N, $Y^2$ = CBr, $Y^3$ = CH and $Y^4$ = CH | $Y^1$ = N, $Y^2$ = CH, $Y^3$ = CH and $Y^4$ = CBr |
| $Y^1$ = N, $Y^2$ = CH, $Y^3$ = CF and $Y^4$ = CH | $Y^1$ = N, $Y^2$ = CCl, $Y^3$ = CH and $Y^4$ = CH |
| $Y^1$ = N, $Y^2$ = CH, $Y^3$ = CH and $Y^4$ = $CCH_3$ | $Y^1$ = N, $Y^2$ = CH, $Y^3$ = $CCH_2CH_3$ and $Y^4$ = CH |
| $Y^1$ = N, $Y^2$ = $CHF_2$, $Y^3$ = CH and $Y^4$ = CH | $Y^1$ = N, $Y^2$ = CH, $Y^3$ = CH and $Y^4$ = $CCHF2$ |
| $Y^1$ = N, $Y^2$ = CCl, $Y^3$ = CH and $Y^4$ = CH | $Y^1$ = N, $Y^2$ = $COCF_3$, $Y^3$ = CH and $Y^4$ = CH |
| $Y^1$ = N, $Y^2$ = CH, $Y^3$ = CCl and $Y^4$ = CH | $Y^1$ = N, $Y^2$ = CH, $Y^3$ = CCN and $Y^4$ = CH |
| $Y^1$ = N, $Y^2$ = CH, $Y^3$ = CH and $Y^4$ = $CCH_2CH_3$ | $Y^1$ = N, $Y^2$ = CH, $Y^3$ = CH and $Y^4$ = $COCF_3$ |
| $Y^1$ = N, $Y^2$ = $COCH_3$, $Y^3$ = CH and $Y^4$ = CH | $Y^1$ = N, $Y^2$ = CH, $Y^3$ = CH and $Y^4$ = $COCHF_2$ |
| $Y^1$ = N, $Y^2$ = $COCHF_2$, $Y^3$ = CH and $Y^4$ = CH | $Y^1$ = N, $Y^2$ = $COCH_3$, $Y^3$ = CH and $Y^4$ = $CCH_3$ |
| $Y^1$ = N, $Y^2$ = CH, $Y^3$ = $COCF_3$ and $Y^4$ = CH | $Y^1$ = N, $Y^2$ = CH, $Y^3$ = CPh and $Y^4$ = CH |
| $Y^1$ = N, $Y^2$ = CH, $Y^3$ = CH and $Y^4$ = CCN | $Y^1$ = N, $Y^2$ = CH, $Y^3$ = CH and $Y^4$ = CC(=O)$OCH_3$ |
| $Y^1$ = N, $Y^2$ = CC(=O)$OCH_3$, $Y^3$ = CH and $Y^4$ = CH | $Y^1$ = N, $Y^2$ = CBr, $Y^3$ = CH and $Y^4$ = CBr |
| $Y^1$ = N, $Y^2$ = CF, $Y^3$ = CH and $Y^4$ = CF | $Y^1$ = N, $Y^2$ = $CCF_3$, $Y^3$ = $CCF_3$ and $Y^4$ = CH |
| $Y^1$ = N, $Y^2$ = $CCF_3$, $Y^3$ = CH and $Y^4$ = $CCF_3$ | $Y^1$ = N, $Y^2$ = CH, $Y^3$ = $COCF_2CF_2H$ and $Y^4$ = CH |
| $Y^1$ = N, $Y^2$ = CH, $Y^3$ = CH and $Y^4$ = CPh | $Y^1$ = N, $Y^2$ = CH, $Y^3$ = C(n-Pr) and $Y^4$ = CH |

TABLE 1-continued

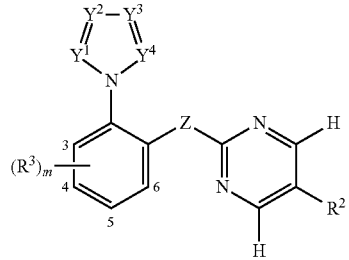

$R^2 = Cl; Z = O;$ and $R^3 = H$ (m = 0)

$Y^1, Y^2, Y^3$ and $Y^4$

- $Y^1 = N, Y^2 = CCF_3, Y^3 = CH$ and $Y^4 = CCH_3$
- $Y^1 = N, Y^2 = CH, Y^3 = CCHF_2$ and $Y^4 = CH$
- $Y^1 = N, Y^2 = CH, Y^3 = CSCF_3$ and $Y^4 = CH$
- $Y^1 = N, Y^2 = CH, Y^3 = CSO_2CH_3$ and $Y^4 = CH$
- $Y^1 = N, Y^2 = CH, Y^3 = COCH_2CHCH_2$ and $Y^4 = CH$
- $Y^1 = N, Y^2 = CH, Y^3 = CCHF_2$ and $Y^4 = CH$
- $Y^1 = N, Y^2 = CH, Y^3 = CI$ and $Y^4 = CH$
- $Y^1 = N, Y^2 = CH, Y^3 = CH$ and $Y^4 = CCl$
- $Y^1 = N, Y^2 = CCN, Y^3 = CH$ and $Y^4 = CH$
- $Y^1 = N, Y^2 = CH, Y^3 = COCH_3$ and $Y^4 = CH$
- $Y^1 = N, Y^2 = CH, Y^3 = COCHF_2$ and $Y^4 = CH$
- $Y^1 = N, Y^2 = CH, Y^3 = CH$ and $Y^4 = COCF_3$
- $Y^1 = N, Y^2 = CH, Y^3 = CPh, Y^3 = CH$ and $Y^4 = CH$
- $Y^1 = N, Y^2 = CH, Y^3 = CC(\!=\!O)OCH_3$ and $Y^4 = CH$
- $Y^1 = N, Y^2 = CCl, Y^3 = CH$ and $Y^4 = CCl$
- $Y^1 = N, Y^2 = CCHF_2, Y^3 = CH$ and $Y^4 = CCHF_2$
- $Y^1 = N, Y^2 = CCH_3, Y^3 = CCH_3$ and $Y^4 = CH$
- $Y^1 = N, Y^2 = CCl, Y^3 = CCl$ and $Y^4 = CH$
- $Y^1 = N, Y^2 = CCH_3, Y^3 = CH$ and $Y^4 = CH$
- $Y^1 = N, Y^2 = CH, Y^3 = CCF_3$ and $Y^4 = CH$
- $Y^1 = N, Y^2 = CH, Y^3 = CBr$ and $Y^4 = CH$
- $Y^1 = N, Y^2 = CH, Y^3 = CH$ and $Y^4 = CF$
- $Y^1 = N, Y^2 = CCH_2CH_3, Y^3 = CH$ and $Y^4 = CH$
- $Y^1 = N, Y^2 = CH, Y^3 = CCF_2CF_3$ and $Y^4 = CH$
- $Y^1 = N, Y^2 = CH, Y^3 = COCH_2CF_3$ and $Y^4 = CH$
- $Y^1 = N, Y^2 = CH, Y^3 = C(c\text{-Pr})$ and $Y^4 = CH$
- $Y^1 = N, Y^2 = CH, Y^3 = CCHCH_2$ and $Y^4 = CH$
- $Y^1 = N, Y^2 = CH, Y^3 = COCH_2CCH$ and $Y^4 = CH$
- $Y^1 = N, Y^2 = CH, Y^3 = CSOCH_3$ and $Y^4 = CH$
- $Y^1 = N, Y^2 = CH, Y^3 = CCH_2OCH_3$ and $Y^4 = CH$
- $Y^1 = CH, Y^2 = N, Y^3 = CF$ and $Y^4 = CH$
- $Y^1 = CH, Y^2 = N, Y^3 = CI$ and $Y^4 = CH$
- $Y^1 = CH, Y^2 = N, Y^3 = CCHF_2$ and $Y^4 = CH$
- $Y^1 = CH, Y^2 = N, Y^3 = CCF_3$ and $Y^4 = CH$
- $Y^1 = CH, Y^2 = N, Y^3 = CBr$ and $Y^4 = CH$
- $Y^1 = CH, Y^2 = N, Y^3 = CCH_2CH_3$ and $Y^4 = CH$
- $Y^1 = CH, Y^2 = N, Y^3 = CCH_2CF_3$ and $Y^4 = CH$
- $Y^1 = CH, Y^2 = N, Y^3 = CCl$ and $Y^4 = CH$
- $Y^1 = N, Y^2 = N, Y^3 = CC\!\equiv\!CH$ and $Y^4 = CH$
- $Y^1 = N, Y^2 = N, Y^3 = CCH\!=\!CH_2$ and $Y^4 = CH$
- $Y^1 = N, Y^2 = N, Y^3 = CC\!\equiv\!CCH_3$ and $Y^4 = CH$
- $Y^1 = N, Y^2 = N, Y^3 = CSCF_3$ and $Y^4 = CH$
- $Y^1 = N, Y^2 = N, Y^3 = CSO_2CH_3$ and $Y^4 = CH$
- $Y^1 = N, Y^2 = N, Y^3 = COCH_2CHCH_2$ and $Y^4 = CH$
- $Y^1 = N, Y^2 = N, Y^3 = COCH_2CH_2CF_3$ and $Y^4 = CH$
- $Y^1 = N, Y^2 = N, Y^3 = COCH_3$ and $Y^4 = CH$
- $Y^1 = N, Y^2 = N, Y^3 = CCF_2CF_3$ and $Y^4 = CH$
- $Y^1 = N, Y^2 = N, Y^3 = COCH_2CF_3$ and $Y^4 = CH$
- $Y^1 = N, Y^2 = N, Y^3 = COCH_2C\!\equiv\!CH$ and $Y^4 = CH$
- $Y^1 = N, Y^2 = N, Y^3 = CSOCH_3$ and $Y^4 = CH$
- $Y^1 = N, Y^2 = N, Y^3 = CCH_2OCH_3$ and $Y^4 = CH$
- $Y^1 = N, Y^2 = N, Y^3 = C(\text{Cyclohexyl})$ and $Y^4 = CH$
- $Y^1 = N, Y^2 = N, Y^3 = C(\text{Cyclopentyl})$ and $Y^4 = CH$
- $Y^1 = N, Y^2 = N, Y^3 = C(\text{Cyclopropyl})$ and $Y^4 = CH$
- $Y^1 = N, Y^2 = N, Y^3 = C(3\text{-thiophenyl})$ and $Y^4 = CH$
- $Y^1 = N, Y^2 = N, Y^3 = C(2\text{-thiophenyl})$ and $Y^4 = CH$
- $Y^1 = N, Y^2 = N, Y^3 = C(3\text{-pyridyl})$ and $Y^4 = CH$
- $Y^1 = N, Y^2 = N, Y^3 = C(2\text{-pyridyl})$ and $Y^4 = CH$
- $Y^1 = N, Y^2 = N, Y^3 = C(4\text{-pyridyl})$ and $Y^4 = CH$ $Y^1, Y^2, Y^3$ and $Y^4$

- $Y^1 = N, Y^2 = CH, Y^3 = CCCH$ and $Y^4 = CH$
- $Y^1 = CH, Y^2 = N, Y^3 = CCH_3$ and $Y^4 = CH$
- $Y^1 = CH, Y^2 = N, Y^3 = CCHO$ and $Y^4 = CH$
- $Y^1 = CH, Y^2 = N, Y^3 = COCH_3$ and $Y^4 = CH$
- $Y^1 = N, Y^2 = CH, Y^3 = N$ and $Y^4 = CH$
- $Y^1 = N, Y^2 = CF_3, Y^3 = N$ and $Y^4 = CH$
- $Y^1 = N, Y^2 = CCl, Y^3 = N$ and $Y^4 = CH$
- $Y^1 = N, Y^2 = CBr, Y^3 = N$ and $Y^4 = CBr$
- $Y^1 = N, Y^2 = CCH_3, Y^3 = N$ and $Y^4 = CH$
- $Y^1 = N, Y^2 = CF, Y^3 = N$ and $Y^4 = CH$
- $Y^1 = N, Y^2 = CCl, Y^3 = N$ and $Y^4 = CCl$
- $Y^1 = N, Y^2 = CHF_2, Y^3 = N$ and $Y^4 = CH$
- $Y^1 = N, Y^2 = CBr, Y^3 = N$ and $Y^4 = CH$
- $Y^1 = N, Y^2 = CPh, Y^3 = N$ and $Y^4 = CH$
- $Y^1 = N, Y^2 = N, Y^3 = CH$ and $Y^4 = CH$
- $Y^1 = N, Y^2 = N, Y^3 = CCF_3$ and $Y^4 = CH$
- $Y^1 = N, Y^2 = N, Y^3 = CI$ and $Y^4 = CH$
- $Y^1 = N, Y^2 = N, Y^3 = CCH_3F$ and $Y^4 = CH$
- $Y^1 = N, Y^2 = N, Y^3 = CCl$ and $Y^4 = CH$
- $Y^1 = N, Y^2 = N, Y^3 = CCHF_2$ and $Y^4 = CH$
- $Y^1 = N, Y^2 = N, Y^3 = CBr$ and $Y^4 = CH$
- $Y^1 = N, Y^2 = N, Y^3 = CCH_3$ and $Y^4 = CH$
- $Y^1 = N, Y^2 = N, Y^3 = CF$ and $Y^4 = CH$
- $Y^1 = N, Y^2 = N, Y^3 = CPh$ and $Y^4 = CH$
- $Y^1 = N, Y^2 = N, Y^3 = COCF_3$ and $Y^4 = CH$
- $Y^1 = N, Y^2 = N, Y^3 = COCHF_2$ and $Y^4 = CH$
- $Y^1 = N, Y^2 = N, Y^3 = COCH_2F$ and $Y^4 = CH$
- $Y^1 = N, Y^2 = N, Y^3 = CCH_2CF_3$ and $Y^4 = CH$
- $Y^1 = N, Y^2 = N, Y^3 = C(i\text{-Pr})$ and $Y^4 = CH$
- $Y^1 = N, Y^2 = N, Y^3 = CCH_2C\!\equiv\!CH$ and $Y^4 = CH$
- $Y^1 = N, Y^2 = N, Y^3 = CSCHF_2$ and $Y^4 = CH$
- $Y^1 = N, Y^2 = N, Y^3 = CSO_2CF_3$ and $Y^4 = CH$
- $Y^1 = N, Y^2 = N, Y^3 = CCH_2SCH_3$ and $Y^4 = CH$
- $Y^1 = N, Y^2 = N, Y^3 = CCH_2CH_3$ and $Y^4 = CH$
- $Y^1 = N, Y^2 = N, Y^3 = CCN$ and $Y^4 = CH$
- $Y^1 = N, Y^2 = N, Y^3 = COCH_2CN$ and $Y^4 = CH$
- $Y^1 = N, Y^2 = N, Y^3 = CCH_2CN$ and $Y^4 = CH$
- $Y^1 = N, Y^2 = N, Y^3 = C(n\text{-Pr})$ and $Y^4 = CH$
- $Y^1 = N, Y^2 = N, Y^3 = C(3\text{-}CF_3\text{---Ph})$ and $Y^4 = CH$
- $Y^1 = N, Y^2 = N, Y^3 = C(3,5\text{-di-F---Ph})$ and $Y^4 = CH$
- $Y^1 = N, Y^2 = N, Y^3 = C(3,5\text{-di-Cl---Ph})$ and $Y^4 = CH$
- $Y^1 = N, Y^2 = N, Y^3 = C(3,5\text{-di-Br---Ph})$ and $Y^4 = CH$
- $Y^1 = N, Y^2 = N, Y^3 = C(C\!=\!O)CH3$ and $Y^4 = CH$
- $Y^1 = N, Y^2 = N, Y^3 = C(C\!=\!CH_2)CH_3$ and $Y^4 = CH$
- $Y^1 = N, Y^2 = N, Y^3 = C(C\!=\!NOH)CH_3$ and $Y^4 = CH$
- $Y^1 = N, Y^2 = N, Y^3 = CSi(CH_3)_3$ and $Y^4 = CH$
- $Y^1 = N, Y^2 = CH, Y^3 = CH$ and $Y^4 = N$
- $Y^1 = N, Y^2 = CCH_3, Y^3 = CH$, and and $Y^4 = N$
- $Y^1 = N, Y^2 = CF, Y^3 = CH$, and and $Y^4 = N$
- $Y^1 = N, Y^2 = CPh, Y^3 = C$, and and $Y^4 = N$
- $Y^1 = N, Y^2 = CCl, Y^3 = CCl$, and and $Y^4 = N$
- $Y^1 = N, Y^2 = CCHF_2, Y^3 = CH$ and $Y^4 = N$
- $Y^1 = N, Y^2 = CBr, Y^3 = CH$ and $Y^4 = N$
- $Y^1 = N, Y^2 = CCF_3, Y^3 = CCF_3$ and $Y^4 = N$
- $Y^1 = N, Y^2 = CCF_3, Y^3 = CH$, and and $Y^4 = N$
- $Y^1 = N, Y^2 = CCl, Y^3 = CH$, and and $Y^4 = N$
- $Y^1 = N, Y^2 = CCH_3, Y^3 = CCH_3$, and and $Y^4 = N$
- $Y^1 = N, Y^2 = CBr, Y^3 = CBr$, and and $Y^4 = N$ The present disclosure also includes Tables 2 through 1584. Each Table is constructed in the the same manner as Table 1 above, except that the row heading in Table 1 (i.e. "$R^2$=Cl; Z=O; and $R^3$=H (m=0)." ) is replaced with the respective row heading shown below.

| Table | Header Row |
|---|---|
| 2 | $R^2$ = F, Z = O, $R^3$ = H (m = 0) |
| 3 | $R^2$ = F, Z = O, $R^3$ = 3-F |
| 4 | $R^2$ = F, Z = O, $R^3$ = 3-Cl |
| 5 | $R^2$ = F, Z = O, $R^3$ = 3-Br |
| 6 | $R^2$ = F, Z = O, $R^3$ = 3-I |
| 7 | $R^2$ = F, Z = O, $R^3$ = 3-CN |
| 8 | $R^2$ = F, Z = O, $R^3$ = 3-$NO_2$ |
| 9 | $R^2$ = F, Z = O, $R^3$ = 3-OMe |
| 10 | $R^2$ = F, Z = O, $R^3$ = 3-$OCF_3$ |
| 11 | $R^2$ = F, Z = O, $R^3$ = 3-$CF_3$ |
| 12 | $R^2$ = F, Z = O, $R^3$ = 3-$CHF_2$ |
| 13 | $R^2$ = F, Z = O, $R^3$ = 3-$CH_2F$ |
| 14 | $R^2$ = F, Z = O, $R^3$ = 3-CHO |
| 15 | $R^2$ = F, Z = O, $R^3$ = 3-Me |
| 16 | $R^2$ = F, Z = O, $R^3$ = 3-Et |
| 17 | $R^2$ = F, Z = O, $R^3$ = 3-Ethynyl |
| 18 | $R^2$ = F, Z = O, $R^3$ = 3-Ethenyl |
| 19 | $R^2$ = F, Z = O, $R^3$ = 3-$SO_2$Me |
| 20 | $R^2$ = F, Z = O, $R^3$ = 3-OAc |
| 21 | $R^2$ = F, Z = O, $R^3$ = 3-c-Pr |
| 22 | $R^2$ = F, Z = O, $R^3$ = 3-i-Pr |
| 23 | $R^2$ = F, Z = O, $R^3$ = 3-Ph |
| 24 | $R^2$ = F, Z = S, $R^3$ = 3-F |
| 25 | $R^2$ = F, Z = S, $R^3$ = 3-Cl |
| 26 | $R^2$ = F, Z = S, $R^3$ = 3-Br |
| 27 | $R^2$ = F, Z = S, $R^3$ = 3-I |
| 28 | $R^2$ = F, Z = S, $R^3$ = 3-CN |
| 29 | $R^2$ = F, Z = S, $R^3$ = 3-$NO_2$ |
| 30 | $R^2$ = F, Z = S, $R^3$ = 3-OMe |
| 31 | $R^2$ = F, Z = S, $R^3$ = 3-$OCF_3$ |
| 32 | $R^2$ = F, Z = S, $R^3$ = 3-$CF_3$ |
| 33 | $R^2$ = F, Z = S, $R^3$ = 3-$CHF_2$ |
| 34 | $R^2$ = F, Z = S, $R^3$ = 3-$CH_2F$ |
| 35 | $R^2$ = F, Z = S, $R^3$ = 3-CHO |
| 36 | $R^2$ = F, Z = S, $R^3$ = 3-Me |
| 37 | $R^2$ = F, Z = S, $R^3$ = 3-Et |
| 38 | $R^2$ = F, Z = S, $R^3$ = 3-Ethynyl |
| 39 | $R^2$ = F, Z = S, $R^3$ = 3-Ethenyl |
| 40 | $R^2$ = F, Z = S, $R^3$ = 3-$SO_2$Me |
| 41 | $R^2$ = F, Z = S, $R^3$ = 3-OAc |
| 42 | $R^2$ = F, Z = S, $R^3$ = 3-c-Pr |
| 43 | $R^2$ = F, Z = S, $R^3$ = 3-i-Pr |
| 44 | $R^2$ = F, Z = S, $R^3$ = 3-Ph |
| 45 | $R^2$ = F, Z = O, $R^3$ = 4-F |
| 46 | $R^2$ = F, Z = O, $R^3$ = 4-Cl |
| 47 | $R^2$ = F, Z = O, $R^3$ = 4-Br |
| 48 | $R^2$ = F, Z = O, $R^3$ = 4-I |
| 49 | $R^2$ = F, Z = O, $R^3$ = 4-CN |
| 50 | $R^2$ = F, Z = O, $R^3$ = 4-$NO_2$ |
| 51 | $R^2$ = F, Z = O, $R^3$ = 4-OMe |
| 52 | $R^2$ = F, Z = O, $R^3$ = 4-$OCF_3$ |
| 53 | $R^2$ = F, Z = O, $R^3$ = 4-$CF_3$ |
| 54 | $R^2$ = F, Z = O, $R^3$ = 4-$CHF_2$ |
| 55 | $R^2$ = F, Z = O, $R^3$ = 4-$CH_2F$ |
| 56 | $R^2$ = F, Z = O, $R^3$ = 4-CHO |
| 57 | $R^2$ = F, Z = O, $R^3$ = 4-Me |
| 58 | $R^2$ = F, Z = O, $R^3$ = 4-Et |
| 59 | $R^2$ = F, Z = O, $R^3$ = 4-Ethynyl |
| 60 | $R^2$ = F, Z = O, $R^3$ = 4-Ethenyl |
| 61 | $R^2$ = F, Z = O, $R^3$ = 4-$SO_2$Me |
| 62 | $R^2$ = F, Z = O, $R^3$ = 4-OAc |
| 63 | $R^2$ = F, Z = O, $R^3$ = 4-c-Pr |
| 64 | $R^2$ = F, Z = O, $R^3$ = 4-i-Pr |
| 65 | $R^2$ = F, Z = O, $R^3$ = 4-Ph |
| 66 | $R^2$ = F, Z = O, $R^3$ = 5-F |
| 67 | $R^2$ = F, Z = O, $R^3$ = 5-Cl |
| 68 | $R^2$ = F, Z = O, $R^3$ = 5-Br |
| 69 | $R^2$ = F, Z = O, $R^3$ = 5-I |
| 70 | $R^2$ = F, Z = O, $R^3$ = 5-CN |
| 71 | $R^2$ = F, Z = O, $R^3$ = 5-$NO_2$ |
| 72 | $R^2$ = F, Z = O, $R^3$ = 5-OMe |
| 73 | $R^2$ = F, Z = O, $R^3$ = 5-$OCF_3$ |

-continued

| Table | Header Row |
|---|---|
| 74 | $R^2$ = F, Z = O, $R^3$ = 5-$CF_3$ |
| 75 | $R^2$ = F, Z = O, $R^3$ = 5-$CHF_2$ |
| 76 | $R^2$ = F, Z = O, $R^3$ = 5-$CH_2F$ |
| 77 | $R^2$ = F, Z = O, $R^3$ = 5-CHO |
| 78 | $R^2$ = F, Z = O, $R^3$ = 5-Me |
| 79 | $R^2$ = F, Z = O, $R^3$ = 5-Et |
| 80 | $R^2$ = F, Z = O, $R^3$ = 5-Ethynyl |
| 81 | $R^2$ = F, Z = O, $R^3$ = 5-Ethenyl |
| 82 | $R^2$ = F, Z = O, $R^3$ = 5-$SO_2$Me |
| 83 | $R^2$ = F, Z = O, $R^3$ = 5-OAc |
| 84 | $R^2$ = F, Z = O, $R^3$ = 5-c-Pr |
| 85 | $R^2$ = F, Z = O, $R^3$ = 5-i-Pr |
| 86 | $R^2$ = F, Z = O, $R^3$ = 5-Ph |
| 87 | $R^2$ = F, Z = O, $R^3$ = 6-F |
| 88 | $R^2$ = F, Z = O, $R^3$ = 6-Cl |
| 89 | $R^2$ = F, Z = O, $R^3$ = 6-Br |
| 90 | $R^2$ = F, Z = O, $R^3$ = 6-I |
| 91 | $R^2$ = F, Z = O, $R^3$ = 6-CN |
| 92 | $R^2$ = F, Z = O, $R^3$ = 6-$NO_2$ |
| 93 | $R^2$ = F, Z = O, $R^3$ = 6-OMe |
| 94 | $R^2$ = F, Z = O, $R^3$ = 6-$OCF_3$ |
| 95 | $R^2$ = F, Z = O, $R^3$ = 6-$CF_3$ |
| 96 | $R^2$ = F, Z = O, $R^3$ = 6-$CHF_2$ |
| 97 | $R^2$ = F, Z = O, $R^3$ = 6-$CH_2F$ |
| 98 | $R^2$ = F, Z = O, $R^3$ = 6-CHO |
| 99 | $R^2$ = F, Z = O, $R^3$ = 6-Me |
| 100 | $R^2$ = F, Z = O, $R^3$ = 6-Et |
| 101 | $R^2$ = F, Z = O, $R^3$ = 6-Ethynyl |
| 102 | $R^2$ = F, Z = O, $R^3$ = 6-Ethenyl |
| 103 | $R^2$ = F, Z = O, $R^3$ = 6-$SO_2$Me |
| 104 | $R^2$ = F, Z = O, $R^3$ = 6-OAc |
| 105 | $R^2$ = F, Z = O, $R^3$ = 6-c-Pr |
| 106 | $R^2$ = F, Z = O, $R^3$ = 6-i-Pr |
| 107 | $R^2$ = F, Z = O, $R^3$ = 6-Ph |
| 108 | $R^2$ = F, Z = O, $R^3$ = 3,4-di-F |
| 109 | $R^2$ = F, Z = O, $R^3$ = 3,5-di-F |
| 110 | $R^2$ = F, Z = O, $R^3$ = 3,6-di-F |
| 111 | $R^2$ = F, Z = O, $R^3$ = 4,5-di-F |
| 112 | $R^2$ = F, Z = O, $R^3$ = 3,4-di-Cl |
| 113 | $R^2$ = F, Z = O, $R^3$ = 3,5-di-Cl |
| 114 | $R^2$ = F, Z = O, $R^3$ = 3,6-di-Cl |
| 115 | $R^2$ = F, Z = O, $R^3$ = 4,5-di-Cl |
| 116 | $R^2$ = F, Z = O, $R^3$ = 3,4-di-Br |
| 117 | $R^2$ = F, Z = O, $R^3$ = 3,5-di-Br |
| 118 | $R^2$ = F, Z = O, $R^3$ = 3,6-di-Br |
| 119 | $R^2$ = F, Z = O, $R^3$ = 4,5-di-Br |
| 120 | $R^2$ = F, Z = O, $R^3$ = 3,4-di-CN |
| 121 | $R^2$ = F, Z = O, $R^3$ = 3,5-di-CN |
| 122 | $R^2$ = F, Z = O, $R^3$ = 3,6-di-CN |
| 123 | $R^2$ = F, Z = O, $R^3$ = 4,5-di-CN |
| 124 | $R^2$ = F, Z = O, $R^3$ = 3,4-di-Me |
| 125 | $R^2$ = F, Z = O, $R^3$ = 3,5-di-Me |
| 126 | $R^2$ = F, Z = O, $R^3$ = 3,6-di-Me |
| 127 | $R^2$ = F, Z = O, $R^3$ = 4,5-di-Me |
| 128 | $R^2$ = F, Z = O, $R^3$ = 3,4-di-OMe |
| 129 | $R^2$ = F, Z = O, $R^3$ = 3,5-di-OMe |
| 130 | $R^2$ = F, Z = O, $R^3$ = 3,6-di-OMe |
| 131 | $R^2$ = F, Z = O, $R^3$ = 4,5-di-OMe |
| 132 | $R^2$ = F, Z = O, $R^3$ = 3,4-di-$CF_3$ |
| 133 | $R^2$ = F, Z = O, $R^3$ = 3,5-di-$CF_3$ |
| 134 | $R^2$ = F, Z = O, $R^3$ = 3,6-di-$CF_3$ |
| 135 | $R^2$ = F, Z = O, $R^3$ = 4,5-di-$CF_3$ |
| 136 | $R^2$ = F, Z = O, $R^3$ = 3-CN, 4-Me |
| 137 | $R^2$ = F, Z = O, $R^3$ = 3-CN, 4-F |
| 138 | $R^2$ = F, Z = O, $R^3$ = 3-CN, 4-Br |
| 139 | $R^2$ = F, Z = O, $R^3$ = 3-CN, 4-OMe |
| 140 | $R^2$ = F, Z = O, $R^3$ = 3-CN, 4-$CF_3$ |
| 141 | $R^2$ = F, Z = O, $R^3$ = 3-CN, 6-Me |
| 142 | $R^2$ = F, Z = O, $R^3$ = 3-CN, 6-F |
| 143 | $R^2$ = F, Z = O, $R^3$ = 3-CN, 6-Br |
| 144 | $R^2$ = F, Z = O, $R^3$ = 3-CN, 6-OMe |
| 145 | $R^2$ = F, Z = O, $R^3$ = 3-CN, 6-$CF_3$ |
| 146 | $R^2$ = Br, Z = O, $R^3$ = H (m = 0) |
| 147 | $R^2$ = Br, Z = O, $R^3$ = 3-F |
| 148 | $R^2$ = Br, Z = O, $R^3$ = 3-Cl |
| 149 | $R^2$ = Br, Z = O, $R^3$ = 3-Br |
| 150 | $R^2$ = Br, Z = O, $R^3$ = 3-I |

-continued

| Table | Header Row |
|---|---|
| 151 | $R^2$ = Br, Z = O, $R^3$ = 3-CN |
| 152 | $R^2$ = Br, Z = O, $R^3$ = 3-$NO_2$ |
| 153 | $R^2$ = Br, Z = O, $R^3$ = 3-OMe |
| 154 | $R^2$ = Br, Z = O, $R^3$ = 3-$OCF_3$ |
| 155 | $R^2$ = Br, Z = O, $R^3$ = 3-$CF_3$ |
| 156 | $R^2$ = Br, Z = O, $R^3$ = 3-$CHF_2$ |
| 157 | $R^2$ = Br, Z = O, $R^3$ = 3-$CH_2F$ |
| 158 | $R^2$ = Br, Z = O, $R^3$ = 3-CHO |
| 159 | $R^2$ = Br, Z = O, $R^3$ = 3-Me |
| 160 | $R^2$ = Br, Z = O, $R^3$ = 3-Et |
| 161 | $R^2$ = Br, Z = O, $R^3$ = 3-Ethynyl |
| 162 | $R^2$ = Br, Z = O, $R^3$ = 3-Ethenyl |
| 163 | $R^2$ = Br, Z = O, $R^3$ = 3-$SO_2Me$ |
| 164 | $R^2$ = Br, Z = O, $R^3$ = 3-OAc |
| 165 | $R^2$ = Br, Z = O, $R^3$ = 3-c-Pr |
| 166 | $R^2$ = Br, Z = O, $R^3$ = 3-i-Pr |
| 167 | $R^2$ = Br, Z = O, $R^3$ = 3-Ph |
| 168 | $R^2$ = Br, Z = S, $R^3$ = 3-F |
| 169 | $R^2$ = Br, Z = S, $R^3$ = 3-Cl |
| 170 | $R^2$ = Br, Z = S, $R^3$ = 3-Br |
| 171 | $R^2$ = Br, Z = S, $R^3$ = 3-I |
| 172 | $R^2$ = Br, Z = S, $R^3$ = 3-CN |
| 173 | $R^2$ = Br, Z = S, $R^3$ = 3-$NO_2$ |
| 174 | $R^2$ = Br, Z = S, $R^3$ = 3-OMe |
| 175 | $R^2$ = Br, Z = S, $R^3$ = 3-$OCF_3$ |
| 176 | $R^2$ = Br, Z = S, $R^3$ = 3-$CF_3$ |
| 177 | $R^2$ = Br, Z = S, $R^3$ = 3-$CHF_2$ |
| 178 | $R^2$ = Br, Z = S, $R^3$ = 3-$CH_2F$ |
| 179 | $R^2$ = Br, Z = S, $R^3$ = 3-CHO |
| 180 | $R^2$ = Br, Z = S, $R^3$ = 3-Me |
| 181 | $R^2$ = Br, Z = S, $R^3$ = 3-Et |
| 182 | $R^2$ = Br, Z = S, $R^3$ = 3-Ethynyl |
| 183 | $R^2$ = Br, Z = S, $R^3$ = 3-Ethenyl |
| 184 | $R^2$ = Br, Z = S, $R^3$ = 3-$SO_2Me$ |
| 185 | $R^2$ = Br, Z = S, $R^3$ = 3-OAc |
| 186 | $R^2$ = Br, Z = S, $R^3$ = 3-c-Pr |
| 187 | $R^2$ = Br, Z = S, $R^3$ = 3-i-Pr |
| 188 | $R^2$ = Br, Z = S, $R^3$ = 3-Ph |
| 189 | $R^2$ = Br, Z = O, $R^3$ = 4-F |
| 190 | $R^2$ = Br, Z = O, $R^3$ = 4-Cl |
| 191 | $R^2$ = Br, Z = O, $R^3$ = 4-Br |
| 192 | $R^2$ = Br, Z = O, $R^3$ = 4-I |
| 193 | $R^2$ = Br, Z = O, $R^3$ = 4-CN |
| 194 | $R^2$ = Br, Z = O, $R^3$ = 4-$NO_2$ |
| 195 | $R^2$ = Br, Z = O, $R^3$ = 4-OMe |
| 196 | $R^2$ = Br, Z = O, $R^3$ = 4-$OCF_3$ |
| 197 | $R^2$ = Br, Z = O, $R^3$ = 4-$CF_3$ |
| 198 | $R^2$ = Br, Z = O, $R^3$ = 4-$CHF_2$ |
| 199 | $R^2$ = Br, Z = O, $R^3$ = 4-$CH_2F$ |
| 200 | $R^2$ = Br, Z = O, $R^3$ = 4-CHO |
| 201 | $R^2$ = Br, Z = O, $R^3$ = 4-Me |
| 202 | $R^2$ = Br, Z = O, $R^3$ = 4-Et |
| 203 | $R^2$ = Br, Z = O, $R^3$ = 4-Ethynyl |
| 204 | $R^2$ = Br, Z = O, $R^3$ = 4-Ethenyl |
| 205 | $R^2$ = Br, Z = O, $R^3$ = 4-$SO_2Me$ |
| 206 | $R^2$ = Br, Z = O, $R^3$ = 4-OAc |
| 207 | $R^2$ = Br, Z = O, $R^3$ = 4-c-Pr |
| 208 | $R^2$ = Br, Z = O, $R^3$ = 4-i-Pr |
| 209 | $R^2$ = Br, Z = O, $R^3$ = 4-Ph |
| 210 | $R^2$ = Br, Z = O, $R^3$ = 5-F |
| 211 | $R^2$ = Br, Z = O, $R^3$ = 5-Cl |
| 212 | $R^2$ = Br, Z = O, $R^3$ = 5-Br |
| 213 | $R^2$ = Br, Z = O, $R^3$ = 5-I |
| 214 | $R^2$ = Br, Z = O, $R^3$ = 5-CN |
| 215 | $R^2$ = Br, Z = O, $R^3$ = 5-$NO_2$ |
| 216 | $R^2$ = Br, Z = O, $R^3$ = 5-OMe |
| 217 | $R^2$ = Br, Z = O, $R^3$ = 5-$OCF_3$ |
| 218 | $R^2$ = Br, Z = O, $R^3$ = 5-$CF_3$ |
| 219 | $R^2$ = Br, Z = O, $R^3$ = 5-$CHF_2$ |
| 220 | $R^2$ = Br, Z = O, $R^3$ = 5-$CH_2F$ |
| 221 | $R^2$ = Br, Z = O, $R^3$ = 5-CHO |
| 222 | $R^2$ = Br, Z = O, $R^3$ = 5-Me |
| 223 | $R^2$ = Br, Z = O, $R^3$ = 5-Et |
| 224 | $R^2$ = Br, Z = O, $R^3$ = 5-Ethynyl |
| 225 | $R^2$ = Br, Z = O, $R^3$ = 5-Ethenyl |
| 226 | $R^2$ = Br, Z = O, $R^3$ = 5-$SO_2Me$ |
| 227 | $R^2$ = Br, Z = O, $R^3$ = 5-OAc |
| 228 | $R^2$ = Br, Z = O, $R^3$ = 5-c-Pr |
| 229 | $R^2$ = Br, Z = O, $R^3$ = 5-i-Pr |
| 230 | $R^2$ = Br, Z = O, $R^3$ = 5-Ph |
| 231 | $R^2$ = Br, Z = O, $R^3$ = 6-F |
| 232 | $R^2$ = Br, Z = O, $R^3$ = 6-Cl |
| 233 | $R^2$ = Br, Z = O, $R^3$ = 6-Br |
| 234 | $R^2$ = Br, Z = O, $R^3$ = 6-I |
| 235 | $R^2$ = Br, Z = O, $R^3$ = 6-CN |
| 236 | $R^2$ = Br, Z = O, $R^3$ = 6-$NO_2$ |
| 237 | $R^2$ = Br, Z = O, $R^3$ = 6-OMe |
| 238 | $R^2$ = Br, Z = O, $R^3$ = 6-$OCF_3$ |
| 239 | $R^2$ = Br, Z = O, $R^3$ = 6-$CF_3$ |
| 240 | $R^2$ = Br, Z = O, $R^3$ = 6-$CHF_2$ |
| 241 | $R^2$ = Br, Z = O, $R^3$ = 6-$CH_2F$ |
| 242 | $R^2$ = Br, Z = O, $R^3$ = 6-CHO |
| 243 | $R^2$ = Br, Z = O, $R^3$ = 6-Me |
| 244 | $R^2$ = Br, Z = O, $R^3$ = 6-Et |
| 245 | $R^2$ = Br, Z = O, $R^3$ = 6-Ethynyl |
| 246 | $R^2$ = Br, Z = O, $R^3$ = 6-Ethenyl |
| 247 | $R^2$ = Br, Z = O, $R^3$ = 6-$SO_2Me$ |
| 248 | $R^2$ = Br, Z = O, $R^3$ = 6-OAc |
| 249 | $R^2$ = Br, Z = O, $R^3$ = 6-c-Pr |
| 250 | $R^2$ = Br, Z = O, $R^3$ = 6-i-Pr |
| 251 | $R^2$ = Br, Z = O, $R^3$ = 6-Ph |
| 252 | $R^2$ = Br, Z = O, $R^3$ = 3,4-di-F |
| 253 | $R^2$ = Br, Z = O, $R^3$ = 3,5-di-F |
| 254 | $R^2$ = Br, Z = O, $R^3$ = 3,6-di-F |
| 255 | $R^2$ = Br, Z = O, $R^3$ = 4,5-di-F |
| 256 | $R^2$ = Br, Z = O, $R^3$ = 3,4-di-Cl |
| 257 | $R^2$ = Br, Z = O, $R^3$ = 3,5-di-Cl |
| 258 | $R^2$ = Br, Z = O, $R^3$ = 3,6-di-Cl |
| 259 | $R^2$ = Br, Z = O, $R^3$ = 4,5-di-Cl |
| 260 | $R^2$ = Br, Z = O, $R^3$ = 3,4-di-Br |
| 261 | $R^2$ = Br, Z = O, $R^3$ = 3,5-di-Br |
| 262 | $R^2$ = Br, Z = O, $R^3$ = 3,6-di-Br |
| 263 | $R^2$ = Br, Z = O, $R^3$ = 4,5-di-Br |
| 264 | $R^2$ = Br, Z = O, $R^3$ = 3,4-di-CN |
| 265 | $R^2$ = Br, Z = O, $R^3$ = 3,5-di-CN |
| 266 | $R^2$ = Br, Z = O, $R^3$ = 3,6-di-CN |
| 267 | $R^2$ = Br, Z = O, $R^3$ = 4,5-di-CN |
| 268 | $R^2$ = Br, Z = O, $R^3$ = 3,4-di-Me |
| 269 | $R^2$ = Br, Z = O, $R^3$ = 3,5-di-Me |
| 270 | $R^2$ = Br, Z = O, $R^3$ = 3,6-di-Me |
| 271 | $R^2$ = Br, Z = O, $R^3$ = 4,5-di-Me |
| 272 | $R^2$ = Br, Z = O, $R^3$ = 3,4-di-OMe |
| 273 | $R^2$ = Br, Z = O, $R^3$ = 3,5-di-OMe |
| 274 | $R^2$ = Br, Z = O, $R^3$ = 3,6-di-OMe |
| 275 | $R^2$ = Br, Z = O, $R^3$ = 4,5-di-OMe |
| 276 | $R^2$ = Br, Z = O, $R^3$ = 3,4-di-$CF_3$ |
| 277 | $R^2$ = Br, Z = O, $R^3$ = 3,5-di-$CF_3$ |
| 278 | $R^2$ = Br, Z = O, $R^3$ = 3,6-di-$CF_3$ |
| 279 | $R^2$ = Br, Z = O, $R^3$ = 4,5-di-$CF_3$ |
| 280 | $R^2$ = Br, Z = O, $R^3$ = 3-CN, 4-Me |
| 281 | $R^2$ = Br, Z = O, $R^3$ = 3-CN, 4-F |
| 282 | $R^2$ = Br, Z = O, $R^3$ = 3-CN, 4-Br |
| 283 | $R^2$ = Br, Z = O, $R^3$ = 3-CN, 4-OMe |
| 284 | $R^2$ = Br, Z = O, $R^3$ = 3-CN, 4-$CF_3$ |
| 285 | $R^2$ = Br, Z = O, $R^3$ = 3-CN, 6-Me |
| 286 | $R^2$ = Br, Z = O, $R^3$ = 3-CN, 6-F |
| 287 | $R^2$ = Br, Z = O, $R^3$ = 3-CN, 6-Br |
| 288 | $R^2$ = Br, Z = O, $R^3$ = 3-CN, 6-OMe |
| 289 | $R^2$ = Br, Z = O, $R^3$ = 3-CN, 6-$CF_3$ |
| 290 | $R^2$ = Cl, Z = O, $R^3$ = H (m = 0) |
| 291 | $R^2$ = Cl, Z = O, $R^3$ = 3-F |
| 292 | $R^2$ = Cl, Z = O, $R^3$ = 3-Cl |
| 293 | $R^2$ = Cl, Z = O, $R^3$ = 3-Br |
| 294 | $R^2$ = Cl, Z = O, $R^3$ = 3-I |
| 295 | $R^2$ = Cl, Z = O, $R^3$ = 3-CN |
| 296 | $R^2$ = Cl, Z = O, $R^3$ = 3-$NO_2$ |
| 297 | $R^2$ = Cl, Z = O, $R^3$ = 3-OMe |
| 298 | $R^2$ = Cl, Z = O, $R^3$ = 3-$OCF_3$ |
| 299 | $R^2$ = Cl, Z = O, $R^3$ = 3-$CF_3$ |
| 300 | $R^2$ = Cl, Z = O, $R^3$ = 3-$CHF_2$ |
| 301 | $R^2$ = Cl, Z = O, $R^3$ = 3-$CH_2F$ |
| 302 | $R^2$ = Cl, Z = O, $R^3$ = 3-CHO |
| 303 | $R^2$ = Cl, Z = O, $R^3$ = 3-Me |
| 304 | $R^2$ = Cl, Z = O, $R^3$ = 3-Et |

| Table | Header Row |
|---|---|
| 305 | $R^2$ = Cl, Z = O, $R^3$ = 3-Ethynyl |
| 306 | $R^2$ = Cl, Z = O, $R^3$ = 3-Ethenyl |
| 307 | $R^2$ = Cl, Z = O, $R^3$ = 3-SO$_2$Me |
| 308 | $R^2$ = Cl, Z = O, $R^3$ = 3-OAc |
| 309 | $R^2$ = Cl, Z = O, $R^3$ = 3-c-Pr |
| 310 | $R^2$ = Cl, Z = O, $R^3$ = 3-i-Pr |
| 311 | $R^2$ = Cl, Z = O, $R^3$ = 3-Ph |
| 312 | $R^2$ = Cl, Z = S, $R^3$ = 3-F |
| 313 | $R^2$ = Cl, Z = S, $R^3$ = 3-Cl |
| 314 | $R^2$ = Cl, Z = S, $R^3$ = 3-Br |
| 315 | $R^2$ = Cl, Z = S, $R^3$ = 3-I |
| 316 | $R^2$ = Cl, Z = S, $R^3$ = 3-CN |
| 317 | $R^2$ = Cl, Z = S, $R^3$ = 3-NO$_2$ |
| 318 | $R^2$ = Cl, Z = S, $R^3$ = 3-OMe |
| 319 | $R^2$ = Cl, Z = S, $R^3$ = 3-OCF$_3$ |
| 320 | $R^2$ = Cl, Z = S, $R^3$ = 3-CF$_3$ |
| 321 | $R^2$ = Cl, Z = S, $R^3$ = 3-CHF$_2$ |
| 322 | $R^2$ = Cl, Z = S, $R^3$ = 3-CH$_2$F |
| 323 | $R^2$ = Cl, Z = S, $R^3$ = 3-CHO |
| 324 | $R^2$ = Cl, Z = S, $R^3$ = 3-Me |
| 325 | $R^2$ = Cl, Z = S, $R^3$ = 3-Et |
| 326 | $R^2$ = Cl, Z = S, $R^3$ = 3-Ethynyl |
| 327 | $R^2$ = Cl, Z = S, $R^3$ = 3-Ethenyl |
| 328 | $R^2$ = Cl, Z = S, $R^3$ = 3-SO$_2$Me |
| 329 | $R^2$ = Cl, Z = S, $R^3$ = 3-OAc |
| 330 | $R^2$ = Cl, Z = S, $R^3$ = 3-c-Pr |
| 331 | $R^2$ = Cl, Z = S, $R^3$ = 3-i-Pr |
| 332 | $R^2$ = Cl, Z = S, $R^3$ = 3-Ph |
| 333 | $R^2$ = Cl, Z = O, $R^3$ = 4-F |
| 334 | $R^2$ = Cl, Z = O, $R^3$ = 4-Cl |
| 335 | $R^2$ = Cl, Z = O, $R^3$ = 4-Br |
| 336 | $R^2$ = Cl, Z = O, $R^3$ = 4-I |
| 337 | $R^2$ = Cl, Z = O, $R^3$ = 4-CN |
| 338 | $R^2$ = Cl, Z = O, $R^3$ = 4-NO$_2$ |
| 339 | $R^2$ = Cl, Z = O, $R^3$ = 4-OMe |
| 340 | $R^2$ = Cl, Z = O, $R^3$ = 4-OCF$_3$ |
| 341 | $R^2$ = Cl, Z = O, $R^3$ = 4-CF$_3$ |
| 342 | $R^2$ = Cl, Z = O, $R^3$ = 4-CHF$_2$ |
| 343 | $R^2$ = Cl, Z = O, $R^3$ = 4-CH$_2$F |
| 344 | $R^2$ = Cl, Z = O, $R^3$ = 4-CHO |
| 345 | $R^2$ = Cl, Z = O, $R^3$ = 4-Me |
| 346 | $R^2$ = Cl, Z = O, $R^3$ = 4-Et |
| 347 | $R^2$ = Cl, Z = O, $R^3$ = 4-Ethynyl |
| 348 | $R^2$ = Cl, Z = O, $R^3$ = 4-Ethenyl |
| 349 | $R^2$ = Cl, Z = O, $R^3$ = 4-SO$_2$Me |
| 350 | $R^2$ = Cl, Z = O, $R^3$ = 4-OAc |
| 351 | $R^2$ = Cl, Z = O, $R^3$ = 4-c-Pr |
| 352 | $R^2$ = Cl, Z = O, $R^3$ = 4-i-Pr |
| 353 | $R^2$ = Cl, Z = O, $R^3$ = 4-Ph |
| 354 | $R^2$ = Cl, Z = O, $R^3$ = 5-F |
| 355 | $R^2$ = Cl, Z = O, $R^3$ = 5-Cl |
| 356 | $R^2$ = Cl, Z = O, $R^3$ = 5-Br |
| 357 | $R^2$ = Cl, Z = O, $R^3$ = 5-I |
| 358 | $R^2$ = Cl, Z = O, $R^3$ = 5-CN |
| 359 | $R^2$ = Cl, Z = O, $R^3$ = 5-NO$_2$ |
| 360 | $R^2$ = Cl, Z = O, $R^3$ = 5-OMe |
| 361 | $R^2$ = Cl, Z = O, $R^3$ = 5-OCF$_3$ |
| 362 | $R^2$ = Cl, Z = O, $R^3$ = 5-CF$_3$ |
| 363 | $R^2$ = Cl, Z = O, $R^3$ = 5-CHF$_2$ |
| 364 | $R^2$ = Cl, Z = O, $R^3$ = 5-CH$_2$F |
| 365 | $R^2$ = Cl, Z = O, $R^3$ = 5-CHO |
| 366 | $R^2$ = Cl, Z = O, $R^3$ = 5-Me |
| 367 | $R^2$ = Cl, Z = O, $R^3$ = 5-Et |
| 368 | $R^2$ = Cl, Z = O, $R^3$ = 5-Ethynyl |
| 369 | $R^2$ = Cl, Z = O, $R^3$ = 5-Ethenyl |
| 370 | $R^2$ = Cl, Z = O, $R^3$ = 5-SO$_2$Me |
| 371 | $R^2$ = Cl, Z = O, $R^3$ = 5-OAc |
| 372 | $R^2$ = Cl, Z = O, $R^3$ = 5-c-Pr |
| 373 | $R^2$ = Cl, Z = O, $R^3$ = 5-i-Pr |
| 374 | $R^2$ = Cl, Z = O, $R^3$ = 5-Ph |
| 375 | $R^2$ = Cl, Z = O, $R^3$ = 6-F |
| 376 | $R^2$ = Cl, Z = O, $R^3$ = 6-Cl |
| 377 | $R^2$ = Cl, Z = O, $R^3$ = 6-Br |
| 378 | $R^2$ = Cl, Z = O, $R^3$ = 6-I |
| 379 | $R^2$ = Cl, Z = O, $R^3$ = 6-CN |
| 380 | $R^2$ = Cl, Z = O, $R^3$ = 6-NO$_2$ |
| 381 | $R^2$ = Cl, Z = O, $R^3$ = 6-OMe |
| 382 | $R^2$ = Cl, Z = O, $R^3$ = 6-OCF$_3$ |
| 383 | $R^2$ = Cl, Z = O, $R^3$ = 6-CF$_3$ |
| 384 | $R^2$ = Cl, Z = O, $R^3$ = 6-CHF$_2$ |
| 385 | $R^2$ = Cl, Z = O, $R^3$ = 6-CH$_2$F |
| 386 | $R^2$ = Cl, Z = O, $R^3$ = 6-CHO |
| 387 | $R^2$ = Cl, Z = O, $R^3$ = 6-Me |
| 388 | $R^2$ = Cl, Z = O, $R^3$ = 6-Et |
| 389 | $R^2$ = Cl, Z = O, $R^3$ = 6-Ethynyl |
| 390 | $R^2$ = Cl, Z = O, $R^3$ = 6-Ethenyl |
| 391 | $R^2$ = Cl, Z = O, $R^3$ = 6-SO$_2$Me |
| 392 | $R^2$ = Cl, Z = O, $R^3$ = 6-OAc |
| 393 | $R^2$ = Cl, Z = O, $R^3$ = 6-c-Pr |
| 394 | $R^2$ = Cl, Z = O, $R^3$ = 6-i-Pr |
| 395 | $R^2$ = Cl, Z = O, $R^3$ = 6-Ph |
| 396 | $R^2$ = Cl, Z = O, $R^3$ = 3,4-di-F |
| 397 | $R^2$ = Cl, Z = O, $R^3$ = 3,5-di-F |
| 398 | $R^2$ = Cl, Z = O, $R^3$ = 3,6-di-F |
| 399 | $R^2$ = Cl, Z = O, $R^3$ = 4,5-di-F |
| 400 | $R^2$ = Cl, Z = O, $R^3$ = 3,4-di-Cl |
| 401 | $R^2$ = Cl, Z = O, $R^3$ = 3,5-di-Cl |
| 402 | $R^2$ = Cl, Z = O, $R^3$ = 3,6-di-Cl |
| 403 | $R^2$ = Cl, Z = O, $R^3$ = 4,5-di-Cl |
| 404 | $R^2$ = Cl, Z = O, $R^3$ = 3,4-di-Br |
| 405 | $R^2$ = Cl, Z = O, $R^3$ = 3,5-di-Br |
| 406 | $R^2$ = Cl, Z = O, $R^3$ = 3,6-di-Br |
| 407 | $R^2$ = Cl, Z = O, $R^3$ = 4,5-di-Br |
| 408 | $R^2$ = Cl, Z = O, $R^3$ = 3,4-di-CN |
| 409 | $R^2$ = Cl, Z = O, $R^3$ = 3,5-di-CN |
| 410 | $R^2$ = Cl, Z = O, $R^3$ = 3,6-di-CN |
| 411 | $R^2$ = Cl, Z = O, $R^3$ = 4,5-di-CN |
| 412 | $R^2$ = Cl, Z = O, $R^3$ = 3,4-di-Me |
| 413 | $R^2$ = Cl, Z = O, $R^3$ = 3,5-di-Me |
| 414 | $R^2$ = Cl, Z = O, $R^3$ = 3,6-di-Me |
| 415 | $R^2$ = Cl, Z = O, $R^3$ = 4,5-di-Me |
| 416 | $R^2$ = Cl, Z = O, $R^3$ = 3,4-di-OMe |
| 417 | $R^2$ = Cl, Z = O, $R^3$ = 3,5-di-OMe |
| 418 | $R^2$ = Cl, Z = O, $R^3$ = 3,6-di-OMe |
| 419 | $R^2$ = Cl, Z = O, $R^3$ = 4,5-di-OMe |
| 420 | $R^2$ = Cl, Z = O, $R^3$ = 3,4-di-CF$_3$ |
| 421 | $R^2$ = Cl, Z = O, $R^3$ = 3,5-di-CF$_3$ |
| 422 | $R^2$ = Cl, Z = O, $R^3$ = 3,6-di-CF$_3$ |
| 423 | $R^2$ = Cl, Z = O, $R^3$ = 4,5-di-CF$_3$ |
| 424 | $R^2$ = Cl, Z = O, $R^3$ = 3-CN, 4-Me |
| 425 | $R^2$ = Cl, Z = O, $R^3$ = 3-CN, 4-F |
| 426 | $R^2$ = Cl, Z = O, $R^3$ = 3-CN, 4-Br |
| 427 | $R^2$ = Cl, Z = O, $R^3$ = 3-CN, 4-OMe |
| 428 | $R^2$ = Cl, Z = O, $R^3$ = 3-CN, 4-CF$_3$ |
| 429 | $R^2$ = Cl, Z = O, $R^3$ = 3-CN, 6-Me |
| 430 | $R^2$ = Cl, Z = O, $R^3$ = 3-CN, 6-F |
| 431 | $R^2$ = Cl, Z = O, $R^3$ = 3-CN, 6-Br |
| 432 | $R^2$ = Cl, Z = O, $R^3$ = 3-CN, 6-OMe |
| 433 | $R^2$ = Cl, Z = O, $R^3$ = 3-CN, 6-CF$_3$ |
| 434 | $R^2$ = I, Z = O, $R^3$ = H (m = 0) |
| 435 | $R^2$ = I, Z = O, $R^3$ = 3-F |
| 436 | $R^2$ = I, Z = O, $R^3$ = 3-Cl |
| 437 | $R^2$ = I, Z = O, $R^3$ = 3-Br |
| 438 | $R^2$ = I, Z = O, $R^3$ = 3-I |
| 439 | $R^2$ = I, Z = O, $R^3$ = 3-CN |
| 440 | $R^2$ = I, Z = O, $R^3$ = 3-NO$_2$ |
| 441 | $R^2$ = I, Z = O, $R^3$ = 3-OMe |
| 442 | $R^2$ = I, Z = O, $R^3$ = 3-OCF$_3$ |
| 443 | $R^2$ = I, Z = O, $R^3$ = 3-CF$_3$ |
| 444 | $R^2$ = I, Z = O, $R^3$ = 3-CHF$_2$ |
| 445 | $R^2$ = I, Z = O, $R^3$ = 3-CH$_2$F |
| 446 | $R^2$ = I, Z = O, $R^3$ = 3-CHO |
| 447 | $R^2$ = I, Z = O, $R^3$ = 3-Me |
| 448 | $R^2$ = I, Z = O, $R^3$ = 3-Et |
| 449 | $R^2$ = I, Z = O, $R^3$ = 3-Ethynyl |
| 450 | $R^2$ = I, Z = O, $R^3$ = 3-Ethenyl |
| 451 | $R^2$ = I, Z = O, $R^3$ = 3-SO$_2$Me |
| 452 | $R^2$ = I, Z = O, $R^3$ = 3-OAc |
| 453 | $R^2$ = I, Z = O, $R^3$ = 3-c-Pr |
| 454 | $R^2$ = I, Z = O, $R^3$ = 3-i-Pr |
| 455 | $R^2$ = I, Z = O, $R^3$ = 3-Ph |
| 456 | $R^2$ = I, Z = S, $R^3$ = 3-F |
| 457 | $R^2$ = I, Z = S, $R^3$ = 3-Cl |
| 458 | $R^2$ = I, Z = S, $R^3$ = 3-Br |

| Table | Header Row |
|---|---|
| 459 | $R^2$ = I, Z = S, $R^3$ = 3-I |
| 460 | $R^2$ = I, Z = S, $R^3$ = 3-CN |
| 461 | $R^2$ = I, Z = S, $R^3$ = 3-$NO_2$ |
| 462 | $R^2$ = I, Z = S, $R^3$ = 3-OMe |
| 463 | $R^2$ = I, Z = S, $R^3$ = 3-$OCF_3$ |
| 464 | $R^2$ = I, Z = S, $R^3$ = 3-$CF_3$ |
| 465 | $R^2$ = I, Z = S, $R^3$ = 3-$CHF_2$ |
| 466 | $R^2$ = I, Z = S, $R^3$ = 3-$CH_2F$ |
| 467 | $R^2$ = I, Z = S, $R^3$ = 3-CHO |
| 468 | $R^2$ = I, Z = S, $R^3$ = 3-Me |
| 469 | $R^2$ = I, Z = S, $R^3$ = 3-Et |
| 470 | $R^2$ = I, Z = S, $R^3$ = 3-Ethynyl |
| 471 | $R^2$ = I, Z = S, $R^3$ = 3-Ethenyl |
| 472 | $R^2$ = I, Z = S, $R^3$ = 3-$SO_2Me$ |
| 473 | $R^2$ = I, Z = S, $R^3$ = 3-OAc |
| 474 | $R^2$ = I, Z = S, $R^3$ = 3-c-Pr |
| 475 | $R^2$ = I, Z = S, $R^3$ = 3-i-Pr |
| 476 | $R^2$ = I, Z = S, $R^3$ = 3-Ph |
| 477 | $R^2$ = I, Z = O, $R^3$ = 4-F |
| 478 | $R^2$ = I, Z = O, $R^3$ = 4-Cl |
| 479 | $R^2$ = I, Z = O, $R^3$ = 4-Br |
| 480 | $R^2$ = I, Z = O, $R^3$ = 4-I |
| 481 | $R^2$ = I, Z = O, $R^3$ = 4-CN |
| 482 | $R^2$ = I, Z = O, $R^3$ = 4-$NO_2$ |
| 483 | $R^2$ = I, Z = O, $R^3$ = 4-OMe |
| 484 | $R^2$ = I, Z = O, $R^3$ = 4-$OCF_3$ |
| 485 | $R^2$ = I, Z = O, $R^3$ = 4-$CF_3$ |
| 486 | $R^2$ = I, Z = O, $R^3$ = 4-$CHF_2$ |
| 487 | $R^2$ = I, Z = O, $R^3$ = 4-$CH_2F$ |
| 488 | $R^2$ = I, Z = O, $R^3$ = 4-CHO |
| 489 | $R^2$ = I, Z = O, $R^3$ = 4-Me |
| 490 | $R^2$ = I, Z = O, $R^3$ = 4-Et |
| 491 | $R^2$ = I, Z = O, $R^3$ = 4-Ethynyl |
| 492 | $R^2$ = I, Z = O, $R^3$ = 4-Ethenyl |
| 493 | $R^2$ = I, Z = O, $R^3$ = 4-$SO_2Me$ |
| 494 | $R^2$ = I, Z = O, $R^3$ = 4-OAc |
| 495 | $R^2$ = I, Z = O, $R^3$ = 4-c-Pr |
| 496 | $R^2$ = I, Z = O, $R^3$ = 4-i-Pr |
| 497 | $R^2$ = I, Z = O, $R^3$ = 4-Ph |
| 498 | $R^2$ = I, Z = O, $R^3$ = 5-F |
| 499 | $R^2$ = I, Z = O, $R^3$ = 5-Cl |
| 500 | $R^2$ = I, Z = O, $R^3$ = 5-Br |
| 501 | $R^2$ = I, Z = O, $R^3$ = 5-I |
| 502 | $R^2$ = I, Z = O, $R^3$ = 5-CN |
| 503 | $R^2$ = I, Z = O, $R^3$ = 5-$NO_2$ |
| 504 | $R^2$ = I, Z = O, $R^3$ = 5-OMe |
| 505 | $R^2$ = I, Z = O, $R^3$ = 5-$OCF_3$ |
| 506 | $R^2$ = I, Z = O, $R^3$ = 5-$CF_3$ |
| 507 | $R^2$ = I, Z = O, $R^3$ = 5-$CHF_2$ |
| 508 | $R^2$ = I, Z = O, $R^3$ = 5-$CH_2F$ |
| 509 | $R^2$ = I, Z = O, $R^3$ = 5-CHO |
| 510 | $R^2$ = I, Z = O, $R^3$ = 5-Me |
| 511 | $R^2$ = I, Z = O, $R^3$ = 5-Et |
| 512 | $R^2$ = I, Z = O, $R^3$ = 5-Ethynyl |
| 513 | $R^2$ = I, Z = O, $R^3$ = 5-Ethenyl |
| 514 | $R^2$ = I, Z = O, $R^3$ = 5-$SO_2Me$ |
| 515 | $R^2$ = I, Z = O, $R^3$ = 5-OAc |
| 516 | $R^2$ = I, Z = O, $R^3$ = 5-c-Pr |
| 517 | $R^2$ = I, Z = O, $R^3$ = 5-i-Pr |
| 518 | $R^2$ = I, Z = O, $R^3$ = 5-Ph |
| 519 | $R^2$ = I, Z = O, $R^3$ = 6-F |
| 520 | $R^2$ = I, Z = O, $R^3$ = 6-Cl |
| 521 | $R^2$ = I, Z = O, $R^3$ = 6-Br |
| 522 | $R^2$ = I, Z = O, $R^3$ = 6-I |
| 523 | $R^2$ = I, Z = O, $R^3$ = 6-CN |
| 524 | $R^2$ = I, Z = O, $R^3$ = 6-$NO_2$ |
| 525 | $R^2$ = I, Z = O, $R^3$ = 6-OMe |
| 526 | $R^2$ = I, Z = O, $R^3$ = 6-$OCF_3$ |
| 527 | $R^2$ = I, Z = O, $R^3$ = 6-$CF_3$ |
| 528 | $R^2$ = I, Z = O, $R^3$ = 6-$CHF_2$ |
| 529 | $R^2$ = I, Z = O, $R^3$ = 6-$CH_2F$ |
| 530 | $R^2$ = I, Z = O, $R^3$ = 6-CHO |
| 531 | $R^2$ = I, Z = O, $R^3$ = 6-Me |
| 532 | $R^2$ = I, Z = O, $R^3$ = 6-Et |
| 533 | $R^2$ = I, Z = O, $R^3$ = 6-Ethynyl |
| 534 | $R^2$ = I, Z = O, $R^3$ = 6-Ethenyl |
| 535 | $R^2$ = I, Z = O, $R^3$ = 6-$SO_2Me$ |
| 536 | $R^2$ = I, Z = O, $R^3$ = 6-OAc |
| 537 | $R^2$ = I, Z = O, $R^3$ = 6-c-Pr |
| 538 | $R^2$ = I, Z = O, $R^3$ = 6-i-Pr |
| 539 | $R^2$ = I, Z = O, $R^3$ = 6-Ph |
| 540 | $R^2$ = I, Z = O, $R^3$ = 3,4-di-F |
| 541 | $R^2$ = I, Z = O, $R^3$ = 3,5-di-F |
| 542 | $R^2$ = I, Z = O, $R^3$ = 3,6-di-F |
| 543 | $R^2$ = I, Z = O, $R^3$ = 4,5-di-F |
| 544 | $R^2$ = I, Z = O, $R^3$ = 3,4-di-Cl |
| 545 | $R^2$ = I, Z = O, $R^3$ = 3,5-di-Cl |
| 546 | $R^2$ = I, Z = O, $R^3$ = 3,6-di-Cl |
| 547 | $R^2$ = I, Z = O, $R^3$ = 4,5-di-Cl |
| 548 | $R^2$ = I, Z = O, $R^3$ = 3,4-di-Br |
| 549 | $R^2$ = I, Z = O, $R^3$ = 3,5-di-Br |
| 550 | $R^2$ = I, Z = O, $R^3$ = 3,6-di-Br |
| 551 | $R^2$ = I, Z = O, $R^3$ = 4,5-di-Br |
| 552 | $R^2$ = I, Z = O, $R^3$ = 3,4-di-CN |
| 553 | $R^2$ = I, Z = O, $R^3$ = 3,5-di-CN |
| 554 | $R^2$ = I, Z = O, $R^3$ = 3,6-di-CN |
| 555 | $R^2$ = I, Z = O, $R^3$ = 4,5-di-CN |
| 556 | $R^2$ = I, Z = O, $R^3$ = 3,4-di-Me |
| 557 | $R^2$ = I, Z = O, $R^3$ = 3,5-di-Me |
| 558 | $R^2$ = I, Z = O, $R^3$ = 3,6-di-Me |
| 559 | $R^2$ = I, Z = O, $R^3$ = 4,5-di-Me |
| 560 | $R^2$ = I, Z = O, $R^3$ = 3,4-di-OMe |
| 561 | $R^2$ = I, Z = O, $R^3$ = 3,5-di-OMe |
| 562 | $R^2$ = I, Z = O, $R^3$ = 3,6-di-OMe |
| 563 | $R^2$ = I, Z = O, $R^3$ = 4,5-di-OMe |
| 564 | $R^2$ = I, Z = O, $R^3$ = 3,4-di-$CF_3$ |
| 565 | $R^2$ = I, Z = O, $R^3$ = 3,5-di-$CF_3$ |
| 566 | $R^2$ = I, Z = O, $R^3$ = 3,6-di-$CF_3$ |
| 567 | $R^2$ = I, Z = O, $R^3$ = 4,5-di-$CF_3$ |
| 568 | $R^2$ = I, Z = O, $R^3$ = 3-CN, 4-Me |
| 569 | $R^2$ = I, Z = O, $R^3$ = 3-CN, 4-F |
| 570 | $R^2$ = I, Z = O, $R^3$ = 3-CN, 4-Br |
| 571 | $R^2$ = I, Z = O, $R^3$ = 3-CN, 4-OMe |
| 572 | $R^2$ = I, Z = O, $R^3$ = 3-CN, 4-$CF_3$ |
| 573 | $R^2$ = I, Z = O, $R^3$ = 3-CN, 6-Me |
| 574 | $R^2$ = I, Z = O, $R^3$ = 3-CN, 6-F |
| 575 | $R^2$ = I, Z = O, $R^3$ = 3-CN, 6-Br |
| 576 | $R^2$ = I, Z = O, $R^3$ = 3-CN, 6-OMe |
| 577 | $R^2$ = I, Z = O, $R^3$ = 3-CN, 6-$CF_3$ |
| 578 | $R^2$ = Me, Z = O, $R^3$ = H (m = 0) |
| 579 | $R^2$ = Me, Z = O, $R^3$ = 3-F |
| 580 | $R^2$ = Me, Z = O, $R^3$ = 3-Cl |
| 581 | $R^2$ = Me, Z = O, $R^3$ = 3-Br |
| 582 | $R^2$ = Me, Z = O, $R^3$ = 3-I |
| 583 | $R^2$ = Me, Z = O, $R^3$ = 3-CN |
| 584 | $R^2$ = Me, Z = O, $R^3$ = 3-$NO_2$ |
| 585 | $R^2$ = Me, Z = O, $R^3$ = 3-OMe |
| 586 | $R^2$ = Me, Z = O, $R^3$ = 3-$OCF_3$ |
| 587 | $R^2$ = Me, Z = O, $R^3$ = 3-$CF_3$ |
| 588 | $R^2$ = Me, Z = O, $R^3$ = 3-$CHF_2$ |
| 589 | $R^2$ = Me, Z = O, $R^3$ = 3-$CH_2F$ |
| 590 | $R^2$ = Me, Z = O, $R^3$ = 3-CHO |
| 591 | $R^2$ = Me, Z = O, $R^3$ = 3-Me |
| 592 | $R^2$ = Me, Z = O, $R^3$ = 3-Et |
| 593 | $R^2$ = Me, Z = O, $R^3$ = 3-Ethynyl |
| 594 | $R^2$ = Me, Z = O, $R^3$ = 3-Ethenyl |
| 595 | $R^2$ = Me, Z = O, $R^3$ = 3-$SO_2Me$ |
| 596 | $R^2$ = Me, Z = O, $R^3$ = 3-OAc |
| 597 | $R^2$ = Me, Z = O, $R^3$ = 3-c-Pr |
| 598 | $R^2$ = Me, Z = O, $R^3$ = 3-i-Pr |
| 599 | $R^2$ = Me, Z = O, $R^3$ = 3-Ph |
| 600 | $R^2$ = Me, Z = S, $R^3$ = 3-F |
| 601 | $R^2$ = Me, Z = S, $R^3$ = 3-Cl |
| 602 | $R^2$ = Me, Z = S, $R^3$ = 3-Br |
| 603 | $R^2$ = Me, Z = S, $R^3$ = 3-I |
| 604 | $R^2$ = Me, Z = S, $R^3$ = 3-CN |
| 605 | $R^2$ = Me, Z = S, $R^3$ = 3-$NO_2$ |
| 606 | $R^2$ = Me, Z = S, $R^3$ = 3-OMe |
| 607 | $R^2$ = Me, Z = S, $R^3$ = 3-$OCF_3$ |
| 608 | $R^2$ = Me, Z = S, $R^3$ = 3-$CF_3$ |
| 609 | $R^2$ = Me, Z = S, $R^3$ = 3-$CHF_2$ |
| 610 | $R^2$ = Me, Z = S, $R^3$ = 3-$CH_2F$ |
| 611 | $R^2$ = Me, Z = S, $R^3$ = 3-CHO |
| 612 | $R^2$ = Me, Z = S, $R^3$ = 3-Me |

-continued

| Table | Header Row |
|---|---|
| 613 | $R^2$ = Me, Z = S, $R^3$ = 3-Et |
| 614 | $R^2$ = Me, Z = S, $R^3$ = 3-Ethynyl |
| 615 | $R^2$ = Me, Z = S, $R^3$ = 3-Ethenyl |
| 616 | $R^2$ = Me, Z = S, $R^3$ = 3-SO$_2$Me |
| 617 | $R^2$ = Me, Z = S, $R^3$ = 3-OAc |
| 618 | $R^2$ = Me, Z = S, $R^3$ = 3-c-Pr |
| 619 | $R^2$ = Me, Z = S, $R^3$ = 3-i-Pr |
| 620 | $R^2$ = Me, Z = S, $R^3$ = 3-Ph |
| 621 | $R^2$ = Me, Z = O, $R^3$ = 4-F |
| 622 | $R^2$ = Me, Z = O, $R^3$ = 4-Cl |
| 623 | $R^2$ = Me, Z = O, $R^3$ = 4-Br |
| 624 | $R^2$ = Me, Z = O, $R^3$ = 4-I |
| 625 | $R^2$ = Me, Z = O, $R^3$ = 4-CN |
| 626 | $R^2$ = Me, Z = O, $R^3$ = 4-NO$_2$ |
| 627 | $R^2$ = Me, Z = O, $R^3$ = 4-OMe |
| 628 | $R^2$ = Me, Z = O, $R^3$ = 4-OCF$_3$ |
| 629 | $R^2$ = Me, Z = O, $R^3$ = 4-CF$_3$ |
| 630 | $R^2$ = Me, Z = O, $R^3$ = 4-CHF$_2$ |
| 631 | $R^2$ = Me, Z = O, $R^3$ = 4-CH$_2$F |
| 632 | $R^2$ = Me, Z = O, $R^3$ = 4-CHO |
| 633 | $R^2$ = Me, Z = O, $R^3$ = 4-Me |
| 634 | $R^2$ = Me, Z = O, $R^3$ = 4-Et |
| 635 | $R^2$ = Me, Z = O, $R^3$ = 4-Ethynyl |
| 636 | $R^2$ = Me, Z = O, $R^3$ = 4-Ethenyl |
| 637 | $R^2$ = Me, Z = O, $R^3$ = 4-SO$_2$Me |
| 638 | $R^2$ = Me, Z = O, $R^3$ = 4-OAc |
| 639 | $R^2$ = Me, Z = O, $R^3$ = 4-c-Pr |
| 640 | $R^2$ = Me, Z = O, $R^3$ = 4-i-Pr |
| 641 | $R^2$ = Me, Z = O, $R^3$ = 4-Ph |
| 642 | $R^2$ = Me, Z = O, $R^3$ = 5-F |
| 643 | $R^2$ = Me, Z = O, $R^3$ = 5-Cl |
| 644 | $R^2$ = Me, Z = O, $R^3$ = 5-Br |
| 645 | $R^2$ = Me, Z = O, $R^3$ = 5-I |
| 646 | $R^2$ = Me, Z = O, $R^3$ = 5-CN |
| 647 | $R^2$ = Me, Z = O, $R^3$ = 5-NO$_2$ |
| 648 | $R^2$ = Me, Z = O, $R^3$ = 5-OMe |
| 649 | $R^2$ = Me, Z = O, $R^3$ = 5-OCF$_3$ |
| 650 | $R^2$ = Me, Z = O, $R^3$ = 5-CF$_3$ |
| 651 | $R^2$ = Me, Z = O, $R^3$ = 5-CHF$_2$ |
| 652 | $R^2$ = Me, Z = O, $R^3$ = 5-CH$_2$F |
| 653 | $R^2$ = Me, Z = O, $R^3$ = 5-CHO |
| 654 | $R^2$ = Me, Z = O, $R^3$ = 5-Me |
| 655 | $R^2$ = Me, Z = O, $R^3$ = 5-Et |
| 656 | $R^2$ = Me, Z = O, $R^3$ = 5-Ethynyl |
| 657 | $R^2$ = Me, Z = O, $R^3$ = 5-Ethenyl |
| 658 | $R^2$ = Me, Z = O, $R^3$ = 5-SO$_2$Me |
| 659 | $R^2$ = Me, Z = O, $R^3$ = 5-OAc |
| 660 | $R^2$ = Me, Z = O, $R^3$ = 5-c-Pr |
| 661 | $R^2$ = Me, Z = O, $R^3$ = 5-i-Pr |
| 662 | $R^2$ = Me, Z = O, $R^3$ = 5-Ph |
| 663 | $R^2$ = Me, Z = O, $R^3$ = 6-F |
| 664 | $R^2$ = Me, Z = O, $R^3$ = 6-Cl |
| 665 | $R^2$ = Me, Z = O, $R^3$ = 6-Br |
| 666 | $R^2$ = Me, Z = O, $R^3$ = 6-I |
| 667 | $R^2$ = Me, Z = O, $R^3$ = 6-CN |
| 668 | $R^2$ = Me, Z = O, $R^3$ = 6-NO$_2$ |
| 669 | $R^2$ = Me, Z = O, $R^3$ = 6-OMe |
| 670 | $R^2$ = Me, Z = O, $R^3$ = 6-OCF$_3$ |
| 671 | $R^2$ = Me, Z = O, $R^3$ = 6-CF$_3$ |
| 672 | $R^2$ = Me, Z = O, $R^3$ = 6-CHF$_2$ |
| 673 | $R^2$ = Me, Z = O, $R^3$ = 6-CH$_2$F |
| 674 | $R^2$ = Me, Z = O, $R^3$ = 6-CHO |
| 675 | $R^2$ = Me, Z = O, $R^3$ = 6-Me |
| 676 | $R^2$ = Me, Z = O, $R^3$ = 6-Et |
| 677 | $R^2$ = Me, Z = O, $R^3$ = 6-Ethynyl |
| 678 | $R^2$ = Me, Z = O, $R^3$ = 6-Ethenyl |
| 679 | $R^2$ = Me, Z = O, $R^3$ = 6-SO$_2$Me |
| 680 | $R^2$ = Me, Z = O, $R^3$ = 6-OAc |
| 681 | $R^2$ = Me, Z = O, $R^3$ = 6-c-Pr |
| 682 | $R^2$ = Me, Z = O, $R^3$ = 6-i-Pr |
| 683 | $R^2$ = Me, Z = O, $R^3$ = 6-Ph |
| 684 | $R^2$ = Me, Z = O, $R^3$ = 3,4-di-F |
| 685 | $R^2$ = Me, Z = O, $R^3$ = 3,5-di-F |
| 686 | $R^2$ = Me, Z = O, $R^3$ = 3,6-di-F |
| 687 | $R^2$ = Me, Z = O, $R^3$ = 4,5-di-F |
| 688 | $R^2$ = Me, Z = O, $R^3$ = 3,4-di-Cl |
| 689 | $R^2$ = Me, Z = O, $R^3$ = 3,5-di-Cl |

-continued

| Table | Header Row |
|---|---|
| 690 | $R^2$ = Me, Z = O, $R^3$ = 3,6-di-Cl |
| 691 | $R^2$ = Me, Z = O, $R^3$ = 4,5-di-Cl |
| 692 | $R^2$ = Me, Z = O, $R^3$ = 3,4-di-Br |
| 693 | $R^2$ = Me, Z = O, $R^3$ = 3,5-di-Br |
| 694 | $R^2$ = Me, Z = O, $R^3$ = 3,6-di-Br |
| 695 | $R^2$ = Me, Z = O, $R^3$ = 4,5-di-Br |
| 696 | $R^2$ = Me, Z = O, $R^3$ = 3,4-di-CN |
| 697 | $R^2$ = Me, Z = O, $R^3$ = 3,5-di-CN |
| 698 | $R^2$ = Me, Z = O, $R^3$ = 3,6-di-CN |
| 699 | $R^2$ = Me, Z = O, $R^3$ = 4,5-di-CN |
| 700 | $R^2$ = Me, Z = O, $R^3$ = 3,4-di-Me |
| 701 | $R^2$ = Me, Z = O, $R^3$ = 3,5-di-Me |
| 702 | $R^2$ = Me, Z = O, $R^3$ = 3,6-di-Me |
| 703 | $R^2$ = Me, Z = O, $R^3$ = 4,5-di-Me |
| 704 | $R^2$ = Me, Z = O, $R^3$ = 3,4-di-OMe |
| 705 | $R^2$ = Me, Z = O, $R^3$ = 3,5-di-OMe |
| 706 | $R^2$ = Me, Z = O, $R^3$ = 3,6-di-OMe |
| 707 | $R^2$ = Me, Z = O, $R^3$ = 4,5-di-OMe |
| 708 | $R^2$ = Me, Z = O, $R^3$ = 3,4-di-CF$_3$ |
| 709 | $R^2$ = Me, Z = O, $R^3$ = 3,5-di-CF$_3$ |
| 710 | $R^2$ = Me, Z = O, $R^3$ = 3,6-di-CF$_3$ |
| 711 | $R^2$ = Me, Z = O, $R^3$ = 4,5-di-CF$_3$ |
| 712 | $R^2$ = Me, Z = O, $R^3$ = 3-CN, 4-Me |
| 713 | $R^2$ = Me, Z = O, $R^3$ = 3-CN, 4-F |
| 714 | $R^2$ = Me, Z = O, $R^3$ = 3-CN, 4-Br |
| 715 | $R^2$ = Me, Z = O, $R^3$ = 3-CN, 4-OMe |
| 716 | $R^2$ = Me, Z = O, $R^3$ = 3-CN, 4-CF$_3$ |
| 717 | $R^2$ = Me, Z = O, $R^3$ = 3-CN, 6-Me |
| 718 | $R^2$ = Me, Z = O, $R^3$ = 3-CN, 6-F |
| 719 | $R^2$ = Me, Z = O, $R^3$ = 3-CN, 6-Br |
| 720 | $R^2$ = Me, Z = O, $R^3$ = 3-CN, 6-OMe |
| 721 | $R^2$ = Me, Z = O, $R^3$ = 3-CN, 6-CF$_3$ |
| 722 | $R^2$ = CN, Z = O, $R^3$ = H (m = 0) |
| 723 | $R^2$ = CN, Z = O, $R^3$ = 3-F |
| 724 | $R^2$ = CN, Z = O, $R^3$ = 3-Cl |
| 725 | $R^2$ = CN, Z = O, $R^3$ = 3-Br |
| 726 | $R^2$ = CN, Z = O, $R^3$ = 3-I |
| 727 | $R^2$ = CN, Z = O, $R^3$ = 3-CN |
| 728 | $R^2$ = CN, Z = O, $R^3$ = 3-NO$_2$ |
| 729 | $R^2$ = CN, Z = O, $R^3$ = 3-OMe |
| 730 | $R^2$ = CN, Z = O, $R^3$ = 3-OCF$_3$ |
| 731 | $R^2$ = CN, Z = O, $R^3$ = 3-CF$_3$ |
| 732 | $R^2$ = CN, Z = O, $R^3$ = 3-CHF$_2$ |
| 733 | $R^2$ = CN, Z = O, $R^3$ = 3-CH$_2$F |
| 734 | $R^2$ = CN, Z = O, $R^3$ = 3-CHO |
| 735 | $R^2$ = CN, Z = O, $R^3$ = 3-Me |
| 736 | $R^2$ = CN, Z = O, $R^3$ = 3-Et |
| 737 | $R^2$ = CN, Z = O, $R^3$ = 3-Ethynyl |
| 738 | $R^2$ = CN, Z = O, $R^3$ = 3-Ethenyl |
| 739 | $R^2$ = CN, Z = O, $R^3$ = 3-SO$_2$Me |
| 740 | $R^2$ = CN, Z = O, $R^3$ = 3-OAc |
| 741 | $R^2$ = CN, Z = O, $R^3$ = 3-c-Pr |
| 742 | $R^2$ = CN, Z = O, $R^3$ = 3-i-Pr |
| 743 | $R^2$ = CN, Z = O, $R^3$ = 3-Ph |
| 744 | $R^2$ = CN, Z = S, $R^3$ = 3-F |
| 745 | $R^2$ = CN, Z = S, $R^3$ = 3-Cl |
| 746 | $R^2$ = CN, Z = S, $R^3$ = 3-Br |
| 747 | $R^2$ = CN, Z = S, $R^3$ = 3-I |
| 748 | $R^2$ = CN, Z = S, $R^3$ = 3-CN |
| 749 | $R^2$ = CN, Z = S, $R^3$ = 3-NO$_2$ |
| 750 | $R^2$ = CN, Z = S, $R^3$ = 3-OMe |
| 751 | $R^2$ = CN, Z = S, $R^3$ = 3-OCF$_3$ |
| 752 | $R^2$ = CN, Z = S, $R^3$ = 3-CF$_3$ |
| 753 | $R^2$ = CN, Z = S, $R^3$ = 3-CHF$_2$ |
| 754 | $R^2$ = CN, Z = S, $R^3$ = 3-CH$_2$F |
| 755 | $R^2$ = CN, Z = S, $R^3$ = 3-CHO |
| 756 | $R^2$ = CN, Z = S, $R^3$ = 3-Me |
| 757 | $R^2$ = CN, Z = S, $R^3$ = 3-Et |
| 758 | $R^2$ = CN, Z = S, $R^3$ = 3-Ethynyl |
| 759 | $R^2$ = CN, Z = S, $R^3$ = 3-Ethenyl |
| 760 | $R^2$ = CN, Z = S, $R^3$ = 3-SO$_2$Me |
| 761 | $R^2$ = CN, Z = S, $R^3$ = 3-OAc |
| 762 | $R^2$ = CN, Z = S, $R^3$ = 3-c-Pr |
| 763 | $R^2$ = CN, Z = S, $R^3$ = 3-i-Pr |
| 764 | $R^2$ = CN, Z = S, $R^3$ = 3-Ph |
| 765 | $R^2$ = CN, Z = O, $R^3$ = 4-F |
| 766 | $R^2$ = CN, Z = O, $R^3$ = 4-Cl |

| Table | Header Row |
|---|---|
| 767 | $R^2$ = CN, Z = O, $R^3$ = 4-Br |
| 768 | $R^2$ = CN, Z = O, $R^3$ = 4-I |
| 769 | $R^2$ = CN, Z = O, $R^3$ = 4-CN |
| 770 | $R^2$ = CN, Z = O, $R^3$ = 4-NO$_2$ |
| 771 | $R^2$ = CN, Z = O, $R^3$ = 4-OMe |
| 772 | $R^2$ = CN, Z = O, $R^3$ = 4-OCF$_3$ |
| 773 | $R^2$ = CN, Z = O, $R^3$ = 4-CF$_3$ |
| 774 | $R^2$ = CN, Z = O, $R^3$ = 4-CHF$_2$ |
| 775 | $R^2$ = CN, Z = O, $R^3$ = 4-CH$_2$F |
| 776 | $R^2$ = CN, Z = O, $R^3$ = 4-CHO |
| 777 | $R^2$ = CN, Z = O, $R^3$ = 4-Me |
| 778 | $R^2$ = CN, Z = O, $R^3$ = 4-Et |
| 779 | $R^2$ = CN, Z = O, $R^3$ = 4-Ethynyl |
| 780 | $R^2$ = CN, Z = O, $R^3$ = 4-Ethenyl |
| 781 | $R^2$ = CN, Z = O, $R^3$ = 4-SO$_2$Me |
| 782 | $R^2$ = CN, Z = O, $R^3$ = 4-OAc |
| 783 | $R^2$ = CN, Z = O, $R^3$ = 4-c-Pr |
| 784 | $R^2$ = CN, Z = O, $R^3$ = 4-i-Pr |
| 785 | $R^2$ = CN, Z = O, $R^3$ = 4-Ph |
| 786 | $R^2$ = CN, Z = O, $R^3$ = 5-F |
| 787 | $R^2$ = CN, Z = O, $R^3$ = 5-Cl |
| 788 | $R^2$ = CN, Z = O, $R^3$ = 5-Br |
| 789 | $R^2$ = CN, Z = O, $R^3$ = 5-I |
| 790 | $R^2$ = CN, Z = O, $R^3$ = 5-CN |
| 791 | $R^2$ = CN, Z = O, $R^3$ = 5-NO$_2$ |
| 792 | $R^2$ = CN, Z = O, $R^3$ = 5-OMe |
| 793 | $R^2$ = CN, Z = O, $R^3$ = 5-OCF$_3$ |
| 794 | $R^2$ = CN, Z = O, $R^3$ = 5-CF$_3$ |
| 795 | $R^2$ = CN, Z = O, $R^3$ = 5-CHF$_2$ |
| 796 | $R^2$ = CN, Z = O, $R^3$ = 5-CH$_2$F |
| 797 | $R^2$ = CN, Z = O, $R^3$ = 5-CHO |
| 798 | $R^2$ = CN, Z = O, $R^3$ = 5-Me |
| 799 | $R^2$ = CN, Z = O, $R^3$ = 5-Et |
| 800 | $R^2$ = CN, Z = O, $R^3$ = 5-Ethynyl |
| 801 | $R^2$ = CN, Z = O, $R^3$ = 5-Ethenyl |
| 802 | $R^2$ = CN, Z = O, $R^3$ = 5-SO$_2$Me |
| 803 | $R^2$ = CN, Z = O, $R^3$ = 5-OAc |
| 804 | $R^2$ = CN, Z = O, $R^3$ = 5-c-Pr |
| 805 | $R^2$ = CN, Z = O, $R^3$ = 5-i-Pr |
| 806 | $R^2$ = CN, Z = O, $R^3$ = 5-Ph |
| 807 | $R^2$ = CN, Z = O, $R^3$ = 6-F |
| 808 | $R^2$ = CN, Z = O, $R^3$ = 6-Cl |
| 809 | $R^2$ = CN, Z = O, $R^3$ = 6-Br |
| 810 | $R^2$ = CN, Z = O, $R^3$ = 6-I |
| 811 | $R^2$ = CN, Z = O, $R^3$ = 6-CN |
| 812 | $R^2$ = CN, Z = O, $R^3$ = 6-NO$_2$ |
| 813 | $R^2$ = CN, Z = O, $R^3$ = 6-OMe |
| 814 | $R^2$ = CN, Z = O, $R^3$ = 6-OCF$_3$ |
| 815 | $R^2$ = CN, Z = O, $R^3$ = 6-CF$_3$ |
| 816 | $R^2$ = CN, Z = O, $R^3$ = 6-CHF$_2$ |
| 817 | $R^2$ = CN, Z = O, $R^3$ = 6-CH$_2$F |
| 818 | $R^2$ = CN, Z = O, $R^3$ = 6-CHO |
| 819 | $R^2$ = CN, Z = O, $R^3$ = 6-Me |
| 820 | $R^2$ = CN, Z = O, $R^3$ = 6-Et |
| 821 | $R^2$ = CN, Z = O, $R^3$ = 6-Ethynyl |
| 822 | $R^2$ = CN, Z = O, $R^3$ = 6-Ethenyl |
| 823 | $R^2$ = CN, Z = O, $R^3$ = 6-SO$_2$Me |
| 824 | $R^2$ = CN, Z = O, $R^3$ = 6-OAc |
| 825 | $R^2$ = CN, Z = O, $R^3$ = 6-c-Pr |
| 826 | $R^2$ = CN, Z = O, $R^3$ = 6-i-Pr |
| 827 | $R^2$ = CN, Z = O, $R^3$ = 6-Ph |
| 828 | $R^2$ = CN, Z = O, $R^3$ = 3,4-di-F |
| 829 | $R^2$ = CN, Z = O, $R^3$ = 3,5-di-F |
| 830 | $R^2$ = CN, Z = O, $R^3$ = 3,6-di-F |
| 831 | $R^2$ = CN, Z = O, $R^3$ = 4,5-di-F |
| 832 | $R^2$ = CN, Z = O, $R^3$ = 3,4-di-Cl |
| 833 | $R^2$ = CN, Z = O, $R^3$ = 3,5-di-Cl |
| 834 | $R^2$ = CN, Z = O, $R^3$ = 3,6-di-Cl |
| 835 | $R^2$ = CN, Z = O, $R^3$ = 4,5-di-Cl |
| 836 | $R^2$ = CN, Z = O, $R^3$ = 3,4-di-Br |
| 837 | $R^2$ = CN, Z = O, $R^3$ = 3,5-di-Br |
| 838 | $R^2$ = CN, Z = O, $R^3$ = 3,6-di-Br |
| 839 | $R^2$ = CN, Z = O, $R^3$ = 4,5-di-Br |
| 840 | $R^2$ = CN, Z = O, $R^3$ = 3,4-di-CN |
| 841 | $R^2$ = CN, Z = O, $R^3$ = 3,5-di-CN |
| 842 | $R^2$ = CN, Z = O, $R^3$ = 3,6-di-CN |
| 843 | $R^2$ = CN, Z = O, $R^3$ = 4,5-di-CN |
| 844 | $R^2$ = CN, Z = O, $R^3$ = 3,4-di-Me |
| 845 | $R^2$ = CN, Z = O, $R^3$ = 3,5-di-Me |
| 846 | $R^2$ = CN, Z = O, $R^3$ = 3,6-di-Me |
| 847 | $R^2$ = CN, Z = O, $R^3$ = 4,5-di-Me |
| 848 | $R^2$ = CN, Z = O, $R^3$ = 3,4-di-OMe |
| 849 | $R^2$ = CN, Z = O, $R^3$ = 3,5-di-OMe |
| 850 | $R^2$ = CN, Z = O, $R^3$ = 3,6-di-OMe |
| 851 | $R^2$ = CN, Z = O, $R^3$ = 4,5-di-OMe |
| 852 | $R^2$ = CN, Z = O, $R^3$ = 3,4-di-CF$_3$ |
| 853 | $R^2$ = CN, Z = O, $R^3$ = 3,5-di-CF$_3$ |
| 854 | $R^2$ = CN, Z = O, $R^3$ = 3,6-di-CF$_3$ |
| 855 | $R^2$ = CN, Z = O, $R^3$ = 4,5-di-CF$_3$ |
| 856 | $R^2$ = CN, Z = O, $R^3$ = 3-CN, 4-Me |
| 857 | $R^2$ = CN, Z = O, $R^3$ = 3-CN, 4-F |
| 858 | $R^2$ = CN, Z = O, $R^3$ = 3-CN, 4-Br |
| 859 | $R^2$ = CN, Z = O, $R^3$ = 3-CN, 4-OMe |
| 860 | $R^2$ = CN, Z = O, $R^3$ = 3-CN, 4-CF$_3$ |
| 861 | $R^2$ = CN, Z = O, $R^3$ = 3-CN, 6-Me |
| 862 | $R^2$ = CN, Z = O, $R^3$ = 3-CN, 6-F |
| 863 | $R^2$ = CN, Z = O, $R^3$ = 3-CN, 6-Br |
| 864 | $R^2$ = CN, Z = O, $R^3$ = 3-CN, 6-OMe |
| 865 | $R^2$ = CN, Z = O, $R^3$ = 3-CN, 6-CF$_3$ |
| 866 | $R^2$ = NO$_2$, Z = O, $R^3$ = H (m = 0) |
| 867 | $R^2$ = NO$_2$, Z = O, $R^3$ = 3-F |
| 868 | $R^2$ = NO$_2$, Z = O, $R^3$ = 3-Cl |
| 869 | $R^2$ = NO$_2$, Z = O, $R^3$ = 3-Br |
| 870 | $R^2$ = NO$_2$, Z = O, $R^3$ = 3-I |
| 871 | $R^2$ = NO$_2$, Z = O, $R^3$ = 3-CN |
| 872 | $R^2$ = NO$_2$, Z = O, $R^3$ = 3-NO$_2$ |
| 873 | $R^2$ = NO$_2$, Z = O, $R^3$ = 3-OMe |
| 874 | $R^2$ = NO$_2$, Z = O, $R^3$ = 3-OCF$_3$ |
| 875 | $R^2$ = NO$_2$, Z = O, $R^3$ = 3-CF$_3$ |
| 876 | $R^2$ = NO$_2$, Z = O, $R^3$ = 3-CHF$_2$ |
| 877 | $R^2$ = NO$_2$, Z = O, $R^3$ = 3-CH$_2$F |
| 878 | $R^2$ = NO$_2$, Z = O, $R^3$ = 3-CHO |
| 879 | $R^2$ = NO$_2$, Z = O, $R^3$ = 3-Me |
| 880 | $R^2$ = NO$_2$, Z = O, $R^3$ = 3-Et |
| 881 | $R^2$ = NO$_2$, Z = O, $R^3$ = 3-Ethynyl |
| 882 | $R^2$ = NO$_2$, Z = O, $R^3$ = 3-Ethenyl |
| 883 | $R^2$ = NO$_2$, Z = O, $R^3$ = 3-SO$_2$Me |
| 884 | $R^2$ = NO$_2$, Z = O, $R^3$ = 3-OAc |
| 885 | $R^2$ = NO$_2$, Z = O, $R^3$ = 3-c-Pr |
| 886 | $R^2$ = NO$_2$, Z = O, $R^3$ = 3-i-Pr |
| 887 | $R^2$ = NO$_2$, Z = O, $R^3$ = 3-Ph |
| 888 | $R^2$ = NO$_2$, Z = S, $R^3$ = 3-F |
| 889 | $R^2$ = NO$_2$, Z = S, $R^3$ = 3-Cl |
| 890 | $R^2$ = NO$_2$, Z = S, $R^3$ = 3-Br |
| 891 | $R^2$ = NO$_2$, Z = S, $R^3$ = 3-I |
| 892 | $R^2$ = NO$_2$, Z = S, $R^3$ = 3-CN |
| 893 | $R^2$ = NO$_2$, Z = S, $R^3$ = 3-NO$_2$ |
| 894 | $R^2$ = NO$_2$, Z = S, $R^3$ = 3-OMe |
| 895 | $R^2$ = NO$_2$, Z = S, $R^3$ = 3-OCF$_3$ |
| 896 | $R^2$ = NO$_2$, Z = S, $R^3$ = 3-CF$_3$ |
| 897 | $R^2$ = NO$_2$, Z = S, $R^3$ = 3-CHF$_2$ |
| 898 | $R^2$ = NO$_2$, Z = S, $R^3$ = 3-CH$_2$F |
| 899 | $R^2$ = NO$_2$, Z = S, $R^3$ = 3-CHO |
| 900 | $R^2$ = NO$_2$, Z = S, $R^3$ = 3-Me |
| 901 | $R^2$ = NO$_2$, Z = S, $R^3$ = 3-Et |
| 902 | $R^2$ = NO$_2$, Z = S, $R^3$ = 3-Ethynyl |
| 903 | $R^2$ = NO$_2$, Z = S, $R^3$ = 3-Ethenyl |
| 904 | $R^2$ = NO$_2$, Z = S, $R^3$ = 3-SO$_2$Me |
| 905 | $R^2$ = NO$_2$, Z = S, $R^3$ = 3-OAc |
| 906 | $R^2$ = NO$_2$, Z = S, $R^3$ = 3-c-Pr |
| 907 | $R^2$ = NO$_2$, Z = S, $R^3$ = 3-i-Pr |
| 908 | $R^2$ = NO$_2$, Z = S, $R^3$ = 3-Ph |
| 909 | $R^2$ = NO$_2$, Z = O, $R^3$ = 4-F |
| 910 | $R^2$ = NO$_2$, Z = O, $R^3$ = 4-Cl |
| 911 | $R^2$ = NO$_2$, Z = O, $R^3$ = 4-Br |
| 912 | $R^2$ = NO$_2$, Z = O, $R^3$ = 4-I |
| 913 | $R^2$ = NO$_2$, Z = O, $R^3$ = 4-CN |
| 914 | $R^2$ = NO$_2$, Z = O, $R^3$ = 4-NO$_2$ |
| 915 | $R^2$ = NO$_2$, Z = O, $R^3$ = 4-OMe |
| 916 | $R^2$ = NO$_2$, Z = O, $R^3$ = 4-OCF$_3$ |
| 917 | $R^2$ = NO$_2$, Z = O, $R^3$ = 4-CF$_3$ |
| 918 | $R^2$ = NO$_2$, Z = O, $R^3$ = 4-CHF$_2$ |
| 919 | $R^2$ = NO$_2$, Z = O, $R^3$ = 4-CH$_2$F |
| 920 | $R^2$ = NO$_2$, Z = O, $R^3$ = 4-CHO |

| Table | Header Row |
|---|---|
| 921 | $R^2 = NO_2$, $Z = O$, $R^3 = 4$-Me |
| 922 | $R^2 = NO_2$, $Z = O$, $R^3 = 4$-Et |
| 923 | $R^2 = NO_2$, $Z = O$, $R^3 = 4$-Ethynyl |
| 924 | $R^2 = NO_2$, $Z = O$, $R^3 = 4$-Ethenyl |
| 925 | $R^2 = NO_2$, $Z = O$, $R^3 = 4$-$SO_2$Me |
| 926 | $R^2 = NO_2$, $Z = O$, $R^3 = 4$-OAc |
| 927 | $R^2 = NO_2$, $Z = O$, $R^3 = 4$-c-Pr |
| 928 | $R^2 = NO_2$, $Z = O$, $R^3 = 4$-i-Pr |
| 929 | $R^2 = NO_2$, $Z = O$, $R^3 = 4$-Ph |
| 930 | $R^2 = NO_2$, $Z = O$, $R^3 = 5$-F |
| 931 | $R^2 = NO_2$, $Z = O$, $R^3 = 5$-Cl |
| 932 | $R^2 = NO_2$, $Z = O$, $R^3 = 5$-Br |
| 933 | $R^2 = NO_2$, $Z = O$, $R^3 = 5$-I |
| 934 | $R^2 = NO_2$, $Z = O$, $R^3 = 5$-CN |
| 935 | $R^2 = NO_2$, $Z = O$, $R^3 = 5$-$NO_2$ |
| 936 | $R^2 = NO_2$, $Z = O$, $R^3 = 5$-OMe |
| 937 | $R^2 = NO_2$, $Z = O$, $R^3 = 5$-$OCF_3$ |
| 938 | $R^2 = NO_2$, $Z = O$, $R^3 = 5$-$CF_3$ |
| 939 | $R^2 = NO_2$, $Z = O$, $R^3 = 5$-$CHF_2$ |
| 940 | $R^2 = NO_2$, $Z = O$, $R^3 = 5$-$CH_2F$ |
| 941 | $R^2 = NO_2$, $Z = O$, $R^3 = 5$-CHO |
| 942 | $R^2 = NO_2$, $Z = O$, $R^3 = 5$-Me |
| 943 | $R^2 = NO_2$, $Z = O$, $R^3 = 5$-Et |
| 944 | $R^2 = NO_2$, $Z = O$, $R^3 = 5$-Ethynyl |
| 945 | $R^2 = NO_2$, $Z = O$, $R^3 = 5$-Ethenyl |
| 946 | $R^2 = NO_2$, $Z = O$, $R^3 = 5$-$SO_2$Me |
| 947 | $R^2 = NO_2$, $Z = O$, $R^3 = 5$-OAc |
| 948 | $R^2 = NO_2$, $Z = O$, $R^3 = 5$-c-Pr |
| 949 | $R^2 = NO_2$, $Z = O$, $R^3 = 5$-i-Pr |
| 950 | $R^2 = NO_2$, $Z = O$, $R^3 = 5$-Ph |
| 951 | $R^2 = NO_2$, $Z = O$, $R^3 = 6$-F |
| 952 | $R^2 = NO_2$, $Z = O$, $R^3 = 6$-Cl |
| 953 | $R^2 = NO_2$, $Z = O$, $R^3 = 6$-Br |
| 954 | $R^2 = NO_2$, $Z = O$, $R^3 = 6$-I |
| 955 | $R^2 = NO_2$, $Z = O$, $R^3 = 6$-CN |
| 956 | $R^2 = NO_2$, $Z = O$, $R^3 = 6$-$NO_2$ |
| 957 | $R^2 = NO_2$, $Z = O$, $R^3 = 6$-OMe |
| 958 | $R^2 = NO_2$, $Z = O$, $R^3 = 6$-$OCF_3$ |
| 959 | $R^2 = NO_2$, $Z = O$, $R^3 = 6$-$CF_3$ |
| 960 | $R^2 = NO_2$, $Z = O$, $R^3 = 6$-$CHF_2$ |
| 961 | $R^2 = NO_2$, $Z = O$, $R^3 = 6$-$CH_2F$ |
| 962 | $R^2 = NO_2$, $Z = O$, $R^3 = 6$-CHO |
| 963 | $R^2 = NO_2$, $Z = O$, $R^3 = 6$-Me |
| 964 | $R^2 = NO_2$, $Z = O$, $R^3 = 6$-Et |
| 965 | $R^2 = NO_2$, $Z = O$, $R^3 = 6$-Ethynyl |
| 966 | $R^2 = NO_2$, $Z = O$, $R^3 = 6$-Ethenyl |
| 967 | $R^2 = NO_2$, $Z = O$, $R^3 = 6$-$SO_2$Me |
| 968 | $R^2 = NO_2$, $Z = O$, $R^3 = 6$-OAc |
| 969 | $R^2 = NO_2$, $Z = O$, $R^3 = 6$-c-Pr |
| 970 | $R^2 = NO_2$, $Z = O$, $R^3 = 6$-i-Pr |
| 971 | $R^2 = NO_2$, $Z = O$, $R^3 = 6$-Ph |
| 972 | $R^2 = NO_2$, $Z = O$, $R^3 = 3,4$-di-F |
| 973 | $R^2 = NO_2$, $Z = O$, $R^3 = 3,5$-di-F |
| 974 | $R^2 = NO_2$, $Z = O$, $R^3 = 3,6$-di-F |
| 975 | $R^2 = NO_2$, $Z = O$, $R^3 = 4,5$-di-F |
| 976 | $R^2 = NO_2$, $Z = O$, $R^3 = 3,4$-di-Cl |
| 977 | $R^2 = NO_2$, $Z = O$, $R^3 = 3,5$-di-Cl |
| 978 | $R^2 = NO_2$, $Z = O$, $R^3 = 3,6$-di-Cl |
| 979 | $R^2 = NO_2$, $Z = O$, $R^3 = 4,5$-di-Cl |
| 980 | $R^2 = NO_2$, $Z = O$, $R^3 = 3,4$-di-Br |
| 981 | $R^2 = NO_2$, $Z = O$, $R^3 = 3,5$-di-Br |
| 982 | $R^2 = NO_2$, $Z = O$, $R^3 = 3,6$-di-Br |
| 983 | $R^2 = NO_2$, $Z = O$, $R^3 = 4,5$-di-Br |
| 984 | $R^2 = NO_2$, $Z = O$, $R^3 = 3,4$-di-CN |
| 985 | $R^2 = NO_2$, $Z = O$, $R^3 = 3,5$-di-CN |
| 986 | $R^2 = NO_2$, $Z = O$, $R^3 = 3,6$-di-CN |
| 987 | $R^2 = NO_2$, $Z = O$, $R^3 = 4,5$-di-CN |
| 988 | $R^2 = NO_2$, $Z = O$, $R^3 = 3,4$-di-Me |
| 989 | $R^2 = NO_2$, $Z = O$, $R^3 = 3,5$-di-Me |
| 990 | $R^2 = NO_2$, $Z = O$, $R^3 = 3,6$-di-Me |
| 991 | $R^2 = NO_2$, $Z = O$, $R^3 = 4,5$-di-Me |
| 992 | $R^2 = NO_2$, $Z = O$, $R^3 = 3,4$-di-OMe |
| 993 | $R^2 = NO_2$, $Z = O$, $R^3 = 3,5$-di-OMe |
| 994 | $R^2 = NO_2$, $Z = O$, $R^3 = 3,6$-di-OMe |
| 995 | $R^2 = NO_2$, $Z = O$, $R^3 = 4,5$-di-OMe |
| 996 | $R^2 = NO_2$, $Z = O$, $R^3 = 3,4$-di-$CF_3$ |
| 997 | $R^2 = NO_2$, $Z = O$, $R^3 = 3,5$-di-$CF_3$ |
| 998 | $R^2 = NO_2$, $Z = O$, $R^3 = 3,6$-di-$CF_3$ |
| 999 | $R^2 = NO_2$, $Z = O$, $R^3 = 4,5$-di-$CF_3$ |
| 1000 | $R^2 = NO_2$, $Z = O$, $R^3 = 3$-CN, $4$-Me |
| 1001 | $R^2 = NO_2$, $Z = O$, $R^3 = 3$-CN, $4$-F |
| 1002 | $R^2 = NO_2$, $Z = O$, $R^3 = 3$-CN, $4$-Br |
| 1003 | $R^2 = NO_2$, $Z = O$, $R^3 = 3$-CN, $4$-OMe |
| 1004 | $R^2 = NO_2$, $Z = O$, $R^3 = 3$-CN, $4$-$CF_3$ |
| 1005 | $R^2 = NO_2$, $Z = O$, $R^3 = 3$-CN, $6$-Me |
| 1006 | $R^2 = NO_2$, $Z = O$, $R^3 = 3$-CN, $6$-F |
| 1007 | $R^2 = NO_2$, $Z = O$, $R^3 = 3$-CN, $6$-Br |
| 1008 | $R^2 = NO_2$, $Z = O$, $R^3 = 3$-CN, $6$-OMe |
| 1009 | $R^2 = NO_2$, $Z = O$, $R^3 = 3$-CN, $6$-$CF_3$ |
| 1010 | $R^2 = $ OMe, $Z = O$, $R^3 = H$ (m = 0) |
| 1011 | $R^2 = $ OMe, $Z = O$, $R^3 = 3$-F |
| 1012 | $R^2 = $ OMe, $Z = O$, $R^3 = 3$-Cl |
| 1013 | $R^2 = $ OMe, $Z = O$, $R^3 = 3$-Br |
| 1014 | $R^2 = $ OMe, $Z = O$, $R^3 = 3$-I |
| 1015 | $R^2 = $ OMe, $Z = O$, $R^3 = 3$-CN |
| 1016 | $R^2 = $ OMe, $Z = O$, $R^3 = 3$-$NO_2$ |
| 1017 | $R^2 = $ OMe, $Z = O$, $R^3 = 3$-OMe |
| 1018 | $R^2 = $ OMe, $Z = O$, $R^3 = 3$-$OCF_3$ |
| 1019 | $R^2 = $ OMe, $Z = O$, $R^3 = 3$-$CF_3$ |
| 1020 | $R^2 = $ OMe, $Z = O$, $R^3 = 3$-$CHF_2$ |
| 1021 | $R^2 = $ OMe, $Z = O$, $R^3 = 3$-$CH_2F$ |
| 1022 | $R^2 = $ OMe, $Z = O$, $R^3 = 3$-CHO |
| 1023 | $R^2 = $ OMe, $Z = O$, $R^3 = 3$-Me |
| 1024 | $R^2 = $ OMe, $Z = O$, $R^3 = 3$-Et |
| 1025 | $R^2 = $ OMe, $Z = O$, $R^3 = 3$-Ethynyl |
| 1026 | $R^2 = $ OMe, $Z = O$, $R^3 = 3$-Ethenyl |
| 1027 | $R^2 = $ OMe, $Z = O$, $R^3 = 3$-$SO_2$Me |
| 1028 | $R^2 = $ OMe, $Z = O$, $R^3 = 3$-OAc |
| 1029 | $R^2 = $ OMe, $Z = O$, $R^3 = 3$-c-Pr |
| 1030 | $R^2 = $ OMe, $Z = O$, $R^3 = 3$-i-Pr |
| 1031 | $R^2 = $ OMe, $Z = O$, $R^3 = 3$-Ph |
| 1032 | $R^2 = $ OMe, $Z = S$, $R^3 = 3$-F |
| 1033 | $R^2 = $ OMe, $Z = S$, $R^3 = 3$-Cl |
| 1034 | $R^2 = $ OMe, $Z = S$, $R^3 = 3$-Br |
| 1035 | $R^2 = $ OMe, $Z = S$, $R^3 = 3$-I |
| 1036 | $R^2 = $ OMe, $Z = S$, $R^3 = 3$-CN |
| 1037 | $R^2 = $ OMe, $Z = S$, $R^3 = 3$-$NO_2$ |
| 1038 | $R^2 = $ OMe, $Z = S$, $R^3 = 3$-OMe |
| 1039 | $R^2 = $ OMe, $Z = S$, $R^3 = 3$-$OCF_3$ |
| 1040 | $R^2 = $ OMe, $Z = S$, $R^3 = 3$-$CF_3$ |
| 1041 | $R^2 = $ OMe, $Z = S$, $R^3 = 3$-$CHF_2$ |
| 1042 | $R^2 = $ OMe, $Z = S$, $R^3 = 3$-$CH_2F$ |
| 1043 | $R^2 = $ OMe, $Z = S$, $R^3 = 3$-CHO |
| 1044 | $R^2 = $ OMe, $Z = S$, $R^3 = 3$-Me |
| 1045 | $R^2 = $ OMe, $Z = S$, $R^3 = 3$-Et |
| 1046 | $R^2 = $ OMe, $Z = S$, $R^3 = 3$-Ethynyl |
| 1047 | $R^2 = $ OMe, $Z = S$, $R^3 = 3$-Ethenyl |
| 1048 | $R^2 = $ OMe, $Z = S$, $R^3 = 3$-$SO_2$Me |
| 1049 | $R^2 = $ OMe, $Z = S$, $R^3 = 3$-OAc |
| 1050 | $R^2 = $ OMe, $Z = S$, $R^3 = 3$-c-Pr |
| 1051 | $R^2 = $ OMe, $Z = S$, $R^3 = 3$-i-Pr |
| 1052 | $R^2 = $ OMe, $Z = S$, $R^3 = 3$-Ph |
| 1053 | $R^2 = $ OMe, $Z = O$, $R^3 = 4$-F |
| 1054 | $R^2 = $ OMe, $Z = O$, $R^3 = 4$-Cl |
| 1055 | $R^2 = $ OMe, $Z = O$, $R^3 = 4$-Br |
| 1056 | $R^2 = $ OMe, $Z = O$, $R^3 = 4$-I |
| 1057 | $R^2 = $ OMe, $Z = O$, $R^3 = 4$-CN |
| 1058 | $R^2 = $ OMe, $Z = O$, $R^3 = 4$-$NO_2$ |
| 1059 | $R^2 = $ OMe, $Z = O$, $R^3 = 4$-OMe |
| 1060 | $R^2 = $ OMe, $Z = O$, $R^3 = 4$-$OCF_3$ |
| 1061 | $R^2 = $ OMe, $Z = O$, $R^3 = 4$-$CF_3$ |
| 1062 | $R^2 = $ OMe, $Z = O$, $R^3 = 4$-$CHF_2$ |
| 1063 | $R^2 = $ OMe, $Z = O$, $R^3 = 4$-$CH_2F$ |
| 1064 | $R^2 = $ OMe, $Z = O$, $R^3 = 4$-CHO |
| 1065 | $R^2 = $ OMe, $Z = O$, $R^3 = 4$-Me |
| 1066 | $R^2 = $ OMe, $Z = O$, $R^3 = 4$-Et |
| 1067 | $R^2 = $ OMe, $Z = O$, $R^3 = 4$-Ethynyl |
| 1068 | $R^2 = $ OMe, $Z = O$, $R^3 = 4$-Ethenyl |
| 1069 | $R^2 = $ OMe, $Z = O$, $R^3 = 4$-$SO_2$Me |
| 1070 | $R^2 = $ OMe, $Z = O$, $R^3 = 4$-OAc |
| 1071 | $R^2 = $ OMe, $Z = O$, $R^3 = 4$-c-Pr |
| 1072 | $R^2 = $ OMe, $Z = O$, $R^3 = 4$-i-Pr |
| 1073 | $R^2 = $ OMe, $Z = O$, $R^3 = 4$-Ph |
| 1074 | $R^2 = $ OMe, $Z = O$, $R^3 = 5$-F |

| Table | Header Row |
|---|---|
| 1075 | $R^2$ = OMe, Z = O, $R^3$ = 5-Cl |
| 1076 | $R^2$ = OMe, Z = O, $R^3$ = 5-Br |
| 1077 | $R^2$ = OMe, Z = O, $R^3$ = 5-I |
| 1078 | $R^2$ = OMe, Z = O, $R^3$ = 5-CN |
| 1079 | $R^2$ = OMe, Z = O, $R^3$ = 5-NO$_2$ |
| 1080 | $R^2$ = OMe, Z = O, $R^3$ = 5-OMe |
| 1081 | $R^2$ = OMe, Z = O, $R^3$ = 5-OCF$_3$ |
| 1082 | $R^2$ = OMe, Z = O, $R^3$ = 5-CF$_3$ |
| 1083 | $R^2$ = OMe, Z = O, $R^3$ = 5-CHF$_2$ |
| 1084 | $R^2$ = OMe, Z = O, $R^3$ = 5-CH$_2$F |
| 1085 | $R^2$ = OMe, Z = O, $R^3$ = 5-CHO |
| 1086 | $R^2$ = OMe, Z = O, $R^3$ = 5-Me |
| 1087 | $R^2$ = OMe, Z = O, $R^3$ = 5-Et |
| 1088 | $R^2$ = OMe, Z = O, $R^3$ = 5-Ethynyl |
| 1089 | $R^2$ = OMe, Z = O, $R^3$ = 5-Ethenyl |
| 1090 | $R^2$ = OMe, Z = O, $R^3$ = 5-SO$_2$Me |
| 1091 | $R^2$ = OMe, Z = O, $R^3$ = 5-OAc |
| 1092 | $R^2$ = OMe, Z = O, $R^3$ = 5-c-Pr |
| 1093 | $R^2$ = OMe, Z = O, $R^3$ = 5-i-Pr |
| 1094 | $R^2$ = OMe, Z = O, $R^3$ = 5-Ph |
| 1095 | $R^2$ = OMe, Z = O, $R^3$ = 6-F |
| 1096 | $R^2$ = OMe, Z = O, $R^3$ = 6-Cl |
| 1097 | $R^2$ = OMe, Z = O, $R^3$ = 6-Br |
| 1098 | $R^2$ = OMe, Z = O, $R^3$ = 6-I |
| 1099 | $R^2$ = OMe, Z = O, $R^3$ = 6-CN |
| 1100 | $R^2$ = OMe, Z = O, $R^3$ = 6-NO$_2$ |
| 1101 | $R^2$ = OMe, Z = O, $R^3$ = 6-OMe |
| 1102 | $R^2$ = OMe, Z = O, $R^3$ = 6-OCF$_3$ |
| 1103 | $R^2$ = OMe, Z = O, $R^3$ = 6-CF$_3$ |
| 1104 | $R^2$ = OMe, Z = O, $R^3$ = 6-CHF$_2$ |
| 1105 | $R^2$ = OMe, Z = O, $R^3$ = 6-CH$_2$F |
| 1106 | $R^2$ = OMe, Z = O, $R^3$ = 6-CHO |
| 1107 | $R^2$ = OMe, Z = O, $R^3$ = 6-Me |
| 1108 | $R^2$ = OMe, Z = O, $R^3$ = 6-Et |
| 1109 | $R^2$ = OMe, Z = O, $R^3$ = 6-Ethynyl |
| 1110 | $R^2$ = OMe, Z = O, $R^3$ = 6-Ethenyl |
| 1111 | $R^2$ = OMe, Z = O, $R^3$ = 6-SO$_2$Me |
| 1112 | $R^2$ = OMe, Z = O, $R^3$ = 6-OAc |
| 1113 | $R^2$ = OMe, Z = O, $R^3$ = 6-c-Pr |
| 1114 | $R^2$ = OMe, Z = O, $R^3$ = 6-i-Pr |
| 1115 | $R^2$ = OMe, Z = O, $R^3$ = 6-Ph |
| 1116 | $R^2$ = OMe, Z = O, $R^3$ = 3,4-di-F |
| 1117 | $R^2$ = OMe, Z = O, $R^3$ = 3,5-di-F |
| 1118 | $R^2$ = OMe, Z = O, $R^3$ = 3,6-di-F |
| 1119 | $R^2$ = OMe, Z = O, $R^3$ = 4,5-di-F |
| 1120 | $R^2$ = OMe, Z = O, $R^3$ = 3,4-di-Cl |
| 1121 | $R^2$ = OMe, Z = O, $R^3$ = 3,5-di-Cl |
| 1122 | $R^2$ = OMe, Z = O, $R^3$ = 3,6-di-Cl |
| 1123 | $R^2$ = OMe, Z = O, $R^3$ = 4,5-di-Cl |
| 1124 | $R^2$ = OMe, Z = O, $R^3$ = 3,4-di-Br |
| 1125 | $R^2$ = OMe, Z = O, $R^3$ = 3,5-di-Br |
| 1126 | $R^2$ = OMe, Z = O, $R^3$ = 3,6-di-Br |
| 1127 | $R^2$ = OMe, Z = O, $R^3$ = 4,5-di-Br |
| 1128 | $R^2$ = OMe, Z = O, $R^3$ = 3,4-di-CN |
| 1129 | $R^2$ = OMe, Z = O, $R^3$ = 3,5-di-CN |
| 1130 | $R^2$ = OMe, Z = O, $R^3$ = 3,6-di-CN |
| 1131 | $R^2$ = OMe, Z = O, $R^3$ = 4,5-di-CN |
| 1132 | $R^2$ = OMe, Z = O, $R^3$ = 3,4-di-Me |
| 1133 | $R^2$ = OMe, Z = O, $R^3$ = 3,5-di-Me |
| 1134 | $R^2$ = OMe, Z = O, $R^3$ = 3,6-di-Me |
| 1135 | $R^2$ = OMe, Z = O, $R^3$ = 4,5-di-Me |
| 1136 | $R^2$ = OMe, Z = O, $R^3$ = 3,4-di-OMe |
| 1137 | $R^2$ = OMe, Z = O, $R^3$ = 3,5-di-OMe |
| 1138 | $R^2$ = OMe, Z = O, $R^3$ = 3,6-di-OMe |
| 1139 | $R^2$ = OMe, Z = O, $R^3$ = 4,5-di-OMe |
| 1140 | $R^2$ = OMe, Z = O, $R^3$ = 3,4-di-CF$_3$ |
| 1141 | $R^2$ = OMe, Z = O, $R^3$ = 3,5-di-CF$_3$ |
| 1142 | $R^2$ = OMe, Z = O, $R^3$ = 3,6-di-CF$_3$ |
| 1143 | $R^2$ = OMe, Z = O, $R^3$ = 4,5-di-CF$_3$ |
| 1144 | $R^2$ = OMe, Z = O, $R^3$ = 3-CN, 4-Me |
| 1145 | $R^2$ = OMe, Z = O, $R^3$ = 3-CN, 4-F |
| 1146 | $R^2$ = OMe, Z = O, $R^3$ = 3-CN, 4-Br |
| 1147 | $R^2$ = OMe, Z = O, $R^3$ = 3-CN, 4-OMe |
| 1148 | $R^2$ = OMe, Z = O, $R^3$ = 3-CN, 4-CF$_3$ |
| 1149 | $R^2$ = OMe, Z = O, $R^3$ = 3-CN, 6-Me |
| 1150 | $R^2$ = OMe, Z = O, $R^3$ = 3-CN, 6-F |
| 1151 | $R^2$ = OMe, Z = O, $R^3$ = 3-CN, 6-Br |
| 1152 | $R^2$ = OMe, Z = O, $R^3$ = 3-CN, 6-OMe |
| 1153 | $R^2$ = OMe, Z = O, $R^3$ = 3-CN, 6-CF$_3$ |
| 1154 | $R^2$ = CF$_3$, Z = O, $R^3$ = H (m = O) |
| 1155 | $R^2$ = CF$_3$, Z = O, $R^3$ = 3-F |
| 1156 | $R^2$ = CF$_3$, Z = O, $R^3$ = 3-Cl |
| 1157 | $R^2$ = CF$_3$, Z = O, $R^3$ = 3-Br |
| 1158 | $R^2$ = CF$_3$, Z = O, $R^3$ = 3-I |
| 1159 | $R^2$ = CF$_3$, Z = O, $R^3$ = 3-CN |
| 1160 | $R^2$ = CF$_3$, Z = O, $R^3$ = 3-NO$_2$ |
| 1161 | $R^2$ = CF$_3$, Z = O, $R^3$ = 3-OMe |
| 1162 | $R^2$ = CF$_3$, Z = O, $R^3$ = 3-OCF$_3$ |
| 1163 | $R^2$ = CF$_3$, Z = O, $R^3$ = 3-CF$_3$ |
| 1164 | $R^2$ = CF$_3$, Z = O, $R^3$ = 3-CHF$_2$ |
| 1165 | $R^2$ = CF$_3$, Z = O, $R^3$ = 3-CH$_2$F |
| 1166 | $R^2$ = CF$_3$, Z = O, $R^3$ = 3-CHO |
| 1167 | $R^2$ = CF$_3$, Z = O, $R^3$ = 3-Me |
| 1168 | $R^2$ = CF$_3$, Z = O, $R^3$ = 3-Et |
| 1169 | $R^2$ = CF$_3$, Z = O, $R^3$ = 3-Ethynyl |
| 1170 | $R^2$ = CF$_3$, Z = O, $R^3$ = 3-Ethenyl |
| 1171 | $R^2$ = CF$_3$, Z = O, $R^3$ = 3-SO$_2$Me |
| 1172 | $R^2$ = CF$_3$, Z = O, $R^3$ = 3-OAc |
| 1173 | $R^2$ = CF$_3$, Z = O, $R^3$ = 3-c-Pr |
| 1174 | $R^2$ = CF$_3$, Z = O, $R^3$ = 3-i-Pr |
| 1175 | $R^2$ = CF$_3$, Z = O, $R^3$ = 3-Ph |
| 1176 | $R^2$ = CF$_3$, Z = S, $R^3$ = 3-F |
| 1177 | $R^2$ = CF$_3$, Z = S, $R^3$ = 3-Cl |
| 1178 | $R^2$ = CF$_3$, Z = S, $R^3$ = 3-Br |
| 1179 | $R^2$ = CF$_3$, Z = S, $R^3$ = 3-I |
| 1180 | $R^2$ = CF$_3$, Z = S, $R^3$ = 3-CN |
| 1181 | $R^2$ = CF$_3$, Z = S, $R^3$ = 3-NO$_2$ |
| 1182 | $R^2$ = CF$_3$, Z = S, $R^3$ = 3-OMe |
| 1183 | $R^2$ = CF$_3$, Z = S, $R^3$ = 3-OCF$_3$ |
| 1184 | $R^2$ = CF$_3$, Z = S, $R^3$ = 3-CF$_3$ |
| 1185 | $R^2$ = CF$_3$, Z = S, $R^3$ = 3-CHF$_2$ |
| 1186 | $R^2$ = CF$_3$, Z = S, $R^3$ = 3-CH$_2$F |
| 1187 | $R^2$ = CF$_3$, Z = S, $R^3$ = 3-CHO |
| 1188 | $R^2$ = CF$_3$, Z = S, $R^3$ = 3-Me |
| 1189 | $R^2$ = CF$_3$, Z = S, $R^3$ = 3-Et |
| 1190 | $R^2$ = CF$_3$, Z = S, $R^3$ = 3-Ethynyl |
| 1191 | $R^2$ = CF$_3$, Z = S, $R^3$ = 3-Ethenyl |
| 1192 | $R^2$ = CF$_3$, Z = S, $R^3$ = 3-SO$_2$Me |
| 1193 | $R^2$ = CF$_3$, Z = S, $R^3$ = 3-OAc |
| 1194 | $R^2$ = CF$_3$, Z = S, $R^3$ = 3-c-Pr |
| 1195 | $R^2$ = CF$_3$, Z = S, $R^3$ = 3-i-Pr |
| 1196 | $R^2$ = CF$_3$, Z = S, $R^3$ = 3-Ph |
| 1197 | $R^2$ = CF$_3$, Z = O, $R^3$ = 4-F |
| 1198 | $R^2$ = CF$_3$, Z = O, $R^3$ = 4-Cl |
| 1199 | $R^2$ = CF$_3$, Z = O, $R^3$ = 4-Br |
| 1200 | $R^2$ = CF$_3$, Z = O, $R^3$ = 4-I |
| 1201 | $R^2$ = CF$_3$, Z = O, $R^3$ = 4-CN |
| 1202 | $R^2$ = CF$_3$, Z = O, $R^3$ = 4-NO$_2$ |
| 1203 | $R^2$ = CF$_3$, Z = O, $R^3$ = 4-OMe |
| 1204 | $R^2$ = CF$_3$, Z = O, $R^3$ = 4-OCF$_3$ |
| 1205 | $R^2$ = CF$_3$, Z = O, $R^3$ = 4-CF$_3$ |
| 1206 | $R^2$ = CF$_3$, Z = O, $R^3$ = 4-CHF$_2$ |
| 1207 | $R^2$ = CF$_3$, Z = O, $R^3$ = 4-CH$_2$F |
| 1208 | $R^2$ = CF$_3$, Z = O, $R^3$ = 4-CHO |
| 1209 | $R^2$ = CF$_3$, Z = O, $R^3$ = 4-Me |
| 1210 | $R^2$ = CF$_3$, Z = O, $R^3$ = 4-Et |
| 1211 | $R^2$ = CF$_3$, Z = O, $R^3$ = 4-Ethynyl |
| 1212 | $R^2$ = CF$_3$, Z = O, $R^3$ = 4-Ethenyl |
| 1213 | $R^2$ = CF$_3$, Z = O, $R^3$ = 4-SO$_2$Me |
| 1214 | $R^2$ = CF$_3$, Z = O, $R^3$ = 4-OAc |
| 1215 | $R^2$ = CF$_3$, Z = O, $R^3$ = 4-c-Pr |
| 1216 | $R^2$ = CF$_3$, Z = O, $R^3$ = 4-i-Pr |
| 1217 | $R^2$ = CF$_3$, Z = O, $R^3$ = 4-Ph |
| 1218 | $R^2$ = CF$_3$, Z = O, $R^3$ = 5-F |
| 1219 | $R^2$ = CF$_3$, Z = O, $R^3$ = 5-Cl |
| 1220 | $R^2$ = CF$_3$, Z = O, $R^3$ = 5-Br |
| 1221 | $R^2$ = CF$_3$, Z = O, $R^3$ = 5-I |
| 1222 | $R^2$ = CF$_3$, Z = O, $R^3$ = 5-CN |
| 1223 | $R^2$ = CF$_3$, Z = O, $R^3$ = 5-NO$_2$ |
| 1224 | $R^2$ = CF$_3$, Z = O, $R^3$ = 5-OMe |
| 1225 | $R^2$ = CF$_3$, Z = O, $R^3$ = 5-OCF$_3$ |
| 1226 | $R^2$ = CF$_3$, Z = O, $R^3$ = 5-CF$_3$ |
| 1227 | $R^2$ = CF$_3$, Z = O, $R^3$ = 5-CHF$_2$ |
| 1228 | $R^2$ = CF$_3$, Z = O, $R^3$ = 5-CH$_2$F |

| Table | Header Row |
|---|---|
| 1229 | $R^2 = CF_3, Z = O, R^3 = 5\text{-CHO}$ |
| 1230 | $R^2 = CF_3, Z = O, R^3 = 5\text{-Me}$ |
| 1231 | $R^2 = CF_3, Z = O, R^3 = 5\text{-Et}$ |
| 1232 | $R^2 = CF_3, Z = O, R^3 = 5\text{-Ethynyl}$ |
| 1233 | $R^2 = CF_3, Z = O, R^3 = 5\text{-Ethenyl}$ |
| 1234 | $R^2 = CF_3, Z = O, R^3 = 5\text{-SO}_2\text{Me}$ |
| 1235 | $R^2 = CF_3, Z = O, R^3 = 5\text{-OAc}$ |
| 1236 | $R^2 = CF_3, Z = O, R^3 = 5\text{-c-Pr}$ |
| 1237 | $R^2 = CF_3, Z = O, R^3 = 5\text{-i-Pr}$ |
| 1238 | $R^2 = CF_3, Z = O, R^3 = 5\text{-Ph}$ |
| 1239 | $R^2 = CF_3, Z = O, R^3 = 6\text{-F}$ |
| 1240 | $R^2 = CF_3, Z = O, R^3 = 6\text{-Cl}$ |
| 1241 | $R^2 = CF_3, Z = O, R^3 = 6\text{-Br}$ |
| 1242 | $R^2 = CF_3, Z = O, R^3 = 6\text{-I}$ |
| 1243 | $R^2 = CF_3, Z = O, R^3 = 6\text{-CN}$ |
| 1244 | $R^2 = CF_3, Z = O, R^3 = 6\text{-NO}_2$ |
| 1245 | $R^2 = CF_3, Z = O, R^3 = 6\text{-OMe}$ |
| 1246 | $R^2 = CF_3, Z = O, R^3 = 6\text{-OCF}_3$ |
| 1247 | $R^2 = CF_3, Z = O, R^3 = 6\text{-CF}_3$ |
| 1248 | $R^2 = CF_3, Z = O, R^3 = 6\text{-CHF}_2$ |
| 1249 | $R^2 = CF_3, Z = O, R^3 = 6\text{-CH}_2\text{F}$ |
| 1250 | $R^2 = CF_3, Z = O, R^3 = 6\text{-CHO}$ |
| 1251 | $R^2 = CF_3, Z = O, R^3 = 6\text{-Me}$ |
| 1252 | $R^2 = CF_3, Z = O, R^3 = 6\text{-Et}$ |
| 1253 | $R^2 = CF_3, Z = O, R^3 = 6\text{-Ethynyl}$ |
| 1254 | $R^2 = CF_3, Z = O, R^3 = 6\text{-Ethenyl}$ |
| 1255 | $R^2 = CF_3, Z = O, R^3 = 6\text{-SO}_2\text{Me}$ |
| 1256 | $R^2 = CF_3, Z = O, R^3 = 6\text{-OAc}$ |
| 1257 | $R^2 = CF_3, Z = O, R^3 = 6\text{-c-Pr}$ |
| 1258 | $R^2 = CF_3, Z = O, R^3 = 6\text{-i-Pr}$ |
| 1259 | $R^2 = CF_3, Z = O, R^3 = 6\text{-Ph}$ |
| 1260 | $R^2 = CF_3, Z = O, R^3 = 3,4\text{-di-F}$ |
| 1261 | $R^2 = CF_3, Z = O, R^3 = 3,5\text{-di-F}$ |
| 1262 | $R^2 = CF_3, Z = O, R^3 = 3,6\text{-di-F}$ |
| 1263 | $R^2 = CF_3, Z = O, R^3 = 4,5\text{-di-F}$ |
| 1264 | $R^2 = CF_3, Z = O, R^3 = 3,4\text{-di-Cl}$ |
| 1265 | $R^2 = CF_3, Z = O, R^3 = 3,5\text{-di-Cl}$ |
| 1266 | $R^2 = CF_3, Z = O, R^3 = 3,6\text{-di-Cl}$ |
| 1267 | $R^2 = CF_3, Z = O, R^3 = 4,5\text{-di-Cl}$ |
| 1268 | $R^2 = CF_3, Z = O, R^3 = 3,4\text{-di-Br}$ |
| 1269 | $R^2 = CF_3, Z = O, R^3 = 3,5\text{-di-Br}$ |
| 1270 | $R^2 = CF_3, Z = O, R^3 = 3,6\text{-di-Br}$ |
| 1271 | $R^2 = CF_3, Z = O, R^3 = 4,5\text{-di-Br}$ |
| 1272 | $R^2 = CF_3, Z = O, R^3 = 3,4\text{-di-CN}$ |
| 1273 | $R^2 = CF_3, Z = O, R^3 = 3,5\text{-di-CN}$ |
| 1274 | $R^2 = CF_3, Z = O, R^3 = 3,6\text{-di-CN}$ |
| 1275 | $R^2 = CF_3, Z = O, R^3 = 4,5\text{-di-CN}$ |
| 1276 | $R^2 = CF_3, Z = O, R^3 = 3,4\text{-di-Me}$ |
| 1277 | $R^2 = CF_3, Z = O, R^3 = 3,5\text{-di-Me}$ |
| 1278 | $R^2 = CF_3, Z = O, R^3 = 3,6\text{-di-Me}$ |
| 1279 | $R^2 = CF_3, Z = O, R^3 = 4,5\text{-di-Me}$ |
| 1280 | $R^2 = CF_3, Z = O, R^3 = 3,4\text{-di-OMe}$ |
| 1281 | $R^2 = CF_3, Z = O, R^3 = 3,5\text{-di-OMe}$ |
| 1282 | $R^2 = CF_3, Z = O, R^3 = 3,6\text{-di-OMe}$ |
| 1283 | $R^2 = CF_3, Z = O, R^3 = 4,5\text{-di-OMe}$ |
| 1284 | $R^2 = CF_3, Z = O, R^3 = 3,4\text{-di-CF}_3$ |
| 1285 | $R^2 = CF_3, Z = O, R^3 = 3,5\text{-di-CF}_3$ |
| 1286 | $R^2 = CF_3, Z = O, R^3 = 3,6\text{-di-CF}_3$ |
| 1287 | $R^2 = CF_3, Z = O, R^3 = 4,5\text{-di-CF}_3$ |
| 1288 | $R^2 = CF_3, Z = O, R^3 = 3\text{-CN, 4-Me}$ |
| 1289 | $R^2 = CF_3, Z = O, R^3 = 3\text{-CN, 4-F}$ |
| 1290 | $R^2 = CF_3, Z = O, R^3 = 3\text{-CN, 4-Br}$ |
| 1291 | $R^2 = CF_3, Z = O, R^3 = 3\text{-CN, 4-OMe}$ |
| 1292 | $R^2 = CF_3, Z = O, R^3 = 3\text{-CN, 4-CF}_3$ |
| 1293 | $R^2 = CF_3, Z = O, R^3 = 3\text{-CN, 6-Me}$ |
| 1294 | $R^2 = CF_3, Z = O, R^3 = 3\text{-CN, 6-F}$ |
| 1295 | $R^2 = CF_3, Z = O, R^3 = 3\text{-CN, 6-Br}$ |
| 1296 | $R^2 = CF_3, Z = O, R^3 = 3\text{-CN, 6-OMe}$ |
| 1297 | $R^2 = CF_3, Z = O, R^3 = 3\text{-CN, 6-CF}_3$ |
| 1298 | $R^2 = CHF_2, Z = O, R^3 = H\ (m = 0)$ |
| 1299 | $R^2 = CHF_2, Z = O, R^3 = 3\text{-F}$ |
| 1300 | $R^2 = CHF_2, Z = O, R^3 = 3\text{-Cl}$ |
| 1301 | $R^2 = CHF_2, Z = O, R^3 = 3\text{-Br}$ |
| 1302 | $R^2 = CHF_2, Z = O, R^3 = 3\text{-I}$ |
| 1303 | $R^2 = CHF_2, Z = O, R^3 = 3\text{-CN}$ |
| 1304 | $R^2 = CHF_2, Z = O, R^3 = 3\text{-NO}_2$ |
| 1305 | $R^2 = CHF_2, Z = O, R^3 = 3\text{-OMe}$ |
| 1306 | $R^2 = CHF_2, Z = O, R^3 = 3\text{-OCF}_3$ |
| 1307 | $R^2 = CHF_2, Z = O, R^3 = 3\text{-CF}_3$ |
| 1308 | $R^2 = CHF_2, Z = O, R^3 = 3\text{-CHF}_2$ |
| 1309 | $R^2 = CHF_2, Z = O, R^3 = 3\text{-CH}_2\text{F}$ |
| 1310 | $R^2 = CHF_2, Z = O, R^3 = 3\text{-CHO}$ |
| 1311 | $R^2 = CHF_2, Z = O, R^3 = 3\text{-Me}$ |
| 1312 | $R^2 = CHF_2, Z = O, R^3 = 3\text{-Et}$ |
| 1313 | $R^2 = CHF_2, Z = O, R^3 = 3\text{-Ethynyl}$ |
| 1314 | $R^2 = CHF_2, Z = O, R^3 = 3\text{-Ethenyl}$ |
| 1315 | $R^2 = CHF_2, Z = O, R^3 = 3\text{-SO}_2\text{Me}$ |
| 1316 | $R^2 = CHF_2, Z = O, R^3 = 3\text{-OAc}$ |
| 1317 | $R^2 = CHF_2, Z = O, R^3 = 3\text{-c-Pr}$ |
| 1318 | $R^2 = CHF_2, Z = O, R^3 = 3\text{-i-Pr}$ |
| 1319 | $R^2 = CHF_2, Z = O, R^3 = 3\text{-Ph}$ |
| 1320 | $R^2 = CHF_2, Z = S, R^3 = 3\text{-F}$ |
| 1321 | $R^2 = CHF_2, Z = S, R^3 = 3\text{-Cl}$ |
| 1322 | $R^2 = CHF_2, Z = S, R^3 = 3\text{-Br}$ |
| 1323 | $R^2 = CHF_2, Z = S, R^3 = 3\text{-I}$ |
| 1324 | $R^2 = CHF_2, Z = S, R^3 = 3\text{-CN}$ |
| 1325 | $R^2 = CHF_2, Z = S, R^3 = 3\text{-NO}_2$ |
| 1326 | $R^2 = CHF_2, Z = S, R^3 = 3\text{-OMe}$ |
| 1327 | $R^2 = CHF_2, Z = S, R^3 = 3\text{-OCF}_3$ |
| 1328 | $R^2 = CHF_2, Z = S, R^3 = 3\text{-CHF}_2$ |
| 1329 | $R^2 = CHF_2, Z = S, R^3 = 3\text{-CH}_2\text{F}$ |
| 1330 | $R^2 = CHF_2, Z = S, R^3 = 3\text{-CHO}$ |
| 1331 | $R^2 = CHF_2, Z = S, R^3 = 3\text{-Me}$ |
| 1332 | $R^2 = CHF_2, Z = S, R^3 = 3\text{-Et}$ |
| 1333 | $R^2 = CHF_2, Z = S, R^3 = 3\text{-Ethynyl}$ |
| 1334 | $R^2 = CHF_2, Z = S, R^3 = 3\text{-Ethenyl}$ |
| 1335 | $R^2 = CHF_2, Z = S, R^3 = 3\text{-SO}_2\text{Me}$ |
| 1336 | $R^2 = CHF_2, Z = S, R^3 = 3\text{-OAc}$ |
| 1337 | $R^2 = CHF_2, Z = S, R^3 = 3\text{-c-Pr}$ |
| 1338 | $R^2 = CHF_2, Z = S, R^3 = 3\text{-i-Pr}$ |
| 1339 | $R^2 = CHF_2, Z = S, R^3 = 3\text{-Ph}$ |
| 1340 | $R^2 = CHF_2, Z = O, R^3 = 4\text{-F}$ |
| 1341 | $R^2 = CHF_2, Z = O, R^3 = 4\text{-Cl}$ |
| 1342 | $R^2 = CHF_2, Z = O, R^3 = 4\text{-Br}$ |
| 1343 | $R^2 = CHF_2, Z = O, R^3 = 4\text{-I}$ |
| 1344 | $R^2 = CHF_2, Z = O, R^3 = 4\text{-CN}$ |
| 1345 | $R^2 = CHF_2, Z = O, R^3 = 4\text{-NO}_2$ |
| 1346 | $R^2 = CHF_2, Z = O, R^3 = 4\text{-OMe}$ |
| 1347 | $R^2 = CHF_2, Z = O, R^3 = 4\text{-OCF}_3$ |
| 1348 | $R^2 = CHF_2, Z = O, R^3 = 4\text{-CF}_3$ |
| 1349 | $R^2 = CHF_2, Z = O, R^3 = 4\text{-CHF}_2$ |
| 1350 | $R^2 = CHF_2, Z = O, R^3 = 4\text{-CH}_2\text{F}$ |
| 1351 | $R^2 = CHF_2, Z = O, R^3 = 4\text{-CHO}$ |
| 1352 | $R^2 = CHF_2, Z = O, R^3 = 4\text{-Me}$ |
| 1353 | $R^2 = CHF_2, Z = O, R^3 = 4\text{-Et}$ |
| 1354 | $R^2 = CHF_2, Z = O, R^3 = 4\text{-Ethynyl}$ |
| 1355 | $R^2 = CHF_2, Z = O, R^3 = 4\text{-Ethenyl}$ |
| 1356 | $R^2 = CHF_2, Z = O, R^3 = 4\text{-SO}_2\text{Me}$ |
| 1357 | $R^2 = CHF_2, Z = O, R^3 = 4\text{-OAc}$ |
| 1358 | $R^2 = CHF_2, Z = O, R^3 = 4\text{-c-Pr}$ |
| 1359 | $R^2 = CHF_2, Z = O, R^3 = 4\text{-i-Pr}$ |
| 1360 | $R^2 = CHF_2, Z = O, R^3 = 4\text{-Ph}$ |
| 1361 | $R^2 = CHF_2, Z = O, R^3 = 5\text{-F}$ |
| 1362 | $R^2 = CHF_2, Z = O, R^3 = 5\text{-Cl}$ |
| 1363 | $R^2 = CHF_2, Z = O, R^3 = 5\text{-Br}$ |
| 1364 | $R^2 = CHF_2, Z = O, R^3 = 5\text{-I}$ |
| 1365 | $R^2 = CHF_2, Z = O, R^3 = 5\text{-CN}$ |
| 1366 | $R^2 = CHF_2, Z = O, R^3 = 5\text{-NO}_2$ |
| 1367 | $R^2 = CHF_2, Z = O, R^3 = 5\text{-OMe}$ |
| 1368 | $R^2 = CHF_2, Z = O, R^3 = 5\text{-OCF}_3$ |
| 1369 | $R^2 = CHF_2, Z = O, R^3 = 5\text{-CF}_3$ |
| 1370 | $R^2 = CHF_2, Z = O, R^3 = 5\text{-CHF}_2$ |
| 1371 | $R^2 = CHF_2, Z = O, R^3 = 5\text{-CH}_2\text{F}$ |
| 1372 | $R^2 = CHF_2, Z = O, R^3 = 5\text{-CHO}$ |
| 1373 | $R^2 = CHF_2, Z = O, R^3 = 5\text{-Me}$ |
| 1374 | $R^2 = CHF_2, Z = O, R^3 = 5\text{-Et}$ |
| 1375 | $R^2 = CHF_2, Z = O, R^3 = 5\text{-Ethynyl}$ |
| 1376 | $R^2 = CHF_2, Z = O, R^3 = 5\text{-Ethenyl}$ |
| 1377 | $R^2 = CHF_2, Z = O, R^3 = 5\text{-SO}_2\text{Me}$ |
| 1378 | $R^2 = CHF_2, Z = O, R^3 = 5\text{-OAc}$ |
| 1379 | $R^2 = CHF_2, Z = O, R^3 = 5\text{-c-Pr}$ |
| 1380 | $R^2 = CHF_2, Z = O, R^3 = 5\text{-i-Pr}$ |
| 1381 | $R^2 = CHF_2, Z = O, R^3 = 5\text{-Ph}$ |
| 1382 | $R^2 = CHF_2, Z = O, R^3 = 6\text{-F}$ |

-continued

| Table | Header Row |
|---|---|
| 1383 | $R^2 = CHF_2$, $Z = O$, $R^3 = 6$-Cl |
| 1384 | $R^2 = CHF_2$, $Z = O$, $R^3 = 6$-Br |
| 1385 | $R^2 = CHF_2$, $Z = O$, $R^3 = 6$-I |
| 1386 | $R^2 = CHF_2$, $Z = O$, $R^3 = 6$-CN |
| 1387 | $R^2 = CHF_2$, $Z = O$, $R^3 = 6$-NO$_2$ |
| 1388 | $R^2 = CHF_2$, $Z = O$, $R^3 = 6$-OMe |
| 1389 | $R^2 = CHF_2$, $Z = O$, $R^3 = 6$-OCF$_3$ |
| 1390 | $R^2 = CHF_2$, $Z = O$, $R^3 = 6$-CF$_3$ |
| 1391 | $R^2 = CHF_2$, $Z = O$, $R^3 = 6$-CHF$_2$ |
| 1392 | $R^2 = CHF_2$, $Z = O$, $R^3 = 6$-CH$_2$F |
| 1393 | $R^2 = CHF_2$, $Z = O$, $R^3 = 6$-CHO |
| 1394 | $R^2 = CHF_2$, $Z = O$, $R^3 = 6$-Me |
| 1395 | $R^2 = CHF_2$, $Z = O$, $R^3 = 6$-Et |
| 1396 | $R^2 = CHF_2$, $Z = O$, $R^3 = 6$-Ethynyl |
| 1397 | $R^2 = CHF_2$, $Z = O$, $R^3 = 6$-Ethenyl |
| 1398 | $R^2 = CHF_2$, $Z = O$, $R^3 = 6$-SO$_2$Me |
| 1399 | $R^2 = CHF_2$, $Z = O$, $R^3 = 6$-OAc |
| 1400 | $R^2 = CHF_2$, $Z = O$, $R^3 = 6$-c-Pr |
| 1401 | $R^2 = CHF_2$, $Z = O$, $R^3 = 6$-i-Pr |
| 1402 | $R^2 = CHF_2$, $Z = O$, $R^3 = 6$-Ph |
| 1403 | $R^2 = CHF_2$, $Z = O$, $R^3 = 3,4$-di-F |
| 1404 | $R^2 = CHF_2$, $Z = O$, $R^3 = 3,5$-di-F |
| 1405 | $R^2 = CHF_2$, $Z = O$, $R^3 = 3,6$-di-F |
| 1406 | $R^2 = CHF_2$, $Z = O$, $R^3 = 4,5$-di-F |
| 1407 | $R^2 = CHF_2$, $Z = O$, $R^3 = 3,4$-di-Cl |
| 1408 | $R^2 = CHF_2$, $Z = O$, $R^3 = 3,5$-di-Cl |
| 1409 | $R^2 = CHF_2$, $Z = O$, $R^3 = 3,6$-di-Cl |
| 1410 | $R^2 = CHF_2$, $Z = O$, $R^3 = 4,5$-di-Cl |
| 1411 | $R^2 = CHF_2$, $Z = O$, $R^3 = 3,4$-di-Br |
| 1412 | $R^2 = CHF_2$, $Z = O$, $R^3 = 3,5$-di-Br |
| 1413 | $R^2 = CHF_2$, $Z = O$, $R^3 = 3,6$-di-Br |
| 1414 | $R^2 = CHF_2$, $Z = O$, $R^3 = 4,5$-di-Br |
| 1415 | $R^2 = CHF_2$, $Z = O$, $R^3 = 3,4$-di-CN |
| 1416 | $R^2 = CHF_2$, $Z = O$, $R^3 = 3,5$-di-CN |
| 1417 | $R^2 = CHF_2$, $Z = O$, $R^3 = 3,6$-di-CN |
| 1418 | $R^2 = CHF_2$, $Z = O$, $R^3 = 4,5$-di-CN |
| 1419 | $R^2 = CHF_2$, $Z = O$, $R^3 = 3,4$-di-Me |
| 1420 | $R^2 = CHF_2$, $Z = O$, $R^3 = 3,5$-di-Me |
| 1421 | $R^2 = CHF_2$, $Z = O$, $R^3 = 3,6$-di-Me |
| 1422 | $R^2 = CHF_2$, $Z = O$, $R^3 = 4,5$-di-Me |
| 1423 | $R^2 = CHF_2$, $Z = O$, $R^3 = 3,4$-di-OMe |
| 1424 | $R^2 = CHF_2$, $Z = O$, $R^3 = 3,5$-di-OMe |
| 1425 | $R^2 = CHF_2$, $Z = O$, $R^3 = 3,6$-di-OMe |
| 1426 | $R^2 = CHF_2$, $Z = O$, $R^3 = 4,5$-di-OMe |
| 1427 | $R^2 = CHF_2$, $Z = O$, $R^3 = 3,4$-di-CF$_3$ |
| 1428 | $R^2 = CHF_2$, $Z = O$, $R^3 = 3,5$-di-CF$_3$ |
| 1429 | $R^2 = CHF_2$, $Z = O$, $R^3 = 3,6$-di-CF$_3$ |
| 1430 | $R^2 = CHF_2$, $Z = O$, $R^3 = 4,5$-di-CF$_3$ |
| 1431 | $R^2 = CHF_2$, $Z = O$, $R^3 = 3$-CN, 4-Me |
| 1432 | $R^2 = CHF_2$, $Z = O$, $R^3 = 3$-CN, 4-F |
| 1433 | $R^2 = CHF_2$, $Z = O$, $R^3 = 3$-CN, 4-Br |
| 1434 | $R^2 = CHF_2$, $Z = O$, $R^3 = 3$-CN, 4-OMe |
| 1435 | $R^2 = CHF_2$, $Z = O$, $R^3 = 3$-CN, 4-CF$_3$ |
| 1436 | $R^2 = CHF_2$, $Z = O$, $R^3 = 3$-CN, 6-Me |
| 1437 | $R^2 = CHF_2$, $Z = O$, $R^3 = 3$-CN, 6-F |
| 1438 | $R^2 = CHF_2$, $Z = O$, $R^3 = 3$-CN, 6-Br |
| 1439 | $R^2 = CHF_2$, $Z = O$, $R^3 = 3$-CN, 6-OMe |
| 1440 | $R^2 = CHF_2$, $Z = O$, $R^3 = 3$-CN, 6-CF$_3$ |
| 1441 | $R^2 = SO_2Me$, $Z = O$, $R^3 = H$ (m = 0) |
| 1442 | $R^2 = SO_2Me$, $Z = O$, $R^3 = 3$-F |
| 1443 | $R^2 = SO_2Me$, $Z = O$, $R^3 = 3$-Cl |
| 1444 | $R^2 = SO_2Me$, $Z = O$, $R^3 = 3$-Br |
| 1445 | $R^2 = SO_2Me$, $Z = O$, $R^3 = 3$-I |
| 1446 | $R^2 = SO_2Me$, $Z = O$, $R^3 = 3$-CN |
| 1447 | $R^2 = SO_2Me$, $Z = O$, $R^3 = 3$-NO$_2$ |
| 1448 | $R^2 = SO_2Me$, $Z = O$, $R^3 = 3$-OMe |
| 1449 | $R^2 = SO_2Me$, $Z = O$, $R^3 = 3$-OCF$_3$ |
| 1450 | $R^2 = SO_2Me$, $Z = O$, $R^3 = 3$-CF$_3$ |
| 1451 | $R^2 = SO_2Me$, $Z = O$, $R^3 = 3$-CHF$_2$ |
| 1452 | $R^2 = SO_2Me$, $Z = O$, $R^3 = 3$-CH$_2$F |
| 1453 | $R^2 = SO_2Me$, $Z = O$, $R^3 = 3$-CHO |
| 1454 | $R^2 = SO_2Me$, $Z = O$, $R^3 = 3$-Me |
| 1455 | $R^2 = SO_2Me$, $Z = O$, $R^3 = 3$-Et |
| 1456 | $R^2 = SO_2Me$, $Z = O$, $R^3 = 3$-Ethynyl |
| 1457 | $R^2 = SO_2Me$, $Z = O$, $R^3 = 3$-Ethenyl |
| 1458 | $R^2 = SO_2Me$, $Z = O$, $R^3 = 3$-SO$_2$Me |
| 1459 | $R^2 = SO_2Me$, $Z = O$, $R^3 = 3$-OAc |

-continued

| Table | Header Row |
|---|---|
| 1460 | $R^2 = SO_2Me$, $Z = O$, $R^3 = 3$-c-Pr |
| 1461 | $R^2 = SO_2Me$, $Z = O$, $R^3 = 3$-i-Pr |
| 1462 | $R^2 = SO_2Me$, $Z = O$, $R^3 = 3$-Ph |
| 1463 | $R^2 = SO_2Me$, $Z = S$, $R^3 = 3$-F |
| 1464 | $R^2 = SO_2Me$, $Z = S$, $R^3 = 3$-Cl |
| 1465 | $R^2 = SO_2Me$, $Z = S$, $R^3 = 3$-Br |
| 1466 | $R^2 = SO_2Me$, $Z = S$, $R^3 = 3$-I |
| 1467 | $R^2 = SO_2Me$, $Z = S$, $R^3 = 3$-CN |
| 1468 | $R^2 = SO_2Me$, $Z = S$, $R^3 = 3$-NO$_2$ |
| 1469 | $R^2 = SO_2Me$, $Z = S$, $R^3 = 3$-OMe |
| 1470 | $R^2 = SO_2Me$, $Z = S$, $R^3 = 3$-OCF$_3$ |
| 1471 | $R^2 = SO_2Me$, $Z = S$, $R^3 = 3$-CF$_3$ |
| 1472 | $R^2 = SO_2Me$, $Z = S$, $R^3 = 3$-CHF$_2$ |
| 1473 | $R^2 = SO_2Me$, $Z = S$, $R^3 = 3$-CH$_2$F |
| 1474 | $R^2 = SO_2Me$, $Z = S$, $R^3 = 3$-CHO |
| 1475 | $R^2 = SO_2Me$, $Z = S$, $R^3 = 3$-Me |
| 1476 | $R^2 = SO_2Me$, $Z = S$, $R^3 = 3$-Et |
| 1477 | $R^2 = SO_2Me$, $Z = S$, $R^3 = 3$-Ethynyl |
| 1478 | $R^2 = SO_2Me$, $Z = S$, $R^3 = 3$-Ethenyl |
| 1479 | $R^2 = SO_2Me$, $Z = S$, $R^3 = 3$-SO$_2$Me |
| 1480 | $R^2 = SO_2Me$, $Z = S$, $R^3 = 3$-OAc |
| 1481 | $R^2 = SO_2Me$, $Z = S$, $R^3 = 3$-c-Pr |
| 1482 | $R^2 = SO_2Me$, $Z = S$, $R^3 = 3$-i-Pr |
| 1483 | $R^2 = SO_2Me$, $Z = S$, $R^3 = 3$-Ph |
| 1484 | $R^2 = SO_2Me$, $Z = O$, $R^3 = 4$-F |
| 1485 | $R^2 = SO_2Me$, $Z = O$, $R^3 = 4$-Cl |
| 1486 | $R^2 = SO_2Me$, $Z = O$, $R^3 = 4$-Br |
| 1487 | $R^2 = SO_2Me$, $Z = O$, $R^3 = 4$-I |
| 1488 | $R^2 = SO_2Me$, $Z = O$, $R^3 = 4$-CN |
| 1489 | $R^2 = SO_2Me$, $Z = O$, $R^3 = 4$-NO$_2$ |
| 1490 | $R^2 = SO_2Me$, $Z = O$, $R^3 = 4$-OMe |
| 1491 | $R^2 = SO_2Me$, $Z = O$, $R^3 = 4$-OCF$_3$ |
| 1492 | $R^2 = SO_2Me$, $Z = O$, $R^3 = 4$-CF$_3$ |
| 1493 | $R^2 = SO_2Me$, $Z = O$, $R^3 = 4$-CHF$_2$ |
| 1494 | $R^2 = SO_2Me$, $Z = O$, $R^3 = 4$-CH$_2$F |
| 1495 | $R^2 = SO_2Me$, $Z = O$, $R^3 = 4$-CHO |
| 1496 | $R^2 = SO_2Me$, $Z = O$, $R^3 = 4$-Me |
| 1497 | $R^2 = SO_2Me$, $Z = O$, $R^3 = 4$-Et |
| 1498 | $R^2 = SO_2Me$, $Z = O$, $R^3 = 4$-Ethynyl |
| 1499 | $R^2 = SO_2Me$, $Z = O$, $R^3 = 4$-Ethenyl |
| 1500 | $R^2 = SO_2Me$, $Z = O$, $R^3 = 4$-SO$_2$Me |
| 1501 | $R^2 = SO_2Me$, $Z = O$, $R^3 = 4$-OAc |
| 1502 | $R^2 = SO_2Me$, $Z = O$, $R^3 = 4$-c-Pr |
| 1503 | $R^2 = SO_2Me$, $Z = O$, $R^3 = 4$-i-Pr |
| 1504 | $R^2 = SO_2Me$, $Z = O$, $R^3 = 4$-Ph |
| 1505 | $R^2 = SO_2Me$, $Z = O$, $R^3 = 5$-F |
| 1506 | $R^2 = SO_2Me$, $Z = O$, $R^3 = 5$-Cl |
| 1507 | $R^2 = SO_2Me$, $Z = O$, $R^3 = 5$-Br |
| 1508 | $R^2 = SO_2Me$, $Z = O$, $R^3 = 5$-I |
| 1509 | $R^2 = SO_2Me$, $Z = O$, $R^3 = 5$-CN |
| 1510 | $R^2 = SO_2Me$, $Z = O$, $R^3 = 5$-NO$_2$ |
| 1511 | $R^2 = SO_2Me$, $Z = O$, $R^3 = 5$-OMe |
| 1512 | $R^2 = SO_2Me$, $Z = O$, $R^3 = 5$-OCF$_3$ |
| 1513 | $R^2 = SO_2Me$, $Z = O$, $R^3 = 5$-CF$_3$ |
| 1514 | $R^2 = SO_2Me$, $Z = O$, $R^3 = 5$-CHF$_2$ |
| 1515 | $R^2 = SO_2Me$, $Z = O$, $R^3 = 5$-CH$_2$F |
| 1516 | $R^2 = SO_2Me$, $Z = O$, $R^3 = 5$-CHO |
| 1517 | $R^2 = SO_2Me$, $Z = O$, $R^3 = 5$-Me |
| 1518 | $R^2 = SO_2Me$, $Z = O$, $R^3 = 5$-Et |
| 1519 | $R^2 = SO_2Me$, $Z = O$, $R^3 = 5$-Ethynyl |
| 1520 | $R^2 = SO_2Me$, $Z = O$, $R^3 = 5$-Ethenyl |
| 1521 | $R^2 = SO_2Me$, $Z = O$, $R^3 = 5$-SO$_2$Me |
| 1522 | $R^2 = SO_2Me$, $Z = O$, $R^3 = 5$-OAc |
| 1523 | $R^2 = SO_2Me$, $Z = O$, $R^3 = 5$-c-Pr |
| 1524 | $R^2 = SO_2Me$, $Z = O$, $R^3 = 5$-i-Pr |
| 1525 | $R^2 = SO_2Me$, $Z = O$, $R^3 = 5$-Ph |
| 1526 | $R^2 = SO_2Me$, $Z = O$, $R^3 = 6$-F |
| 1527 | $R^2 = SO_2Me$, $Z = O$, $R^3 = 6$-Cl |
| 1528 | $R^2 = SO_2Me$, $Z = O$, $R^3 = 6$-Br |
| 1529 | $R^2 = SO_2Me$, $Z = O$, $R^3 = 6$-I |
| 1530 | $R^2 = SO_2Me$, $Z = O$, $R^3 = 6$-CN |
| 1531 | $R^2 = SO_2Me$, $Z = O$, $R^3 = 6$-NO$_2$ |
| 1532 | $R^2 = SO_2Me$, $Z = O$, $R^3 = 6$-OMe |
| 1533 | $R^2 = SO_2Me$, $Z = O$, $R^3 = 6$-OCF$_3$ |
| 1534 | $R^2 = SO_2Me$, $Z = O$, $R^3 = 6$-CF$_3$ |
| 1535 | $R^2 = SO_2Me$, $Z = O$, $R^3 = 6$-CHF$_2$ |
| 1536 | $R^2 = SO_2Me$, $Z = O$, $R^3 = 6$-CH$_2$F |

-continued

| Table | Header Row |
|---|---|
| 1537 | $R^2 = SO_2Me, Z = O, R^3 = 6\text{-CHO}$ |
| 1538 | $R^2 = SO_2Me, Z = O, R^3 = 6\text{-Me}$ |
| 1539 | $R^2 = SO_2Me, Z = O, R^3 = 6\text{-Et}$ |
| 1540 | $R^2 = SO_2Me, Z = O, R^3 = 6\text{-Ethynyl}$ |
| 1541 | $R^2 = SO_2Me, Z = O, R^3 = 6\text{-Ethenyl}$ |
| 1542 | $R^2 = SO_2Me, Z = O, R^3 = 6\text{-}SO_2Me$ |
| 1543 | $R^2 = SO_2Me, Z = O, R^3 = 6\text{-OAc}$ |
| 1544 | $R^2 = SO_2Me, Z = O, R^3 = 6\text{-c-Pr}$ |
| 1545 | $R^2 = SO_2Me, Z = O, R^3 = 6\text{-i-Pr}$ |
| 1546 | $R^2 = SO_2Me, Z = O, R^3 = 6\text{-Ph}$ |
| 1547 | $R^2 = SO_2Me, Z = O, R^3 = 3,4\text{-di-F}$ |
| 1548 | $R^2 = SO_2Me, Z = O, R^3 = 3,5\text{-di-F}$ |
| 1549 | $R^2 = SO_2Me, Z = O, R^3 = 3,6\text{-di-F}$ |
| 1550 | $R^2 = SO_2Me, Z = O, R^3 = 4,5\text{-di-F}$ |
| 1551 | $R^2 = SO_2Me, Z = O, R^3 = 3,4\text{-di-Cl}$ |
| 1552 | $R^2 = SO_2Me, Z = O, R^3 = 3,5\text{-di-Cl}$ |
| 1553 | $R^2 = SO_2Me, Z = O, R^3 = 3,6\text{-di-Cl}$ |
| 1554 | $R^2 = SO_2Me, Z = O, R^3 = 4,5\text{-di-Cl}$ |
| 1555 | $R^2 = SO_2Me, Z = O, R^3 = 3,4\text{-di-Br}$ |
| 1556 | $R^2 = SO_2Me, Z = O, R^3 = 3,5\text{-di-Br}$ |
| 1557 | $R^2 = SO_2Me, Z = O, R^3 = 3,6\text{-di-Br}$ |
| 1558 | $R^2 = SO_2Me, Z = O, R^3 = 4,5\text{-di-Br}$ |
| 1559 | $R^2 = SO_2Me, Z = O, R^3 = 3,4\text{-di-CN}$ |
| 1560 | $R^2 = SO_2Me, Z = O, R^3 = 3,5\text{-di-CN}$ |
| 1561 | $R^2 = SO_2Me, Z = O, R^3 = 3,6\text{-di-CN}$ |
| 1562 | $R^2 = SO_2Me, Z = O, R^3 = 4,5\text{-di-CN}$ |
| 1563 | $R^2 = SO_2Me, Z = O, R^3 = 3,4\text{-di-Me}$ |
| 1564 | $R^2 = SO_2Me, Z = O, R^3 = 3,5\text{-di-Me}$ |
| 1565 | $R^2 = SO_2Me, Z = O, R^3 = 3,6\text{-di-Me}$ |
| 1566 | $R^2 = SO_2Me, Z = O, R^3 = 4,5\text{-di-Me}$ |
| 1567 | $R^2 = SO_2Me, Z = O, R^3 = 3,4\text{-di-OMe}$ |
| 1568 | $R^2 = SO_2Me, Z = O, R^3 = 3,5\text{-di-OMe}$ |
| 1569 | $R^2 = SO_2Me, Z = O, R^3 = 3,6\text{-di-OMe}$ |
| 1570 | $R^2 = SO_2Me, Z = O, R^3 = 4,5\text{-di-OMe}$ |
| 1571 | $R^2 = SO_2Me, Z = O, R^3 = 3,4\text{-di-}CF_3$ |
| 1572 | $R^2 = SO_2Me, Z = O, R^3 = 3,5\text{-di-}CF_3$ |
| 1573 | $R^2 = SO_2Me, Z = O, R^3 = 3,6\text{-di-}CF_3$ |
| 1574 | $R^2 = SO_2Me, Z = O, R^3 = 4,5\text{-di-}CF_3$ |
| 1575 | $R^2 = SO_2Me, Z = O, R^3 = 3\text{-CN, 4-Me}$ |
| 1576 | $R^2 = SO_2Me, Z = O, R^3 = 3\text{-CN, 4-F}$ |
| 1577 | $R^2 = SO_2Me, Z = O, R^3 = 3\text{-CN, 4-Br}$ |
| 1578 | $R^2 = SO_2Me, Z = O, R^3 = 3\text{-CN, 4-OMe}$ |
| 1579 | $R^2 = SO_2Me, Z = O, R^3 = 3\text{-CN, 4-}CF_3$ |
| 1580 | $R^2 = SO_2Me, Z = O, R^3 = 3\text{-CN, 6-Me}$ |
| 1581 | $R^2 = SO_2Me, Z = O, R^3 = 3\text{-CN, 6-F}$ |
| 1582 | $R^2 = SO_2Me, Z = O, R^3 = 3\text{-CN, 6-Br}$ |
| 1583 | $R^2 = SO_2Me, Z = O, R^3 = 3\text{-CN, 6-OMe}$ |
| 1584 | $R^2 = SO_2Me, Z = O, R^3 = 3\text{-CN, 6-}CF_3$ |

A compound of this invention will generally be used as a herbicidal active ingredient in a composition, i.e. formulation, with at least one additional component selected from the group consisting of surfactants, solid diluents and liquid diluents, which serves as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions, oil-in-water emulsions, flowable concentrates and/or suspoemulsions) and the like, which optionally can be thickened into gels. The general types of aqueous liquid compositions are soluble concentrate, suspension concentrate, capsule suspension, concentrated emulsion, microemulsion, oil-in-water emulsion, flowable concentrate and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water, but occasionally another suitable medium like an aromatic or paraffinic hydrocarbon or vegetable oil. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), alkyl phosphates (e.g., triethyl phosphate), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters, alkyl and aryl benzoates and y-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol, cresol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food—Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
| --- | --- |
| Compound 2 | 98.5% |
| silica aerogel | 0.5% |
| synthetic amorphous fine silica | 1.0% |

Example B

| Wettable Powder | |
| --- | --- |
| Compound 5 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
| --- | --- |
| Compound 7 | 10.0% |
| attapulgite granules (low volatile matter, 0.71/0.30 mm; U.S.S. No. 25-50 sieves) | 90.0% |

Example D

| Extruded Pellet | |
| --- | --- |
| Compound 10 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
| --- | --- |
| Compound 18 | 10.0% |
| polyoxyethylene sorbitol hexoleate | 20.0% |
| $C_6$-$C_{10}$ fatty acid methyl ester | 70.0% |

Example F

| Microemulsion | |
| --- | --- |
| Compound 52 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

| Suspension Concentrate | |
| --- | --- |
| Compound 54 | 35% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |

-continued

| Suspension Concentrate | |
|---|---|
| propylene glycol | 5.0% |
| silicone based defoamer | 0.1% |
| 1,2-benzisothiazolin-3-one | 0.1% |
| water | 53.7% |

Example H

| Emulsion in Water | |
|---|---|
| Compound 58 | 10.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0 |
| water | 58.7% |

Example I

| Oil Dispersion | |
|---|---|
| Compound 59 | 25% |
| polyoxyethylene sorbitol hexaoleate | 15% |
| organically modified bentonite clay | 2.5% |
| fatty acid methyl ester | 57.5% |

Example J

| Suspoemulsion | |
|---|---|
| Compound 2 | 10.0% |
| imidacloprid | 5.0% |
| butyl polyoxyethylene/polypropylene block copolymer | 4.0% |
| stearic acid/polyethylene glycol copolymer | 1.0% |
| styrene acrylic polymer | 1.0% |
| xanthan gum | 0.1% |
| propylene glycol | 5.0% |
| silicone based defoamer | 0.1% |
| 1,2-benzisothiazolin-3-one | 0.1% |
| aromatic petroleum based hydrocarbon | 20.0% |
| water | 53.7% |

Test results indicate that the compounds of the present invention are highly active preemergent and/or postemergent herbicides and/or plant growth regulants. The compounds of the invention generally show highest activity for postemergence weed control (i.e. applied after weed seedlings emerge from the soil) and preemergence weed control (i.e. applied before weed seedlings emerge from the soil). Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Many of the compounds of this invention, by virtue of selective metabolism in crops versus weeds, or by selective activity at the locus of physiological inhibition in crops and weeds, or by selective placement on or within the environment of a mixture of crops and weeds, are useful for the selective control of grass and broadleaf weeds within a crop/weed mixture. One skilled in the art will recognize that the preferred combination of these selectivity factors within a compound or group of compounds can readily be determined by performing routine biological and/or biochemical assays. Compounds of this invention may show tolerance to important agronomic crops including, but is not limited to, alfalfa, barley, cotton, wheat, rape, sugar beets, corn (maize), *sorghum*, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as *eucalyptus* and conifers (e.g., loblolly pine), and turf species (e.g., Kentucky bluegrass, St. Augustine grass, Kentucky fescue and Bermuda grass). Compounds of this invention can be used in crops genetically transformed or bred to incorporate resistance to herbicides, express proteins toxic to invertebrate pests (such as *Bacillus thuringiensis* toxin), and/or express other useful traits. Those skilled in the art will appreciate that not all compounds are equally effective against all weeds. Alternatively, the subject compounds are useful to modify plant growth.

As the compounds of the invention have both preemergent and postemergent herbicidal activity, to control undesired vegetation by killing or injuring the vegetation or reducing its growth, the compounds can be usefully applied by a variety of methods involving contacting a herbicidally effective amount of a compound of the invention, or a composition comprising said compound and at least one of a surfactant, a solid diluent or a liquid diluent, to the foliage or other part of the undesired vegetation or to the environment of the undesired vegetation such as the soil or water in which the undesired vegetation is growing or which surrounds the seed or other propagule of the undesired vegetation.

A herbicidally effective amount of the compounds of this invention is determined by a number of factors. These factors include: formulation selected, method of application, amount and type of vegetation present, growing conditions, etc. In general, a herbicidally effective amount of compounds of this invention is about 0.001 to 20 kg/ha with a preferred range of about 0.004 to 1 kg/ha. One skilled in the art can easily determine the herbicidally effective amount necessary for the desired level of weed control.

Compounds of the invention are useful in treating all plants and plant parts. Plant varieties and cultivars can be obtained by conventional propagation and breeding methods or by genetic engineering methods. Genetically modified plants (transgenic plants) are those in which a heterologous gene (transgene) has been stably integrated into the plant's genome. A transgene that is defined by its particular location in the plant genome is called a transformation or transgenic event.

Genetically modified plant cultivars which can be treated according to the invention include those that are resistant against one or more biotic stresses (pests such as nematodes, insects, mites, fungi, etc.) or abiotic stresses (drought, cold temperature, soil salinity, etc.), or that contain other desirable characteristics. Plants can be genetically modified to exhibit traits of, for example, herbicide tolerance, insect-resistance, modified oil profiles or drought tolerance. Useful genetically modified plants containing single gene transformation events or combinations of transformation events are listed in Exhibit A. Additional information for the genetic modifications listed in Exhibit A can be obtained from publicly available databases maintained, for example, by the U.S. Department of Agriculture.

The following abbreviations, T1 through T37, are used in Exhibit A for traits. A "-" means the entry is not available.

| Trait | Description |
|---|---|
| T1 | Glyphosate tolerance |
| T2 | High lauric acid oil |
| T3 | Glufosinate tolerance |
| T4 | Phytate breakdown |
| T5 | Oxynil tolerance |
| T6 | Disease resistance |
| T7 | Insect resistance |
| T9 | Modified flower color |
| T11 | ALS Herbicide Tol. |
| T12 | Dicamba Tolerance |
| T13 | Anti-allergy |
| T14 | Salt tolerance |
| T15 | Cold tolerance |
| T16 | Imidazolinone herb. tol. |
| T17 | Modified alpha-amylase |
| T18 | Pollination control |
| T19 | 2,4-D tolerance |
| T20 | Increased lysine |
| T21 | Drought tolerance |
| T22 | Delayed ripening/senescence |
| T23 | Modified product quality |
| T24 | High cellulose |
| T25 | Modified starch/carbohydrate |
| T26 | Insect & disease resist. |
| T27 | High tryptophan |
| T28 | Erect leaves semidwarf |
| T29 | Semidwarf |
| T30 | Low iron tolerance |
| T31 | Modified oil/fatty acid |
| T32 | HPPD tolerance |
| T33 | High oil |
| T34 | Aryloxyalkanoate tol. |
| T35 | Mesotrione tolerance |
| T36 | Reduced nicotine |
| T37 | Modified product |

Exhibit A

| Crop | Event Name | Event Code | Trait(s) | Gene(s) |
|---|---|---|---|---|
| Alfalfa | J101 | MON-00101-8 | T1 | cp4 epsps (aroA:CP4) |
| Alfalfa | J163 | MON-ØØ163-7 | T1 | cp4 epsps (aroA:CP4) |
| Canola* | 23-18-17 (Event 18) | CGN-89465-2 | T2 | te |
| Canola* | 23-198 (Event 23) | CGN-89465-2 | T2 | te |
| Canola* | 61061 | DP-Ø61Ø61-7 | T1 | gat4621 |
| Canola* | 73496 | DP-Ø73496-4 | T1 | gat4621 |
| Canola* | GT200 (RT200) | MON-89249-2 | T1 | cp4 epsps (aroA:CP4); goxv247 |
| Canola* | GT73 (RT73) | MON-ØØØ73-7 | T1 | cp4 epsps (aroA:CP4); goxv247 |
| Canola* | HCN10 (Topas 19/2) | — | T3 | bar |
| Canola* | HCN28 (T45) | ACS-BNØØ8-2 | T3 | pat (syn) |
| Canola* | HCN92 (Topas 19/2) | ACS-BNØØ7-1 | T3 | bar |
| Canola* | MON88302 | MON-883Ø2-9 | T1 | cp4 epsps (aroA:CP4) |
| Canola* | MPS961 | — | T4 | phyA |
| Canola* | MPS962 | — | T4 | phyA |
| Canola* | MPS963 | — | T4 | phyA |
| Canola* | MPS964 | — | T4 | phyA |
| Canola* | MPS965 | — | T4 | phyA |
| Canola* | MS1 (B91-4) | ACS-BNØØ4-7 | T3 | bar |
| Canola* | MS8 | ACS-BNØØ5-8 | T3 | bar |
| Canola* | OXY-235 | ACS-BNØ11-5 | T5 | bxn |
| Canola* | PHY14 | — | T3 | bar |
| Canola* | PHY23 | — | T3 | bar |
| Canola* | PHY35 | — | T3 | bar |
| Canola* | PHY36 | — | T3 | bar |
| Canola* | RF1 (B93-101) | ACS-BNØØ1-4 | T3 | bar |
| Canola* | RF2 (B94-2) | ACS-BNØØ2-5 | T3 | bar |
| Canola* | RF3 | ACS-BNØØ3-6 | T3 | bar |
| Bean | EMBRAPA 5.1 | EMB-PV051-1 | T6 | acl (sense and antisense) |
| Brinjal # | EE-1 | — | T7 | cry1Ac |
| Cotton | 19-51a | DD-Ø1951A-7 | T11 | S4-HrA |
| Cotton | 281-24-236 | DAS-24236-5 | T3, T7 | pat (syn); cry1F |
| Cotton | 3006-210-23 | DAS-21Ø23-5 | T3, T7 | pat (syn); cry1Ac |
| Cotton | 31707 | — | T5, T7 | bxn; cry1Ac |
| Cotton | 31803 | — | T5, T7 | bxn; cry1Ac |
| Cotton | 31807 | — | T5, T7 | bxn; cry1Ac |
| Cotton | 31808 | — | T5, T7 | bxn; cry1Ac |
| Cotton | 42317 | — | T5, T7 | bxn; cry1Ac |
| Cotton | BNLA-601 | — | T7 | cry1Ac |
| Cotton | BXN10211 | BXN10211-9 | T5 | bxn; cry1Ac |
| Cotton | BXN10215 | BXN10215-4 | T5 | bxn; cry1Ac |
| Cotton | BXN10222 | BXN10222-2 | T5 | bxn; cry1Ac |
| Cotton | BXN10224 | BXN10224-4 | T5 | bxn; cry1Ac |
| Cotton | COT102 | SYN-IR102-7 | T7 | vip3A(a) |
| Cotton | COT67B | SYN-IR67B-1 | T7 | cry1Ab |
| Cotton | COT202 | — | T7 | vip3A |
| Cotton | Event 1 | — | T7 | cry1Ac |
| Cotton | GMF Cry1A | GTL-GMF311-7 | T7 | cry1Ab-Ac |
| Cotton | GHB119 | BCS-GH005-8 | T7 | cry2Ac |
| Cotton | GHB614 | BCS-GH002-5 | T1 | 2mepsps |
| Cotton | GK12 | — | T7 | cry1Ab-Ac |

-continued

| Crop | Event Name | Event Code | Trait(s) | Gene(s) |
|---|---|---|---|---|
| Cotton | LLCotton25 | ACS-GH001-3 | T3 | bar |
| Cotton | MLS 9124 | — | T7 | cry1C |
| Cotton | MON1076 | MON-89924-2 | T7 | cry1Ac |
| Cotton | MON1445 | MON-01445-2 | T1 | cp4 epsps (aroA:CP4) |
| Cotton | MON15985 | MON-15985-7 | T7 | cry1Ac; cry2Ab2 |
| Cotton | MON1698 | MON-89383-1 | T7 | cp4 epsps (aroA:CP4) |
| Cotton | MON531 | MON-00531-6 | T7 | cry1Ac |
| Cotton | MON757 | MON-00757-7 | T7 | cry1Ac |
| Cotton | MON88913 | MON-88913-8 | T1 | cp4 epsps (aroA:CP4) |
| Cotton | Nqwe Chi 6 Bt | — | T7 | — |
| Cotton | SKG321 | — | T7 | cry1A; CpTI |
| Cotton | T303-3 | BCS-GH003-6 | T3, T7 | cry1Ab; bar |
| Cotton | T304-40 | BCS-GH004-7 | T3, T7 | cry1Ab; bar |
| Cotton | CE43-67B | — | T7 | cry1Ab |
| Cotton | CE46-02A | — | T7 | cry1Ab |
| Cotton | CE44-69D | — | T7 | cry1Ab |
| Cotton | 1143-14A | — | T7 | cry1Ab |
| Cotton | 1143-51B | — | T7 | cry1Ab |
| Cotton | T342-142 | — | T7 | cry1Ab |
| Cotton | PV-GHGT07 (1445) | — | T1 | cp4 epsps (aroA:CP4) |
| Cotton | EE-GH3 | — | T1 | mepsps |
| Cotton | EE-GH5 | — | T7 | cry1Ab |
| Cotton | MON88701 | MON-88701-3 | T3, T12 | Modified dmo; bar |
| Cotton | OsCr11 | — | T13 | Modified Cry j |
| Flax | FP967 | CDC-FL001-2 | T11 | als |
| Lentil | RH44 | — | T16 | als |
| Maize | 3272 | SYN-E3272-5 | T17 | amy797E |
| Maize | 5307 | SYN-05307-1 | T7 | ecry3.1Ab |
| Maize | 59122 | DAS-59122-7 | T3, T7 | cry34Ab1; cry35Ab1; pat |
| Maize | 676 | PH-000676-7 | T3, T18 | pat; dam |
| Maize | 678 | PH-000678-9 | T3, T18 | pat; dam |
| Maize | 680 | PH-000680-2 | T3, T18 | pat; dam |
| Maize | 98140 | DP-098140-6 | T1, T11 | gat4621; zm-hra |
| Maize | Bt10 | — | T3, T7 | cry1Ab; pat |
| Maize | Bt176 (176) | SYN-EV176-9 | T3, T7 | cry1Ab; bar |
| Maize | BVLA430101 | — | T4 | phyA2 |
| Maize | CBH-351 | ACS-ZM004-3 | T3, T7 | cry9C; bar |
| Maize | DAS40278-9 | DAS40278-9 | T19 | aad-1 |
| Maize | DBT418 | DKB-89614-9 | T3, T7 | cry1Ac; pinII; bar |
| Maize | DLL25 (B16) | DKB-89790-5 | T3 | bar |
| Maize | GA21 | MON-00021-9 | T1 | mepsps |
| Maize | GG25 | — | T1 | mepsps |
| Maize | GJ11 | — | T1 | mepsps |
| Maize | Fl117 | — | T1 | mepsps |
| Maize | GAT-ZM1 | — | T3 | pat |
| Maize | LY038 | REN-00038-3 | T20 | cordapA |
| Maize | MIR162 | SYN-IR162-4 | T7 | vip3Aa20 |
| Maize | MIR604 | SYN-IR604-5 | T7 | mcry3A |
| Maize | MON801 (MON80100) | MON801 | T1, T7 | cry1Ab; cp4 epsps (aroA:CP4); goxv247 |
| Maize | MON802 | MON-80200-7 | T1, T7 | cry1Ab; cp4 epsps (aroA:CP4); goxv247 |
| Maize | MON809 | PH-MON-809-2 | T1, T7 | cry1Ab; cp4 epsps (aroA:CP4); goxv247 |
| Maize | MON810 | MON-00810-6 | T1, T7 | cry1Ab; cp4 epsps (aroA:CP4); goxv247 |
| Maize | MON832 | — | T1 | cp4 epsps (aroA:CP4); goxv247 |
| Maize | MON863 | MON-00863-5 | T7 | cry3Bb1 |
| Maize | MON87427 | MON-87427-7 | T1 | cp4 epsps (aroA:CP4) |
| Maize | MON87460 | MON-87460-4 | T21 | cspB |
| Maize | MON88017 | MON-88017-3 | T1, T7 | cry3Bb1; cp4 epsps (aroA:CP4) |
| Maize | MON89034 | MON-89034-3 | T7 | cry2Ab2; cry1A.105 |
| Maize | MS3 | ACS-ZM001-9 | T3, T18 | bar; barnase |
| Maize | MS6 | ACS-ZM005-4 | T3, T18 | bar; barnase |
| Maize | NK603 | MON-00603-6 | T1 | cp4 epsps (aroA:CP4) |
| Maize | T14 | ACS-ZM002-1 | T3 | pat (syn) |
| Maize | T25 | ACS-ZM003-2 | T3 | pat (syn) |
| Maize | TC1507 | DAS-01507-1 | T3, T7 | cry1Fa2; pat |
| Maize | TC6275 | DAS-06275-8 | T3, T7 | mocry1F; bar |
| Maize | VIP1034 | — | T3, T7 | vip3A; pat |
| Maize | 43A47 | DP-043A47-3 | T3, T7 | cry1F; cry34Ab1; cry35Ab1; pat |
| Maize | 40416 | DP-040416-8 | T3, T7 | cry1F; cry34Ab1; cry35Ab1; pat |
| Maize | 32316 | DP-032316-8 | T3, T7 | cry1F; cry34Ab1; cry35Ab1; pat |
| Maize | 4114 | DP-004114-3 | T3, T7 | cry1F; cry34Ab1; cry35Ab1; pat |
| Melon | Melon A | — | T22 | sam-k |
| Melon | Melon B | — | T22 | sam-k |
| Papaya | 55-1 | CUH-CP551-8 | T6 | prsv cp |

| Crop | Event Name | Event Code | Trait(s) | Gene(s) |
| --- | --- | --- | --- | --- |
| Papaya | 63-1 | CUH-CP631-7 | T6 | prsv cp |
| Papaya | Huanong No. 1 | — | T6 | prsv rep |
| Papaya | X17-2 | UFL-X17CP-6 | T6 | prsv cp |
| Plum | C-5 | ARS-PLMC5-6 | T6 | ppv cp |
| Canola** | ZSR500 | — | T1 | cp4 epsps (aroA:CP4); goxv247 |
| Canola** | ZSR502 | — | T1 | cp4 epsps (aroA:CP4); goxv247 |
| Canola** | ZSR503 | — | T1 | cp4 epsps (aroA:CP4); goxv247 |
| Rice | 7Crp#242-95-7 | — | T13 | 7crp |
| Rice | 7Crp#10 | — | T13 | 7crp |
| Rice | GM Shanyou 63 | — | T7 | cry1Ab; cry1Ac |
| Rice | Huahui-1/TT51-1 | — | T7 | cry1Ab; cry1Ac |
| Rice | LLRICE06 | ACS-OS001-4 | T3 | bar |
| Rice | LLRICE601 | BCS-OS003-7 | T3 | bar |
| Rice | LLRICE62 | ACS-OS002-5 | T3 | bar |
| Rice | Tarom molaii + cry1Ab | — | T7 | cry1Ab (truncated) |
| Rice | GAT-OS2 | — | T3 | bar |
| Rice | GAT-OS3 | — | T3 | bar |
| Rice | PE-7 | — | T7 | Cry1Ac |
| Rice | 7Crp#10 | — | T13 | 7crp |
| Rice | KPD627-8 | — | T27 | OASA1D |
| Rice | KPD722-4 | — | T27 | OASA1D |
| Rice | KA317 | — | T27 | OASA1D |
| Rice | HW5 | — | T27 | OASA1D |
| Rice | HW1 | — | T27 | OASA1D |
| Rice | B-4-1-18 | — | T28 | Δ OsBRI1 |
| Rice | G-3-3-22 | — | T29 | OSGA2ox1 |
| Rice | AD77 | — | T6 | DEF |
| Rice | AD51 | — | T6 | DEF |
| Rice | AD48 | — | T6 | DEF |
| Rice | AD41 | — | T6 | DEF |
| Rice | 13pNasNaatAprt1 | — | T30 | HvNAS1; HvNAAT-A; APRT |
| Rice | 13pAprt1 | — | T30 | APRT |
| Rice | gHvNAS1-gHvNAAT-1 | — | T30 | HvNAS1; HvNAAT-A; HvNAAT-B |
| Rice | gHvIDS3-1 | — | T30 | HvIDS3 |
| Rice | gHvNAAT1 | — | T30 | HvNAAT-A; HvNAAT-B |
| Rice | gHvNAS1-1 | — | T30 | HvNAS1 |
| Rice | NIA-OS006-4 | — | T6 | WRKY45 |
| Rice | NIA-OS005-3 | — | T6 | WRKY45 |
| Rice | NIA-OS004-2 | — | T6 | WRKY45 |
| Rice | NIA-OS003-1 | — | T6 | WRKY45 |
| Rice | NIA-OS002-9 | — | T6 | WRKY45 |
| Rice | NIA-OS001-8 | — | T6 | WRKY45 |
| Rice | OsCrl1 | — | T13 | Modified Cry j |
| Rice | 17053 | — | T1 | cp4 epsps (aroA:CP4) |
| Rice | 17314 | — | T1 | cp4 epsps (aroA:CP4) |
| Rose | WKS82/130-4-1 | IFD-52401-4 | T9 | 5AT; bp40 (f3'5'h) |
| Rose | WKS92/130-9-1 | IFD-52901-9 | T9 | 5AT; bp40 (f3'5'h) |
| Soybean | 260-05 (G94-1, G94-19, G168) | — | T9 | gm-fad2-1 (silencing locus) |
| Soybean | A2704-12 | ACS-GM005-3 | T3 | pat |
| Soybean | A2704-21 | ACS-GM004-2 | T3 | pat |
| Soybean | A5547-127 | ACS-GM006-4 | T3 | pat |
| Soybean | A5547-35 | ACS-GM008-6 | T3 | pat |
| Soybean | CV127 | BPS-CV127-9 | T16 | csr1-2 |
| Soybean | DAS68416-4 | DAS68416-4 | T3 | pat |
| Soybean | DP305423 | DP-305423-1 | T11, T31 | gm-fad2-1 (silencing locus); gm-hra |
| Soybean | DP356043 | DP-356043-5 | T1, T31 | gm-fad2-1 (silencing locus); gat4601 |
| Soybean | FG72 | MST-FG072-3 | T32, T1 | 2mepsps; hppdPF W336 |
| Soybean | GTS 40-3-2 (40-3-2) | MON-04032-6 | T1 | cp4 epsps (aroA:CP4) |
| Soybean | GU262 | ACS-GM003-1 | T3 | pat |
| Soybean | MON87701 | MON-87701-2 | T7 | cry1Ac |
| Soybean | MON87705 | MON-87705-6 | T1, T31 | fatb1-A (sense & antisense); fad2-1A (sense & antisense); cp4 epsps (aroA:CP4) |
| Soybean | MON87708 | MON-87708-9 | T1, T12 | dmo; cp4 epsps (aroA:CP4) |
| Soybean | MON87769 | MON-87769-7 | T1, T31 | Pj.D6D; Nc.Fad3; cp4 epsps (aroA:CP4) |
| Soybean | MON89788 | MON-89788-1 | T1 | cp4 epsps (aroA:CP4) |
| Soybean | W62 | ACS-GM002-9 | T3 | bar |
| Soybean | W98 | ACS-GM001-8 | T3 | bar |
| Soybean | MON87754 | MON-87754-1 | T33 | dgat2A |
| Soybean | DAS21606 | DAS-21606 | T34, T3 | Modified aad-12; pat |
| Soybean | DAS44406 | DAS-44406-6 | T1, T3, T34 | Modified aad-12; 2mepsps; pat |
| Soybean | SYHT04R | SYN-0004R-8 | T35 | Modified avhppd |
| Soybean | 9582.814.19.1 | — | T3, T7 | cry1Ac, cry1F, PAT |
| Squash | CZW3 | SEM-ØCZW3-2 | T6 | cmv cp, zymv cp, wmv cp |

-continued

| Crop | Event Name | Event Code | Trait(s) | Gene(s) |
|---|---|---|---|---|
| Squash | ZW20 | SEM-0ZW20-7 | T6 | zymv cp, wmv cp |
| Sugar Beet | GTSB77 (T9100152) | SY-GTSB77-8 | T1 | cp4 epsps (aroA:CP4); goxv247 |
| Sugar Beet | H7-1 | KM-000H71-4 | T1 | cp4 epsps (aroA:CP4) |
| Sugar Beet | T120-7 | ACS-BV001-3 | T3 | pat |
| Sugar Beet | T227-1 | — | T1 | cp4 epsps (aroA:CP4) |
| Sugarcane | NXI-1T | — | T21 | EcbetA |
| Sunflower | X81359 | — | T16 | als |
| Pepper | PK-SP01 | — | T6 | cmv cp |
| Tobacco | C/F/93/08-02 | — | T5 | bxn |
| Tobacco | Vector 21-41 | — | T36 | NtQPT1 (antisense) |
| Sunflower | X81359 | — | T16 | als |
| Wheat | MON71800 | MON-718ØØ-3 | T1 | cp4 epsps (aroA:CP4) |

*Argentine (*Brassica napus*),
**Polish (*B. rapa*),
Eggplant

Treatment of genetically modified plants with compounds of the invention may result in super-additive or synergistic effects. For example, reduction in application rates, broadening of the activity spectrum, increased tolerance to biotic/abiotic stresses or enhanced storage stability may be greater than expected from just simple additive effects of the application of compounds of the invention on genetically modified plants.

Compounds of this invention can also be mixed with one or more other biologically active compounds or agents including herbicides, herbicide safeners, fungicides, insecticides, nematocides, bactericides, acaricides, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Mixtures of the compounds of the invention with other herbicides can broaden the spectrum of activity against additional weed species, and suppress the proliferation of any resistant biotypes. Thus the present invention also pertains to a composition comprising a compound of Formula 1 (in a herbicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

A mixture of one or more of the following herbicides with a compound of this invention may be particularly useful for weed control: acetochlor, acifluorfen and its sodium salt, aclonifen, acrolein (2-propenal), alachlor, alloxydim, ametryn, amicarbazone, amidosulfuron, aminocyclopyrachlor and its esters (e.g., methyl, ethyl) and salts (e.g., sodium, potassium), aminopyralid, amitrole, ammonium sulfamate, anilofos, asulam, atrazine, azimsulfuron, beflubutamid, benazolin, benazolin-ethyl, bencarbazone, benfluralin, benfuresate, bensulfuron-methyl, bensulide, bentazone, benzobicyclon, benzofenap, bicyclopyrone, bifenox, bilanafos, bispyribac and its sodium salt, bromacil, bromobutide, bromofenoxim, bromoxynil, bromoxynil octanoate, butachlor, butafenacil, butamifos, butralin, butroxydim, butylate, cafenstrole, carbetamide, carfentrazone-ethyl, catechin, chlomethoxyfen, chloramben, chlorbromuron, chlorflurenol-methyl, chloridazon, chlorimuron-ethyl, chlorotoluron, chlorpropham, chlorsulfuron, chlorthal-dimethyl, chlorthiamid, cinidon-ethyl, cinmethylin, cinosulfuron, clacyfos, clefoxydim, clethodim, clodinafop-propargyl, clomazone, clomeprop, clopyralid, clopyralid-olamine, cloransulam-methyl, cumyluron, cyanazine, cycloate, cyclopyrimorate, cyclosulfamuron, cycloxydim, cyhalofop-butyl, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, diclosulam, difenzoquat metilsulfate, diflufenican, diflufenzopyr, dimefuron, dimepiperate, dimethachlor, dimethametryn, dimethenamid, dimethenamid-P, dimethipin, dimethylarsinic acid and its sodium salt, dinitramine, dinoterb, diphenamid, diquat dibromide, dithiopyr, diuron, DNOC, endothal, EPTC, esprocarb, ethalfluralin, ethametsulfuron-methyl, ethiozin, ethofumesate, ethoxyfen, ethoxysulfuron, etobenzanid, fenoxaprop-ethyl, fenoxaprop-P-ethyl, fenoxasulfone, fenquinotrione, fentrazamide, fenuron, fenuron-TCA, flamprop-methyl, flamprop-M-isopropyl, flamprop-M-methyl, flazasulfuron, florasulam, fluazifop-butyl, fluazifop-P-butyl, fluazolate, flucarbazone, flucetosulfuron, fluchloralin, flufenacet, flufenpyr, flufenpyr-ethyl, flumetsulam, flumiclorac-pentyl, flumioxazin, fluometuron, fluoroglycofen-ethyl, flupoxam, flupyrsulfuron-methyl and its sodium salt, flurenol, flurenol-butyl, fluridone, flurochloridone, fluroxypyr, flurtamone, fluthiacet-methyl, fomesafen, foramsulfuron, fosamine-ammonium, glufosinate, glufosinate-ammonium, glufosinate-P, glyphosate and its salts such as ammonium, isopropylammonium, potassium, sodium (including sesquisodium) and trimesium (alternatively named sulfosate), halauxifen, halauxifen-methyl, halosulfuron-methyl, haloxyfop-etotyl, haloxyfop-methyl, hexazinone, imazamethabenz-methyl, imazamox, imazapic, imazapyr, imazaquin, imazaquin-ammonium, imazethapyr, imazethapyr-ammonium, imazosulfuron, indanofan, indaziflam, iofensulfuron, iodosulfuron-methyl, ioxynil, ioxynil octanoate, ioxynil-sodium, ipfencarbazone, isoproturon, isouron, isoxaben, isoxaflutole, isoxachlortole, lactofen, lenacil, linuron, maleic hydrazide, MCPA and its salts (e.g., MCPA-dimethylammonium, MCPA-potassium and MCPA-sodium, esters (e.g., MCPA-2-ethylhexyl, MCPA-butotyl) and thioesters (e.g., MCPA-thioethyl), MCPB and its salts (e.g., MCPB-sodium) and esters (e.g., MCPB-ethyl), mecoprop, mecoprop-P, mefenacet, mefluidide, mesosulfuron-methyl, mesotrione, metam-sodium, metamifop, metamitron, metazachlor, metazosulfuron, methabenzthiazuron, methylarsonic acid and its calcium, monoammonium, monosodium and disodium salts, methyldymron, metobenzuron, metobromuron, metolachlor, S-metolachlor, metosulam, metoxuron, metribuzin, metsulfuron-methyl, molinate, monolinuron, naproanilide, napropamide, napropamide-M, naptalam, neburon, nicosulfuron, norflurazon, orbencarb, orthosulfamuron, oryzalin, oxadiargyl, oxadiazon, oxasulfuron, oxaziclomefone, oxyfluorfen, paraquat dichloride, pebulate, pelargonic acid, pendimethalin, penoxsulam, pentanochlor, pentoxazone, perfluidone, pethoxamid, pethoxyamid, phenmedipham, picloram, picloram-potassium, picolinafen, pinoxaden, piperophos, pretilachlor, primisulfuron-methyl, prodiamine, profoxydim, prometon, prometryn, propachlor, propanil, propaquizafop, propazine, propham, propisochlor, propoxycarbazone, propyrisulfuron, propyzamide, prosulfocarb, prosulfuron, pyraclonil, pyraflufen-ethyl, pyrasulfotole, pyrazogyl, pyrazolynate, pyrazoxyfen, pyrazosulfuron-ethyl, pyribenzoxim, pyributicarb, pyridate, pyriftalid, pyriminobac-methyl, pyrimisulfan, pyrithiobac, pyrithiobac-sodium, pyroxasulfone, pyroxsulam, quinclorac, quinmerac, quinoclamine, quizalofop-ethyl, quizalofop-P-ethyl, quizalofop-P-tefuryl, rimsulfuron, saflufenacil, sethoxydim, siduron, simazine, simetryn, sulcotrione, sulfentrazone, sulfometuron-methyl, sulfosulfuron, 2,3,6-TBA, TCA, TCA-sodium, tebutam, tebuthiuron, tefuryltrione, tembotrione, tepraloxydim, terbacil, terbumeton, terbuthylazine, terbutryn, thenylchlor, thiazopyr, thiencarbazone, thifensulfuron-methyl, thiobencarb, tiafenacil, tiocarbazil, topramezone, tralkoxydim, tri-allate, triafamone, triasulfuron, triaziflam, tribenuron-methyl, triclopyr, triclopyr-butotyl, triclopyr-triethylammonium, tridiphane, trietazine, trifloxysulfuron, trifluralin, triflusulfuron-methyl, tritosulfuron, vernolate, 3-(2-chloro-3,6-difluorophenyl)-4-hydroxy-1-methyl-1,5-naphthyridin-2(1H)-one, 5-chloro-3-[(2-hydroxy-6-oxo-1-cyclohexen-1-yl)carbonyl]-1-(4-methoxyphenyl)-2(1H)-quinoxalinone, 2-chloro-N-(1-methyl-1H-tetrazol-5-yl)-6-(trifluoromethyl)-3-pyridinecarboxamide, 7-(3,5-dichloro-4-pyridinyl)-5-(2,2-difluoroethyl)-8-hydroxypyrido[2,3-b]pyrazin-6(5H)-one), 4-(2,6-diethyl-4-methylphenyl)-5-hydroxy-2,6-dimethyl-3(2H)-pyridazinone), 5-[[(2,6-difluorophenyl)methoxy]methyl]-4,5-dihydro-5-methyl-3-(3-methyl-2-thienyl)isoxazole (previously methioxolin), 3-[7-fluoro-3,4-dihydro-3-oxo-4-(2-propyn-1-yl)-2H-1,4-benzoxazin-6-yl]dihydro-1,5-dimethyl-6-thioxo-1,3,5-triazine-2,4(1H,3H)-dione, 4-(4-fluorophenyl)-6-[(2-hydroxy-6-oxo-1-cyclohexen-1-yl)carbonyl]-2-methyl-1,2,4-triazine-3,5(2H,4H)-dione, methyl 4-amino-3-chloro-6-(4-chloro-2-fluoro-3-methoxyphenyl)-5-fluoro-2-pyridinecarboxylate, 2-methyl-3-(methylsulfonyl)-N-(1-methyl-1H-tetrazol-5-yl)-4-(trifluoromethyl)benzamide, and 2-methyl-N-(4-methyl-1,2,5-oxadiazol-3-yl)-3-(methylsulfinyl)-4-(trifluoromethyl)benzamide. Other herbicides also include bioherbicides such as *Alternaria destruens* Simmons, *Colletotrichum gloeosporioides* (Penz.) Penz. & Sacc., *Drechsiera monoceras* (MTB-951), *Myrothecium verrucaria* (Albertini & Schweinitz) Ditmar: Fries, *Phytophthora palmivora* (Butl.) Butl. and *Puccinia thlaspeos* Schub.

Compounds of this invention can also be used in combination with plant growth regulators such as aviglycine, N-(phenylmethyl)-1H-purin-6-amine, epocholeone, gibberellic acid, gibberellin $A_4$ and $A_7$, harpin protein, mepiquat chloride, prohexadione calcium, prohydrojasmon, sodium nitrophenolate and trinexapac-methyl, and plant growth modifying organisms such as *Bacillus cereus* strain BP01.

General references for agricultural protectants (i.e. herbicides, herbicide safeners, insecticides, fungicides, nematocides, acaricides and biological agents) include *The Pesticide Manual*, 13th Edition, C. D. S. Tomlin, Ed., British Crop Protection Council, Farnham, Surrey, U. K., 2003 and *The BioPesticide Manual*, 2nd Edition, L. G. Copping, Ed., British Crop Protection Council, Farnham, Surrey, U. K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of weeds controlled beyond the spectrum controlled by the compound of Formula 1 alone.

In certain instances, combinations of a compound of this invention with other biologically active (particularly herbicidal) compounds or agents (i.e. active ingredients) can result in a greater-than-additive (i.e. synergistic) effect on weeds and/or a less-than-additive effect (i.e. safening) on crops or other desirable plants. Reducing the quantity of active ingredients released in the environment while ensuring effective pest control is always desirable. Ability to use greater amounts of active ingredients to provide more effective weed control without excessive crop injury is also desirable. When synergism of herbicidal active ingredients occurs on weeds at application rates giving agronomically satisfactory levels of weed control, such combinations can be advantageous for reducing crop production cost and decreasing environmental load. When safening of herbicidal active ingredients occurs on crops, such combinations can be advantageous for increasing crop protection by reducing weed competition.

Of note is a combination of a compound of the invention with at least one other herbicidal active ingredient. Of particular note is such a combination where the other herbicidal active ingredient has different site of action from the compound of the invention. In certain instances, a combination with at least one other herbicidal active ingredient having a similar spectrum of control but a different site of action will be particularly advantageous for resistance management. Thus, a composition of the present invention can further comprise (in a herbicidally effective amount) at least one additional herbicidal active ingredient having a similar spectrum of control but a different site of action.

Compounds of this invention can also be used in combination with herbicide safeners such as allidochlor, benoxacor, cloquintocet-mexyl, cumyluron, cyometrinil, cyprosulfonamide, daimuron, dichlormid, dicyclonon, dietholate, dimepiperate, fenchlorazole-ethyl, fenclorim, flurazole, fluxofenim, furilazole, isoxadifen-ethyl, mefenpyr-diethyl, mephenate, methoxyphenone naphthalic anhydride (1,8-naphthalic anhydride), oxabetrinil, N-(aminocarbonyl)-2-methylbenzenesulfonamide, N-(aminocarbonyl)-2-fluorobenzenesulfonamide, 1-bromo-4-[(chloromethyl)sulfonyl]benzene (BCS), 4-(dichloroacetyl)-1-oxa-4-azospiro[4.5]decane (MON 4660), 2-(dichloromethyl)-2- methyl-1,3-dioxolane (MG 191), ethyl 1,6-dihydro-1-(2-methoxyphenyl)-6-oxo-2-phenyl-5-pyrimidinecarboxylate, 2-hydroxy-N,N-dimethyl-6-(trifluoromethyl)pyridine-3-carboxamide, and 3-oxo-1-cyclohexen-1-yl 1-(3,4-dimethylphenyl)-1,6-dihydro-6-oxo-2-phenyl-5-pyrimidinecarboxylate to increase safety to certain crops. Antidotally effective amounts of the herbicide safeners can be applied at the same time as the compounds of this invention, or applied as seed treatments. Therefore an aspect of the present invention relates to a herbicidal mixture comprising a compound of this invention and an antidotally effective amount of a herbicide safener. Seed treatment is particularly useful for selective weed control, because it physically restricts antidoting to the crop plants. Therefore a particularly useful embodiment of the present invention is a method for selectively controlling the growth of undesired vegetation in a crop comprising contacting the locus of the crop with a herbicidally effective amount of a compound of this invention wherein seed from which the crop is grown is treated with an antidotally effective amount of safener. Antidotally effective amounts of safeners can be easily determined by one skilled in the art through simple experimentation.

Of note is a composition comprising a compound of the invention (in a herbicidally effective amount), at least one additional active ingredient selected from the group consisting of other herbicides and herbicide safeners (in an effective amount), and at least one component selected from the group consisting of surfactants, solid diluents and liquid diluents.

Table A1 lists specific combinations of a Component (a) with Component (b) illustrative of the mixtures, compositions and methods of the present invention. Compound 2 in the Component (a) column is identified in Index Table A. The second column of Table A1 lists the specific Component (b) compound (e.g., "2,4-D" in the first line). The third, fourth and fifth columns of Table A1 lists ranges of weight ratios for rates at which the Component (a) compound is typically applied to a field-grown crop relative to Component (b) (i.e. (a):(b)). Thus, for example, the first line of Table A1 specifically discloses the combination of Component (a) (i.e. Compound 2 in Index Table A) with 2,4-D is typically applied in a weight ratio between 1:192-6:1. The remaining lines of Table A1 are to be construed similarly.

TABLE A1

| Component (a) (Compound #) | Component (b) | Typical Weight Ratio | More Typical Weight Ratio | Most Typical Weight Ratio |
|---|---|---|---|---|
| 2 | 2,4-D | 1:192-6:1 | 1:64-2:1 | 1:24-1:3 |
| 2 | Acetochlor | 1:768-2:1 | 1:256-1:2 | 1:96-1:11 |
| 2 | Acifluorfen | 1:96-12:1 | 1:32-4:1 | 1:12-1:2 |
| 2 | Aclonifen | 1:857-2:1 | 1:285-1:3 | 1:107-1:12 |
| 2 | Alachlor | 1:768-2:1 | 1:256-1:2 | 1:96-1:11 |
| 2 | Ametryn | 1:384-3:1 | 1:128-1:1 | 1:48-1:6 |
| 2 | Amicarbazone | 1:192-6:1 | 1:64-2:1 | 1:24-1:3 |
| 2 | Amidosulfuron | 1:6-168:1 | 1:2-56:1 | 1:1-11:1 |
| 2 | Aminocyclopyrachlor | 1:48-24:1 | 1:16-8:1 | 1:6-2:1 |
| 2 | Aminopyralid | 1:20-56:1 | 1:6-19:1 | 1:2-4:1 |
| 2 | Amitrole | 1:768-2:1 | 1:256-1:2 | 1:96-1:11 |
| 2 | Anilofos | 1:96-12:1 | 1:32-4:1 | 1:12-1:2 |
| 2 | Asulam | 1:960-2:1 | 1:320-1:3 | 1:120-1:14 |
| 2 | Atrazine | 1:192-6:1 | 1:64-2:1 | 1:24-1:3 |
| 2 | Azimsulfuron | 1:6-168:1 | 1:2-56:1 | 1:1-11:1 |
| 2 | Beflubutamid | 1:342-4:1 | 1:114-2:1 | 1:42-1:5 |
| 2 | Benfuresate | 1:617-2:1 | 1:205-1:2 | 1:77-1:9 |
| 2 | Bensulfuron-methyl | 1:25-45:1 | 1:8-15:1 | 1:3-3:1 |
| 2 | Bentazone | 1:192-6:1 | 1:64-2:1 | 1:24-1:3 |
| 2 | Benzobicyclon | 1:85-14:1 | 1:28-5:1 | 1:10-1:2 |
| 2 | Benzofenap | 1:257-5:1 | 1:85-2:1 | 1:32-1:4 |
| 2 | Bicyclopyrone | 1:42-27:1 | 1:14-9:1 | 1:5-2:1 |
| 2 | Bifenox | 1:257-5:1 | 1:85-2:1 | 1:32-1:4 |
| 2 | Bispyribac-sodium | 1:10-112:1 | 1:3-38:1 | 1:1-7:1 |
| 2 | Bromacil | 1:384-3:1 | 1:128-1:1 | 1:48-1:6 |
| 2 | Bromobutide | 1:384-3:1 | 1:128-1:1 | 1:48-1:6 |
| 2 | Bromoxynil | 1:96-12:1 | 1:32-4:1 | 1:12-1:2 |
| 2 | Butachlor | 1:768-2:1 | 1:256-1:2 | 1:96-1:11 |
| 2 | Butafenacil | 1:42-27:1 | 1:14-9:1 | 1:5-2:1 |
| 2 | Butylate | 1:1542-1:2 | 1:514-1:5 | 1:192-1:22 |
| 2 | Carfenstrole | 1:192-6:1 | 1:64-2:1 | 1:24-1:3 |
| 2 | Carfentrazone-ethyl | 1:128-9:1 | 1:42-3:1 | 1:16-1:2 |
| 2 | Chlorimuron-ethyl | 1:8-135:1 | 1:2-45:1 | 1:1-9:1 |
| 2 | Chlorotoluron | 1:768-2:1 | 1:256-1:2 | 1:96-1:11 |
| 2 | Chlorsulfuron | 1:6-168:1 | 1:2-56:1 | 1:1-11:1 |
| 2 | Cincosulfuron | 1:17-68:1 | 1:5-23:1 | 1:2-5:1 |
| 2 | Cinidon-ethyl | 1:384-3:1 | 1:128-1:1 | 1:48-1:6 |
| 2 | Cinmethylin | 1:34-34:1 | 1:11-12:1 | 1:4-3:1 |
| 2 | Clacyfos | 1:34-34:1 | 1:11-12:1 | 1:4-3:1 |
| 2 | Clethodim | 1:48-24:1 | 1:16-8:1 | 1:6-2:1 |
| 2 | Clodinafop-propargyl | 1:20-56:1 | 1:6-19:1 | 1:2-4:1 |
| 2 | Clomazone | 1:384-3:1 | 1:128-1:1 | 1:48-1:6 |
| 2 | Clomeprop | 1:171-7:1 | 1:57-3:1 | 1:21-1:3 |
| 2 | Clopyralid | 1:192-6:1 | 1:64-2:1 | 1:24-1:3 |
| 2 | Cloransulam-methyl | 1:12-96:1 | 1:4-32:1 | 1:1-6:1 |
| 2 | Cumyluron | 1:384-3:1 | 1:128-1:1 | 1:48-1:6 |
| 2 | Cyanazine | 1:384-3:1 | 1:128-1:1 | 1:48-1:6 |
| 2 | Cyclopyrimorate | 1:17-68:1 | 1:5-23:1 | 1:2-5:1 |
| 2 | Cyclosulfamuron | 1:17-68:1 | 1:5-23:1 | 1:2-5:1 |
| 2 | Cycloxydim | 1:96-12:1 | 1:32-4:1 | 1:12-1:2 |

TABLE A1-continued

| Component (a) (Compound #) | Component (b) | Typical Weight Ratio | More Typical Weight Ratio | Most Typical Weight Ratio |
|---|---|---|---|---|
| 2 | Cyhalofop | 1:25-45:1 | 1:8-15:1 | 1:3-3:1 |
| 2 | Daimuron | 1:192-6:1 | 1:64-2:1 | 1:24-1:3 |
| 2 | Desmedipham | 1:322-4:1 | 1:107-2:1 | 1:40-1:5 |
| 2 | Dicamba | 1:192-6:1 | 1:64-2:1 | 1:24-1:3 |
| 2 | Dichlobenil | 1:1371-1:2 | 1:457-1:4 | 1:171-1:20 |
| 2 | Dichlorprop | 1:925-2:1 | 1:308-1:3 | 1:115-1:13 |
| 2 | Diclofop-methyl | 1:384-3:1 | 1:128-1:1 | 1:48-1:6 |
| 2 | Diclosulam | 1:10-112:1 | 1:3-38:1 | 1:1-7:1 |
| 2 | Difenzoquat | 1:288-4:1 | 1:96-2:1 | 1:36-1:4 |
| 2 | Diflufenican | 1:857-2:1 | 1:285-1:3 | 1:107-1:12 |
| 2 | Diflufenzopyr | 1:12-96:1 | 1:4-32:1 | 1:1-6:1 |
| 2 | Dimethachlor | 1:768-2:1 | 1:256-1:2 | 1:96-1:11 |
| 2 | Dimethametryn | 1:192-6:1 | 1:64-2:1 | 1:24-1:3 |
| 2 | Dimethenamid-P | 1:384-3:1 | 1:128-1:1 | 1:48-1:6 |
| 2 | Dithiopyr | 1:192-6:1 | 1:64-2:1 | 1:24-1:3 |
| 2 | Diuron | 1:384-3:1 | 1:128-1:1 | 1:48-1:6 |
| 2 | EPTC | 1:768-2:1 | 1:256-1:2 | 1:96-1:11 |
| 2 | Esprocarb | 1:1371-1:2 | 1:457-1:4 | 1:171-1:20 |
| 2 | Ethalfluralin | 1:384-3:1 | 1:128-1:1 | 1:48-1:6 |
| 2 | Ethametsulfuron-methyl | 1:17-68:1 | 1:5-23:1 | 1:2-5:1 |
| 2 | Ethoxyfen | 1:8-135:1 | 1:2-45:1 | 1:1-9:1 |
| 2 | Ethoxysulfuron | 1:20-56:1 | 1:6-19:1 | 1:2-4:1 |
| 2 | Etobenzanid | 1:257-5:1 | 1:85-2:1 | 1:32-1:4 |
| 2 | Fenoxaprop-ethyl | 1:120-10:1 | 1:40-4:1 | 1:15-1:2 |
| 2 | Fenoxasulfone | 1:85-14:1 | 1:28-5:1 | 1:10-1:2 |
| 2 | Fenquinotrione | 1:17-68:1 | 1:5-23:1 | 1:2-5:1 |
| 2 | Fentrazamide | 1:17-68:1 | 1:5-23:1 | 1:2-5:1 |
| 2 | Flazasulfuron | 1:17-68:1 | 1:5-23:1 | 1:2-5:1 |
| 2 | Florasulam | 1:2-420:1 | 1:1-140:1 | 2:1-27:1 |
| 2 | Fluazifop-butyl | 1:192-6:1 | 1:64-2:1 | 1:24-1:3 |
| 2 | Flucarbazone | 1:8-135:1 | 1:2-45:1 | 1:1-9:1 |
| 2 | Flucetosulfuron | 1:8-135:1 | 1:2-45:1 | 1:1-9:1 |
| 2 | Flufenacet | 1:257-5:1 | 1:85-2:1 | 1:32-1:4 |
| 2 | Flumetsulam | 1:24-48:1 | 1:8-16:1 | 1:3-3:1 |
| 2 | Flumiclorac-pentyl | 1:10-112:1 | 1:3-38:1 | 1:1-7:1 |
| 2 | Flumioxazin | 1:25-45:1 | 1:8-15:1 | 1:3-3:1 |
| 2 | Fluometuron | 1:384-3:1 | 1:128-1:1 | 1:48-1:6 |
| 2 | Flupyrsulfuron-methyl | 1:3-336:1 | 1:1-112:1 | 2:1-21:1 |
| 2 | Fluridone | 1:384-3:1 | 1:128-1:1 | 1:48-1:6 |
| 2 | Fluroxypyr | 1:96-12:1 | 1:32-4:1 | 1:12-1:2 |
| 2 | Flurtamone | 1:857-2:1 | 1:285-1:3 | 1:107-1:12 |
| 2 | Fluthiacet-methyl | 1:48-42:1 | 1:16-14:1 | 1:3-3:1 |
| 2 | Fomesafen | 1:96-12:1 | 1:32-4:1 | 1:12-1:2 |
| 2 | Foramsulfuron | 1:13-84:1 | 1:4-28:1 | 1:1-6:1 |
| 2 | Glufosinate | 1:288-4:1 | 1:96-2:1 | 1:36-1:4 |
| 2 | Glyphosate | 1:288-4:1 | 1:96-2:1 | 1:36-1:4 |
| 2 | Halauxifen | 1:20-56:1 | 1:6-19:1 | 1:2-4:1 |
| 2 | Halauxifen-methyl | 1:20-56:1 | 1:6-19:1 | 1:2-4:1 |
| 2 | Halosulfuron-methyl | 1:17-68:1 | 1:5-23:1 | 1:2-5:1 |
| 2 | Haloxyfop-methyl | 1:34-34:1 | 1:11-12:1 | 1:4-3:1 |
| 2 | Hexazinone | 1:192-6:1 | 1:64-2:1 | 1:24-1:3 |
| 2 | Imazamox | 1:13-84:1 | 1:4-28:1 | 1:1-6:1 |
| 2 | Imazapic | 1:20-56:1 | 1:6-19:1 | 1:2-4:1 |
| 2 | Imazapyr | 1:85-14:1 | 1:28-5:1 | 1:10-1:2 |
| 2 | Imazaquin | 1:34-34:1 | 1:11-12:1 | 1:4-3:1 |
| 2 | Imazethabenz-methyl | 1:171-7:1 | 1:57-3:1 | 1:21-1:3 |
| 2 | Imazethapyr | 1:24-48:1 | 1:8-16:1 | 1:3-3:1 |
| 2 | Imazosulfuron | 1:27-42:1 | 1:9-14:1 | 1:3-3:1 |
| 2 | Indanofan | 1:342-4:1 | 1:114-2:1 | 1:42-1:5 |
| 2 | Indaziflam | 1:25-45:1 | 1:8-15:1 | 1:3-3:1 |
| 2 | Iodosulfuron-methyl | 1:3-336:1 | 1:1-112:1 | 2:1-21:1 |
| 2 | Ioxynil | 1:192-6:1 | 1:64-2:1 | 1:24-1:3 |
| 2 | Ipfencarbazone | 1:85-14:1 | 1:28-5:1 | 1:10-1:2 |
| 2 | Isoproturon | 1:384-3:1 | 1:128-1:1 | 1:48-1:6 |
| 2 | Isoxaben | 1:288-4:1 | 1:96-2:1 | 1:36-1:4 |
| 2 | Isoxaflutole | 1:60-20:1 | 1:20-7:1 | 1:7-2:1 |
| 2 | Lactofen | 1:42-27:1 | 1:14-9:1 | 1:5-2:1 |
| 2 | Lenacil | 1:384-3:1 | 1:128-1:1 | 1:48-1:6 |
| 2 | Linuron | 1:384-3:1 | 1:128-1:1 | 1:48-1:6 |
| 2 | MCPA | 1:192-6:1 | 1:64-2:1 | 1:24-1:3 |
| 2 | MCPB | 1:288-4:1 | 1:96-2:1 | 1:36-1:4 |
| 2 | Mecoprop | 1:768-2:1 | 1:256-1:2 | 1:96-1:11 |

TABLE A1-continued

| Component (a)<br>(Compound #) | Component (b) | Typical<br>Weight Ratio | More Typical<br>Weight Ratio | Most Typical<br>Weight Ratio |
|---|---|---|---|---|
| 2 | Mefenacet | 1:384-3:1 | 1:128-1:1 | 1:48-1:6 |
| 2 | Mefluidide | 1:192-6:1 | 1:64-2:1 | 1:24-1:3 |
| 2 | Mesosulfuron-methyl | 1:5-224:1 | 1:1-75:1 | 1:1-14:1 |
| 2 | Mesotrione | 1:42-27:1 | 1:14-9:1 | 1:5-2:1 |
| 2 | Metamifop | 1:42-27:1 | 1:14-9:1 | 1:5-2:1 |
| 2 | Metazachlor | 1:384-3:1 | 1:128-1:1 | 1:48-1:6 |
| 2 | Metazosulfuron | 1:25-45:1 | 1:8-15:1 | 1:3-3:1 |
| 2 | Methabenzthiazuron | 1:768-2:1 | 1:256-1:2 | 1:96-1:11 |
| 2 | Metolachlor | 1:768-2:1 | 1:256-1:2 | 1:96-1:11 |
| 2 | Metosulam | 1:8-135:1 | 1:2-45:1 | 1:1-9:1 |
| 2 | Metribuzin | 1:192-6:1 | 1:64-2:1 | 1:24-1:3 |
| 2 | Metsulfuron-methyl | 1:2-560:1 | 1:1-187:1 | 3:1-35:1 |
| 2 | Molinate | 1:1028-2:1 | 1:342-1:3 | 1:128-1:15 |
| 2 | Napropamide | 1:384-3:1 | 1:128-1:1 | 1:48-1:6 |
| 2 | Napropamide-M | 1:192-6:1 | 1:64-2:1 | 1:24-1:3 |
| 2 | Naptalam | 1:192-6:1 | 1:64-2:1 | 1:24-1:3 |
| 2 | Nicosulfuron | 1:12-96:1 | 1:4-32:1 | 1:1-6:1 |
| 2 | Norflurazon | 1:1152-1:1 | 1:384-1:3 | 1:144-1:16 |
| 2 | Orbencarb | 1:1371-1:2 | 1:457-1:4 | 1:171-1:20 |
| 2 | Orthosulfamuron | 1:20-56:1 | 1:6-19:1 | 1:2-4:1 |
| 2 | Oryzalin | 1:514-3:1 | 1:171-1:2 | 1:64-1:8 |
| 2 | Oxadiargyl | 1:384-3:1 | 1:128-1:1 | 1:48-1:6 |
| 2 | Oxadiazon | 1:548-3:1 | 1:182-1:2 | 1:68-1:8 |
| 2 | Oxasulfuron | 1:27-42:1 | 1:9-14:1 | 1:3-3:1 |
| 2 | Oxaziclomefone | 1:42-27:1 | 1:14-9:1 | 1:5-2:1 |
| 2 | Oxyfluorfen | 1:384-3:1 | 1:128-1:1 | 1:48-1:6 |
| 2 | Paraquat | 1:192-6:1 | 1:64-2:1 | 1:24-1:3 |
| 2 | Pendimethalin | 1:384-3:1 | 1:128-1:1 | 1:48-1:6 |
| 2 | Penoxsulam | 1:10-112:1 | 1:3-38:1 | 1:1-7:1 |
| 2 | Penthoxamid | 1:384-3:1 | 1:128-1:1 | 1:48-1:6 |
| 2 | Pentoxazone | 1:102-12:1 | 1:34-4:1 | 1:12-1:2 |
| 2 | Phenmedipham | 1:102-12:1 | 1:34-4:1 | 1:12-1:2 |
| 2 | Picloram | 1:96-12:1 | 1:32-4:1 | 1:12-1:2 |
| 2 | Picolinafen | 1:34-34:1 | 1:11-12:1 | 1:4-3:1 |
| 2 | Pinoxaden | 1:25-45:1 | 1:8-15:1 | 1:3-3:1 |
| 2 | Pretilachlor | 1:192-6:1 | 1:64-2:1 | 1:24-1:3 |
| 2 | Primisulfuron-methyl | 1:8-135:1 | 1:2-45:1 | 1:1-9:1 |
| 2 | Prodiamine | 1:384-3:1 | 1:128-1:1 | 1:48-1:6 |
| 2 | Profoxydim | 1:42-27:1 | 1:14-9:1 | 1:5-2:1 |
| 2 | Prometryn | 1:384-3:1 | 1:128-1:1 | 1:48-1:6 |
| 2 | Propachlor | 1:1152-1:1 | 1:384-1:3 | 1:144-1:16 |
| 2 | Propanil | 1:384-3:1 | 1:128-1:1 | 1:48-1:6 |
| 2 | Propaquizafop | 1:48-24:1 | 1:16-8:1 | 1:6-2:1 |
| 2 | Propoxycarbazone | 1:17-68:1 | 1:5-23:1 | 1:2-5:1 |
| 2 | Propyrisulfuron | 1:17-68:1 | 1:5-23:1 | 1:2-5:1 |
| 2 | Propyzamide | 1:384-3:1 | 1:128-1:1 | 1:48-1:6 |
| 2 | Prosulfocarb | 1:1200-1:2 | 1:400-1:4 | 1:150-1:17 |
| 2 | Prosulfuron | 1:6-168:1 | 1:2-56:1 | 1:1-11:1 |
| 2 | Pyraclonil | 1:42-27:1 | 1:14-9:1 | 1:5-2:1 |
| 2 | Pyraflufen-ethyl | 1:5-224:1 | 1:1-75:1 | 1:1-14:1 |
| 2 | Pyrasulfotole | 1:13-84:1 | 1:4-28:1 | 1:1-6:1 |
| 2 | Pyrazolynate | 1:857-2:1 | 1:285-1:3 | 1:107-1:12 |
| 2 | Pyrazosulfuron-ethyl | 1:10-112:1 | 1:3-38:1 | 1:1-7:1 |
| 2 | Pyrazoxyfen | 1:5-224:1 | 1:1-75:1 | 1:1-14:1 |
| 2 | Pyribenzoxim | 1:10-112:1 | 1:3-38:1 | 1:1-7:1 |
| 2 | Pyributicarb | 1:384-3:1 | 1:128-1:1 | 1:48-1:6 |
| 2 | Pyridate | 1:288-4:1 | 1:96-2:1 | 1:36-1:4 |
| 2 | Pyriftalid | 1:10-112:1 | 1:3-38:1 | 1:1-7:1 |
| 2 | Pyriminobac-methyl | 1:20-56:1 | 1:6-19:1 | 1:2-4:1 |
| 2 | Pyrimisulfan | 1:17-68:1 | 1:5-23:1 | 1:2-5:1 |
| 2 | Pyrithiobac | 1:24-48:1 | 1:8-16:1 | 1:3-3:1 |
| 2 | Pyroxasulfone | 1:85-14:1 | 1:28-5:1 | 1:10-1:2 |
| 2 | Pyroxsulam | 1:5-224:1 | 1:1-75:1 | 1:1-14:1 |
| 2 | Quinclorac | 1:192-6:1 | 1:64-2:1 | 1:24-1:3 |
| 2 | Quizalofop-ethyl | 1:42-27:1 | 1:14-9:1 | 1:5-2:1 |
| 2 | Rimsulfuron | 1:13-84:1 | 1:4-28:1 | 1:1-6:1 |
| 2 | Saflufenacil | 1:25-45:1 | 1:8-15:1 | 1:3-3:1 |
| 2 | Sethoxydim | 1:96-12:1 | 1:32-4:1 | 1:12-1:2 |
| 2 | Simazine | 1:384-3:1 | 1:128-1:1 | 1:48-1:6 |

TABLE A1-continued

| Component (a) (Compound #) | Component (b) | Typical Weight Ratio | More Typical Weight Ratio | Most Typical Weight Ratio |
|---|---|---|---|---|
| 2 | Sulcotrione | 1:120-10:1 | 1:40-4:1 | 1:15-1:2 |
| 2 | Sulfentrazone | 1:147-8:1 | 1:49-3:1 | 1:18-1:3 |
| 2 | Sulfometuron-methyl | 1:34-34:1 | 1:11-12:1 | 1:4-3:1 |
| 2 | Sulfosulfuron | 1:8-135:1 | 1:2-45:1 | 1:1-9:1 |
| 2 | Tebuthiuron | 1:384-3:1 | 1:128-1:1 | 1:48-1:6 |
| 2 | Tefuryltrione | 1:42-27:1 | 1:14-9:1 | 1:5-2:1 |
| 2 | Tembotrione | 1:31-37:1 | 1:10-13:1 | 1:3-3:1 |
| 2 | Tepraloxydim | 1:25-45:1 | 1:8-15:1 | 1:3-3:1 |
| 2 | Terbacil | 1:288-4:1 | 1:96-2:1 | 1:36-1:4 |
| 2 | Terbuthylazine | 1:857-2:1 | 1:285-1:3 | 1:107-1:12 |
| 2 | Terbutryn | 1:192-6:1 | 1:64-2:1 | 1:24-1:3 |
| 2 | Thenylchlor | 1:85-14:1 | 1:28-5:1 | 1:10-1:2 |
| 2 | Thiazopyr | 1:384-3:1 | 1:128-1:1 | 1:48-1:6 |
| 2 | Thiencarbazone | 1:3-336:1 | 1:1-112:1 | 2:1-21:1 |
| 2 | Thifensulfuron-methyl | 1:5-224:1 | 1:1-75:1 | 1:1-14:1 |
| 2 | Tiafenacil | 1:17-68:1 | 1:5-23:1 | 1:2-5:1 |
| 2 | Thiobencarb | 1:768-2:1 | 1:256-1:2 | 1:96-1:11 |
| 2 | Topramezone | 1:6-168:1 | 1:2-56:1 | 1:1-11:1 |
| 2 | Tralkoxydim | 1:68-17:1 | 1:22-6:1 | 1:8-2:1 |
| 2 | Triallate | 1:768-2:1 | 1:256-1:2 | 1:96-1:11 |
| 2 | Triasulfuron | 1:5-224:1 | 1:1-75:1 | 1:1-14:1 |
| 2 | Triaziflam | 1:171-7:1 | 1:57-3:1 | 1:21-1:3 |
| 2 | Tribenuron-methyl | 1:3-336:1 | 1:1-112:1 | 2:1-21:1 |
| 2 | Triclopyr | 1:192-6:1 | 1:64-2:1 | 1:24-1:3 |
| 2 | Trifloxysulfuron | 1:2-420:1 | 1:1-140:1 | 2:1-27:1 |
| 2 | Trifluralin | 1:288-4:1 | 1:96-2:1 | 1:36-1:4 |
| 2 | Triflusulfuron-methyl | 1:17-68:1 | 1:5-23:1 | 1:2-5:1 |
| 2 | Tritosulfuron | 1:13-84:1 | 1:4-28:1 | 1:1-6:1 |

Table A2 is constructed the same as Table A1 above except that entries below the "Component (a)" column heading are replaced with the respective Component (a) Column Entry shown below. Compound 2 in the Component (a) column is identified in Index Table A. Thus, for example, in Table A2 the entries below the "Component (a)" column heading all recite "Compound 7" (i.e. Compound 5 identified in Index Table A), and the first line below the column headings in Table A2 specifically discloses a mixture of Compound 5 with 2,4-D. Tables A3 through A20 are constructed similarly.

| Table Number | Component (a) Column Entries |
|---|---|
| A2 | Compound 5 |
| A3 | Compound 7 |
| A4 | Compound 10 |
| A5 | Compound 18 |
| A6 | Compound 52 |
| A7 | Compound 54 |
| A8 | Compound 58 |
| A9 | Compound 59 |
| A10 | Compound 141 |
| A11 | Compound 166 |
| A12 | Compound 147 |
| A13 | Compound 79 |
| A14 | Compound 178 |
| A15 | Compound 274 |
| A16 | Compound 138 |
| A17 | Compound 194 |
| A18 | Compound 253 |
| A19 | Compound 252 |
| A20 | Compound 305 |

Preferred for better control of undesired vegetation (e.g., lower use rate such as from synergism, broader spectrum of weeds controlled, or enhanced crop safety) or for preventing the development of resistant weeds are mixtures of a compound of this invention with a herbicide selected from the group consisting of aminocyclopyrachlor, diuron, hexazinone, nicosulfuron, chlorimuron-ethyl, metsulfuron-methyl, thifensulfuron-methyl and tribenuron.

The following Tests demonstrate the control efficacy of the compounds of this invention against specific weeds. The weed control afforded by the compounds is not limited, however, to these species. See Index Tables A for compound descriptions. The following abbreviations are used in the Index Table A which follow: c is cyclo, Me is methyl, Et is ethyl, Pr is propyl, i-Pr is isopropyl, t-Bu is tert-butyl, —CN is cyano, —$NO_2$ is nitro. The abbreviation "Ex." stands for "Example" and is followed by a number indicating in which example the compound is prepared.

Representative compounds of this invention prepared by the methods described herein are shown in Index Table A. See Index Table B for $^1$H NMR data. For mass spectral data (AP$^+$(M+1)), the numerical value reported is the molecular weight of the parent molecular ion (M) formed by addition of H+(molecular weight of 1) to the molecule to give a M+1 peak observed by mass spectrometry using atmospheric pressure chemical ionization (AP$^+$). The alternate molecular ion peaks (e.g., M+2 or M+4) that occur with compounds containing multiple halogens are not reported. The reported M+1 peaks were observed by mass spectrometry using atmospheric pressure chemical ionization (AP$^+$) or electrospray ionization (ESI).

INDEX TABLE A

[Structure 1: A bicyclic scaffold with a 5-membered ring containing Y1, Y2, Y3, Y4, N attached to a benzene ring (positions 3,4,5,6) bearing (R3)m, connected via Z to a pyrimidine bearing R2]

| Cmpd No. | Y¹ | Y² | Y³ | Y⁴ | Z | R² | (R³)ₘ | mp or MS |
|---|---|---|---|---|---|---|---|---|
| 1 | N | CCF₃ | CH | CH | O | Br | H (m is 0) | * |
| 2 | N | CCF₃ | CH | CH | O | Cl | H (m is 0) | * |
| 3 | N | CH | CCl | CH | O | Cl | H (m is 0) | * |
| 4 | N | CCF₃ | CH | CH | O | CF₃ | H (m is 0) | * |
| 5 | N | CH | CCl | CH | O | Br | H (m is 0) | * |
| 6 | N | CH | CCl | CH | O | CF₃ | H (m is 0) | * |
| 7 | N | CH | CBr | CH | O | Cl | H (m is 0) | * |
| 8 | N | CH | CBr | CH | O | Br | H (m is 0) | * |
| 9 | N | CH | CBr | CH | O | CH₃ | H (m is 0) | * |
| 10 | N | CH | CBr | CH | O | F | H (m is 0) | * |
| 11 | N | CH | CCl | CH | O | F | H (m is 0) | * |
| 12 | N | CH | CH | CH | O | Cl | H (m is 0) | * |
| 13 | N | CH | CH | CH | O | Br | H (m is 0) | * |
| 14 | N | CH | CH | CH | O | F | H (m is 0) | * |
| 15 | N | CH | CCl | CH | O | CH₃ | H (m is 0) | * |
| 16 | N | CH | CCF₃ | CH | O | Cl | H (m is 0) | * |
| 17 | N | CH | CCF₃ | CH | O | CF₃ | H (m is 0) | * |
| 18 | N | CH | CCF₃ | CH | O | Br | H (m is 0) | * |
| 19 | N | CBr | CBr | CH | O | Cl | H (m is 0) | * |
| 20 | N | CBr | CH | CH | O | Br | H (m is 0) | * |
| 21 | N | CBr | CH | CH | O | Cl | H (m is 0) | * |
| 22 | N | CH | CPh | CH | O | Cl | H (m is 0) | * |
| 23 | N | CH | CCH₃ | CH | O | Cl | H (m is 0) | * |
| 24 | N | CBr | CBr | CH | O | Br | H (m is 0) | * |
| 25 | N | CH | Cl | CH | O | Cl | H (m is 0) | * |
| 26 | N | CH | Cl | CH | O | C | H (m is 0) | * |
| 27 | N | CH | CCH=CHCH₃ | CH | O | Cl | H (m is 0) | * |
| 28 | N | CCF₃ | CH | CH | S | Cl | H (m is 0) | 357 |
| 29 | N | C(t-Bu) | CH | CH | O | Cl | H (m is 0) | * |
| 30 | N | C(t-Bu) | CH | CH | O | Br | H (m is 0) | * |
| 31 | N | CH | CCH=CH₂ | CH | O | Cl | H (m is 0) | * |
| 32 | N | CH | C(CH₃)=CH₂ | CH | O | Cl | H (m is 0) | * |
| 33 | N | CH | CCN | CH | O | Cl | H (m is 0) | * |
| 34 | CH | N | CBr | CH | O | Cl | H (m is 0) | * |
| 35 | N | CH | CBr | CH | O | Cl | 5-OCH₃ | 323 |
| 36 | N | CCH₃ | CH | CH | O | Cl | H (m is 0) | * |
| 37 | N | CCH₃ | CBr | CH | O | Cl | H (m is 0) | * |
| 38 | N | CCH₃ | Cl | CH | O | Cl | H (m is 0) | * |
| 39 | N | CCH₃ | CCl | CH | O | Cl | H (m is 0) | * |
| 40 | N | CH | CBr | CH | O | Cl | 4-CH₃ | 366 |
| 41 | N | CH | CBr | CH | O | Cl | 6-OCH₃ | 382 |
| 42 | N | CH | CBr | CH | O | Cl | 4-OCH₃ | 382 |
| 43 | N | CH | CBr | CH | O | Br | 4-OCH₃ | 425 |
| 44 | N | CH | CBr | CH | O | Cl | 3-CH₃ | 366 |
| 45 | N | CH | CBr | CH | O | Br | 3-CH₃ | 411 |
| 46 | N | CBr | N | CH | O | Cl | H (m is 0) | * |
| 47 | N | CH | CCF₃ | CH | O | F | H (m is 0) | * |
| 48 | N | CH | CBr | CH | O | Cl | 4-CF₃ | 420 |
| 49 | N | CH | CH | CH | O | Cl | 5-Cl | * |
| 50 | N | CH | CH | CH | O | Br | 5-Cl | * |
| 51 | N | CH | CBr | CH | O | Cl | 5-Cl | * |
| 52 | N | CH | CBr | CH | O | Cl | 3-CN | 376 |
| 53 | N | CH | CBr | CH | O | Cl | 4-F | 124-127 |
| 54 | N | CBr | CH | N | O | Cl | H (m is 0) | 352 |
| 55 | N | CCN | CH | N | O | Cl | H (m is 0) | 299 |
| 56 | N | CCN | CH | N | O | Br | H (m is 0) | * |
| 57 | N | CH | CBr | CH | O | Br | 3-CN | 422 |
| 58 | N | CH | CCF₃ | CH | O | Cl | 3-CN | * |
| 59 | N | CH | CCF₃ | CH | O | Br | 3-CN | * |
| 60 | N | CH | CBr | CH | O | I | 3-CN | 470 |
| 61 | N | CH | CBr | CH | O | Cl | 3-CHO | 379 |
| 62 | N | CH | CBr | CH | O | F | 3-CN | 362 |

INDEX TABLE A-continued

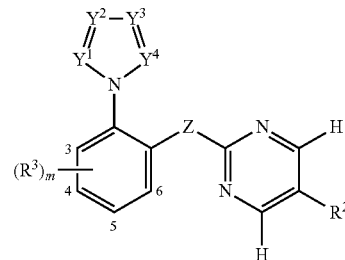

| Cmpd No. | Y¹ | Y² | Y³ | Y⁴ | Z | R² | (R³)ₘ | mp or MS |
|---|---|---|---|---|---|---|---|---|
| 63 | N | CH | CBr | CH | O | Cl | 3-NO2 | 398 |
| 64 | N | CH | CBr | CH | O | Cl | 3-CF₃ | 420 |
| 65 | N | CH | CBr | CH | O | Cl | 3-Br | * |
| 66 | N | CH | CBr | CH | O | Cl | 3-I | * |
| 67 | N | CH | CBr | CH | O | Cl | 3-O(C=O)CH₃ | * |
| 68 | N | CH | CBr | CH | O | Cl | 3-OH | * |
| 69 | N | CH | CBr | CH | O | Cl | 3-OCH₂CF₃ | * |
| 70 | N | CH | CBr | CH | O | Cl | 3-OCH₂CN | 406 |
| 71 | N | CH | CCl | CH | O | Br | 3-CN | 378 |
| 72 | N | CH | CCl | CH | O | Cl | 3-CN | 332 |
| 73 | N | CH | CCl | CH | O | F | 3-CN | 316 |
| 74 | CH | CBr | N | CH | O | Cl | 3-CN | * |
| 75 | N | CH | CCl | CH | O | I | 3-CN | 424 |
| 76 | N | CH | CBr | CH | O | CH₃ | 3-CN | 358 |
| 77 | N | CH | CBr | CH | O | Br | 3-CF₃ | 465 |
| 78 | N | CH | CBr | CH | O | Cl | 3-OCF₃ | 436 |
| 79 | N | CH | CCF₃ | CH | O | F | 3-CN | * |
| 80 | N | CH | CF₂H | CH | O | Cl | H (m is 0) | * |
| 81 | N | CH | CF₂H | CH | O | Br | H (m is 0) | * |
| 82 | N | CH | C(t-Bu) | CH | O | Cl | 3-CN | 354 |
| 83 | N | CH | CBr | CH | O | Cl | 3-CH₂F | 384 |
| 84 | N | N | COEt | CH | O | Cl | 3-Br | 398 |
| 85 | N | CH | C(i-Pr) | CH | O | Cl | 3-CN | 340 |
| 86 | N | CH | Cl | CH | O | F | 3-CN | 408 |
| 87 | N | CH | Cl | CH | O | I | 3-CN | 516 |
| 88 | N | CH | Cl | CH | O | Br | 3-CN | 470 |
| 89 | N | CH | COEt | CH | O | F | 3-CN | * |
| 90 | N | CH | CCN | CH | O | CH₃ | 3-CN | 303 |
| 91 | N | CH | CCN | CH | O | I | 3-CN | 415 |
| 92 | N | CH | COEt | CH | O | Cl | 3-CN | 342 |
| 93 | N | CH | CCl | CH | O | F | 3-CHO | 319 |
| 94 | N | CH | CCl | CH | O | F | 3-CHF₂ | 341 |
| 95 | N | CH | CCH₃ | CH | O | Cl | 3-CN | 311 |
| 96 | N | CH | CBr | CH | O | Cl | 3-C(=O)CH₃ | 395 |
| 97 | N | CH | COCHF₂ | CH | O | Cl | 3-CN | 364 |
| 98 | N | CH | COCHF₂ | CH | O | Cl | H (m is 0) | 339 |
| 99 | N | CH | COCH₂CHF₂ | CH | O | Cl | 3-CN | * |
| 100 | CH | N | CH | CH | O | Cl | H (m is 0) | 273 |
| 101 | N | CH | COCHF₂ | CH | O | F | 3-Cl | * |
| 102 | N | N | C(cyclohexyl) | CH | O | Cl | 3-F | 374 |
| 103 | N | CH | CO(i-Pr) | CH | O | Cl | 3-Cl | * |
| 104 | N | CH | CCF₃ | CH | O | Cl | 3-I | 467 |
| 105 | N | CH | CCHF₂ | CH | O | Cl | 3-I | * |
| 106 | N | N | C(cyclopentyl) | CH | O | Cl | 3-F | 360 |
| 107 | N | N | CCH₂CH(Me)₂ | CH | O | Cl | 3-F | 348 |
| 108 | N | N | CCH₂CH₂F | CH | O | Cl | 3-F | 338 |
| 109 | N | CH | COCH₂CF₃ | CH | O | F | 3-Cl | 389 |
| 110 | N | CH | COCH₂CF₃ | CH | O | Cl | 3-Cl | * |
| 111 | N | CH | CCN | CH | O | F | 3-CN | * |
| 112 | N | CH | CBr | CH | O | F | 3-CHF₂ | 386 |
| 113 | N | CH | CBr | CH | O | CF₃ | 3-CN | 410 |
| 114 | N | N | CC(=CH₂)CH₃ | CH | O | Cl | 3-Br | 394 |
| 115 | N | N | CC(=NOH)CH₃ | CH | O | Cl | 3-Br | 411 |
| 116 | N | N | CCN | CH | O | Cl | 3-Br | 377 |
| 117 | N | N | CI | CH | O | Cl | 3-Br | 480 |
| 118 | N | CH | CCF₃ | CH | O | F | 3-CH₂F | 357 |
| 119 | N | CH | CCF₃ | CH | O | Cl | 3-CH₂F | 373 |
| 120 | N | CH | CCF₃ | CH | O | Br | 3-CH₂F | 418 |
| 121 | N | CH | COMe | CH | O | Cl | 3-F | 321 |
| 122 | N | CH | COCHF₂ | CH | O | Cl | 3-Br | 418 |
| 123 | N | N | CCH₂F | CH | O | Cl | H (m is 0) | 306 |
| 124 | CH | CH | CCHO | CH | O | Cl | H (m is 0) | * |

INDEX TABLE A-continued

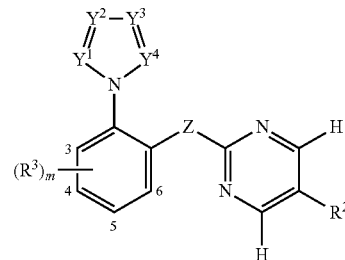

| Cmpd No. | Y$^1$ | Y$^2$ | Y$^3$ | Y$^4$ | Z | R$^2$ | (R$^3$)$_m$ | mp or MS |
|---|---|---|---|---|---|---|---|---|
| 125 | N | CH | CBr | CH | O | Br | 3-CH$_2$F | 429 |
| 126 | N | CH | COCH$_2$CF$_3$ | CH | O | F | 3-F | * |
| 127 | N | CH | CO(n-Pr) | CH | O | Cl | 3-F | 349 |
| 128 | N | CH | COCH$_2$CF$_3$ | CH | O | Cl | 3-Br | 450 |
| 129 | N | N | CBr | CH | O | Cl | 3-Br | 432 |
| 130 | N | CH | CBr | CH | O | i-Pr | 3-CN | 386 |
| 131 | N | CH | CBr | CH | O | n-Pr | 3-CN | 384 |
| 132 | N | CH | CSCF$_3$ | CH | O | Cl | H (m is 0) | * |
| 133 | N | CH | CSCF$_3$ | CH | O | Cl | 3-I | * |
| 134 | N | CH | CSCF$_3$ | CH | O | Cl | 3-CN | * |
| 135 | N | CH | CCN | CH | O | Br | 3-CN | 369 |
| 136 | N | CH | CI | CH | O | CH$_3$ | 3-CN | 404 |
| 137 | N | CH | COMe | CH | O | Cl | 3-CN | 328 |
| 138 | N | CH | COCH$_2$CF$_3$ | CH | O | Cl | H (m is 0) | 371 |
| 139 | N | N | CCHO | CH | O | Cl | 3-F | 320 |
| 140 | N | CH | CCN | CH | O | Cl | 3-Br | 378 |
| 141 | N | N | CCHF$_2$ | CH | O | Cl | 3-F | 342 |
| 142 | N | CH | CBr | CH | O | Cl | 3-SO$_2$CH$_3$ | 429 |
| 143 | N | CH | CS(O)CF$_3$ | CH | O | Cl | H (m is 0) | * |
| 144 | N | CH | CCN | CH | O | Cl | 3-Cl | 332 |
| 145 | N | CH | CBr | CH | O | F | 3-CHF$_2$ | 368 |
| 146 | N | CH | CBr | CH | O | Cl | 3-CHF(CH$_3$) | 398 |
| 147 | N | N | CCHF$_2$ | CH | O | Cl | H (m is 0) | 324 |
| 148 | N | CH | CO(i-Pr) | CH | O | Cl | 3-Br | * |
| 149 | N | CH | CO(i-Pr) | CH | O | Cl | 3-CN | 356 |
| 150 | N | CH | CO(n-Pr) | CH | O | Cl | 3-CN | 356 |
| 151 | N | CH | CCN | CH | O | F | 3-CH$_2$F | 314 |
| 152 | N | CH | CI | CH | O | F | 3-CH$_2$F | 415 |
| 153 | N | CH | CO(n-Pr) | CH | O | F | 3-F | 333 |
| 154 | N | N | CCH$_2$F | CH | O | Cl | 3-F | 324 |
| 155 | N | N | C(c-Pr) | CH | O | Cl | 3-F | 332 |
| 156 | N | CH | CO(i-Pr) | CH | O | F | 3-Br | * |
| 157 | N | CH | COCH$_2$CF$_3$ | CH | O | F | 3-Br | * |
| 158 | N | CH | CO(i-Pr) | CH | O | F | 3-CN | 340 |
| 159 | N | N | CH | CH | O | Cl | 3-F | 292 |
| 160 | N | N | C(c-Pr) | CH | O | Cl | H (m is 0) | 314 |
| 161 | N | CH | CCF$_3$ | CH | O | Br | 3-CHO | 414 |
| 162 | N | CH | CCF$_3$ | CH | O | F | 3-CHO | 353 |
| 163 | N | CH | CCF$_3$ | CH | O | Br | 3-CHF$_2$ | 436 |
| 164 | N | CH | CCF$_3$ | CH | O | F | 3-CHF$_2$ | 375 |
| 165 | N | CH | CH | CH | O | Br | 3-CN | 342 |
| 166 | N | N | CCF$_3$ | CH | O | Cl | H (m is 0) | 342 |
| 167 | N | CH | CCF$_3$ | CH | O | Cl | 3-Cl | 375 |
| 168 | N | CH | CCF$_3$ | CH | O | Br | 3-Cl | 421 |
| 169 | N | CH | CCl | CH | O | Cl | 3-OMe | 337 |
| 170 | N | CH | CCF$_3$ | CH | O | Cl | 3-CHF$_2$ | 391 |
| 171 | N | CH | CCF$_3$ | CH | O | Cl | 3-CHO | 369 |
| 172 | N | CH | CBr | CH | O | I | 3-CHO | 472 |
| 173 | N | CH | CBr | CH | O | I | 3-CHF$_2$ | 494 |
| 174 | N | CH | CBr | CH | O | CN | 3-CHO | 371 |
| 175 | N | CH | CBr | CH | O | CN | 3-CHF$_2$ | 393 |
| 176 | N | CH | CH | CH | O | Cl | 3-F | 291 |
| 177 | N | CH | CCl | CH | O | Cl | 3-F | 325 |
| 178 | N | CH | CBr | CH | O | Cl | 3-F | 369 |
| 179 | N | CH | CI | CH | O | Cl | 3-F | 417 |
| 180 | N | CH | CCF$_3$ | CH | O | CH$_3$ | 3-CN | * |
| 181 | N | CH | CI | CH | O | Cl | 3-Cl | 435 |
| 182 | N | CH | CI | CH | O | Cl | 3-CHO | 425 |
| 183 | N | CH | CI | CH | O | Br | 3-CHO | 472 |
| 184 | N | CH | CI | CH | O | Cl | 3-CHF$_2$ | 449 |
| 185 | N | CH | CI | CH | O | Br | 3-CHF$_2$ | 494 |
| 186 | N | CH | COMe | CH | O | Cl | H (m is 0) | * |

INDEX TABLE A-continued

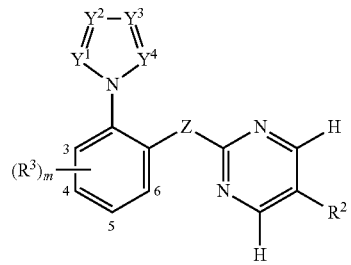

| Cmpd No. | $Y^1$ | $Y^2$ | $Y^3$ | $Y^4$ | Z | $R^2$ | $(R^3)_m$ | mp or MS |
|---|---|---|---|---|---|---|---|---|
| 187 | N | CH | COEt | CH | O | Cl | H (m is 0) | 317 |
| 188 | N | CH | CC=CH | CH | O | Cl | H (m is 0) | 297 |
| 189 | N | CH | CC=CMe | CH | O | Cl | H (m is 0) | 311 |
| 190 | N | CH | C(2-pyridinyl) | CH | O | Cl | H (m is 0) | 350 |
| 191 | N | CH | $CCF_3$ | CH | O | Cl | 3-Br | 419 |
| 192 | N | CH | $CCHF_2$ | CH | O | Cl | 3-Cl | 358 |
| 193 | N | CH | N | CH | O | Cl | 3-CN | 299 |
| 194 | N | CH | CBr | CH | O | Cl | 3-$CHF_2$ | 402 |
| 195 | N | CH | CBr | CH | O | Cl | 3-Ph | 428 |
| 196 | N | CH | CBr | CH | O | Cl | 4,5-diF | 389 |
| 197 | N | CH | CBr | CH | O | Cl | 3-CH=$CH_2$ | 392 |
| 198 | N | CH | CBr | CH | O | Cl | 3-C(Me)=$CH_2$ | 392 |
| 199 | N | CH | CBr | CH | O | Cl | 3-C≡CH | 377 |
| 200 | N | CH | CCN | CH | O | Cl | 3-CN | 323 |
| 201 | N | CH | CBr | CH | O | Cl | 3-Br, 6-OMe | 461 |
| 202 | N | CH | CBr | CH | O | Cl | 3-Br, 4-Me | 445 |
| 203 | N | CH | CBr | CH | O | Cl | 3-CH=NOMe | * |
| 204 | N | CH | CI | CH | O | Cl | 3-CN | 424 |
| 205 | N | CH | CCl | CH | O | Cl | 3-CHO | 334 |
| 206 | N | CH | CCl | CH | O | Br | 3-CHO | 380 |
| 207 | N | CH | CBr | CH | O | Cl | 3-I, 6-OMe | 508 |
| 208 | N | CH | CH | CH | O | Cl | 3-CN | 298 |
| 209 | N | CH | CCl | CH | O | Cl | 3-$CHF_2$ | 358 |
| 210 | N | CH | CCl | CH | O | Br | 3-$CHF_2$ | 402 |
| 211 | N | CH | CBr | CH | O | Cl | 3-$CO_2$Me | 411 |
| 212 | N | CH | CBr | CH | O | Cl | 3-CN, 6-OMe | 407 |
| 213 | N | CH | CBr | CH | O | Cl | 4-CN | * |
| 214 | N | CH | CBr | CH | O | CN | 3-CN | 369 |
| 215 | N | CH | CBr | CH | O | C≡CH | 3-CN | 368 |
| 216 | N | CH | CCl | CH | O | Cl | 3-OC(=O)Me | 365 |
| 217 | N | N | CH | CH | O | Cl | H (m is 0) | 274 |
| 218 | N | CH | CBr | CH | O | OMe | 3-CN | 372 |
| 219 | N | CH | CBr | CH | O | Cl | 3-Cl | 387 |
| 220 | N | CH | CCl | CH | O | Cl | 3-Cl | 341 |
| 221 | N | CH | CCl | CH | O | Cl | 3-Br | 387 |
| 222 | N | N | CI | CH | O | Cl | H (m is 0) | 400 |
| 223 | N | N | CBr | CH | O | Cl | H (m is 0) | 354 |
| 224 | N | N | CCl | CH | O | Cl | H (m is 0) | 308 |
| 225 | N | CH | CBr | CH | O | $NO_2$ | H (m is 0) | * |
| 226 | N | CH | CH | CH | O | CN | H (m is 0) | * |
| 227 | N | CH | CH | CH | O | OMe | H (m is 0) | * |
| 228 | N | CH | $CCHF_2$ | CH | O | F | H (m is 0) | 307 |
| 229 | N | CH | CCl | CH | O | Cl | 3-OH | 324 |
| 230 | N | CH | CBr | CH | O | Br | 3-CHO | 425 |
| 231 | N | CH | CBr | CH | O | Br | 3-$CHF_2$ | 447 |
| 232 | N | CH | $CCHF_2$ | CH | O | Cl | 3-Br | * |
| 233 | N | CH | CBr | CH | O | CN | H (m is 0) | * |
| 234 | N | CH | CBr | CH | O | OMe | H (m is 0) | * |
| 235 | N | CH | CBr | CH | O | Cl | 3-CN | 377 |
| 236 | N | CH | CCN | CH | O | Cl | 3-$CHF_2$ | 348 |
| 237 | N | CH | CCN | CH | O | Cl | 3-CHO | 326 |
| 238 | N | CH | CBr | CH | O | Cl | 3-CN, 5-F | 395 |
| 239 | N | CH | CBr | CH | O | Br | 3-CN, 5-F | 440 |
| 240 | N | CH | CCN | CH | O | F | 3-$CHF_2$ | 332 |
| 241 | N | CH | $COCH_2CF_3$ | CH | O | F | H (m is 0) | 355 |
| 242 | N | CH | CCN | CH | O | Cl | 3-$CH_2F$ | 330 |
| 243 | N | CH | CCN | CH | O | Br | 3-$CH_2F$ | 375 |
| 244 | N | CH | CI | CH | O | Br | 3-$CH_2F$ | 476 |
| 245 | N | CH | CI | CH | O | Cl | 3-$CH_2F$ | 431 |
| 246 | N | CH | $CSCF_3$ | CH | O | Br | H (m is 0) | 417 |
| 247 | N | CH | $CSCF_3$ | CH | O | F | H (m is 0) | 357 |
| 248 | N | CH | $CCF_3$ | CH | O | Cl | 3-$CO_2$Me | 399 |

INDEX TABLE A-continued

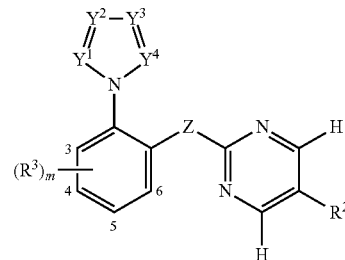

| Cmpd No. | Y¹ | Y² | Y³ | Y⁴ | Z | R² | (R³)ₘ | mp or MS |
|---|---|---|---|---|---|---|---|---|
| 249 | N | CH | CCl | CH | O | F | 3-CH₂F | 322 |
| 250 | N | CH | CCl | CH | O | Cl | 3-CH₂F | 340 |
| 251 | N | CH | CCl | CH | O | Br | 3-CH₂F | 384 |
| 252 | CH | N | CCF₃ | CH | O | Cl | 3-CN | 366 |
| 253 | N | CH | CCHF₂ | CH | O | Cl | 3-CN | 348 |
| 254 | N | CH | CO(i-Pr) | CH | O | Br | 3-CN | * |
| 255 | N | CH | CCF₃ | CH | O | Cl | 3-C(=O)NMe₂ | 412 |
| 256 | N | CH | CCF₃ | CH | O | Cl | 3-C(=O)NHMe | 398 |
| 257 | N | CH | CCF₃ | CH | O | Cl | 3-C(=O)NHEt | 412 |
| 258 | N | CH | COCHF₂ | CH | O | Cl | 3-Cl | * |
| 259 | CH | N | CH | CBr | O | Cl | 3-CHF₂ | 402 |
| 260 | CH | N | CMe | CH | O | Cl | 3-CN | 312 |
| 261 | CH | N | CH | CH | O | Cl | 3-CN | 298 |
| 262 | N | CH | CCF₃ | CH | O | Cl | 3-C(=O)N(Me)Et | 426 |
| 263 | N | CH | CCF₃ | CH | O | Cl | 3-C(=O)NEt₂ | 440 |
| 264 | N | CMe | CH | CMe | O | Cl | H (m is 0) | 301 |
| 265 | N | CMe | CH | CCF₂ | O | Cl | H (m is 0) | 334 |
| 266 | N | CCF₃ | CH | CMe | O | Cl | H (m is 0) | 355 |
| 267 | N | CCHF₂ | CH | CMe | O | Cl | H (m is 0) | 337 |
| 268 | N | CCHF₂ | CH | CCF₂ | O | Cl | H (m is 0) | 121 |
| 269 | CH | CH | CH | CH | O | Cl | H (m is 0) | * |
| 270 | N | CH | COCH₂CF₃ | CH | O | Cl | 3-F | 389 |
| 271 | N | CH | COCHF₂ | CH | O | Cl | 3-F | 357 |
| 272 | N | N | CCHO | CH | O | Cl | H (m is 0) | 302 |
| 273 | N | N | CCN | CH | O | Cl | 3-CN | 324 |
| 274 | N | CH | COCH₂CF₃ | CH | O | Cl | 3-CN | 396 |
| 275 | N | CH | CBr | CH | O | H | H (m is 0) | 318 |
| 276 | N | N | C(3-CF₃—Ph) | CH | O | Cl | 3-F | 436 |
| 277 | N | N | C(3-thienyl) | CH | O | Cl | 3-F | 374 |
| 278 | N | CH | CCF₃ | CH | O | Cl | 3-C(=O)NH₂ | 384 |
| 279 | N | CH | CCF₃ | CH | O | Cl | 3-[3-(1,2,4-oxadiazole)] | 409 |
| 280 | N | N | CC(=O)CH₃ | CH | O | Cl | 3-Br | 396 |
| 281 | N | CH | CC(=O)NH₂ | CH | O | Cl | H (m is 0) | 316 |
| 282 | N | CH | CSO₂NH₂ | CH | O | Cl | H (m is 0) | 352 |
| 283 | N | CH | CSO₂NH(t-Bu) | CH | O | Cl | H (m is 0) | 408 |
| 284 | N | CH | C(3-CF₃-pyrazol-1-yl) | CH | O | Cl | 3-CN | 432 |
| 285 | N | CH | CB(OCMe₂CMe₂O) | CH | O | Cl | 3-CN | 424 |
| 286 | N | CH | C(4-pyridinyl) | CH | O | Cl | H (m is 0) | 350 |
| 287 | N | CH | CBr | CH | O | Cl | 3-(2-oxazolyl) | 419 |
| 288 | N | CH | CBr | CH | O | Cl | 3-CH=NNH₂ | 394 |
| 289 | N | CH | CBr | CH | O | Cl | 3-CH=NNHMe | 408 |
| 290 | N | CH | CBr | CH | O | Cl | 3-(3-pyridinyl) | 429 |
| 291 | N | CH | CBr | CH | O | Cl | 3-(4-isoxazolyl) | 419 |
| 292 | N | CH | CCl | CH | O | Cl | 3-C(=S)NH₂ | 365 |
| 293 | N | CH | CBr | CH | O | Cl | 3-C≡CSi(Me)₃ | 449 |
| 294 | N | CH | CCO₂Et | CH | O | Br | 3-CN | 416 |
| 295 | N | CH | CCl | CH | O | Cl | 3-CH=NNH₂ | 350 |
| 296 | N | CH | CCl | CH | O | Cl | 3-CH=NNHMe | 363 |
| 297 | N | N | CSi(Me)₃ | CH | O | Cl | H (m is 0) | 346 |
| 298 | N | CH | CCF₃ | CH | O | Cl | 3-[2-(1,3,4-oxadiazole)] | 409 |
| 299 | N | CH | CCF₃ | CH | O | Cl | 3-[5-(3-Me-1,2,4-oxadiazole)] | 423 |
| 300 | N | N | CSi(Me)₃ | CH | O | Cl | 3-Br | * |
| 301 | N | CH | CCO₂Et | CH | O | Cl | 3-CN | * |
| 302 | N | N | CCO₂Et | CH | O | Cl | H (m is 0) | 346 |
| 303 | N | N | C(3,5-diF—Ph) | CH | O | Cl | 3-Br | 466 |
| 304 | N | CH | CNO₂ | CH | O | Cl | 3-CN | 343 |
| 305 | N | N | CCHF₂ | CH | O | Br | 3-F | 386 |

* See Index Table B for ¹H NMR data.

INDEX TABLE B

| No. | ¹H NMR Data (CDCl₃ solution unless indicated otherwise)ᵃ |
|---|---|
| 1 | 8.48 (s, 2H), 7.96 (s, 1H), 7.80 (d, 1H), 7.49 (t, 1H), 7.44 (t, 1H), 7.35 (d, 1H), 6.57 (s, 1H) |
| 2 | 8.39 (s, 2H), 7.93 (s, 1H), 7.81 (d, 1H), 7.48 (t, 1H), 7.42 (t, 1H), 7.35 (d, 1H), 6.58 (s, 1H) |
| 3 | 8.42 (s, 2H), 7.92 (s, 1H), 7.77 (d, 1H), 7.52 (s, 1H), 7.42 (m, 2H), 7.31 (d, 1H) |
| 4 | 8.70 (s, 2H), 7.90 (s, 1H), 7.78 (d, 1H), 7.52 (t, 1H), 7.47 (t, 1H), 7.38 (d, 1H), 6.57 (s, 1H) |
| 5 | 8.49 (s, 2H), 7.91 (s, 1H), 7.77 (d, 1H), 7.52 (s, 1H), 7.42 (m, 2H), 7.30 (d, 1H) |
| 6 | 8.72 (s, 2H), 7.88 (s, 1H), 7.77 (d, 1H), 7.50 (s, 1H), 7.44-7.46 (m, 2H), 7.32 (d, 1H) |
| 7 | 8.41 (s, 2H), 7.94 (s, 1H), 7.77 (d, 1H), 7.55 (s, 1H), 7.42 (m, 2H), 7.32 (d, 1H) |
| 8 | 8.49 (s, 2H), 7.96 (s, 1H), 7.78 (d, 1H), 7.56 (s, 1H), 7.41-7.46 (m, 2H), 7.32 (d, 1H) |
| 9 | 8.30 (s, 2H), 7.99 (s, 1H), 7.78 (d, 1H), 7.55 (s, 1H), 7.36-7.43 (m, 2H), 7.28 (d, 1H), 2.23 (s, 1H) |
| 10 | 8.34 (s, 2H), 7.97 (s, 1H), 7.78 (d, 1H), 7.55 (s, 1H), 7.41-7.47 (m, 2H), 7.32 (d, 1H) |
| 11 | 8.34 (s, 2H), 7.92 (s, 1H), 7.78 (d, 1H), 7.51 (s, 1H), 7.39-7.45 (m, 2H), 7.30 (d, 1H) |
| 12 | 8.38 (s, 2H), 7.90 (s, 1H), 7.82 (d, 1H), 7.59 (s, 1H), 7.43 (m, 2H), 7.32 (d, 1H), 6.31 (s, 1H) |
| 13 | 8.46 (s, 2H), 7.90 (s, 1H), 7.81 (d, 1H), 7.59 (s, 1H), 7.41 (m, 2H), 7.31 (d, 1H), 6.32 (s, 1H) |
| 14 | 8.29 (s, 2H), 7.91 (s, 1H), 7.83 (d, 1H), 7.59 (s, 1H), 7.41 (m, 2H), 7.32 (d, 1H), 6.30 (s, 1H) |
| 15 | 8.30 (s, 2H), 7.96 (s, 1H), 7.80 (d, 1H), 7.51 (s, 1H), 7.35-7.44 (m, 2H), 7.28 (d, 1H), 2.23 (s, 1H) |
| 16 | 8.41 (s, 2H), 8.18 (s, 1H), 7.77 (m, 2H), 7.48 (t, 1H), 7.44 (t, 1H), 7.35 (d, 1H) |
| 17 | 8.71 (s, 2H), 8.14 (s, 1H), 7.75 (m, 2H), 7.51 (t, 1H), 7.48 (t, 1H), 7.38 (d, 1H) |
| 18 | 8.49 (s, 2H), 8.18 (s, 1H), 7.78 (m, 2H), 7.48 (t, 1H), 7.44 (t, 1H), 7.34 (d, 1H) |
| 19 | 8.44 (s, 2H), 7.92 (s, 1H), 7.78 (d, 1H), 7.39-7.47 (m, 2H), 7.30 (d, 1H) |
| 20 | 8.48 (s, 2H), 7.82 (s, 1H), 7.81 (d, 1H), 7.38-7.46 (m, 2H), 7.30 (d, 1H), 6.32 (s, 1H) |
| 21 | 8.40 (s, 2H), 7.82 (s, 1H), 7.81 (d, 1H), 7.38-7.45 (m, 2H), 7.31 (d, 1H), 6.32 (s, 1H) |
| 22 | 8.37 (s, 2H), 8.18 (s, 1H), 7.86 (s, 1H), 7.85 (d, 2H), 7.41-7.47 (m, 4H), 7.32-7.38 (m, 3H), 7.23 (d, 1H) |
| 23 | 8.38 (s, 2H), 7.80 (d, 1H), 7.68 (s, 1H), 7.35-7.42 (m, 3H), 7.28 (d, 1H), 6.30 (s, 1H), 2.03 (s, 3H) |
| 24 | 8.52 (s, 2H), 7.92 (s, 1H), 7.78 (d, 1H), 7.39-7.47 (m, 2H), 7.29 (d, 1H) |
| 25 | 8.41 (s, 2H), 7.95 (s, 1H), 7.77 (d, 1H), 7.58 (s, 1H), 7.38-7.47 (m, 2H), 7.31 (d, 1H) |
| 26 | 8.48 (s, 2H), 7.95 (s, 1H), 7.77 (d, 1H), 7.58 (s, 1H), 7.39-7.45 (m, 2H), 7.29 (d, 1H) |
| 27 | 8.38 (s, 2H), 7.81 (s, 1H), 7.80 (d, 1H), 7.60 (s, 1H), 7.37-7.41 (m, 2H), 7.29 (m, 1H), 6.17 (d, 1H), 5.98 (d, 1H), 1.81 (d, 3H) |
| 29 | 8.37 (s, 2H), 7.76 (d, 1H), 7.71 (s, 1H), 7.38 (m, 2H), 7.32 (d, 1H), 6.1 (s, 1H), 1.21 (s, 9H) |
| 30 | 8.46 (s, 2H), 7.76 (d, 1H), 7.71 (s, 1H), 7.38 (m, 2H), 7.31 (d, 1H), 6.12 (s, 1H), 1.22 (s, 9H) |
| 31 | 8.39 (s, 2H), 7.91 (s, 1H), 7.8 (d, 1H), 7.68 (s, 1H), 7.40 (m, 2H), 7.30 (d, 1H), 6.49 (m, 1H), 5.47 (dd, 1H), 5.08 (dd, 1H) |
| 32 | 8.38 (s, 2H), 7.90 (d, 1H), 7.82 (s, 1H), 7.60 (d, 1H), 7.40 (m, 2H), 7.31 (d, 1H), 5.98 (dd, 1H), 5.63 (dd, 1H), 1.81 (t, 3H) |
| 33 | 8.43 (s, 2H), 8.34 (s, 1H), 7.88 (s, 1H), 7.80 (d, 1H), 7.56 (t, 1H), 7.46 (t, 1H), 7.34 (d, 1H) |
| 34 | 8.39 (s, 2H), 7.59 (s, 1H), 7.51 (m, 1H), 7.42 (d, 2H), 7.34 (d, 1H), 7.15 (s, 1H) |
| 36 | 8.38 (s, 2H), 7.80 (m, 2H), 7.37 (m, 2H), 7.28 (d, 1H), 6.08 (s, 1H), 2.25 (s, 3H) |
| 37 | 8.41 (s, 2H), 7.88 (s, 1H), 7.76 (d, 1H), 7.38 (m, 2H), 7.28 (d, 1H), 2.22 (s, 3H) |
| 38 | 8.41 (s, 2H), 7.88 (s, 1H), 7.76 (d, 1H), 7.37-4.40 (m, 2H), 7.28 (d, 1H), 2.22 (s, 3H) |
| 39 | 8.42 (s, 2H), 7.87 (s, 1H), 7.78 (d, 1H), 7.38 (m, 2H), 7.28 (d, 1H), 2.22 (s, 3H) |
| 46 | 8.51 (s, 1H), 8.44 (s, 2H), 7.82 (d, 1H), 7.51 (t, 1H), 7.45 (t, 1H), 7.35 (d, 1H) |
| 47 | 8.33 (s, 2H), 8.19 (s, 1H), 7.80 (s, 1H), 7.78 (d, 1H), 7.48 (t, 1H), 7.44 (t, 1H), 7.33 (d, 1H) |
| 49 | 8.39 (s, 2H), 7.89 (d, 1H), 7.77 (d, 1H), 7.58 (1H), 7.39 (d, 1H), 7.33 (1H), 6.30 (d, 1H) |
| 50 | 8.47 (s, 2H), 7.89 (d, 1H), 7.78 (d, 1H), 7.59 (s, 1H), 7.39 (d, 1H), 7.33 (1H), 6.30 (d, 1H) |
| 51 | 8.43 (s, 2H), 7.93 (s, 1H), 7.73 (d, 1H), 7.55 (s, 1H), 7.40 (d, 1H), 7.33 (s, 1H) |
| 56 | 8.53 (s, 2H), 8.03 (s, 1H), 7.96 (dd, 1H), 7.65-7.54 (m, 1H), 7.50-7.47 (m, 1H), 7.41 (dd, 1H) |
| 58 | 8.40 (s, 2H), 8.05 (s, 1H), 7.85 (s, 1H), 7.78 (d, 1H), 7.6-7.7 (m, 2H) |
| 59 | 8.49 (s, 2H), 8.05 (s, 1H), 7.85 (s, 1H), 7.79 (d, 1H), 7.62-7.65 (m, 2H) |
| 65 | 8.41 (s, 2H), 7.66-7.64 (m, 1H), 7.53 (s, 1H), 7.53 (s, 1H), 7.45-7.40 (m, 1H), 7.32-7.28 (m, 1H) |
| 66 | 8.41 (s, 2H), 7.90-7.86 (m, 1H), 7.54 (d, 1H), 7.50 (d, 1H), 7.33-7.26 (m, 2H) |
| 67 | 8.40 (s, 2H), 7.56 (s, 1H), 7.54-7.50 (m, 2H), 7.24 (dd, 1H), 7.22-7.18 (m, 1H), 2.13 (s, 3H) |
| 68 | 10.06 (s, 1H), 8.43 (s, 2H), 8.16 (s, 1H), 7.64 (s, 1H), 7.26 (t, 1H), 7.04 (dd, 1H), 6.79 (dd, 1H) |
| 69 | 8.40 (s, 2H), 7.55 (d, 1H), 7.53-7.45 (m, 3H), 7.08 (dd, 1H), 7.01 (dd, 1H), 4.32 (q, 3H) |
| 74 | 8.39 (s, 2H), 7.76 (d, 1H), 7.66 (t, 1H), 7.60 (d, 1H), 7.55 (s, 1H), 7.11 (s, 1H) |
| 79 | 8.32 (s, 2H), 8.05 (s, 1H), 7.84 (s, 1H), 7.77 (d, 1H), 7.63-7.65 (m, 2H) |
| 80 | 8.40 (s, 2H), 8.08 (s, 1H), 7.80 (d, 1H), 7.72 (s, 1H), 7.41-7.50 (m, 2H), 7.33 (d, 1H), 6.67 (t, 1H) |
| 81 | 8.48 (s, 2H), 8.08 (s, 1H), 7.80 (d, 1H), 7.72 (s, 1H), 7.42-7.47 (m, 2H), 7.33 (d, 1H), 6.67 (t, 1H) |
| 89 | 8.30 (s, 2H), 7.72 (m, 1H), 7.47-7.60 (m, 2H), 7.40 (m, 2H), 3.89 (m, 2H), 1.34 (m, 3H) |
| 99 | 8.39 (s, 2H), 7.73 (m, 1H), 7.52-7.61 (m, 2H), 7.49 (m, 1H), 7.46 (m, 1H), 5.83-6.13 (m, 2H), 4.03-4.09 (m, 2H) |
| 101 | 8.30 (s, 2H), 7.44-7.50 (m, 4H), 7.28 (m, 1H), 6.32-6.47 (s, 1H) |
| 103 | 8.38 (s, 2H), 7.38-7.51 (m, 2H), 7.30 (m, 1H), 7.25 (m, 1H), 7.15 (m, 1H), 4.03-4.18 (m, 1H), 1.25 (m, 6H) |
| 105 | 8.39 (s, 2H), 7.89 (d, 1H), 7.71 (s, 1H), 7.64 (s, 1H), 7.27-7.33 (m, 2H), 7.69 (t, 1H) |
| 110 | 8.40 (s, 2H), 7.48 (s, 1H), 7.47 (m, 1H), 7.39 (m, 1H), 7.29 (m, 1H), 7.25-7.27 (m, 2H), 4.20 (m, 2H) |
| 111 | 7.60-7.65 (m, 1H), 7.65-7.72 (m, 1H), 7.79 (d, J = 7.83 Hz, 1H), 7.96 (s, 1H), 8.21 (s, 1H), 8.36 (s, 2H) |
| 124 | 9.74 (s, 1H), 8.35 (s, 2H), 7.40-7.53 (m, 4H), 7.33-7.36 (m, 1H), 6.91-6.94 (m, 1H), 6.61 (dd, 1H) |
| 126 | 8.31 (s, 2H), 7.48-7.42 (m, 1H), 7.38-7.36 (m, 2H), 7.22-7.14 (m, 2H), 4.26-4.17 (m, 2H) |
| 132 | 8.37 (s, 2H), 8.14 (s, 1H), 7.80 (d, 1H), 7.71 (s, 1H), 7.41-7.50 (2 × t, 1H each), 7.35 (d, 1H) |
| 133 | 8.38 (s, 2H), 7.91 (d, 1H), 7.72 (d, 2H), 7.28-7.37 (m, 2H) |
| 134 | 8.36 (s, 2H), 8.01 (s, 1H), 7.78 (s + d, 2H), 7.63 (2 × t, 2H) |
| 143 | 8.43 (s, 1H), 8.40 (s, 2H), 8.01 (s, 1H), 7.82 (d, 1H), 7.53 (t, 1H), 7.46 (t, 1H), 7.37 (d, 1H) |
| 148 | 8.38 (s, 2H), 7.68-7.56 (m, 1H), 7.44-7.33 (m, 1H), 7.31-7.27 (m, 2H), 7.15-7.11 (m, 1H), 4.16-4.05 (m, 1H), 1.27-1.24 (m, 6H) |
| 156 | 8.38 (s, 2H), 7.68-7.56 (m, 1H), 7.44-7.33 (m, 1H), 7.31-7.27 (m, 2H), 7.15-7.11 (m, 1H), 4.16-4.05 (m, 1H), 1.27-1.24 (m, 6H) |

INDEX TABLE B-continued

| No. | $^1$H NMR Data (CDCl$_3$ solution unless indicated otherwise)$^a$ |
|---|---|
| 157 | 8.32 (s, 2H), 7.73-7.54 (m, 1H), 7.43-7.36 (m, 2H), 7.31-7.27 (m, 2H), 4.26-4.17 (m, 2H) |
| 180 | 8.28 (s, 2H), 8.08-7.99 (m, 1H), 7.84 (s, 1H), 7.78-7.72 (m, 1H), 7.67-7.57 (m, 2H), 2.42-2.07 (m, 4H) |
| 186 | 8.39 (s, 2H), 7.80-7.77 (m, 1H), 7.61-7.60 (m, 1H), 7.40-7.36 (m, 2H), 7.36-7.33 (m, 1H), 7.32-7.27 (m, 1H), 3.70 (s, 3H) |
| 203 | 3.95 (s, 3H), 7.31 (d, 1H), 7.51 (m, 1H), 7.53 (s, 1H), 7.57 (s, 1H), 7.69 (s, 1H), 7.94 (d, 1H), 8.40 (s, 2H) |
| 213 | 7.42 (d, 1H), 7.61 (s, 1H), 7.67 (m, 1H), 8.05 (s, 1H), 8.2 (m, 1H), 8.45 (s, 2H) |
| 225 | 9.24 (s, 2H), 7.87 (s, 1H), 7.73 (d, 1H), 7.49 (m, 3H), 7.32 (d, 1H) |
| 226 | 8.69 (s, 2H), 7.82 (s, 1H), 7.75 (d, 1H), 7.54 (s, 1H), 7.45 (m, 2H), 7.35 (d, 1H), 6.30 (s, 1H) |
| 227 | 8.12 (s, 2H), 7.98 (s, 1H), 7.85 (d, 1H), 7.59 (s, 1H), 7.38 (m, 2H), 7.29 (d, 1H), 6.29 (s, 1H), 3.82 (s, 3H) |
| 232 | 8.39 (s, 2H), 7.71 (s, 1H), 7.65-7.69 (m, 2H), 7.45 (t, 1H), 7.32 (d, 2H), 6.68 (t, 1H) |
| 233 | 8.73 (s, 2H), 7.87 (s, 1H), 7.73 (d, 1H), 7.52 (s, 1H), 7.47 (m, 2H), 7.33 (d, 1H) |
| 234 | 8.15 (s, 2H), 8.00 (s, 1H), 7.79 (d, 1H), 7.56 (s, 1H), 7.38 (m, 2H), 7.28 (d, 1H), 3.85 (s, 3H) |
| 254 | 8.45 (s, 2H), 7.77-7.66 (m, 1H), 7.61-7.45 (m, 2H), 7.39 (s, 2H), 4.17-4.08 (m, 1H), 1.28-1.24 (m, 6H) |
| 258 | 8.39 (s, 2H), 7.50-7.44 (m, 4H), 7.29-7.26 (m, 1H), 6.46-6.16 (m, 1H) |
| 269 | 8.32 (s, 2H), 7.28-7.47 (m, 4H), 6.89 (t, 2H), 6.13 (t, 2H) |
| 300 | 8.37 (s, 2H), 7.69 (dd, J = 8.2, 1.3 Hz, 1H), 7.66 (s, 1H), 7.47 (t, J = 8.2 Hz, 1H), 7.34 (dd, J = 8.3, 1.3 Hz, 1H), 0.30 (m, 9H) |
| 301 | 8.48-8.37 (m, 2H), 8.22 (s, 1H), 8.04 (s, 1H), 7.85-7.71 (m, 1H), 7.68-7.57 (m, 2H), 4.36-4.24 (m, 2H), 1.41-1.26 (m, 3H) |

$^a$$^1$H NMR data are in ppm downfield from tetramethylsilane at 500 MHz. Couplings are designated by (s)-singlet, (d)-doublet, (t)-triplet, (m)-multiplet and (dd)-doublet of doublets.

Biological Examples of the Invention

Test A

Seeds of plant species selected from barnyardgrass (*Echinochloa crus-galli*), kochia (*Kochia scoparia*), ragweed (common ragweed, *Ambrosia elatior*), Italian ryegrass (*Lolium multiflorum*), large (Lg) crabgrass (*Digitaria sanguinalis*), giant foxtail (*Setaria faberii*), morningglory (*Ipomoea* spp.), pigweed (*Amaranthus retroflexus*), velvetleaf (*Abutilon theophrasti*), wheat (*Triticum aestivum*), and corn (*Zea mays*) were planted into a blend of loam soil and sand and treated preemergence with a directed soil spray using test chemicals formulated in a non-phytotoxic solvent mixture which included a surfactant.

At the same time, plants selected from these crop and weed species and also blackgrass (*Alopecurus myosuroides*), and galium (catchweed bedstraw, *Galium aparine*) were planted in pots containing the same blend of loam soil and sand and treated with postemergence applications of test chemicals formulated in the same manner. Plants ranged in height from 2 to 10 cm and were in the one- to two-leaf stage for the postemergence treatment. Treated plants and untreated controls were maintained in a greenhouse for approximately 10 days, after which time all treated plants were compared to untreated controls and visually evaluated for injury. Plant response ratings, summarized in Table A, are based on a 0 to 100 scale where 0 is no effect and 100 is complete control. A dash (-) response means no test result.

TABLE A

| | Postemergence 1000 g ai/ha Compounds | | | | | | | | | | | | | | | | | |
|---|---|---|---|---|---|---|---|---|---|---|---|---|---|---|---|---|---|---|
| | 12 | 13 | 14 | 53 | 54 | 55 | 56 | 65 | 66 | 67 | 69 | 70 | 102 | 114 | 115 | 116 | 123 | 139 |
| Barnyardgrass | 90 | 90 | 20 | 90 | 30 | 10 | 30 | 100 | 80 | 20 | 50 | 80 | 50 | 100 | 90 | 90 | 100 | 0 |
| Blackgrass | — | — | — | — | — | — | — | — | — | — | — | — | 40 | — | — | — | 90 | 0 |
| Corn | 30 | 40 | 20 | 30 | 50 | 20 | 20 | 70 | 40 | 10 | 20 | 10 | 20 | 70 | 90 | 60 | 70 | 20 |
| Crabgrass, Large | 80 | 90 | 30 | 70 | 100 | 40 | 40 | 100 | 100 | 10 | 80 | 60 | — | 90 | 90 | 100 | — | — |
| Foxtail, Giant | 80 | 100 | 40 | 80 | 70 | 60 | 30 | 100 | 100 | 10 | 70 | 60 | 40 | 90 | 90 | 90 | 90 | 0 |
| Galium | — | — | — | — | — | — | — | — | — | — | — | — | 70 | — | — | — | 100 | 10 |
| Kochia | — | — | — | — | — | — | — | — | — | — | — | — | 30 | — | — | — | 100 | 0 |
| Morningglory | 90 | 90 | 70 | 100 | 100 | 80 | 0 | 100 | 100 | 10 | 30 | 20 | — | 80 | 100 | 100 | — | — |
| Pigweed | 100 | 100 | 100 | 100 | 100 | 90 | 90 | 100 | 100 | 100 | 100 | 70 | 80 | 100 | 100 | 100 | 100 | 30 |
| Ragweed | — | — | — | — | — | — | — | — | — | — | — | — | 20 | — | — | — | 100 | 0 |
| Ryegrass, Italian | — | — | — | — | — | — | — | — | — | — | — | — | 0 | — | — | — | 90 | 0 |
| Velvetleaf | 100 | 100 | 90 | 100 | 80 | 100 | 100 | 100 | 100 | 70 | 60 | 70 | — | 100 | 100 | 100 | — | — |
| Wheat | 20 | 60 | 20 | 30 | 0 | 0 | 0 | 60 | 20 | 0 | 30 | 0 | 0 | 60 | 90 | 50 | 70 | 0 |

| | Postemergence 1000 g ai/ha Compounds | | | | | | | | | | | | | | | | | |
|---|---|---|---|---|---|---|---|---|---|---|---|---|---|---|---|---|---|---|
| | 154 | 155 | 159 | 160 | 193 | 207 | 216 | 217 | 222 | 223 | 224 | 229 | 248 | 255 | 256 | 257 | 262 | |
| Barnyardgrass | 100 | 100 | 70 | 100 | 90 | 10 | 0 | 30 | 100 | 100 | 90 | 0 | 70 | 10 | 10 | 10 | 10 | |
| Blackgrass | 90 | 100 | 50 | 100 | — | — | — | — | — | — | — | — | 30 | 10 | 10 | 10 | 10 | |
| Corn | 90 | 100 | 40 | 100 | 60 | 0 | 0 | 0 | 50 | 60 | 50 | 0 | 80 | 0 | 0 | 0 | 0 | |
| Crabgrass, Large | — | — | — | — | 80 | 40 | 40 | 60 | 100 | 100 | 80 | 0 | — | — | — | — | — | |

TABLE A-continued

| | | | | | | | | | | | | | | | | |
|---|---|---|---|---|---|---|---|---|---|---|---|---|---|---|---|---|
| Foxtail, Giant | 100 | 100 | 90 | 100 | 80 | 60 | 30 | 50 | 90 | 90 | 90 | 0 | 100 | 10 | 10 | 10 | 10 |
| *Galium* | 100 | 100 | 90 | 100 | — | — | — | — | — | — | — | — | 100 | 10 | 30 | 30 | 10 |
| *Kochia* | 100 | 100 | 100 | 100 | — | — | — | — | — | — | — | — | 90 | 50 | 30 | 60 | 30 |
| Morningglory | — | — | — | — | 90 | 30 | 40 | 90 | 100 | 100 | 100 | 0 | — | — | — | — | — |
| Pigweed | 100 | 100 | 100 | 100 | 100 | 70 | 100 | 100 | 100 | 100 | 100 | 60 | 100 | 30 | 10 | 40 | 50 |
| Ragweed | 100 | 100 | 80 | 100 | — | — | — | — | — | — | — | — | 50 | 10 | 10 | 30 | 10 |
| Ryegrass, Italian | 90 | 100 | 30 | 90 | — | — | — | — | — | — | — | — | 50 | 0 | 0 | 0 | 0 |
| Velvetleaf | — | — | — | — | 90 | 30 | 100 | 100 | 100 | 100 | 100 | 0 | — | — | — | — | — |
| Wheat | 80 | 90 | 30 | 100 | 20 | 0 | 0 | 20 | 40 | 70 | 60 | 0 | 20 | 0 | 0 | 0 | 0 |

| | Postemergence | | | | | | | | | | | | | | | |
|---|---|---|---|---|---|---|---|---|---|---|---|---|---|---|---|---|
| | 1000 g ai/ha Compounds | | | | | | | | | | | 500 g ai/ha Compounds | | | | |
| | 263 | 276 | 280 | 281 | 282 | 283 | 297 | 298 | 299 | 300 | 302 | 303 | 1 | 2 | 3 | 4 | 5 |
| Barnyardgrass | 0 | 20 | 90 | 0 | 90 | 0 | 10 | 90 | 80 | 0 | 0 | 20 | 30 | 70 | 90 | 0 | 60 |
| Blackgrass | 20 | 20 | — | 0 | 100 | 10 | — | 80 | 80 | 0 | 0 | — | — | — | — | — | — |
| Corn | 0 | 10 | 50 | 10 | 50 | 0 | 0 | 70 | 70 | 10 | 0 | 10 | 10 | 40 | 40 | 0 | 30 |
| Crabgrass, Large | — | — | 90 | — | — | — | 30 | — | — | — | — | 20 | 50 | 60 | 80 | 0 | 80 |
| Foxtail, Giant | 0 | 20 | 90 | 0 | 60 | 0 | 10 | 90 | 90 | 30 | 0 | 20 | 60 | 80 | 90 | 0 | 100 |
| *Galium* | 10 | 20 | — | 60 | 30 | 30 | — | 80 | 80 | 40 | 0 | — | — | — | — | — | — |
| *Kochia* | 10 | 40 | — | 70 | 90 | 10 | — | 100 | 70 | 20 | 0 | — | — | — | — | — | — |
| Morningglory | — | — | 30 | — | — | — | 30 | — | — | — | — | 30 | 20 | 70 | 70 | 0 | 90 |
| Pigweed | 10 | 80 | 100 | 70 | 80 | 20 | 70 | 100 | 100 | 60 | 0 | 90 | 100 | 100 | 100 | 20 | 100 |
| Ragweed | 0 | 30 | — | 70 | 100 | 20 | — | 90 | 30 | 0 | 0 | — | — | — | — | — | — |
| Ryegrass, Italian | 0 | 0 | — | 0 | 80 | 0 | — | 70 | 70 | 0 | 0 | — | — | — | — | — | — |
| Velvetleaf | — | — | 90 | — | — | — | 60 | — | — | — | — | 70 | 70 | 60 | 100 | 0 | 100 |
| Wheat | 0 | 0 | 40 | 0 | 0 | 0 | 0 | 40 | 20 | 0 | 0 | 0 | 0 | 0 | 0 | 0 | 40 |

| | Postemergence 500 g ai/ha Compounds | | | | | | | | | | | | | | | |
|---|---|---|---|---|---|---|---|---|---|---|---|---|---|---|---|---|
| | 6 | 7 | 8 | 9 | 10 | 11 | 15 | 16 | 17 | 18 | 19 | 20 | 21 | 22 | 23 | 24 | 25 |
| Barnyardgrass | 100 | 100 | 90 | 90 | 90 | 90 | 60 | 100 | 20 | 100 | 20 | 30 | 40 | 70 | 40 | 0 | 100 |
| Blackgrass | — | — | — | — | — | — | — | — | — | — | — | — | — | — | — | — | — |
| Corn | 60 | 50 | 30 | 50 | 50 | 50 | 20 | 80 | 40 | 90 | 30 | 30 | 30 | 30 | 60 | 0 | 40 |
| Crabgrass, Large | 100 | 100 | 90 | 80 | 80 | 90 | 60 | 100 | 90 | 100 | 20 | 30 | 50 | 70 | 60 | 0 | 100 |
| Foxtail, Giant | 100 | 100 | 90 | 90 | 90 | 90 | 70 | 100 | 90 | 100 | 30 | 60 | 90 | 90 | 90 | 0 | 100 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 70 | 100 | 100 | 30 | 100 | 100 | 20 | 100 | 50 | 100 | 40 | 40 | 80 | 90 | 90 | 0 | 90 |
| Pigweed | 100 | 100 | 90 | 100 | 100 | 100 | 100 | 100 | 100 | 100 | 90 | 100 | 100 | 100 | 100 | 60 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 100 | 100 | 100 | 100 | 100 | 100 | 100 | 60 | 70 | 80 | 100 | 100 | 0 | 100 |
| Wheat | 90 | 50 | 20 | 30 | 60 | 20 | 10 | 80 | 50 | 50 | 0 | 20 | 20 | 0 | 20 | 0 | 60 |

| | Postemergence 500 g ai/ha Compounds | | | | | | | | | | | | | | | |
|---|---|---|---|---|---|---|---|---|---|---|---|---|---|---|---|---|
| | 26 | 27 | 28 | 29 | 30 | 31 | 32 | 33 | 34 | 35 | 36 | 37 | 38 | 39 | 40 | 41 | 42 |
| Barnyardgrass | 90 | 10 | 10 | 0 | 10 | 50 | 20 | 100 | 50 | 0 | 0 | 0 | 0 | 0 | 20 | 50 | 0 |
| Blackgrass | — | — | — | — | — | — | — | — | — | — | — | — | — | — | — | — | — |
| Corn | 30 | 10 | 20 | 0 | 0 | 20 | 20 | 100 | 20 | 20 | 0 | 0 | 0 | 10 | 0 | 20 | 0 |
| Crabgrass, Large | 100 | 60 | 20 | 40 | 40 | 60 | 50 | 80 | 60 | 0 | 10 | 0 | 10 | 10 | 70 | 70 | 50 |
| Foxtail, Giant | 90 | 30 | 10 | 30 | 10 | 50 | 30 | 100 | 70 | 0 | 0 | 0 | 0 | 0 | 60 | 80 | 30 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 90 | 50 | 10 | 0 | 0 | 30 | 0 | — | 80 | — | — | — | — | — | 100 | 30 | 40 |
| Pigweed | 100 | 70 | 30 | 50 | 30 | 70 | 70 | 100 | 100 | 40 | 20 | 10 | 10 | 40 | 60 | 80 | 30 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 70 | 30 | 40 | 30 | 100 | 100 | 100 | 100 | 70 | 40 | 20 | 30 | 100 | 100 | 70 | |
| Wheat | 30 | 0 | 0 | 0 | 0 | 0 | 0 | 90 | 20 | 0 | 0 | 0 | 0 | 0 | 0 | 0 | 0 |

| | Postemergence 500 g ai/ha Compounds | | | | | | | | | | | | | | | |
|---|---|---|---|---|---|---|---|---|---|---|---|---|---|---|---|---|
| | 43 | 44 | 45 | 46 | 47 | 48 | 49 | 50 | 51 | 52 | 57 | 58 | 59 | 60 | 61 | 62 | 63 |
| Barnyardgrass | 10 | 90 | 100 | 20 | 100 | 10 | 10 | 10 | 10 | 100 | 100 | 100 | 100 | 50 | 0 | 100 | 70 |
| Blackgrass | — | — | — | — | — | — | — | — | — | — | — | — | — | — | — | — | — |
| Corn | 10 | 40 | 70 | 30 | 90 | 0 | 0 | 0 | 20 | 90 | 90 | 100 | 100 | 30 | 0 | 90 | 30 |

TABLE A-continued

| | | | | | | | | | | | | | | | | | |
|---|---|---|---|---|---|---|---|---|---|---|---|---|---|---|---|---|---|
| Crabgrass, Large | 20 | 100 | 100 | 20 | 100 | 20 | 10 | 10 | 20 | 100 | 100 | 100 | 100 | 70 | 0 | 100 | 90 |
| Foxtail, Giant | 40 | 90 | 90 | 20 | 100 | 20 | 10 | 0 | 10 | 100 | 100 | 100 | 100 | 80 | 0 | 100 | 80 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 50 | 60 | 20 | 50 | 100 | 30 | 20 | 30 | 20 | 100 | 80 | 100 | 100 | 50 | 0 | 100 | 80 |
| Pigweed | 40 | 100 | 80 | 80 | 100 | 50 | 40 | 30 | 70 | 100 | 100 | 100 | 100 | 100 | 0 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 40 | 100 | 10 | 30 | 10 | 60 | 100 | 100 | 100 | 100 | 100 | 30 | 100 | 100 |
| Wheat | 0 | 30 | 40 | 0 | 100 | 0 | 0 | 0 | 0 | 100 | 30 | 100 | 100 | 10 | 0 | 100 | 10 |

| | Postemergence 500 g ai/ha Compounds | | | | | | | | | | | | | | | |
|---|---|---|---|---|---|---|---|---|---|---|---|---|---|---|---|---|
| | 64 | 68 | 71 | 72 | 73 | 74 | 75 | 76 | 77 | 78 | 79 | 80 | 81 | 82 | 83 | 84 | 85 |
| Barnyardgrass | 100 | 0 | 90 | 100 | 90 | 90 | 70 | 100 | 70 | 50 | 100 | 100 | 100 | 20 | 100 | 100 | 90 |
| Blackgrass | — | 0 | — | — | — | — | — | — | — | — | — | — | — | 50 | 100 | 100 | 80 |
| Corn | 90 | 0 | 60 | 60 | 80 | 70 | 40 | 80 | 40 | 30 | 100 | 10 | 30 | 10 | 60 | 70 | 70 |
| Crabgrass, Large | 100 | — | 100 | 100 | 100 | 90 | 70 | 100 | 90 | 100 | 100 | 100 | 90 | — | — | — | — |
| Foxtail, Giant | 100 | 0 | 90 | 100 | 100 | 90 | 80 | 90 | 90 | 90 | 90 | 100 | 90 | 20 | 100 | 100 | 90 |
| *Galium* | — | 0 | — | — | — | — | — | — | — | — | — | — | — | 20 | 100 | 100 | 100 |
| *Kochia* | — | 0 | — | — | — | — | — | — | — | — | — | — | — | 10 | 100 | 100 | 100 |
| Morningglory | 80 | — | 90 | 100 | 100 | 100 | 60 | 90 | 100 | 90 | 100 | 100 | 100 | — | — | — | — |
| Pigweed | 100 | 0 | 100 | 100 | 100 | 100 | 100 | 100 | 100 | 100 | 100 | 100 | 100 | 40 | 100 | 100 | 100 |
| Ragweed | — | 0 | — | — | — | — | — | — | — | — | — | — | — | 10 | 80 | 90 | 60 |
| Ryegrass, Italian | — | 0 | — | — | — | — | — | — | — | — | — | — | — | 20 | 80 | 80 | 100 |
| Velvetleaf | 100 | — | 100 | 100 | 100 | 100 | 70 | 100 | 100 | 100 | 100 | 100 | 100 | — | — | — | — |
| Wheat | 30 | 0 | 40 | 50 | 50 | 50 | 0 | 10 | 30 | 20 | 90 | 80 | 60 | 30 | 60 | 80 | 70 |

| | Postemergence 500 g ai/ha Compounds | | | | | | | | | | | | | | | |
|---|---|---|---|---|---|---|---|---|---|---|---|---|---|---|---|---|
| | 86 | 87 | 88 | 89 | 90 | 91 | 92 | 93 | 94 | 95 | 96 | 97 | 98 | 111 | 112 | 113 | 117 |
| Barnyardgrass | 100 | 20 | 80 | 90 | 100 | 10 | 100 | 0 | 90 | 80 | 30 | 100 | 90 | 90 | 90 | 80 | 90 |
| Blackgrass | 100 | 50 | 100 | 90 | 70 | 30 | — | — | — | — | — | — | — | — | — | — | 80 |
| Corn | 100 | 20 | 50 | 90 | 80 | 0 | 80 | 0 | 50 | 70 | 10 | 90 | 70 | 90 | 70 | 60 | 50 |
| Crabgrass, Large | — | — | — | — | — | — | 90 | 0 | 90 | 90 | 30 | 100 | 100 | 90 | 100 | 70 | — |
| Foxtail, Giant | 100 | 60 | 80 | 90 | 90 | 10 | 90 | 0 | 90 | 80 | 20 | 90 | 90 | 90 | 90 | 60 | 90 |
| *Galium* | 100 | 90 | 100 | 90 | 100 | 70 | — | — | — | — | — | — | — | — | — | — | 100 |
| *Kochia* | 100 | 90 | 100 | 90 | 100 | 30 | — | — | — | — | — | — | — | — | — | — | 100 |
| Morningglory | — | — | — | — | — | — | 100 | 0 | 100 | 90 | 10 | 100 | 100 | 90 | 100 | 30 | — |
| Pigweed | 100 | 100 | 100 | 100 | 100 | 50 | 100 | 0 | 100 | 100 | 40 | 100 | 100 | 100 | 100 | 80 | 100 |
| Ragweed | 100 | 70 | 30 | 90 | 80 | 30 | — | — | — | — | — | — | — | — | — | — | 100 |
| Ryegrass, Italian | 100 | 40 | 90 | 90 | 80 | 0 | — | — | — | — | — | — | — | — | — | — | 90 |
| Velvetleaf | — | — | — | — | — | — | 100 | 0 | 100 | 100 | 10 | 100 | 100 | 100 | 100 | 80 | — |
| Wheat | 90 | 0 | 50 | 70 | 50 | 10 | 70 | 0 | 50 | 40 | 0 | 70 | 60 | 80 | 70 | 60 | 70 |

| | Postemergence 500 g ai/ha Compounds | | | | | | | | | | | | | | | |
|---|---|---|---|---|---|---|---|---|---|---|---|---|---|---|---|---|
| | 129 | 130 | 131 | 132 | 134 | 135 | 136 | 137 | 138 | 142 | 143 | 145 | 146 | 147 | 150 | 161 | 162 |
| Barnyardgrass | 90 | 0 | 0 | 70 | 90 | 100 | 90 | 100 | 100 | 0 | 80 | 100 | 60 | 90 | — | 0 | 10 |
| Blackgrass | 90 | 0 | 0 | 90 | 90 | 90 | 100 | 90 | 90 | 0 | 90 | 100 | 70 | 100 | 100 | — | — |
| Corn | 50 | 0 | 0 | 50 | 60 | 80 | 60 | 80 | 90 | 0 | 40 | 60 | 30 | 90 | 90 | 0 | 10 |
| Crabgrass, Large | — | — | — | — | — | — | — | — | — | — | — | — | — | — | — | 0 | 10 |
| Foxtail, Giant | 100 | 0 | 0 | 90 | 100 | 100 | 90 | 100 | 100 | 0 | 100 | 100 | 80 | 90 | 100 | 0 | 0 |
| *Galium* | 100 | 0 | 0 | 100 | 100 | 90 | 100 | 100 | 100 | 0 | 100 | 100 | 100 | 100 | 100 | — | — |
| *Kochia* | 100 | 0 | 0 | 100 | 100 | 70 | 100 | 100 | 100 | 70 | 90 | 100 | 100 | 100 | 100 | — | — |
| Morningglory | — | — | — | — | — | — | — | — | — | — | — | — | — | — | — | 0 | 10 |
| Pigweed | 100 | 0 | 0 | 100 | 100 | 100 | 100 | 100 | 100 | 0 | 100 | 100 | 100 | 100 | 100 | 80 | 70 |
| Ragweed | 90 | 0 | 0 | 30 | 60 | 100 | 100 | 100 | 60 | 0 | 100 | 100 | 10 | 100 | 60 | — | — |
| Ryegrass, Italian | 90 | 0 | 0 | 60 | 100 | 70 | 90 | 80 | 90 | 0 | 90 | 100 | 40 | 90 | 100 | — | — |
| Velvetleaf | — | — | — | — | — | — | — | — | — | — | — | — | — | — | — | 20 | 50 |
| Wheat | 70 | 0 | 0 | 60 | 70 | 60 | 50 | 70 | 90 | 0 | 30 | 70 | 0 | 80 | 90 | 0 | 0 |

| | Postemergence 500 g ai/ha Compounds | | | | | | | | | | | | | | | |
|---|---|---|---|---|---|---|---|---|---|---|---|---|---|---|---|---|
| | 163 | 164 | 165 | 166 | 167 | 168 | 170 | 171 | 172 | 173 | 174 | 175 | 176 | 177 | 178 | 179 | 180 |
| Barnyardgrass | 100 | 100 | 0 | 100 | 100 | 90 | 90 | 0 | 60 | 30 | 0 | 0 | 40 | 100 | 100 | 100 | 100 |
| Blackgrass | — | — | — | — | — | — | — | — | — | — | — | — | — | — | — | — | — |
| Corn | 50 | 90 | 0 | 60 | 50 | 30 | 90 | 0 | 20 | 20 | 0 | 0 | 20 | 70 | 70 | 60 | 90 |

TABLE A-continued

| | | | | | | | | | | | | | | | | | |
|---|---|---|---|---|---|---|---|---|---|---|---|---|---|---|---|---|---|
| Crabgrass, Large | 90 | 100 | 10 | 100 | 90 | 90 | 90 | 0 | 30 | 40 | 0 | 0 | 40 | 100 | 100 | 100 | 90 |
| Foxtail, Giant | 90 | 100 | 20 | 90 | 90 | 90 | 90 | 0 | 20 | 50 | 0 | 0 | 50 | 100 | 100 | 90 | 90 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 100 | 100 | 20 | 100 | 100 | 100 | 90 | 0 | 90 | 0 | 0 | 0 | 80 | 100 | 100 | 100 | 100 |
| Pigweed | 100 | 100 | 80 | 100 | 100 | 100 | 100 | 100 | 100 | 100 | 0 | 0 | 100 | 100 | 100 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 30 | 100 | 100 | 100 | 100 | 70 | 100 | 70 | 0 | 0 | 90 | 100 | 100 | 100 | 100 |
| Wheat | 60 | 90 | 0 | 70 | 60 | 50 | 70 | 0 | 0 | 0 | 0 | 0 | 10 | 90 | 80 | 60 | 80 |

| | Postemergence 500 g ai/ha Compounds | | | | | | | | | | | | | | | | |
|---|---|---|---|---|---|---|---|---|---|---|---|---|---|---|---|---|---|
| | 181 | 182 | 183 | 184 | 185 | 186 | 187 | 188 | 189 | 190 | 191 | 192 | 194 | 195 | 196 | 197 | 198 |
| Barnyardgrass | 90 | 0 | 0 | 90 | 80 | 70 | 90 | 90 | 90 | 10 | 90 | 90 | 90 | 20 | 50 | 60 | 50 |
| Blackgrass | — | — | — | — | — | — | — | — | — | — | — | — | — | — | — | — | — |
| Corn | 40 | 0 | 0 | 70 | 20 | 30 | 70 | 50 | 40 | 20 | 40 | 60 | 60 | 20 | 40 | 10 | 20 |
| Crabgrass, Large | 90 | 0 | 0 | 80 | 90 | 70 | 100 | 80 | 80 | 50 | 90 | 90 | 100 | 60 | 90 | 70 | 90 |
| Foxtail, Giant | 90 | 0 | 0 | 80 | 80 | 80 | 90 | 90 | 80 | 40 | 90 | 90 | 100 | 50 | 80 | 70 | 80 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 100 | 0 | 0 | 90 | 90 | 100 | 100 | 100 | 100 | 90 | 100 | 100 | 100 | 70 | 80 | 30 | 70 |
| Pigweed | 100 | 90 | 50 | 100 | 100 | 100 | 100 | 100 | 100 | 100 | 100 | 100 | 100 | 80 | 100 | 60 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 30 | 30 | 90 | 100 | 90 | 100 | 100 | 100 | 80 | 100 | 100 | 100 | 100 | 100 | 100 | 100 |
| Wheat | 30 | 0 | 0 | 90 | 40 | 60 | 60 | 30 | 50 | 0 | 40 | 50 | 60 | 0 | 10 | 0 | 10 |

| | Postemergence 500 g ai/ha Compounds | | | | | | | | | | | | | | | | |
|---|---|---|---|---|---|---|---|---|---|---|---|---|---|---|---|---|---|
| | 199 | 200 | 201 | 202 | 203 | 204 | 205 | 206 | 208 | 209 | 210 | 211 | 212 | 213 | 214 | 215 | 218 |
| Barnyardgrass | 80 | 90 | 10 | 0 | 70 | 90 | 0 | 0 | 0 | 100 | 40 | 50 | 0 | 10 | 0 | 30 | 70 |
| Blackgrass | — | — | — | — | — | — | — | — | — | — | — | — | 50 | — | — | — | — |
| Corn | 60 | 60 | 0 | 0 | 50 | 60 | 0 | 0 | 20 | 70 | 30 | 0 | 0 | 30 | 0 | 20 | 40 |
| Crabgrass, Large | 90 | 90 | 30 | 50 | 80 | 100 | 0 | 0 | 20 | 90 | 70 | 50 | — | 70 | 0 | 30 | 70 |
| Foxtail, Giant | 90 | 90 | 40 | 30 | 80 | 100 | 0 | 0 | 20 | 90 | 60 | 60 | 50 | 30 | 0 | 10 | 70 |
| *Galium* | — | — | — | — | — | — | — | — | — | — | — | — | 30 | — | — | — | — |
| *Kochia* | — | — | — | — | — | — | — | — | — | — | — | — | 10 | — | — | — | — |
| Morningglory | 60 | 100 | 20 | 20 | 70 | 100 | 0 | 0 | 80 | 90 | 30 | 100 | — | 30 | 0 | 10 | 90 |
| Pigweed | 100 | 100 | 40 | 50 | 90 | 100 | 0 | 0 | 100 | 100 | 100 | 100 | 30 | 100 | 0 | 80 | 100 |
| Ragweed | — | — | — | — | — | — | — | — | — | — | — | — | 10 | — | — | — | — |
| Ryegrass, Italian | — | — | — | — | — | — | — | — | — | — | — | — | 30 | — | — | — | — |
| Velvetleaf | 100 | 100 | 70 | 70 | 90 | 100 | 20 | 20 | 60 | 100 | 80 | 90 | — | 20 | 0 | 50 | 100 |
| Wheat | 30 | 60 | 0 | 0 | 20 | 70 | 0 | 0 | 0 | 70 | 0 | 0 | 30 | 0 | 0 | 0 | 20 |

| | Postemergence 500 g ai/ha Compounds | | | | | | | | | | | | | | | | |
|---|---|---|---|---|---|---|---|---|---|---|---|---|---|---|---|---|---|
| | 219 | 220 | 221 | 225 | 226 | 227 | 228 | 230 | 231 | 232 | 233 | 234 | 235 | 236 | 237 | 238 | 239 |
| Barnyardgrass | 100 | 100 | 100 | 10 | 0 | 0 | 90 | 20 | 90 | 90 | 20 | 70 | 0 | 100 | 0 | 100 | 80 |
| Blackgrass | — | — | — | — | — | — | — | — | — | — | — | — | — | — | — | — | — |
| Corn | 70 | 70 | 50 | 0 | 0 | 0 | 10 | 0 | 90 | 90 | 0 | 30 | 0 | 100 | 0 | 80 | 20 |
| Crabgrass, Large | 100 | 100 | 100 | 10 | 0 | 10 | 90 | 10 | 90 | 90 | 10 | 60 | 30 | 100 | 0 | 90 | 70 |
| Foxtail, Giant | 90 | 90 | 90 | 0 | 0 | 10 | 90 | 20 | 90 | 90 | 20 | 70 | 30 | 100 | 0 | 90 | 70 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 100 | 100 | 100 | 0 | 0 | 10 | 100 | 0 | 90 | 90 | 0 | 60 | 30 | 100 | 0 | 60 | 40 |
| Pigweed | 100 | 100 | 100 | 0 | 10 | 60 | 100 | 60 | 100 | 100 | 50 | 100 | 100 | 100 | 70 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 0 | 10 | 90 | 100 | 30 | 100 | 100 | 30 | 100 | 30 | 100 | 30 | 100 | 60 |
| Wheat | 70 | 60 | 30 | 0 | 0 | 0 | 70 | 0 | 50 | 50 | 0 | 20 | 0 | 100 | 0 | 60 | 0 |

| | Postemergence 500 g ai/ha Compounds | | | | | | | | | | | | | | | | |
|---|---|---|---|---|---|---|---|---|---|---|---|---|---|---|---|---|---|
| | 240 | 252 | 273 | 274 | 275 | 284 | 285 | 287 | 288 | 289 | 290 | 291 | 292 | 293 | 294 | 295 | 296 |
| Barnyardgrass | 100 | 100 | 90 | 100 | 0 | 90 | 30 | 0 | 10 | 20 | 0 | 40 | 90 | 10 | 60 | 0 | 0 |
| Blackgrass | 100 | 100 | 80 | — | — | 70 | — | — | — | — | — | — | — | — | — | — | — |
| Corn | 90 | 90 | 50 | 90 | 0 | 40 | 30 | 0 | 10 | 10 | 10 | 10 | 80 | 20 | 40 | 0 | 10 |

TABLE A-continued

| | | | | | | | | | | | | | | | | | |
|---|---|---|---|---|---|---|---|---|---|---|---|---|---|---|---|---|---|
| Crabgrass, Large | — | — | — | 90 | 20 | — | 40 | 20 | 20 | 20 | 10 | 60 | 90 | 30 | 50 | 0 | 0 |
| Foxtail, Giant | 100 | 100 | 90 | 90 | 30 | 90 | 60 | 0 | 20 | 30 | 10 | 50 | 90 | 30 | 50 | 0 | 0 |
| *Galium* | 100 | 100 | 100 | — | — | 60 | — | — | — | — | — | — | — | — | — | — | — |
| *Kochia* | 60 | 100 | 100 | — | — | 100 | — | — | — | — | — | — | — | — | — | — | — |
| Morningglory | — | — | — | 100 | 50 | — | 40 | 20 | 40 | 50 | 10 | 40 | 100 | 30 | 30 | 40 | 20 |
| Pigweed | 100 | 100 | 100 | 100 | 90 | 100 | 100 | 50 | 100 | 100 | 20 | 70 | 100 | 90 | 90 | 70 | 100 |
| Ragweed | 100 | 90 | 90 | — | — | 20 | — | — | — | — | — | — | — | — | — | — | — |
| Ryegrass, Italian | 100 | 70 | 80 | — | — | 60 | — | — | — | — | — | — | — | — | — | — | — |
| Velvetleaf | — | — | — | 100 | 90 | — | 80 | 20 | 30 | 40 | 30 | 60 | 100 | 80 | 60 | 30 | 30 |
| Wheat | 90 | 90 | 50 | 80 | 0 | 20 | 20 | 0 | 0 | 0 | 0 | 0 | 60 | 0 | 40 | 0 | 20 |

| | Postemergence | | | | | | | | | | | | | | | | |
|---|---|---|---|---|---|---|---|---|---|---|---|---|---|---|---|---|---|
| | 500 g ai/ha Compounds | | 125 g ai/ha Compounds | | | | | | | | | | | | | | |
| | 301 | 304 | 1 | 2 | 3 | 4 | 5 | 6 | 7 | 8 | 9 | 10 | 11 | 15 | 16 | 17 | 18 |
| Barnyardgrass | 0 | 0 | 10 | 30 | 10 | 0 | 10 | 40 | 90 | 30 | 30 | 40 | 10 | 0 | 60 | 0 | 60 |
| Blackgrass | — | — | — | — | — | — | — | — | — | — | — | — | — | — | — | — | — |
| Corn | 0 | 0 | 0 | 0 | 0 | 0 | 0 | 20 | 30 | 0 | 20 | 20 | 10 | 0 | 70 | 0 | 30 |
| Crabgrass, Large | 0 | 0 | 20 | 20 | 10 | 0 | 30 | 50 | 80 | 50 | 30 | 50 | 70 | 10 | 80 | 20 | 70 |
| Foxtail, Giant | 0 | 0 | 10 | 10 | 30 | 0 | 40 | 80 | 90 | 50 | 30 | 50 | 70 | 10 | 100 | 20 | 80 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 0 | 0 | 0 | 30 | 10 | 0 | 80 | 40 | 70 | 70 | 20 | 90 | 60 | 10 | 90 | 20 | 60 |
| Pigweed | 30 | 50 | 50 | 60 | 90 | 0 | 100 | 100 | 100 | 100 | 80 | 100 | 100 | 70 | 100 | 70 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 0 | 0 | 20 | — | 100 | 0 | 100 | 100 | 100 | 100 | 100 | 100 | 100 | 90 | 100 | 50 | 100 |
| Wheat | 0 | 0 | 0 | 0 | 0 | 0 | 0 | 40 | 30 | 0 | 0 | 0 | 0 | 0 | 70 | 0 | 50 |

| | Postemergence 125 g ai/ha Compounds | | | | | | | | | | | | | | | | |
|---|---|---|---|---|---|---|---|---|---|---|---|---|---|---|---|---|---|
| | 19 | 20 | 21 | 22 | 23 | 24 | 25 | 26 | 27 | 28 | 29 | 30 | 31 | 32 | 33 | 34 | 35 |
| Barnyardgrass | 0 | 0 | 0 | 50 | 0 | 0 | 30 | 20 | 0 | 0 | 0 | 10 | 10 | 0 | 0 | 20 | 0 |
| Blackgrass | — | — | — | — | — | — | — | — | — | — | — | — | — | — | — | — | — |
| Corn | 0 | 0 | 0 | 0 | 0 | 0 | 20 | 20 | 0 | 0 | 0 | 0 | 0 | 0 | 0 | 10 | 0 |
| Crabgrass, Large | 0 | 0 | 20 | 30 | 20 | 0 | 80 | 60 | 20 | 0 | 10 | 30 | 50 | 50 | 20 | 50 | 0 |
| Foxtail, Giant | 0 | 0 | 30 | 40 | 40 | 0 | 90 | 70 | 0 | 0 | 20 | 10 | 40 | 0 | 70 | 30 | 0 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 0 | 40 | 40 | 80 | 50 | 0 | 80 | 60 | 10 | 10 | 0 | 0 | 0 | 0 | — | 60 | — |
| Pigweed | 30 | 80 | 90 | 50 | 90 | 0 | 100 | 100 | 60 | 10 | 20 | 0 | 40 | 50 | 100 | 90 | 0 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 30 | 20 | 50 | 50 | 80 | — | 90 | 90 | 50 | 0 | 20 | 20 | 100 | 80 | 100 | 80 | 20 |
| Wheat | 0 | 0 | 0 | 0 | 0 | 0 | 30 | 0 | 0 | 0 | 0 | 0 | 0 | 0 | 0 | 0 | 0 |

| | Postemergence 125 g ai/ha Compounds | | | | | | | | | | | | | | | | |
|---|---|---|---|---|---|---|---|---|---|---|---|---|---|---|---|---|---|
| | 36 | 37 | 38 | 39 | 40 | 41 | 42 | 43 | 44 | 45 | 46 | 47 | 48 | 49 | 50 | 51 | 52 |
| Barnyardgrass | 0 | 0 | 0 | 0 | 0 | 10 | 0 | 0 | 30 | 40 | 0 | 30 | 0 | 0 | 0 | 0 | 90 |
| Blackgrass | — | — | — | — | — | — | — | — | — | — | — | — | — | — | — | — | — |
| Corn | 0 | 0 | 0 | 0 | 0 | 0 | 0 | 0 | 20 | 10 | 0 | 40 | 0 | 0 | 0 | 0 | 90 |
| Crabgrass, Large | 0 | 0 | 0 | 0 | 50 | 20 | 10 | 10 | 80 | 60 | 0 | 70 | 10 | 0 | 0 | 0 | 90 |
| Foxtail, Giant | 0 | 0 | 0 | 0 | 10 | 20 | 0 | 0 | 50 | 70 | 0 | 80 | 0 | 0 | 0 | 0 | 90 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | — | — | — | — | 70 | 20 | 20 | 30 | 20 | 10 | 20 | 80 | 20 | 0 | 20 | 10 | 100 |
| Pigweed | 0 | 0 | 0 | 10 | 40 | 50 | 0 | 30 | 70 | 60 | 40 | 100 | 20 | 0 | 20 | 30 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 20 | 20 | 10 | 20 | 100 | 70 | 60 | 60 | 100 | 100 | 0 | 100 | 0 | 10 | 0 | 50 | 100 |
| Wheat | 0 | 0 | 0 | 0 | 0 | 0 | 0 | 0 | 0 | 0 | 0 | 60 | 0 | 0 | 0 | 0 | 40 |

| | Postemergence 125 g ai/ha | | | | | | | | | | | | | | | | |
|---|---|---|---|---|---|---|---|---|---|---|---|---|---|---|---|---|---|
| | 57 | 58 | 59 | 60 | 61 | 62 | 63 | 64 | 71 | 72 | 73 | 74 | 75 | 76 | 77 | 79 | 80 |
| Barnyardgrass | 90 | 100 | 100 | 20 | 0 | 90 | 30 | 60 | 80 | 90 | 90 | 90 | 30 | 60 | 40 | 100 | 70 |
| Blackgrass | — | — | — | — | — | — | — | — | — | — | — | — | — | — | — | — | — |

TABLE A-continued

| | | | | | | | | | | | | | | | | | |
|---|---|---|---|---|---|---|---|---|---|---|---|---|---|---|---|---|---|
| Corn | 30 | 100 | 60 | 0 | 0 | 70 | 0 | 30 | 30 | 50 | 40 | 30 | 0 | 10 | 20 | 80 | 70 |
| Crabgrass, Large | 90 | 100 | 100 | 10 | 0 | 90 | 30 | 80 | 70 | 100 | 90 | 70 | 20 | 70 | 50 | 100 | 80 |
| Foxtail, Giant | 80 | 100 | 100 | 20 | 0 | 90 | 20 | 80 | 80 | 90 | 90 | 80 | 10 | 60 | 50 | 100 | 80 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 90 | 100 | 90 | 10 | 0 | 90 | 30 | 60 | 70 | 90 | 90 | 80 | 50 | 60 | 70 | 100 | 90 |
| Pigweed | 100 | 100 | 100 | 50 | 0 | 100 | 70 | 100 | 100 | 100 | 100 | 100 | 70 | 90 | 100 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 50 | 20 | 100 | 60 | 100 | 90 | 100 | 100 | 90 | 40 | 80 | 80 | 100 | 100 |
| Wheat | 0 | 90 | 70 | 0 | 0 | 20 | 0 | 0 | 10 | 20 | 20 | 0 | 0 | 0 | 0 | 80 | 40 |

| | Postemergence 125 g ai/ha Compounds | | | | | | | | | | | | | | | | |
|---|---|---|---|---|---|---|---|---|---|---|---|---|---|---|---|---|---|
| | 81 | 82 | 83 | 84 | 85 | 86 | 87 | 88 | 89 | 90 | 91 | 92 | 93 | 94 | 95 | 96 | 97 |
| Barnyardgrass | 50 | 0 | 90 | 70 | 90 | 90 | 20 | 60 | 40 | 90 | 0 | 90 | 0 | 20 | 50 | 10 | 90 |
| Blackgrass | — | 10 | 100 | 80 | 70 | 90 | 40 | 70 | 40 | 50 | 0 | — | — | — | — | — | 60 |
| Corn | 50 | 0 | 40 | 20 | 30 | 50 | 20 | 30 | 60 | 0 | 0 | 50 | 0 | 30 | 10 | 0 | 60 |
| Crabgrass, Large | 40 | — | — | — | — | — | — | — | — | — | — | 80 | 0 | 50 | 40 | 10 | 90 |
| Foxtail, Giant | 50 | 0 | 90 | 100 | 70 | 90 | 20 | 50 | 80 | 80 | 10 | 80 | 0 | 70 | 40 | 0 | 90 |
| *Galium* | — | 10 | 100 | 100 | 90 | 100 | 60 | 100 | 90 | 90 | 40 | — | — | — | — | — | — |
| *Kochia* | — | 0 | 100 | 100 | 70 | 100 | 50 | 80 | 80 | 90 | 10 | — | — | — | — | — | — |
| Morningglory | 50 | — | — | — | — | — | — | — | — | — | — | 100 | 0 | 80 | 60 | 0 | 90 |
| Pigweed | 100 | 10 | 100 | 100 | 80 | 100 | 60 | 100 | 90 | 100 | 10 | 100 | 0 | 100 | 100 | 10 | 100 |
| Ragweed | — | 0 | 70 | 50 | 50 | 90 | 50 | 10 | 30 | 60 | 10 | — | — | — | — | — | — |
| Ryegrass, Italian | — | 0 | 50 | 50 | 60 | 80 | 30 | 50 | 0 | 30 | 0 | — | — | — | — | — | — |
| Velvetleaf | 100 | — | — | — | — | — | — | — | — | — | — | 100 | 0 | 90 | 70 | 0 | 100 |
| Wheat | 10 | 0 | 0 | 30 | 0 | 50 | 0 | 0 | 20 | 0 | 0 | 60 | 0 | 0 | 0 | 0 | 50 |

| | Postemergence 125 g ai/ha Compounds | | | | | | | | | | | | | | | | |
|---|---|---|---|---|---|---|---|---|---|---|---|---|---|---|---|---|---|
| | 98 | 99 | 100 | 101 | 103 | 106 | 107 | 108 | 109 | 110 | 111 | 112 | 113 | 117 | 118 | 119 | 120 |
| Barnyardgrass | 80 | 100 | 0 | 20 | 0 | 50 | 40 | 60 | 60 | 90 | 60 | 40 | 0 | 70 | 80 | 70 | 80 |
| Blackgrass | — | 90 | 0 | 20 | 0 | 50 | 50 | 80 | 70 | 80 | — | — | — | 40 | 90 | 70 | 80 |
| Corn | 40 | 90 | 0 | 20 | 0 | 20 | 20 | 30 | 40 | 50 | 30 | 30 | 10 | 30 | 50 | 50 | 50 |
| Crabgrass, Large | 80 | — | — | — | — | — | — | — | — | — | 60 | 60 | 20 | — | — | — | — |
| Foxtail, Giant | 80 | 100 | 0 | 60 | 0 | 70 | 70 | 70 | 70 | 90 | 80 | 30 | 10 | 90 | 80 | 80 | 70 |
| *Galium* | — | 100 | 10 | 60 | 0 | 70 | 80 | 90 | 90 | 90 | — | — | — | 100 | 90 | 100 | 100 |
| *Kochia* | — | 100 | 0 | 100 | 0 | 50 | 20 | 90 | 60 | 100 | — | — | — | 100 | 100 | 90 | 90 |
| Morningglory | 100 | — | — | — | — | — | — | — | — | — | 80 | 50 | 20 | — | — | — | — |
| Pigweed | 100 | 100 | 10 | 90 | 0 | 60 | 60 | 80 | 90 | 100 | 100 | 100 | 60 | 100 | 100 | 100 | 100 |
| Ragweed | — | 60 | 0 | 20 | 0 | 50 | 40 | 30 | 30 | 50 | — | — | — | 50 | 80 | 50 | 50 |
| Ryegrass, Italian | — | 60 | 0 | 0 | 0 | 0 | 0 | 20 | 10 | 60 | — | — | — | 50 | 100 | 60 | 80 |
| Velvetleaf | 100 | — | — | — | — | — | — | — | — | — | 80 | 100 | 30 | — | — | — | — |
| Wheat | 40 | 80 | 0 | 40 | 0 | 10 | 30 | 20 | 20 | 40 | 20 | 0 | 20 | 0 | 70 | 60 | 20 |

| | Postemergence 125 g ai/ha Compounds | | | | | | | | | | | | | | | | |
|---|---|---|---|---|---|---|---|---|---|---|---|---|---|---|---|---|---|
| | 121 | 122 | 125 | 126 | 127 | 128 | 129 | 130 | 131 | 132 | 134 | 135 | 136 | 137 | 138 | 140 | 141 |
| Barnyardgrass | 20 | 40 | 90 | 40 | 10 | 50 | 90 | 0 | 0 | 50 | 80 | 40 | 30 | 0 | 80 | 70 | 100 |
| Blackgrass | 30 | 80 | 80 | 20 | 10 | 40 | 70 | 0 | 0 | 60 | 30 | 30 | 20 | 20 | 50 | 70 | 100 |
| Corn | 10 | 30 | 50 | 20 | 10 | 30 | 30 | 0 | 0 | 20 | 40 | 10 | 10 | 30 | 60 | 30 | 60 |
| Crabgrass, Large | — | — | — | — | — | — | — | — | — | — | — | — | — | — | — | — | — |
| Foxtail, Giant | 30 | 60 | 80 | 50 | 20 | 60 | 90 | 0 | 0 | 60 | 70 | 70 | 30 | 70 | 90 | 90 | 100 |
| *Galium* | 30 | 40 | 90 | 60 | 20 | 80 | 100 | 0 | 0 | 100 | 100 | 60 | 80 | 70 | 90 | 90 | 100 |
| *Kochia* | 40 | 90 | 40 | 100 | 30 | 80 | 100 | 0 | 0 | 90 | 90 | 20 | 70 | 80 | 90 | 100 | 100 |
| Morningglory | — | — | — | — | — | — | — | — | — | — | — | — | — | — | — | — | — |
| Pigweed | 40 | 100 | 70 | 80 | 30 | 100 | 100 | 0 | 0 | 100 | 100 | 70 | 80 | 70 | 100 | 100 | 100 |
| Ragweed | 40 | 30 | 10 | 50 | 10 | 20 | 80 | 0 | 0 | 10 | 50 | 60 | 50 | 20 | 30 | 70 | 100 |
| Ryegrass, Italian | 0 | 20 | 10 | 10 | 0 | 30 | 50 | 0 | 0 | 10 | 50 | 20 | 30 | 20 | 40 | 30 | 80 |
| Velvetleaf | — | — | — | — | — | — | — | — | — | — | — | — | — | — | — | — | — |
| Wheat | 0 | 10 | 20 | 10 | 0 | 10 | 0 | 0 | 0 | 0 | 10 | 0 | 30 | 50 | 0 | 80 |  |

| | Postemergence 125 g ai/ha Compounds | | | | | | | | | | | | | | | | |
|---|---|---|---|---|---|---|---|---|---|---|---|---|---|---|---|---|---|
| | 142 | 143 | 144 | 145 | 146 | 147 | 148 | 149 | 150 | 151 | 152 | 153 | 156 | 157 | 158 | 161 | 162 |
| Barnyardgrass | 0 | 0 | 90 | 70 | 10 | 90 | 30 | 70 | 100 | 60 | 30 | 0 | 10 | 80 | 80 | 0 | 0 |
| Blackgrass | 0 | 0 | 90 | 80 | 20 | 100 | 10 | 80 | 100 | 50 | 90 | 0 | 20 | 50 | 60 | — | — |

TABLE A-continued

| | | | | | | | | | | | | | | | | | |
|---|---|---|---|---|---|---|---|---|---|---|---|---|---|---|---|---|---|
| Corn | 0 | 30 | 40 | 10 | 10 | 40 | 20 | 20 | 50 | 40 | 30 | 0 | 10 | 40 | 30 | 0 | 0 |
| Crabgrass, Large | — | — | — | — | — | — | — | — | — | — | — | — | — | — | — | 0 | 0 |
| Foxtail, Giant | 0 | 0 | 100 | 80 | 20 | 90 | 40 | 90 | 100 | 40 | 40 | 0 | 10 | 80 | 70 | 0 | 0 |
| *Galium* | 0 | 30 | 90 | 100 | 50 | 100 | 60 | 100 | 90 | 40 | 90 | 0 | 30 | 90 | 100 | — | — |
| *Kochia* | 0 | 30 | 100 | 60 | 70 | 100 | 30 | 70 | 70 | 90 | 80 | 0 | 40 | 100 | 80 | — | — |
| Morningglory | — | — | — | — | — | — | — | — | — | — | — | — | — | — | — | 0 | 0 |
| Pigweed | 0 | 70 | 100 | 100 | 100 | 100 | 50 | 100 | 100 | 70 | 90 | 0 | 20 | 100 | 50 | 50 | 30 |
| Ragweed | 0 | 0 | 80 | 90 | 10 | 100 | 20 | 80 | 20 | 100 | 20 | 0 | 40 | 50 | 80 | — | — |
| Ryegrass, Italian | 0 | 0 | 50 | 50 | 0 | 70 | 0 | 30 | 40 | 30 | 20 | 0 | 0 | 20 | 50 | — | — |
| Velvetleaf | — | — | — | — | — | — | — | — | — | — | — | — | — | — | — | 10 | 10 |
| Wheat | 0 | 0 | 20 | 40 | 0 | 50 | 0 | 0 | 30 | 30 | 40 | 0 | 0 | 0 | 0 | 0 | 0 |

| | Postemergence 125 g ai/ha Compounds | | | | | | | | | | | | | | | | |
|---|---|---|---|---|---|---|---|---|---|---|---|---|---|---|---|---|---|
| | 163 | 164 | 165 | 166 | 167 | 168 | 169 | 170 | 171 | 172 | 173 | 174 | 175 | 177 | 178 | 179 | 180 |
| Barnyardgrass | 30 | 70 | 0 | 90 | 70 | 50 | 20 | 70 | 0 | 30 | 0 | 0 | 0 | 40 | 70 | 80 | 90 |
| Blackgrass | — | — | — | — | — | — | 30 | — | — | — | — | — | — | — | — | — | — |
| Corn | 30 | 40 | 0 | 50 | 40 | 20 | 0 | 80 | 0 | 0 | 0 | 0 | 0 | 40 | 30 | 30 | 70 |
| Crabgrass, Large | 30 | 80 | 0 | 90 | 80 | 70 | — | 70 | 0 | 20 | 0 | 0 | 0 | 80 | 90 | 90 | 90 |
| Foxtail, Giant | 50 | 90 | 10 | 90 | 90 | 70 | 40 | 70 | 0 | 0 | 10 | 0 | 0 | 80 | 90 | 80 | 90 |
| *Galium* | — | — | — | — | — | — | 40 | — | — | — | — | — | — | — | — | — | — |
| *Kochia* | — | — | — | — | — | — | 10 | — | — | — | — | — | — | — | — | — | — |
| Morningglory | 90 | 80 | 10 | 100 | 80 | 50 | — | 60 | 0 | 80 | 0 | 0 | 0 | 90 | 70 | 70 | 100 |
| Pigweed | 100 | 100 | 30 | 100 | 100 | 100 | 20 | 100 | 100 | 100 | 100 | 0 | 0 | 100 | 100 | 100 | 100 |
| Ragweed | — | — | — | — | — | — | 60 | — | — | — | — | — | — | — | — | — | — |
| Ryegrass, Italian | — | — | — | — | — | — | 0 | — | — | — | — | — | — | — | — | — | — |
| Velvetleaf | 100 | 100 | 10 | 100 | 100 | 90 | — | 70 | 40 | 90 | 60 | 0 | 0 | 100 | 100 | 100 | 100 |
| Wheat | 10 | 70 | 0 | 60 | 20 | 10 | 0 | 30 | 0 | 0 | 0 | 0 | 0 | 20 | 40 | 30 | 40 |

| | Postemergence 125 g ai/ha Compounds | | | | | | | | | | | | | | | | |
|---|---|---|---|---|---|---|---|---|---|---|---|---|---|---|---|---|---|
| | 181 | 182 | 183 | 184 | 185 | 186 | 187 | 188 | 189 | 190 | 191 | 192 | 194 | 195 | 196 | 197 | 198 |
| Barnyardgrass | 60 | 0 | 0 | 60 | 50 | 20 | 80 | 30 | 10 | 0 | 50 | 60 | 80 | 0 | 10 | 20 | 30 |
| Blackgrass | — | — | — | — | — | — | — | — | — | — | — | — | — | — | — | — | — |
| Corn | 40 | 0 | 0 | 20 | 10 | 0 | 10 | 20 | 10 | 0 | 20 | 10 | 30 | 0 | 10 | 0 | 20 |
| Crabgrass, Large | 70 | 0 | 0 | 70 | 60 | 40 | 60 | 50 | 30 | 10 | 50 | 50 | 90 | 40 | 30 | 30 | 60 |
| Foxtail, Giant | 70 | 0 | 0 | 70 | 50 | 20 | 60 | 60 | 40 | 0 | 50 | 70 | 90 | 10 | 30 | 20 | 30 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 90 | 0 | 0 | 60 | 70 | 60 | 70 | 40 | 50 | 30 | 80 | 80 | 90 | 30 | 20 | 0 | 60 |
| Pigweed | 100 | 30 | 20 | 100 | 100 | 100 | 70 | 100 | 100 | 100 | 100 | 100 | 100 | 60 | 100 | 30 | 90 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 30 | 20 | 80 | 90 | 80 | 100 | 90 | 90 | 60 | 90 | 90 | 100 | 50 | 100 | 60 | 90 |
| Wheat | 0 | 0 | 0 | 30 | 0 | 0 | 20 | 0 | 20 | 0 | 20 | 0 | 30 | 0 | 0 | 0 | 0 |

| | Postemergence 125 g ai/ha Compounds | | | | | | | | | | | | | | | | |
|---|---|---|---|---|---|---|---|---|---|---|---|---|---|---|---|---|---|
| | 199 | 200 | 201 | 202 | 203 | 204 | 205 | 206 | 208 | 209 | 210 | 211 | 212 | 213 | 214 | 215 | 218 |
| Barnyardgrass | 30 | 80 | 0 | 0 | 40 | 80 | 0 | 0 | 0 | 40 | 20 | 10 | 0 | 0 | 0 | 0 | 30 |
| Blackgrass | — | — | — | — | — | — | — | — | — | — | — | — | 10 | — | — | — | — |
| Corn | 20 | 50 | 0 | 0 | 30 | 50 | 0 | 0 | 0 | 30 | 10 | 0 | 0 | 0 | 0 | 0 | 0 |
| Crabgrass, Large | 40 | 90 | 0 | 10 | 60 | 90 | 0 | 0 | 0 | 70 | 40 | 10 | — | 20 | 0 | 10 | 50 |
| Foxtail, Giant | 70 | 90 | 0 | 10 | 70 | 80 | 0 | 0 | 0 | 70 | 30 | 30 | 10 | 0 | 0 | 0 | 20 |
| *Galium* | — | — | — | — | — | — | — | — | — | — | — | — | 10 | — | — | — | — |
| *Kochia* | — | — | — | — | — | — | — | — | — | — | — | — | 0 | — | — | — | — |
| Morningglory | 40 | 90 | 20 | 0 | 20 | 80 | 0 | 0 | 20 | 50 | 20 | 90 | — | 20 | 0 | 10 | 70 |
| Pigweed | 80 | 100 | 20 | 30 | 70 | 100 | 0 | 0 | 30 | 100 | 100 | 90 | 20 | 100 | 0 | 70 | 90 |
| Ragweed | — | — | — | — | — | — | — | — | — | — | — | — | 0 | — | — | — | — |
| Ryegrass, Italian | — | — | — | — | — | — | — | — | — | — | — | — | 20 | — | — | — | — |
| Velvetleaf | 70 | 100 | 30 | 50 | 80 | 100 | 10 | 10 | 40 | 100 | 60 | 50 | — | 10 | 0 | 40 | 30 |
| Wheat | 0 | 40 | 0 | 0 | 0 | 40 | 0 | 0 | 0 | 0 | 0 | 0 | 0 | 0 | 0 | 0 | 0 |

| | Postemergence 125 g ai/ha Compounds | | | | | | | | | | | | | | | |
|---|---|---|---|---|---|---|---|---|---|---|---|---|---|---|---|---|
| | 219 | 220 | 221 | 225 | 226 | 227 | 228 | 230 | 231 | 232 | 233 | 234 | 235 | 236 | 237 | 238 | 239 |
| Barnyardgrass | 50 | 90 | 50 | 0 | 0 | 0 | 10 | 0 | 40 | 30 | 0 | 20 | 0 | 100 | 0 | 40 | 0 |
| Blackgrass | — | — | — | — | — | — | — | — | — | — | — | — | — | — | — | — | — |

TABLE A-continued

| | | | | | | | | | | | | | | | | | |
|---|---|---|---|---|---|---|---|---|---|---|---|---|---|---|---|---|---|
| Corn | 20 | 40 | 10 | 0 | 0 | 0 | 50 | 0 | 20 | 30 | 0 | 20 | 0 | 70 | 0 | 0 | 0 |
| Crabgrass, Large | 90 | 100 | 60 | 0 | 0 | 0 | 40 | 0 | 70 | 60 | 0 | 20 | 10 | 80 | 0 | 60 | 10 |
| Foxtail, Giant | 70 | 80 | 50 | 0 | 0 | 0 | 50 | 0 | 70 | 70 | 0 | 30 | 0 | 90 | 0 | 60 | 20 |
| *Galium* | — | — | — | — | — | — | — | — | — | — | — | — | — | — | — | — | — |
| *Kochia* | — | — | — | — | — | — | — | — | — | — | — | — | — | — | — | — | — |
| Morningglory | 70 | 50 | 90 | 0 | 0 | 0 | 80 | 0 | 30 | 80 | 0 | 40 | 30 | 80 | 0 | 40 | 40 |
| Pigweed | 100 | 100 | 100 | 0 | 0 | 10 | 100 | 30 | 100 | 100 | 20 | 100 | 90 | 100 | 30 | 100 | 90 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 0 | 0 | 50 | 100 | 0 | 100 | 80 | 0 | 70 | 30 | 90 | 20 | 60 | 50 |
| Wheat | 0 | 10 | 0 | 0 | 0 | 0 | 0 | 0 | 20 | 20 | 0 | 20 | 0 | 50 | 0 | 0 | 0 |

Postemergence
125 g ai/ha
Compounds

| | 240 | 241 | 242 | 243 | 244 | 245 | 246 | 247 | 249 | 250 | 251 | 252 | 253 | 254 | 258 | 259 | 260 |
|---|---|---|---|---|---|---|---|---|---|---|---|---|---|---|---|---|---|
| Barnyardgrass | 90 | 10 | 60 | 0 | 10 | 30 | 0 | 20 | 60 | 60 | 30 | 100 | 100 | 60 | 90 | 30 | 0 |
| Blackgrass | 90 | 20 | 90 | 30 | 30 | 70 | 0 | 40 | 80 | 100 | 70 | 60 | 80 | 60 | 50 | 50 | 0 |
| Corn | 30 | 10 | 60 | 0 | 20 | 40 | 20 | 20 | 10 | 30 | 20 | 60 | 60 | 20 | 40 | 10 | 10 |
| Crabgrass, Large | — | — | — | — | — | — | — | — | — | — | — | — | — | — | — | — | — |
| Foxtail, Giant | 90 | 20 | 50 | 10 | 10 | 80 | 0 | 10 | 60 | 80 | 60 | 100 | 100 | 60 | 70 | 40 | 0 |
| *Galium* | 100 | 60 | 30 | 10 | 100 | 100 | 70 | 30 | 30 | 60 | 30 | 90 | 100 | 100 | 90 | 80 | 60 |
| *Kochia* | 100 | 90 | 80 | 30 | 80 | 100 | 70 | 40 | 80 | 90 | 60 | 100 | 100 | 60 | 100 | 80 | 60 |
| Morningglory | — | — | — | — | — | — | — | — | — | — | — | — | — | — | — | — | — |
| Pigweed | 100 | 80 | 80 | 20 | 100 | 90 | 40 | 20 | 100 | 90 | 70 | 100 | 100 | 30 | 100 | 90 | 60 |
| Ragweed | 100 | 30 | 50 | 20 | 0 | 20 | 0 | 0 | 70 | 100 | 20 | 70 | 80 | 20 | 50 | 70 | 40 |
| Ryegrass, Italian | 40 | 0 | 30 | 0 | 0 | 20 | 0 | 0 | 0 | 0 | 10 | 40 | 50 | 20 | 20 | 10 | 0 |
| Velvetleaf | — | — | — | — | — | — | — | — | — | — | — | — | — | — | — | — | — |
| Wheat | 30 | 10 | 60 | 20 | 20 | 40 | 0 | 20 | 0 | 0 | 0 | 30 | 30 | 30 | 50 | 0 | 0 |

Postemergence
125 g ai/ha
Compounds

| | 261 | 264 | 265 | 266 | 267 | 268 | 269 | 270 | 271 | 272 | 273 | 274 | 275 | 277 | 278 | 279 | 284 |
|---|---|---|---|---|---|---|---|---|---|---|---|---|---|---|---|---|---|
| Barnyardgrass | 0 | 0 | 0 | 0 | 0 | 0 | 0 | 80 | 80 | 0 | 70 | 90 | 0 | 40 | 0 | 30 | 30 |
| Blackgrass | 0 | 0 | 0 | 0 | 0 | 0 | 0 | 40 | 80 | 0 | 60 | — | — | 50 | 0 | 40 | 30 |
| Corn | 0 | 0 | 0 | 0 | 0 | 0 | 0 | 50 | 30 | 0 | 40 | 80 | 0 | 20 | 0 | 10 | 20 |
| Crabgrass, Large | — | — | — | — | — | — | — | — | — | — | — | 90 | 0 | — | — | — | — |
| Foxtail, Giant | 10 | 0 | 0 | 0 | 0 | 0 | 0 | 90 | 90 | 0 | 70 | 90 | 0 | 70 | 0 | 50 | 90 |
| *Galium* | 50 | 0 | 0 | 0 | 10 | 0 | 0 | 90 | 100 | 0 | 80 | — | — | 100 | 10 | 80 | 20 |
| *Kochia* | 70 | 0 | 0 | 0 | 0 | 0 | 0 | 70 | 100 | 0 | 70 | — | — | 70 | 0 | 90 | 60 |
| Morningglory | — | — | — | — | — | — | — | — | — | — | — | 90 | 10 | — | — | — | — |
| Pigweed | 60 | 0 | 0 | 0 | 0 | 20 | 0 | 100 | 100 | 0 | 100 | 100 | 80 | 70 | 10 | 80 | 100 |
| Ragweed | 30 | 0 | 0 | 0 | 0 | 10 | 0 | 20 | 80 | 0 | 40 | — | — | 60 | 10 | 40 | 20 |
| Ryegrass, Italian | 0 | 0 | 0 | 0 | 0 | 0 | 0 | 30 | 30 | 0 | 50 | — | — | 50 | 0 | 50 | 20 |
| Velvetleaf | — | — | — | — | — | — | — | — | — | — | — | 100 | 60 | — | — | — | — |
| Wheat | 0 | 0 | 0 | 0 | 0 | 0 | 0 | 30 | 40 | 0 | 10 | 70 | 0 | 0 | 0 | 30 | 20 |

Postemergence
125 g ai/ha
Compounds

| | 285 | 287 | 288 | 289 | 290 | 291 | 292 | 293 | 294 | 295 | 296 | 301 | 304 |
|---|---|---|---|---|---|---|---|---|---|---|---|---|---|
| Barnyardgrass | 0 | 0 | 0 | 0 | 0 | 0 | 60 | 10 | 20 | 0 | 0 | 0 | 0 |
| Blackgrass | — | — | — | — | — | — | — | — | — | — | — | — | — |
| Corn | 0 | 0 | 0 | 0 | 0 | 0 | 50 | 0 | 0 | 0 | 0 | 0 | 0 |
| Crabgrass, Large | 10 | 10 | 10 | 0 | 0 | 10 | 60 | 20 | 0 | 0 | 0 | 0 | 0 |
| Foxtail, Giant | 0 | 0 | 10 | 0 | 0 | 0 | 70 | 20 | 10 | 0 | 0 | 0 | 0 |
| *Galium* | — | — | — | — | — | — | — | — | — | — | — | — | — |
| *Kochia* | — | — | — | — | — | — | — | — | — | — | — | — | — |
| Morningglory | 30 | 10 | 20 | 20 | 0 | 30 | 90 | 10 | 20 | 40 | 20 | 0 | 0 |
| Pigweed | 80 | 30 | 90 | 100 | 10 | 30 | 100 | 60 | 60 | 40 | 30 | 0 | 30 |
| Ragweed | — | — | — | — | — | — | — | — | — | — | — | — | — |
| Ryegrass, Italian | — | — | — | — | — | — | — | — | — | — | — | — | — |
| Velvetleaf | 30 | 10 | 20 | 10 | 10 | 50 | 70 | 60 | 50 | 30 | 30 | 0 | 0 |
| Wheat | 0 | 0 | 0 | 0 | 0 | 0 | 10 | 0 | 0 | 0 | 0 | 0 | 0 |

Postemergence
31 g ai/ha
Compounds

| | 99 | 100 | 101 | 103 | 106 | 107 | 108 | 109 | 110 | 118 | 119 | 120 | 121 | 122 | 125 | 126 | 127 |
|---|---|---|---|---|---|---|---|---|---|---|---|---|---|---|---|---|---|
| Barnyardgrass | 100 | 0 | 20 | 0 | 0 | 20 | 10 | 10 | 30 | 40 | 20 | 0 | 10 | 0 | 10 | 0 |
| Blackgrass | 50 | 0 | 20 | 0 | 30 | 10 | 30 | 20 | 20 | 60 | 40 | 60 | 10 | 30 | 40 | 10 | 0 |

TABLE A-continued

| | | | | | | | | | | | | | | | | |
|---|---|---|---|---|---|---|---|---|---|---|---|---|---|---|---|---|
| Corn | 20 | 0 | 10 | 0 | 0 | 0 | 20 | 10 | 10 | 10 | 10 | 10 | 0 | 10 | 20 | 0 | 0 |
| Foxtail, Giant | 90 | 0 | 20 | 0 | 50 | 20 | 20 | 10 | 20 | 30 | 30 | 20 | 0 | 10 | 0 | 10 | 0 |
| *Galium* | 90 | 0 | 40 | 0 | 50 | 30 | 70 | 50 | 40 | 70 | 70 | 90 | 10 | 20 | 20 | 20 | 10 |
| *Kochia* | 100 | 0 | 70 | 0 | 0 | 0 | 70 | 40 | 90 | 60 | 70 | 60 | 20 | 50 | 40 | 40 | 0 |
| Pigweed | 100 | 0 | 90 | 0 | 50 | 40 | 50 | 70 | 100 | 70 | 70 | 60 | 10 | 70 | 30 | 50 | 20 |
| Ragweed | 30 | 0 | 50 | 0 | 20 | 30 | 20 | 10 | 10 | 70 | 30 | 30 | 10 | 10 | 0 | 10 | 0 |
| Ryegrass, Italian | 20 | 0 | 0 | 0 | 0 | 0 | 0 | 0 | 0 | 20 | 30 | 0 | 0 | 0 | 0 | 0 | 0 |
| Wheat | 50 | 0 | 20 | 0 | 0 | 10 | 10 | 0 | 0 | 20 | 10 | 0 | 0 | 0 | 0 | 0 | 0 |

| | Postemergence 31 g ai/ha Compounds | | | | | | | | | | | | | | | |
|---|---|---|---|---|---|---|---|---|---|---|---|---|---|---|---|---|
| | 128 | 140 | 141 | 144 | 148 | 149 | 151 | 152 | 153 | 156 | 157 | 158 | 169 | 241 | 242 | 243 | 244 |
| Barnyardgrass | 10 | 30 | 60 | 20 | 0 | 20 | 0 | 0 | 0 | 0 | 10 | 20 | 0 | 0 | 0 | 0 | 0 |
| Blackgrass | 30 | 30 | 90 | 20 | 0 | 50 | 20 | 50 | 0 | 0 | 30 | 50 | 0 | 0 | 30 | 0 | 0 |
| Corn | 0 | 20 | 30 | 20 | 0 | 0 | 0 | 20 | 0 | 0 | 0 | 0 | 0 | 0 | 0 | 0 | 0 |
| Foxtail, Giant | 20 | 30 | 90 | 20 | 10 | 20 | 0 | 0 | 0 | 0 | 10 | 20 | 0 | 0 | 0 | 0 | 0 |
| *Galium* | 50 | 80 | 100 | 80 | 20 | 70 | 10 | 90 | 0 | 20 | 60 | 60 | 10 | 40 | 10 | 0 | 70 |
| *Kochia* | 50 | 90 | 100 | 50 | 0 | 60 | 60 | 20 | 0 | 0 | 60 | 60 | 0 | 50 | 30 | 20 | 20 |
| Pigweed | 80 | 90 | 100 | 80 | 50 | 60 | 20 | 0 | 0 | 10 | 90 | 40 | 10 | 40 | 30 | 10 | 20 |
| Ragweed | 0 | 60 | 80 | 20 | 10 | 50 | 50 | 20 | 0 | 0 | 20 | 60 | 10 | 10 | 20 | 20 | 0 |
| Ryegrass, Italian | 0 | 0 | 60 | 0 | 0 | 0 | 0 | 0 | 0 | 0 | 0 | 20 | 0 | 0 | 0 | 0 | 0 |
| Wheat | 0 | 0 | 10 | 20 | 0 | 0 | 20 | 20 | 0 | 0 | 0 | 0 | 0 | 0 | 0 | 0 | 0 |

| | Postemergence 31 g ai/ha Compounds | | | | | | | | | | | | | | | |
|---|---|---|---|---|---|---|---|---|---|---|---|---|---|---|---|---|
| | 245 | 246 | 247 | 249 | 250 | 251 | 252 | 253 | 254 | 258 | 259 | 260 | 261 | 264 | 265 | 266 | 267 |
| Barnyardgrass | 0 | 0 | 0 | 0 | 10 | 10 | 20 | 20 | 10 | 10 | 0 | 0 | 0 | 0 | 0 | 0 | 0 |
| Blackgrass | 30 | 0 | 0 | 60 | 70 | 50 | 10 | 20 | 0 | 20 | 20 | 0 | 0 | 0 | 0 | 0 | 0 |
| Corn | 20 | 0 | 0 | 0 | 10 | 0 | 20 | 20 | 10 | 10 | 0 | 0 | 0 | 0 | 0 | 0 | 0 |
| Foxtail, Giant | 0 | 0 | 0 | 0 | 10 | 30 | 20 | 20 | 10 | 20 | 10 | 0 | 0 | 0 | 0 | 0 | 0 |
| *Galium* | 100 | 20 | 10 | 20 | 10 | 20 | 60 | 60 | 20 | 70 | 50 | 30 | 0 | 0 | 0 | 0 | 0 |
| *Kochia* | 60 | 20 | 20 | 20 | 60 | 40 | 70 | 100 | 20 | 90 | 60 | 50 | 50 | 0 | 0 | 0 | 0 |
| Pigweed | 0 | 20 | 10 | 60 | 60 | 60 | 80 | 90 | 10 | 80 | 70 | 50 | 30 | 0 | 0 | 0 | 0 |
| Ragweed | 0 | 0 | 0 | 10 | 50 | 10 | 20 | 20 | 10 | 10 | 50 | 30 | 20 | 0 | 0 | 0 | 0 |
| Ryegrass, Italian | 0 | 0 | 0 | 0 | 0 | 0 | 0 | 0 | 0 | 0 | 0 | 0 | 0 | 0 | 0 | 0 | 0 |
| Wheat | 20 | 0 | 0 | 0 | 0 | 0 | 20 | 20 | 0 | 0 | 0 | 0 | 0 | 0 | 0 | 0 | 0 |

| | Postemergence 31 g ai/ha Compounds | | | | | | | |
|---|---|---|---|---|---|---|---|---|
| | 268 | 269 | 270 | 271 | 272 | 277 | 278 | 279 |
| Barnyardgrass | 0 | 0 | 10 | 10 | 0 | 20 | 0 | 0 |
| Blackgrass | 0 | 0 | 10 | 10 | 0 | 30 | 0 | 10 |
| Corn | 0 | 0 | 20 | 20 | 0 | 0 | 0 | 10 |
| Foxtail, Giant | 0 | 0 | 10 | 10 | 0 | 40 | 0 | 10 |
| *Galium* | 0 | 0 | 60 | 70 | 0 | 100 | 0 | 20 |
| *Kochia* | 0 | 0 | 60 | 70 | 0 | 60 | 0 | 40 |
| Pigweed | 0 | 0 | 60 | 70 | 0 | 60 | 0 | 50 |
| Ragweed | 0 | 0 | 0 | 0 | 0 | 50 | 0 | 20 |
| Ryegrass, Italian | 0 | 0 | 0 | 0 | 0 | 30 | 0 | 0 |
| Wheat | 0 | 0 | 0 | 0 | 0 | 0 | 0 | 0 |

| | Preemergence 1000 g ai/ha Compounds | | | | | | | | | | | | | | | |
|---|---|---|---|---|---|---|---|---|---|---|---|---|---|---|---|---|
| | 12 | 13 | 14 | 53 | 54 | 55 | 56 | 65 | 66 | 67 | 69 | 70 | 102 | 114 | 115 | 116 | 123 |
| Barnyardgrass | 100 | 80 | 30 | 100 | 0 | 40 | 0 | 100 | 90 | 0 | 70 | 50 | 50 | 90 | 100 | 90 | 100 |
| Corn | 0 | 0 | 0 | 10 | 20 | 0 | 20 | 40 | 30 | 0 | 0 | 0 | — | 20 | 60 | 30 | — |
| Crabgrass, Large | 100 | 100 | 90 | 100 | 100 | 90 | 80 | 100 | 100 | 20 | 90 | 90 | — | 100 | 100 | 100 | — |
| Foxtail, Giant | 100 | 100 | 90 | 100 | 100 | 90 | 30 | 100 | 100 | 10 | 90 | 60 | 100 | 100 | 100 | 100 | 100 |
| *Kochia* | — | — | — | — | — | — | — | — | — | — | — | — | 0 | — | — | — | 100 |
| Morningglory | 0 | 0 | 20 | 60 | 70 | 0 | 0 | 100 | 40 | 0 | 10 | 10 | — | 10 | 50 | 100 | — |
| Pigweed | 100 | 100 | 100 | 100 | 100 | 90 | 100 | 100 | 100 | 100 | 100 | 90 | 20 | 100 | 100 | 100 | 100 |
| Ragweed | — | — | — | — | — | — | — | — | — | — | — | — | 0 | — | — | — | 90 |

TABLE A-continued

| | | | | | | | | | | | | | | | | | |
|---|---|---|---|---|---|---|---|---|---|---|---|---|---|---|---|---|---|
| Ryegrass, Italian | — | — | — | — | — | — | — | — | — | — | — | — | 0 | — | — | — | 70 |
| Velvetleaf | 100 | 100 | 90 | 100 | 100 | 100 | 90 | 100 | 90 | 10 | 80 | 70 | — | 100 | 100 | 100 | — |
| Wheat | 20 | 20 | 20 | 0 | 0 | 0 | 0 | 30 | 10 | 0 | 20 | 0 | — | 40 | 40 | 40 | — |

Preemergence
1000 g ai/ha
Compounds

| | 139 | 154 | 155 | 159 | 160 | 193 | 207 | 216 | 217 | 222 | 223 | 224 | 229 | 248 | 255 | 256 | 257 |
|---|---|---|---|---|---|---|---|---|---|---|---|---|---|---|---|---|---|
| Barnyardgrass | 0 | 100 | 100 | 100 | 100 | 60 | 0 | 30 | 70 | 100 | 100 | 100 | 0 | 80 | 10 | 20 | 50 |
| Corn | — | — | — | — | — | 20 | 0 | 0 | 0 | 60 | 80 | 40 | 0 | — | — | — | — |
| Crabgrass, Large | — | — | — | — | — | 100 | 50 | 70 | 100 | 100 | 100 | 100 | 10 | — | — | — | — |
| Foxtail, Giant | 0 | 100 | 100 | 100 | 100 | 100 | 50 | 40 | 90 | 100 | 100 | 100 | 0 | 100 | 10 | 30 | 70 |
| *Kochia* | 0 | 100 | 100 | 100 | 100 | — | — | — | — | — | — | — | — | 100 | 70 | 70 | 70 |
| Morningglory | — | — | — | — | — | 100 | 0 | 0 | 40 | 100 | 100 | 90 | 0 | — | — | — | — |
| Pigweed | 50 | 100 | 100 | 100 | 100 | 100 | 0 | 100 | 100 | 100 | 100 | 100 | 100 | 100 | 60 | 30 | 80 |
| Ragweed | 0 | 100 | 90 | 100 | 100 | — | — | — | — | — | — | — | — | 40 | 20 | 30 | 70 |
| Ryegrass, Italian | 0 | 90 | 60 | 30 | 90 | — | — | — | — | — | — | — | — | 50 | 20 | 20 | 20 |
| Velvetleaf | — | — | — | — | — | 90 | 30 | 30 | 100 | 100 | 100 | 100 | 0 | — | — | — | — |
| Wheat | — | — | — | — | — | 20 | 0 | 0 | 0 | 70 | 80 | 60 | 0 | — | — | — | — |

Preemergence

| | 1000 g ai/ha Compounds | | | | | | | | | | | | | 500 g ai/ha Compounds | | | |
|---|---|---|---|---|---|---|---|---|---|---|---|---|---|---|---|---|---|
| | 262 | 263 | 276 | 280 | 281 | 282 | 283 | 297 | 298 | 299 | 300 | 302 | 303 | 1 | 2 | 3 | 4 |
| Barnyardgrass | 0 | 0 | 0 | 100 | 0 | 90 | 0 | 10 | 100 | 90 | 20 | 0 | 0 | 70 | 90 | 100 | 0 |
| Corn | — | — | — | 50 | — | — | 0 | — | — | — | — | — | 0 | 0 | 30 | 10 | 0 |
| Crabgrass, Large | — | — | — | 100 | — | — | — | 90 | — | — | — | — | 60 | 100 | 100 | 100 | 0 |
| Foxtail, Giant | 50 | 50 | 0 | 100 | 0 | 100 | 0 | 80 | 100 | 100 | 80 | 0 | 50 | 100 | 100 | 100 | 0 |
| *Kochia* | 20 | 20 | 0 | — | 0 | 100 | 0 | — | 90 | 100 | 60 | 0 | — | — | — | — | — |
| Morningglory | — | — | — | 0 | — | — | 0 | — | — | — | — | — | 0 | 0 | 20 | 20 | 0 |
| Pigweed | 10 | 10 | 0 | 100 | 60 | 100 | 0 | 70 | 100 | 100 | 100 | 0 | 80 | 100 | 100 | 100 | 0 |
| Ragweed | 0 | 0 | 0 | — | 30 | 100 | 0 | — | 90 | 70 | 0 | 0 | — | — | — | — | — |
| Ryegrass, Italian | 0 | 0 | 0 | — | 10 | 50 | 0 | — | 50 | 60 | 20 | 0 | — | — | — | — | — |
| Velvetleaf | — | — | — | 100 | — | — | 50 | — | — | — | — | — | 0 | 20 | 70 | 90 | 0 |
| Wheat | — | — | — | 40 | — | — | 0 | — | — | — | — | — | 0 | 0 | 0 | 10 | 0 |

Preemergence
500 g ai/ha
Compounds

| | 5 | 6 | 7 | 8 | 9 | 10 | 11 | 15 | 16 | 17 | 18 | 19 | 20 | 21 | 22 | 23 | 24 |
|---|---|---|---|---|---|---|---|---|---|---|---|---|---|---|---|---|---|
| Barnyardgrass | 80 | 90 | 100 | 90 | 100 | 90 | 100 | 100 | 100 | 60 | 100 | 20 | 20 | 30 | 20 | 50 | 0 |
| Corn | 0 | 20 | 30 | 0 | 20 | 20 | 30 | 0 | 30 | 0 | 10 | 0 | 0 | 0 | 0 | 20 | 0 |
| Crabgrass, Large | 90 | 100 | 100 | 100 | 100 | 100 | 100 | 100 | 100 | 90 | 100 | 90 | 90 | 100 | 90 | 90 | 0 |
| Foxtail, Giant | 100 | 100 | 100 | 100 | 90 | 100 | 100 | 100 | 90 | 100 | 90 | 80 | 100 | 90 | 90 | 0 |
| *Kochia* | — | — | — | — | — | — | — | — | — | — | — | — | — | — | — | — | — |
| Morningglory | 20 | 10 | 70 | 30 | 0 | 60 | 60 | 0 | 90 | 20 | 40 | 0 | 0 | 0 | 0 | 0 | 0 |
| Pigweed | 100 | 100 | 100 | 100 | 100 | 100 | 100 | 100 | 100 | 100 | 100 | 100 | 90 | 100 | 90 | 100 | 0 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 100 | 100 | 100 | 100 | 100 | 100 | 100 | 100 | 90 | 90 | 20 | 0 | 20 | 20 | 90 | 0 |
| Wheat | 20 | 30 | 20 | 0 | 0 | 20 | 0 | 0 | 60 | 70 | 70 | 0 | 0 | 0 | 0 | 0 | 0 |

Preemergence
500 g ai/ha
Compounds

| | 25 | 26 | 27 | 28 | 29 | 30 | 31 | 32 | 33 | 34 | 35 | 36 | 37 | 38 | 39 | 40 | 41 |
|---|---|---|---|---|---|---|---|---|---|---|---|---|---|---|---|---|---|
| Barnyardgrass | 100 | 90 | 20 | 10 | 20 | 10 | 50 | 60 | 70 | 50 | 0 | 0 | 10 | 0 | 10 | 50 | 50 |
| Corn | 30 | 10 | 0 | 0 | 0 | 0 | 0 | 0 | 0 | 0 | 0 | 0 | 0 | 0 | 0 | 0 | 0 |
| Crabgrass, Large | 100 | 90 | 50 | 10 | 40 | 60 | 90 | 60 | 100 | 90 | 10 | 70 | 80 | 40 | 90 | 80 | 70 |
| Foxtail, Giant | 100 | 90 | 40 | 10 | 20 | 30 | 90 | 70 | 100 | 100 | 10 | 20 | 30 | 20 | 50 | 60 | 80 |
| *Kochia* | — | — | — | — | — | — | — | — | — | — | — | — | — | — | — | — | — |
| Morningglory | 0 | 0 | 0 | 0 | 0 | 0 | 0 | 0 | — | — | — | — | 0 | 0 | 0 | 0 | 0 |
| Pigweed | 90 | 90 | 20 | 40 | 0 | 0 | 60 | 40 | 100 | 100 | 20 | 20 | 0 | 0 | 0 | 50 | 100 |
| Ragweed | — | — | — | — | — | — | — | — | — | — | — | — | — | — | — | — | — |

TABLE A-continued

| | | | | | | | | | | | | | | | | |
|---|---|---|---|---|---|---|---|---|---|---|---|---|---|---|---|---|
| Ryegrass, Italian | — | — | — | — | — | — | — | — | — | — | — | — | — | — | — | — |
| Velvetleaf | 90 | 80 | 10 | 0 | 40 | 40 | 90 | 70 | 100 | 80 | 20 | 20 | 10 | 10 | 20 | 70 | 70 |
| Wheat | 0 | 0 | 0 | 0 | 0 | 0 | 0 | 0 | 0 | 0 | 0 | 0 | 0 | 0 | 0 | 0 | 0 |

Preemergence 500 g ai/ha Compounds

| | 42 | 43 | 44 | 45 | 46 | 47 | 48 | 49 | 50 | 51 | 52 | 57 | 58 | 59 | 60 | 61 | 62 |
|---|---|---|---|---|---|---|---|---|---|---|---|---|---|---|---|---|---|
| Barnyardgrass | 10 | 10 | 100 | 100 | 20 | 100 | 0 | 0 | 0 | 30 | 100 | 100 | 100 | 100 | 70 | 20 | 100 |
| Corn | 0 | 0 | 20 | 20 | 0 | 90 | 0 | 0 | 0 | 0 | 80 | 70 | 70 | 30 | 0 | 0 | 90 |
| Crabgrass, Large | 30 | 50 | 100 | 100 | 100 | 100 | 80 | 20 | 40 | 90 | 100 | 100 | 100 | 100 | 100 | 20 | 100 |
| Foxtail, Giant | 20 | 20 | 100 | 100 | 80 | 100 | 50 | 10 | 0 | 80 | 100 | 100 | 100 | 100 | 90 | 0 | 100 |
| Kochia | — | — | — | — | — | — | — | — | — | — | — | — | — | — | — | — | — |
| Morningglory | 0 | 0 | 60 | 10 | 0 | 100 | 0 | 0 | 0 | 0 | 100 | 40 | 100 | 100 | 0 | 0 | 90 |
| Pigweed | 20 | 20 | 100 | 100 | 90 | 100 | 0 | 0 | 0 | 80 | 100 | 100 | 100 | 100 | 100 | 30 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 60 | 50 | 100 | 100 | 0 | 100 | 0 | 20 | 0 | 0 | 100 | 100 | 100 | 100 | 40 | 0 | 100 |
| Wheat | 0 | 0 | 20 | 0 | 0 | 40 | 0 | 0 | 0 | 0 | 80 | 50 | 90 | 40 | 0 | 0 | 80 |

Preemergence 500 g ai/ha Compounds

| | 63 | 64 | 68 | 71 | 72 | 73 | 74 | 75 | 76 | 77 | 78 | 79 | 80 | 81 | 82 | 83 | 84 |
|---|---|---|---|---|---|---|---|---|---|---|---|---|---|---|---|---|---|
| Barnyardgrass | 70 | 100 | 0 | 100 | 100 | 100 | 100 | 70 | 100 | 90 | 80 | 100 | 100 | 70 | 30 | 90 | 90 |
| Corn | 0 | 70 | — | 40 | 50 | 70 | 40 | 10 | 30 | 0 | 10 | 100 | 40 | 10 | — | — | — |
| Crabgrass, Large | 100 | 90 | — | 100 | 100 | 100 | 100 | 100 | 100 | 100 | 100 | 100 | 100 | 100 | — | — | — |
| Foxtail, Giant | 100 | 90 | 0 | 100 | 100 | 100 | 100 | 100 | 100 | 100 | 100 | 100 | 100 | 100 | 70 | 100 | 100 |
| Kochia | — | — | 0 | — | — | — | — | — | — | — | — | — | — | — | 0 | 100 | 100 |
| Morningglory | 0 | 20 | — | 90 | 100 | 100 | 100 | 30 | 80 | 60 | 20 | 100 | 80 | 60 | — | — | — |
| Pigweed | 100 | 100 | 30 | 100 | 100 | 100 | 100 | 100 | 100 | 100 | 100 | 0 | 0 | 60 | 100 | 100 | 100 |
| Ragweed | — | — | 0 | — | — | — | — | — | — | — | — | — | — | — | 0 | 50 | 40 |
| Ryegrass, Italian | — | — | 0 | — | — | — | — | — | — | — | — | — | — | — | 0 | 60 | 20 |
| Velvetleaf | 20 | 90 | — | 100 | 100 | 100 | 100 | 80 | 100 | 100 | 50 | 100 | 90 | 100 | — | — | — |
| Wheat | 0 | 30 | — | 40 | 60 | 80 | 40 | 0 | 30 | 0 | 10 | 100 | 50 | 10 | — | — | — |

Preemergence 500 g ai/ha Compounds

| | 85 | 86 | 87 | 88 | 89 | 90 | 91 | 92 | 93 | 94 | 95 | 96 | 97 | 98 | 111 | 112 | 113 |
|---|---|---|---|---|---|---|---|---|---|---|---|---|---|---|---|---|---|
| Barnyardgrass | 100 | 100 | 10 | 80 | 90 | 100 | 0 | 100 | 0 | 100 | 100 | 30 | 100 | 100 | 100 | 100 | 90 |
| Corn | — | — | — | — | — | — | — | 40 | 0 | 30 | 40 | 0 | 60 | 10 | 50 | 50 | 20 |
| Crabgrass, Large | — | — | — | — | — | — | — | 100 | 30 | 100 | 100 | 90 | 100 | 100 | 100 | 100 | 100 |
| Foxtail, Giant | 100 | 100 | 70 | 100 | 90 | 100 | 30 | 100 | 0 | 100 | 100 | 60 | 100 | 100 | 100 | 100 | 90 |
| Kochia | 100 | 100 | 60 | 100 | 100 | 100 | 90 | — | — | — | — | — | — | — | — | — | — |
| Morningglory | — | — | — | — | — | — | — | 100 | 0 | 90 | 100 | 0 | 100 | 80 | 100 | 90 | 30 |
| Pigweed | 100 | 100 | 100 | 100 | 100 | 100 | 90 | 100 | 30 | 100 | 100 | 100 | 100 | 100 | 100 | 100 | 100 |
| Ragweed | 60 | 100 | 20 | 60 | 70 | 80 | 0 | — | — | — | — | — | — | — | — | — | — |
| Ryegrass, Italian | 40 | 60 | 0 | 30 | 10 | 30 | 30 | — | — | — | — | — | — | — | — | — | — |
| Velvetleaf | — | — | — | — | — | — | — | 100 | 0 | 100 | 100 | 10 | 100 | 100 | 100 | 100 | 50 |
| Wheat | — | — | — | — | — | — | — | 80 | 0 | 30 | 10 | 0 | 80 | 50 | 40 | 50 | 30 |

Preemergence 500 g ai/ha Compounds

| | 117 | 129 | 130 | 131 | 132 | 134 | 135 | 136 | 137 | 138 | 142 | 143 | 145 | 146 | 147 | 150 | 161 |
|---|---|---|---|---|---|---|---|---|---|---|---|---|---|---|---|---|---|
| Barnyardgrass | 90 | 90 | 0 | 0 | 100 | 100 | 90 | 100 | 100 | 100 | 0 | 100 | 100 | 90 | 100 | 100 | 10 |
| Corn | — | — | — | — | — | — | — | — | — | — | — | — | — | — | — | — | 0 |
| Crabgrass, Large | — | — | — | — | — | — | — | — | — | — | — | — | — | — | — | — | 0 |
| Foxtail, Giant | 100 | 100 | 0 | 0 | 100 | 100 | 100 | 100 | 100 | 100 | 0 | 100 | 100 | 100 | 100 | 100 | 0 |
| Kochia | 100 | 100 | 0 | 0 | 100 | 100 | 100 | 100 | 100 | 100 | 50 | 100 | 100 | 100 | 100 | 100 | — |
| Morningglory | — | — | — | — | — | — | — | — | — | — | — | — | — | — | — | — | 0 |
| Pigweed | 100 | 100 | 0 | 0 | 100 | 100 | 100 | 100 | 100 | 100 | 0 | 100 | 100 | 100 | 100 | 100 | 100 |
| Ragweed | 60 | 80 | 0 | 0 | 10 | 80 | 90 | 100 | 60 | 60 | 20 | 20 | 80 | 100 | 100 | 70 | — |

TABLE A-continued

| | | | | | | | | | | | | | | | | | |
|---|---|---|---|---|---|---|---|---|---|---|---|---|---|---|---|---|---|
| Ryegrass, Italian | 30 | 30 | 0 | 0 | 40 | 40 | 20 | 30 | 20 | 50 | 0 | 20 | 50 | 50 | 100 | 50 | — |
| Velvetleaf | — | — | — | — | — | — | — | — | — | — | — | — | — | — | — | — | 20 |
| Wheat | — | — | — | — | — | — | — | — | — | — | — | — | — | — | — | — | 0 |

Preemergence
500 g ai/ha
Compounds

| | 162 | 163 | 164 | 165 | 166 | 167 | 168 | 170 | 171 | 172 | 173 | 174 | 175 | 176 | 177 | 178 | 179 |
|---|---|---|---|---|---|---|---|---|---|---|---|---|---|---|---|---|---|
| Barnyardgrass | 50 | 100 | 100 | 20 | 100 | 100 | 80 | 100 | 60 | 0 | 30 | 0 | 0 | 60 | 100 | 100 | 100 |
| Corn | 0 | 10 | 60 | 0 | 30 | 40 | 20 | 20 | 0 | 0 | 0 | 0 | 0 | 0 | 50 | 30 | 10 |
| Crabgrass, Large | 10 | 100 | 100 | 90 | 100 | 100 | 100 | 100 | 0 | 30 | 80 | 0 | 0 | 100 | 100 | 100 | 100 |
| Foxtail, Giant | 0 | 100 | 100 | 90 | 100 | 100 | 100 | 90 | 0 | 0 | 70 | 0 | 0 | 100 | 100 | 100 | 100 |
| Kochia | — | — | — | — | — | — | — | — | — | — | — | — | — | — | — | — | — |
| Morningglory | 0 | 70 | 100 | — | 100 | 100 | 80 | 90 | 0 | 0 | 0 | 0 | 0 | 0 | 80 | 90 | 80 |
| Pigweed | 100 | 100 | 100 | 90 | 100 | 100 | 100 | 100 | 100 | 50 | 100 | 0 | 0 | 100 | 100 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 50 | 100 | 100 | 20 | 100 | 100 | 90 | 100 | 70 | 0 | 0 | 0 | 0 | 90 | 100 | 100 | 80 |
| Wheat | 0 | 10 | 90 | 0 | 80 | 50 | 20 | 20 | 0 | 0 | 0 | 0 | 0 | 0 | 50 | 40 | 30 |

Preemergence
500 g ai/ha
Compounds

| | 180 | 181 | 182 | 183 | 184 | 185 | 186 | 187 | 188 | 189 | 190 | 191 | 192 | 194 | 195 | 196 | 197 |
|---|---|---|---|---|---|---|---|---|---|---|---|---|---|---|---|---|---|
| Barnyardgrass | 100 | 100 | 20 | 0 | 100 | 80 | 100 | 100 | 100 | 90 | 10 | 100 | 100 | 100 | 0 | 40 | 70 |
| Corn | 90 | 30 | 0 | 0 | 20 | 10 | 0 | 40 | 20 | 0 | 0 | 30 | 50 | 50 | 0 | 0 | 0 |
| Crabgrass, Large | 100 | 100 | 30 | 0 | 100 | 100 | 100 | 100 | 100 | 100 | 90 | 100 | 100 | 100 | 70 | 100 | 90 |
| Foxtail, Giant | 100 | 100 | 20 | 0 | 100 | 100 | 100 | 100 | 100 | 100 | 80 | 100 | 100 | 100 | 80 | 90 | 80 |
| Kochia | — | — | — | — | — | — | — | — | — | — | — | — | — | — | — | — | — |
| Morningglory | 100 | 30 | 0 | 0 | 90 | 30 | 20 | 50 | 90 | 30 | 20 | 70 | 100 | 100 | 10 | 0 | 0 |
| Pigweed | 100 | 100 | 100 | 90 | 100 | 100 | 100 | 100 | 100 | 100 | 100 | 100 | 100 | 100 | 40 | 100 | 70 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 40 | 0 | 0 | 60 | 80 | 100 | 100 | 100 | 80 | 60 | 90 | 100 | 100 | 20 | 40 | 30 |
| Wheat | 80 | 10 | 0 | 0 | 30 | 10 | 20 | 40 | 30 | 10 | 0 | 40 | — | 30 | 0 | 0 | 0 |

Preemergence
500 g ai/ha
Compounds

| | 198 | 199 | 200 | 201 | 202 | 203 | 204 | 205 | 206 | 208 | 209 | 210 | 211 | 212 | 213 | 214 | 215 |
|---|---|---|---|---|---|---|---|---|---|---|---|---|---|---|---|---|---|
| Barnyardgrass | 80 | 80 | 90 | 0 | 10 | 40 | 100 | 0 | 0 | 70 | 100 | 70 | 60 | 20 | 10 | 0 | 10 |
| Corn | 0 | 0 | 50 | 0 | 0 | 0 | 30 | 0 | 0 | 0 | 20 | 0 | 0 | — | 0 | 0 | 0 |
| Crabgrass, Large | 100 | 100 | 100 | 40 | 70 | 100 | 100 | 0 | 0 | 100 | 100 | 100 | 100 | — | 100 | 0 | 80 |
| Foxtail, Giant | 100 | 100 | 100 | 50 | 70 | 100 | 100 | 0 | 0 | 90 | 100 | 100 | 100 | 50 | 100 | 0 | 50 |
| Kochia | — | — | — | — | — | — | — | — | — | — | — | — | — | 40 | — | — | — |
| Morningglory | 10 | 20 | 100 | 0 | 0 | 10 | 90 | 0 | 0 | 30 | 70 | 0 | 70 | — | 10 | 0 | 0 |
| Pigweed | 100 | 100 | 100 | 0 | 0 | 100 | 100 | 10 | 50 | 100 | 100 | 100 | 100 | 90 | 100 | 0 | 100 |
| Ragweed | — | — | — | — | — | — | — | — | — | — | — | — | — | 0 | — | — | — |
| Ryegrass, Italian | — | — | — | — | — | — | — | — | — | — | — | — | — | 20 | — | — | — |
| Velvetleaf | 80 | 90 | 100 | 0 | 0 | 40 | 100 | 10 | 0 | 50 | 90 | 60 | 90 | — | 0 | 0 | 10 |
| Wheat | 0 | 0 | 50 | 0 | 0 | 0 | 60 | 0 | 0 | 20 | 20 | 0 | 0 | — | 0 | 0 | 0 |

Preemergence
500 g ai/ha
Compounds

| | 218 | 219 | 220 | 221 | 225 | 226 | 227 | 228 | 230 | 231 | 232 | 233 | 234 | 235 | 236 | 237 | 238 |
|---|---|---|---|---|---|---|---|---|---|---|---|---|---|---|---|---|---|
| Barnyardgrass | 70 | 90 | 100 | 90 | 0 | 0 | 0 | 100 | 0 | 100 | 100 | 0 | 100 | 10 | 100 | 10 | 100 |
| Corn | 0 | 10 | 10 | 0 | 0 | 0 | 0 | 40 | 0 | 20 | 60 | 0 | 90 | 0 | 90 | 0 | 90 |
| Crabgrass, Large | 100 | 100 | 100 | 100 | 0 | 0 | 10 | 100 | 0 | 100 | 100 | 10 | 100 | 100 | 100 | 10 | 100 |
| Foxtail, Giant | 100 | 100 | 100 | 100 | 0 | 0 | 10 | 100 | 0 | 100 | 90 | 0 | 90 | 100 | 100 | 0 | 100 |
| Kochia | — | — | — | — | — | — | — | — | — | — | — | — | — | — | — | — | — |
| Morningglory | 10 | 10 | 40 | 10 | 0 | 0 | 0 | 80 | 0 | 30 | 90 | 0 | 100 | 0 | 100 | 0 | 100 |
| Pigweed | 100 | 100 | 100 | 100 | 0 | 0 | 60 | 0 | 70 | 100 | 100 | 20 | 100 | 100 | 100 | 80 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |

TABLE A-continued

| | | | | | | | | | | | | | | | | | |
|---|---|---|---|---|---|---|---|---|---|---|---|---|---|---|---|---|---|
| Velvetleaf | 50 | 20 | 70 | 70 | 0 | 0 | 20 | 100 | 0 | 100 | 100 | 0 | 100 | 0 | 100 | 10 | 90 |
| Wheat | 0 | 0 | 20 | 10 | 0 | 0 | 0 | 0 | 0 | 20 | 10 | 0 | 0 | 0 | 100 | 0 | 30 |

| | Preemergence 500 g ai/ha Compounds | | | | | | | | | | | | | | | |
|---|---|---|---|---|---|---|---|---|---|---|---|---|---|---|---|---|
| | 239 | 240 | 252 | 273 | 274 | 275 | 284 | 285 | 287 | 288 | 289 | 290 | 291 | 292 | 293 | 294 | 295 |
| Barnyardgrass | 100 | 100 | 100 | 90 | 100 | 0 | 90 | 30 | 0 | 10 | 20 | 0 | 50 | 100 | 10 | 20 | 0 |
| Corn | 10 | — | — | — | 50 | 0 | — | 20 | 0 | 0 | 0 | 0 | 0 | 30 | 0 | 0 | 0 |
| Crabgrass, Large | 100 | — | — | — | 100 | 70 | — | 100 | 70 | 10 | 10 | 10 | 90 | 100 | 90 | 60 | 0 |
| Foxtail, Giant | 100 | 100 | 100 | 90 | 100 | 70 | 90 | 100 | 40 | 0 | 10 | 10 | 80 | 100 | 90 | 70 | 0 |
| *Kochia* | — | 100 | 100 | 100 | — | — | 100 | — | — | — | — | — | — | — | — | — | — |
| Morningglory | 30 | — | — | — | 100 | 0 | — | 40 | 0 | 0 | 0 | 0 | 0 | 90 | 0 | 0 | 0 |
| Pigweed | 100 | 100 | 100 | 100 | 100 | 90 | 100 | 100 | 100 | 90 | 100 | 0 | 90 | 100 | 80 | 100 | 60 |
| Ragweed | — | 100 | 100 | 80 | — | — | 0 | — | — | — | — | — | — | — | — | — | — |
| Ryegrass, Italian | — | 70 | 90 | 40 | — | — | 20 | — | — | — | — | — | — | — | — | — | — |
| Velvetleaf | 20 | — | — | — | 100 | 60 | — | 40 | 0 | 10 | 10 | 0 | 60 | 100 | 0 | 70 | 0 |
| Wheat | 20 | — | — | — | 80 | 0 | — | 20 | 0 | 0 | 0 | 0 | 0 | 30 | 0 | 0 | 0 |

| | Preemergence | | | | | | | | | | | | | | | | |
|---|---|---|---|---|---|---|---|---|---|---|---|---|---|---|---|---|---|
| | 500 g ai/ha Compounds | | | 125 g ai/ha Compounds | | | | | | | | | | | | | |
| | 296 | 301 | 304 | 1 | 2 | 3 | 4 | 5 | 6 | 7 | 8 | 9 | 10 | 11 | 15 | 16 | 17 |
| Barnyardgrass | 10 | 0 | 0 | 20 | 30 | 60 | 0 | 10 | 20 | 80 | 50 | 30 | 60 | 70 | 20 | 100 | 50 |
| Corn | 0 | 0 | 0 | 0 | 0 | 0 | 0 | 0 | 0 | 0 | 0 | 0 | 0 | 0 | 0 | 10 | 0 |
| Crabgrass, Large | 60 | 0 | 10 | 50 | 80 | 90 | 0 | 90 | 90 | 100 | 80 | 90 | 100 | 90 | 40 | 100 | 40 |
| Foxtail, Giant | 10 | 0 | 0 | 60 | 80 | 90 | 0 | 90 | 90 | 100 | 70 | 80 | 90 | 90 | 30 | 100 | 60 |
| *Kochia* | — | — | — | — | — | — | — | — | — | — | — | — | — | — | — | — | — |
| Morningglory | 0 | 0 | 0 | 0 | — | 0 | 0 | 0 | 0 | 20 | 20 | 0 | 40 | 30 | 0 | 30 | 0 |
| Pigweed | 90 | 0 | 0 | 60 | 90 | 90 | 0 | 100 | 100 | 90 | 90 | 100 | 100 | 90 | 90 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 10 | 0 | 0 | 0 | 30 | 70 | 0 | 90 | 100 | 100 | 100 | 80 | 100 | 90 | 60 | 100 | 70 |
| Wheat | 0 | 0 | 0 | 0 | 0 | 0 | 0 | 0 | 0 | 0 | 0 | 0 | 0 | 0 | 0 | 20 | 0 |

| | Preemergence 125 g ai/ha Compounds | | | | | | | | | | | | | | | |
|---|---|---|---|---|---|---|---|---|---|---|---|---|---|---|---|---|---|
| | 18 | 19 | 20 | 21 | 22 | 23 | 24 | 25 | 26 | 27 | 28 | 29 | 30 | 31 | 32 | 33 | 34 |
| Barnyardgrass | 90 | 0 | 0 | 20 | 0 | 20 | 0 | 90 | 30 | 0 | 0 | 0 | 0 | 20 | 0 | 0 | 0 |
| Corn | 0 | 0 | 0 | 0 | 0 | 0 | 0 | 0 | 0 | 0 | 0 | 0 | 0 | 0 | 0 | 0 | 0 |
| Crabgrass, Large | 100 | 0 | 20 | 90 | 20 | 90 | 0 | 90 | 70 | 0 | 0 | 10 | 40 | 50 | 0 | 90 | 70 |
| Foxtail, Giant | 100 | 20 | 20 | 70 | 20 | 70 | 0 | 80 | 60 | 0 | 0 | 10 | 0 | 20 | 0 | 90 | 30 |
| *Kochia* | — | — | — | — | — | — | — | — | — | — | — | — | — | — | — | — | — |
| Morningglory | 0 | 0 | 0 | 0 | 0 | 0 | 0 | 0 | 0 | 0 | 0 | 0 | 0 | 0 | 0 | — | — |
| Pigweed | 100 | 0 | 30 | 90 | 20 | 100 | 0 | 90 | 80 | 10 | 0 | 0 | 0 | 40 | 0 | 100 | 80 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 90 | 0 | 0 | 0 | 0 | 90 | 0 | — | 60 | 0 | 0 | 0 | 10 | 50 | 10 | 50 | 60 |
| Wheat | 0 | 0 | 0 | 0 | 0 | 0 | 0 | 0 | 0 | 0 | 0 | 0 | 0 | 0 | 0 | 0 | 0 |

| | Preemergence 125 g ai/ha Compounds | | | | | | | | | | | | | | | |
|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 |
| Barnyardgrass | 0 | 0 | 0 | 0 | 0 | 40 | 10 | 0 | 0 | 50 | 30 | 0 | 20 | 0 | 0 | 0 | 20 |
| Corn | 0 | 0 | 0 | 0 | 0 | 0 | 0 | 0 | 0 | 0 | 0 | 0 | 0 | 0 | 0 | 0 | 0 |
| Crabgrass, Large | 0 | 0 | 10 | 0 | 10 | 60 | 30 | 10 | 10 | 90 | 90 | 20 | 90 | 50 | 0 | 0 | 40 |
| Foxtail, Giant | 0 | 0 | 10 | 0 | 10 | 10 | 10 | 10 | 10 | 60 | 90 | 0 | 100 | 10 | 0 | 0 | 20 |
| *Kochia* | — | — | — | — | — | — | — | — | — | — | — | — | — | — | — | — | — |
| Morningglory | — | — | 0 | 0 | 0 | 0 | 0 | 0 | 0 | 50 | 0 | 0 | 0 | 0 | 0 | 0 | 0 |
| Pigweed | 0 | 0 | 0 | 0 | 0 | 0 | 70 | 0 | 0 | 100 | 100 | 20 | 100 | 0 | 0 | 0 | 10 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |

TABLE A-continued

| | | | | | | | | | | | | | | | | | |
|---|---|---|---|---|---|---|---|---|---|---|---|---|---|---|---|---|---|
| Velvetleaf | 0 | 0 | 10 | 0 | 10 | 50 | 60 | 60 | 30 | 70 | 100 | 0 | 100 | 0 | 0 | 0 | 0 |
| Wheat | 0 | 0 | 0 | 0 | 0 | 0 | 0 | 0 | 0 | 0 | 0 | 0 | 0 | 0 | 0 | 0 | 0 |

| | Preemergence 125 g ai/ha Compounds | | | | | | | | | | | | | | | | |
|---|---|---|---|---|---|---|---|---|---|---|---|---|---|---|---|---|---|
| | 52 | 57 | 58 | 59 | 60 | 61 | 62 | 63 | 64 | 71 | 72 | 73 | 74 | 75 | 76 | 77 | 79 |
| Barnyardgrass | 90 | 60 | 100 | 80 | 0 | 0 | 60 | 0 | 60 | 60 | 80 | 90 | 70 | 20 | 50 | 50 | 100 |
| Corn | 20 | 0 | 40 | 20 | 0 | 0 | 0 | 0 | 0 | 30 | 30 | 20 | 0 | 0 | 20 | 0 | 80 |
| Crabgrass, Large | 100 | 90 | 100 | 100 | 40 | 0 | 90 | 80 | 90 | 100 | 100 | 100 | 100 | 70 | 100 | 90 | 100 |
| Foxtail, Giant | 100 | 80 | 100 | 100 | 20 | 0 | 90 | 20 | 90 | 100 | 100 | 100 | 90 | 40 | 80 | 90 | 100 |
| *Kochia* | — | — | — | — | — | — | — | — | — | — | — | — | — | — | — | — | — |
| Morningglory | 90 | 0 | 100 | 80 | 0 | 0 | 0 | 0 | 0 | 90 | 80 | 90 | 70 | 20 | 0 | 10 | 100 |
| Pigweed | 100 | 100 | 100 | 100 | 30 | 0 | 100 | 90 | 90 | 100 | 100 | 100 | 100 | 100 | 100 | 100 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 40 | 90 | 100 | 0 | 0 | 50 | 0 | 40 | 70 | 90 | 100 | 70 | 40 | 90 | 60 | 100 |
| Wheat | 20 | 0 | 60 | 20 | 0 | 0 | 0 | 0 | 0 | 20 | 20 | 0 | 0 | 0 | 0 | 0 | 70 |

| | Preemergence 125 g ai/ha Compounds | | | | | | | | | | | | | | | | |
|---|---|---|---|---|---|---|---|---|---|---|---|---|---|---|---|---|---|
| | 80 | 81 | 82 | 83 | 84 | 85 | 86 | 87 | 88 | 89 | 90 | 91 | 92 | 93 | 94 | 95 | 96 |
| Barnyardgrass | 60 | 0 | 0 | 60 | 50 | 20 | 80 | 0 | 60 | 60 | 70 | 0 | 60 | 0 | 80 | 50 | 0 |
| Corn | 0 | 0 | — | — | — | — | — | — | — | — | — | — | 10 | 0 | 0 | 0 | 0 |
| Crabgrass, Large | 100 | 90 | — | — | — | — | — | — | — | — | — | — | 100 | 0 | 100 | 100 | 30 |
| Foxtail, Giant | 90 | 80 | 10 | 100 | 70 | 100 | 100 | 60 | 100 | 90 | 90 | 10 | 100 | 0 | 100 | 100 | 10 |
| *Kochia* | — | — | 0 | 100 | 100 | 80 | 100 | 30 | 100 | 90 | 100 | 30 | — | — | — | — | — |
| Morningglory | 30 | 0 | — | — | — | — | — | — | — | — | — | — | 90 | 0 | 40 | 50 | 0 |
| Pigweed | 0 | 0 | 0 | 100 | 100 | 100 | 100 | 90 | 100 | 90 | 100 | 70 | 100 | 0 | 100 | 90 | 50 |
| Ragweed | — | — | 0 | 20 | 10 | 40 | 90 | 10 | — | 50 | 50 | 0 | — | — | — | — | — |
| Ryegrass, Italian | — | — | 0 | 50 | 0 | 0 | 10 | 0 | 20 | 0 | 0 | 0 | — | — | — | — | — |
| Velvetleaf | 80 | 50 | — | — | — | — | — | — | — | — | — | — | 100 | 0 | 90 | 90 | 0 |
| Wheat | 10 | 10 | — | — | — | — | — | — | — | — | — | — | 0 | 0 | 0 | 0 | 0 |

| | Preemergence 125 g ai/ha Compounds | | | | | | | | | | | | | | | | |
|---|---|---|---|---|---|---|---|---|---|---|---|---|---|---|---|---|---|
| | 97 | 98 | 99 | 100 | 101 | 103 | 106 | 107 | 108 | 109 | 110 | 111 | 112 | 113 | 117 | 118 | 119 |
| Barnyardgrass | 80 | 50 | 90 | 0 | 70 | 0 | 40 | 60 | 70 | 60 | 90 | 90 | 70 | 0 | 30 | 100 | 90 |
| Corn | 40 | 0 | — | — | — | — | — | — | — | — | — | 20 | 0 | 0 | — | — | — |
| Crabgrass, Large | 100 | 100 | — | — | — | — | — | — | — | — | — | 100 | 100 | 80 | — | — | — |
| Foxtail, Giant | 100 | 100 | 100 | 0 | 90 | 0 | 70 | 80 | 90 | 90 | 100 | 100 | 100 | 20 | 90 | 100 | 100 |
| *Kochia* | — | — | 100 | 0 | 70 | 0 | 0 | 0 | 70 | 60 | 80 | — | — | — | 70 | 100 | 100 |
| Morningglory | 100 | 60 | — | — | — | — | — | — | — | — | — | 90 | 80 | 0 | — | — | — |
| Pigweed | 100 | 100 | 100 | 0 | 100 | 0 | 60 | 50 | 100 | 100 | 100 | 100 | 100 | 100 | 100 | 100 | 100 |
| Ragweed | — | — | 90 | 0 | 30 | 0 | 0 | 0 | 80 | 10 | 10 | — | — | — | 20 | 90 | 60 |
| Ryegrass, Italian | — | — | 30 | 0 | 0 | 0 | 0 | 0 | 30 | 0 | 20 | — | — | — | 20 | 50 | 80 |
| Velvetleaf | 100 | 90 | — | — | — | — | — | — | — | — | — | 70 | 90 | 10 | — | — | — |
| Wheat | 0 | 0 | — | — | — | — | — | — | — | — | — | 0 | 0 | 0 | — | — | — |

| | Preemergence 125 g ai/ha Compounds | | | | | | | | | | | | | | | | |
|---|---|---|---|---|---|---|---|---|---|---|---|---|---|---|---|---|---|
| | 120 | 121 | 122 | 125 | 126 | 127 | 128 | 129 | 130 | 131 | 132 | 134 | 135 | 136 | 137 | 138 | 140 |
| Barnyardgrass | 70 | 30 | 70 | 80 | 80 | 40 | 70 | 70 | 0 | 0 | 50 | 70 | 40 | 60 | 20 | 80 | 70 |
| Corn | — | — | — | — | — | — | — | — | — | — | — | — | — | — | — | — | — |
| Crabgrass, Large | — | — | — | — | — | — | — | — | — | — | — | — | — | — | — | — | — |
| Foxtail, Giant | 100 | 50 | 100 | 100 | 100 | 60 | 100 | 100 | 0 | 0 | 90 | 100 | 70 | 60 | 90 | 90 | 100 |
| *Kochia* | 90 | 60 | 100 | 50 | 90 | 0 | 70 | 100 | 0 | 0 | 100 | 100 | 100 | 90 | 90 | 90 | 100 |
| Morningglory | — | — | — | — | — | — | — | — | — | — | — | — | — | — | — | — | — |
| Pigweed | 100 | 90 | 100 | 100 | 100 | 10 | 100 | 100 | 0 | 0 | 100 | 100 | 100 | 90 | 90 | 90 | 100 |
| Ragweed | 0 | 10 | 0 | 10 | 20 | 0 | 0 | 30 | 0 | 0 | 60 | 90 | 80 | 30 | 30 | 70 |
| Ryegrass, Italian | 30 | 0 | 0 | 20 | 0 | 0 | 10 | 10 | 0 | 0 | 30 | 20 | 0 | 0 | 0 | 0 | 0 |

TABLE A-continued

| | | | | | | | | | | | | | | | | | |
|---|---|---|---|---|---|---|---|---|---|---|---|---|---|---|---|---|---|
| Velvetleaf | — | — | — | — | — | — | — | — | — | — | — | — | — | — | — | — | |
| Wheat | — | — | — | — | — | — | — | — | — | — | — | — | — | — | — | — | |

| | Preemergence 125 g ai/ha Compounds | | | | | | | | | | | | | | | | |
|---|---|---|---|---|---|---|---|---|---|---|---|---|---|---|---|---|---|
| | 141 | 142 | 143 | 144 | 145 | 146 | 147 | 148 | 149 | 150 | 151 | 152 | 153 | 156 | 157 | 158 | 161 |
| Barnyardgrass | 100 | 0 | 30 | 90 | 50 | 20 | 100 | 50 | 90 | 90 | 60 | 70 | 0 | 30 | 80 | 70 | 0 |
| Corn | — | — | — | — | — | — | — | — | — | — | — | — | — | — | — | — | 0 |
| Crabgrass, Large | — | — | — | — | — | — | — | — | — | — | — | — | — | — | — | — | 0 |
| Foxtail, Giant | 100 | 0 | 80 | 100 | 80 | 70 | 100 | 70 | 100 | 100 | 100 | 100 | 0 | 70 | 100 | 90 | 0 |
| *Kochia* | 100 | 0 | 50 | 100 | 90 | 40 | 100 | 0 | 100 | 100 | 90 | 90 | 0 | 10 | 90 | 70 | — |
| Morningglory | — | — | — | — | — | — | — | — | — | — | — | — | — | — | — | — | 0 |
| Pigweed | 100 | 0 | 90 | 100 | 100 | 60 | 100 | 10 | 100 | 100 | 90 | 90 | 0 | 0 | 90 | 70 | 90 |
| Ragweed | 100 | 0 | 0 | 100 | 50 | 0 | 90 | 0 | 60 | 30 | 80 | 40 | 0 | 0 | 30 | 80 | — |
| Ryegrass, Italian | 80 | 0 | 0 | 20 | 10 | 0 | 10 | 0 | 20 | 20 | 0 | 0 | 0 | 0 | 0 | 50 | — |
| Velvetleaf | — | — | — | — | — | — | — | — | — | — | — | — | — | — | — | — | 10 |
| Wheat | — | — | — | — | — | — | — | — | — | — | — | — | — | — | — | — | 0 |

| | Preemergence 125 g ai/ha Compounds | | | | | | | | | | | | | | | | |
|---|---|---|---|---|---|---|---|---|---|---|---|---|---|---|---|---|---|
| | 162 | 163 | 164 | 165 | 166 | 167 | 168 | 169 | 170 | 171 | 172 | 173 | 174 | 175 | 177 | 178 | 179 |
| Barnyardgrass | 10 | 50 | 90 | 0 | 90 | 80 | 50 | 50 | 90 | 20 | 0 | 0 | 0 | 0 | 70 | 90 | 20 |
| Corn | 0 | 0 | 10 | 0 | 30 | 10 | 0 | — | 0 | 0 | 0 | 0 | 0 | 0 | 0 | 0 | 0 |
| Crabgrass, Large | 0 | 100 | 100 | 50 | 100 | 100 | 100 | — | 100 | 0 | 0 | 20 | 0 | 0 | 100 | 100 | 100 |
| Foxtail, Giant | 0 | 100 | 90 | 20 | 100 | 100 | 100 | 80 | 100 | 0 | 0 | 50 | 0 | 0 | 100 | 100 | 100 |
| *Kochia* | — | — | — | — | — | — | — | 0 | — | — | — | — | — | — | — | — | — |
| Morningglory | 0 | 0 | 80 | 0 | 100 | 90 | 20 | — | 20 | 0 | 0 | 0 | 0 | 0 | 20 | 10 | 10 |
| Pigweed | 100 | 100 | 100 | 60 | 100 | 100 | 100 | 80 | 100 | 90 | 0 | 80 | 0 | 0 | 100 | 100 | 100 |
| Ragweed | — | — | — | — | — | — | — | 0 | — | — | — | — | — | — | — | — | — |
| Ryegrass, Italian | — | — | — | — | — | — | — | 0 | — | — | — | — | — | — | — | — | — |
| Velvetleaf | 10 | 20 | 100 | 10 | 100 | 80 | 70 | — | 80 | 30 | 0 | 0 | 0 | 0 | 80 | 80 | 60 |
| Wheat | 0 | 0 | 20 | 0 | 50 | 0 | 20 | — | 20 | 0 | 0 | 0 | 0 | 0 | 0 | 0 | 0 |

| | Preemergence 125 g ai/ha Compounds | | | | | | | | | | | | | | | | |
|---|---|---|---|---|---|---|---|---|---|---|---|---|---|---|---|---|---|
| | 180 | 181 | 182 | 183 | 184 | 185 | 186 | 187 | 188 | 189 | 190 | 191 | 192 | 194 | 195 | 196 | 197 |
| Barnyardgrass | 100 | 50 | 0 | 0 | 30 | 40 | 30 | 80 | 30 | 20 | 0 | 70 | 60 | 80 | 0 | 0 | 30 |
| Corn | 60 | 0 | 0 | 0 | 20 | 0 | 0 | 0 | 0 | 0 | 0 | 0 | 0 | 30 | 0 | 0 | 0 |
| Crabgrass, Large | 100 | 100 | 0 | 0 | 100 | 90 | 100 | 100 | 90 | 90 | 20 | 100 | 100 | 100 | — | 60 | 40 |
| Foxtail, Giant | 100 | 90 | 0 | 0 | 100 | 90 | 80 | 100 | 90 | 70 | 10 | 100 | 100 | 100 | 10 | 50 | 20 |
| *Kochia* | — | — | — | — | — | — | — | — | — | — | — | — | — | — | — | — | — |
| Morningglory | 90 | 0 | 0 | 0 | 0 | 10 | 0 | 0 | 10 | 0 | 0 | 50 | 30 | 60 | 0 | 0 | 0 |
| Pigweed | 100 | 100 | 90 | 20 | 100 | 100 | 100 | 100 | 100 | 100 | 100 | 100 | 100 | 100 | 0 | 90 | 50 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 100 | 20 | 0 | 0 | 20 | 40 | 70 | 80 | 70 | 60 | 50 | 80 | 90 | 80 | 0 | 20 | 0 |
| Wheat | 20 | 0 | 0 | 0 | 0 | 0 | 0 | 0 | 0 | 0 | 0 | 20 | 0 | 20 | 0 | 0 | 0 |

| | Preemergence 125 g ai/ha Compounds | | | | | | | | | | | | | | | | |
|---|---|---|---|---|---|---|---|---|---|---|---|---|---|---|---|---|---|
| | 198 | 199 | 200 | 201 | 202 | 203 | 204 | 205 | 206 | 208 | 209 | 210 | 211 | 212 | 213 | 214 | 215 |
| Barnyardgrass | 50 | 20 | 80 | 0 | 0 | 10 | 70 | 0 | 0 | 0 | 60 | 10 | 0 | 0 | 0 | 0 | 0 |
| Corn | 0 | 0 | 40 | 0 | 0 | 0 | 0 | 0 | 0 | 0 | 0 | 0 | 0 | — | 0 | 0 | 0 |
| Crabgrass, Large | 80 | 100 | 100 | 20 | 40 | 100 | 100 | 0 | 0 | 20 | 100 | 100 | 80 | — | 10 | 0 | 20 |
| Foxtail, Giant | 70 | 90 | 100 | 20 | 10 | 90 | 100 | 0 | 0 | 20 | 100 | 100 | 100 | 0 | 20 | 0 | 0 |
| *Kochia* | — | — | — | — | — | — | — | — | — | — | — | — | — | 0 | — | — | — |
| Morningglory | 0 | 0 | 90 | 0 | 0 | 0 | 90 | 0 | 0 | 0 | 10 | 0 | 20 | — | 0 | 0 | 0 |
| Pigweed | 100 | 90 | 100 | 0 | 0 | 90 | 100 | 0 | 0 | 30 | 100 | 100 | 90 | 70 | 50 | 0 | 90 |
| Ragweed | — | — | — | — | — | — | — | — | — | — | — | — | — | 0 | — | — | — |
| Ryegrass, Italian | — | — | — | — | — | — | — | — | — | — | — | — | — | 0 | — | — | — |

TABLE A-continued

| | | | | | | | | | | | | | | | | | |
|---|---|---|---|---|---|---|---|---|---|---|---|---|---|---|---|---|---|
| Velvetleaf | 40 | 20 | 100 | 0 | 0 | 30 | 80 | 0 | 0 | 0 | 90 | 20 | 60 | — | 0 | 0 | 0 |
| Wheat | 0 | 0 | 30 | 0 | 0 | 0 | 40 | 0 | 0 | 0 | 0 | 0 | 0 | — | 0 | 0 | 0 |

Preemergence
125 g ai/ha
Compounds

| | 218 | 219 | 220 | 221 | 225 | 226 | 227 | 228 | 230 | 231 | 232 | 233 | 234 | 235 | 236 | 237 | 238 |
|---|---|---|---|---|---|---|---|---|---|---|---|---|---|---|---|---|---|
| Barnyardgrass | 10 | 30 | 60 | 10 | 0 | 0 | 0 | 20 | 0 | 20 | 60 | 0 | 20 | 0 | 100 | 0 | 70 |
| Corn | 0 | 0 | 0 | 0 | 0 | 0 | 0 | 0 | 0 | 0 | 0 | 0 | 0 | 0 | 20 | 0 | 0 |
| Crabgrass, Large | 80 | 100 | 100 | 100 | 0 | 0 | 0 | 90 | 0 | 90 | 90 | 0 | 90 | 70 | 100 | 0 | 100 |
| Foxtail, Giant | 20 | 100 | 100 | 100 | 0 | 0 | 0 | 90 | 0 | 90 | 90 | 0 | 60 | 30 | 100 | 0 | 100 |
| *Kochia* | — | — | — | — | — | — | — | — | — | — | — | — | — | — | — | — | — |
| Morningglory | 0 | 0 | 0 | 0 | 0 | 0 | 0 | 10 | 0 | 0 | 20 | 0 | 0 | 0 | 30 | 0 | 10 |
| Pigweed | 100 | 100 | 100 | 100 | 0 | 0 | 10 | 0 | 0 | 90 | 100 | 0 | 90 | 90 | 100 | 0 | 100 |
| Ragweed | — | — | — | — | — | — | — | — | — | — | — | — | — | — | — | — | — |
| Ryegrass, Italian | — | — | — | — | — | — | — | — | — | — | — | — | — | — | — | — | — |
| Velvetleaf | 10 | 10 | 20 | 10 | 0 | 0 | 10 | 70 | 0 | 0 | 20 | 0 | 40 | 0 | 100 | 0 | 70 |
| Wheat | 0 | 0 | 0 | 0 | 0 | 0 | 0 | 0 | 0 | 0 | 0 | 0 | 0 | 0 | 0 | 0 | 0 |

Preemergence
125 g ai/ha
Compounds

| | 239 | 240 | 241 | 242 | 243 | 244 | 245 | 246 | 247 | 249 | 250 | 251 | 252 | 253 | 254 | 258 | 259 |
|---|---|---|---|---|---|---|---|---|---|---|---|---|---|---|---|---|---|
| Barnyardgrass | 20 | 90 | 60 | 70 | 30 | 20 | 70 | 30 | 70 | 0 | 90 | 50 | 100 | 100 | 80 | 90 | 70 |
| Corn | 0 | — | — | — | — | — | — | — | — | — | — | — | — | — | — | — | — |
| Crabgrass, Large | 100 | — | — | — | — | — | — | — | — | — | — | — | — | — | — | — | — |
| Foxtail, Giant | 90 | 100 | 100 | 100 | 100 | 80 | 100 | 70 | 100 | 0 | 100 | 80 | 100 | 100 | 90 | 100 | 100 |
| *Kochia* | — | 100 | 100 | 100 | 90 | 40 | 30 | 0 | 60 | 40 | 0 | 70 | 100 | 100 | 80 | 90 | 80 |
| Morningglory | 0 | — | — | — | — | — | — | — | — | — | — | — | — | — | — | — | — |
| Pigweed | 100 | 100 | 100 | 100 | 80 | 100 | 90 | 20 | 80 | 90 | 100 | 90 | 100 | 100 | 90 | 100 | 100 |
| Ragweed | — | 90 | 40 | 80 | 20 | 0 | 0 | 0 | 0 | 0 | — | 30 | 70 | 80 | 0 | 40 | 70 |
| Ryegrass, Italian | — | 20 | 0 | 0 | 0 | 0 | 0 | 0 | 0 | 30 | 0 | 0 | 20 | 20 | 40 | 10 | 0 |
| Velvetleaf | 10 | — | — | — | — | — | — | — | — | — | — | — | — | — | — | — | — |
| Wheat | 0 | — | — | — | — | — | — | — | — | — | — | — | — | — | — | — | — |

Preemergence
125 g ai/ha
Compounds

| | 260 | 261 | 264 | 265 | 266 | 267 | 268 | 269 | 270 | 271 | 272 | 273 | 274 | 275 | 277 | 278 | 279 |
|---|---|---|---|---|---|---|---|---|---|---|---|---|---|---|---|---|---|
| Barnyardgrass | 0 | 0 | 0 | 0 | 0 | 0 | 0 | 0 | 100 | 100 | 0 | 70 | 90 | 0 | 0 | 0 | 10 |
| Corn | — | — | — | — | — | — | — | — | — | — | — | — | 50 | 0 | — | — | — |
| Crabgrass, Large | — | — | — | — | — | — | — | — | — | — | — | — | 100 | 0 | — | — | — |
| Foxtail, Giant | 0 | 0 | 0 | 0 | 0 | 0 | 0 | 0 | 100 | 100 | 0 | 90 | 100 | 0 | 70 | 0 | 50 |
| *Kochia* | 0 | 0 | 0 | 0 | 0 | 0 | 0 | 0 | 100 | 100 | 0 | 100 | — | — | 0 | 0 | 90 |
| Morningglory | — | — | — | — | — | — | — | — | — | — | — | — | 100 | 0 | — | — | — |
| Pigweed | 30 | 0 | 0 | 0 | 0 | 0 | 0 | 0 | 100 | 100 | 0 | 100 | 100 | 80 | 60 | 10 | 100 |
| Ragweed | 0 | 0 | 0 | 0 | 0 | 0 | 0 | 0 | 20 | 20 | 0 | 70 | — | — | 0 | 0 | 10 |
| Ryegrass, Italian | 0 | 0 | 0 | 0 | 0 | 0 | 0 | 0 | 10 | 10 | 0 | 20 | — | — | 0 | 0 | 0 |
| Velvetleaf | — | — | — | — | — | — | — | — | — | — | — | — | 100 | 20 | — | — | — |
| Wheat | — | — | — | — | — | — | — | — | — | — | — | — | 40 | 0 | — | — | — |

Preemergence
125 g ai/ha
Compounds

| | 284 | 285 | 287 | 288 | 289 | 290 | 291 | 292 | 293 | 294 | 295 | 296 | 301 | 304 |
|---|---|---|---|---|---|---|---|---|---|---|---|---|---|---|
| Barnyardgrass | 60 | 0 | 0 | 0 | 0 | 0 | 0 | 80 | 0 | 0 | 0 | 0 | 0 | 0 |
| Corn | — | 0 | 0 | 0 | 0 | 0 | 0 | 20 | 0 | 0 | 0 | 0 | 0 | 0 |
| Crabgrass, Large | — | 80 | 0 | 0 | 0 | 0 | 50 | 100 | 40 | 30 | 0 | 0 | 0 | 0 |
| Foxtail, Giant | 90 | 20 | 0 | 0 | 0 | 0 | 20 | 100 | 20 | 30 | 0 | 0 | 0 | 0 |
| *Kochia* | 80 | — | — | — | — | — | — | — | — | — | — | — | — | — |
| Morningglory | — | 0 | 0 | 0 | 0 | 0 | 0 | 30 | 0 | 0 | 0 | 0 | 0 | 0 |
| Pigweed | 100 | 80 | 0 | 20 | 20 | 0 | 60 | 100 | 20 | 100 | 20 | 0 | 0 | 0 |
| Ragweed | 0 | — | — | — | — | — | — | — | — | — | — | — | — | — |
| Ryegrass, Italian | 20 | — | — | — | — | — | — | — | — | — | — | — | — | — |

TABLE A-continued

| | | | | | | | | | | | | | | | | |
|---|---|---|---|---|---|---|---|---|---|---|---|---|---|---|---|---|
| Velvetleaf | — | 10 | 0 | 0 | 0 | 0 | 40 | 30 | 0 | 10 | 0 | 0 | 0 | 0 | 0 |
| Wheat | — | 0 | 0 | 0 | 0 | 0 | 0 | 10 | 0 | 0 | 0 | 0 | 0 | 0 | 0 |

| | Preemergence 31 g ai/ha Compounds | | | | | | | | | | | | | | | | |
|---|---|---|---|---|---|---|---|---|---|---|---|---|---|---|---|---|---|
| | 99 | 100 | 101 | 103 | 106 | 107 | 108 | 109 | 110 | 118 | 119 | 120 | 121 | 122 | 125 | 126 | 127 |
| Barnyardgrass | 80 | 0 | 60 | 0 | 0 | 10 | 10 | 20 | 30 | 50 | 30 | 20 | 0 | 10 | 10 | 10 | 0 |
| Foxtail, Giant | 100 | 0 | 70 | 0 | 30 | 30 | 20 | 70 | 100 | 80 | 90 | 50 | 10 | 50 | 20 | 50 | 10 |
| Kochia | 100 | 0 | 70 | 0 | 0 | 0 | 40 | 20 | 20 | 100 | 50 | 20 | 0 | 20 | 20 | 40 | 0 |
| Pigweed | 100 | 0 | 90 | 0 | 10 | 0 | 90 | 100 | 100 | 100 | 100 | 100 | 60 | 80 | 70 | 80 | 0 |
| Ragweed | 70 | 0 | 0 | 0 | 0 | 0 | 70 | 0 | 0 | 50 | 0 | 0 | 0 | 0 | 0 | 0 | 0 |
| Ryegrass, Italian | 0 | 0 | 0 | 0 | 0 | 0 | 0 | 0 | 0 | 0 | 10 | 0 | 0 | 0 | 0 | 0 | 0 |

| | Preemergence 31 g ai/ha Compounds | | | | | | | | | | | | | | | | |
|---|---|---|---|---|---|---|---|---|---|---|---|---|---|---|---|---|---|
| | 128 | 140 | 141 | 144 | 148 | 149 | 151 | 152 | 153 | 156 | 157 | 158 | 169 | 241 | 242 | 243 | 244 |
| Barnyardgrass | 10 | 30 | 90 | 20 | 0 | 40 | 20 | 20 | 0 | 0 | 20 | 10 | 10 | 10 | 20 | 0 | 0 |
| Foxtail, Giant | 60 | 50 | 100 | 70 | 10 | 60 | 100 | 10 | 0 | 0 | 70 | 60 | 30 | 50 | 100 | 0 | 0 |
| Kochia | 0 | 60 | 100 | 70 | 0 | 70 | 80 | 20 | 0 | 0 | 60 | 50 | 0 | 50 | 30 | 0 | 0 |
| Pigweed | 100 | 90 | 100 | 90 | 0 | 100 | 90 | 90 | 0 | 0 | 90 | 50 | 0 | 80 | 90 | 0 | 0 |
| Ragweed | 0 | 30 | 90 | 0 | 0 | 0 | 20 | 20 | 0 | 0 | — | 40 | 0 | 0 | 50 | 0 | 0 |
| Ryegrass, Italian | 0 | 0 | 30 | 20 | 0 | 0 | 0 | 0 | 0 | 0 | 0 | 30 | 0 | 0 | 0 | 0 | 0 |

| | Preemergence 31 g ai/ha Compounds | | | | | | | | | | | | | | | | |
|---|---|---|---|---|---|---|---|---|---|---|---|---|---|---|---|---|---|
| | 245 | 246 | 247 | 249 | 250 | 251 | 252 | 253 | 254 | 258 | 259 | 260 | 261 | 264 | 265 | 266 | 267 |
| Barnyardgrass | 0 | 0 | 0 | 0 | 10 | 30 | 70 | 50 | 20 | 50 | 10 | 0 | 0 | 0 | 0 | 0 | 0 |
| Foxtail, Giant | 60 | 0 | 0 | 0 | 30 | 50 | 70 | 70 | 30 | 60 | 30 | 0 | 0 | 0 | 0 | 0 | 0 |
| Kochia | 0 | 0 | 0 | 0 | 90 | 10 | 80 | 90 | 20 | 90 | 20 | 0 | 0 | 0 | 0 | 0 | 0 |
| Pigweed | 90 | 0 | 0 | 90 | 80 | 70 | 100 | 100 | 30 | 100 | 70 | 0 | 0 | 0 | 0 | 0 | 0 |
| Ragweed | 0 | 0 | 0 | 0 | — | 0 | 20 | 20 | 0 | 0 | 10 | 0 | 0 | 0 | 0 | 0 | 0 |
| Ryegrass, Italian | 0 | 0 | 0 | 0 | 0 | 0 | 20 | 20 | 0 | 0 | 0 | 0 | 0 | 0 | 0 | 0 | 0 |

| | Preemergence 31 g ai/ha Compounds | | | | | | | |
|---|---|---|---|---|---|---|---|---|
| | 268 | 269 | 270 | 271 | 272 | 277 | 278 | 279 |
| Barnyardgrass | 0 | 0 | 20 | 20 | 0 | 0 | 0 | 0 |
| Foxtail, Giant | 0 | 0 | 40 | 40 | 0 | 30 | 0 | 40 |
| Kochia | 0 | 0 | 80 | 70 | 0 | 0 | 0 | 40 |
| Pigweed | 0 | 0 | 100 | 90 | 0 | 30 | 0 | 90 |
| Ragweed | 0 | 0 | 0 | 0 | 0 | 0 | 0 | 0 |
| Ryegrass, Italian | 0 | 0 | 0 | 0 | 0 | 0 | 0 | 0 |

Test B

Plant species in the flooded paddy test selected from rice (*Oryza sativa*), sedge, umbrella (small-flower umbrella sedge, *Cyperus difformis*), (*Heteranthera limosa*), and barnyardgrass (*Echinochloa crus-galli*) were grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table B, are based on a scale of 0 to 100 where 0 is no effect and 100 is complete control. A dash (-) response means no test result.

TABLE B

| 250 g ai/ha | Compounds | | | | | | | | | | | | | |
|---|---|---|---|---|---|---|---|---|---|---|---|---|---|---|
| | 1 | 2 | 3 | 4 | 5 | 6 | 7 | 8 | 9 | 10 | 11 | 13 | 15 | 16 |
| | Flood | | | | | | | | | | | | | |
| Barnyardgrass | 0 | 0 | 0 | 0 | 0 | 0 | 30 | 0 | 0 | 0 | 0 | 0 | 20 | 40 |
| Ducksalad | 0 | 45 | 90 | 0 | 50 | 65 | 80 | 100 | 80 | 75 | 50 | 30 | 75 | 90 |

TABLE B-continued

| | | | | | | | | | | | | | | |
|---|---|---|---|---|---|---|---|---|---|---|---|---|---|---|
| Rice | 0 | 0 | 0 | 0 | 10 | 15 | 20 | 30 | 0 | 0 | 0 | 0 | 20 | 40 |
| Sedge, Umbrella | 0 | 0 | 75 | 0 | 50 | 55 | 75 | 80 | 60 | 50 | 0 | 0 | 85 | 90 |

| | Compounds | | | | | | | | | | | | | |
|---|---|---|---|---|---|---|---|---|---|---|---|---|---|---|
| 250 g ai/ha | 17 | 18 | 19 | 20 | 21 | 22 | 23 | 24 | 25 | 26 | 27 | 28 | 29 | 30 |

| | Flood | | | | | | | | | | | | | |
|---|---|---|---|---|---|---|---|---|---|---|---|---|---|---|
| Barnyardgrass | 0 | 30 | 0 | 20 | 25 | 20 | 20 | 0 | 20 | 0 | 0 | 0 | 0 | 0 |
| Ducksalad | 75 | 90 | 40 | 60 | 40 | 65 | 80 | 0 | 85 | 80 | 75 | 35 | 0 | 0 |
| Rice | 25 | 0 | 20 | 45 | 15 | 40 | 35 | 35 | 20 | 25 | 0 | 0 | 0 | 0 |
| Sedge, Umbrella | 90 | 90 | 30 | 75 | 70 | 80 | 70 | 60 | 85 | 80 | 75 | 0 | 0 | 0 |

| | Compounds | | | | | | | | | | | | | |
|---|---|---|---|---|---|---|---|---|---|---|---|---|---|---|
| 250 g ai/ha | 31 | 32 | 33 | 34 | 35 | 36 | 37 | 38 | 39 | 40 | 39 41 | 42 | 43 | 44 |

| | Flood | | | | | | | | | | | | | |
|---|---|---|---|---|---|---|---|---|---|---|---|---|---|---|
| Barnyardgrass | 0 | 0 | 10 | 20 | 0 | 0 | 0 | 0 | 0 | 20 | 0 | 0 | 0 | 20 |
| Ducksalad | 80 | 0 | 80 | 90 | 0 | 0 | 0 | 0 | 50 | 80 | 70 | 45 | 75 | 100 |
| Rice | 25 | 15 | 0 | 30 | 0 | 0 | 0 | 0 | 15 | 0 | 15 | 0 | 0 | 45 |
| Sedge, Umbrella | 30 | 0 | 20 | 90 | 0 | 0 | 0 | 30 | 30 | 80 | 70 | 0 | 0 | 90 |

| | Compounds | | | | | | | | | | | | | |
|---|---|---|---|---|---|---|---|---|---|---|---|---|---|---|
| 250 g ai/ha | 45 | 46 | 47 | 48 | 49 | 50 | 51 | 52 | 53 | 54 | 57 | 58 | 59 | 60 |

| | Flood | | | | | | | | | | | | | |
|---|---|---|---|---|---|---|---|---|---|---|---|---|---|---|
| Barnyardgrass | 30 | 0 | 10 | 0 | 0 | 0 | 0 | 30 | 0 | 0 | 0 | 80 | 40 | 0 |
| Ducksalad | 85 | 0 | 95 | 0 | 0 | 0 | 40 | 70 | 75 | 0 | 60 | 90 | 80 | 0 |
| Rice | 0 | 0 | 35 | 0 | 0 | 0 | 0 | 20 | 0 | 0 | 0 | 50 | 20 | 0 |
| Sedge, Umbrella | 75 | 0 | 70 | 0 | 0 | 0 | 65 | 95 | 0 | 0 | 80 | 90 | 90 | 0 |

| | Compounds | | | | | | | | | | | | | |
|---|---|---|---|---|---|---|---|---|---|---|---|---|---|---|
| 250 g ai/ha | 61 | 62 | 63 | 64 | 65 | 66 | 69 | 71 | 72 | 73 | 74 | 75 | 76 | 77 |

| | Flood | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 0 |
| Ducksalad | 0 | 80 | 0 | 70 | 95 | 30 | 0 | 0 | 75 | 70 | 40 | 60 | 70 | 40 |
| Rice | 0 | 0 | 0 | 0 | 0 | 0 | 0 | 30 | 0 | 0 | 0 | 0 | 0 | 20 |
| Sedge, Umbrella | 0 | 80 | 0 | 80 | 95 | 0 | 0 | 70 | 85 | 85 | 70 | 50 | 75 | 70 |

| | Compounds | | | | | | | | | | | | | |
|---|---|---|---|---|---|---|---|---|---|---|---|---|---|---|
| 250 g ai/ha | 79 | 80 | 81 | 82 | 83 | 84 | 85 | 86 | 87 | 88 | 89 | 90 | 91 | 92 |

| | Flood | | | | | | | | | | | | | |
|---|---|---|---|---|---|---|---|---|---|---|---|---|---|---|
| Barnyardgrass | 40 | 0 | 0 | 0 | 0 | 0 | 0 | 0 | 0 | 0 | 10 | 0 | 0 | 20 |
| Ducksalad | 95 | 100 | 90 | 30 | 45 | 50 | 30 | 75 | 0 | 25 | 95 | 40 | 0 | 95 |
| Rice | 45 | 0 | 0 | 0 | 0 | 0 | 10 | 0 | 0 | 0 | 20 | 0 | 0 | 20 |
| Sedge, Umbrella | 95 | 80 | 80 | 0 | 45 | 30 | 30 | 65 | 0 | 0 | 85 | 40 | 0 | 90 |

| | Compounds | | | | | | | | | | | | | |
|---|---|---|---|---|---|---|---|---|---|---|---|---|---|---|
| 250 g ai/ha | 93 | 94 | 95 | 96 | 97 | 98 | 99 | 100 | 101 | 103 | 106 | 107 | 108 | 109 |

| | Flood | | | | | | | | | | | | | |
|---|---|---|---|---|---|---|---|---|---|---|---|---|---|---|
| Barnyardgrass | 0 | 0 | 0 | 0 | 40 | 35 | 0 | 15 | 0 | 0 | 0 | 30 | 0 | 0 |
| Ducksalad | 0 | 40 | 40 | 0 | 95 | 85 | 0 | 0 | 0 | 0 | 75 | 40 | 85 | 80 |
| Rice | 0 | 0 | 0 | 0 | 0 | 15 | 0 | 0 | 0 | 0 | 0 | 0 | 35 | 0 |
| Sedge, Umbrella | 0 | 30 | 50 | 0 | 90 | 85 | 0 | 0 | 0 | 0 | 90 | 70 | 80 | 85 |

| | Compounds | | | | | | | | | | | | | |
|---|---|---|---|---|---|---|---|---|---|---|---|---|---|---|
| 250 g ai/ha | 110 | 111 | 112 | 113 | 114 | 115 | 116 | 117 | 118 | 119 | 120 | 121 | 122 | 123 |

| | Flood | | | | | | | | | | | | | |
|---|---|---|---|---|---|---|---|---|---|---|---|---|---|---|
| Barnyardgrass | 45 | 0 | 0 | 0 | 0 | 0 | 0 | 0 | 50 | 40 | 0 | 20 | 0 | 35 |
| Ducksalad | 95 | 70 | 90 | 0 | 50 | 70 | 60 | 40 | 90 | 95 | 95 | 45 | 80 | 80 |

TABLE B-continued

| | | | | | | | | | | | | | | |
|---|---|---|---|---|---|---|---|---|---|---|---|---|---|---|
| Rice | 0 | 0 | 0 | 0 | 0 | 0 | 0 | 0 | 60 | 25 | 0 | 0 | 0 | 0 |
| Sedge, Umbrella | 95 | 75 | 85 | 0 | 30 | 20 | 30 | 20 | 95 | 95 | 95 | 0 | 75 | 40 |

Compounds

| 250 g ai/ha | 125 | 126 | 127 | 128 | 129 | 130 | 131 | 132 | 134 | 135 | 136 | 137 | 138 | 140 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 30 | 20 | 0 | 0 | 20 |
| Ducksalad | 70 | 65 | 60 | 85 | 65 | 0 | 0 | 0 | 30 | 70 | 70 | 30 | 90 | 80 |
| Rice | 0 | 0 | 0 | 0 | 0 | 0 | 0 | 0 | 0 | 15 | 0 | 0 | 0 | 0 |
| Sedge, Umbrella | 70 | 20 | 0 | 85 | 65 | 0 | 0 | 0 | 30 | 75 | 70 | 0 | 75 | 80 |

Compounds

| 250 g ai/ha | 141 | 142 | 143 | 144 | 145 | 146 | 147 | 148 | 149 | 150 | 151 | 152 | 153 | 154 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 100 | 0 | 0 | 0 | 20 | 20 | 35 | 0 | 0 | 0 | 0 | 0 | 0 | 20 |
| Ducksalad | 100 | 0 | 40 | 95 | 75 | 40 | 80 | 40 | 70 | 90 | 70 | 60 | 30 | 80 |
| Rice | 45 | 0 | 0 | 0 | 20 | 0 | 35 | 0 | 0 | 0 | 20 | 0 | 0 | 10 |
| Sedge, Umbrella | 90 | 0 | 0 | 80 | 65 | 40 | 75 | 30 | 65 | 85 | 0 | 50 | 0 | 30 |

Compounds

| 250 g ai/ha | 155 | 156 | 157 | 158 | 159 | 160 | 161 | 162 | 163 | 164 | 165 | 166 | 167 | 168 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 40 | 0 | 35 | 0 | 0 | 35 | 0 | 0 | 0 | 20 | 0 | 60 | 35 | 0 |
| Ducksalad | 100 | 0 | 80 | 50 | 0 | 80 | 0 | 35 | 90 | 100 | 0 | 95 | 100 | 90 |
| Rice | 50 | 0 | 35 | 40 | 0 | 35 | 0 | 0 | 25 | 0 | 0 | 75 | 0 | 30 |
| Sedge, Umbrella | 80 | 0 | 75 | 0 | 0 | 75 | 0 | 40 | 90 | 90 | 0 | 95 | 98 | 80 |

Compounds

| 250 g ai/ha | 169 | 170 | 171 | 172 | 173 | 174 | 175 | 177 | 178 | 179 | 180 | 181 | 182 | 183 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 25 | 70 | 0 | 0 | 0 | 0 | 0 | 30 | 0 | 20 | 60 | 0 | 0 | 0 |
| Ducksalad | 65 | 95 | 0 | 0 | 0 | 0 | 0 | 90 | 0 | 80 | 80 | 75 | 0 | 0 |
| Rice | 15 | 50 | 0 | 0 | 0 | 0 | 0 | 15 | 0 | 0 | 40 | 0 | 0 | 0 |
| Sedge, Umbrella | 75 | 90 | 0 | 0 | 0 | 0 | 0 | 100 | 0 | 85 | 80 | 85 | 0 | 0 |

Compounds

| 250 g ai/ha | 184 | 185 | 186 | 187 | 188 | 189 | 190 | 191 | 192 | 193 | 194 | 195 | 196 | 197 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 0 | 0 | 0 | 0 | 30 | 0 | 0 | 40 | 0 | 0 | 0 | 0 | 20 | 0 |
| Ducksalad | 100 | 95 | 0 | 65 | 90 | 70 | 0 | 95 | 90 | 0 | 98 | 20 | 85 | 0 |
| Rice | 10 | 0 | 0 | 0 | 0 | 0 | 0 | 0 | 0 | 0 | 0 | 20 | 0 | 0 |
| Sedge, Umbrella | 95 | 90 | 0 | 50 | 90 | 70 | 0 | 95 | 85 | 0 | 95 | 30 | 70 | 65 |

Compounds

| 250 g ai/ha | 198 | 199 | 200 | 201 | 202 | 203 | 204 | 205 | 206 | 208 | 209 | 210 | 211 | 212 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 0 | 0 | 20 | 0 | 0 | 0 | 20 | 0 | 0 | 0 | 30 | 0 | 0 | 0 |
| Ducksalad | 25 | 70 | 95 | 40 | 30 | 90 | 70 | 0 | 0 | 0 | 75 | 75 | 0 | 0 |
| Rice | 0 | 20 | 20 | 0 | 0 | 10 | 20 | 0 | 0 | 0 | 0 | 15 | 0 | 0 |
| Sedge, Umbrella | 20 | 70 | 85 | 20 | 10 | 90 | 90 | 0 | 0 | 0 | 60 | 60 | 0 | 0 |

Compounds

| 250 g ai/ha | 213 | 214 | 215 | 216 | 217 | 218 | 219 | 220 | 221 | 222 | 223 | 225 | 226 | 227 |
|---|---|---|---|---|---|---|---|---|---|---|---|---|---|---|

Flood

| | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 35 | 0 | 0 | 0 |
| Ducksalad | 0 | 0 | 0 | 0 | 0 | 50 | 100 | 100 | 0 | 50 | 90 | 0 | 0 | 0 |

TABLE B-continued

| | | | | | | | | | | | | | | |
|---|---|---|---|---|---|---|---|---|---|---|---|---|---|---|
| Rice | 0 | 0 | 0 | 0 | 0 | 0 | 0 | 0 | 0 | 0 | 50 | 0 | 0 | 0 |
| Sedge, Umbrella | 70 | 0 | 0 | 0 | 0 | 40 | 85 | 90 | 0 | 70 | 85 | 0 | 0 | 0 |

| | Compounds | | | | | | | | | | | | | |
|---|---|---|---|---|---|---|---|---|---|---|---|---|---|---|
| 250 g ai/ha | 228 | 230 | 231 | 232 | 233 | 234 | 235 | 236 | 237 | 238 | 239 | 240 | 241 | 242 |

| | Flood | | | | | | | | | | | | | |
|---|---|---|---|---|---|---|---|---|---|---|---|---|---|---|
| Barnyardgrass | 0 | 20 | 20 | 10 | 10 | 20 | 0 | 30 | 0 | 0 | 0 | 0 | 0 | 20 |
| Ducksalad | 75 | 20 | 80 | 95 | 50 | 90 | 0 | 100 | 0 | 70 | 65 | 50 | 40 | 70 |
| Rice | 0 | 35 | 30 | 35 | 20 | 20 | 0 | 0 | 0 | 0 | 30 | 0 | 0 | 0 |
| Sedge, Umbrella | 60 | 50 | 80 | 80 | 50 | 90 | 0 | 100 | 0 | 90 | 70 | 30 | 0 | 75 |

| | Compounds | | | | | | | | | | | | | |
|---|---|---|---|---|---|---|---|---|---|---|---|---|---|---|
| 250 g ai/ha | 243 | 244 | 245 | 246 | 247 | 248 | 249 | 250 | 251 | 252 | 253 | 254 | 258 | 259 |

| | Flood | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 40 | 40 | 0 | 60 | 0 |
| Ducksalad | 30 | 40 | 75 | 0 | 65 | 50 | 70 | 70 | 75 | 75 | 75 | 65 | 100 | 70 |
| Rice | 0 | 0 | 0 | 0 | 0 | 15 | 0 | 0 | 0 | 0 | 25 | 0 | 30 | 0 |
| Sedge, Umbrella | 0 | 0 | 60 | 0 | 50 | 70 | 60 | 35 | 40 | 80 | 85 | 60 | 95 | 75 |

| | Compounds | | | | | | | | | | | | | |
|---|---|---|---|---|---|---|---|---|---|---|---|---|---|---|
| 250 g ai/ha | 260 | 261 | 264 | 265 | 266 | 267 | 268 | 269 | 270 | 271 | 272 | 273 | 274 | 275 |

| | Flood | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 35 | 0 | 0 | 0 | 65 | 15 |
| Ducksalad | 0 | 0 | 0 | 0 | 0 | 0 | 0 | 0 | 100 | 90 | 0 | 75 | 95 | 30 |
| Rice | 0 | 0 | 0 | 0 | 0 | 0 | 0 | 0 | 0 | 0 | 0 | 0 | 60 | 15 |
| Sedge, Umbrella | 0 | 0 | 0 | 0 | 0 | 0 | 50 | 0 | 90 | 60 | 0 | 75 | 95 | 0 |

| | Compounds | | | | | | | | | | | | | |
|---|---|---|---|---|---|---|---|---|---|---|---|---|---|---|
| 250 g ai/ha | 277 | 278 | 279 | 280 | 282 | 284 | 285 | 287 | 288 | 289 | 290 | 291 | 292 | 293 |

| | Flood | | | | | | | | | | | | | |
|---|---|---|---|---|---|---|---|---|---|---|---|---|---|---|
| Barnyardgrass | 0 | 0 | 75 | 10 | 0 | 0 | 0 | 0 | 0 | 0 | 0 | 0 | 20 | 0 |
| Ducksalad | 80 | 0 | 90 | 30 | 0 | 80 | 0 | 0 | 0 | 0 | 0 | 0 | 45 | 80 |
| Rice | 0 | 0 | 50 | 10 | 0 | 0 | 0 | 0 | 0 | 0 | 0 | 0 | 20 | 0 |
| Sedge, Umbrella | 80 | 0 | 90 | 10 | 0 | 85 | 0 | 0 | 0 | 0 | 0 | 0 | 75 | 80 |

| | Compounds | | | | | | | |
|---|---|---|---|---|---|---|---|---|
| 250 g ai/ha | 294 | 295 | 296 | 297 | 298 | 299 | 301 | 304 |

| | Flood | | | | | | | |
|---|---|---|---|---|---|---|---|---|
| Barnyardgrass | 0 | 0 | 0 | 0 | 0 | 20 | 0 | 0 |
| Ducksalad | 0 | 0 | 0 | 0 | 0 | 20 | 0 | 0 |
| Rice | 0 | 0 | 0 | 0 | 0 | 15 | 0 | 0 |
| Sedge, Umbrella | 0 | 0 | 0 | 0 | 30 | 70 | 0 | 0 |

Test C

Seeds of plant species selected from blackgrass (*Alopecurus myosuroides*), Italian ryegrass (*Lolium multiflorum*), wheat, winter (winter wheat, *Triticum aestivum*), galium (catchweed bedstraw, *Galium aparine*), corn (*Zea mays*), large (Lg) crabgrass (*Digitaria sanguinalis*), giant foxtail (*Setaria faberii*), johnsongrass (*Sorghum halepense*), lambsquarters (*Chenopodium album*), morningglory (*Ipomoea coccinea*), yellow nutsedge (*Cyperus esculentus*), pigweed (*Amaranthus retroflexus*), ragweed (common ragweed, *Ambrosia elatior*), soybean (*Glycine max*), barnyardgrass (*Echinochloa crus-galli*), oilseed rape (*Brassica napus*), waterhemp (common waterhemp, *Amaranthus rudis*), kochia (*Kochia scoparia*), wild oat (*Avena fatua*), surinam grass (*Brachiaria decumbens*), foxtail, green (green foxtail, *Setaria viridis*), goosegrass (*Eleusine indica*), bromegrass, downy (downy bromegrass, *Bromus tectorum*), nightshade (eastern black nightshade, *Solanum ptycanthum*), cocklebur (common cocklebur, *Xanthium strumarium*), cupgrass, woolly (woolly cupgrass, *Eriochloa villosa*), bermudagrass (*Cynodon dactylon*), sunflower, (common oilseed sunflower, *Helianthus annuus*), Russian thistle (*Salsola kali*), and velvetleaf (*Abutilon theophrasti*) were planted into a blend of loam soil and sand and treated preemergence with test chemicals formulated in a non-phytotoxic solvent mixture which included a surfactant.

At the same time, plants selected from these crop and weed species and also barley, winter (winter barley, *Hordeum vulgare*), windgrass (*Apera spica-venti*), chickweed (common chickweed, *Stellaria media*), deadnettle (henbit deadnettle, *Lamium amplexicaule*), and canarygrass (littleseed canarygrass, *Phalaris minor*) were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of test chemicals formulated in the same manner. Plants ranged in height from 2 to 18 cm (1- to 4-leaf stage) for postemergence treatments. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

Plant species in the flooded paddy test consisted of rice (*Oryza sativa*), sedge, umbrella (small-flower umbrella sedge, *Cyperus difformis*), ducksalad (*Heteranthera limosa*), and barnyardgrass (*Echinochloa crus-galli*) grown to the 2-leaf stage for testing. At time of treatment, test pots were flooded to 3 cm above the soil surface, treated by application of test compounds directly to the paddy water, and then maintained at that water depth for the duration of the test. Treated plants and controls were maintained in a greenhouse for 13 to 15 days, after which time all species were compared to controls and visually evaluated. Plant response ratings, summarized in Table C, are based on a scale of 0 to 100 where 0 is no effect and 100 is complete control. A dash (-) response means no test result.

TABLE C

| 250 g ai/ha | Compounds | | | | | | | | | | | | | |
|---|---|---|---|---|---|---|---|---|---|---|---|---|---|---|
| | 5 | 7 | 10 | 16 | 25 | 47 | 52 | 57 | 58 | 59 | 62 | 72 | 73 | 74 |
| Postemergence | | | | | | | | | | | | | | |
| Barley | 10 | 15 | 10 | 35 | — | — | — | — | — | — | — | — | — | — |
| Barnyardgrass | — | — | — | — | 25 | 5 | 10 | 15 | 75 | 25 | 10 | 40 | 35 | 15 |
| Bermudagrass | 35 | 70 | 50 | 55 | — | — | — | — | — | — | — | — | — | — |
| Blackgrass | 45 | 50 | 75 | 70 | 85 | 40 | 25 | 30 | 55 | 40 | 50 | 15 | 25 | 5 |
| Bromegrass, Downy | 10 | 10 | 15 | 5 | — | — | — | — | — | — | — | — | — | — |
| Canarygrass | 40 | 80 | 40 | 80 | — | — | — | — | — | — | — | — | — | — |
| Chickweed | 45 | 98 | 98 | 90 | 98 | 50 | 95 | 80 | 100 | 98 | 90 | 80 | 80 | 50 |
| Cocklebur | 65 | 80 | 100 | 80 | — | — | — | — | — | — | — | — | — | — |
| Corn | 70 | 75 | 20 | 20 | 15 | 5 | 10 | 20 | 45 | 20 | 20 | 20 | 10 | 20 |
| Crabgrass, Large | 20 | 20 | 35 | 85 | 30 | 10 | 40 | 30 | 85 | 40 | 35 | 60 | 20 | 20 |
| Cupgrass, Woolly | 30 | 25 | 15 | 30 | — | — | — | — | — | — | — | — | — | — |
| Deadnettle | 90 | 100 | 95 | — | — | — | — | — | — | — | — | — | — | — |
| Foxtail, Giant | 10 | 10 | 5 | 85 | 30 | 80 | 70 | 30 | 95 | 90 | 25 | 65 | 30 | 20 |
| Foxtail, Green | 70 | 98 | 30 | 100 | — | — | — | — | — | — | — | — | — | — |
| Galium | 95 | 98 | 95 | — | 90 | 65 | 90 | 95 | 95 | 90 | 95 | 95 | 70 | 65 |
| Goosegrass | 15 | 15 | 10 | 30 | — | — | — | — | — | — | — | — | — | — |
| Johnsongrass | 10 | 10 | 10 | 10 | 15 | 5 | 10 | 20 | 85 | 85 | 15 | 25 | 25 | 25 |
| *Kochia* | 100 | 100 | 98 | 100 | 100 | 60 | 95 | 100 | 100 | 100 | 95 | 95 | 90 | 90 |
| Lambsquarters | 98 | 98 | 98 | 100 | 100 | 90 | 100 | 85 | 98 | 90 | 90 | 98 | 80 | 85 |
| Morningglory | 90 | — | 85 | 85 | — | 75 | 100 | 95 | 98 | 95 | 90 | 90 | 85 | 85 |
| Nutsedge, Yellow | 15 | 20 | 5 | 20 | 10 | 10 | 30 | 15 | 15 | 10 | 15 | 10 | 5 | 0 |
| Oat, Wild | 30 | 55 | 30 | 45 | 35 | 5 | 15 | 35 | 55 | 40 | 35 | 35 | 15 | 10 |
| Oilseed Rape | — | — | — | — | — | 55 | 85 | 85 | 85 | 95 | 75 | 90 | 80 | 65 |
| Pigweed | 100 | 100 | 100 | 100 | 98 | 70 | 95 | 95 | 100 | 98 | 80 | 95 | 90 | 80 |
| Ragweed | 85 | 60 | 80 | 90 | 65 | 85 | 95 | 65 | 90 | 55 | 50 | 60 | 65 | 60 |
| Ryegrass, Italian | 25 | 40 | 10 | 20 | — | 0 | 10 | 15 | 35 | 30 | 15 | 10 | 5 | 5 |
| Soybean | 95 | 98 | 95 | 90 | 80 | 65 | 95 | 100 | 98 | 98 | 95 | 95 | 90 | 80 |
| Surinam Grass | — | — | 15 | 40 | — | — | — | — | — | — | — | — | — | — |
| Velvetleaf | 98 | 85 | 90 | 75 | 65 | 100 | 90 | 60 | 85 | 70 | 85 | 75 | 70 | 65 |
| Waterhemp | — | — | — | — | 98 | 100 | 95 | 90 | 100 | 98 | 75 | 95 | 90 | 80 |
| Wheat | 40 | 15 | 10 | 35 | 10 | 0 | 5 | 15 | 30 | 20 | 20 | 5 | 5 | 5 |
| Windgrass | 85 | 80 | 65 | 50 | — | — | — | — | — | — | — | — | — | — |

| 250 g ai/ha | Compounds | | | | |
|---|---|---|---|---|---|
| | 79 | 194 | 200 | 204 | 284 |
| Postemergence | | | | | |
| Barley | — | — | — | — | — |
| Barnyardgrass | 75 | 55 | 15 | 35 | 15 |
| Bermudagrass | — | — | — | — | — |
| Blackgrass | 80 | 35 | 35 | 25 | 5 |
| Bromegrass, Downy | — | — | — | — | — |
| Canarygrass | — | — | — | — | — |
| Chickweed | 95 | 85 | 98 | 100 | 100 |
| Cocklebur | — | — | — | — | — |
| Corn | 35 | 30 | 20 | 20 | 20 |
| Crabgrass, Large | 65 | 50 | 20 | 65 | 10 |
| Cupgrass, Woolly | — | — | — | — | — |
| Deadnettle | — | — | — | — | — |
| Foxtail, Giant | 65 | 15 | 15 | 90 | 25 |
| Foxtail, Green | — | — | — | — | — |
| Galium | 95 | 90 | 95 | 100 | 100 |
| Goosegrass | — | — | — | — | — |
| Johnsongrass | 85 | 35 | 30 | 30 | 20 |
| *Kochia* | 95 | 95 | 100 | 100 | 100 |
| Lambsquarters | 98 | 98 | 95 | 95 | 98 |

TABLE C-continued

| | | | | | |
|---|---|---|---|---|---|
| Morningglory | 98 | 95 | 95 | 95 | 100 |
| Nutsedge, Yellow | 25 | 5 | 35 | 5 | 5 |
| Oat, Wild | 50 | 45 | 20 | 15 | 5 |
| Oilseed Rape | 90 | 90 | 70 | 75 | 80 |
| Pigweed | 98 | 95 | 95 | 98 | 100 |
| Ragweed | 85 | 50 | 85 | 75 | 80 |
| Ryegrass, Italian | 20 | 15 | 5 | 10 | 5 |
| Soybean | 95 | 85 | 90 | 95 | 65 |
| Surinam Grass | — | — | — | — | — |
| Velvetleaf | 90 | 75 | 70 | 70 | 70 |
| Waterhemp | 100 | 90 | 95 | 95 | 100 |
| Wheat | 35 | 5 | 5 | 10 | 5 |
| Windgrass | — | — | — | — | — |

| | Compounds | | | | | | | | | | | | |
|---|---|---|---|---|---|---|---|---|---|---|---|---|---|
| 125 g ai/ha | 5 | 7 | 10 | 16 | 25 | 47 | 52 | 57 | 58 | 59 | 62 | 65 | 72 | 73 |
| | Postemergence | | | | | | | | | | | | |
| Barley | 5 | 10 | 5 | 10 | — | — | — | — | — | — | — | — | — | — |
| Barnyardgrass | — | — | — | — | 20 | 0 | 5 | 10 | 15 | 10 | 5 | 10 | 10 | 10 |
| Bermudagrass | 10 | 15 | 5 | 50 | — | — | — | — | — | — | — | — | — | — |
| Blackgrass | 20 | 45 | 40 | 30 | 60 | 5 | 10 | 30 | 30 | 25 | 30 | 15 | 15 | 5 |
| Bromegrass, Downy | 5 | 10 | 10 | 5 | — | — | — | — | — | — | — | — | — | — |
| Canarygrass | 30 | 30 | 25 | 60 | — | — | — | — | — | — | — | — | — | — |
| Chickweed | — | 90 | 35 | 75 | 98 | 50 | 90 | 80 | 100 | 80 | 75 | 98 | 80 | 50 |
| Cocklebur | 50 | 55 | 55 | — | — | — | — | — | — | — | — | — | — | — |
| Corn | 60 | 60 | 5 | 10 | — | 5 | 10 | 20 | 25 | 15 | 15 | 10 | 15 | 10 |
| Crabgrass, Large | 20 | 10 | 5 | 30 | 20 | 5 | 20 | 10 | 50 | 30 | 10 | 5 | 55 | 10 |
| Cupgrass, Woolly | 10 | 25 | 5 | 20 | — | — | — | — | — | — | — | — | — | — |
| Deadnettle | 90 | 98 | 80 | — | — | — | — | — | — | — | — | — | — | — |
| Foxtail, Giant | 5 | 10 | 5 | 15 | 30 | 25 | 70 | 15 | 80 | 45 | 20 | 10 | 10 | 10 |
| Foxtail, Green | 40 | 50 | 0 | 30 | — | — | — | — | — | — | — | — | — | — |
| Galium | 80 | 90 | 80 | — | 90 | 55 | 85 | 70 | 85 | 90 | 80 | 98 | 95 | 70 |
| Goosegrass | 10 | 15 | 5 | 15 | — | — | — | — | — | — | — | — | — | — |
| Johnsongrass | 5 | 5 | 5 | 10 | 10 | 5 | 5 | 5 | 35 | 35 | 10 | 5 | 5 | 5 |
| Kochia | 70 | 100 | 95 | 98 | 100 | 25 | 90 | 90 | 100 | 100 | 90 | 98 | 95 | 90 |
| Lambsquarters | 98 | 98 | 75 | 100 | 98 | 60 | 90 | 70 | 98 | 90 | 85 | 90 | 85 | 70 |
| Morningglory | 60 | 95 | 65 | 80 | 98 | 70 | 95 | 85 | 98 | 95 | 85 | 95 | 85 | 85 |
| Nutsedge, Yellow | 15 | 15 | 5 | 5 | 10 | 0 | 5 | 5 | 15 | 5 | 5 | 15 | 0 | 5 |
| Oat, Wild | 10 | 35 | 5 | 35 | 30 | 0 | 10 | 30 | 45 | 40 | 30 | 5 | 30 | 10 |
| Oilseed Rape | — | — | — | — | 90 | 55 | 70 | 80 | 85 | 85 | 60 | 90 | 70 | 60 |
| Pigweed | 100 | 100 | 100 | 100 | 90 | 65 | 80 | — | 98 | 95 | 75 | 98 | 85 | 80 |
| Ragweed | 55 | 55 | 55 | 40 | 65 | 50 | 80 | 55 | 85 | 25 | 50 | 35 | 60 | 50 |
| Ryegrass, Italian | 10 | 10 | 5 | 20 | — | 0 | 10 | 10 | 10 | 10 | 5 | 5 | 10 | 0 |
| Soybean | 95 | 98 | 85 | 90 | 80 | 65 | 95 | 95 | 98 | 98 | 95 | 85 | 90 | 80 |
| Surinam Grass | 45 | 30 | 15 | 40 | — | — | — | — | — | — | — | — | — | — |
| Velvetleaf | 80 | 85 | 70 | 75 | 50 | 70 | 70 | 40 | 60 | 55 | 75 | 65 | 55 | 50 |
| Waterhemp | — | — | — | — | 90 | 100 | 75 | 80 | 90 | 90 | 75 | 90 | 75 | 75 |
| Wheat | 10 | 10 | 5 | 35 | 10 | 0 | 5 | 10 | 25 | 20 | 5 | 10 | 0 | 0 |
| Windgrass | 60 | 55 | 50 | 50 | — | — | — | — | — | — | — | — | — | — |

| | Compounds | | | | | | | | | | | | |
|---|---|---|---|---|---|---|---|---|---|---|---|---|---|
| 125 g ai/ha | 74 | 79 | 80 | 83 | 84 | 85 | 86 | 88 | 89 | 90 | 92 | 94 | 97 | 98 |
| | Postemergence | | | | | | | | | | | | |
| Barley | — | — | — | — | — | — | — | — | — | — | — | — | — | — |
| Barnyardgrass | 5 | 20 | 5 | 5 | 15 | 5 | 5 | 10 | 5 | 10 | 10 | 10 | 15 | 15 |
| Bermudagrass | — | — | — | — | — | — | — | — | — | — | — | — | — | — |
| Blackgrass | 0 | 35 | 40 | 20 | 20 | 10 | 10 | 10 | 5 | 15 | 35 | 5 | 40 | 20 |
| Bromegrass, Downy | — | — | — | — | — | — | — | — | — | — | — | — | — | — |
| Canarygrass | — | — | — | — | — | — | — | — | — | — | — | — | — | — |
| Chickweed | 50 | 90 | 70 | 70 | 50 | 40 | 80 | 90 | 60 | 50 | 70 | 70 | 90 | 85 |
| Cocklebur | — | — | — | — | — | — | — | — | — | — | — | — | — | — |
| Corn | 15 | 15 | 5 | 10 | 5 | 10 | 10 | 10 | 5 | 5 | 5 | 5 | 15 | 20 |
| Crabgrass, Large | 15 | 30 | 5 | 10 | 30 | 10 | 5 | 10 | 5 | 10 | 10 | 10 | 55 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 10 | 20 | 5 | 40 | 50 | 15 | 25 | 40 | 10 | 20 | 10 | 10 | 15 | 10 |
| Foxtail, Green | — | — | — | — | — | — | — | — | — | — | — | — | — | — |
| Galium | 65 | 80 | 95 | 60 | 95 | 75 | 80 | 95 | 55 | 85 | 80 | 80 | 90 | 80 |
| Goosegrass | — | — | — | — | — | — | — | — | — | — | — | — | — | — |
| Johnsongrass | 25 | 40 | 5 | 10 | 0 | 10 | 5 | 10 | 5 | 5 | 5 | 5 | 5 | 10 |
| Kochia | 90 | 95 | 95 | 95 | 80 | 90 | 95 | 100 | 50 | 90 | 85 | 90 | 100 | 98 |
| Lambsquarters | 75 | 95 | 55 | 80 | 80 | 70 | 85 | 75 | 55 | 60 | 75 | 85 | 98 | 98 |
| Morningglory | 75 | 95 | 60 | 85 | 85 | 40 | 85 | 95 | 85 | 85 | 85 | 55 | 95 | 85 |
| Nutsedge, Yellow | 0 | 5 | 5 | 5 | — | 10 | 5 | 10 | 5 | 10 | 5 | 10 | 5 | 5 |

TABLE C-continued

| | | | | | | | | | | | | | | |
|---|---|---|---|---|---|---|---|---|---|---|---|---|---|---|
| Oat, Wild | 10 | 20 | 10 | 5 | 15 | 5 | 10 | 10 | 15 | 5 | 15 | 5 | 25 | 20 |
| Oilseed Rape | 40 | 50 | 90 | 80 | 60 | 15 | 45 | 45 | 60 | 40 | 70 | 80 | 80 | 98 |
| Pigweed | 65 | 95 | 75 | 85 | 85 | 70 | 80 | 90 | 40 | 70 | 75 | 85 | 95 | 75 |
| Ragweed | 40 | 70 | 45 | 70 | 80 | 65 | 85 | 60 | 70 | 65 | 55 | 45 | 70 | 40 |
| Ryegrass, Italian | 0 | 20 | 5 | 5 | 0 | 5 | 5 | 0 | 5 | 0 | 35 | 5 | 15 | 25 |
| Soybean | 75 | 90 | 80 | 90 | 90 | 90 | 75 | 65 | 95 | 60 | 95 | 80 | 95 | 90 |
| Surinam Grass | — | — | — | — | — | — | — | — | — | — | — | — | — | — |
| Velvetleaf | 50 | 70 | 75 | 65 | 90 | 55 | 65 | 55 | 40 | 60 | 60 | 40 | 70 | 90 |
| Waterhemp | 60 | 90 | 90 | 90 | 70 | 60 | 75 | 90 | 60 | 75 | 80 | 70 | 95 | 85 |
| Wheat | 0 | 5 | 30 | 5 | 0 | 0 | 0 | 5 | 5 | 0 | 5 | 0 | 10 | 10 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 111 | 116 | 117 | 120 | 123 | 129 | 132 | 134 | 136 | 138 | 140 | 141 | 145 | 147 |
| | Postemergence | | | | | | | | | | | | | |
| Barley | — | — | — | — | — | — | — | — | — | — | — | — | — | — |
| Barnyardgrass | 35 | 20 | 10 | 10 | 15 | 5 | 5 | 10 | 5 | 5 | 10 | 40 | 5 | 10 |
| Bermudagrass | — | — | — | — | — | — | — | — | — | — | — | — | — | — |
| Blackgrass | 10 | 25 | 10 | 30 | 0 | 10 | 5 | 10 | 5 | 10 | 5 | 60 | 10 | 10 |
| Bromegrass, Downy | — | — | — | — | — | — | — | — | — | — | — | — | — | — |
| Canarygrass | — | — | — | — | — | — | — | — | — | — | — | — | — | — |
| Chickweed | 95 | 80 | 80 | 80 | 60 | 55 | 40 | 80 | 60 | 55 | 70 | 100 | 65 | 90 |
| Cocklebur | — | — | — | — | — | — | — | — | — | — | — | — | — | — |
| Corn | 15 | 5 | 5 | 10 | 5 | 15 | 10 | 5 | 5 | 10 | 10 | 20 | 5 | 10 |
| Crabgrass, Large | 35 | 30 | 20 | 10 | 5 | 10 | 10 | 15 | 15 | 15 | 20 | 45 | 5 | 10 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 65 | 10 | 55 | 35 | 20 | 10 | 10 | 5 | 10 | 50 | 20 | 70 | 25 | 50 |
| Foxtail, Green | — | — | — | — | — | — | — | — | — | — | — | — | — | — |
| Galium | 100 | 80 | 80 | 60 | 90 | 85 | 70 | 85 | 60 | 85 | 95 | 100 | 60 | 90 |
| Goosegrass | — | — | — | — | — | — | — | — | — | — | — | — | — | — |
| Johnsongrass | 10 | 15 | 5 | 10 | 10 | 5 | 5 | 15 | — | 10 | 25 | 30 | 10 | 10 |
| Kochia | 95 | 95 | 100 | 100 | 85 | 100 | 95 | 95 | 70 | 95 | 90 | 100 | 90 | 100 |
| Lambsquarters | 90 | 80 | 75 | 85 | 85 | 85 | 50 | 65 | 75 | 75 | 85 | 100 | 85 | 98 |
| Morningglory | 98 | 80 | 90 | 80 | 75 | 85 | 65 | 95 | 40 | 85 | 70 | 100 | 60 | 80 |
| Nutsedge, Yellow | 5 | — | 5 | 25 | 10 | 10 | 10 | 10 | 10 | 10 | 5 | 15 | 0 | 5 |
| Oat, Wild | 5 | 15 | 20 | 5 | 0 | 10 | 5 | 10 | 5 | 10 | 5 | 30 | 5 | 5 |
| Oilseed Rape | 80 | 40 | 70 | 15 | 70 | 60 | 95 | 60 | 5 | 80 | 50 | 98 | 70 | 95 |
| Pigweed | 85 | 95 | 90 | 95 | 85 | 90 | 80 | 85 | 55 | 80 | 90 | 98 | 75 | 85 |
| Ragweed | 90 | 70 | 60 | 60 | 75 | 85 | 35 | 55 | 45 | 45 | 75 | 90 | 50 | 85 |
| Ryegrass, Italian | 0 | 5 | 5 | 5 | 0 | 5 | 5 | 0 | 0 | 5 | 0 | 40 | 0 | 5 |
| Soybean | 95 | 95 | 50 | 80 | 90 | 60 | 50 | 90 | 90 | 95 | 75 | 95 | 65 | 90 |
| Surinam Grass | — | — | — | — | — | — | — | — | — | — | — | — | — | — |
| Velvetleaf | 80 | 85 | 45 | 50 | 100 | 40 | 45 | 55 | 25 | 55 | 60 | 100 | 80 | 75 |
| Waterhemp | 90 | 95 | 90 | 85 | 80 | 85 | 75 | 85 | 30 | 85 | 85 | 100 | 80 | 70 |
| Wheat | 5 | 5 | 20 | 0 | 5 | 5 | 5 | 25 | 5 | 5 | 10 | 25 | 0 | 15 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 150 | 154 | 155 | 160 | 163 | 164 | 166 | 167 | 177 | 178 | 180 | 181 | 191 | 192 |
| | Postemergence | | | | | | | | | | | | | |
| Barley | — | — | — | — | — | — | — | — | — | — | — | — | — | — |
| Barnyardgrass | 5 | 20 | 10 | 5 | 5 | 5 | 15 | 10 | 10 | 10 | 20 | 10 | 15 | 10 |
| Bermudagrass | — | — | — | — | — | — | — | — | — | — | — | — | — | — |
| Blackgrass | 10 | 0 | 5 | 15 | 15 | 15 | 60 | 30 | 35 | 60 | 30 | 25 | 10 | 10 |
| Bromegrass, Downy | — | — | — | — | — | — | — | — | — | — | — | — | — | — |
| Canarygrass | — | — | — | — | — | — | — | — | — | — | — | — | — | — |
| Chickweed | 70 | 60 | 90 | 70 | 95 | 90 | 95 | 80 | 85 | 80 | 80 | 85 | 98 | 60 |
| Cocklebur | — | — | — | — | — | — | — | — | — | — | — | — | — | — |
| Corn | 10 | 0 | 10 | 5 | 10 | 5 | 15 | 15 | 10 | 10 | 10 | 5 | 10 | 5 |
| Crabgrass, Large | 10 | 10 | 15 | 10 | 10 | 10 | 15 | 10 | 10 | 10 | 35 | 10 | 10 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 25 | 15 | 25 | 10 | 10 | 10 | 35 | 30 | 20 | 25 | 80 | 10 | 15 | 10 |
| Foxtail, Green | — | — | — | — | — | — | — | — | — | — | — | — | — | — |
| Galium | 80 | 85 | 100 | 85 | 95 | 65 | 95 | 90 | 98 | 98 | 90 | 80 | 98 | 85 |
| Goosegrass | — | — | — | — | — | — | — | — | — | — | — | — | — | — |
| Johnsongrass | 5 | 5 | 5 | 5 | 10 | 10 | 5 | 25 | 10 | 35 | 5 | 20 | 10 | 10 |
| Kochia | 85 | 80 | 100 | 100 | 100 | 95 | 100 | 95 | 95 | 95 | 60 | 100 | 100 | 90 |
| Lambsquarters | 80 | 70 | 98 | 95 | 95 | 65 | 98 | 100 | 90 | 98 | 85 | 100 | 95 | 90 |
| Morningglory | 80 | 80 | 85 | 65 | 90 | 80 | 95 | 90 | 85 | 65 | 90 | 98 | 50 | 35 |
| Nutsedge, Yellow | 5 | 10 | 5 | 5 | 5 | 5 | 5 | 20 | 10 | 10 | 10 | — | 5 | 40 |
| Oat, Wild | 5 | 0 | 25 | 0 | 20 | 15 | 50 | 35 | 30 | 30 | 30 | 5 | 10 | 5 |
| Oilseed Rape | 50 | 80 | 80 | 60 | 80 | 60 | 98 | 70 | 90 | 98 | 55 | 100 | 50 | 60 |

TABLE C-continued

| | | | | | | | | | | | | | | |
|---|---|---|---|---|---|---|---|---|---|---|---|---|---|---|
| Pigweed | 65 | 75 | 98 | 85 | 90 | 80 | 98 | 98 | 95 | 98 | 70 | 98 | 98 | 70 |
| Ragweed | 65 | 90 | 85 | 70 | 60 | 55 | 80 | 55 | 60 | 65 | 70 | 45 | 35 | 45 |
| Ryegrass, Italian | 5 | 0 | 10 | 5 | 10 | 0 | 30 | 30 | 0 | 20 | 10 | 10 | 5 | 5 |
| Soybean | 95 | 75 | 80 | 60 | 75 | 65 | 95 | 60 | 95 | 95 | 95 | 95 | 30 | 80 |
| Surinam Grass | — | — | — | — | — | — | — | — | — | — | — | — | — | — |
| Velvetleaf | 30 | 80 | 85 | 90 | — | 65 | 85 | 70 | 80 | 100 | 85 | 70 | 65 | 75 |
| Waterhemp | 65 | 70 | 98 | 85 | 80 | 75 | 90 | 98 | 100 | 100 | 75 | 98 | 95 | 85 |
| Wheat | 25 | 5 | 35 | 5 | 5 | 0 | 20 | 5 | 5 | 0 | 5 | 5 | 0 | 5 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 125 g ai/ha | 194 | 200 | 204 | 220 | 221 | 223 | 228 | 232 | 236 | 240 | 245 | 253 | 258 | 273 |
| | Postemergence | | | | | | | | | | | | | |
| Barley | — | — | — | — | — | — | — | — | — | — | — | — | — | — |
| Barnyardgrass | 15 | 10 | 5 | 15 | 10 | 5 | 5 | 20 | 10 | 20 | 5 | 20 | 10 | 10 |
| Bermudagrass | — | — | — | — | — | — | — | — | — | — | — | — | — | — |
| Blackgrass | 30 | 10 | 10 | 50 | 5 | 0 | 40 | 25 | 20 | 5 | 5 | 10 | 10 | 10 |
| Bromegrass, Downy | — | — | — | — | — | — | — | — | — | — | — | — | — | — |
| Canarygrass | — | — | — | — | — | — | — | — | — | — | — | — | — | — |
| Chickweed | 70 | 95 | 98 | 80 | 50 | 60 | 50 | 60 | 50 | 55 | 100 | 90 | 95 | 70 |
| Cocklebur | — | — | — | — | — | — | — | — | — | — | — | — | — | — |
| Corn | 25 | 15 | 20 | 10 | 10 | 5 | 5 | 15 | 10 | 15 | 5 | 25 | 20 | 5 |
| Crabgrass, Large | 10 | 15 | 15 | 5 | 25 | 5 | 5 | 5 | 5 | 20 | 15 | 20 | 15 | 10 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 15 | 5 | 10 | 5 | 5 | 5 | 5 | 15 | 15 | 40 | 15 | 20 | 45 | 20 |
| Foxtail, Green | — | — | — | — | — | — | — | — | — | — | — | — | — | — |
| Galium | 85 | 85 | 75 | 95 | 90 | 100 | 80 | 95 | 85 | 70 | 85 | 100 | 100 | 80 |
| Goosegrass | — | — | — | — | — | — | — | — | — | — | — | — | — | — |
| Johnsongrass | 25 | 5 | 10 | 5 | 20 | 5 | 10 | 5 | 20 | 10 | 10 | 10 | 5 | 5 |
| Kochia | 90 | 98 | 100 | 95 | 95 | 90 | 85 | 98 | 90 | 90 | 98 | 100 | 100 | 95 |
| Lambsquarters | 90 | 85 | 90 | 75 | 65 | 95 | 65 | 75 | 90 | 90 | 98 | 95 | 90 | 80 |
| Morningglory | 80 | 95 | 98 | 50 | 55 | 80 | 35 | 85 | 75 | 90 | 85 | 85 | 95 | 85 |
| Nutsedge, Yellow | 5 | 30 | 0 | 5 | 10 | 5 | 5 | 5 | 5 | 5 | 10 | 5 | 5 | 25 |
| Oat, Wild | 40 | 25 | 15 | 50 | 30 | 5 | 5 | 20 | 5 | 0 | 5 | 10 | 15 | 10 |
| Oilseed Rape | 85 | 50 | 85 | 90 | 80 | 85 | 85 | 60 | 65 | 60 | 80 | 80 | 98 | 25 |
| Pigweed | 90 | 95 | 95 | 90 | 85 | 90 | 55 | 85 | 95 | 75 | 85 | 95 | 90 | 90 |
| Ragweed | 50 | 55 | 35 | 25 | 10 | 75 | 45 | 60 | 75 | 75 | 60 | 80 | 75 | 80 |
| Ryegrass, Italian | 0 | 5 | 10 | 10 | 5 | 5 | 10 | 10 | 0 | 0 | 5 | 0 | 30 | 10 |
| Soybean | 75 | 95 | 95 | 95 | 80 | 95 | 80 | 75 | 95 | 75 | 90 | 90 | 95 | 90 |
| Surinam Grass | — | — | — | — | — | — | — | — | — | — | — | — | — | — |
| Velvetleaf | 70 | 75 | 60 | 60 | 75 | 90 | 70 | 65 | 80 | 80 | 55 | 85 | 80 | 30 |
| Waterhemp | 85 | 90 | 90 | 85 | 80 | 95 | 75 | 85 | 90 | 70 | 75 | 85 | 90 | 80 |
| Wheat | 0 | 5 | 10 | 0 | 0 | 5 | 0 | 5 | 0 | 5 | 5 | 0 | 5 | 10 |
| Windgrass | — | — | — | — | — | — | — | — | — | — | — | — | — | — |

| | Compounds | |
|---|---|---|
| 125 g ai/ha | 274 | 284 |
| | Postemergence | |
| Barley | — | — |
| Barnyardgrass | 15 | 15 |
| Bermudagrass | — | — |
| Blackgrass | 20 | 5 |
| Bromegrass, Downy | — | — |
| Canarygrass | — | — |
| Chickweed | 98 | 100 |
| Cocklebur | — | — |
| Corn | 15 | 20 |
| Crabgrass, Large | 60 | 10 |
| Cupgrass, Woolly | — | — |
| Deadnettle | — | — |
| Foxtail, Giant | 60 | 20 |
| Foxtail, Green | — | — |
| Galium | 98 | 85 |
| Goosegrass | — | — |
| Johnsongrass | 10 | 20 |
| Kochia | 100 | 100 |
| Lambsquarters | 98 | 98 |
| Morningglory | 95 | 85 |
| Nutsedge, Yellow | 10 | 0 |
| Oat, Wild | 30 | 5 |
| Oilseed Rape | 90 | 80 |
| Pigweed | 98 | 100 |
| Ragweed | 75 | 50 |

TABLE C-continued

|  |  |  |
|---|---|---|
| Ryegrass, Italian | 35 | 5 |
| Soybean | 98 | 85 |
| Surinam Grass | — | — |
| Velvetleaf | 75 | 30 |
| Waterhemp | 98 | 98 |
| Wheat | 15 | 5 |
| Windgrass | — | — |

| | Compounds | | | | | | | | | | | | | |
|---|---|---|---|---|---|---|---|---|---|---|---|---|---|---|
| 62 g ai/ha | 5 | 7 | 10 | 16 | 25 | 47 | 52 | 57 | 58 | 59 | 62 | 65 | 72 | 73 |
| Postemergence | | | | | | | | | | | | | | |
| Barley | 0 | 0 | 5 | 5 | — | — | — | — | — | — | — | — | — | — |
| Barnyardgrass | — | — | — | — | 20 | 0 | 5 | 10 | 5 | 5 | 5 | 5 | 5 | 0 |
| Bermudagrass | 0 | 5 | 5 | 15 | — | — | — | — | — | — | — | — | — | — |
| Blackgrass | 5 | 10 | 5 | 30 | 50 | 0 | 5 | 15 | 15 | 10 | 5 | 40 | 10 | 0 |
| Bromegrass, Downy | 5 | 5 | 5 | 5 | — | — | — | — | — | — | — | — | — | — |
| Canarygrass | 10 | 10 | 0 | 30 | — | — | — | — | — | — | — | — | — | — |
| Chickweed | 15 | — | 30 | 65 | 90 | 5 | 60 | 50 | 95 | 70 | 50 | 70 | 65 | 50 |
| Cocklebur | 50 | 45 | 55 | 55 | — | — | — | — | — | — | — | — | — | — |
| Corn | 20 | 25 | 5 | 5 | 15 | 0 | 10 | 15 | 15 | 15 | 15 | 10 | 10 | 5 |
| Crabgrass, Large | 15 | 5 | 5 | 20 | 20 | 5 | 15 | 5 | 20 | 10 | 5 | 5 | 10 | 10 |
| Cupgrass, Woolly | 10 | 20 | 5 | 15 | — | — | — | — | — | — | — | — | — | — |
| Deadnettle | 50 | 98 | 60 | — | — | — | — | — | — | — | — | — | — | — |
| Foxtail, Giant | 5 | 5 | 0 | 10 | 15 | 25 | 50 | 10 | 40 | 45 | 10 | 10 | 10 | 5 |
| Foxtail, Green | 40 | — | 0 | 30 | — | — | — | — | — | — | — | — | — | — |
| Galium | 70 | 80 | 80 | — | 80 | 50 | 60 | 50 | 70 | 80 | 65 | 85 | 80 | 55 |
| Goosegrass | 5 | 5 | 5 | 10 | — | — | — | — | — | — | — | — | — | — |
| Johnsongrass | 5 | 0 | — | 5 | 5 | 5 | 5 | 5 | 15 | 35 | 5 | 5 | 5 | 5 |
| Kochia | 55 | 98 | 40 | 80 | 98 | 10 | 90 | 90 | 95 | 100 | 90 | 98 | 90 | 85 |
| Lambsquarters | 95 | 98 | 55 | 100 | 80 | 45 | 90 | 70 | 90 | 80 | 60 | 75 | 75 | 55 |
| Morningglory | 60 | 80 | 65 | 80 | 98 | 70 | 80 | 80 | 95 | 85 | 70 | 65 | 75 | 65 |
| Nutsedge, Yellow | 5 | 15 | 5 | 5 | 10 | 0 | 5 | 5 | 5 | 5 | 5 | 5 | 0 | 0 |
| Oat, Wild | 5 | 35 | 0 | 35 | 15 | 0 | 5 | 15 | 40 | 25 | 0 | 5 | 5 | 5 |
| Oilseed Rape | — | — | — | — | 85 | 50 | 40 | 40 | 70 | 50 | 20 | 60 | 70 | 30 |
| Pigweed | 98 | 100 | 98 | 98 | 90 | 55 | 60 | 85 | 95 | 90 | 65 | 95 | 80 | 70 |
| Ragweed | 45 | 55 | 50 | 30 | 65 | 50 | 45 | 40 | 45 | 25 | 40 | 25 | 40 | 35 |
| Ryegrass, Italian | 5 | 10 | 0 | 15 | — | 0 | 5 | 5 | 5 | 10 | 0 | 0 | 5 | 0 |
| Soybean | 90 | 98 | 75 | 85 | 80 | 45 | 90 | 85 | 95 | 85 | 85 | 60 | 80 | 70 |
| Surinam Grass | 35 | 20 | 10 | 15 | — | — | — | — | — | — | — | — | — | — |
| Velvetleaf | 55 | 50 | 70 | — | 40 | 50 | 60 | 35 | 50 | 30 | 20 | 55 | 40 | 30 |
| Waterhemp | — | — | — | — | 80 | 100 | 70 | 80 | 90 | 85 | 60 | 95 | 75 | 60 |
| Wheat | 5 | 5 | 5 | 15 | 5 | 0 | 0 | 5 | 15 | 5 | 0 | 5 | 0 | 0 |
| Windgrass | 40 | 55 | 10 | 40 | — | — | — | — | — | — | — | — | — | — |

| | Compounds | | | | | | | | | | | | |
|---|---|---|---|---|---|---|---|---|---|---|---|---|---|
| 62 g ai/ha | 74 | 79 | 80 | 83 | 84 | 85 | 86 | 88 | 89 | 90 | 92 | 94 | 97 | 98 |
| Postemergence | | | | | | | | | | | | | | |
| Barley | — | — | — | — | — | — | — | — | — | — | — | — | — | — |
| Barnyardgrass | 5 | 5 | 5 | 5 | 0 | 5 | 5 | 5 | 5 | 5 | 5 | 10 | 10 | 10 |
| Bermudagrass | — | — | — | — | — | — | — | — | — | — | — | — | — | — |
| Blackgrass | 0 | 30 | 10 | 5 | 5 | 5 | 5 | 10 | 5 | 5 | 10 | 5 | 10 | 30 |
| Bromegrass, Downy | — | — | — | — | — | — | — | — | — | — | — | — | — | — |
| Canarygrass | — | — | — | — | — | — | — | — | — | — | — | — | — | — |
| Chickweed | 30 | 65 | 65 | 60 | 40 | 50 | 60 | 20 | 50 | 15 | 60 | 60 | 80 | 75 |
| Cocklebur | — | — | — | — | — | — | — | — | — | — | — | — | — | — |
| Corn | 10 | 5 | 5 | 5 | 0 | 10 | 5 | 10 | 5 | 5 | 5 | 35 | 10 | 5 |
| Crabgrass, Large | 5 | 20 | 5 | 10 | 5 | 5 | 5 | 10 | 5 | 10 | 5 | 10 | 15 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 5 | 10 | 5 | 10 | 5 | 10 | 15 | 30 | 5 | 20 | 5 | 10 | 10 | 5 |
| Foxtail, Green | — | — | — | — | — | — | — | — | — | — | — | — | — | — |
| Galium | 55 | 75 | 85 | 70 | 60 | 50 | 80 | 70 | 50 | 65 | 65 | 80 | 85 | 75 |
| Goosegrass | — | — | — | — | — | — | — | — | — | — | — | — | — | — |
| Johnsongrass | 0 | 10 | 5 | 10 | 0 | 5 | 5 | 5 | 5 | 5 | 5 | 5 | 15 | 5 |
| Kochia | 90 | 90 | 95 | 90 | 70 | 80 | 90 | 95 | 60 | 45 | 80 | 90 | 95 | 90 |
| Lambsquarters | 75 | 95 | 55 | 60 | 55 | 75 | 65 | 60 | 65 | 60 | 40 | 75 | 80 | 80 |
| Morningglory | 75 | 95 | 60 | 75 | 85 | 25 | 85 | 85 | 55 | 75 | 90 | 75 | 85 | 65 |
| Nutsedge, Yellow | 0 | 5 | 5 | 5 | — | 5 | 5 | 10 | 20 | 10 | 5 | 45 | 5 | 5 |
| Oat, Wild | 0 | 15 | 5 | 10 | 5 | 5 | 5 | 10 | 5 | 5 | 10 | 0 | 15 | 10 |
| Oilseed Rape | 40 | 50 | 80 | 55 | 45 | 30 | 60 | 55 | 55 | 50 | 60 | 50 | 80 | 95 |
| Pigweed | 60 | 95 | 65 | 75 | 80 | 70 | 65 | 85 | 35 | 45 | 55 | 80 | 85 | 75 |
| Ragweed | 40 | 70 | 40 | 60 | 40 | 20 | 55 | 55 | 60 | 50 | 50 | 55 | 60 | 30 |
| Ryegrass, Italian | 0 | 10 | 20 | 5 | 0 | 0 | 5 | 10 | 5 | 5 | 5 | 0 | 5 | 5 |
| Soybean | 65 | 85 | 75 | 70 | 90 | 65 | 70 | 95 | 90 | 75 | 90 | 85 | 90 | 60 |

TABLE C-continued

| | | | | | | | | | | | | | | |
|---|---|---|---|---|---|---|---|---|---|---|---|---|---|---|
| Surinam Grass | — | — | — | — | — | — | — | — | — | — | — | — | — | — |
| Velvetleaf | 35 | 70 | 65 | 50 | 70 | 45 | 65 | 40 | 25 | 60 | 50 | 65 | 75 | 70 |
| Waterhemp | 60 | 80 | 70 | 70 | 70 | 70 | 60 | 85 | 30 | 65 | 75 | 75 | 90 | 80 |
| Wheat | 0 | 5 | 5 | 0 | 0 | 5 | 0 | 5 | 0 | 0 | 0 | 0 | 5 | 5 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 62 g ai/ha | 111 | 116 | 117 | 120 | 123 | 129 | 132 | 134 | 136 | 138 | 140 | 141 | 145 | 147 |
| | Postemergence | | | | | | | | | | | | | |
| Barley | — | — | — | — | — | — | — | — | — | — | — | — | — | — |
| Barnyardgrass | 5 | 5 | 5 | 10 | 15 | 5 | 5 | 5 | 0 | 5 | 10 | 20 | 0 | 5 |
| Bermudagrass | — | — | — | — | — | — | — | — | — | — | — | — | — | — |
| Blackgrass | 5 | 10 | 5 | 5 | 0 | 5 | 10 | 5 | 5 | 5 | 0 | 35 | 5 | 0 |
| Bromegrass, Downy | — | — | — | — | — | — | — | — | — | — | — | — | — | — |
| Canarygrass | — | — | — | — | — | — | — | — | — | — | — | — | — | — |
| Chickweed | 75 | 55 | 70 | 70 | 50 | 70 | 30 | 55 | 5 | 50 | 45 | 95 | 45 | 75 |
| Cocklebur | — | — | — | — | — | — | — | — | — | — | — | — | — | — |
| Corn | 10 | 5 | 5 | 5 | 5 | 10 | 5 | 10 | 0 | 5 | 10 | 5 | 5 | 5 |
| Crabgrass, Large | 10 | 15 | 20 | 10 | 5 | 5 | 5 | 10 | 5 | 15 | 15 | 10 | 5 | 10 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 35 | 40 | 40 | 10 | 20 | 5 | 5 | 5 | 5 | 10 | 20 | 45 | 25 | 20 |
| Foxtail, Green | — | — | — | — | — | — | — | — | — | — | — | — | — | — |
| Galium | 90 | 80 | 70 | 30 | 85 | 55 | 65 | 85 | 55 | 65 | 90 | 98 | 55 | 90 |
| Goosegrass | — | — | — | — | — | — | — | — | — | — | — | — | — | — |
| Johnsongrass | 5 | 0 | 5 | 5 | 10 | 5 | 5 | 5 | 0 | 5 | 5 | 10 | 0 | 5 |
| Kochia | 90 | 90 | 100 | 95 | 70 | 95 | 85 | 95 | 60 | 95 | 85 | 100 | 85 | 95 |
| Lambsquarters | 80 | 50 | 50 | 70 | 85 | 80 | 60 | 75 | 60 | 60 | 80 | 100 | 85 | 90 |
| Morningglory | 80 | 60 | 90 | 35 | 55 | 80 | 75 | 85 | 50 | 65 | 75 | 95 | 50 | 75 |
| Nutsedge, Yellow | 5 | — | 5 | 10 | 10 | 5 | 0 | 10 | 5 | 5 | 5 | 15 | 5 | 0 |
| Oat, Wild | 5 | 5 | 10 | 5 | 0 | 15 | 5 | 10 | 5 | 5 | 0 | 10 | 0 | 0 |
| Oilseed Rape | 60 | 10 | 60 | 5 | 60 | 60 | 70 | 70 | 5 | 60 | 50 | 95 | 60 | 75 |
| Pigweed | 85 | 90 | 85 | 85 | 85 | 80 | 75 | 85 | 55 | 80 | 90 | 100 | 65 | 75 |
| Ragweed | 70 | 25 | 35 | 25 | 70 | 40 | 10 | 55 | 45 | 40 | 60 | 98 | 35 | 75 |
| Ryegrass, Italian | 0 | 5 | 0 | 0 | 0 | 20 | 5 | 5 | 0 | 0 | 0 | 5 | 0 | 0 |
| Soybean | 80 | 60 | 50 | 30 | 65 | 85 | 35 | 65 | 75 | 65 | 65 | 90 | 35 | 85 |
| Surinam Grass | — | — | — | — | — | — | — | — | — | — | — | — | — | — |
| Velvetleaf | 75 | 60 | 30 | 35 | 80 | 40 | 40 | 50 | 10 | 20 | 45 | 100 | 60 | 85 |
| Waterhemp | 80 | 80 | 85 | 80 | 80 | 65 | 65 | 60 | 35 | 75 | 80 | 100 | 55 | 85 |
| Wheat | 0 | 5 | 5 | 0 | 0 | 0 | 0 | 5 | 5 | 0 | 0 | 5 | 0 | 10 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 62 g ai/ha | 150 | 154 | 155 | 160 | 163 | 164 | 166 | 167 | 172 | 177 | 178 | 180 | 181 | 191 |
| | Postemergence | | | | | | | | | | | | | |
| Barley | — | — | — | — | — | — | — | — | — | — | — | — | — | — |
| Barnyardgrass | 5 | 10 | 5 | 5 | 5 | 5 | 10 | 10 | 5 | 10 | 5 | 5 | 10 | 15 |
| Bermudagrass | — | — | — | — | — | — | — | — | — | — | — | — | — | — |
| Blackgrass | 10 | 0 | 5 | 5 | 5 | 5 | 45 | 5 | 0 | 5 | 20 | 5 | 15 | 5 |
| Bromegrass, Downy | — | — | — | — | — | — | — | — | — | — | — | — | — | — |
| Canarygrass | — | — | — | — | — | — | — | — | — | — | — | — | — | — |
| Chickweed | 65 | 10 | 75 | 80 | 80 | 80 | 90 | 70 | 70 | 55 | 65 | 70 | 80 | 80 |
| Cocklebur | — | — | — | — | — | — | — | — | — | — | — | — | — | — |
| Corn | 10 | 0 | 5 | 5 | 10 | 5 | 10 | 10 | 0 | 10 | 10 | 5 | 5 | 10 |
| Crabgrass, Large | 5 | 10 | 5 | 5 | 10 | 5 | 10 | 5 | 0 | 10 | 5 | 5 | 10 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 20 | 5 | 15 | 5 | 10 | 10 | 10 | 10 | 5 | 10 | 5 | 10 | 25 | 10 |
| Foxtail, Green | — | — | — | — | — | — | — | — | — | — | — | — | — | — |
| Galium | 75 | 80 | 98 | 95 | 85 | 80 | 90 | 70 | 10 | 85 | 85 | 60 | 70 | 98 |
| Goosegrass | — | — | — | — | — | — | — | — | — | — | — | — | — | — |
| Johnsongrass | 5 | 0 | 5 | 0 | 5 | 5 | 5 | 15 | 10 | 5 | 15 | 0 | 5 | 15 |
| Kochia | 55 | 80 | 98 | 98 | 100 | 90 | 90 | 90 | 30 | 90 | 95 | 50 | 100 | 98 |
| Lambsquarters | 35 | 60 | 98 | 70 | 85 | 40 | 95 | 98 | 0 | 75 | 85 | 75 | 100 | 75 |
| Morningglory | 65 | 65 | 80 | 75 | 65 | 55 | 85 | 98 | 10 | 80 | 85 | 75 | 75 | 85 |
| Nutsedge, Yellow | 15 | 10 | 5 | 5 | 5 | 5 | 5 | 5 | 5 | 5 | 5 | 10 | 5 | 5 |
| Oat, Wild | 5 | 0 | 5 | 0 | 10 | 5 | 35 | 35 | 0 | 10 | 10 | 20 | 5 | 5 |
| Oilseed Rape | 45 | 50 | 50 | 60 | 60 | 55 | 95 | 85 | 0 | 90 | 90 | 40 | 60 | 50 |
| Pigweed | 55 | 60 | 98 | 75 | 90 | 75 | 90 | 95 | 5 | 85 | 95 | 60 | 85 | 95 |
| Ragweed | 35 | 100 | 70 | 60 | 35 | 60 | 60 | 30 | 0 | 55 | 30 | 80 | 30 | 30 |
| Ryegrass, Italian | 5 | 0 | 10 | 0 | 0 | 0 | 15 | 5 | 5 | 0 | 0 | 5 | 5 | 5 |
| Soybean | 65 | 65 | 75 | 60 | 80 | 75 | 90 | 60 | 5 | 85 | 65 | 98 | 50 | 60 |
| Surinam Grass | — | — | — | — | — | — | — | — | — | — | — | — | — | — |
| Velvetleaf | 30 | 70 | 70 | 80 | — | 40 | 80 | 40 | 10 | 70 | 85 | 65 | 40 | 75 |

TABLE C-continued

| | | | | | | | | | | | | | | |
|---|---|---|---|---|---|---|---|---|---|---|---|---|---|---|
| Waterhemp | 35 | 65 | 80 | 70 | 85 | 65 | 90 | 85 | 5 | 95 | 90 | 70 | 85 | 95 |
| Wheat | 5 | 0 | 15 | 5 | 0 | 0 | 35 | 5 | 0 | 0 | 0 | 0 | 0 | 0 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 62 g ai/ha | 192 | 194 | 200 | 204 | 220 | 221 | 222 | 223 | 228 | 232 | 236 | 240 | 245 | 253 |

Postemergence

| | | | | | | | | | | | | | | |
|---|---|---|---|---|---|---|---|---|---|---|---|---|---|---|
| Barley | — | — | — | — | — | — | — | — | — | — | — | — | — | — |
| Barnyardgrass | 10 | 5 | 5 | 10 | 10 | 5 | 15 | 5 | 5 | 10 | 5 | 10 | 5 | 10 |
| Bermudagrass | — | — | — | — | — | — | — | — | — | — | — | — | — | — |
| Blackgrass | 5 | 20 | 5 | 5 | 40 | 5 | 60 | 5 | 0 | 5 | 5 | 0 | 5 | 0 |
| Bromegrass, Downy | — | — | — | — | — | — | — | — | — | — | — | — | — | — |
| Canarygrass | — | — | — | — | — | — | — | — | — | — | — | — | — | — |
| Chickweed | 70 | 70 | 75 | 95 | 80 | 60 | 100 | 50 | 50 | 50 | 65 | 55 | 80 | 90 |
| Cocklebur | — | — | — | — | — | — | — | — | — | — | — | — | — | — |
| Corn | 5 | — | 10 | 20 | 10 | 10 | 0 | 5 | 0 | 10 | 5 | 5 | 5 | 5 |
| Crabgrass, Large | 5 | 10 | 5 | 10 | 5 | 5 | 5 | 5 | 5 | 5 | 5 | 5 | 10 | 15 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 5 | 10 | 5 | 5 | 10 | 5 | 5 | 5 | 0 | 5 | 15 | 20 | 20 | 25 |
| Foxtail, Green | — | — | — | — | — | — | — | — | — | — | — | — | — | — |
| Galium | 80 | 65 | 65 | 75 | 80 | 55 | 85 | 80 | 70 | 80 | 80 | 55 | 80 | 80 |
| Goosegrass | — | — | — | — | — | — | — | — | — | — | — | — | — | — |
| Johnsongrass | 5 | 5 | 5 | 5 | 5 | 5 | 10 | 0 | 5 | 5 | 15 | 5 | 10 | 5 |
| *Kochia* | 85 | 90 | 95 | 100 | 95 | 95 | 100 | 80 | 80 | 90 | 85 | 45 | 90 | 100 |
| Lambsquarters | 90 | 80 | 80 | 80 | 55 | 50 | 75 | 75 | 75 | 70 | 75 | 75 | 80 | 80 |
| Morningglory | 35 | 80 | 80 | 65 | 40 | 50 | 70 | 70 | 25 | 55 | 70 | 75 | 65 | 75 |
| Nutsedge, Yellow | 0 | 5 | 5 | 10 | 0 | 5 | 5 | 5 | 5 | 5 | 0 | 0 | 5 | 5 |
| Oat, Wild | 5 | 15 | 15 | 15 | 35 | 10 | 30 | 0 | 0 | 5 | 5 | 0 | 5 | 10 |
| Oilseed Rape | 60 | 40 | 55 | 70 | 85 | 60 | 20 | 80 | 60 | 5 | 30 | 55 | 50 | 10 |
| Pigweed | 80 | 75 | 90 | 95 | 85 | 50 | 85 | 80 | 60 | 60 | 90 | 45 | 75 | 98 |
| Ragweed | 15 | 25 | 40 | 40 | 15 | 20 | 60 | 55 | 55 | 50 | 40 | 55 | 45 | 55 |
| Ryegrass, Italian | 5 | 0 | 10 | 5 | 5 | 5 | 0 | 0 | 0 | 5 | 0 | 0 | 0 | 0 |
| Soybean | 75 | 50 | 95 | 95 | 60 | 65 | 60 | 85 | 60 | 70 | 85 | 60 | 60 | 40 |
| Surinam Grass | — | — | — | — | — | — | — | — | — | — | — | — | — | — |
| Velvetleaf | 65 | 45 | 50 | 40 | 65 | 45 | 50 | 80 | 60 | 30 | 85 | 45 | 35 | 70 |
| Waterhemp | 65 | 80 | 98 | 90 | 75 | 80 | 90 | 85 | 60 | 70 | 90 | 55 | 85 | 80 |
| Wheat | 5 | 0 | 0 | 5 | 0 | 0 | 5 | 0 | 0 | 0 | 0 | 5 | 0 | 0 |
| Windgrass | — | — | — | — | — | — | — | — | — | — | — | — | — | — |

| | Compounds | | | |
|---|---|---|---|---|
| 62 g ai/ha | 258 | 273 | 274 | 284 |

Postemergence

| | | | | |
|---|---|---|---|---|
| Barley | — | — | — | — |
| Barnyardgrass | 10 | 5 | 10 | 10 |
| Bermudagrass | — | — | — | — |
| Blackgrass | 5 | 10 | 15 | 5 |
| Bromegrass, Downy | — | — | — | — |
| Canarygrass | — | — | — | — |
| Chickweed | 90 | 35 | 90 | 100 |
| Cocklebur | — | — | — | — |
| Corn | 10 | 5 | 10 | 10 |
| Crabgrass, Large | 10 | 10 | 30 | 5 |
| Cupgrass, Woolly | — | — | — | — |
| Deadnettle | — | — | — | — |
| Foxtail, Giant | 25 | 10 | 10 | 10 |
| Foxtail, Green | — | — | — | — |
| Galium | 95 | 60 | 90 | 85 |
| Goosegrass | — | — | — | — |
| Johns ongrass | 5 | 5 | 5 | 5 |
| *Kochia* | 100 | 80 | 100 | 100 |
| Lambsquarters | 90 | 85 | 95 | 85 |
| Morningglory | 85 | 65 | 95 | 100 |
| Nutsedge, Yellow | 5 | 5 | 20 | 0 |
| Oat, Wild | 10 | 5 | 35 | 5 |
| Oilseed Rape | 95 | 5 | 85 | 70 |
| Pigweed | 85 | 65 | 90 | 98 |
| Ragweed | 50 | 55 | 40 | 55 |
| Ryegrass, Italian | 0 | 5 | 30 | 5 |
| Soybean | 70 | 90 | 90 | 40 |
| Surinam Grass | — | — | — | — |
| Velvetleaf | 75 | 25 | 65 | 15 |

TABLE C-continued

|  | | | | | | | | | | | | | |
|---|---|---|---|---|---|---|---|---|---|---|---|---|---|
| Waterhemp | | | 80 | | 65 | | | 95 | | | 85 | | |
| Wheat | | | 5 | | 0 | | | 5 | | | 5 | | |
| Windgrass | | | — | | — | | | — | | | — | | |

| Compounds | | | | | | | | | | | | | |
|---|---|---|---|---|---|---|---|---|---|---|---|---|---|
| 31 g ai/ha | 5 | 7 | 10 | 16 | 25 | 47 | 52 | 57 | 58 | 59 | 62 | 65 | 72 | 73 |

Postemergence

| | | | | | | | | | | | | | | |
|---|---|---|---|---|---|---|---|---|---|---|---|---|---|---|
| Barley | 0 | 0 | 0 | 0 | — | — | — | — | — | — | — | — | — | — |
| Barnyardgrass | — | — | — | — | 15 | 0 | 0 | 5 | 5 | 5 | 0 | 5 | 5 | 0 |
| Bermudagrass | 0 | 0 | 0 | 10 | — | — | — | — | — | — | — | — | — | — |
| Blackgrass | 0 | 5 | 5 | 5 | 5 | 0 | 5 | 10 | 10 | 5 | 0 | 10 | 10 | 0 |
| Bromegrass, Downy | 5 | 5 | 5 | 0 | — | — | — | — | — | — | — | — | — | — |
| Canarygrass | 5 | 5 | 5 | 10 | — | — | — | — | — | — | — | — | — | — |
| Chickweed | 5 | 80 | 5 | 40 | 80 | 5 | 40 | 50 | 95 | 40 | 50 | 50 | 50 | 50 |
| Cocklebur | 25 | 35 | 45 | 50 | — | — | — | — | — | — | — | — | — | — |
| Corn | 15 | — | 5 | 5 | 5 | 0 | 5 | 10 | 10 | 10 | 5 | 10 | 5 | 5 |
| Crabgrass, Large | 5 | 5 | 5 | 10 | 15 | 5 | 5 | 5 | 5 | 10 | 5 | 5 | 5 | 5 |
| Cupgrass, Woolly | 0 | 10 | 0 | 5 | — | — | — | — | — | — | — | — | — | — |
| Deadnettle | 50 | 85 | 50 | — | — | — | — | — | — | — | — | — | — | — |
| Foxtail, Giant | 5 | 0 | 0 | 5 | 10 | 10 | 45 | 10 | 15 | 10 | 5 | 10 | 10 | 0 |
| Foxtail, Green | 0 | 0 | 0 | 10 | — | — | — | — | — | — | — | — | — | — |
| Galium | 55 | 65 | 65 | — | 70 | 35 | 60 | 50 | 60 | 65 | 65 | 50 | 75 | 40 |
| Goosegrass | 0 | 0 | 0 | 0 | — | — | — | — | — | — | — | — | — | — |
| Johnsongrass | 5 | 0 | 5 | 0 | 5 | 0 | 5 | 5 | 15 | 15 | 5 | 5 | 0 | 0 |
| Kochia | 20 | 98 | 20 | 35 | 95 | 5 | 75 | 85 | 95 | 95 | 80 | 90 | 90 | 80 |
| Lambsquarters | 80 | 60 | 55 | 75 | 75 | 30 | 85 | 70 | 75 | 70 | 60 | 80 | 75 | 25 |
| Morningglory | 40 | 75 | 40 | 65 | 60 | 20 | 80 | 45 | 80 | 80 | 65 | 30 | 75 | 65 |
| Nutsedge, Yellow | 5 | 10 | 0 | 5 | 0 | 0 | 0 | 5 | 5 | 0 | 0 | 5 | 0 | 0 |
| Oat, Wild | 0 | 5 | 0 | 25 | 0 | 0 | 0 | 10 | 35 | 25 | 0 | 0 | 5 | 5 |
| Oilseed Rape | — | — | — | — | 50 | 15 | 25 | 30 | 60 | 50 | 20 | 25 | 55 | 10 |
| Pigweed | 98 | 100 | 75 | 80 | 90 | 40 | 60 | 65 | 90 | 80 | 50 | 90 | 70 | 45 |
| Ragweed | 15 | 50 | 50 | 15 | 15 | 20 | 40 | 35 | 40 | 10 | 40 | 5 | 40 | 30 |
| Ryegrass, Italian | 0 | 5 | 0 | 10 | — | 0 | 0 | 0 | 5 | 5 | 0 | 0 | 5 | 0 |
| Soybean | 55 | 85 | 50 | 75 | 60 | 35 | 40 | 65 | 95 | 75 | 45 | 40 | — | 40 |
| Surinam Grass | 10 | 15 | 0 | 10 | — | — | — | — | — | — | — | — | — | — |
| Velvetleaf | 45 | 40 | 50 | 60 | 30 | 45 | 50 | 25 | 45 | 15 | 20 | 50 | 40 | 30 |
| Waterhemp | — | — | — | — | 75 | 100 | 70 | 75 | 85 | 85 | 40 | 75 | 75 | 50 |
| Wheat | 0 | 5 | 5 | 5 | 5 | 0 | 0 | 0 | 10 | 5 | 0 | 0 | 0 | 0 |
| Windgrass | 10 | 10 | 10 | 30 | — | — | — | — | — | — | — | — | — | — |

| Compounds | | | | | | | | | | | | | |
|---|---|---|---|---|---|---|---|---|---|---|---|---|---|
| 31 g ai/ha | 74 | 79 | 80 | 83 | 84 | 85 | 86 | 88 | 89 | 90 | 92 | 94 | 97 | 98 |

Postemergence

| | | | | | | | | | | | | | | |
|---|---|---|---|---|---|---|---|---|---|---|---|---|---|---|
| Barley | — | — | — | — | — | — | — | — | — | — | — | — | — | — |
| Barnyardgrass | 0 | 5 | 5 | 5 | 0 | 5 | 5 | 5 | 5 | 5 | 5 | 10 | 10 | 5 |
| Bermudagrass | — | — | — | — | — | — | — | — | — | — | — | — | — | — |
| Blackgrass | 0 | 10 | 5 | 5 | 5 | 0 | 5 | 10 | 0 | 0 | 0 | 5 | 5 | 5 |
| Bromegrass, Downy | — | — | — | — | — | — | — | — | — | — | — | — | — | — |
| Canarygrass | — | — | — | — | — | — | — | — | — | — | — | — | — | — |
| Chickweed | 25 | 50 | 60 | 40 | 10 | 40 | 55 | 15 | 50 | 30 | 60 | 60 | 60 | 50 |
| Cocklebur | — | — | — | — | — | — | — | — | — | — | — | — | — | — |
| Corn | 10 | 5 | 0 | 5 | 0 | 5 | 5 | 10 | 5 | 5 | 5 | 5 | 5 | 10 |
| Crabgrass, Large | 5 | 20 | 5 | 5 | 5 | 10 | 5 | 5 | 5 | 5 | 5 | 5 | 10 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 5 | 10 | 5 | 35 | 5 | 10 | 5 | 35 | 5 | 15 | 5 | 10 | 5 | 5 |
| Foxtail, Green | — | — | — | — | — | — | — | — | — | — | — | — | — | — |
| Galium | 40 | 65 | 70 | 65 | 75 | 50 | 60 | 80 | 40 | 55 | 80 | 70 | 75 | 60 |
| Goosegrass | — | — | — | — | — | — | — | — | — | — | — | — | — | — |
| Johnsongrass | — | 5 | 0 | 0 | 0 | 0 | 5 | 0 | 5 | 5 | 0 | 5 | 5 | 0 |
| Kochia | 80 | 90 | 90 | 70 | 55 | 50 | 60 | 95 | 50 | 70 | 60 | 80 | 90 | 80 |
| Lambsquarters | 40 | 90 | 60 | 80 | 30 | 55 | 45 | 75 | 30 | 75 | 35 | 65 | 75 | 35 |
| Morningglory | 60 | 70 | 10 | 65 | 70 | 60 | 80 | 90 | 70 | 60 | 85 | 75 | 85 | 30 |
| Nutsedge, Yellow | 0 | 5 | 5 | 0 | — | 5 | 0 | 5 | 5 | 5 | 5 | 5 | 5 | 10 |
| Oat, Wild | 0 | 10 | 0 | 0 | 0 | 0 | 0 | 5 | 5 | 0 | 5 | 0 | 10 | 5 |
| Oilseed Rape | 35 | 30 | 70 | 50 | 20 | 5 | 40 | 50 | 25 | 5 | 45 | 50 | 60 | 80 |
| Pigweed | 40 | 75 | 60 | 75 | 50 | 55 | 65 | 85 | 35 | 45 | 60 | 80 | 85 | 75 |
| Ragweed | 40 | 55 | 40 | 40 | 10 | 20 | 50 | 55 | 40 | 40 | 40 | 15 | 40 | 10 |
| Ryegrass, Italian | 0 | 5 | 0 | 0 | 0 | 0 | 5 | 0 | 5 | 5 | 0 | 5 | 0 | 0 |
| Soybean | 40 | 65 | 60 | 60 | 55 | 75 | 60 | 65 | 65 | 65 | 70 | 45 | 60 | 40 |
| Surinam Grass | — | — | — | — | — | — | — | — | — | — | — | — | — | — |
| Velvetleaf | 30 | 55 | 45 | 55 | 45 | 45 | 25 | 35 | 15 | 55 | 45 | 20 | 40 | 50 |

TABLE C-continued

| | | | | | | | | | | | | | | |
|---|---|---|---|---|---|---|---|---|---|---|---|---|---|---|
| Waterhemp | 35 | 75 | 65 | 50 | 50 | 55 | 70 | 75 | 40 | 35 | 45 | 80 | 85 | 50 |
| Wheat | 0 | 0 | 0 | 0 | 0 | 0 | 0 | 5 | 0 | 0 | 0 | 0 | 5 | 0 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 31 g ai/ha | 111 | 115 | 116 | 117 | 120 | 123 | 129 | 132 | 134 | 136 | 138 | 140 | 141 | 145 |

| | Postemergence | | | | | | | | | | | | | |
|---|---|---|---|---|---|---|---|---|---|---|---|---|---|---|
| Barley | — | — | — | — | — | — | — | — | — | — | — | — | — | — |
| Barnyardgrass | 5 | 5 | 5 | 5 | 5 | 15 | 5 | 0 | 5 | 0 | 5 | 10 | 15 | 0 |
| Bermudagrass | — | — | — | — | — | — | — | — | — | — | — | — | — | — |
| Blackgrass | 0 | 5 | 5 | 10 | 5 | 0 | 5 | 5 | 25 | 5 | 5 | 0 | 35 | 0 |
| Bromegrass, Downy | — | — | — | — | — | — | — | — | — | — | — | — | — | — |
| Canarygrass | — | — | — | — | — | — | — | — | — | — | — | — | — | — |
| Chickweed | 60 | 5 | 60 | 75 | 50 | 20 | 60 | 30 | 50 | 5 | 40 | 40 | 90 | 40 |
| Cocklebur | — | — | — | — | — | — | — | — | — | — | — | — | — | — |
| Corn | 5 | 5 | 0 | 5 | 5 | 5 | 5 | 5 | 5 | 0 | 5 | 5 | 5 | 5 |
| Crabgrass, Large | 5 | 5 | 5 | 10 | 10 | 5 | 5 | 5 | 5 | 5 | 15 | 15 | 10 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 20 | 25 | 35 | 20 | 5 | 0 | 5 | 5 | 5 | 5 | 10 | 15 | 35 | 0 |
| Foxtail, Green | — | — | — | — | — | — | — | — | — | — | — | — | — | — |
| Galium | 80 | 50 | 55 | 65 | 30 | 75 | 50 | 60 | 75 | 40 | 60 | 90 | 95 | 50 |
| Goosegrass | — | — | — | — | — | — | — | — | — | — | — | — | — | — |
| Johnsongrass | 5 | 5 | 0 | 5 | 5 | 10 | 5 | 5 | 5 | 0 | 5 | 5 | 5 | 0 |
| *Kochia* | 65 | 5 | 75 | 95 | 80 | 60 | 95 | 45 | 90 | 30 | 95 | 85 | 100 | 45 |
| Lambsquarters | 65 | 25 | 5 | 50 | 65 | 60 | 75 | 50 | 65 | 40 | 30 | 65 | 85 | 55 |
| Morningglory | 85 | 10 | 80 | 40 | 35 | 25 | 80 | 55 | 75 | 25 | 65 | 65 | 85 | 30 |
| Nutsedge, Yellow | 0 | 0 | — | 5 | 5 | 5 | 0 | 0 | 10 | 0 | 0 | 5 | 15 | 0 |
| Oat, Wild | 0 | 5 | 5 | 15 | 5 | 0 | 10 | 0 | 5 | 5 | 5 | 0 | 0 | 0 |
| Oilseed Rape | 60 | 0 | 5 | 30 | 5 | 40 | 15 | 50 | 10 | 0 | 80 | 30 | 55 | 40 |
| Pigweed | 75 | 60 | 85 | 85 | 85 | 80 | 75 | 45 | 80 | 20 | 85 | 85 | 90 | 60 |
| Ragweed | 45 | 10 | 15 | 40 | 15 | 45 | 20 | 0 | 20 | 35 | 35 | 60 | 98 | 35 |
| Ryegrass, Italian | 0 | 5 | 5 | 5 | 0 | 0 | 10 | 0 | 5 | 0 | 0 | 0 | 0 | 0 |
| Soybean | 75 | 5 | 50 | 40 | 55 | 50 | 35 | 35 | 60 | 65 | 75 | 50 | 80 | 25 |
| Surinam Grass | — | — | — | — | — | — | — | — | — | — | — | — | — | — |
| Velvetleaf | 60 | 5 | 40 | 15 | 10 | 70 | 20 | 20 | 35 | 15 | 45 | 25 | 85 | 30 |
| Waterhemp | 65 | 40 | 70 | 65 | 80 | 55 | 65 | 20 | 75 | 30 | 70 | 75 | 85 | 35 |
| Wheat | 0 | 0 | 5 | 0 | 0 | 0 | 0 | 0 | 0 | 5 | 0 | 0 | 0 | 0 |
| Windgrass | — | — | — | — | — | — | — | — | — | — | — | — | — | — |

| | Compounds | | | | | | | | | | | | |
|---|---|---|---|---|---|---|---|---|---|---|---|---|---|
| 31 g ai/ha | 147 | 150 | 152 | 154 | 155 | 160 | 163 | 164 | 166 | 167 | 172 | 177 | 178 | 180 |

| | Postemergence | | | | | | | | | | | | |
|---|---|---|---|---|---|---|---|---|---|---|---|---|---|
| Barley | — | — | — | — | — | — | — | — | — | — | — | — | — | — |
| Barnyardgrass | 5 | 5 | 5 | 5 | 5 | 5 | 5 | 0 | 10 | 5 | 5 | 5 | 5 | 5 |
| Bermudagrass | — | — | — | — | — | — | — | — | — | — | — | — | — | — |
| Blackgrass | 0 | 5 | 0 | 0 | 5 | 0 | 5 | 0 | 10 | 5 | 20 | 5 | 5 | 10 |
| Bromegrass, Downy | — | — | — | — | — | — | — | — | — | — | — | — | — | — |
| Canarygrass | — | — | — | — | — | — | — | — | — | — | — | — | — | — |
| Chickweed | 70 | 65 | 30 | 5 | 80 | 55 | 80 | 50 | 80 | 80 | 50 | 50 | 50 | 60 |
| Cocklebur | — | — | — | — | — | — | — | — | — | — | — | — | — | — |
| Corn | 5 | 10 | 5 | 0 | 5 | 5 | 5 | 5 | 5 | 5 | 0 | 5 | 10 | 5 |
| Crabgrass, Large | 5 | 5 | 5 | 10 | 5 | 5 | 5 | 5 | 5 | 5 | 0 | 5 | 10 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 0 | 20 | 5 | 10 | 5 | 5 | 5 | 20 | 5 | 10 | 0 | 10 | 5 | 5 |
| Foxtail, Green | — | — | — | — | — | — | — | — | — | — | — | — | — | — |
| Galium | 90 | 65 | 55 | 65 | 95 | 80 | 50 | 55 | 85 | 70 | 0 | 50 | 75 | 55 |
| Goosegrass | — | — | — | — | — | — | — | — | — | — | — | — | — | — |
| Johnsongrass | 5 | 0 | 5 | 0 | 0 | 0 | 5 | 0 | 5 | 15 | 10 | 5 | 5 | 0 |
| *Kochia* | 90 | 55 | 40 | 50 | 98 | 90 | 90 | 90 | 90 | 90 | 0 | 70 | 90 | 50 |
| Lambsquarters | 75 | 30 | 80 | 55 | 90 | 65 | 80 | 25 | 80 | 90 | 0 | 65 | 80 | 55 |
| Morningglory | 70 | 60 | 40 | 65 | 80 | 75 | 50 | 35 | 70 | 60 | 20 | 10 | 70 | 65 |
| Nutsedge, Yellow | 0 | 0 | 0 | 10 | 5 | 5 | 5 | 5 | 5 | 0 | 5 | 5 | 5 | 0 |
| Oat, Wild | 0 | 5 | 5 | 0 | 0 | 0 | 5 | 5 | 10 | 25 | 0 | 0 | 0 | 10 |
| Oilseed Rape | 40 | 40 | 60 | 50 | 50 | 55 | 30 | 10 | 90 | 50 | 0 | 80 | 85 | 25 |
| Pigweed | 60 | 55 | 60 | 30 | 75 | 75 | 85 | 75 | 85 | 90 | 10 | 80 | 85 | 55 |
| Ragweed | 65 | 30 | 40 | 45 | 55 | 45 | 35 | 15 | 45 | 10 | 0 | 15 | 55 | 65 |
| Ryegrass, Italian | 0 | 0 | 0 | 0 | 0 | 0 | 0 | 5 | 10 | 0 | 0 | 0 | 0 | 0 |
| Soybean | 65 | 65 | 60 | 65 | 70 | 55 | 50 | 35 | 95 | 30 | 0 | 65 | 70 | 85 |
| Surinam Grass | — | — | — | — | — | — | — | — | — | — | — | — | — | — |
| Velvetleaf | 70 | 25 | 45 | 45 | 75 | 65 | — | 15 | 55 | 40 | 10 | 70 | 70 | 40 |

TABLE C-continued

| | | | | | | | | | | | | | | |
|---|---|---|---|---|---|---|---|---|---|---|---|---|---|---|
| Waterhemp | 55 | 35 | 60 | 60 | 65 | 35 | 75 | 45 | 85 | 75 | 5 | 75 | 90 | 60 |
| Wheat | 5 | 5 | 0 | 0 | 10 | 5 | 0 | 0 | 5 | 0 | 0 | 0 | 0 | 0 |
| Windgrass | — | — | — | — | — | — | — | — | — | — | — | — | — | — |

| | Compounds | | | | | | | | | | | | | |
|---|---|---|---|---|---|---|---|---|---|---|---|---|---|---|
| 31 g ai/ha | 181 | 191 | 192 | 194 | 200 | 204 | 220 | 221 | 222 | 223 | 228 | 232 | 236 | 240 |

| | Postemergence | | | | | | | | | | | | | |
|---|---|---|---|---|---|---|---|---|---|---|---|---|---|---|
| Barley | — | — | — | — | — | — | — | — | — | — | — | — | — | — |
| Barnyardgrass | 5 | 10 | 10 | 5 | 0 | 5 | 10 | 5 | 10 | 0 | 0 | 5 | 5 | 10 |
| Bermudagrass | — | — | — | — | — | — | — | — | — | — | — | — | — | — |
| Blackgrass | 5 | 0 | 0 | 15 | 5 | 5 | 60 | 0 | 30 | 30 | 0 | 0 | 5 | 0 |
| Bromegrass, Downy | — | — | — | — | — | — | — | — | — | — | — | — | — | — |
| Canarygrass | — | — | — | — | — | — | — | — | — | — | — | — | — | — |
| Chickweed | 75 | 80 | 50 | 50 | 55 | 75 | 70 | 60 | 85 | 50 | 30 | 30 | 50 | 5 |
| Cocklebur | — | — | — | — | — | — | — | — | — | — | — | — | — | — |
| Corn | 5 | 5 | 5 | 5 | 5 | 10 | 10 | 5 | 5 | 5 | 0 | 10 | 5 | 5 |
| Crabgrass, Large | 5 | 5 | 10 | 10 | 5 | 5 | 5 | 5 | 5 | 5 | 5 | 5 | 5 | 5 |
| Cupgrass, Woolly | — | — | — | — | — | — | — | — | — | — | — | — | — | — |
| Deadnettle | — | — | — | — | — | — | — | — | — | — | — | — | — | — |
| Foxtail, Giant | 10 | 10 | 5 | 10 | 5 | 5 | 5 | 5 | 5 | 5 | 0 | 5 | 50 | 35 |
| Foxtail, Green | — | — | — | — | — | — | — | — | — | — | — | — | — | — |
| Galium | 65 | 80 | 80 | 60 | 60 | 70 | 70 | 55 | 85 | 80 | 50 | 70 | 75 | 40 |
| Goosegrass | — | — | — | — | — | — | — | — | — | — | — | — | — | — |
| Johnsongrass | 5 | 10 | 10 | — | 5 | 5 | 0 | 5 | 10 | 0 | 0 | 0 | 25 | 5 |
| *Kochia* | 100 | 95 | 45 | 90 | 80 | 90 | 90 | 80 | 100 | 85 | 60 | 85 | 80 | 45 |
| Lambsquarters | 100 | 60 | 25 | 60 | 80 | 85 | 50 | 60 | 65 | 75 | 40 | 60 | 85 | 45 |
| Morningglory | 20 | 85 | 50 | 50 | 85 | 60 | 50 | 40 | 45 | 45 | 10 | 80 | 45 | 65 |
| Nutsedge, Yellow | 0 | 0 | 5 | 5 | 5 | 0 | 0 | 0 | 5 | 5 | 0 | 5 | 0 | 0 |
| Oat, Wild | 5 | 5 | 0 | 5 | 15 | 20 | 25 | 5 | 10 | 0 | 0 | 0 | 0 | 0 |
| Oilseed Rape | 60 | 45 | 5 | 30 | 55 | 40 | 65 | 50 | 10 | 50 | 60 | 50 | 10 | 35 |
| Pigweed | 98 | 85 | 65 | 75 | 75 | 80 | 75 | 75 | 80 | 70 | 50 | 70 | 90 | 30 |
| Ragweed | 35 | 20 | 25 | 15 | 25 | 25 | 10 | 5 | 45 | 20 | 20 | 35 | 15 | 40 |
| Ryegrass, Italian | 0 | 0 | 0 | 0 | 5 | 5 | 0 | 0 | 0 | 0 | 0 | 0 | 0 | 0 |
| Soybean | 50 | 55 | 30 | 30 | 90 | 70 | 65 | 55 | 65 | 65 | 35 | 55 | 75 | 40 |
| Surinam Grass | — | — | — | — | — | — | — | — | — | — | — | — | — | — |
| Velvetleaf | 20 | 65 | 60 | 40 | 20 | 35 | 50 | 35 | 35 | 55 | 55 | 60 | 65 | 25 |
| Waterhemp | 85 | 85 | 50 | 80 | 70 | 85 | 70 | 70 | 90 | 60 | 45 | 65 | 70 | 25 |
| Wheat | 0 | 0 | 0 | 0 | 0 | 5 | 0 | 0 | 0 | 0 | 0 | 0 | 0 | 0 |
| Windgrass | — | — | — | — | — | — | — | — | — | — | — | — | — | — |

| | Compounds | | | | | |
|---|---|---|---|---|---|---|
| 31 g ai/ha | 245 | 253 | 258 | 273 | 274 | 284 |

| | Postemergence | | | | | |
|---|---|---|---|---|---|---|
| Barley | — | — | — | — | — | — |
| Barnyardgrass | 5 | 5 | 10 | 5 | 10 | 10 |
| Bermudagrass | — | — | — | — | — | — |
| Blackgrass | 0 | 0 | 5 | 5 | 5 | 5 |
| Bromegrass, Downy | — | — | — | — | — | — |
| Canarygrass | — | — | — | — | — | — |
| Chickweed | 60 | 70 | 50 | 30 | 70 | 65 |
| Cocklebur | — | — | — | — | — | — |
| Corn | 5 | 5 | 5 | 5 | 10 | 5 |
| Crabgrass, Large | 5 | 5 | 5 | 5 | 5 | 5 |
| Cupgrass, Woolly | — | — | — | — | — | — |
| Deadnettle | — | — | — | — | — | — |
| Foxtail, Giant | 35 | 45 | 20 | 40 | 10 | 10 |
| Foxtail, Green | — | — | — | — | — | — |
| Galium | 60 | 80 | 90 | 60 | 80 | 100 |
| Goosegrass | — | — | — | — | — | — |
| Johnsongrass | 5 | 5 | 5 | 0 | 5 | 5 |
| *Kochia* | 75 | 98 | 95 | 65 | 90 | 100 |
| Lambsquarters | 70 | 80 | 65 | 40 | 95 | 70 |
| Morningglory | 30 | 75 | 85 | 65 | 85 | 70 |
| Nutsedge, Yellow | 5 | 5 | 0 | 5 | 5 | 0 |
| Oat, Wild | 0 | 0 | 5 | 5 | — | 5 |
| Oilseed Rape | 50 | 60 | 85 | 0 | 80 | 70 |
| Pigweed | 55 | 85 | 85 | 80 | 85 | 98 |
| Ragweed | 40 | 45 | 50 | 55 | 60 | 55 |
| Ryegrass, Italian | 0 | 0 | 0 | 5 | 5 | 5 |
| Soybean | 60 | 60 | 75 | 70 | 70 | 35 |
| Surinam Grass | — | — | — | — | — | — |
| Velvetleaf | 10 | 70 | 65 | 10 | 50 | 15 |

TABLE C-continued

| | | | | | | | |
|---|---|---|---|---|---|---|---|
| Waterhemp | 65 | 75 | 70 | 40 | 85 | 85 | |
| Wheat | 0 | 0 | 0 | 0 | 5 | 0 | |
| Windgrass | — | — | — | — | — | — | |

| | Compounds | | | | | | | | | | | | |
|---|---|---|---|---|---|---|---|---|---|---|---|---|---|
| 16 g ai/ha | 65 | 80 | 83 | 84 | 85 | 86 | 88 | 89 | 90 | 92 | 94 | 97 | 98 | 111 |
| | Postemergence | | | | | | | | | | | | |
| Barnyardgrass | 5 | 0 | 5 | 0 | 10 | 0 | 5 | 0 | 5 | 5 | 10 | 10 | 5 | 5 |
| Blackgrass | 0 | 0 | 0 | 5 | 0 | 5 | 5 | 0 | 0 | 0 | 0 | 10 | 0 | 0 |
| Chickweed | 60 | 50 | 35 | 10 | 5 | 40 | 5 | 20 | 5 | 50 | 10 | 70 | 30 | 50 |
| Corn | 5 | 0 | 0 | 0 | 5 | 5 | 5 | 5 | 0 | 5 | 5 | 5 | 5 | 5 |
| Crabgrass, Large | 5 | 0 | 5 | 5 | 10 | 5 | 5 | 5 | 5 | 5 | 5 | 5 | 5 | 5 |
| Foxtail, Giant | 5 | 0 | 35 | 40 | 5 | 5 | 20 | 5 | 35 | 5 | 10 | 10 | 5 | 20 |
| Galium | 100 | 55 | 50 | 60 | 40 | 55 | 70 | 45 | 70 | 70 | 45 | 55 | 50 | 80 |
| Johnsongrass | 5 | 0 | 0 | 0 | 0 | 0 | 0 | 0 | 0 | 0 | 5 | 5 | 0 | 5 |
| *Kochia* | 90 | 60 | 60 | 55 | 50 | 50 | 90 | 45 | 45 | 40 | 30 | 80 | 70 | 60 |
| Lambsquarters | 55 | 50 | 60 | 50 | 35 | 15 | 25 | 30 | 35 | 15 | 70 | 15 | 10 | 70 |
| Morningglory | 45 | 5 | 10 | 55 | 45 | 75 | 30 | 70 | 40 | 70 | 70 | 80 | 50 | 50 |
| Nutsedge, Yellow | 0 | 10 | 0 | — | 0 | 0 | 0 | 0 | 0 | 5 | 5 | 0 | 0 | 0 |
| Oat, Wild | 0 | 0 | 0 | 0 | 0 | 0 | 5 | 0 | 5 | 5 | 0 | 5 | 0 | 0 |
| Oilseed Rape | 10 | 50 | 30 | 10 | 10 | 20 | 50 | 25 | 0 | 40 | 10 | 35 | 75 | 40 |
| Pigweed | 65 | 45 | 70 | 50 | 30 | 65 | 80 | 10 | 25 | 30 | 75 | 70 | 50 | 65 |
| Ragweed | 5 | 5 | 30 | 5 | 40 | 40 | 35 | 35 | 35 | 50 | 5 | 40 | 10 | 40 |
| Ryegrass, Italian | 0 | 10 | 0 | 0 | 0 | 0 | 0 | 0 | 5 | 0 | 0 | 5 | 0 | 0 |
| Soybean | 30 | 55 | 15 | 55 | 30 | 55 | 30 | 55 | 30 | 80 | 50 | 35 | 50 | 60 |
| Velvetleaf | 35 | 20 | 30 | 40 | 40 | 20 | 25 | 10 | 55 | 35 | 25 | 35 | 35 | 40 |
| Waterhemp | 75 | 40 | 65 | 35 | 25 | 35 | 75 | 25 | 35 | 35 | 80 | 80 | 55 | 50 |
| Wheat | 0 | 0 | 0 | 0 | 0 | 0 | 0 | 0 | 0 | 0 | 0 | 5 | 0 | 0 |

| | Compounds | | | | | | | | | | | | |
|---|---|---|---|---|---|---|---|---|---|---|---|---|---|
| 16 g ai/ha | 115 | 116 | 117 | 120 | 123 | 129 | 132 | 134 | 136 | 138 | 140 | 141 | 145 | 147 |
| | Postemergence | | | | | | | | | | | | |
| Barnyardgrass | 0 | 0 | 5 | 5 | 10 | 5 | 0 | 0 | 0 | 5 | 5 | 15 | 0 | 0 |
| Blackgrass | 0 | 0 | 5 | 0 | 0 | 5 | 5 | 5 | 0 | 0 | 0 | 5 | 0 | 0 |
| Chickweed | 5 | 40 | 50 | 40 | 5 | 50 | 10 | 45 | 5 | 5 | 30 | 70 | 15 | 15 |
| Corn | 5 | 0 | 5 | 5 | 0 | 5 | 5 | 5 | 0 | 5 | 0 | 5 | 5 | 5 |
| Crabgrass, Large | 5 | 5 | 10 | 5 | 0 | 5 | 5 | 5 | 5 | 10 | 10 | 5 | 0 | 5 |
| Foxtail, Giant | 5 | 30 | 20 | 5 | 0 | 5 | 0 | 5 | 5 | 5 | 5 | 10 | 0 | 0 |
| Galium | 40 | 55 | 80 | 30 | 40 | 50 | 50 | 65 | 20 | 50 | 50 | 90 | 45 | 85 |
| Johnsongrass | 5 | 0 | 0 | 0 | 10 | 5 | 5 | 5 | 0 | 5 | 0 | 5 | 0 | 5 |
| *Kochia* | 0 | 70 | 90 | 75 | 50 | 90 | 10 | 75 | 5 | 80 | 70 | 100 | 30 | 40 |
| Lambsquarters | 10 | 5 | 45 | 55 | 60 | 35 | 10 | 5 | 20 | 20 | 35 | 85 | 25 | 60 |
| Morningglory | 40 | 50 | 80 | 20 | 5 | 75 | 10 | 70 | 5 | 65 | 0 | 85 | 5 | 70 |
| Nutsedge, Yellow | 0 | — | 5 | 0 | 5 | 0 | 0 | 0 | 0 | 0 | 0 | 10 | 0 | 0 |
| Oat, Wild | 0 | 5 | 10 | 0 | 0 | 0 | 5 | 0 | 5 | 0 | 0 | 0 | 0 | 0 |
| Oilseed Rape | 0 | 5 | 25 | 5 | 30 | 5 | 40 | 5 | 0 | 5 | 5 | 50 | 5 | 25 |
| Pigweed | 50 | 80 | 80 | 40 | 70 | 70 | 25 | 75 | 45 | 60 | 85 | 90 | 35 | 35 |
| Ragweed | 5 | 5 | 25 | 10 | 35 | 15 | 0 | 10 | 25 | 40 | 25 | 80 | 5 | 40 |
| Ryegrass, Italian | 0 | 5 | 0 | 0 | 0 | 0 | 0 | 10 | 0 | 0 | 0 | 0 | 0 | 0 |
| Soybean | 10 | 15 | 35 | 30 | 45 | 35 | 20 | 60 | 35 | 40 | 25 | 85 | 25 | 65 |
| Velvetleaf | 5 | 25 | 10 | 10 | 60 | 15 | 5 | 30 | 10 | 30 | 5 | 80 | 15 | 55 |
| Waterhemp | 30 | 65 | 60 | 75 | 25 | 65 | 45 | 55 | 40 | 60 | 75 | 85 | 15 | 40 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 16 g ai/ha | 150 | 152 | 154 | 155 | 160 | 163 | 164 | 166 | 167 | 172 | 177 | 178 | 180 | 181 |
| | Postemergence | | | | | | | | | | | | |
| Barnyardgrass | 5 | 5 | 5 | 0 | 5 | 5 | 0 | 5 | 5 | 5 | 5 | 5 | — | 5 |
| Blackgrass | 5 | 0 | 0 | 0 | 0 | 0 | 0 | 5 | 0 | 0 | 0 | 0 | 0 | 5 |
| Chickweed | 50 | 10 | 5 | 90 | 50 | 40 | 45 | 60 | 55 | 0 | 50 | 40 | 50 | 55 |
| Corn | 5 | 5 | 0 | 5 | 0 | 5 | 0 | 5 | 5 | 0 | 5 | 5 | 0 | 5 |
| Crabgrass, Large | 5 | 5 | 5 | 5 | 5 | 5 | 5 | 5 | 5 | 0 | 5 | 5 | 5 | 5 |
| Foxtail, Giant | 5 | 5 | 5 | 0 | 0 | 5 | 0 | 5 | 10 | 10 | 5 | 5 | 5 | 10 |
| Galium | 60 | 35 | 60 | 75 | 80 | 70 | 50 | 80 | 70 | 0 | 60 | 80 | 50 | 60 |
| Johnsongrass | 0 | 5 | 0 | 0 | 0 | 5 | 0 | 5 | 5 | 0 | 5 | 0 | 0 | 0 |
| *Kochia* | 50 | 15 | 50 | 80 | 85 | 90 | 80 | 90 | 90 | 0 | 70 | 60 | 40 | 70 |
| Lambsquarters | 10 | 40 | 20 | 65 | 65 | 60 | 15 | 40 | 80 | 0 | 60 | 70 | 35 | 75 |
| Morningglory | 40 | 10 | 55 | 70 | 5 | 20 | 35 | 85 | 80 | 0 | 20 | 10 | 45 | 15 |
| Nutsedge, Yellow | 0 | 0 | 5 | 5 | 5 | 5 | 5 | 0 | 0 | 0 | 0 | 5 | 0 | 0 |
| Oat, Wild | 5 | 0 | 0 | 0 | 0 | 0 | 0 | 5 | 5 | 0 | 5 | 0 | 5 | 0 |
| Oilseed Rape | 5 | 35 | 40 | 60 | 10 | 45 | 10 | 60 | 15 | 0 | 60 | 70 | 15 | 55 |

TABLE C-continued

| | | | | | | | | | | | | | | |
|---|---|---|---|---|---|---|---|---|---|---|---|---|---|---|
| Pigweed | 40 | 50 | 25 | 80 | 80 | 80 | 50 | 80 | 80 | 10 | 75 | 80 | 10 | 85 |
| Ragweed | 30 | 10 | 35 | 50 | 10 | 10 | 20 | 35 | 10 | 0 | 10 | 20 | 35 | 5 |
| Ryegrass, Italian | 0 | 0 | 0 | 0 | 0 | 0 | 0 | 0 | 0 | 0 | 0 | 0 | 0 | 0 |
| Soybean | 65 | 35 | 40 | 5 | 40 | 35 | 40 | 40 | 20 | 0 | 45 | 50 | 85 | 35 |
| Velvetleaf | 20 | 20 | 25 | 45 | 45 | — | — | 45 | 35 | 5 | 50 | 50 | 30 | 25 |
| Waterhemp | 35 | 45 | 5 | 45 | 70 | 75 | 50 | 75 | 65 | 5 | 70 | 80 | 25 | 80 |
| Wheat | 5 | 0 | 0 | 5 | 0 | 0 | 0 | 5 | 0 | 0 | 0 | 0 | 0 | 0 |

| | Compounds | | | | | | | | | | | | | |
|---|---|---|---|---|---|---|---|---|---|---|---|---|---|---|
| 16 g ai/ha | 191 | 192 | 220 | 221 | 222 | 223 | 228 | 232 | 236 | 240 | 245 | 253 | 258 | 273 |
| | Postemergence | | | | | | | | | | | | | |
| Barnyardgrass | 10 | 5 | 5 | 5 | 5 | 0 | 0 | 10 | 5 | 0 | 5 | 5 | 5 | 5 |
| Blackgrass | 0 | 0 | 0 | 0 | 5 | 0 | 0 | 10 | 0 | 0 | 0 | 0 | 0 | 5 |
| Chickweed | 10 | 45 | 65 | 20 | 60 | 35 | 10 | 5 | 40 | 5 | 5 | 60 | 50 | 10 |
| Corn | 5 | 0 | 5 | 0 | 5 | 5 | 0 | 5 | 5 | 0 | 5 | 5 | 5 | 5 |
| Crabgrass, Large | 5 | 5 | 5 | 5 | 5 | 5 | 0 | 5 | 5 | 10 | 5 | 5 | 5 | 5 |
| Foxtail, Giant | 10 | 5 | 0 | 0 | 5 | 5 | 0 | 5 | 5 | 0 | 35 | 10 | 5 | 10 |
| Galium | 80 | 60 | 50 | 60 | 70 | 75 | 50 | 65 | 60 | 35 | 60 | 45 | 85 | 55 |
| Johnsongrass | 30 | 5 | 5 | 5 | 0 | 0 | 5 | 0 | 10 | 10 | 5 | 0 | 0 | 0 |
| *Kochia* | 85 | 30 | 90 | 90 | 85 | 70 | 30 | 85 | 30 | 40 | 45 | 80 | 90 | 70 |
| Lambsquarters | 85 | 10 | 15 | 15 | 65 | 60 | 25 | 55 | 80 | 15 | 50 | 30 | 50 | 25 |
| Morningglory | 40 | 30 | 15 | 45 | 90 | 5 | 5 | 70 | 10 | 30 | 5 | 60 | 65 | 60 |
| Nutsedge, Yellow | 0 | 5 | 10 | 0 | 5 | 5 | 0 | 5 | 0 | 0 | 5 | 5 | 0 | 10 |
| Oat, Wild | 5 | 0 | 5 | 5 | 10 | 0 | 0 | 0 | 0 | 0 | 0 | 0 | 5 | 5 |
| Oilseed Rape | 10 | 10 | 50 | 40 | 5 | 10 | 40 | 5 | 30 | 30 | 40 | 5 | 70 | 0 |
| Pigweed | 95 | 60 | 65 | 60 | 70 | 70 | 25 | 60 | 60 | 15 | 40 | 85 | 75 | 65 |
| Ragweed | 5 | 10 | 10 | 5 | 40 | 10 | 5 | 25 | 10 | 35 | 35 | 20 | 25 | 30 |
| Ryegrass, Italian | 0 | 0 | 0 | 0 | 0 | 0 | 0 | 0 | 0 | 0 | 0 | 0 | 0 | 5 |
| Soybean | 40 | 30 | 40 | 30 | 55 | 60 | 25 | 30 | 60 | 30 | 40 | 40 | 50 | 60 |
| Velvetleaf | 50 | 35 | 30 | 35 | 40 | 30 | 15 | 35 | 55 | 10 | 5 | 30 | 55 | 5 |
| Waterhemp | 80 | 40 | 65 | 65 | 70 | 70 | 15 | 65 | 70 | 10 | 60 | 75 | 65 | 35 |
| Wheat | 0 | 0 | 0 | 0 | 0 | 0 | 0 | 0 | 0 | 0 | 0 | 0 | 0 | 0 |

| 16 g ai/ha | Compound 274 |
|---|---|
| | Postemergence |
| Barnyardgrass | 5 |
| Blackgrass | 5 |
| Chickweed | 70 |
| Corn | 5 |
| Crabgrass, Large | 5 |
| Foxtail, Giant | 5 |
| Galium | 70 |
| Johnsongrass | 5 |
| *Kochia* | 85 |
| Lambsquarters | 85 |
| Morningglory | 85 |
| Nutsedge, Yellow | 10 |
| Oat, Wild | 30 |
| Oilseed Rape | 60 |
| Pigweed | 95 |
| Ragweed | 50 |
| Ryegrass, Italian | 5 |
| Soybean | 45 |
| Velvetleaf | 30 |
| Waterhemp | 70 |
| Wheat | 5 |

| | Compounds | | | |
|---|---|---|---|---|
| 8 g ai/ha | 115 | 152 | 172 | 222 |
| | Postemergence | | | |
| Barnyardgrass | 0 | 0 | 0 | 5 |
| Blackgrass | 0 | 0 | 0 | 0 |
| Chickweed | 5 | 5 | 0 | 10 |
| Corn | 10 | 0 | 0 | 0 |
| Crabgrass, Large | 5 | 5 | 0 | 5 |
| Foxtail, Giant | 5 | 0 | 0 | 0 |
| Galium | 5 | 15 | 0 | 65 |
| Johnsongrass | 5 | 0 | 0 | 0 |
| *Kochia* | 0 | 10 | 0 | 60 |
| Lambsquarters | 10 | 60 | 0 | 50 |
| Morningglory | 0 | 0 | 0 | 40 |

TABLE C-continued

|  | | | | |
|---|---|---|---|---|
| Nutsedge, Yellow | 0 | 0 | 0 | 0 |
| Oat, Wild | 0 | 0 | 0 | 5 |
| Oilseed Rape | 0 | 5 | 0 | 10 |
| Pigweed | 15 | 30 | 5 | 65 |
| Ragweed | 5 | 15 | 0 | 20 |
| Ryegrass, Italian | 0 | 0 | 0 | 0 |
| Soybean | 5 | 30 | 0 | 40 |
| Velvetleaf | 5 | 5 | 5 | 35 |
| Waterhemp | 5 | 15 | 0 | 60 |
| Wheat | 0 | 0 | 0 | 0 |

| | Compounds | |
|---|---|---|
| 4 g ai/ha | 115 | 152 |

Postemergence

| | | |
|---|---|---|
| Barnyardgrass | 0 | 0 |
| Blackgrass | 0 | 0 |
| Chickweed | 0 | 5 |
| Corn | 5 | 0 |
| Crabgrass, Large | 0 | 5 |
| Foxtail, Giant | 5 | 0 |
| Galium | 5 | 5 |
| Johnsongrass | 5 | 0 |
| *Kochia* | 0 | 0 |
| Lambsquarters | 10 | 25 |
| Morningglory | 0 | 0 |
| Nutsedge, Yellow | 0 | 0 |
| Oat, Wild | 0 | 0 |
| Oilseed Rape | 0 | 5 |
| Pigweed | 10 | 10 |
| Ragweed | 5 | 15 |
| Ryegrass, Italian | 0 | 0 |
| Soybean | 5 | 35 |
| Velvetleaf | 5 | 5 |
| Waterhemp | 5 | 20 |
| Wheat | 0 | 0 |

| | Compounds | | | | | | | | | | | | |
|---|---|---|---|---|---|---|---|---|---|---|---|---|---|
| 250 g ai/ha | 7 | 16 | 18 | 25 | 52 | 58 | 59 | 72 | 73 | 79 | 194 | 200 | 204 |

Preemergence

| | 7 | 16 | 18 | 25 | 52 | 58 | 59 | 72 | 73 | 79 | 194 | 200 | 204 |
|---|---|---|---|---|---|---|---|---|---|---|---|---|---|
| Barnyardgrass | — | — | — | 98 | 100 | 100 | 100 | 100 | 100 | 100 | 100 | 100 | 100 |
| Bermudagrass | 100 | 98 | 100 | — | — | — | — | — | — | — | — | — | — |
| Blackgrass | 85 | 90 | 90 | 85 | 90 | 90 | 90 | 95 | 90 | 90 | 90 | 98 | 95 |
| Bromegrass, Downy | 75 | 95 | 95 | — | — | — | — | — | — | — | — | — | — |
| Cocklebur | 5 | 20 | 15 | — | — | — | — | — | — | — | — | — | — |
| Corn | 5 | 35 | 35 | 10 | 70 | 98 | 90 | 65 | 70 | 95 | 25 | 75 | 35 |
| Crabgrass, Large | 100 | 100 | 100 | 100 | 100 | 100 | 100 | 100 | 100 | 100 | 100 | 100 | 100 |
| Cupgrass, Woolly | 98 | 98 | 100 | — | — | — | — | — | — | — | — | — | — |
| Foxtail, Giant | 100 | 100 | 100 | 100 | 100 | 100 | 100 | 100 | 100 | 100 | 100 | 100 | 100 |
| Foxtail, Green | 95 | 90 | 90 | — | — | — | — | — | — | — | — | — | — |
| Galium | 100 | 100 | 100 | 100 | 100 | 100 | 100 | 95 | 95 | 90 | 100 | 100 | 100 |
| Goosegrass | 100 | 100 | 100 | — | — | — | — | — | — | — | — | — | — |
| Johnsongrass | 75 | 100 | 98 | 45 | 100 | 100 | 100 | 100 | 98 | 100 | 95 | 98 | 98 |
| *Kochia* | 100 | 100 | 98 | — | — | — | — | — | — | — | — | — | — |
| Lambsquarters | 95 | 90 | 80 | 100 | 100 | 100 | 100 | 100 | 98 | 100 | 100 | 98 | 98 |
| Morningglory | 40 | 98 | 98 | 30 | 100 | 100 | 100 | 100 | 98 | 100 | 98 | 98 | 98 |
| Nightshade | 98 | 98 | 95 | — | — | — | — | — | — | — | — | — | — |
| Nutsedge, Yellow | 15 | 65 | 35 | 30 | 45 | 95 | 90 | 80 | 15 | 75 | 25 | 95 | 60 |
| Oat, Wild | 80 | 90 | 85 | — | — | — | — | — | — | — | — | — | — |
| Oilseed Rape | — | — | — | 100 | 100 | 100 | 100 | 100 | 100 | 100 | 95 | 100 | 98 | 100 |
| Pigweed | 100 | 100 | 100 | 95 | 100 | 100 | 100 | 100 | 100 | 100 | 100 | 100 | 98 |
| Ragweed | 40 | 60 | 30 | 35 | 100 | 100 | 100 | 95 | 85 | 90 | 75 | 98 | 85 |
| Russian Thistle | — | 90 | 95 | — | — | — | — | — | — | — | — | — | — |
| Ryegrass, Italian | 40 | 90 | 85 | 25 | 90 | 90 | 90 | 80 | 70 | 90 | 90 | 95 | 95 |
| Soybean | 98 | 90 | 85 | 75 | 90 | 98 | 95 | 85 | 90 | 95 | 45 | 100 | 80 |
| Sunflower | 10 | 0 | 40 | — | — | — | — | — | — | — | — | — | — |
| Surinam Grass | 85 | 100 | 100 | — | — | — | — | — | — | — | — | — | — |

TABLE C-continued

| | | | | | | | | | | | | | |
|---|---|---|---|---|---|---|---|---|---|---|---|---|---|
| Velvetleaf | 100 | 100 | 100 | 100 | 100 | 100 | 100 | 100 | 100 | 100 | 100 | 100 | 98 |
| Waterhemp | — | — | — | 95 | 100 | 100 | 100 | 100 | 100 | 100 | 100 | 100 | 98 |
| Wheat | 40 | 60 | 35 | 0 | 45 | 90 | 90 | 35 | 85 | 90 | 35 | 95 | 60 |

| | Compounds | | | | | | | | | | | | |
|---|---|---|---|---|---|---|---|---|---|---|---|---|---|
| 125 g ai/ha | 7 | 16 | 18 | 25 | 52 | 58 | 59 | 72 | 73 | 79 | 83 | 84 | 85 | 86 |

| | Preemergence | | | | | | | | | | | | |
|---|---|---|---|---|---|---|---|---|---|---|---|---|---|
| Barnyardgrass | — | — | — | 35 | 100 | 100 | 100 | 100 | 100 | 100 | 90 | 85 | 95 | 95 |
| Bermudagrass | 100 | 98 | 98 | — | — | — | — | — | — | — | — | — | — | — |
| Blackgrass | 50 | 90 | 90 | 85 | 90 | 90 | 90 | 90 | 90 | 90 | 85 | 85 | 90 | 98 |
| Bromegrass, Downy | 45 | 90 | 50 | — | — | — | — | — | — | — | — | — | — | — |
| Cocklebur | 5 | 5 | — | — | — | — | — | — | — | — | — | — | — | — |
| Corn | 5 | 25 | 10 | 0 | 60 | 98 | 75 | 65 | 5 | 80 | 15 | 5 | 45 | 80 |
| Crabgrass, Large | 100 | 100 | 100 | 100 | 100 | 100 | 100 | 100 | 100 | 100 | 100 | 100 | 100 | 100 |
| Cupgrass, Woolly | 98 | 98 | 98 | — | — | — | — | — | — | — | — | — | — | — |
| Foxtail, Giant | 98 | 100 | 100 | 75 | 100 | 100 | 100 | 100 | 100 | 100 | 100 | 100 | 100 | 100 |
| Foxtail, Green | 90 | 90 | 90 | — | — | — | — | — | — | — | — | — | — | — |
| Galium | 100 | 100 | 100 | 100 | 100 | 100 | 100 | 90 | 90 | 90 | 100 | 100 | 85 | 90 |
| Goosegrass | 95 | 100 | 95 | — | — | — | — | — | — | — | — | — | — | — |
| Johnsongrass | 10 | 100 | 80 | 5 | 90 | 100 | 98 | 100 | 75 | 100 | 85 | 85 | 85 | 95 |
| Kochia | 100 | 85 | 80 | — | — | — | — | — | — | — | — | — | — | — |
| Lambsquarters | 85 | 80 | 65 | 100 | 100 | 100 | 100 | 98 | 100 | 100 | 100 | 100 | 100 | 100 |
| Morningglory | 10 | 90 | 80 | 5 | 100 | 100 | 100 | 100 | 95 | 100 | 10 | 100 | 20 | 100 |
| Nightshade | 95 | 80 | 80 | — | — | — | — | — | — | — | — | — | — | — |
| Nutsedge, Yellow | 15 | 65 | 25 | 0 | 40 | 90 | 85 | 10 | 5 | 65 | 15 | 40 | 20 | 35 |
| Oat, Wild | 50 | 90 | 80 | — | — | — | — | — | — | — | — | — | — | — |
| Oilseed Rape | — | — | — | 100 | 100 | 100 | 100 | 100 | 100 | 95 | 100 | 100 | 98 | 100 |
| Pigweed | 100 | 100 | 100 | 95 | 100 | 100 | 100 | 100 | 100 | 100 | 100 | 100 | 100 | 100 |
| Ragweed | 5 | 55 | 10 | 35 | 95 | 100 | 100 | 85 | 85 | 90 | 45 | 85 | 65 | 100 |
| Russian Thistle | — | 90 | 95 | — | — | — | — | — | — | — | — | — | — | — |
| Ryegrass, Italian | 5 | 80 | 45 | 20 | 80 | 90 | 90 | 40 | 55 | 90 | 50 | 5 | 50 | 35 |
| Soybean | 60 | 90 | 85 | 60 | 90 | 98 | 90 | 80 | 75 | 90 | 75 | 70 | 60 | 85 |
| Sunflower | 10 | 0 | 0 | — | — | — | — | — | — | — | — | — | — | — |
| Surinam Grass | 30 | 100 | 100 | — | — | — | — | — | — | — | — | — | — | — |
| Velvetleaf | 100 | 100 | 100 | 100 | 100 | 100 | 100 | 100 | 100 | 100 | 100 | 100 | 100 | 100 |
| Waterhemp | — | — | — | 95 | 100 | 100 | 100 | 100 | 100 | 100 | 100 | 100 | 100 | 100 |
| Wheat | 10 | 35 | 35 | 0 | 30 | 80 | 85 | 30 | 5 | 85 | 0 | 0 | 5 | 35 |

| | Compounds | | | | | | | | | | | | |
|---|---|---|---|---|---|---|---|---|---|---|---|---|---|
| 125 g ai/ha | 88 | 89 | 90 | 92 | 94 | 97 | 111 | 112 | 116 | 118 | 129 | 132 | 134 | 136 |

| | Preemergence | | | | | | | | | | | | |
|---|---|---|---|---|---|---|---|---|---|---|---|---|---|
| Barnyardgrass | 95 | 100 | 85 | 100 | 100 | 100 | 100 | 90 | 70 | 100 | 90 | 75 | 85 | 100 |
| Bermudagrass | — | — | — | — | — | — | — | — | — | — | — | — | — | — |
| Blackgrass | 90 | 50 | 85 | 90 | 90 | 90 | 90 | 95 | 85 | 95 | 90 | 95 | 98 | 80 |
| Bromegrass, Downy | — | — | — | — | — | — | — | — | — | — | — | — | — | — |
| Cocklebur | — | — | — | — | — | — | — | — | — | — | — | — | — | — |
| Corn | 15 | 5 | 45 | 65 | 55 | 80 | 65 | 20 | 25 | 85 | 30 | 35 | 40 | 15 |
| Crabgrass, Large | 100 | 100 | 100 | 100 | 100 | 100 | 100 | 100 | 100 | 100 | 100 | 100 | 100 | 100 |
| Cupgrass, Woolly | — | — | — | — | — | — | — | — | — | — | — | — | — | — |
| Foxtail, Giant | 100 | 100 | 100 | 100 | 100 | 100 | 100 | 100 | 95 | 100 | 100 | 98 | 100 | 100 |
| Foxtail, Green | — | — | — | — | — | — | — | — | — | — | — | — | — | — |
| Galium | 80 | 100 | 98 | 98 | 100 | 95 | 75 | 95 | 100 | 100 | 100 | 90 | 98 | 85 |
| Goosegrass | — | — | — | — | — | — | — | — | — | — | — | — | — | — |
| Johnsongrass | 85 | 75 | 80 | 85 | 70 | 90 | 80 | 40 | 70 | 100 | 90 | 35 | 85 | 60 |
| Kochia | — | — | — | — | — | — | — | — | — | — | — | — | — | — |
| Lambsquarters | 100 | 100 | 100 | 98 | 100 | 98 | 100 | 98 | 100 | 100 | 100 | 100 | 100 | 100 |
| Morningglory | 90 | 98 | 100 | 98 | 90 | 100 | 100 | 75 | 20 | 100 | 75 | 5 | 40 | 60 |
| Nightshade | — | — | — | — | — | — | — | — | — | — | — | — | — | — |
| Nutsedge, Yellow | 5 | 70 | 60 | 75 | 65 | 90 | 50 | 40 | 40 | 70 | 25 | 15 | 10 | 35 |
| Oat, Wild | — | — | — | — | — | — | — | — | — | — | — | — | — | — |
| Oilseed Rape | 100 | 98 | 100 | 95 | 98 | 90 | 100 | 100 | 100 | 100 | 100 | 100 | 100 | 100 |
| Pigweed | 100 | 100 | 100 | 100 | 100 | 100 | 100 | 100 | 100 | 100 | 100 | 100 | 100 | 100 |
| Ragweed | 60 | 100 | 95 | 85 | 25 | 100 | 100 | 100 | 45 | 100 | 85 | 30 | 50 | 70 |
| Russian Thistle | — | — | — | — | — | — | — | — | — | — | — | — | — | — |
| Ryegrass, Italian | 5 | 50 | 50 | 85 | 50 | 90 | 60 | 30 | 35 | 100 | 35 | 30 | 70 | 15 |
| Soybean | 90 | 98 | 95 | 95 | 95 | 98 | 95 | 95 | 70 | 95 | 80 | 55 | 55 | 85 |
| Sunflower | — | — | — | — | — | — | — | — | — | — | — | — | — | — |
| Surinam Grass | — | — | — | — | — | — | — | — | — | — | — | — | — | — |
| Velvetleaf | 100 | 100 | 100 | 100 | 100 | 100 | 100 | 100 | 100 | 100 | 100 | 100 | 100 | 90 |

TABLE C-continued

| | | | | | | | | | | | | | | |
|---|---|---|---|---|---|---|---|---|---|---|---|---|---|---|
| Waterhemp | 100 | 100 | 100 | 100 | 100 | 100 | 100 | 100 | 100 | 100 | 100 | 100 | 100 | 100 |
| Wheat | 5 | 5 | 0 | 80 | 5 | 90 | 20 | 10 | 5 | 90 | 15 | 0 | 15 | 0 |

| | Compounds | | | | | | | | | | | | | |
|---|---|---|---|---|---|---|---|---|---|---|---|---|---|---|
| 125 g ai/ha | 137 | 138 | 141 | 145 | 147 | 150 | 151 | 154 | 164 | 166 | 167 | 170 | 179 | 180 |

Preemergence

| | | | | | | | | | | | | | | |
|---|---|---|---|---|---|---|---|---|---|---|---|---|---|---|
| Barnyardgrass | 40 | 95 | 100 | 75 | 100 | 80 | 100 | 100 | 100 | 100 | 100 | 100 | 100 | 100 |
| Bermudagrass | — | — | — | — | — | — | — | — | — | — | — | — | — | — |
| Blackgrass | 10 | 90 | 95 | 95 | 90 | 50 | 90 | 90 | 90 | 100 | 90 | 90 | 90 | 90 |
| Bromegrass, Downy | — | — | — | — | — | — | — | — | — | — | — | — | — | — |
| Cocklebur | — | — | — | — | — | — | — | — | — | — | — | — | — | — |
| Corn | 10 | 25 | 90 | 5 | 35 | 45 | 70 | 10 | 45 | 80 | 60 | 40 | 15 | 65 |
| Crabgrass, Large | 100 | 100 | 100 | 100 | 100 | 100 | 100 | 100 | 100 | 100 | 100 | 100 | 100 | 100 |
| Cupgrass, Woolly | — | — | — | — | — | — | — | — | — | — | — | — | — | — |
| Foxtail, Giant | 90 | 100 | 100 | 100 | 100 | 100 | 100 | 100 | 100 | 100 | 100 | 100 | 100 | 100 |
| Foxtail, Green | — | — | — | — | — | — | — | — | — | — | — | — | — | — |
| Galium | 95 | 100 | 100 | 98 | 98 | 100 | — | 95 | 95 | 95 | 100 | 100 | 100 | 100 |
| Goosegrass | — | — | — | — | — | — | — | — | — | — | — | — | — | — |
| Johnsongrass | 45 | 65 | 100 | 65 | 90 | 80 | 65 | 85 | 80 | 95 | 95 | 85 | 98 | 98 |
| *Kochia* | — | — | — | — | — | — | — | — | — | — | — | — | — | — |
| Lambsquarters | 100 | 100 | 100 | 100 | 100 | 100 | 100 | 100 | 98 | 98 | 100 | 100 | 100 | 100 |
| Morningglory | 90 | 35 | 100 | 35 | 100 | 75 | 25 | 85 | 100 | 100 | 100 | 100 | 90 | 100 |
| Nightshade | — | — | — | — | — | — | — | — | — | — | — | — | — | — |
| Nutsedge, Yellow | 10 | 55 | 95 | 10 | 55 | 40 | 25 | 65 | 25 | 80 | 60 | 55 | 15 | 85 |
| Oat, Wild | — | — | — | — | — | — | — | — | — | — | — | — | — | — |
| Oilseed Rape | 95 | 100 | 100 | 100 | 100 | 100 | 100 | 100 | 100 | 100 | 98 | 95 | 100 | 100 |
| Pigweed | 100 | 100 | 100 | 100 | 100 | 100 | 100 | 98 | 100 | 100 | 100 | 100 | 100 | 100 |
| Ragweed | 95 | 10 | 100 | 70 | 100 | 55 | 100 | 90 | 85 | 95 | 20 | 65 | 10 | 98 |
| Russian Thistle | — | — | — | — | — | — | — | — | — | — | — | — | — | — |
| Ryegrass, Italian | 0 | 60 | 100 | 75 | 70 | 50 | 45 | 25 | 98 | 90 | 90 | 90 | 70 | 80 |
| Soybean | 85 | 90 | 98 | 95 | 95 | 90 | 95 | 95 | 95 | 95 | 90 | 55 | 65 | 98 |
| Sunflower | — | — | — | — | — | — | — | — | — | — | — | — | — | — |
| Surinam Grass | — | — | — | — | — | — | — | — | — | — | — | — | — | — |
| Velvetleaf | 85 | 100 | 100 | 100 | 100 | 70 | 100 | 100 | 100 | 100 | 100 | 100 | 100 | 100 |
| Waterhemp | 100 | 100 | 100 | 100 | 100 | 98 | 100 | 100 | 100 | 100 | 100 | 100 | 100 | 100 |
| Wheat | 0 | 5 | 60 | 0 | 25 | 5 | 40 | 5 | 35 | 90 | 50 | 60 | 5 | 50 |

| | Compounds | | | | | | | | | | | | | |
|---|---|---|---|---|---|---|---|---|---|---|---|---|---|---|
| 125 g ai/ha | 187 | 194 | 200 | 204 | 236 | 240 | 250 | 252 | 253 | 258 | 270 | 273 | 274 | 292 |

Preemergence

| | | | | | | | | | | | | | | |
|---|---|---|---|---|---|---|---|---|---|---|---|---|---|---|
| Barnyardgrass | 90 | 100 | 100 | 100 | 100 | 100 | 100 | 100 | 100 | 100 | 100 | 85 | 100 | 100 |
| Bermudagrass | — | — | — | — | — | — | — | — | — | — | — | — | — | — |
| Blackgrass | 100 | 90 | 98 | 90 | 90 | 95 | 90 | 95 | 90 | 90 | 95 | 70 | 90 | 90 |
| Bromegrass, Downy | — | — | — | — | — | — | — | — | — | — | — | — | — | — |
| Cocklebur | — | — | — | — | — | — | — | — | — | — | — | — | — | — |
| Corn | 5 | 15 | 60 | 5 | 90 | 35 | 10 | 70 | 90 | 65 | 55 | 35 | 80 | 45 |
| Crabgrass, Large | 100 | 100 | 100 | 100 | 100 | 100 | 100 | 100 | 100 | 100 | 100 | 100 | 100 | 100 |
| Cupgrass, Woolly | — | — | — | — | — | — | — | — | — | — | — | — | — | — |
| Foxtail, Giant | 85 | 100 | 100 | 100 | 100 | 100 | 100 | 100 | 100 | 100 | 100 | 90 | 100 | 100 |
| Foxtail, Green | — | — | — | — | — | — | — | — | — | — | — | — | — | — |
| Galium | 98 | 90 | 100 | 100 | 100 | 100 | 98 | 98 | 95 | 100 | 100 | 98 | 98 | 100 |
| Goosegrass | — | — | — | — | — | — | — | — | — | — | — | — | — | — |
| Johnsongrass | 45 | 80 | 98 | 95 | 85 | 45 | 70 | 100 | 100 | 90 | 95 | 80 | 98 | 85 |
| *Kochia* | — | — | — | — | — | — | — | — | — | — | — | — | — | — |
| Lambsquarters | 100 | 100 | 98 | 95 | 100 | 100 | 100 | 100 | 100 | 98 | 100 | 100 | 98 | 100 |
| Morningglory | 5 | 95 | 98 | 98 | 98 | 75 | 50 | 100 | 100 | 98 | 100 | 85 | 100 | 70 |
| Nightshade | — | — | — | — | — | — | — | — | — | — | — | — | — | — |
| Nutsedge, Yellow | 5 | 0 | 90 | 60 | 75 | 40 | 5 | 60 | 65 | 100 | 45 | 35 | 95 | 35 |
| Oat, Wild | — | — | — | — | — | — | — | — | — | — | — | — | — | — |
| Oilseed Rape | 90 | 90 | 98 | 98 | 100 | 100 | 100 | 100 | 100 | 100 | 100 | 100 | 95 | 98 |
| Pigweed | 100 | 100 | 100 | 98 | 100 | 65 | 100 | 100 | 100 | 100 | 100 | 100 | 100 | 100 |
| Ragweed | 55 | 20 | 100 | 5 | 90 | 80 | 75 | 100 | 100 | 90 | 70 | 85 | 75 | 70 |
| Russian Thistle | — | — | — | — | — | — | — | — | — | — | — | — | — | — |
| Ryegrass, Italian | 5 | 70 | 85 | 75 | 85 | 50 | 15 | 90 | 80 | 70 | 50 | 60 | 90 | 85 |
| Soybean | 85 | 25 | 95 | 65 | 95 | 98 | 90 | 98 | 98 | 95 | 85 | 65 | 98 | 90 |
| Sunflower | — | — | — | — | — | — | — | — | — | — | — | — | — | — |
| Surinam Grass | — | — | — | — | — | — | — | — | — | — | — | — | — | — |
| Velvetleaf | 100 | 100 | 100 | 98 | 100 | 85 | 100 | 100 | 100 | 100 | 100 | 85 | 100 | 100 |

TABLE C-continued

| | | | | | | | | | | | | | | |
|---|---|---|---|---|---|---|---|---|---|---|---|---|---|---|
| Waterhemp | 95 | 100 | 100 | 100 | 100 | 100 | 100 | 100 | 100 | 100 | 100 | 100 | 100 | 100 |
| Wheat | 0 | 0 | 90 | 30 | 60 | 5 | 0 | 45 | 60 | 25 | 5 | 5 | 90 | 15 |

| | Compounds | | | | | | | | | | | | | |
|---|---|---|---|---|---|---|---|---|---|---|---|---|---|---|
| 62 g ai/ha | 7 | 16 | 18 | 25 | 52 | 58 | 59 | 72 | 73 | 79 | 83 | 84 | 85 | 86 |
| | Preemergence | | | | | | | | | | | | | |
| Barnyardgrass | — | — | — | 10 | 95 | 100 | 100 | 100 | 80 | 100 | 45 | 40 | 75 | 40 |
| Bermudagrass | 100 | 98 | 98 | — | — | — | — | — | — | — | — | — | — | — |
| Blackgrass | 10 | 90 | 80 | 5 | 85 | 90 | 85 | 90 | 80 | 90 | 90 | 40 | 10 | 90 |
| Bromegrass, Downy | 5 | 60 | 10 | — | — | — | — | — | — | — | — | — | — | — |
| Cocklebur | 5 | 5 | 0 | — | — | — | — | — | — | — | — | — | — | — |
| Corn | 5 | 15 | 10 | 0 | 5 | 90 | 55 | 25 | 0 | — | 0 | 0 | 5 | 30 |
| Crabgrass, Large | 98 | 100 | 100 | 85 | 100 | 100 | 100 | 100 | 100 | 100 | 100 | 100 | 100 | 100 |
| Cupgrass, Woolly | 55 | 90 | 55 | — | — | — | — | — | — | — | — | — | — | — |
| Foxtail, Giant | 80 | 98 | 100 | 60 | 100 | 100 | 98 | 100 | 100 | 100 | 100 | 98 | 90 | 100 |
| Foxtail, Green | 90 | 90 | 90 | — | — | — | — | — | — | — | — | — | — | — |
| Galium | 100 | 100 | 95 | 90 | 100 | 100 | 100 | 90 | 90 | 90 | 85 | 100 | 50 | 98 |
| Goosegrass | 85 | 98 | 85 | — | — | — | — | — | — | — | — | — | — | — |
| Johnsongrass | 5 | 85 | 30 | 0 | 25 | 100 | 85 | 55 | 35 | 90 | 50 | 40 | 55 | 60 |
| *Kochia* | 95 | 80 | 60 | — | — | — | — | — | — | — | — | — | — | — |
| Lambsquarters | 80 | 80 | 50 | 100 | 100 | 100 | 100 | 100 | 98 | 100 | 100 | 100 | 100 | 100 |
| Morningglory | 0 | 75 | 30 | 5 | 95 | 100 | 100 | 85 | 45 | 100 | 0 | 25 | 0 | 60 |
| Nightshade | 95 | 65 | 30 | — | — | — | — | — | — | — | — | — | — | — |
| Nutsedge, Yellow | 0 | 25 | 15 | 0 | 10 | 85 | 65 | 0 | 0 | 15 | 0 | 5 | 5 | 5 |
| Oat, Wild | 5 | 90 | 50 | — | — | — | — | — | — | — | — | — | — | — |
| Oilseed Rape | — | — | — | 98 | 100 | 100 | 100 | 100 | 95 | 95 | 98 | 100 | 90 | 100 |
| Pigweed | 100 | 100 | 100 | 95 | 100 | 100 | 100 | 100 | 100 | 100 | 100 | 100 | 100 | 100 |
| Ragweed | 0 | 25 | 0 | 20 | 90 | 100 | 95 | 75 | 75 | 90 | 40 | 60 | 50 | 100 |
| Russian Thistle | — | 80 | 0 | — | — | — | — | — | — | — | — | — | — | — |
| Ryegrass, Italian | 0 | 30 | 5 | 5 | 55 | 90 | 85 | 10 | 5 | 90 | 30 | 5 | 0 | 30 |
| Soybean | 40 | 90 | 65 | 20 | 85 | 95 | 90 | 55 | 60 | 75 | 60 | 60 | 40 | 75 |
| Sunflower | 10 | 0 | 0 | — | — | — | — | — | — | — | — | — | — | — |
| Surinam Grass | 5 | 100 | 30 | — | — | — | — | — | — | — | — | — | — | — |
| Velvetleaf | 100 | 100 | 100 | 85 | 100 | 100 | 100 | 95 | 75 | 100 | 100 | 85 | 100 | 100 |
| Waterhemp | — | — | — | 95 | 100 | 100 | 100 | 100 | 100 | 100 | 100 | 100 | 100 | 100 |
| Wheat | 5 | 0 | 5 | 0 | 0 | 80 | 50 | 0 | 0 | 35 | 0 | 0 | 0 | 0 |

| | Compounds | | | | | | | | | | | | | |
|---|---|---|---|---|---|---|---|---|---|---|---|---|---|---|
| 62 g ai/ha | 88 | 89 | 90 | 92 | 94 | 97 | 111 | 112 | 116 | 118 | 129 | 132 | 134 | 135 |
| | Preemergence | | | | | | | | | | | | | |
| Barnyardgrass | 35 | 70 | 75 | 100 | 85 | 100 | 90 | 30 | 45 | 100 | 40 | 10 | 60 | 60 |
| Bermudagrass | — | — | — | — | — | — | — | — | — | — | — | — | — | — |
| Blackgrass | 60 | 5 | 30 | 70 | 90 | 90 | 40 | 40 | 60 | 90 | 5 | 40 | 85 | 20 |
| Bromegrass, Downy | — | — | — | — | — | — | — | — | — | — | — | — | — | — |
| Cocklebur | — | — | — | — | — | — | — | — | — | — | — | — | — | — |
| Corn | 5 | 0 | 10 | 5 | 5 | 45 | 5 | 5 | 5 | 70 | 5 | 20 | 40 | 30 |
| Crabgrass, Large | 100 | 100 | 98 | 100 | 100 | 100 | 100 | 100 | 100 | 85 | 100 | 98 | 98 | 100 |
| Cupgrass, Woolly | — | — | — | — | — | — | — | — | — | — | — | — | — | — |
| Foxtail, Giant | 98 | 100 | 75 | 100 | 100 | 100 | 100 | 100 | 85 | 95 | 100 | 70 | 100 | 70 |
| Foxtail, Green | — | — | — | — | — | — | — | — | — | — | — | — | — | — |
| Galium | 90 | 85 | 100 | 95 | 98 | 98 | 100 | 100 | 100 | 100 | 95 | 90 | 90 | 90 |
| Goosegrass | — | — | — | — | — | — | — | — | — | — | — | — | — | — |
| Johnsongrass | 40 | 20 | 20 | 70 | 35 | 90 | 25 | 20 | 55 | 85 | 40 | 0 | 45 | 45 |
| *Kochia* | — | — | — | — | — | — | — | — | — | — | — | — | — | — |
| Lambsquarters | 100 | 95 | 100 | 100 | 100 | 100 | 100 | 100 | 85 | 100 | 100 | 100 | 100 | 85 |
| Morningglory | 40 | 95 | 55 | 98 | 40 | 100 | 85 | 65 | 20 | 100 | 45 | 5 | 35 | 80 |
| Nightshade | — | — | — | — | — | — | — | — | — | — | — | — | — | — |
| Nutsedge, Yellow | 5 | 10 | 5 | 50 | 55 | 60 | 15 | 15 | 10 | 25 | 5 | 15 | 0 | 15 |
| Oat, Wild | — | — | — | — | — | — | — | — | — | — | — | — | — | — |
| Oilseed Rape | 70 | 95 | 98 | 85 | 98 | 98 | 98 | 95 | 98 | 100 | 100 | 100 | 100 | 95 |
| Pigweed | 100 | 100 | 98 | 100 | 100 | 100 | 100 | 100 | 100 | 100 | 100 | 70 | 100 | 98 |
| Ragweed | 5 | 75 | 100 | 50 | 10 | 85 | 100 | 35 | 45 | 100 | 60 | 40 | 55 | 65 |
| Russian Thistle | — | — | — | — | — | — | — | — | — | — | — | — | — | — |
| Ryegrass, Italian | 0 | 45 | 0 | 50 | 10 | 85 | 40 | 5 | 10 | 70 | 10 | 5 | 15 | 10 |
| Soybean | 40 | 90 | 65 | 80 | 85 | 95 | 80 | 50 | 40 | 90 | 40 | 5 | 20 | 85 |
| Sunflower | — | — | — | — | — | — | — | — | — | — | — | — | — | — |
| Surinam Grass | — | — | — | — | — | — | — | — | — | — | — | — | — | — |
| Velvetleaf | 100 | 100 | 98 | 100 | 100 | 100 | 90 | 100 | 100 | 100 | 100 | 100 | 85 | 85 |

TABLE C-continued

| | | | | | | | | | | | | | | |
|---|---|---|---|---|---|---|---|---|---|---|---|---|---|---|
| Waterhemp | 100 | 100 | 100 | 100 | 100 | 100 | 100 | 100 | 100 | 100 | 100 | 100 | 100 | 100 |
| Wheat | 0 | 0 | 0 | 30 | 0 | 60 | 0 | 0 | 0 | 10 | 0 | 0 | 0 | 0 |

| | Compounds | | | | | | | | | | | | | |
|---|---|---|---|---|---|---|---|---|---|---|---|---|---|---|
| 62 g ai/ha | 136 | 137 | 138 | 141 | 145 | 147 | 150 | 151 | 154 | 164 | 166 | 167 | 170 | 179 |

| | Preemergence | | | | | | | | | | | | | |
|---|---|---|---|---|---|---|---|---|---|---|---|---|---|---|
| Barnyardgrass | 60 | 10 | 65 | 100 | 50 | 90 | 65 | 70 | 70 | 98 | 100 | 100 | 100 | 90 |
| Bermudagrass | — | — | — | — | — | — | — | — | — | — | — | — | — | — |
| Blackgrass | 75 | 5 | 80 | 95 | 85 | 50 | 50 | 10 | 20 | 90 | 90 | 90 | 90 | 40 |
| Bromegrass, Downy | — | — | — | — | — | — | — | — | — | — | — | — | — | — |
| Cocklebur | — | — | — | — | — | — | — | — | — | — | — | — | — | — |
| Corn | 5 | 5 | 0 | 80 | 0 | 20 | 25 | 15 | 5 | 5 | 40 | 25 | 15 | 5 |
| Crabgrass, Large | 100 | 98 | 100 | 100 | 100 | 100 | 100 | 98 | 100 | 100 | 100 | 100 | 100 | 98 |
| Cupgrass, Woolly | — | — | — | — | — | — | — | — | — | — | — | — | — | — |
| Foxtail, Giant | 80 | 60 | 100 | 100 | 75 | 100 | 100 | 80 | 85 | 100 | 100 | 100 | 98 | 100 |
| Foxtail, Green | — | — | — | — | — | — | — | — | — | — | — | — | — | — |
| Galium | 30 | 10 | 90 | 100 | 90 | 98 | 90 | — | 95 | 95 | 95 | 100 | 100 | 98 |
| Goosegrass | — | — | — | — | — | — | — | — | — | — | — | — | — | — |
| Johnsongrass | 20 | 5 | 40 | 100 | 25 | 80 | 70 | 50 | 40 | 75 | 85 | 80 | 70 | 65 |
| *Kochia* | — | — | — | — | — | — | — | — | — | — | — | — | — | — |
| Lambsquarters | 80 | 100 | 100 | 100 | 100 | 100 | 80 | 100 | 90 | 100 | 98 | 100 | 100 | 100 |
| Morningglory | 10 | 45 | 10 | 100 | 0 | 95 | 45 | 10 | 50 | 85 | 98 | 50 | 40 | 35 |
| Nightshade | — | — | — | — | — | — | — | — | — | — | — | — | — | — |
| Nutsedge, Yellow | 10 | 5 | 25 | 70 | 0 | 15 | 25 | 5 | 5 | 20 | 35 | 10 | 15 | 10 |
| Oat, Wild | — | — | — | — | — | — | — | — | — | — | — | — | — | — |
| Oilseed Rape | 50 | 85 | 100 | 100 | 100 | 100 | 90 | 100 | 100 | 100 | 100 | 90 | 98 | 98 |
| Pigweed | 40 | 90 | 100 | 100 | 100 | 100 | 100 | 100 | 100 | 100 | 100 | 100 | 100 | 100 |
| Ragweed | 20 | 80 | 5 | 100 | 100 | 98 | 25 | 85 | 95 | 75 | 95 | 15 | 55 | 0 |
| Russian Thistle | — | — | — | — | — | — | — | — | — | — | — | — | — | — |
| Ryegrass, Italian | 0 | 0 | 20 | 75 | 40 | 50 | 30 | 35 | 20 | 65 | 90 | 80 | 75 | 30 |
| Soybean | 50 | 80 | 90 | 90 | 90 | 95 | 45 | 85 | 80 | 65 | 95 | 90 | 45 | 45 |
| Sunflower | — | — | — | — | — | — | — | — | — | — | — | — | — | — |
| Surinam Grass | — | — | — | — | — | — | — | — | — | — | — | — | — | — |
| Velvetleaf | 30 | 65 | 98 | 100 | 100 | 100 | 60 | 100 | 100 | 100 | 100 | 100 | 80 | 98 |
| Waterhemp | 75 | 95 | 100 | 100 | 100 | 100 | 98 | 100 | 100 | 100 | 100 | 100 | 100 | 98 |
| Wheat | 0 | 0 | 5 | 40 | 0 | 0 | 5 | 0 | 0 | 30 | 60 | 5 | 20 | 0 |

| | Compounds | | | | | | | | | | | | | |
|---|---|---|---|---|---|---|---|---|---|---|---|---|---|---|
| 62 g ai/ha | 180 | 187 | 194 | 200 | 204 | 236 | 240 | 250 | 252 | 253 | 258 | 270 | 273 | 274 |

| | Preemergence | | | | | | | | | | | | | |
|---|---|---|---|---|---|---|---|---|---|---|---|---|---|---|
| Barnyardgrass | 100 | 65 | 85 | 100 | 95 | 98 | 60 | 50 | 100 | 100 | 90 | 90 | 25 | 100 |
| Bermudagrass | — | — | — | — | — | — | — | — | — | — | — | — | — | — |
| Blackgrass | 90 | 30 | 50 | 95 | 80 | 90 | 95 | 70 | 90 | 90 | 90 | 70 | 5 | 90 |
| Bromegrass, Downy | — | — | — | — | — | — | — | — | — | — | — | — | — | — |
| Cocklebur | — | — | — | — | — | — | — | — | — | — | — | — | — | — |
| Corn | 30 | 5 | 0 | 5 | 0 | 10 | 5 | 0 | 40 | 35 | 45 | 20 | 45 | 85 |
| Crabgrass, Large | 100 | 100 | 98 | 100 | 100 | 100 | 100 | 98 | 100 | 100 | 100 | 100 | 95 | 100 |
| Cupgrass, Woolly | — | — | — | — | — | — | — | — | — | — | — | — | — | — |
| Foxtail, Giant | 100 | 85 | 90 | 100 | 98 | 100 | 100 | 100 | 100 | 98 | 100 | 100 | 75 | 100 |
| Foxtail, Green | — | — | — | — | — | — | — | — | — | — | — | — | — | — |
| Galium | 100 | 90 | 90 | 100 | 100 | 100 | 100 | 70 | 90 | 100 | 100 | 95 | 95 | 98 |
| Goosegrass | — | — | — | — | — | — | — | — | — | — | — | — | — | — |
| Johnsongrass | 75 | 30 | 25 | 98 | 80 | 60 | 10 | 35 | 80 | 60 | 75 | 40 | 55 | 95 |
| *Kochia* | — | — | — | — | — | — | — | — | — | — | — | — | — | — |
| Lambsquarters | 100 | 98 | 100 | 98 | 98 | 100 | 100 | 100 | 100 | 100 | 98 | 100 | 100 | 100 |
| Morningglory | 100 | 0 | 0 | 95 | 98 | 55 | 75 | 50 | 95 | 98 | 45 | 55 | 55 | 100 |
| Nightshade | — | — | — | — | — | — | — | — | — | — | — | — | — | — |
| Nutsedge, Yellow | 65 | 5 | 0 | 40 | 0 | 60 | 15 | — | 40 | 20 | 95 | 15 | 5 | 85 |
| Oat, Wild | — | — | — | — | — | — | — | — | — | — | — | — | — | — |
| Oilseed Rape | 100 | 90 | 30 | 98 | 95 | 100 | 100 | 100 | 100 | 100 | 100 | 100 | 80 | 95 |
| Pigweed | 100 | 90 | 100 | 100 | 100 | 100 | 55 | 100 | 100 | 100 | 100 | 100 | 100 | 100 |
| Ragweed | 80 | 45 | 10 | 100 | 5 | 85 | 100 | 40 | 98 | 85 | 80 | 45 | 55 | 35 |
| Russian Thistle | — | — | — | — | — | — | — | — | — | — | — | — | — | — |
| Ryegrass, Italian | 50 | 0 | 20 | 70 | 35 | 45 | 0 | 5 | 60 | 35 | 25 | 10 | 0 | 90 |
| Soybean | 98 | 55 | 20 | 90 | 35 | 90 | 85 | 65 | 95 | 95 | 75 | 25 | 40 | 95 |
| Sunflower | — | — | — | — | — | — | — | — | — | — | — | — | — | — |
| Surinam Grass | — | — | — | — | — | — | — | — | — | — | — | — | — | — |
| Velvetleaf | 100 | 95 | 75 | 100 | 85 | 100 | 80 | 100 | 100 | 100 | 100 | 98 | 85 | 100 |

TABLE C-continued

| | | | | | | | | | | | | | | |
|---|---|---|---|---|---|---|---|---|---|---|---|---|---|---|
| Waterhemp | 100 | 85 | 100 | 100 | 100 | 98 | 100 | 100 | 100 | 100 | 98 | 100 | 98 | 100 |
| Wheat | 5 | 0 | 0 | 65 | 5 | 0 | 0 | 0 | 0 | 0 | 5 | 0 | 0 | 90 |

| 62 g ai/ha | Compound 292 |
|---|---|
| Preemergence | |
| Barnyardgrass | 85 |
| Bermudagrass | — |
| Blackgrass | 90 |
| Bromegrass, Downy | — |
| Cocklebur | — |
| Corn | 10 |
| Crabgrass, Large | 100 |
| Cupgrass, Woolly | — |
| Foxtail, Giant | 100 |
| Foxtail, Green | — |
| Galium | 100 |
| Goosegrass | — |
| Johnsongrass | 40 |
| *Kochia* | — |
| Lambsquarters | 98 |
| Morningglory | 35 |
| Nightshade | — |
| Nutsedge, Yellow | 0 |
| Oat, Wild | — |
| Oilseed Rape | 98 |
| Pigweed | 100 |
| Ragweed | 35 |
| Russian Thistle | — |
| Ryegrass, Italian | 10 |
| Soybean | 85 |
| Sunflower | — |
| Surinam Grass | — |
| Velvetleaf | 98 |
| Waterhemp | 100 |
| Wheat | 10 |

| 31 g ai/ha | Compounds | | | | | | | | | | | | |
|---|---|---|---|---|---|---|---|---|---|---|---|---|---|
| | 7 | 16 | 18 | 25 | 52 | 58 | 59 | 72 | 73 | 79 | 83 | 84 | 85 | 86 |
| Preemergence | | | | | | | | | | | | | | |
| Barnyardgrass | — | — | — | 0 | 50 | 98 | 80 | 75 | 60 | 100 | 5 | 25 | 15 | 10 |
| Bermudagrass | 85 | 95 | 95 | — | — | — | — | — | — | — | — | — | — | — |
| Blackgrass | 5 | 85 | 10 | 0 | — | 90 | 5 | 50 | 0 | 90 | 5 | 5 | 5 | 20 |
| Bromegrass, Downy | 0 | 30 | 0 | — | — | — | — | — | — | — | — | — | — | — |
| Cocklebur | 0 | 0 | — | — | — | — | — | — | — | — | — | — | — | — |
| Corn | 0 | 0 | 0 | 0 | 5 | 60 | — | — | 0 | 40 | 0 | 0 | 10 | 25 |
| Crabgrass, Large | 80 | 98 | 75 | 55 | 100 | 100 | 100 | 100 | 100 | 100 | 85 | 98 | 90 | 100 |
| Cupgrass, Woolly | 15 | 75 | 40 | — | — | — | — | — | — | — | — | — | — | — |
| Foxtail, Giant | 40 | 95 | 65 | 10 | 100 | 100 | 95 | 100 | 85 | 98 | 75 | 55 | 35 | 75 |
| Foxtail, Green | 50 | 90 | 85 | — | — | — | — | — | — | — | — | — | — | — |
| Galium | 85 | 95 | 90 | 80 | 100 | 100 | 100 | 80 | 85 | 90 | 0 | 90 | 0 | 80 |
| Goosegrass | 65 | 75 | 75 | — | — | — | — | — | — | — | — | — | — | — |
| Johnsongrass | 0 | 0 | 30 | 0 | 15 | 85 | 60 | 35 | 10 | 75 | 0 | 20 | 20 | 20 |
| *Kochia* | 55 | 50 | 15 | — | — | — | — | — | — | — | — | — | — | — |
| Lambsquarters | 80 | 20 | 30 | 100 | 100 | 100 | 100 | 98 | 60 | 100 | 100 | 85 | 100 | 100 |
| Morningglory | 0 | 10 | 10 | 0 | 55 | 100 | 95 | 15 | 45 | 95 | 0 | 10 | 0 | 25 |
| Nightshade | 80 | 20 | — | — | — | — | — | — | — | — | — | — | — | — |
| Nutsedge, Yellow | 0 | 15 | 10 | — | 0 | 70 | — | 0 | 0 | 10 | 0 | 0 | 0 | 0 |
| Oat, Wild | 0 | 50 | 0 | — | — | — | — | — | — | — | — | — | — | — |
| Oilseed Rape | — | — | — | 85 | 100 | 100 | 90 | 65 | 85 | 90 | 95 | 85 | 40 | 100 |
| Pigweed | 100 | 100 | 100 | 80 | 100 | 100 | 100 | 100 | 100 | 100 | 100 | 100 | 40 | 100 |
| Ragweed | 0 | 0 | 0 | 20 | 90 | 85 | 90 | 55 | — | 90 | 35 | 60 | 0 | 20 |
| Russian Thistle | — | 0 | 0 | — | — | — | — | — | — | — | — | — | — | — |
| Ryegrass, Italian | 0 | 0 | 0 | 0 | 5 | 90 | 50 | 5 | 0 | 40 | 0 | 5 | 0 | 0 |
| Soybean | 15 | 75 | 25 | 0 | 5 | 90 | 85 | 40 | — | 75 | 10 | 20 | 15 | 45 |
| Sunflower | 0 | 0 | 0 | — | — | — | — | — | — | — | — | — | — | — |
| Surinam Grass | 0 | 25 | 20 | — | — | — | — | — | — | — | — | — | — | — |
| Velvetleaf | 40 | 98 | 60 | 75 | 75 | 100 | 100 | 60 | 60 | 90 | 100 | 60 | 80 | 50 |

TABLE C-continued

| | | | | | | | | | | | | | | |
|---|---|---|---|---|---|---|---|---|---|---|---|---|---|---|
| Waterhemp | — | — | — | 80 | 100 | 100 | 100 | 100 | 100 | 100 | 100 | 75 | 85 | 100 |
| Wheat | 0 | 0 | 0 | 0 | 0 | 45 | 0 | 0 | 0 | 10 | 0 | 0 | 0 | 0 |

| | Compounds | | | | | | | | | | | | | |
|---|---|---|---|---|---|---|---|---|---|---|---|---|---|---|
| 31 g ai/ha | 88 | 89 | 90 | 92 | 94 | 97 | 111 | 112 | 116 | 118 | 129 | 132 | 134 | 135 |

| Preemergence | | | | | | | | | | | | | | |
|---|---|---|---|---|---|---|---|---|---|---|---|---|---|---|
| Barnyardgrass | 5 | 35 | 5 | 75 | 10 | 95 | 55 | 5 | 25 | 80 | 15 | 0 | 15 | 15 |
| Bermudagrass | — | — | — | — | — | — | — | — | — | — | — | — | — | — |
| Blackgrass | 5 | 0 | 5 | 5 | 20 | 70 | 10 | 30 | 10 | 80 | 50 | 5 | 45 | 5 |
| Bromegrass, Downy | — | — | — | — | — | — | — | — | — | — | — | — | — | — |
| Cocklebur | — | — | — | — | — | — | — | — | — | — | — | — | — | — |
| Corn | 5 | 0 | 0 | 0 | 5 | 5 | 5 | 0 | 0 | 40 | 5 | 10 | 30 | 5 |
| Crabgrass, Large | 70 | 100 | 98 | 100 | 98 | 100 | 100 | 100 | 100 | 80 | 95 | 85 | 98 | 100 |
| Cupgrass, Woolly | — | — | — | — | — | — | — | — | — | — | — | — | — | — |
| Foxtail, Giant | 65 | 35 | 45 | 98 | 65 | 100 | 100 | 85 | 10 | 75 | 80 | 55 | 65 | 70 |
| Foxtail, Green | — | — | — | — | — | — | — | — | — | — | — | — | — | — |
| Galium | 50 | 100 | 5 | 85 | 98 | 90 | 100 | 98 | 100 | 95 | 80 | 0 | 0 | 80 |
| Goosegrass | — | — | — | — | — | — | — | — | — | — | — | — | — | — |
| Johnsongrass | 0 | 0 | 10 | 5 | 25 | 40 | 5 | 5 | 25 | 25 | 10 | 0 | 25 | 5 |
| *Kochia* | — | — | — | — | — | — | — | — | — | — | — | — | — | — |
| Lambsquarters | 100 | 80 | 98 | 98 | 85 | 98 | 100 | 100 | 95 | 100 | 40 | 55 | 100 | 85 |
| Morningglory | 5 | 35 | 20 | 25 | 30 | 98 | 45 | 15 | 5 | 75 | 35 | 0 | 20 | 50 |
| Nightshade | — | — | — | — | — | — | — | — | — | — | — | — | — | — |
| Nutsedge, Yellow | 0 | 5 | 0 | 5 | 0 | 20 | 0 | 5 | 5 | 5 | 0 | 0 | 0 | 0 |
| Oat, Wild | — | — | — | — | — | — | — | — | — | — | — | — | — | — |
| Oilseed Rape | 100 | 80 | 80 | 80 | 98 | 85 | 90 | 90 | 5 | 100 | 85 | 85 | 45 | 95 |
| Pigweed | 100 | 90 | 85 | 85 | 100 | 100 | 95 | 100 | 100 | 100 | 100 | 45 | 100 | 80 |
| Ragweed | 0 | 55 | 60 | 5 | 0 | 35 | 50 | 0 | 5 | 100 | 20 | 10 | 25 | 55 |
| Russian Thistle | — | — | — | — | — | — | — | — | — | — | — | — | — | — |
| Ryegrass, Italian | 0 | 5 | 0 | 10 | 0 | 60 | 0 | 0 | 0 | 40 | 0 | 0 | 5 | 5 |
| Soybean | 5 | 45 | 35 | 65 | 50 | 90 | 60 | 35 | 25 | 75 | 10 | 0 | 15 | 65 |
| Sunflower | — | — | — | — | — | — | — | — | — | — | — | — | — | — |
| Surinam Grass | — | — | — | — | — | — | — | — | — | — | — | — | — | — |
| Velvetleaf | 98 | 70 | 65 | 90 | 100 | 95 | 60 | 70 | 70 | 100 | 70 | 85 | 35 | 45 |
| Waterhemp | 100 | 100 | 100 | 98 | 100 | 100 | 100 | 98 | 100 | 100 | 100 | 98 | 100 | 100 |
| Wheat | 0 | 0 | 0 | 0 | 0 | 10 | 30 | 0 | 0 | 0 | 0 | 0 | 0 | 0 |

| | Compounds | | | | | | | | | | | | | |
|---|---|---|---|---|---|---|---|---|---|---|---|---|---|---|
| 31 g ai/ha | 136 | 137 | 138 | 141 | 145 | 147 | 150 | 151 | 154 | 164 | 166 | 167 | 170 | 179 |

| Preemergence | | | | | | | | | | | | | | |
|---|---|---|---|---|---|---|---|---|---|---|---|---|---|---|
| Barnyardgrass | 10 | 5 | 25 | 100 | 0 | 80 | 20 | 5 | 25 | 70 | 100 | 85 | 55 | 10 |
| Bermudagrass | — | — | — | — | — | — | — | — | — | — | — | — | — | — |
| Blackgrass | 0 | 0 | 20 | 95 | 65 | 40 | 10 | 0 | 10 | 50 | 85 | 30 | 80 | 50 |
| Bromegrass, Downy | — | — | — | — | — | — | — | — | — | — | — | — | — | — |
| Cocklebur | — | — | — | — | — | — | — | — | — | — | — | — | — | — |
| Corn | 0 | 5 | 0 | 20 | 0 | 0 | 0 | 5 | 0 | 5 | 25 | 5 | 5 | 5 |
| Crabgrass, Large | 100 | 70 | 90 | 100 | 75 | 100 | 98 | 85 | 90 | 85 | 100 | 98 | 95 | 90 |
| Cupgrass, Woolly | — | — | — | — | — | — | — | — | — | — | — | — | — | — |
| Foxtail, Giant | 5 | 5 | 90 | 100 | 55 | 100 | 75 | 35 | 70 | 95 | 100 | 95 | 85 | 85 |
| Foxtail, Green | — | — | — | — | — | — | — | — | — | — | — | — | — | — |
| Galium | 0 | 5 | 90 | 98 | 85 | 98 | 80 | — | 95 | 100 | 100 | 100 | 98 | 95 |
| Goosegrass | — | — | — | — | — | — | — | — | — | — | — | — | — | — |
| Johnsongrass | 0 | 0 | 5 | 70 | 0 | 35 | 30 | 5 | 0 | 20 | 40 | 40 | 25 | 0 |
| *Kochia* | — | — | — | — | — | — | — | — | — | — | — | — | — | — |
| Lambsquarters | 10 | 30 | 100 | 100 | 100 | 100 | 100 | 100 | 85 | 98 | 98 | 100 | 98 | 100 |
| Morningglory | 30 | 10 | 0 | 90 | 0 | 80 | 5 | 0 | 25 | 55 | 70 | 35 | 15 | 0 |
| Nightshade | — | — | — | — | — | — | — | — | — | — | — | — | — | — |
| Nutsedge, Yellow | 0 | 0 | 5 | 30 | 0 | 5 | 0 | 0 | 5 | 5 | 10 | 10 | 0 | 0 |
| Oat, Wild | — | — | — | — | — | — | — | — | — | — | — | — | — | — |
| Oilseed Rape | 0 | 60 | 100 | 100 | 100 | 100 | 5 | 100 | 100 | 98 | 100 | 80 | 80 | 95 |
| Pigweed | 50 | 75 | 95 | 100 | 100 | 100 | 70 | 100 | 100 | 100 | 100 | 100 | 100 | 100 |
| Ragweed | 25 | 25 | 5 | 100 | 75 | 100 | — | 70 | 85 | 10 | 65 | 30 | 25 | 5 |
| Russian Thistle | — | — | — | — | — | — | — | — | — | — | — | — | — | — |
| Ryegrass, Italian | 0 | 0 | 0 | 45 | 5 | 35 | 5 | 0 | 5 | 40 | 40 | 40 | 10 | 10 |
| Soybean | 30 | 40 | 55 | 85 | 45 | 80 | 35 | 65 | 70 | 25 | 90 | 70 | 10 | 10 |
| Sunflower | — | — | — | — | — | — | — | — | — | — | — | — | — | — |
| Surinam Grass | — | — | — | — | — | — | — | — | — | — | — | — | — | — |

TABLE C-continued

| | | | | | | | | | | | | | | |
|---|---|---|---|---|---|---|---|---|---|---|---|---|---|---|
| Velvetleaf | — | 25 | 80 | 100 | 100 | 100 | 10 | 100 | 100 | 100 | 100 | 85 | 55 | 75 |
| Waterhemp | 40 | 100 | 100 | 100 | 100 | 98 | 50 | 100 | 95 | 100 | 100 | 100 | 100 | 98 |
| Wheat | 0 | 0 | 0 | 5 | 0 | 0 | 0 | 0 | 0 | 5 | 15 | 0 | 10 | 0 |

| 31 g ai/ha | Compound 292 |
|---|---|
| Preemergence | |
| Barnyardgrass | 15 |
| Bermudagrass | — |
| Blackgrass | 70 |
| Bromegrass, Downy | — |
| Cocklebur | — |
| Corn | 5 |
| Crabgrass, Large | 100 |
| Cupgrass, Woolly | — |
| Foxtail, Giant | 100 |
| Foxtail, Green | — |
| Galium | 98 |
| Goosegrass | — |
| Johnsongrass | 5 |
| *Kochia* | — |
| Lambsquarters | 80 |
| Morningglory | 30 |
| Nightshade | — |
| Nutsedge, Yellow | 0 |
| Oat, Wild | — |
| Oilseed Rape | 80 |
| Pigweed | 100 |
| Ragweed | 35 |
| Russian Thistle | — |
| Ryegrass, Italian | 0 |
| Soybean | 40 |
| Sunflower | — |
| Surinam Grass | — |
| Velvetleaf | 35 |
| Waterhemp | 100 |
| Wheat | 0 |

| | Compounds | | | | | | | | | | | | |
|---|---|---|---|---|---|---|---|---|---|---|---|---|---|
| 16 g ai/ha | 83 | 84 | 85 | 86 | 88 | 89 | 90 | 92 | 94 | 97 | 111 | 112 | 116 | 118 |
| Preemergence | | | | | | | | | | | | | | |
| Barnyardgrass | 5 | 0 | 0 | 5 | 5 | 5 | 0 | 5 | 5 | 35 | 5 | 0 | 0 | 20 |
| Blackgrass | 0 | 0 | 0 | 0 | 0 | 0 | 5 | 0 | 5 | 0 | 20 | 0 | 0 | 35 |
| Corn | 0 | 0 | 5 | 0 | 5 | 0 | 0 | 0 | 5 | 0 | 5 | 0 | 0 | 10 |
| Crabgrass, Large | 65 | 45 | 65 | 85 | 45 | 80 | 25 | 90 | 25 | 98 | 98 | 35 | 5 | 30 |
| Foxtail, Giant | 5 | 5 | 20 | 35 | 5 | 5 | 5 | 30 | 5 | 60 | 15 | 15 | 0 | 25 |
| Galium | 0 | 80 | 0 | 90 | 0 | 30 | 5 | 80 | 80 | 85 | 90 | 55 | 0 | 95 |
| Johnsongrass | 0 | 0 | 15 | 10 | 0 | 0 | 5 | 0 | 0 | 10 | 0 | 0 | 0 | 0 |
| Lambsquarters | 100 | 75 | 65 | 100 | 70 | 45 | 100 | 65 | 40 | 95 | 50 | 98 | 10 | 100 |
| Morningglory | 0 | 0 | 0 | 10 | 0 | 45 | 0 | 10 | 0 | 40 | 20 | 5 | 0 | 40 |
| Nutsedge, Yellow | 0 | 0 | 0 | 0 | 0 | 0 | 35 | 5 | 0 | 10 | 0 | 0 | 0 | 0 |
| Oilseed Rape | 75 | 50 | 0 | 25 | 10 | 80 | 60 | 80 | 85 | 85 | 60 | 65 | 0 | 98 |
| Pigweed | 85 | 85 | 50 | 90 | 100 | 55 | 40 | 90 | 90 | 100 | 75 | 100 | 75 | 90 |
| Ragweed | 0 | 0 | 0 | 5 | 0 | 40 | 10 | 10 | 0 | 35 | 10 | 0 | 0 | 70 |
| Ryegrass, Italian | 0 | 0 | 0 | 0 | 0 | 0 | 0 | 0 | 0 | 0 | 0 | 0 | 0 | 0 |
| Soybean | 5 | 0 | 0 | 35 | 0 | 30 | 25 | 30 | 35 | 50 | 30 | 10 | 0 | 60 |
| Velvetleaf | 60 | 50 | 35 | 20 | 15 | 20 | 35 | 30 | 40 | 40 | 60 | 65 | 20 | 100 |
| Waterhemp | 75 | 100 | 55 | 100 | 98 | 80 | 85 | 95 | 80 | 100 | 100 | 90 | 100 | 85 |
| Wheat | 0 | 0 | 0 | 0 | 0 | 0 | 0 | 0 | 0 | 0 | 0 | 0 | 0 | 0 |

| | Compounds | | | | | | | | | | | | |
|---|---|---|---|---|---|---|---|---|---|---|---|---|---|
| 16 g ai/ha | 129 | 132 | 134 | 135 | 136 | 137 | 138 | 141 | 145 | 147 | 150 | 151 | 154 | 164 |
| Preemergence | | | | | | | | | | | | | | |
| Barnyardgrass | 5 | 0 | 0 | 0 | 0 | 0 | 10 | 80 | 0 | 10 | 5 | 5 | 5 | 15 |
| Blackgrass | 0 | 0 | 0 | 0 | 0 | 0 | 5 | 80 | 0 | 0 | 0 | 0 | 0 | 0 |
| Corn | 0 | 0 | 0 | 10 | 5 | 0 | 0 | 5 | 0 | 0 | 0 | 0 | 5 | 0 |
| Crabgrass, Large | 75 | 65 | 60 | 60 | 35 | 10 | 100 | 100 | 70 | 98 | 70 | 5 | 75 | 75 |
| Foxtail, Giant | 0 | 5 | 10 | 5 | 0 | 35 | 30 | 90 | 10 | 70 | 5 | 5 | 5 | 40 |
| Galium | 50 | 0 | 0 | 0 | 0 | 5 | 90 | 98 | 0 | 90 | 0 | — | 80 | 75 |
| Johnsongrass | 0 | 0 | 20 | 0 | 0 | 0 | 0 | 30 | 0 | 10 | 0 | 0 | 0 | 5 |
| Lambsquarters | 50 | 75 | 60 | 30 | — | 100 | 100 | 85 | 55 | 100 | 10 | 100 | 70 | 70 |
| Morningglory | 5 | 25 | 5 | 50 | 20 | 25 | 0 | 75 | 0 | 40 | 0 | 0 | 10 | 10 |

TABLE C-continued

| | | | | | | | | | | | | | | |
|---|---|---|---|---|---|---|---|---|---|---|---|---|---|---|
| Nutsedge, Yellow | 0 | 100 | 0 | 0 | 0 | 0 | 5 | — | 0 | 0 | 0 | 0 | 0 | 0 |
| Oilseed Rape | 50 | 20 | 20 | 55 | 0 | 50 | 80 | 100 | 95 | 100 | 0 | 95 | 98 | 70 |
| Pigweed | 98 | 30 | 100 | 85 | 0 | 75 | 85 | 100 | 25 | 100 | 55 | 100 | 85 | 98 |
| Ragweed | 0 | 10 | 0 | 40 | 0 | 45 | 0 | 85 | 20 | 75 | 0 | 55 | 75 | 0 |
| Ryegrass, Italian | 0 | 0 | 0 | 0 | 0 | 0 | 0 | 40 | 0 | 0 | 0 | 0 | 0 | 0 |
| Soybean | 10 | 0 | 0 | 20 | 20 | 10 | 20 | 65 | 35 | 85 | 0 | 35 | 50 | 0 |
| Velvetleaf | 35 | 75 | 30 | 40 | 5 | 40 | 60 | 100 | 55 | 100 | 5 | 85 | 85 | 50 |
| Waterhemp | 100 | 85 | 85 | 75 | 0 | 100 | 100 | 100 | 95 | 100 | 20 | 95 | 100 | 85 |
| Wheat | 0 | 0 | 0 | 0 | 0 | 0 | 0 | 0 | 0 | 0 | 0 | 0 | 0 | 0 |

| | Compounds | | | | | | | | | | | | | |
|---|---|---|---|---|---|---|---|---|---|---|---|---|---|---|
| 16 g ai/ha | 166 | 167 | 170 | 179 | 180 | 187 | 236 | 240 | 250 | 252 | 253 | 258 | 270 | 273 |

Preemergence

| | | | | | | | | | | | | | | |
|---|---|---|---|---|---|---|---|---|---|---|---|---|---|---|
| Barnyardgrass | 85 | 5 | 10 | 5 | 60 | 5 | 10 | 5 | 5 | 10 | 30 | 45 | 0 | 0 |
| Blackgrass | 40 | 30 | 0 | 0 | 20 | 0 | 5 | 0 | 0 | 10 | 0 | 0 | 0 | 0 |
| Corn | 0 | 0 | 0 | 0 | 5 | 0 | 0 | 5 | 0 | 10 | 0 | 0 | 0 | 0 |
| Crabgrass, Large | 100 | 75 | 25 | 55 | 100 | 5 | 90 | 75 | 75 | 60 | 85 | 100 | 50 | 90 |
| Foxtail, Giant | 100 | 35 | 80 | 40 | 90 | 0 | 35 | 10 | 5 | 35 | 35 | 75 | 5 | 0 |
| Galium | 98 | 98 | 95 | 90 | 80 | 30 | 90 | 5 | 0 | 80 | 70 | 80 | 70 | 0 |
| Johnsongrass | 5 | 5 | 0 | 0 | 0 | 0 | 5 | 5 | 0 | 5 | 15 | 5 | 0 | 0 |
| Lambsquarters | 90 | 75 | 90 | 85 | 85 | 5 | 98 | 70 | 90 | 98 | 100 | 65 | 80 | 35 |
| Morningglory | 15 | 30 | 0 | 10 | 35 | 0 | 0 | 15 | 0 | 45 | 40 | 10 | 0 | 5 |
| Nutsedge, Yellow | 0 | 0 | 0 | 0 | 5 | 0 | 0 | 0 | 0 | 0 | 0 | 5 | 0 | 0 |
| Oilseed Rape | 90 | 80 | 70 | 60 | 55 | 70 | 80 | 70 | 100 | 80 | 75 | 80 | 95 | 0 |
| Pigweed | 100 | 100 | 100 | 100 | 85 | 45 | 100 | 5 | 85 | 98 | 100 | 100 | 100 | 55 |
| Ragweed | 50 | 15 | 85 | 0 | 20 | 55 | 15 | 10 | 15 | 40 | 35 | 0 | 0 | 10 |
| Ryegrass, Italian | 5 | 5 | 5 | 0 | 5 | 0 | 0 | 0 | 0 | 0 | 0 | 0 | 0 | 0 |
| Soybean | 60 | 10 | 5 | 0 | 90 | 5 | 35 | 40 | — | 65 | 40 | 35 | 0 | 5 |
| Velvetleaf | 80 | 45 | 25 | 60 | 75 | 25 | 65 | 25 | 100 | 75 | 55 | 80 | 0 | 10 |
| Waterhemp | 100 | 100 | 100 | 90 | 90 | 25 | 98 | 50 | 85 | 100 | 100 | 100 | 80 | 45 |
| Wheat | 0 | 0 | 0 | 0 | 0 | 0 | 0 | 0 | 0 | 0 | 0 | 0 | 0 | 0 |

| | Compounds | | | Compound |
|---|---|---|---|---|
| 16 g ai/ha | 274 | 292 | 8 g ai/ha | 135 |

Preemergence

| | | | | |
|---|---|---|---|---|
| Barnyardgrass | 90 | 0 | Barnyardgrass | 0 |
| Blackgrass | 50 | 0 | Blackgrass | 0 |
| Corn | 5 | 0 | Corn | 5 |
| Crabgrass, Large | 100 | 100 | Crabgrass, Large | 45 |
| Foxtail, Giant | 98 | 45 | Foxtail, Giant | 0 |
| Galium | 90 | 80 | Galium | 0 |
| Johnsongrass | 10 | 0 | Johnsongrass | 0 |
| Lambsquarters | 100 | 35 | Morningglory | 5 |
| Morningglory | 35 | 25 | Nutsedge, Yellow | 0 |
| Nutsedge, Yellow | 20 | 0 | Oilseed Rape | 30 |
| Oilseed Rape | 80 | 70 | Pigweed | 50 |
| Pigweed | 100 | 100 | Ragweed | 0 |
| Ragweed | 10 | 25 | Ryegrass, Italian | 0 |
| Ryegrass, Italian | 25 | 0 | Soybean | 10 |
| Soybean | 35 | 5 | Velvetleaf | 5 |
| Velvetleaf | 80 | 15 | Waterhemp | 55 |
| Waterhemp | 100 | 100 | Wheat | 0 |
| Wheat | 20 | 0 | | |

| | Compound | | Compound |
|---|---|---|---|
| 2000 g ai/ha | 80 | 500 g ai/ha | 80 |

Flood

| | | | |
|---|---|---|---|
| Barnyardgrass | 0 | Barnyardgrass | 0 |
| Ducksalad | 80 | Ducksalad | 75 |
| Rice | 0 | Rice | 0 |
| Sedge, Umbrella | 85 | Sedge, Umbrella | 0 |

| | Compound |
|---|---|
| 1000 g ai/ha | 80 |

Flood

| | |
|---|---|
| Barnyardgrass | 0 |
| Ducksalad | 80 |

TABLE C-continued

|  | | |
|---|---|---|
| Rice | | 0 |
| Sedge, Umbrella | | 60 |

| Compounds | | | | | | | | | | | | | |
|---|---|---|---|---|---|---|---|---|---|---|---|---|---|
| 250 g ai/ha | 3 | 8 | 18 | 25 | 26 | 34 | 40 | 59 | 62 | 65 | 80 | 81 | 89 | 97 |

Flood

| | 3 | 8 | 18 | 25 | 26 | 34 | 40 | 59 | 62 | 65 | 80 | 81 | 89 | 97 |
|---|---|---|---|---|---|---|---|---|---|---|---|---|---|---|
| Barnyardgrass | 0 | 0 | 20 | 0 | 0 | 10 | 15 | 40 | 40 | 0 | 0 | 0 | 20 | 0 |
| Ducksalad | 85 | 70 | 90 | 90 | 85 | 75 | 60 | 95 | 100 | 85 | 50 | 90 | 80 | 80 |
| Rice | 0 | 10 | 10 | 0 | 0 | 0 | 0 | 20 | 25 | 0 | 0 | 0 | 0 | 0 |
| Sedge, Umbrella | 70 | 85 | 90 | 85 | 85 | 70 | 75 | 95 | 100 | 85 | 0 | 90 | 70 | 80 |

| Compounds | | | | | | | | | | | | | |
|---|---|---|---|---|---|---|---|---|---|---|---|---|---|
| 250 g ai/ha | 120 | 141 | 150 | 164 | 167 | 177 | 179 | 184 | 185 | 188 | 191 | 192 | 194 | 200 |

Flood

| | 120 | 141 | 150 | 164 | 167 | 177 | 179 | 184 | 185 | 188 | 191 | 192 | 194 | 200 |
|---|---|---|---|---|---|---|---|---|---|---|---|---|---|---|
| Barnyardgrass | 85 | 20 | 0 | 0 | 0 | 0 | 0 | 0 | 0 | 0 | 20 | 0 | 0 | 25 |
| Ducksalad | 90 | 100 | 75 | 95 | 80 | 95 | 95 | 75 | 40 | 60 | 80 | 75 | 100 | 80 |
| Rice | 60 | 60 | 0 | 0 | 0 | 10 | 10 | 0 | 15 | 0 | 0 | 0 | 10 | 0 |
| Sedge, Umbrella | 85 | 100 | 85 | 95 | 85 | 85 | 80 | 75 | 85 | 75 | 98 | 85 | 95 | 90 |

| Compounds | | | | |
|---|---|---|---|---|
| 250 g ai/ha | 231 | 234 | 236 | 270 |

Flood

| | 231 | 234 | 236 | 270 |
|---|---|---|---|---|
| Barnyardgrass | 0 | 0 | 20 | 60 |
| Ducksalad | 75 | 30 | 90 | 95 |
| Rice | 0 | 0 | 20 | 30 |
| Sedge, Umbrella | 80 | 40 | 80 | 95 |

| Compounds | | | | | | | | | | | | | |
|---|---|---|---|---|---|---|---|---|---|---|---|---|---|
| 125 g ai/ha | 3 | 8 | 18 | 25 | 26 | 34 | 40 | 59 | 62 | 65 | 81 | 89 | 97 | 120 |

Flood

| | 3 | 8 | 18 | 25 | 26 | 34 | 40 | 59 | 62 | 65 | 81 | 89 | 97 | 120 |
|---|---|---|---|---|---|---|---|---|---|---|---|---|---|---|
| Barnyardgrass | 0 | 0 | 10 | 0 | 0 | 0 | 15 | 30 | 0 | 0 | 0 | 15 | 0 | 60 |
| Ducksalad | 70 | 50 | 85 | 85 | 65 | 20 | 40 | 95 | 85 | 85 | 60 | 65 | 75 | 80 |
| Rice | 0 | 10 | 0 | 0 | 0 | 0 | 0 | 20 | 15 | 0 | 0 | 0 | 0 | 15 |
| Sedge, Umbrella | 20 | 75 | 85 | 80 | 75 | 0 | 75 | 90 | 90 | 75 | 70 | 50 | 75 | 60 |

| Compounds | | | | | | | | | | | | | |
|---|---|---|---|---|---|---|---|---|---|---|---|---|---|
| 125 g ai/ha | 141 | 150 | 164 | 167 | 177 | 179 | 184 | 185 | 188 | 191 | 192 | 194 | 200 | 203 |

Flood

| | 141 | 150 | 164 | 167 | 177 | 179 | 184 | 185 | 188 | 191 | 192 | 194 | 200 | 203 |
|---|---|---|---|---|---|---|---|---|---|---|---|---|---|---|
| Barnyardgrass | 15 | 0 | 0 | 0 | 0 | 0 | 0 | 0 | 0 | 0 | 0 | 0 | 0 | 50 |
| Ducksalad | 95 | 70 | 75 | 60 | 85 | 85 | 30 | 0 | 40 | 75 | 70 | 90 | 20 | 70 |
| Rice | 40 | 0 | 0 | 0 | 10 | 10 | 0 | 0 | 0 | 0 | 0 | 10 | 0 | 20 |
| Sedge, Umbrella | 75 | 75 | 75 | 80 | 60 | 40 | 50 | 50 | 50 | 85 | 50 | 85 | 90 | 85 |

| Compounds | | | | | |
|---|---|---|---|---|---|
| 125 g ai/ha | 231 | 234 | 236 | 270 | 293 |

Flood

| | 231 | 234 | 236 | 270 | 293 |
|---|---|---|---|---|---|
| Barnyardgrass | 0 | 0 | 0 | 45 | 0 |
| Ducksalad | 70 | 0 | 80 | 80 | 75 |
| Rice | 0 | 0 | 10 | 0 | 0 |
| Sedge, Umbrella | 70 | 0 | 60 | 60 | 85 |

| Compounds | | | | | | | | | | | | | |
|---|---|---|---|---|---|---|---|---|---|---|---|---|---|
| 62 g ai/ha | 3 | 8 | 18 | 25 | 26 | 34 | 40 | 59 | 62 | 65 | 81 | 89 | 97 | 120 |

Flood

| | 3 | 8 | 18 | 25 | 26 | 34 | 40 | 59 | 62 | 65 | 81 | 89 | 97 | 120 |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 0 |
| Ducksalad | 50 | 40 | 80 | 70 | 30 | 0 | 0 | 75 | 70 | 30 | 40 | 0 | 40 | 40 |

TABLE C-continued

| | | | | | | | | | | | | | | |
|---|---|---|---|---|---|---|---|---|---|---|---|---|---|---|
| Rice | 0 | 0 | 0 | 0 | 0 | 0 | 0 | 15 | 15 | 0 | 0 | 0 | 0 | 0 |
| Sedge, Umbrella | 0 | 50 | 75 | 50 | 0 | 0 | 75 | 80 | 50 | 65 | 50 | 0 | 60 | 0 |

| | Compounds | | | | | | | | | | | | | |
|---|---|---|---|---|---|---|---|---|---|---|---|---|---|---|
| 62 g ai/ha | 141 | 150 | 164 | 167 | 177 | 179 | 184 | 185 | 188 | 191 | 192 | 194 | 200 | 203 |

| Flood | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 50 |
| Ducksalad | 80 | 40 | 0 | 50 | 60 | 60 | 30 | 0 | 0 | 50 | 0 | 80 | 0 | 50 |
| Rice | 0 | 0 | 0 | 0 | 0 | 0 | 0 | 0 | 0 | 0 | 0 | 10 | 0 | 20 |
| Sedge, Umbrella | 40 | 50 | 20 | 70 | 0 | 0 | 0 | 50 | 0 | 60 | 0 | 75 | 80 | 75 |

| | Compounds | | | | |
|---|---|---|---|---|---|
| 62 g ai/ha | 231 | 234 | 236 | 270 | 293 |

| Flood | | | | | |
|---|---|---|---|---|---|
| Barnyardgrass | 0 | 0 | 0 | 30 | 0 |
| Ducksalad | 30 | 0 | 40 | 60 | 40 |
| Rice | 0 | 0 | 0 | 0 | 0 |
| Sedge, Umbrella | 50 | 0 | 20 | 25 | 75 |

| | Compounds | | | | | | | | | | | | | |
|---|---|---|---|---|---|---|---|---|---|---|---|---|---|---|
| 31 g ai/ha | 3 | 8 | 18 | 25 | 26 | 34 | 40 | 59 | 62 | 65 | 81 | 97 | 120 | 141 |

| Flood | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 0 | 0 |
| Ducksalad | 0 | 0 | 80 | 0 | 0 | 0 | 0 | 50 | 30 | 0 | 30 | 0 | 0 | 65 |
| Rice | 0 | 0 | 0 | 0 | 0 | 0 | 0 | 0 | 15 | 0 | 0 | 0 | 0 | 0 |
| Sedge, Umbrella | 0 | 0 | 70 | 0 | 0 | 0 | 50 | 60 | 0 | 50 | 0 | 60 | 0 | 0 |

| | Compounds | | | | | | | | | | | | | |
|---|---|---|---|---|---|---|---|---|---|---|---|---|---|---|
| 31 g ai/ha | 150 | 164 | 167 | 177 | 179 | 184 | 185 | 188 | 191 | 192 | 194 | 200 | 203 | 231 |

| Flood | | | | | | | | | | | | | | |
|---|---|---|---|---|---|---|---|---|---|---|---|---|---|---|
| Barnyardgrass | 0 | 0 | 0 | 0 | 0 | 0 | 0 | 0 | 0 | 0 | 0 | 0 | 40 | 0 |
| Ducksalad | 0 | 0 | 0 | 20 | 20 | 0 | 0 | 0 | 30 | 0 | 65 | 0 | 0 | 0 |
| Rice | 0 | 0 | 0 | 0 | 0 | 0 | 0 | 0 | 0 | 0 | 10 | 0 | 0 | 0 |
| Sedge, Umbrella | 0 | 0 | 60 | 0 | 0 | 0 | 0 | 0 | 40 | 0 | 50 | 0 | 50 | 0 |

| | Compounds | | | |
|---|---|---|---|---|
| 31 g ai/ha | 234 | 236 | 270 | 293 |

| Flood | | | | |
|---|---|---|---|---|
| Barnyardgrass | 0 | 0 | 0 | 0 |
| Ducksalad | 0 | 0 | 20 | 30 |
| Rice | 0 | 0 | 0 | 0 |
| Sedge, Umbrella | 0 | 0 | 0 | 60 |

Test D

Seeds of plant species selected from bluegrass (annual bluegrass, *Poa annua*), blackgrass (*Alopecurus myosuroides*), canarygrass (littleseed canarygrass, *Phalaris minor*), chickweed (common chickweed, *Stellaria media*), galium (catchweed bedstraw, *Galium aparine*), bromegrass, downy (downy bromegrass, *Bromus tectorum*), field poppy (*Papaver rhoeas*), field violet (*Viola arvensis*), green foxtail (*Setaria viridis*), deadnettle (henbit deadnettle, *Lamium amplexicaule*), Italian ryegrass (*Lolium multiflorum*), kochia (*Kochia scoparia*), lambsquarters (*Chenopodium album*), oilseed rape (*Brassica napus*), pigweed (*Amaranthus retroflexus*), chamomile (scentless chamomile, *Matricaria inodora*), Russian thistle (*Salsola kali*), speedwell (bird's-eye speedwell, *Veronica persica*), spring barley (*Hordeum vulgare*), spring wheat (*Triticum aestivum*), wild buckwheat (*Polygonum convolvulus*), wild mustard (*Sinapis arvensis*), wild oat (*Avena fatua*), wild radish (*Raphanus raphanistrum*), windgrass (*Apera spica-venti*), winter barley (*Hordeum vulgare*), and winter wheat (*Triticum aestivum*) were planted into a silt loam soil and treated preemergence with test chemicals formulated in a non-phytotoxic solvent mixture which included a surfactant.

At the same time, these species were planted in pots containing Redi-Earth® planting medium (Scotts Company, 14111 Scottslawn Road, Marysville, Ohio 43041) comprising spaghnum peat moss, vermiculite, wetting agent and starter nutrients and treated with postemergence applications of the test chemicals formulated in the same manner. Plants ranged in height from 2 to 18 cm (1- to 4-leaf stage). Treated plants and controls were maintained in a controlled growth environment for 7 to 21 days after which time all species were compared to controls and visually evaluated. Plant response ratings, summarized in Table D, are based on a scale of 0 to 100 where 0 is no effect and 100 is complete control. A dash (-) response means no test result.

TABLE D

| | Postemergence | | | | | | | | | | | | | | | |
|---|---|---|---|---|---|---|---|---|---|---|---|---|---|---|---|---|
| | 250 g ai/ha Compounds | | | | | | | 125 g ai/ha Compounds | | | | | | | | |
| | 3 | 7 | 18 | 52 | 58 | 59 | 284 | 3 | 7 | 18 | 25 | 52 | 58 | 59 | 138 | 141 | 145 |
| Barley, Spring | 10 | 5 | 25 | 20 | 40 | 35 | 25 | 0 | 5 | 15 | 15 | 15 | 30 | 20 | 15 | 25 | 10 |
| Barley, Winter | 0 | 0 | 20 | 20 | 50 | 25 | 25 | 0 | 0 | 15 | 5 | 15 | 25 | 15 | 10 | 35 | 15 |
| Blackgrass | 10 | 25 | 35 | 65 | 90 | 70 | 35 | 0 | 10 | 20 | 25 | 40 | 70 | 40 | 15 | 55 | 35 |
| Bluegrass | 10 | 15 | 40 | 25 | 55 | 40 | 45 | 0 | 10 | 40 | 55 | 15 | 45 | 20 | 10 | 40 | 45 |
| Bromegrass, Downy | 0 | 5 | 15 | 25 | 35 | 30 | 45 | 0 | 5 | 20 | 30 | 20 | 35 | 25 | 5 | 45 | 25 |
| Buckwheat, Wild | 80 | 100 | 95 | 100 | 100 | 100 | 100 | 60 | 85 | 100 | 100 | 100 | 100 | 100 | 80 | 100 | 100 |
| Canarygrass | 10 | 25 | 35 | 60 | 70 | 35 | 25 | 0 | 10 | 20 | 40 | 50 | 50 | 35 | 15 | 55 | 35 |
| Chamomile | 0 | 0 | 10 | 15 | 35 | 15 | 10 | 0 | 0 | 10 | 5 | 20 | 35 | 10 | 0 | 20 | 10 |
| Chickweed | 40 | 80 | 95 | 90 | 100 | 95 | 100 | 30 | 60 | 60 | 100 | 85 | 100 | 95 | 55 | 100 | 80 |
| Deadnettle | 20 | 40 | 100 | 100 | 100 | 100 | 100 | 10 | 30 | 90 | 55 | 70 | 100 | 100 | 25 | 100 | 85 |
| Field Poppy | 0 | 60 | 100 | 100 | 100 | 100 | 100 | — | 50 | 100 | 75 | 80 | 100 | 100 | 75 | 85 | 100 |
| Field Violet | 20 | 70 | 90 | 100 | 100 | 100 | 100 | 5 | 70 | 80 | 100 | 100 | 100 | 100 | 75 | 95 | 75 |
| Foxtail, Green | 10 | 20 | 25 | 75 | 80 | 80 | 85 | 0 | 10 | 20 | 20 | 40 | 65 | 50 | 30 | 100 | 50 |
| *Galium* | 75 | 90 | 70 | 100 | 100 | 95 | 95 | 45 | 80 | 65 | 90 | 95 | 100 | 95 | 75 | 98 | 75 |
| *Kochia* | 55 | 100 | 100 | 90 | 95 | 95 | 100 | 25 | 100 | 100 | 100 | 90 | 95 | 95 | 75 | 100 | 75 |
| Lambsquarters | 85 | 100 | 95 | 95 | 90 | 95 | 100 | 80 | 90 | 95 | 95 | 75 | 95 | 80 | 60 | 98 | 85 |
| Mustard, Wild | 85 | 98 | 100 | 100 | 100 | 100 | 100 | 35 | 95 | 80 | 100 | 95 | 100 | 100 | 75 | 100 | 100 |
| Oat, Wild | 0 | 25 | 25 | 35 | 55 | 50 | 35 | 0 | 10 | 20 | 50 | 30 | 35 | 35 | 10 | 30 | 25 |
| Oilseed Rape | 95 | 100 | 100 | 95 | 95 | 100 | 100 | 90 | 100 | 100 | 55 | 85 | 95 | 75 | 75 | 100 | 95 |
| Pigweed | 90 | 100 | 95 | 95 | 100 | 95 | 100 | 70 | 100 | 95 | 100 | 85 | 100 | 95 | 90 | 100 | 100 |
| Radish, Wild | 75 | — | 100 | 90 | 95 | 85 | 100 | 50 | — | 100 | 100 | 80 | 90 | 80 | 90 | 100 | 100 |
| Russian Thistle | 20 | 70 | 100 | — | — | — | 95 | 10 | 30 | 60 | — | — | — | — | — | 95 | 65 |
| Ryegrass, Italian | 0 | 0 | 15 | 35 | 65 | 50 | 15 | 0 | 0 | 10 | 15 | 20 | 50 | 40 | 5 | 25 | 15 |
| Speedwell | 75 | 100 | 100 | 100 | 100 | 100 | 100 | 60 | 100 | 100 | 100 | 100 | 100 | 100 | 75 | 100 | 100 |
| Wheat, Spring | 0 | 10 | 25 | 15 | 35 | 25 | 35 | 0 | 10 | 20 | 20 | 10 | 20 | 20 | 15 | 35 | 15 |
| Wheat, Winter | 0 | 10 | 20 | 25 | 40 | 20 | 25 | 0 | 10 | 15 | 10 | 20 | 25 | 20 | 15 | 50 | 15 |
| Windgrass | 10 | 25 | 10 | 40 | 90 | 45 | 30 | 0 | 10 | 10 | 35 | 25 | 55 | 35 | 20 | 60 | 15 |

| | Postemergence | | | | | | | | | | | | | | | |
|---|---|---|---|---|---|---|---|---|---|---|---|---|---|---|---|---|
| | 125 g ai/ha Compound | | | | | 62 g ai/ha Compounds | | | | | | | | | | |
| | 166 | 178 | 245 | 274 | 284 | 3 | 7 | 18 | 25 | 52 | 58 | 59 | 138 | 141 | 145 | 166 | 178 |
| Barley, Spring | 45 | 10 | 30 | 35 | 20 | 0 | 0 | 10 | 10 | 15 | 20 | 20 | 10 | 25 | 5 | 30 | 5 |
| Barley, Winter | 35 | 10 | 20 | 30 | 20 | 0 | 0 | 10 | 5 | 10 | 15 | 15 | 5 | 25 | 15 | 25 | 5 |
| Blackgrass | 65 | — | 25 | 30 | 30 | 0 | 5 | 15 | 10 | 30 | 45 | 30 | 10 | 35 | 25 | 40 | 25 |
| Bluegrass | 65 | 55 | 30 | 30 | 40 | 0 | 0 | 30 | 50 | 20 | 35 | 15 | 5 | 35 | 30 | 55 | 35 |
| Bromegrass, Downy | 50 | 20 | 30 | 40 | 45 | 0 | 0 | 15 | 20 | 20 | 30 | 20 | 5 | 30 | 25 | 35 | 10 |
| Buckwheat, Wild | 100 | 85 | 90 | 100 | 100 | 50 | 60 | 70 | 100 | 95 | 100 | 100 | 65 | 100 | 60 | 95 | 75 |
| Canarygrass | 55 | 35 | 35 | 30 | 25 | 0 | 5 | 15 | 25 | 35 | 40 | 30 | 10 | 35 | 25 | 50 | 20 |
| Chamomile | 15 | 5 | 40 | 25 | 10 | 0 | 0 | 5 | 5 | 15 | 25 | 10 | 0 | 15 | 10 | 10 | 5 |
| Chickweed | 90 | 75 | 98 | 80 | 90 | 25 | 20 | 45 | 75 | 70 | 90 | 75 | 40 | 95 | 35 | 80 | 65 |
| Deadnettle | 70 | 65 | 100 | 70 | 100 | 10 | 20 | 75 | 35 | 70 | 100 | 75 | 15 | 100 | 90 | 65 | 50 |
| Field Poppy | 75 | 75 | 100 | 80 | 100 | 0 | 50 | 75 | 60 | 75 | 85 | 65 | 40 | 90 | 55 | 80 | 65 |
| Field Violet | 85 | 70 | 90 | 85 | 100 | 5 | 70 | 65 | 100 | 100 | 100 | 100 | 65 | 85 | 65 | 70 | 65 |
| Foxtail, Green | 35 | 35 | 45 | 45 | 50 | 0 | 0 | 15 | 15 | 20 | 40 | 35 | 20 | 45 | 20 | 20 | 30 |
| *Galium* | 90 | 80 | 98 | 85 | 85 | 40 | 70 | 70 | 75 | 80 | 100 | 80 | 75 | 98 | 40 | 80 | 75 |
| *Kochia* | 95 | 85 | 90 | 95 | 100 | 5 | 100 | 90 | 85 | 90 | 95 | 95 | 55 | 100 | 65 | 90 | 75 |
| Lambsquarters | 95 | 85 | 95 | 95 | 100 | 60 | 80 | 90 | 95 | 75 | 90 | 85 | 60 | 95 | 85 | 95 | 75 |
| Mustard, Wild | 100 | 100 | 98 | 100 | 100 | 35 | 75 | 70 | 100 | 80 | 100 | 95 | 75 | 100 | 75 | 85 | 75 |
| Oat, Wild | 40 | 25 | 10 | 40 | 25 | 0 | 0 | 15 | 40 | 35 | 35 | 30 | 5 | 15 | 15 | 35 | 25 |
| Oilseed Rape | 100 | 90 | 75 | 75 | 100 | 80 | 95 | 100 | 60 | 65 | 85 | 65 | 75 | 100 | 75 | 95 | 80 |
| Pigweed | 95 | 90 | 100 | 95 | 100 | 70 | 100 | 75 | 100 | 85 | 100 | 100 | 90 | 100 | 95 | 95 | 85 |
| Radish, Wild | 95 | 80 | 85 | 90 | 100 | 40 | — | 100 | 100 | 70 | 70 | 70 | 80 | 100 | 98 | 95 | 70 |
| Russian Thistle | — | — | 80 | — | 85 | 10 | 30 | 50 | — | — | — | — | — | 85 | 55 | — | — |
| Ryegrass, Italian | 40 | 15 | 20 | 35 | 15 | 0 | 0 | 5 | 10 | 5 | 20 | 10 | 0 | 20 | 10 | 25 | 5 |
| Speedwell | 100 | 100 | 100 | 100 | 100 | 45 | 100 | 100 | 100 | 95 | 100 | 75 | 75 | 100 | 100 | 100 | 100 |
| Wheat, Spring | 35 | 5 | 20 | 25 | 30 | 0 | 0 | 15 | 15 | 10 | 15 | 15 | 5 | 25 | 20 | 25 | 0 |
| Wheat, Winter | 40 | 10 | 10 | 30 | 20 | 0 | 0 | 10 | 5 | 15 | 20 | 15 | 5 | 20 | 10 | 30 | 0 |
| Windgrass | 55 | 20 | 25 | 35 | 30 | 0 | 0 | 10 | 20 | 20 | 35 | 25 | 15 | 50 | 5 | 35 | 15 |

| | Postemergence | | | | | | | | | | | | | | | |
|---|---|---|---|---|---|---|---|---|---|---|---|---|---|---|---|---|
| | 62 g ai/ha Compounds | | | 31 g ai/ha Compounds | | | | | | | | | | | | |
| | 245 | 274 | 284 | 3 | 7 | 18 | 25 | 52 | 58 | 59 | 138 | 141 | 145 | 166 | 178 | 245 | 274 |
| Barley, Spring | 20 | 30 | 15 | 0 | 0 | 5 | 5 | 10 | 15 | 10 | 10 | 20 | 0 | 20 | 5 | 20 | 25 |
| Barley, Winter | 20 | 25 | 15 | 0 | 0 | 10 | 0 | 10 | 10 | 10 | 5 | 20 | 15 | 15 | 0 | 15 | 20 |
| Blackgrass | 20 | 20 | 25 | 0 | 5 | 15 | 5 | 30 | 20 | 25 | 5 | 25 | 25 | 20 | 10 | 10 | 15 |

TABLE D-continued

| | | | | | | | | | | | | | | | | | |
|---|---|---|---|---|---|---|---|---|---|---|---|---|---|---|---|---|---|
| Bluegrass | 15 | 30 | 35 | 0 | 0 | 25 | 35 | 15 | 25 | 15 | 5 | 20 | 10 | 40 | 30 | 20 | 25 |
| Bromegrass, Downy | 25 | 35 | 40 | 0 | 0 | 15 | 15 | 15 | 25 | 20 | 0 | 20 | 25 | 20 | 5 | 20 | 25 |
| Buckwheat, Wild | 75 | 100 | 100 | 10 | 30 | 55 | 85 | 80 | 90 | 80 | 70 | 100 | 30 | 95 | 75 | 70 | 85 |
| Canarygrass | 25 | 25 | 20 | 0 | 0 | 15 | 20 | 35 | 35 | 20 | 10 | 25 | 15 | 35 | 15 | 20 | 20 |
| Chamomile | 45 | 25 | 0 | 0 | 0 | 10 | 0 | 10 | 10 | 5 | 0 | 20 | 0 | 5 | 0 | 30 | 10 |
| Chickweed | 95 | 70 | 85 | 0 | 10 | 40 | 65 | 60 | 70 | 70 | 20 | 90 | 30 | 65 | 60 | 75 | 65 |
| Deadnettle | 100 | 60 | 100 | 10 | 10 | 65 | 35 | 65 | 80 | 70 | 5 | 100 | 85 | 60 | 45 | 100 | 45 |
| Field Poppy | 80 | 40 | 70 | 0 | 20 | 75 | 25 | 60 | 80 | 70 | 35 | 95 | 25 | 60 | 55 | 95 | 40 |
| Field Violet | 90 | 70 | 85 | 5 | 20 | 80 | 75 | 100 | 100 | 100 | 50 | 75 | 45 | 65 | 60 | 80 | 75 |
| Foxtail, Green | 35 | 25 | 10 | 0 | 0 | 10 | 10 | 15 | 20 | 20 | 20 | 20 | 15 | 15 | 20 | 20 | 20 |
| *Galium* | 90 | 75 | 85 | 30 | 40 | 60 | 65 | 70 | 70 | 75 | 70 | 98 | 35 | 75 | 75 | 75 | 70 |
| *Kochia* | 90 | 90 | 100 | 5 | 70 | 85 | 70 | 80 | 95 | 95 | 40 | 85 | 50 | 65 | 70 | 70 | 70 |
| Lambsquarters | 85 | 95 | 98 | 20 | 70 | 50 | 80 | 80 | 75 | 90 | 60 | 95 | 70 | 90 | 70 | 80 | 80 |
| Mustard, Wild | 100 | 100 | 100 | 20 | 50 | 90 | 80 | 70 | 85 | 100 | 75 | 100 | 70 | 80 | 75 | 70 | 75 |
| Oat, Wild | 10 | 35 | 25 | 0 | 0 | 10 | 35 | 20 | 30 | 25 | 0 | 10 | 10 | 30 | 25 | 0 | 30 |
| Oilseed Rape | 60 | 65 | 70 | 80 | 80 | 70 | 75 | 55 | 55 | 65 | 70 | 95 | 60 | 65 | 65 | 45 | 55 |
| Pigweed | 100 | 95 | 100 | 70 | 90 | 75 | 100 | 80 | 90 | 100 | 70 | 98 | 90 | 85 | 80 | 95 | 95 |
| Radish, Wild | 55 | 70 | 100 | 30 | — | 90 | 60 | 65 | 65 | 35 | 65 | 95 | 100 | 70 | 65 | 45 | 70 |
| Russian Thistle | 70 | — | 75 | 10 | 0 | 5 | — | — | — | — | — | 40 | 55 | — | — | 75 | — |
| Ryegrass, Italian | 20 | 35 | 10 | 0 | 0 | 5 | 5 | 5 | 10 | 10 | 0 | 15 | 0 | 20 | 0 | 10 | 25 |
| Speedwell | 100 | 85 | 75 | 30 | 70 | 100 | 90 | 70 | 100 | 100 | 70 | 100 | 100 | 85 | 80 | 100 | 100 |
| Wheat, Spring | 10 | 15 | 25 | 0 | 0 | 10 | 5 | 5 | 10 | 10 | 5 | 20 | 15 | 10 | 0 | 10 | 15 |
| Wheat, Winter | 10 | 20 | 25 | 0 | 0 | 5 | 0 | 10 | 15 | 10 | 0 | 5 | 10 | 15 | 0 | 10 | 20 |
| Windgrass | 15 | 35 | 20 | 0 | 0 | 10 | 15 | 15 | 20 | 15 | 0 | 10 | 5 | 25 | 10 | 15 | 25 |

| | Postemergence | | | | | | | | | | | |
|---|---|---|---|---|---|---|---|---|---|---|---|---|
| | 31 g ai/ha Compound | 16 g ai/ha Compounds | | | | | | | | | | |
| | 284 | 3 | 7 | 18 | 25 | 138 | 141 | 145 | 166 | 178 | 245 | 274 |
| Barley, Spring | 5 | 50 | 0 | 5 | 0 | 10 | 10 | 0 | 10 | 0 | 10 | 20 |
| Barley, Winter | 15 | 50 | 0 | 10 | 0 | 5 | 20 | 5 | 5 | 0 | 25 | 10 |
| Blackgrass | 20 | 70 | 0 | 10 | 0 | 5 | 10 | 5 | 15 | 5 | 5 | 10 |
| Bluegrass | 25 | 40 | 0 | 15 | 5 | 0 | 5 | 15 | 20 | 20 | 10 | 20 |
| Bromegrass, Downy | 30 | 50 | 0 | 15 | 5 | 0 | 15 | 10 | 15 | 5 | 20 | 20 |
| Buckwheat, Wild | 100 | 50 | 20 | 60 | 80 | 65 | 100 | 10 | 70 | 65 | 70 | 65 |
| Canarygrass | 20 | 30 | 0 | 10 | 10 | 5 | 10 | 0 | 20 | 5 | 0 | 15 |
| Chamomile | 0 | 0 | 0 | 5 | 0 | 0 | 10 | 0 | 5 | 0 | 30 | 5 |
| Chickweed | 80 | 40 | 10 | 15 | 60 | 20 | 70 | 15 | 55 | 55 | 45 | 65 |
| Deadnettle | 70 | 10 | 10 | 50 | 15 | 5 | 100 | 85 | 40 | 40 | 100 | 50 |
| Field Poppy | 65 | 10 | 10 | 80 | 20 | 30 | 40 | 35 | 40 | 45 | 90 | 25 |
| Field Violet | 100 | 20 | 10 | 55 | 100 | 25 | 45 | 30 | 60 | 50 | 25 | — |
| Foxtail, Green | 10 | 10 | 0 | 10 | 5 | 20 | 15 | 5 | 10 | 15 | 10 | 15 |
| *Galium* | 70 | 40 | 20 | 40 | 55 | 70 | 95 | 35 | 70 | 75 | 70 | 70 |
| *Kochia* | 100 | 20 | 30 | 35 | 60 | 25 | 70 | 35 | 65 | 60 | 25 | 60 |
| Lambsquarters | 85 | 25 | 70 | 15 | 70 | 55 | 80 | 65 | 80 | 65 | 65 | 75 |
| Mustard, Wild | 100 | 75 | 20 | 60 | 65 | 65 | 80 | 65 | 75 | 70 | 80 | 70 |
| Oat, Wild | 20 | 70 | 0 | 10 | 20 | 5 | 5 | 5 | 25 | 20 | 0 | 20 |
| Oilseed Rape | 65 | 90 | 75 | 35 | 100 | 70 | 75 | 55 | 60 | 60 | 30 | 40 |
| Pigweed | 100 | 70 | 70 | 65 | 90 | 65 | 98 | 95 | 80 | 75 | 95 | 75 |
| Radish, Wild | 75 | 70 | — | 95 | 70 | 60 | 90 | 95 | 70 | 60 | 35 | 70 |
| Russian Thistle | 65 | 0 | 0 | 10 | — | — | 40 | 25 | — | — | 55 | — |
| Ryegrass, Italian | 10 | 60 | 0 | 5 | 0 | 5 | 5 | 0 | 10 | 0 | 0 | 15 |
| Speedwell | 70 | 60 | 30 | 100 | 70 | 70 | 100 | 100 | 70 | 70 | 100 | 75 |
| Wheat, Spring | 15 | 60 | 0 | 10 | 0 | 5 | 15 | 10 | 5 | 0 | 10 | 10 |
| Wheat, Winter | 10 | 65 | 0 | 5 | 0 | 0 | 5 | 5 | 5 | 0 | 5 | 10 |
| Windgrass | 20 | 70 | 0 | 5 | 10 | 0 | 5 | 0 | 15 | 5 | 10 | 15 |

| | Preemergence | | | | | | | | | | | | | | |
|---|---|---|---|---|---|---|---|---|---|---|---|---|---|---|---|
| | 250 g ai/ha Compounds | | | | | | | 125 g ai/ha Compounds | | | | | | | |
| | 3 | 7 | 18 | 52 | 58 | 59 | 284 | 3 | 7 | 18 | 25 | 52 | 58 | 59 | 138 | 141 | 145 |
| Barley, Spring | 0 | 0 | 30 | 50 | 100 | 75 | 35 | 0 | 0 | 0 | 0 | 10 | 85 | 50 | 15 | 90 | 20 |
| Barley, Winter | 20 | — | 25 | 35 | 100 | 80 | 20 | 10 | — | 15 | 5 | 5 | 80 | 40 | 15 | 90 | 60 |
| Blackgrass | 0 | 15 | 100 | 95 | 100 | 85 | 65 | 0 | 0 | 100 | 55 | 30 | 100 | 70 | 30 | 95 | 90 |
| Bluegrass | 40 | 40 | 100 | 60 | 100 | 85 | 25 | 20 | 30 | 100 | 15 | 10 | 100 | 35 | 10 | 90 | 85 |
| Bromegrass, Downy | 0 | 0 | 50 | 0 | 75 | 40 | 10 | 0 | 0 | 10 | 0 | 0 | 35 | 10 | 10 | 95 | 55 |
| Buckwheat, Wild | 100 | 90 | 100 | 100 | 100 | 100 | 100 | 60 | 80 | 100 | 50 | 100 | 100 | 100 | 75 | 100 | 100 |
| Canarygrass | 25 | 25 | 100 | 55 | 100 | 100 | 60 | 0 | 0 | 100 | 30 | 35 | 100 | 65 | 40 | 100 | 80 |
| Chamomile | 40 | 25 | 55 | 80 | 100 | 85 | 100 | 20 | 20 | 50 | 15 | 60 | 80 | 95 | — | 100 | 100 |
| Chickweed | 90 | 95 | 100 | 100 | 100 | 95 | 30 | — | 90 | 90 | 100 | 100 | 100 | 100 | 100 | 100 | 100 |
| Deadnettle | 50 | 80 | 100 | 100 | 100 | 100 | 100 | 40 | 20 | 70 | 100 | 100 | 100 | 100 | 30 | 100 | 100 |
| Field Poppy | 80 | 100 | 100 | 100 | 100 | 100 | 100 | 70 | 60 | 95 | 100 | 90 | 100 | 100 | 100 | 100 | 100 |
| Field Violet | 85 | 80 | 90 | 100 | 100 | 100 | 100 | 85 | 70 | 85 | 60 | 100 | 100 | 100 | 75 | 100 | 100 |
| Foxtail, Green | 30 | 20 | 100 | 100 | 100 | 100 | 80 | 10 | 0 | 95 | 50 | 100 | 100 | 100 | 100 | 100 | 85 |

TABLE D-continued

| | | | | | | | | | | | | | | | | |
|---|---|---|---|---|---|---|---|---|---|---|---|---|---|---|---|---|
| *Galium* | 100 | 40 | 100 | 70 | 100 | 100 | 25 | 70 | 30 | 100 | 65 | 75 | 100 | 60 | 100 | 100 | 90 |
| *Kochia* | 50 | 70 | 100 | 95 | 95 | 100 | 95 | 30 | 0 | 100 | 100 | 95 | 95 | 100 | 55 | 100 | 100 |
| Lambsquarters | 50 | 60 | 100 | 100 | 100 | 100 | 100 | 25 | 40 | 100 | 95 | 100 | 100 | 95 | 100 | 100 | 100 |
| Mustard, Wild | 100 | 100 | 100 | 100 | 100 | 100 | 100 | 90 | 90 | 90 | 100 | 90 | 100 | 100 | 100 | 100 | 100 |
| Oat, Wild | 10 | 10 | 30 | 20 | 100 | 55 | 50 | 0 | 10 | 5 | 15 | 0 | 60 | 20 | 0 | 98 | 75 |
| Oilseed Rape | 100 | 100 | 100 | 100 | 100 | 100 | 10 | 100 | 100 | 100 | 70 | 100 | 100 | 100 | 65 | 100 | 100 |
| Pigweed | 100 | 90 | 100 | 100 | 100 | 100 | 100 | 80 | 90 | 100 | 100 | 100 | 100 | 100 | 100 | 100 | 100 |
| Radish, Wild | 95 | — | 100 | 100 | 100 | 100 | 35 | 90 | — | 100 | 100 | 95 | 100 | 95 | 85 | 100 | 100 |
| Russian Thistle | 40 | 0 | 95 | — | — | — | 30 | 40 | 0 | 40 | — | — | — | — | — | 100 | 50 |
| Ryegrass, Italian | 0 | 5 | 50 | 50 | 100 | 70 | 30 | 0 | 0 | 25 | 10 | 5 | 100 | 60 | 10 | 75 | 65 |
| Speedwell | 100 | 100 | — | 100 | 100 | 100 | 100 | 100 | 100 | — | — | 100 | 100 | 100 | 100 | 100 | 100 |
| Wheat, Spring | 0 | 0 | 15 | 30 | 100 | 55 | 30 | 0 | 0 | 5 | 0 | 0 | 75 | 40 | 15 | 75 | 20 |
| Wheat, Winter | 0 | 10 | 40 | 35 | 90 | 35 | 25 | 0 | 5 | 5 | 0 | 25 | 50 | 5 | 5 | 60 | 20 |
| Windgrass | 20 | 30 | 100 | 100 | 100 | 100 | 55 | 10 | 0 | 100 | 80 | 100 | 100 | 100 | 15 | 100 | 80 |

| | Preemergence | | | | | | | | | | | | | | | |
|---|---|---|---|---|---|---|---|---|---|---|---|---|---|---|---|---|
| | 125 g ai/ha Compounds | | | | | 62 g ai/ha Compounds | | | | | | | | | | |
| | 166 | 178 | 245 | 274 | 284 | 3 | 7 | 18 | 25 | 52 | 58 | 59 | 138 | 141 | 145 | 166 | 178 |
| Barley, Spring | 60 | — | 35 | 15 | 25 | 0 | 0 | 5 | 0 | 10 | 50 | 5 | 10 | 65 | 15 | 30 | — |
| Barley, Winter | 50 | — | 40 | 55 | 15 | 0 | — | 15 | 0 | 0 | 35 | 10 | 5 | 65 | 20 | 35 | — |
| Blackgrass | 95 | 85 | 65 | 95 | 35 | 0 | 0 | 50 | 25 | 5 | 55 | 55 | 25 | 90 | 80 | 70 | 35 |
| Bluegrass | 100 | 70 | 20 | 70 | 20 | 0 | 0 | 70 | 0 | 0 | 50 | 10 | 0 | 90 | 40 | 65 | 20 |
| Bromegrass, Downy | 50 | 10 | 40 | 35 | 0 | 0 | 0 | 5 | 0 | 0 | 15 | 0 | 0 | 85 | 50 | 25 | 0 |
| Buckwheat, Wild | 100 | 100 | 35 | 100 | 70 | 0 | 75 | 80 | 25 | 50 | 100 | 100 | 55 | 100 | 80 | 100 | 100 |
| Canarygrass | 100 | 95 | 35 | 85 | 35 | 0 | 0 | 65 | 20 | 0 | 55 | 15 | 20 | 100 | 75 | 70 | 60 |
| Chamomile | 55 | 60 | 100 | 65 | 100 | 0 | 0 | 520 | 15 | 65 | 50 | 15 | — | 70 | 98 | 50 | 55 |
| Chickweed | 100 | 90 | 100 | 100 | 20 | 0 | 10 | — | 100 | 100 | 100 | 100 | 100 | 100 | 100 | 95 | 85 |
| Deadnettle | 100 | 100 | 15 | 100 | 75 | 40 | 10 | 55 | 5 | 75 | 100 | 100 | 20 | 98 | 70 | 100 | 75 |
| Field Poppy | 100 | 85 | 100 | 100 | 100 | 40 | 30 | 85 | 75 | 80 | 100 | 100 | 100 | 100 | 100 | 100 | 85 |
| Field Violet | 100 | 100 | 100 | 100 | 100 | 80 | 20 | 85 | 30 | 95 | 100 | 85 | 70 | 100 | 100 | 100 | 90 |
| Foxtail, Green | 100 | 95 | 35 | 100 | 10 | 10 | 0 | 50 | 20 | 60 | 100 | 100 | 20 | 100 | 25 | 100 | 5 |
| *Galium* | 100 | 60 | 85 | 100 | 20 | 10 | 20 | 80 | 50 | 20 | 100 | 95 | 90 | 100 | 85 | 100 | 45 |
| *Kochia* | 100 | 100 | 75 | 100 | 100 | 30 | 0 | 75 | 55 | 95 | 95 | 80 | 35 | 100 | 100 | 95 | 85 |
| Lambsquarters | 100 | 85 | 100 | 100 | 100 | 0 | 30 | 100 | 80 | 100 | 100 | 100 | 60 | 100 | 100 | 100 | 80 |
| Mustard, Wild | 100 | 95 | 100 | 100 | 90 | 80 | 80 | 100 | 80 | 55 | 100 | 100 | 100 | 100 | 95 | 100 | 95 |
| Oat, Wild | 75 | 25 | 15 | 25 | 20 | 0 | 0 | 0 | 0 | 0 | 25 | 0 | 0 | 80 | 55 | 55 | 10 |
| Oilseed Rape | 100 | 100 | 100 | 75 | 10 | 70 | 25 | 100 | 60 | 80 | 100 | 60 | 50 | 100 | 100 | 100 | — |
| Pigweed | 100 | 100 | 100 | 100 | 100 | 40 | 90 | 100 | 100 | 100 | 100 | 100 | 100 | 100 | 100 | 100 | 100 |
| Radish, Wild | 100 | 100 | 85 | 85 | 0 | 60 | — | 100 | 90 | 80 | 100 | 100 | 70 | 100 | 85 | 100 | 100 |
| Russian Thistle | — | — | 70 | — | 20 | 30 | 0 | 25 | — | — | — | — | — | 75 | 30 | — | — |
| Ryegrass, Italian | 85 | 20 | 40 | 70 | 0 | 0 | 0 | 20 | 10 | 0 | 35 | 5 | 0 | 70 | 25 | 60 | 15 |
| Speedwell | 100 | 100 | 100 | 100 | 100 | 100 | 100 | — | — | 100 | 100 | 100 | 100 | 100 | 100 | 100 | 100 |
| Wheat, Spring | 60 | — | 20 | 55 | 20 | 0 | 0 | 0 | 0 | 0 | 15 | 5 | 15 | 65 | 20 | 10 | — |
| Wheat, Winter | 25 | — | 30 | 35 | 20 | 0 | 0 | 5 | 0 | 0 | 20 | 5 | 5 | 60 | 10 | 0 | — |
| Windgrass | 100 | 95 | 60 | 100 | 45 | 0 | 0 | 75 | 25 | 70 | 100 | 100 | 0 | 85 | 65 | 100 | 70 |

| | Preemergence | | | | | | | | | | | | | | | |
|---|---|---|---|---|---|---|---|---|---|---|---|---|---|---|---|---|
| | 62 g ai/ha Compounds | | | 31 g ai/ha Compounds | | | | | | | | | | | | |
| | 245 | 274 | 284 | 3 | 7 | 18 | 25 | 52 | 58 | 59 | 138 | 141 | 145 | 166 | 178 | 245 | 274 |
| Barley, Spring | 15 | 10 | 15 | 0 | 0 | 5 | 0 | 5 | 10 | 5 | 10 | 20 | 0 | 0 | — | 5 | 0 |
| Barley, Winter | 25 | 10 | 0 | 0 | — | 10 | 0 | 0 | 10 | 0 | 0 | 35 | 5 | 0 | — | 35 | 0 |
| Blackgrass | 10 | 70 | 10 | 0 | 0 | 5 | 15 | 5 | 20 | 25 | 0 | 65 | 15 | 55 | 10 | 0 | 30 |
| Bluegrass | 0 | 30 | 15 | 0 | 0 | 30 | 0 | 0 | 10 | 5 | 0 | 35 | 20 | 20 | 10 | 0 | 5 |
| Bromegrass, Downy | 35 | 5 | 0 | 0 | 0 | 0 | 0 | 0 | 10 | 0 | 0 | 45 | 30 | 5 | 0 | 0 | 5 |
| Buckwheat, Wild | 25 | 100 | 20 | 0 | 0 | 70 | 10 | 10 | 100 | 60 | 35 | 100 | 25 | 95 | 55 | 0 | 100 |
| Canarygrass | 15 | 60 | 25 | 0 | 0 | 25 | 20 | 0 | 20 | 5 | 10 | 75 | 45 | 50 | 60 | 0 | 20 |
| Chamomile | 55 | 35 | 100 | 0 | 0 | 5 | 5 | 15 | 30 | 10 | — | 100 | 85 | 25 | 70 | 30 | — |
| Chickweed | 100 | 100 | 15 | — | 0 | — | 75 | 100 | 100 | 100 | 100 | 100 | 100 | 95 | 50 | 85 | 85 |
| Deadnettle | 0 | 100 | 45 | 30 | 0 | 5 | 5 | 70 | 100 | 100 | 5 | 100 | 55 | 75 | 60 | 0 | 100 |
| Field Poppy | 100 | 100 | 100 | — | 0 | 70 | 70 | 95 | 95 | 95 | 100 | 100 | 100 | 100 | 70 | 100 | 100 |
| Field Violet | 100 | 100 | 100 | 80 | 0 | 70 | 25 | 75 | 100 | 65 | 25 | 100 | 90 | 100 | — | 95 | 100 |
| Foxtail, Green | 0 | 100 | 5 | — | 0 | 15 | 15 | 20 | 100 | 35 | 0 | 100 | 5 | 65 | 0 | 0 | 75 |
| *Galium* | 5 | 100 | 20 | 0 | 0 | 15 | 15 | 10 | 65 | 0 | 40 | 100 | 15 | 80 | 30 | 0 | 60 |

TABLE D-continued

| | | | | | | | | | | | | | | | | | |
|---|---|---|---|---|---|---|---|---|---|---|---|---|---|---|---|---|---|
| Kochia | 75 | 65 | 20 | 30 | 0 | 90 | 15 | 95 | 95 | 90 | 20 | 100 | 95 | 65 | 35 | 0 | 70 |
| Lambsquarters | 100 | 100 | 100 | 0 | 0 | 80 | 25 | 80 | 100 | 95 | 10 | 100 | 100 | 95 | 70 | 100 | 90 |
| Mustard, Wild | 85 | 95 | 15 | 80 | 20 | 85 | 0 | 20 | 90 | 15 | 65 | 100 | 100 | 95 | 35 | 80 | 25 |
| Oat, Wild | 20 | 15 | 0 | 0 | 0 | 0 | 0 | 0 | 15 | 0 | 0 | 65 | 15 | 30 | 0 | 5 | 0 |
| Oilseed Rape | 30 | 65 | 0 | 75 | 10 | 30 | 10 | 0 | 100 | 65 | 30 | 100 | 70 | 50 | 75 | 0 | 30 |
| Pigweed | 100 | 100 | 100 | 0 | 30 | 100 | 95 | 100 | 100 | 100 | 25 | 100 | 100 | 100 | 100 | 100 | 100 |
| Radish, Wild | 0 | 40 | 0 | 20 | — | 100 | 20 | 30 | 100 | 95 | 85 | 98 | 75 | 80 | 90 | 0 | 5 |
| Russian Thistle | 30 | — | 10 | 0 | 0 | 10 | — | — | — | — | — | 50 | 15 | — | — | 10 | — |
| Ryegrass, Italian | 20 | 50 | 0 | 0 | 0 | 10 | 0 | 0 | 10 | 0 | 0 | 55 | 15 | 40 | 0 | 15 | 0 |
| Speedwell | 100 | 100 | 100 | 100 | 50 | — | — | 100 | 100 | 15 | 100 | 100 | 100 | 100 | 100 | 100 | 100 |
| Wheat, Spring | 20 | 10 | 10 | 0 | 0 | 0 | 0 | 0 | 0 | 0 | 10 | 30 | 15 | 0 | — | 10 | 0 |
| Wheat, Winter | 20 | 5 | 15 | 0 | 0 | 0 | 0 | 0 | 0 | 0 | 5 | 20 | 0 | 0 | — | 15 | 0 |
| Windgrass | 35 | 100 | 35 | 0 | 0 | 20 | 5 | 50 | 100 | 70 | 0 | 70 | 35 | 75 | 75 | 15 | 90 |

| | Preemergence | | | | | | | | | | | |
|---|---|---|---|---|---|---|---|---|---|---|---|---|
| | 31 g ai/ha Compound | 16 g ai/ha Compounds | | | | | | | | | | |
| | 284 | 3 | 7 | 18 | 25 | 138 | 141 | 145 | 166 | 178 | 245 | 274 |
| Barley, Spring | 10 | 0 | 0 | 0 | 0 | 10 | 15 | 5 | 0 | — | 0 | 0 |
| Barley, Winter | 0 | 0 | — | 0 | 0 | 0 | 15 | 0 | 0 | — | 0 | 0 |
| Blackgrass | 0 | 0 | 0 | 0 | 20 | 0 | 40 | 0 | 10 | 5 | 0 | 10 |
| Bluegrass | 0 | 0 | 0 | 10 | 0 | 0 | 15 | 0 | 5 | 0 | 0 | 0 |
| Bromegrass, Downy | 0 | 0 | 0 | 0 | 0 | 0 | 30 | 15 | 5 | 0 | 0 | 0 |
| Buckwheat, Wild | 10 | 0 | 0 | 10 | 10 | 60 | 100 | 0 | 60 | 15 | 25 | 10 |
| Canarygrass | 30 | 0 | 0 | 10 | 20 | 10 | 35 | 40 | 30 | 10 | 0 | 20 |
| Chamomile | 100 | — | 0 | 5 | 0 | — | 90 | 30 | 5 | 0 | 25 | 5 |
| Chickweed | 10 | 0 | 0 | — | 50 | 100 | 100 | 75 | 85 | 0 | 55 | 60 |
| Deadnettle | 35 | 30 | 0 | 10 | 5 | 5 | 90 | 35 | 70 | 50 | 0 | 55 |
| Field Poppy | 100 | 40 | 0 | — | 0 | 100 | 98 | 90 | 100 | 20 | 100 | 75 |
| Field Violet | 45 | 40 | 0 | 65 | 25 | 70 | 100 | 60 | 70 | 20 | 55 | 75 |
| Foxtail, Green | 10 | 10 | 0 | 5 | 0 | 0 | 10 | 5 | 25 | 0 | 0 | 15 |
| Galium | 20 | 0 | 0 | 0 | 20 | 25 | 75 | 10 | 65 | 10 | 0 | 0 |
| Kochia | 0 | 0 | 0 | 15 | 15 | 20 | 85 | 5 | 35 | 0 | 0 | 0 |
| Lambsquarters | 30 | 0 | 0 | 70 | 25 | 45 | 100 | 85 | 85 | 20 | 85 | 20 |
| Mustard, Wild | 15 | 30 | 20 | 80 | 0 | 55 | 90 | 90 | 65 | 25 | 80 | 15 |
| Oat, Wild | 0 | 0 | 0 | 0 | 0 | 0 | 30 | 0 | 0 | 0 | 0 | 0 |
| Oilseed Rape | 0 | 10 | 0 | 40 | 5 | 35 | 100 | 35 | 35 | 65 | 0 | 35 |
| Pigweed | 75 | 0 | 0 | 30 | 60 | 0 | 98 | 100 | 100 | 75 | 98 | 70 |
| Radish, Wild | 0 | 0 | — | 100 | 10 | 90 | 40 | 75 | 55 | 55 | 0 | 5 |
| Russian Thistle | 0 | 0 | — | — | — | — | 15 | 0 | — | — | 5 | — |
| Ryegrass, Italian | 0 | 0 | 0 | 10 | 0 | 0 | 35 | 0 | 20 | 0 | 15 | 0 |
| Speedwell | 0 | 100 | 20 | 50 | — | 70 | 100 | 35 | 100 | 100 | 5 | 100 |
| Wheat, Spring | 10 | 0 | 0 | 0 | 0 | 0 | 25 | 15 | 0 | — | 5 | 0 |
| Wheat, Winter | 15 | 0 | 0 | 0 | 0 | 0 | 15 | 0 | 0 | — | 10 | 0 |
| Windgrass | 20 | 0 | 0 | 5 | 0 | 0 | 35 | 15 | 50 | 75 | 5 | 20 |

Test E

Seeds of plant species selected from corn (*Zea mays*), soybean (*Glycine max*), velvetleaf (*Abutilon theophrasti*), lambsquarters (*Chenopodium album*), wild poinsettia (*Euphorbia heterophylla*), palmer pigweed (*Amaranthus palmeri*), waterhemp (common waterhemp, *Amaranthus rudis*), surinam grass (*Brachiaria decumbens*), large (Lg) crabgrass (*Digitaria sanguinalis*), Brazilian crabgrass (*Digitaria horizontalis*), fall *panicum* (*Panicum dichotomiflorum*), giant foxtail (*Setaria faberii*), green foxtail (*Setaria viridis*), goosegrass (*Eleusine indica*), johnsongrass (*Sorghum halepense*), ragweed (common ragweed, *Ambrosia elatior*), barnyardgrass (*Echinochloa crus-galli*), sandbur (southern sandbur, *Cenchrus echinatus*), arrowleaf *sida* (*Sida rhombifolia*), Italian ryegrass (*Lolium multiflorum*), dayflower (Virginia (VA) dayflower, *Commelina virginica*), field bindweed (*Convolvulus arvensis*), morningglory (*Ipomoea coccinea*), nightshade (eastern black nightshade, *Solanum ptycanthum*), kochia (*Kochia scoparia*), yellow nutsedge (*Cyperus esculentus*), cocklebur (common cocklebur, *Xanthium strumarium*), smartweed (ladysthumb smartweed, and hairy beggarticks (*Bidens pilosa*), were planted into a silt loam soil and treated preemergence with test chemicals formulated in a non-phytotoxic solvent mixture which included a surfactant.

At the same time, plants from these crop and weed species and also horseweed (Canada horseweed, *Conyza canadensis*), waterhemp_RES1, (ALS & Triazine resistant common waterhemp, *Amaranthus rudis*), and waterhemp_RES2, (ALS & HPPD resistant common waterhemp, *Amaranthus rudis*) were planted in pots containing Redi-Earth® planting medium (Scotts Company, 14111 Scottslawn Road, Marysville, Ohio 43041) comprising spaghnum peat moss, vermiculite, wetting agent and starter nutrients were treated with postemergence applications of test chemicals formulated in the same manner. Plants ranged in height from 2 to 18 cm for postemergence treatments (1- to 4-leaf stage). Treated plants and controls were maintained in a greenhouse for 14 to 21 days, after which time all species were compared to controls and visually evaluated. Plant response ratings, summarized in Table E, are based on a scale of 0 to 100 where 0 is no effect and 100 is complete control. A dash (-) response means no test result.

TABLE E

| 250 g ai/ha | Compounds | | | | | | |
|---|---|---|---|---|---|---|---|
| | 5 | 10 | 16 | 25 | 58 | 59 | 200 |
| Postemergence | | | | | | | |
| Arrowleaf Sida | 85 | 85 | 90 | 95 | 98 | 90 | 98 |
| Barnyardgrass | 10 | 0 | 15 | 15 | 70 | 30 | 40 |
| Beggarticks | 70 | 80 | 60 | 50 | 95 | 95 | 95 |
| Corn | 0 | 0 | 15 | 15 | 15 | 15 | 25 |
| Crabgrass, Brazil | 20 | 5 | 40 | 35 | 75 | 50 | 60 |
| Dayflower, VA | 75 | 75 | 40 | 75 | 100 | 100 | 70 |
| Field Bindweed | 40 | 50 | 60 | 70 | 80 | 80 | 95 |
| *Panicum*, Fall | 0 | 0 | 25 | 40 | 60 | 45 | 50 |
| Pigweed, Palmer | 98 | 95 | — | 100 | 100 | 100 | 100 |
| Poinsettia, Wild | 50 | 60 | 80 | 70 | 90 | 80 | 90 |
| Ryegrass, Italian | 0 | 0 | 0 | 5 | 60 | 60 | 0 |
| Sandbur | 20 | 0 | 0 | 15 | 55 | 20 | 10 |
| Smartweed | — | — | — | — | 100 | 100 | — |
| Soybean | 95 | 95 | 95 | 98 | 100 | 98 | 98 |
| Waterhemp | 98 | 95 | 90 | 100 | 100 | 100 | 100 |
| Waterhemp_RES1 | — | — | 95 | — | 100 | 100 | 100 |
| Waterhemp_RES2 | 95 | 90 | 85 | — | 100 | 100 | 100 |

| 125 g ai/ha | Compounds | | | | | | | | | | | | | |
|---|---|---|---|---|---|---|---|---|---|---|---|---|---|---|
| | 5 | 7 | 10 | 16 | 25 | 52 | 58 | 59 | 65 | 72 | 79 | 181 | 191 | 200 |
| Postemergence | | | | | | | | | | | | | | |
| Arrowleaf Sida | 80 | 95 | 80 | 80 | 90 | 70 | 95 | 85 | 80 | 75 | 98 | 95 | 100 | 90 |
| Barnyardgrass | 0 | 10 | 0 | 10 | 10 | 30 | 30 | 15 | 0 | 10 | 20 | 25 | 0 | 20 |
| Beggarticks | 60 | 60 | 50 | 50 | 50 | 75 | 90 | 70 | 50 | 80 | 80 | 60 | 50 | 90 |
| Corn | 0 | 5 | 0 | 10 | 10 | 25 | 10 | 10 | 10 | 10 | 15 | 15 | 15 | 20 |
| Crabgrass, Brazil | 10 | 30 | 0 | 30 | 20 | 40 | 55 | 25 | 15 | 20 | 30 | 30 | 20 | 50 |
| Dayflower, VA | 40 | 90 | 50 | 30 | 70 | 60 | 90 | 70 | 20 | 60 | 50 | 60 | 10 | 60 |
| Field Bindweed | 30 | 70 | 40 | 50 | 60 | 65 | 70 | 70 | 40 | 80 | 80 | 50 | 50 | 95 |
| Horseweed | — | — | — | — | — | — | — | — | — | — | 30 | 5 | — | — |
| *Kochia* | — | — | — | — | 80 | — | — | — | — | — | 75 | 90 | — | — |
| *Panicum*, Fall | 0 | 0 | 0 | 20 | 40 | 40 | 60 | 30 | 15 | 10 | 30 | 30 | 20 | 50 |
| Pigweed, Palmer | 95 | 85 | 85 | — | 75 | 95 | 100 | 100 | 60 | 90 | 90 | 98 | 85 | 98 |
| Poinsettia, Wild | 35 | 60 | 30 | 70 | 60 | 70 | — | 65 | 40 | 60 | 60 | 60 | 60 | 90 |
| Ragweed | — | — | — | — | — | 60 | — | — | — | — | 60 | 50 | — | — |
| Ryegrass, Italian | 0 | 0 | 0 | 0 | 0 | 10 | 35 | 25 | 0 | 5 | 0 | 20 | 0 | 0 |
| Sandbur | 10 | 0 | 0 | 0 | 5 | 20 | 20 | 10 | 0 | 0 | 10 | 20 | 10 | 0 |
| Smartweed | — | 100 | — | — | — | 100 | 100 | — | — | — | — | — | — | — |
| Soybean | 80 | 98 | 90 | 95 | 80 | 95 | 95 | 95 | 98 | 95 | 95 | 95 | 95 | 95 |
| Waterhemp | 95 | 90 | 95 | 90 | 85 | 95 | 100 | 90 | 95 | 98 | 100 | 98 | 95 | 95 |
| Waterhemp_RES1 | — | 90 | — | 75 | — | — | 95 | 95 | 98 | 95 | 100 | 95 | 95 | 100 |
| Waterhemp_RES2 | 90 | 95 | 80 | 70 | — | 90 | 95 | 95 | 98 | 90 | 95 | 100 | 100 | 100 |

| 125 g ai/ha | Compounds | |
|---|---|---|
| | 223 | 274 |
| Postemergence | | |
| Arrowleaf Sida | 90 | 85 |
| Barnyardgrass | 0 | 60 |
| Beggarticks | 85 | 95 |
| Corn | 5 | 15 |
| Crabgrass, Brazil | 20 | 50 |
| Dayflower, VA | 65 | 70 |
| Field Bindweed | 50 | 75 |
| Horseweed | — | — |
| *Kochia* | — | — |
| *Panicum*, Fall | 0 | 20 |
| Pigweed, Palmer | 85 | 100 |
| Poinsettia, Wild | 60 | 70 |
| Ragweed | — | — |
| Ryegrass, Italian | 0 | 40 |
| Sandbur | 0 | 0 |
| Smartweed | — | — |
| Soybean | 98 | 95 |
| Waterhemp | 98 | 98 |

TABLE E-continued

|  |  |  |  |  |  |  |  |  |  |  |  |  |  |  |
|---|---|---|---|---|---|---|---|---|---|---|---|---|---|---|
| Waterhemp_RES1 |  |  |  |  |  |  | 95 |  |  |  | 100 |  |  |  |
| Waterhemp_RES2 |  |  |  |  |  |  | 95 |  |  |  | 100 |  |  |  |

| | Compounds |
|---|---|
| 62 g ai/ha | 5 | 7 | 10 | 16 | 25 | 52 | 58 | 59 | 65 | 72 | 79 | 181 | 191 | 200 |

| Postemergence |
|---|

| | | | | | | | | | | | | | | |
|---|---|---|---|---|---|---|---|---|---|---|---|---|---|---|
| Arrowleaf Sida | 70 | 90 | 70 | 75 | 80 | 70 | 90 | 80 | 80 | 50 | 85 | 70 | 70 | 80 |
| Barnyardgrass | 0 | 10 | 0 | 0 | 10 | 20 | 20 | 10 | 0 | 0 | 10 | 15 | 0 | 0 |
| Beggarticks | 60 | 50 | 40 | 50 | 40 | 70 | 80 | 60 | 50 | 70 | 75 | 50 | 50 | 70 |
| Corn | 0 | 10 | 0 | 0 | 10 | 20 | 20 | 10 | 10 | 15 | 10 | 15 | 10 | 15 |
| Crabgrass, Brazil | 10 | 20 | 0 | 10 | 20 | 30 | 40 | 20 | 10 | 10 | 20 | 30 | 10 | 30 |
| Dayflower, VA | 10 | 70 | 40 | 15 | 60 | 50 | 75 | 50 | 10 | 50 | 50 | 40 | 10 | 40 |
| Field Bindweed | 30 | 50 | 30 | 40 | 50 | 65 | 70 | 65 | 40 | 70 | 80 | 40 | 40 | 90 |
| Horseweed | — | — | — | — | — | — | — | — | — | — | 20 | 5 | — | — |
| *Kochia* | — | — | — | — | — | 55 | — | — | — | — | 80 | 50 | — | — |
| *Panicum*, Fall | 0 | 50 | 0 | 10 | 30 | 10 | 40 | 20 | 0 | 10 | 30 | 50 | 10 | 20 |
| Pigweed, Palmer | 85 | 75 | 75 | — | 70 | 95 | 100 | 85 | 50 | 75 | 95 | 90 | 75 | 75 |
| Poinsettia, Wild | 30 | 60 | 30 | 60 | 50 | 50 | — | 60 | 20 | 55 | 50 | 50 | 50 | 70 |
| Ragweed | — | — | — | — | — | 55 | — | — | — | — | 50 | 30 | — | — |
| Ryegrass, Italian | 0 | 0 | 0 | 0 | 0 | 0 | 20 | 15 | 0 | 0 | 0 | 10 | 0 | 0 |
| Sandbur | 0 | 0 | 0 | 0 | 0 | 25 | 10 | 0 | 0 | 0 | 0 | 10 | 0 | 0 |
| Smartweed | — | 70 | — | — | — | — | 85 | 80 | — | — | — | — | — | — |
| Soybean | 70 | 98 | 75 | 80 | 80 | 90 | 95 | 95 | 50 | 95 | 95 | 90 | 50 | 95 |
| Waterhemp | 90 | 90 | 85 | 85 | 80 | 75 | 95 | 90 | 75 | 80 | 85 | 95 | 90 | 95 |
| Waterhemp_RES1 | — | 95 | — | 60 | — | — | 95 | 90 | 90 | 75 | 75 | 90 | 90 | 90 |
| Waterhemp_RES2 | 80 | 90 | 75 | 60 | — | 95 | 90 | 90 | 95 | 80 | 90 | 98 | 95 | 90 |

| | Compounds |
|---|---|
| 62 g ai/ha | 223 | 274 |

| Postemergence |
|---|

| | | |
|---|---|---|
| Arrowleaf Sida | 80 | 75 |
| Barnyardgrass | 0 | 10 |
| Beggarticks | 75 | 70 |
| Corn | 0 | 10 |
| Crabgrass, Brazil | 10 | 35 |
| Dayflower, VA | 55 | 40 |
| Field Bindweed | 50 | 70 |
| Horseweed | — | — |
| *Kochia* | — | — |
| *Panicum*, Fall | 0 | 50 |
| Pigweed, Palmer | 60 | 95 |
| Poinsettia, Wild | 50 | 70 |
| Ragweed | — | — |
| Ryegrass, Italian | 0 | 10 |
| Sandbur | 0 | 15 |
| Smartweed | — | — |
| Soybean | 98 | 95 |
| Waterhemp | 85 | 95 |
| Waterhemp_RES1 | 70 | 90 |
| Waterhemp_RES2 | 80 | 95 |

| | Compounds |
|---|---|
| 31 g ai/ha | 5 | 7 | 10 | 16 | 25 | 52 | 58 | 59 | 65 | 79 | 181 | 191 | 200 | 223 |

| Postemergence |
|---|

| | | | | | | | | | | | | | | |
|---|---|---|---|---|---|---|---|---|---|---|---|---|---|---|
| Arrowleaf Sida | 60 | 80 | 50 | 70 | 70 | 60 | 80 | 70 | 60 | 75 | 75 | 70 | 80 | 70 |
| Barnyardgrass | 0 | 0 | 0 | 0 | 10 | 10 | 5 | 0 | 0 | 0 | 20 | 0 | 0 | 0 |
| Beggarticks | 40 | 40 | 30 | 30 | 30 | 60 | 65 | 60 | 40 | 50 | 40 | 40 | 60 | 60 |
| Corn | 0 | 0 | 0 | 0 | 10 | 10 | 10 | 5 | 0 | 0 | 5 | 10 | 10 | 0 |
| Crabgrass, Brazil | 5 | 10 | 0 | 0 | 10 | 30 | 20 | 15 | 10 | 10 | 20 | 10 | 15 | 10 |
| Dayflower, VA | 10 | 50 | 10 | 10 | 60 | 40 | 60 | 35 | 10 | 30 | 30 | 5 | 25 | 25 |
| Field Bindweed | 20 | 30 | 30 | 30 | 50 | 50 | 60 | 60 | 20 | 70 | 40 | 50 | 70 | 35 |
| Horseweed | — | — | — | — | — | — | — | — | — | 0 | 0 | — | — | — |
| *Kochia* | — | — | — | — | — | 50 | — | — | — | 70 | 60 | — | — | — |
| *Panicum*, Fall | — | 15 | 0 | 0 | 30 | 10 | 30 | 20 | 5 | 35 | 20 | 5 | 10 | 0 |
| Pigweed, Palmer | 75 | 50 | 70 | — | 50 | 70 | 95 | 80 | 50 | 50 | 70 | 75 | 70 | 50 |
| Poinsettia, Wild | 20 | 30 | 20 | 60 | 50 | 40 | — | 50 | 20 | 40 | 50 | 50 | 80 | 40 |
| Ragweed | — | — | — | — | — | 50 | — | — | — | 40 | 25 | — | — | — |
| Ryegrass, Italian | 0 | 0 | 0 | 0 | 0 | 10 | 0 | 0 | — | 5 | 0 | 0 | 0 | 0 |
| Sandbur | 0 | 0 | 0 | 0 | 0 | 10 | 10 | 0 | 0 | 15 | 0 | 0 | 0 | 0 |
| Smartweed | — | 40 | — | — | — | 65 | — | — | — | — | — | — | — | — |
| Soybean | 30 | 90 | 50 | 30 | 80 | 75 | 95 | 65 | 20 | 70 | 80 | 60 | 95 | 95 |

TABLE E-continued

| | | | | | | | | | | | | | | |
|---|---|---|---|---|---|---|---|---|---|---|---|---|---|---|
| Waterhemp | 80 | 90 | 80 | 60 | 80 | 70 | 85 | 65 | 70 | 90 | 95 | 90 | 90 | 70 |
| Waterhemp_RES1 | — | 80 | — | 50 | — | — | 80 | 80 | 85 | 60 | 95 | 80 | 80 | 80 |
| Waterhemp_RES2 | 70 | 80 | 60 | 50 | — | 90 | 90 | 85 | 90 | 80 | 95 | 95 | 90 | 80 |

| 31 g ai/ha | Compound 274 |
|---|---|
| Postemergence | |
| Arrowleaf Sida | 60 |
| Barnyardgrass | 20 |
| Beggarticks | 60 |
| Corn | 10 |
| Crabgrass, Brazil | 25 |
| Dayflower, VA | 20 |
| Field Bindweed | 50 |
| Horseweed | — |
| *Kochia* | — |
| *Panicum*, Fall | 20 |
| Pigweed, Palmer | 85 |
| Poinsettia, Wild | 70 |
| Ragweed | — |
| Ryegrass, Italian | 10 |
| Sandbur | 10 |
| Smartweed | — |
| Soybean | 75 |
| Waterhemp | 90 |
| Waterhemp_RES1 | 80 |
| Waterhemp_RES2 | 85 |

| 16 g ai/ha | Compounds | | | | | | | | | | | | |
|---|---|---|---|---|---|---|---|---|---|---|---|---|---|
| | 5 | 7 | 10 | 16 | 25 | 52 | 58 | 59 | 65 | 79 | 181 | 191 | 200 | 223 |
| Postemergence | | | | | | | | | | | | | | |
| Arrowleaf Sida | 60 | 75 | 40 | 50 | 60 | 50 | 70 | 65 | 50 | 65 | 60 | 60 | 60 | 60 |
| Barnyardgrass | 0 | 0 | 0 | 0 | 0 | 5 | 0 | 0 | 0 | 0 | 10 | 0 | 0 | 0 |
| Beggarticks | 30 | 35 | 10 | 30 | 20 | 30 | 60 | 50 | 35 | 40 | 40 | 20 | 50 | 50 |
| Corn | 0 | 0 | 0 | 0 | 0 | 10 | 5 | 5 | 0 | 0 | 5 | 0 | 10 | 0 |
| Crabgrass, Brazil | 0 | 0 | 0 | 0 | 10 | 15 | 10 | 15 | 0 | 0 | 20 | 10 | 10 | 0 |
| Dayflower, VA | 0 | 40 | 5 | 0 | 50 | 30 | 50 | 20 | 5 | 10 | 20 | 0 | 15 | 0 |
| Field Bindweed | 10 | 20 | 15 | 10 | 40 | 50 | 50 | 50 | 10 | 60 | 25 | 40 | 70 | 20 |
| Horseweed | — | — | — | — | — | — | — | — | 0 | 0 | — | — | — | — |
| *Kochia* | — | — | — | — | — | 40 | — | — | — | 50 | 35 | — | — | — |
| *Panicum*, Fall | 0 | 0 | 0 | 0 | 10 | 5 | 20 | 10 | 0 | 20 | 20 | 0 | 10 | 0 |
| Pigweed, Palmer | 60 | 60 | 60 | — | 50 | 60 | 90 | 75 | 20 | 50 | 80 | 40 | 40 | 25 |
| Poinsettia, Wild | 10 | 30 | 5 | 50 | 20 | 45 | — | 50 | 20 | 40 | 40 | 40 | 50 | 30 |
| Ragweed | — | — | — | — | — | 40 | — | — | — | 30 | 20 | — | — | — |
| Ryegrass, Italian | 0 | 0 | 0 | 0 | 0 | 0 | 10 | 0 | 0 | 0 | 5 | 0 | 0 | 0 |
| Sandbur | 0 | 0 | 0 | 0 | 0 | 15 | 0 | 0 | 0 | 0 | 5 | 0 | 0 | 0 |
| Smartweed | — | 30 | — | — | — | 50 | 55 | — | — | — | — | — | — | — |
| Soybean | 20 | 80 | 30 | 15 | 75 | 70 | 75 | 60 | 20 | 60 | 50 | 30 | 95 | 60 |
| Waterhemp | 70 | 80 | — | 60 | 80 | 65 | 75 | — | 50 | 70 | 65 | 70 | 80 | 50 |
| Waterhemp_RES1 | — | 70 | — | 50 | — | — | 80 | 70 | 70 | 40 | 90 | 70 | 70 | 60 |
| Waterhemp_RES2 | 60 | 75 | 50 | 25 | — | 80 | 80 | 75 | 80 | 75 | 85 | 90 | 90 | 75 |

| 16 g ai/ha | Compound 274 |
|---|---|
| Postemergence | |
| Arrowleaf Sida | 75 |
| Barnyardgrass | 10 |
| Beggarticks | 50 |
| Corn | 15 |
| Crabgrass, Brazil | 20 |
| Dayflower, VA | 10 |
| Field Bindweed | 50 |
| Horseweed | — |
| *Kochia* | — |
| *Panicum*, Fall | 15 |
| Pigweed, Palmer | 65 |
| Poinsettia, Wild | 65 |
| Ragweed | — |
| Ryegrass, Italian | 5 |
| Sandbur | 0 |
| Smartweed | — |
| Soybean | 35 |
| Waterhemp | 95 |

TABLE E-continued

|  |  |  |  |  |  |
|---|---|---|---|---|---|
| Waterhemp_RES1 |  |  | 75 |  |  |
| Waterhemp_RES2 |  |  | 80 |  |  |

| | Compounds | | | | |
|---|---|---|---|---|---|
| 8 g ai/ha | 7 | 65 | 191 | 223 | 274 |

| Postemergence | | | | | |
|---|---|---|---|---|---|
| Arrowleaf Sida | 65 | 55 | 50 | 50 | 55 |
| Barnyardgrass | 0 | 0 | 0 | 0 | 5 |
| Beggarticks | 25 | 20 | 10 | 40 | 30 |
| Corn | 0 | 0 | 0 | 0 | 10 |
| Crabgrass, Brazil | 0 | 0 | 10 | 0 | 10 |
| Dayflower, VA | 10 | 5 | 0 | 0 | 5 |
| Field Bindweed | 15 | 0 | 20 | 20 | 60 |
| *Panicum*, Fall | 0 | 0 | 0 | 0 | 10 |
| Pigweed, Palmer | 40 | 10 | 20 | 15 | 70 |
| Poinsettia, Wild | 0 | 15 | 20 | 30 | 50 |
| Ryegrass, Italian | 0 | 0 | 0 | 0 | 0 |
| Sandbur | 0 | 0 | 0 | 0 | 0 |
| Smartweed | 15 | — | — | — | — |
| Soybean | 60 | 15 | 20 | 30 | 20 |
| Waterhemp | 70 | 60 | 60 | 60 | 70 |
| Waterhemp_RES1 | 65 | 65 | 50 | 30 | 60 |

| | Compounds | | | | | | | | |
|---|---|---|---|---|---|---|---|---|---|
| 250 g ai/ha | 16 | 18 | 52 | 58 | 59 | 72 | 73 | 89 | 180 | 200 |

| Preemergence | | | | | | | | | | |
|---|---|---|---|---|---|---|---|---|---|---|
| Arrowleaf Sida | 98 | 95 | 100 | 100 | 100 | 100 | 100 | 100 | 85 | 100 |
| Barnyardgrass | 40 | 20 | 98 | 98 | 95 | 90 | 75 | 98 | 100 | 95 |
| Beggarticks | 0 | 0 | 65 | 100 | 25 | 30 | 75 | 95 | 90 | 95 |
| Cocklebur | — | — | 25 | 50 | 0 | 15 | 25 | — | — | 95 |
| Corn | 25 | 0 | 40 | 70 | 50 | 0 | 5 | 70 | 65 | 75 |
| Crabgrass, Brazil | 100 | 100 | 100 | 100 | 100 | 100 | 100 | 100 | 100 | 100 |
| Crabgrass, Large | 100 | 100 | 100 | 100 | 100 | 100 | 100 | 100 | 100 | 100 |
| Dayflower, VA | 98 | 98 | 98 | 98 | 98 | 95 | 95 | 98 | 90 | 85 |
| Field Bindweed | 60 | 40 | 95 | 100 | 100 | 95 | 85 | 90 | 90 | 95 |
| Foxtail, Giant | 100 | 98 | 100 | 100 | 100 | 100 | 100 | 100 | 100 | 70 |
| Foxtail, Green | 100 | 100 | 100 | 100 | 100 | 100 | 95 | 85 | 100 | 100 |
| Goosegrass | 95 | 98 | 100 | 100 | 98 | 100 | 100 | 50 | 100 | 90 |
| Johnsongrass | 40 | — | 98 | 100 | 100 | 98 | 85 | 100 | 80 | 75 |
| *Kochia* | 100 | 100 | 100 | 100 | 100 | 100 | 100 | 100 | 100 | 100 |
| Lambsquarters | 98 | 98 | 100 | 98 | 100 | 100 | 100 | 100 | 100 | 100 |
| Morningglory | 95 | 35 | 98 | 100 | 100 | 35 | 60 | 100 | 100 | 98 |
| Nightshade | 100 | 100 | 100 | 100 | 100 | 100 | 100 | 100 | 100 | 100 |
| Nutsedge, Yellow | 35 | 10 | 50 | 80 | 50 | 50 | 30 | 35 | 75 | 70 |
| *Panicum*, Fall | 100 | 100 | 100 | 100 | 100 | 100 | 100 | 100 | 100 | 100 |
| Pigweed, Palmer | — | — | 100 | 100 | 100 | 100 | 100 | 100 | 90 | 100 |
| Poinsettia, Wild | 100 | 50 | 100 | 100 | 100 | 70 | 85 | 85 | 98 | 95 |
| Ragweed | 65 | 0 | 70 | 85 | 50 | 95 | 80 | 90 | 100 | 95 |
| Ryegrass, Italian | 75 | 35 | 90 | 98 | 95 | 75 | 65 | 0 | 70 | 80 |
| Sandbur | 95 | 75 | 80 | 95 | 95 | 50 | 35 | 20 | 90 | 70 |
| Smartweed | — | — | — | — | — | 98 | 98 | — | — | — |
| Soybean | 95 | 90 | 90 | 95 | 95 | 90 | 80 | 80 | 98 | 90 |
| Surinam Grass | 50 | 20 | 10 | 90 | 65 | 30 | 35 | 75 | 100 | 100 |
| Velvetleaf | 100 | 100 | 90 | 100 | 100 | 100 | 95 | 100 | 100 | 100 |
| Waterhemp | 100 | 100 | 100 | 100 | 100 | 100 | 100 | 100 | 100 | 100 |

| | Compounds | | | | | | | | | | | | |
|---|---|---|---|---|---|---|---|---|---|---|---|---|---|
| 125 g ai/ha | 7 | 16 | 18 | 25 | 52 | 58 | 59 | 72 | 73 | 86 | 88 | 89 | 90 | 111 |

| Preemergence | | | | | | | | | | | | | | |
|---|---|---|---|---|---|---|---|---|---|---|---|---|---|---|
| Arrowleaf Sida | 80 | 95 | 85 | 65 | 80 | 100 | 100 | 100 | 100 | 100 | 35 | 100 | 90 | 98 |
| Barnyardgrass | 0 | 10 | 5 | 0 | 75 | 95 | 75 | 35 | 20 | 30 | 0 | 70 | 40 | 35 |
| Beggarticks | 0 | 0 | 0 | 50 | 40 | 15 | 0 | 5 | 50 | 70 | 0 | 80 | 30 | 80 |
| Cocklebur | 0 | — | — | — | — | 0 | — | 0 | — | — | — | — | — | — |
| Corn | 0 | 20 | 0 | 0 | 0 | 65 | 30 | 0 | 0 | 5 | 35 | 30 | 0 | 15 |
| Crabgrass, Brazil | 100 | 100 | 100 | 100 | 100 | 100 | 100 | 100 | 100 | 95 | 60 | 100 | 80 | 100 |
| Crabgrass, Large | 98 | 80 | 100 | 95 | 100 | 100 | 100 | 100 | 100 | 98 | 95 | 100 | 98 | 100 |
| Dayflower, VA | 65 | 70 | 95 | 40 | 70 | 98 | 85 | 65 | 65 | 65 | 60 | 80 | 0 | 20 |
| Field Bindweed | 0 | 30 | 40 | 65 | 80 | 98 | 60 | 60 | 75 | 90 | 50 | 95 | 65 | 80 |
| Foxtail, Giant | 90 | 100 | 95 | 80 | 100 | 100 | 100 | 98 | 95 | 100 | 25 | 65 | 50 | 100 |
| Foxtail, Green | 75 | 90 | 100 | 80 | 80 | 100 | 100 | 100 | 80 | 75 | 35 | 65 | 50 | 90 |
| Goosegrass | 75 | 75 | 90 | 75 | 98 | 100 | 98 | 98 | 98 | 50 | 5 | 5 | 50 | 65 |

TABLE E-continued

| | | | | | | | | | | | | | |
|---|---|---|---|---|---|---|---|---|---|---|---|---|---|
| Johnsongrass | 50 | 25 | 80 | 60 | 70 | 95 | 75 | 95 | 35 | 65 | 15 | 50 | 15 | 70 |
| *Kochia* | 95 | 100 | 100 | 85 | 100 | 100 | 100 | 100 | 98 | 100 | 50 | 100 | 100 | 95 |
| Lambsquarters | 100 | 98 | 98 | 98 | 98 | 98 | 100 | 100 | 100 | 100 | 100 | 95 | 100 | 100 |
| Morningglory | 0 | 25 | 0 | 50 | 95 | 100 | 75 | 15 | 30 | 75 | 15 | 75 | 35 | 75 |
| Nightshade | 98 | 100 | 100 | 98 | 98 | 100 | 100 | 98 | 98 | 98 | 0 | 100 | 80 | 95 |
| Nutsedge, Yellow | 0 | 35 | 0 | 0 | 25 | 60 | 30 | 25 | 40 | 20 | 0 | 20 | 0 | 15 |
| *Panicum*, Fall | — | 100 | 100 | — | 100 | 100 | 100 | 100 | 98 | 100 | 10 | 100 | 80 | 100 |
| Pigweed, Palmer | 100 | — | — | 100 | 100 | 100 | 100 | 100 | 100 | 100 | 75 | 40 | 65 | 100 |
| Poinsettia, Wild | 0 | 50 | 0 | 40 | 50 | 100 | 20 | 70 | 65 | 65 | 0 | 70 | 75 | 85 |
| Ragweed | 0 | 30 | 0 | 5 | 5 | 50 | 5 | 50 | 60 | 20 | 65 | 80 | 75 | 90 |
| Ryegrass, Italian | 20 | 40 | 20 | 10 | 60 | 98 | 75 | 35 | 35 | 5 | 0 | 0 | 0 | 20 |
| Sandbur | 35 | 70 | 5 | 15 | 35 | 90 | 50 | 35 | 30 | 10 | 10 | 10 | 0 | 0 |
| Smartweed | — | — | — | — | — | — | — | 90 | 98 | — | — | — | — | — |
| Soybean | 50 | 90 | 90 | 30 | 60 | 75 | 50 | 70 | 70 | 60 | 20 | 60 | 35 | 70 |
| Surinam Grass | 35 | 30 | 0 | 35 | 10 | 65 | 20 | 10 | 20 | 0 | 10 | 10 | 0 | 25 |
| Velvetleaf | 100 | 100 | 100 | 80 | 85 | 100 | 100 | 65 | 70 | 80 | 65 | 90 | 85 | 75 |
| Waterhemp | 100 | 100 | 100 | 100 | 100 | 100 | 100 | 100 | 100 | 100 | 100 | 80 | 100 | 100 |

| | Compounds | | | | | | | | | | |
|---|---|---|---|---|---|---|---|---|---|---|---|
| 125 g ai/ha | 138 | 145 | 151 | 164 | 167 | 170 | 179 | 180 | 200 | 250 | 292 |
| | Preemergence | | | | | | | | | | |
| Arrowleaf Sida | 100 | 100 | 100 | 100 | 100 | 100 | 100 | 70 | 100 | 100 | 80 |
| Barnyardgrass | 60 | 0 | 75 | 65 | 75 | 75 | 20 | 100 | 60 | 25 | 40 |
| Beggarticks | 0 | 35 | 100 | 20 | 0 | 0 | 0 | 40 | 75 | 20 | 35 |
| Cocklebur | — | — | — | — | 90 | — | — | — | 75 | — | — |
| Corn | 35 | 10 | 0 | 0 | 25 | 30 | 0 | 40 | 30 | 20 | 0 |
| Crabgrass, Brazil | 98 | 85 | 75 | 100 | 100 | 100 | 100 | 100 | 100 | 98 | 100 |
| Crabgrass, Large | 100 | 90 | 100 | 100 | 100 | 100 | 98 | 100 | 80 | 100 | 100 |
| Dayflower, VA | 40 | 80 | 85 | 90 | 100 | 95 | 60 | 85 | 65 | 70 | 85 |
| Field Bindweed | 50 | 0 | 35 | 50 | 10 | 30 | 30 | 65 | 70 | 0 | 65 |
| Foxtail, Giant | 75 | 70 | 95 | 95 | 100 | 100 | 100 | 100 | 25 | 98 | 95 |
| Foxtail, Green | 98 | 65 | 75 | 100 | 90 | 100 | 100 | 100 | 75 | 90 | 75 |
| Goosegrass | 70 | 25 | 85 | 75 | 98 | 98 | 70 | 98 | 80 | 65 | 70 |
| Johnsongrass | 40 | 75 | 70 | 70 | 70 | 70 | 25 | 75 | 30 | 50 | 35 |
| *Kochia* | 100 | 90 | 100 | 100 | 90 | 98 | 75 | 100 | 100 | 98 | 98 |
| Lambsquarters | 100 | 100 | 100 | 100 | 100 | 100 | 100 | 100 | 98 | 100 | 100 |
| Morningglory | 40 | 35 | 0 | 98 | 65 | 95 | 30 | 60 | 90 | 20 | 50 |
| Nightshade | 90 | 80 | 90 | 95 | 100 | 98 | 95 | 98 | 100 | 98 | 80 |
| Nutsedge, Yellow | 40 | 20 | 0 | 20 | 0 | 40 | 30 | 60 | 40 | 40 | 35 |
| *Panicum*, Fall | 100 | 98 | 98 | 98 | 0 | 100 | 98 | 100 | 100 | 100 | 100 |
| Pigweed, Palmer | 70 | 95 | 100 | 80 | 100 | 100 | 100 | 75 | 100 | 100 | 100 |
| Poinsettia, Wild | 25 | 35 | 100 | 30 | 25 | 40 | 35 | 65 | 90 | 20 | 60 |
| Ragweed | 0 | 60 | 100 | 60 | 35 | 35 | 0 | 100 | 80 | 0 | 35 |
| Ryegrass, Italian | 20 | 0 | 65 | 60 | 40 | 70 | 15 | 30 | 60 | 0 | 35 |
| Sandbur | 15 | 20 | 35 | 10 | 65 | 35 | 15 | 75 | 40 | 25 | 35 |
| Smartweed | — | — | — | — | — | — | — | — | — | — | — |
| Soybean | 35 | 65 | 75 | 70 | 50 | 60 | 40 | 90 | 65 | 65 | 50 |
| Surinam Grass | 50 | 0 | 100 | 20 | 0 | 25 | 0 | 75 | 100 | 0 | 20 |
| Velvetleaf | 100 | 100 | 100 | 100 | 100 | 100 | 100 | 100 | 100 | 100 | 90 |
| Waterhemp | 100 | 100 | 100 | 90 | 100 | 80 | 98 | 100 | 100 | 100 | 100 |

| | Compounds | | | | | | | | | | | | |
|---|---|---|---|---|---|---|---|---|---|---|---|---|---|
| 62 g ai/ha | 7 | 16 | 18 | 25 | 52 | 58 | 59 | 72 | 73 | 86 | 88 | 89 | 90 | 111 |
| | Preemergence | | | | | | | | | | | | |
| Arrowleaf Sida | 50 | 70 | 70 | 35 | 60 | 100 | 75 | 40 | 80 | 60 | 10 | 75 | 75 | 70 |
| Barnyardgrass | 0 | 0 | 0 | 0 | 30 | 90 | 50 | 15 | 0 | 0 | 0 | 20 | 0 | 0 |
| Beggarticks | 0 | 0 | 0 | 50 | 0 | 0 | 0 | 5 | 20 | 35 | 0 | 60 | 10 | 60 |
| Cocklebur | — | — | 0 | — | 0 | — | 0 | — | — | — | 0 | — | — | — |
| Corn | 0 | 0 | 0 | 0 | 0 | 40 | 0 | 0 | 0 | 0 | 35 | 0 | 0 | 0 |
| Crabgrass, Brazil | 100 | 100 | 98 | 100 | 100 | 100 | 100 | 100 | 100 | 75 | 60 | 90 | 50 | 75 |
| Crabgrass, Large | 75 | 65 | 40 | 50 | 98 | 100 | 90 | 100 | 95 | 65 | 85 | 75 | 90 |
| Dayflower, VA | 20 | 35 | 35 | 25 | 5 | 70 | 25 | 35 | 25 | 30 | 0 | 60 | — | 20 |
| Field Bindweed | 0 | 0 | 30 | 60 | 25 | 70 | 60 | 10 | 50 | 20 | 0 | 75 | 70 | 60 |
| Foxtail, Giant | 40 | 100 | 65 | 50 | 70 | 100 | 85 | 95 | 50 | 30 | 0 | 20 | 15 | 70 |
| Foxtail, Green | 35 | 70 | 65 | 60 | 75 | 100 | 95 | 70 | 15 | 0 | 35 | 10 | 70 |
| Goosegrass | 40 | 50 | 30 | 25 | 65 | 95 | 65 | 80 | 70 | 50 | 5 | 0 | 5 | 40 |
| Johnsongrass | 40 | 0 | 0 | 25 | 30 | 95 | 60 | 40 | 20 | 65 | 15 | 10 | 0 | 15 |
| *Kochia* | 50 | 65 | 80 | 35 | 65 | 100 | 100 | 98 | 98 | 100 | 35 | 75 | 100 | 95 |
| Lambsquarters | 98 | 98 | 98 | 98 | 98 | 100 | 100 | 100 | 100 | 100 | 100 | 5 | 50 | 98 |
| Morningglory | 0 | 0 | 0 | 25 | 35 | 100 | 65 | 15 | 10 | 30 | 10 | 65 | 20 | 75 |
| Nightshade | 98 | 100 | 98 | 98 | 75 | 100 | 90 | 100 | 90 | 0 | — | 80 | 80 | 80 |
| Nutsedge, Yellow | 0 | 0 | 0 | 0 | 0 | 25 | 0 | 0 | 50 | 0 | 0 | 0 | 0 | 0 |
| *Panicum*, Fall | — | 100 | 70 | — | 100 | 100 | 98 | 98 | 98 | 90 | 0 | 65 | 0 | 80 |
| Pigweed, Palmer | 100 | — | — | 100 | 100 | 100 | 100 | 100 | 100 | 100 | 0 | 0 | 0 | 100 |

TABLE E-continued

| | | | | | | | | | | | | | | |
|---|---|---|---|---|---|---|---|---|---|---|---|---|---|---|
| Poinsettia, Wild | — | 50 | 0 | 0 | 25 | 90 | 10 | 15 | 35 | 20 | 0 | 40 | 70 | 70 |
| Ragweed | 0 | 0 | 0 | 0 | 0 | 5 | 0 | 5 | 30 | 5 | 0 | 80 | 50 | 70 |
| Ryegrass, Italian | 0 | 15 | 0 | 10 | 0 | 75 | 50 | 20 | 35 | 0 | 0 | 0 | 0 | 0 |
| Sandbur | 0 | 20 | 0 | 5 | 10 | 75 | 30 | 30 | 20 | 10 | 0 | 10 | 0 | 0 |
| Smartweed | — | — | — | — | — | — | — | 0 | 20 | — | — | — | — | — |
| Soybean | 40 | 60 | 60 | 0 | 0 | 60 | — | 25 | 25 | 35 | 20 | 30 | 30 | 40 |
| Surinam Grass | 10 | 0 | 0 | 40 | 0 | 25 | 5 | 20 | 5 | 0 | 0 | 0 | 0 | 0 |
| Velvetleaf | 98 | 85 | 100 | 80 | 75 | 90 | 75 | 40 | 60 | 50 | 20 | 65 | 60 | 60 |
| Waterhemp | 100 | 100 | 100 | 100 | 100 | 100 | 100 | 100 | 100 | 100 | 35 | 70 | 20 | 80 |

| | Compounds | | | | | | | | | | |
|---|---|---|---|---|---|---|---|---|---|---|---|
| 62 g ai/ha | 138 | 145 | 151 | 164 | 167 | 170 | 179 | 180 | 194 | 200 | 250 | 292 |
| | Preemergence | | | | | | | | | | |
| Arrowleaf Sida | 40 | 100 | 100 | 100 | 100 | 90 | 100 | 30 | 100 | 70 | 60 | 5 |
| Barnyardgrass | 15 | 0 | 10 | 0 | 25 | 35 | 10 | 98 | 0 | 10 | 0 | 0 |
| Beggarticks | 0 | 30 | 95 | 20 | 0 | 0 | 0 | 20 | 0 | 35 | 0 | 15 |
| Cocklebur | — | — | — | — | 100 | — | — | — | — | — | — | — |
| Corn | 15 | 0 | 0 | 0 | 15 | 10 | 0 | 15 | 0 | 30 | 0 | 0 |
| Crabgrass, Brazil | 90 | 50 | 70 | 75 | 75 | 100 | 65 | 100 | 98 | 100 | 5 | 100 |
| Crabgrass, Large | 98 | 35 | 60 | 75 | 100 | 98 | 75 | 98 | 95 | 65 | 0 | 90 |
| Dayflower, VA | 30 | 0 | 65 | 65 | 65 | 80 | 0 | 35 | 40 | 65 | 50 | 35 |
| Field Bindweed | 40 | 0 | 20 | 30 | 0 | 20 | 0 | 25 | 40 | 40 | 0 | 30 |
| Foxtail, Giant | 30 | 20 | 60 | 60 | 100 | 100 | 65 | 100 | 75 | 0 | 15 | 80 |
| Foxtail, Green | 20 | 35 | 70 | 60 | 70 | 90 | 25 | 100 | 80 | 30 | 0 | 25 |
| Goosegrass | 50 | 0 | 70 | 20 | 75 | 75 | 35 | 90 | 75 | 60 | 0 | 50 |
| Johnsongrass | 35 | 0 | 35 | 10 | 30 | 25 | 20 | 50 | 50 | 25 | 0 | 20 |
| Kochia | 90 | 0 | 90 | 75 | 65 | 90 | 25 | 20 | 35 | 95 | 0 | 70 |
| Lambsquarters | 100 | 100 | 100 | 98 | 100 | 100 | 95 | 100 | 100 | 80 | 0 | 25 |
| Morningglory | 0 | 20 | 0 | 35 | 40 | 35 | 10 | 15 | 0 | 50 | 0 | 15 |
| Nightshade | 98 | 65 | 75 | 80 | 100 | 98 | 80 | 98 | 95 | 85 | 35 | 70 |
| Nutsedge, Yellow | 15 | 0 | 0 | 0 | 0 | 30 | 30 | 30 | 20 | 0 | 0 | 15 |
| Panicum, Fall | 100 | 90 | 100 | 30 | 100 | 98 | 75 | 100 | 100 | 95 | 0 | 90 |
| Pigweed, Palmer | 75 | 50 | 100 | 75 | 98 | 100 | 100 | 0 | 100 | 100 | 0 | 100 |
| Poinsettia, Wild | 35 | 20 | 100 | 5 | 20 | 25 | 30 | 15 | 0 | 50 | 0 | 35 |
| Ragweed | 0 | 0 | 95 | 25 | 35 | 5 | 0 | 90 | 20 | 80 | 0 | 0 |
| Ryegrass, Italian | 0 | 0 | 10 | 30 | 10 | 35 | 15 | 0 | 0 | 20 | 0 | 0 |
| Sandbur | 10 | 0 | 0 | 0 | 20 | 30 | 15 | 20 | 20 | 5 | 0 | 0 |
| Smartweed | — | — | — | — | — | — | — | 90 | — | — | — | — |
| Soybean | — | 65 | — | 15 | 20 | 30 | 25 | 70 | 20 | 35 | 15 | 40 |
| Surinam Grass | 20 | 0 | 35 | 20 | 0 | 15 | 0 | 25 | 0 | 70 | 0 | 10 |
| Velvetleaf | 90 | 95 | 100 | 100 | 65 | 65 | 100 | 80 | 25 | 80 | 75 | 35 |
| Waterhemp | 90 | 100 | 98 | 90 | 98 | 90 | 90 | 98 | 100 | 100 | 0 | 80 |

| | Compounds | | | | | | | | | | | | |
|---|---|---|---|---|---|---|---|---|---|---|---|---|---|
| 31 g ai/ha | 7 | 16 | 18 | 25 | 52 | 58 | 59 | 72 | 73 | 86 | 88 | 89 | 90 | 111 |
| | Preemergence | | | | | | | | | | | | |
| Arrowleaf Sida | 25 | 35 | 5 | 35 | 40 | 100 | 50 | 40 | 40 | 5 | 40 | 50 | 50 | 50 |
| Barnyardgrass | 0 | 0 | 0 | 0 | 0 | 40 | 20 | 0 | 0 | 0 | 0 | 0 | 0 | 0 |
| Beggarticks | 0 | 0 | 0 | 35 | 0 | 0 | 0 | 0 | 5 | 0 | 0 | 35 | 5 | 30 |
| Cocklebur | — | — | — | — | 0 | 0 | 0 | — | 0 | — | — | — | — | — |
| Corn | 0 | 0 | 0 | 0 | 0 | 5 | 0 | 0 | 0 | 0 | 0 | 0 | 0 | 0 |
| Crabgrass, Brazil | 80 | — | 95 | 100 | 90 | 100 | 100 | 98 | 95 | 0 | 0 | 20 | 20 | 30 |
| Crabgrass, Large | 70 | 0 | 0 | 20 | 35 | 100 | 95 | 80 | 30 | 0 | 35 | 35 | 40 | 35 |
| Dayflower, VA | 0 | 0 | 0 | 25 | 0 | 20 | 5 | 0 | 0 | 0 | 0 | 0 | 0 | 0 |
| Field Bindweed | 0 | 0 | 0 | 60 | 0 | 20 | 5 | 5 | 15 | 10 | 0 | 35 | 50 | 15 |
| Foxtail, Giant | 20 | 20 | 15 | 35 | 70 | 100 | 10 | 35 | 20 | 15 | 0 | 0 | 0 | 0 |
| Foxtail, Green | 30 | 20 | 0 | 20 | 20 | 95 | 60 | 30 | 20 | 0 | 0 | 0 | 0 | 10 |
| Goosegrass | 35 | 35 | 0 | 25 | 50 | 70 | 25 | 60 | 20 | 0 | 0 | 0 | 0 | 5 |
| Johnsongrass | 0 | 0 | 0 | — | 0 | 35 | 0 | 0 | 20 | 0 | 0 | 0 | 0 | 0 |
| Kochia | 0 | 0 | 0 | 25 | 25 | 100 | 80 | 75 | 75 | 90 | 0 | 60 | 50 | 10 |
| Lambsquarters | 75 | 80 | 90 | 50 | 75 | 98 | 98 | 90 | 65 | 65 | 50 | 20 | 75 | 80 |
| Morningglory | 0 | 0 | 0 | 0 | 5 | 50 | 15 | 0 | 0 | 10 | 0 | 30 | 0 | 35 |
| Nightshade | 98 | 98 | 95 | 98 | 0 | 98 | 50 | 65 | 80 | 0 | 0 | — | 10 | 50 |
| Nutsedge, Yellow | 0 | 0 | 0 | 0 | 0 | 5 | 0 | 0 | 0 | 0 | 0 | 0 | 0 | 0 |
| Panicum, Fall | — | 80 | 50 | — | 0 | 98 | 75 | 65 | 40 | 35 | 0 | 0 | 0 | 5 |
| Pigweed, Palmer | 85 | — | — | 100 | 100 | 100 | 100 | 100 | 75 | 0 | 0 | 0 | 0 | 20 |
| Poinsettia, Wild | 0 | 0 | 0 | 0 | 0 | 15 | 0 | 0 | 5 | 30 | 10 | 0 | 20 | 35 | 30 |
| Ragweed | 0 | 0 | 0 | 0 | 0 | 0 | 0 | 0 | 0 | 5 | 0 | 0 | 65 | 50 | 50 |
| Ryegrass, Italian | 0 | 0 | 0 | 0 | 0 | 35 | 0 | 15 | 20 | 0 | 0 | 0 | 0 | 0 |
| Sandbur | 0 | 20 | 0 | 0 | 0 | 20 | 15 | 40 | 20 | 10 | 0 | 0 | 0 | 0 |
| Smartweed | — | — | — | — | — | — | — | 0 | 0 | — | — | — | — | — |
| Soybean | 0 | 60 | 0 | 0 | 0 | 0 | 0 | 10 | 25 | 0 | 0 | — | 15 | 20 |

TABLE E-continued

| | | | | | | | | | | | | | | |
|---|---|---|---|---|---|---|---|---|---|---|---|---|---|---|
| Surinam Grass | 0 | 0 | 0 | 65 | 0 | 0 | 0 | 20 | 0 | 0 | 0 | 0 | 0 | 0 |
| Velvetleaf | 65 | 50 | 95 | 60 | 0 | 70 | 25 | 0 | 20 | 0 | 0 | 20 | 20 | 10 |
| Waterhemp | 100 | 100 | 100 | 100 | 100 | 100 | 100 | 98 | 100 | 70 | 35 | 0 | 0 | 65 |

| | Compounds | | | | | | | | | | |
|---|---|---|---|---|---|---|---|---|---|---|---|
| 31 g ai/ha | 138 | 145 | 151 | 164 | 167 | 170 | 180 | 194 | 200 | 250 | 292 |

Preemergence

| | | | | | | | | | | | |
|---|---|---|---|---|---|---|---|---|---|---|---|
| Arrowleaf Sida | 0 | 100 | 80 | 100 | 65 | 10 | 15 | 35 | 20 | 20 | 5 |
| Barnyardgrass | 0 | 0 | 20 | 0 | 20 | 0 | 20 | 0 | 0 | 0 | 0 |
| Beggarticks | 0 | 0 | 65 | 0 | 0 | 0 | 10 | 0 | 10 | 0 | 15 |
| Cocklebur | — | — | — | — | 0 | — | — | — | 0 | — | — |
| Corn | 0 | 0 | 0 | 0 | 0 | 20 | 0 | 0 | 5 | 0 | 0 |
| Crabgrass, Brazil | 40 | 0 | 35 | 20 | 0 | 100 | 90 | 65 | 85 | 0 | 40 |
| Crabgrass, Large | 70 | 0 | 5 | 35 | 65 | 70 | 90 | 85 | 35 | 0 | 20 |
| Dayflower, VA | 5 | 0 | 10 | 20 | 5 | 30 | 0 | 0 | 35 | 0 | 20 |
| Field Bindweed | 20 | 0 | 0 | 0 | 0 | 0 | 10 | 0 | 10 | 0 | 5 |
| Foxtail, Giant | 0 | 0 | 25 | 20 | 0 | 25 | 75 | 25 | 0 | 0 | 5 |
| Foxtail, Green | 0 | 0 | 20 | 25 | 35 | 40 | 65 | 35 | 5 | 0 | 10 |
| Goosegrass | 30 | 0 | 0 | 5 | 60 | 40 | 70 | 40 | 5 | 0 | 20 |
| Johnsongrass | 0 | 0 | 0 | 0 | 10 | 15 | 0 | 0 | 15 | 0 | 15 |
| *Kochia* | 75 | 0 | 80 | 0 | 40 | 30 | 0 | 5 | 60 | 0 | 0 |
| Lambsquarters | 50 | 100 | 100 | 75 | 98 | 98 | 98 | 80 | 65 | 0 | 0 |
| Morningglory | 0 | 0 | 0 | 65 | 25 | 10 | 0 | 0 | 20 | 0 | 0 |
| Nightshade | 0 | 0 | 30 | 50 | 98 | 50 | 75 | 95 | 10 | 0 | 5 |
| Nutsedge, Yellow | 10 | 0 | 0 | 0 | 0 | 20 | 0 | 0 | 0 | 0 | 0 |
| *Panicum*, Fall | 25 | 0 | 60 | 0 | 65 | 20 | 95 | 80 | 75 | 0 | 0 |
| Pigweed, Palmer | 70 | 0 | 100 | 0 | 0 | 95 | 0 | 98 | 40 | 0 | 35 |
| Poinsettia, Wild | 25 | 0 | 60 | 0 | 0 | 20 | 10 | 10 | 50 | 0 | 5 |
| Ragweed | 0 | 0 | 90 | 0 | 15 | 0 | 70 | 0 | 0 | 0 | 0 |
| Ryegrass, Italian | 0 | 0 | 10 | 0 | 0 | 20 | 0 | 0 | 0 | 0 | 0 |
| Sandbur | 0 | 0 | 0 | 0 | 0 | 0 | 0 | 20 | 0 | 0 | 20 |
| Smartweed | — | — | — | — | — | — | — | 0 | — | — | — |
| Soybean | 0 | 15 | 30 | 0 | 0 | 0 | 35 | 0 | 25 | 0 | 0 |
| Surinam Grass | 0 | 0 | 0 | 0 | 0 | 0 | 10 | 0 | 5 | 0 | 0 |
| Velvetleaf | 70 | 90 | 95 | 50 | 20 | 60 | 35 | 5 | 35 | 75 | 30 |
| Waterhemp | 100 | 98 | 75 | 65 | 98 | 80 | 98 | 98 | 100 | 0 | 20 |

| | Compounds | | | | | | | | | | | | |
|---|---|---|---|---|---|---|---|---|---|---|---|---|---|
| 16 g ai/ha | 7 | 16 | 18 | 25 | 52 | 58 | 59 | 72 | 73 | 86 | 88 | 90 | 111 | 138 |

Preemergence

| | | | | | | | | | | | | | |
|---|---|---|---|---|---|---|---|---|---|---|---|---|---|
| Arrowleaf Sida | 0 | 5 | 0 | 20 | 35 | 80 | 50 | 20 | 5 | 0 | 30 | 20 | 40 | 0 |
| Barnyardgrass | 0 | 0 | 0 | 0 | 0 | 20 | 0 | 0 | 0 | 0 | 0 | 0 | 0 | 0 |
| Beggarticks | 0 | 0 | 0 | 20 | 0 | 0 | 0 | 0 | 5 | 0 | 0 | 0 | 20 | 0 |
| Cocklebur | — | 0 | — | — | 0 | — | — | 0 | 0 | — | — | — | — | — |
| Corn | 0 | 0 | 0 | 0 | 0 | 0 | 0 | 0 | 0 | 0 | 0 | 0 | 0 | 0 |
| Crabgrass, Brazil | 0 | — | 0 | 0 | 0 | 100 | 80 | 90 | 25 | 0 | 0 | 0 | 0 | 0 |
| Crabgrass, Large | 0 | 0 | 0 | 15 | 0 | 75 | 5 | 50 | 0 | 0 | 0 | 30 | 15 | 0 |
| Dayflower, VA | 0 | 0 | 0 | 35 | 0 | 5 | 0 | 0 | 0 | 0 | 0 | 0 | 0 | 0 |
| Field Bindweed | 0 | 0 | 0 | 60 | 0 | 0 | 0 | 0 | 0 | 0 | 0 | 0 | 35 | 15 | 0 |
| Foxtail, Giant | 20 | 15 | 0 | 10 | 0 | 75 | 5 | 35 | 0 | 0 | 0 | 0 | 0 | 0 |
| Foxtail, Green | 0 | 0 | 0 | 20 | 0 | 65 | 0 | 30 | 0 | 0 | 0 | 0 | 0 | 0 |
| Goosegrass | 0 | 0 | 0 | 20 | 5 | 10 | 15 | 0 | 0 | 0 | 0 | 0 | 0 | 10 |
| Johnsongrass | 0 | 0 | 0 | 0 | 0 | — | 0 | 0 | 0 | 0 | 0 | 0 | 0 | 0 |
| *Kochia* | 0 | 0 | 0 | 0 | — | 35 | 20 | 10 | 5 | 0 | 0 | 0 | 0 | 60 |
| Lambsquarters | 0 | 50 | 80 | 0 | 0 | 98 | 98 | 0 | 10 | 0 | 75 | 5 | 50 | 0 |
| Morningglory | 0 | 0 | 0 | 0 | 0 | — | 0 | 0 | 0 | 0 | 0 | 0 | 20 | 0 |
| Nightshade | 65 | 0 | 0 | 0 | 0 | 90 | 0 | 0 | 65 | 0 | — | 10 | 65 | 0 |
| Nutsedge, Yellow | 0 | 0 | 0 | 0 | 0 | 0 | 0 | 0 | 0 | 0 | 0 | 0 | 0 | 0 |
| *Panicum*, Fall | — | 0 | 0 | — | 0 | 95 | 50 | 0 | 0 | 0 | 0 | 0 | 0 | 0 |
| Pigweed, Palmer | 95 | — | — | 70 | 25 | 100 | 35 | 95 | 0 | — | 0 | 0 | 10 | 0 |
| Poinsettia, Wild | 0 | 0 | 0 | 0 | 0 | 5 | 0 | 15 | 0 | 0 | 0 | 10 | 15 | 0 |
| Ragweed | 0 | 0 | 0 | 0 | 0 | 0 | 0 | 0 | 0 | 0 | 0 | 0 | 25 | 0 |
| Ryegrass, Italian | 0 | 0 | 0 | 0 | 0 | 30 | 0 | 0 | 0 | 0 | 0 | 0 | 0 | 0 |
| Sandbur | 0 | 0 | 0 | 0 | 0 | 0 | 0 | 25 | 10 | 0 | 0 | 0 | 0 | 0 |
| Smartweed | — | — | — | — | — | — | 0 | 0 | — | — | — | — | — | — |
| Soybean | 0 | 0 | 0 | 0 | 0 | 0 | 0 | 0 | 15 | 0 | 35 | — | 0 | 0 |
| Surinam Grass | 0 | 0 | 0 | 50 | 0 | 0 | 0 | 20 | 0 | 0 | 0 | 0 | 0 | 0 |

TABLE E-continued

| | | | | | | | | | | | | | | |
|---|---|---|---|---|---|---|---|---|---|---|---|---|---|---|
| Velvetleaf | 50 | 0 | 25 | 35 | 0 | 40 | 0 | 0 | 0 | 0 | 0 | 0 | 5 | 40 |
| Waterhemp | 100 | 100 | 100 | 100 | 80 | 98 | 100 | 95 | 65 | 0 | 20 | 0 | 0 | 0 |

| | Compounds | | | | | | | | |
|---|---|---|---|---|---|---|---|---|---|
| 16 g ai/ha | 145 | 151 | 164 | 167 | 170 | 179 | 200 | 250 | 292 |
| Preemergence | | | | | | | | | |
| Arrowleaf Sida | 35 | 60 | 40 | 65 | 0 | 20 | 20 | 0 | 0 |
| Barnyardgrass | 0 | 0 | 0 | 20 | 0 | 0 | 0 | 0 | 0 |
| Beggarticks | 0 | 65 | 0 | 0 | 0 | 0 | 0 | 0 | 0 |
| Cocklebur | — | — | — | 0 | — | — | 0 | — | — |
| Corn | 0 | 0 | 0 | 0 | 0 | 0 | 0 | 0 | 0 |
| Crabgrass, Brazil | 0 | 0 | 0 | 0 | 40 | 0 | 30 | 0 | 10 |
| Crabgrass, Large | 0 | 0 | 35 | 0 | 0 | 0 | 5 | 0 | 0 |
| Dayflower, VA | 0 | 0 | 0 | 0 | 30 | 0 | 0 | 0 | 20 |
| Field Bindweed | 0 | 0 | 0 | 0 | 0 | 0 | 5 | 0 | 0 |
| Foxtail, Giant | 0 | 0 | 0 | 0 | 0 | 0 | 0 | 0 | 0 |
| Foxtail, Green | 0 | 20 | 0 | 10 | 0 | 0 | 0 | 0 | 0 |
| Goosegrass | 0 | 0 | 0 | 0 | 0 | 30 | 10 | 0 | 0 |
| Johnsongrass | 0 | 0 | 0 | 10 | 15 | 0 | 0 | 0 | 15 |
| *Kochia* | 0 | 5 | 0 | 0 | 0 | 0 | 40 | 0 | 0 |
| Lambsquarters | 0 | 98 | 65 | 40 | 0 | 0 | 0 | 0 | 0 |
| Morningglory | 0 | 0 | 20 | 25 | 0 | 0 | 10 | 0 | 0 |
| Nightshade | 0 | 0 | 60 | 0 | 0 | 0 | 0 | 0 | 0 |
| Nutsedge, Yellow | 0 | 0 | 0 | 0 | 0 | 0 | 0 | 0 | 0 |
| *Panicum*, Fall | 0 | 80 | 0 | 0 | 0 | 30 | 20 | 0 | 0 |
| Pigweed, Palmer | 0 | 25 | 0 | 0 | 50 | 0 | 0 | 0 | 0 |
| Poinsettia, Wild | 0 | 20 | 0 | 0 | 0 | 0 | 20 | 0 | 15 |
| Ragweed | 0 | 65 | 0 | 0 | 0 | 0 | 0 | 0 | 0 |
| Ryegrass, Italian | 0 | 0 | 0 | 0 | 0 | 0 | 0 | 0 | 0 |
| Sandbur | 0 | 0 | 0 | 0 | 0 | 0 | 0 | 0 | 0 |
| Smartweed | — | — | — | — | — | — | — | — | — |
| Soybean | 0 | 25 | 0 | 0 | 0 | 0 | 0 | 0 | 0 |
| Surinam Grass | 0 | 0 | 0 | 0 | 0 | 0 | 0 | 0 | 0 |
| Velvetleaf | 35 | 50 | 20 | 20 | 20 | 25 | 0 | 20 | 20 |
| Waterhemp | 0 | 75 | 0 | 20 | 35 | 70 | 30 | 0 | 0 |

| | Compounds | | | | |
|---|---|---|---|---|---|
| 8 g ai/ha | 7 | 25 | 170 | 179 | 292 |
| Preemergence | | | | | |
| Arrowleaf Sida | 0 | 0 | 0 | 0 | 0 |
| Barnyardgrass | 0 | 0 | 0 | 0 | 0 |
| Beggarticks | 0 | 0 | 0 | 0 | 0 |
| Corn | 0 | 0 | 0 | 0 | 0 |
| Crabgrass, Brazil | 0 | — | 30 | 0 | 0 |
| Crabgrass, Large | 0 | 0 | 0 | 0 | 0 |
| Dayflower, VA | 0 | 30 | 0 | 0 | 20 |
| Field Bindweed | 0 | 30 | 0 | 0 | 0 |
| Foxtail, Giant | 15 | 15 | 0 | 0 | 0 |
| Foxtail, Green | 0 | 20 | 0 | 0 | 0 |
| Goosegrass | 0 | 25 | 0 | 0 | 0 |
| Johnsongrass | 0 | 0 | 15 | 0 | 0 |
| *Kochia* | 0 | 0 | 0 | 0 | 0 |
| Lambsquarters | 0 | 0 | 0 | 0 | 0 |
| Morningglory | 0 | 0 | 0 | 0 | 0 |
| Nightshade | 0 | 0 | 0 | 0 | 0 |
| Nutsedge, Yellow | 0 | 0 | 0 | 0 | 0 |
| *Panicum*, Fall | — | — | 0 | 0 | 0 |
| Pigweed, Palmer | 0 | 35 | 0 | 0 | 0 |
| Poinsettia, Wild | 0 | 0 | 0 | 0 | 0 |
| Ragweed | 0 | 0 | 0 | 0 | 0 |
| Ryegrass, Italian | 0 | 0 | 0 | 0 | 0 |
| Sandbur | 0 | 0 | 0 | 0 | 0 |
| Soybean | 0 | 0 | 0 | 0 | 0 |
| Surinam Grass | 0 | 35 | 0 | 0 | 0 |
| Velvetleaf | 20 | — | 0 | 20 | 0 |
| Waterhemp | 95 | 95 | 0 | 0 | 0 |

Test F

Seeds of plant species selected from bermudagrass (*Cynodon dactylon*), surinam grass (*Brachiaria decumbens*), large (Lg) crabgrass (*Digitaria sanguinalis*), crabgrass, naked (naked crabgrass, *Digitaria nuda*), foxtail, green (green foxtail, *Setaria viridis*), johnsongrass (*Sorghum halepense*), kochia (*Kochia scoparia*), morningglory (pitted morningglory, *Ipomoea lacunosa*), nutsedge, purple (purple nutsedge, *Cyperus rotundus*), ragweed (common ragweed, *Ambrosia elatior*), mustard, black (black mustard, *Brassica nigra*), guineagrass (*Panicum maximum*), dallisgrass (*Paspalum dilatatum*), barnyardgrass (*Echinochloa crus-galli*), sandbur (southern sandbur, *Cenchrus echinatus*), sowthistle (common sowthistle, *Sonchus oleraceous*), Italian ryegrass (*Lolium multiflorum*), signalgrass (broadleaf signalgrass, *Brachiaria platyphylla*), dayflower (Virginia (VA) dayflower, *Commelina virginica*), bluegrass (annual bluegrass, *Poa annua*), quackgrass (*Elytrigia repens*), mallow (common mallow, *Malva sylvestris*), buckwheat, wild (wild buckwheat, *Polygonum convolvulus*), leafy spurge (*Euphorbia esula*), chickweed (common chickweed, *Stellaria media*), wild poinsettia (*Euphorbia heterophylla*), and pigweed (*Amaranthus retroflexus*) were planted into a blend of loam soil and sand and treated preemergence with test chemicals formulated in a non-phytotoxic solvent mixture which included a surfactant.

Treated plants and controls were maintained in a greenhouse for 21 days, after which time all species were compared to controls and visually evaluated. Plant response ratings, summarized in Table F, are based on a scale of 0 to 100 where 0 is no effect and 100 is complete control. A dash (-) response means no test result.

TABLE F

|  | Compounds | | | |
|---|---|---|---|---|
|  | 58 | 79 | 97 | 274 |
| 250 g ai/ha Preemergence | | | | |
| Barnyardgrass | 100 | 100 | 100 | 100 |
| Bermudagrass | 100 | 100 | 100 | 100 |
| Bluegrass | 100 | 100 | 100 | 100 |
| Buckwheat, Wild | 100 | 100 | 100 | 100 |
| Chickweed | 100 | 100 | 100 | 100 |
| Crabgrass, Large | 100 | 100 | 100 | 100 |
| Crabgrass, Naked | 100 | 100 | 100 | 100 |
| Dallisgrass | 100 | 100 | 100 | 100 |
| Dayflower, VA | 100 | 100 | 100 | 100 |
| Foxtail, Green | 100 | 100 | 100 | 100 |
| Guineagrass | 100 | 100 | 100 | 100 |
| Johnsongrass | 100 | 100 | 100 | 100 |
| *Kochia* | 100 | 100 | 100 | 100 |
| Leafy Spurge | 100 | 100 | 100 | 100 |
| Mallow | 100 | 100 | 100 | 100 |
| Morningglory | 100 | 100 | 100 | 100 |
| Mustard, Black | 100 | 100 | 100 | 100 |
| Nutsedge, Purple | 80 | 85 | 90 | 98 |
| Pigweed | 100 | 100 | 100 | 100 |
| Poinsettia, Wild | 100 | 100 | 98 | 100 |
| Quackgrass | 100 | 100 | 100 | 98 |
| Ragweed | 95 | 100 | 100 | 100 |
| Ryegrass, Italian | 100 | 100 | 100 | 100 |
| Sandbur | 100 | 100 | 100 | 100 |
| Signalgrass | 100 | 100 | 100 | 100 |
| Sowthistle | 100 | 100 | 100 | 100 |
| Surinam Grass | 100 | 100 | 100 | 100 |
| 125 g ai/ha Preemergence | | | | |
| Barnyardgrass | 100 | 100 | 100 | 100 |
| Bermudagrass | 100 | 100 | 100 | 100 |
| Bluegrass | 98 | 100 | 98 | 85 |
| Buckwheat, Wild | 100 | 100 | 100 | 100 |
| Chickweed | 100 | 100 | 100 | 100 |
| Crabgrass, Large | 100 | 100 | 100 | 100 |
| Crabgrass, Naked | 100 | 100 | 100 | 100 |
| Dallisgrass | 100 | 100 | 100 | 100 |
| Dayflower, VA | 100 | 100 | 98 | 100 |
| Foxtail, Green | 100 | 100 | 100 | 100 |
| Guineagrass | 100 | 100 | 100 | 100 |
| Johnsongrass | 100 | 100 | 100 | 100 |
| *Kochia* | 100 | 100 | 100 | 100 |
| Leafy Spurge | 100 | 100 | 100 | 100 |
| Mallow | 100 | 100 | 100 | 100 |
| Morningglory | 100 | 100 | 98 | 98 |
| Mustard, Black | 100 | 100 | 100 | 100 |

TABLE F-continued

|  | Compounds | | | |
|---|---|---|---|---|
|  | 58 | 79 | 97 | 274 |
| Nutsedge, Purple | 70 | 70 | 75 | 85 |
| Pigweed | 100 | 100 | 100 | 100 |
| Poinsettia, Wild | 100 | 100 | 98 | 95 |
| Quackgrass | 100 | 98 | 95 | 85 |
| Ragweed | 75 | 100 | 95 | 70 |
| Ryegrass, Italian | 100 | 100 | 85 | 75 |
| Sandbur | 100 | 98 | 100 | 95 |
| Signalgrass | 100 | 100 | 100 | 100 |
| Sowthistle | 100 | 100 | 100 | 100 |
| Surinam Grass | 100 | 100 | 90 | 100 |
| 62 g ai/ha Preemergence | | | | |
| Barnyardgrass | 100 | 100 | 95 | 100 |
| Bermudagrass | 100 | 100 | 100 | 100 |
| Bluegrass | 98 | 98 | 75 | 50 |
| Buckwheat, Wild | 100 | 100 | 100 | 100 |
| Chickweed | 100 | 100 | 100 | 100 |
| Crabgrass, Large | 100 | 100 | 100 | 100 |
| Crabgrass, Naked | 100 | 100 | 100 | 100 |
| Dallisgrass | 100 | 100 | 100 | 100 |
| Dayflower, VA | 100 | 100 | 98 | 98 |
| Foxtail, Green | 100 | 100 | 100 | 100 |
| Guineagrass | 100 | 100 | 100 | 100 |
| Johnsongrass | 100 | 100 | 95 | 100 |
| *Kochia* | 100 | 100 | 100 | 100 |
| Leafy Spurge | 100 | 100 | 100 | 100 |
| Mallow | 98 | 100 | 98 | 98 |
| Morningglory | 100 | 100 | 90 | 65 |
| Mustard, Black | 100 | 100 | 100 | 100 |
| Nutsedge, Purple | 40 | 70 | 30 | 65 |
| Pigweed | 100 | 100 | 100 | 100 |
| Poinsettia, Wild | 100 | 98 | 75 | 70 |
| Quackgrass | 98 | 95 | 50 | 70 |
| Ragweed | 70 | 98 | 85 | 30 |
| Ryegrass, Italian | 98 | 98 | 70 | 70 |
| Sandbur | 95 | 95 | 25 | 70 |
| Signalgrass | 100 | 100 | 85 | 100 |
| Sowthistle | 100 | 100 | 100 | 100 |
| Surinam Grass | 98 | 95 | 50 | 70 |
| 31 g ai/ha Preemergence | | | | |
| Barnyardgrass | 100 | 100 | 90 | 100 |
| Bermudagrass | 100 | 100 | 95 | 100 |
| Bluegrass | 80 | 75 | 35 | 20 |
| Buckwheat, Wild | 100 | 100 | 100 | 100 |
| Chickweed | 100 | 100 | 100 | 98 |
| Crabgrass, Large | 100 | 100 | 100 | 100 |
| Crabgrass, Naked | 100 | 100 | 100 | 100 |
| Dallisgrass | 100 | 98 | 98 | 100 |
| Dayflower, VA | 95 | 98 | 80 | 95 |
| Foxtail, Green | 100 | 100 | 100 | 100 |
| Guineagrass | 100 | 100 | 100 | 100 |
| Johnsongrass | 98 | 100 | 65 | 70 |
| *Kochia* | 100 | 100 | 100 | 100 |
| Leafy Spurge | 95 | 98 | 98 | 98 |
| Mallow | 100 | 100 | 75 | 98 |
| Morningglory | 98 | 100 | 60 | 50 |
| Mustard, Black | 100 | 100 | 100 | 100 |
| Nutsedge, Purple | 60 | 10 | 35 | 50 |
| Pigweed | 100 | 100 | 100 | 100 |
| Poinsettia, Wild | 65 | 85 | 20 | 10 |
| Quackgrass | 70 | 70 | 35 | 40 |
| Ragweed | 65 | 70 | 75 | 30 |
| Ryegrass, Italian | 95 | 75 | 35 | 40 |
| Sandbur | 35 | 15 | 10 | 20 |
| Signalgrass | 100 | 100 | 90 | 70 |
| Sowthistle | 100 | 100 | 100 | 100 |
| Surinam Grass | 60 | 90 | 10 | 35 |
| 16 g ai/ha Preemergence | | | | |
| Barnyardgrass | 70 | 75 | 0 | 75 |
| Bermudagrass | 95 | 98 | 80 | 85 |
| Bluegrass | 50 | 50 | 5 | 0 |

TABLE F-continued

| | Compounds | | | |
|---|---|---|---|---|
| | 58 | 79 | 97 | 274 |
| Buckwheat, Wild | 90 | 98 | 85 | 100 |
| Chickweed | 100 | 98 | 100 | 98 |
| Crabgrass, Large | 100 | 98 | 98 | 100 |
| Crabgrass, Naked | 100 | 100 | 100 | 100 |
| Dallisgrass | 90 | 65 | 75 | 95 |
| Dayflower, VA | 90 | 95 | 35 | 90 |
| Foxtail, Green | 75 | 95 | 75 | 100 |
| Guineagrass | 100 | 100 | 100 | 100 |
| Johnsongrass | 65 | 65 | 0 | 65 |
| Kochia | 98 | 100 | 100 | 100 |
| Leafy Spurge | 100 | 95 | 98 | 100 |
| Mallow | 60 | 98 | 30 | 98 |
| Morningglory | 100 | 98 | 10 | 35 |
| Mustard, Black | 100 | 100 | 90 | 98 |
| Nutsedge, Purple | 0 | 0 | 15 | 35 |
| Pigweed | 100 | 100 | 100 | 100 |
| Poinsettia, Wild | 25 | 50 | 10 | 5 |
| Quackgrass | 50 | 40 | 0 | 40 |
| Ragweed | 60 | 25 | 10 | 30 |
| Ryegrass, Italian | 35 | 30 | 0 | 35 |
| Sandbur | 10 | 10 | 0 | 5 |
| Signalgrass | 95 | 98 | 25 | 75 |
| Sowthistle | 100 | 100 | 100 | 100 |
| Surinam Grass | 25 | 75 | 0 | 10 |

Test G

Three plastic pots (ca. 16-cm diameter) per rate were partially filled with sterilized Tama silt loam soil comprising a 35:50:15 ratio of sand, silt and clay and 2.6% organic matter. Separate plantings for each of the three pots were as follows. Seeds from the U.S. of monochoria (*Monochoria vaginalis*), sedge, umbrella (small-flower umbrella sedge, *Cyperus difformis*), hardstem bulrush (*Scirpus juncoides*), and redstem (purple redstem, *Ammannia coccinea*), were planted into one 16-cm pot for each rate. Seeds from the U.S. of rice flatsedge (*Cyperus iria*), bearded sprangletop (*Leptochloa fascicularis*), one stand of 9 or 10 water seeded rice seedlings (*Oryza sativa* cv. 'Japonica—M202'), and two stands of 3 or 4 transplanted rice seedlings (*Oryza sativa* cv. 'Japonica—M202') were planted into one 16-cm pot for each rate. Seeds from the U.S. of barnyardgrass (*Echinochloa crus-galli*), and late watergrass (*Echinochloa oryzicola*) were planted into one 16-cm pot for each rate. Plantings were sequential so that crop and weed species were at the 2.0 to 2.5-leaf stage at time of treatment.

Potted plants were grown in a greenhouse with day/night temperature settings of 30/27° C., and supplemental balanced lighting was provided to maintain a 16-hour photoperiod. Test pots were maintained in the greenhouse until test completion.

At time of treatment, test pots were flooded to 3 cm above the soil surface, treated by application of test compounds directly to the paddy water, and then maintained at that water depth for the duration of the test. Effects of treatments on rice and weeds were visually evaluated by comparison to untreated controls after 21 days. Plant response ratings, summarized in Table G, are based on a scale of 0 to 100 where 0 is no effect and 100 is complete control. A dash (-) response means no test result.

TABLE G

| | Compounds | |
|---|---|---|
| | 16 | 18 |
| 250 g ai/ha Flood | | |
| Barnyardgrass | 100 | 100 |
| Bulrush, Hardstem | 80 | 85 |
| Flatsedge, Rice | 100 | 100 |
| Monochoria | 100 | 100 |
| Redstem | 95 | 90 |
| Rice, Transplanted | — | 20 |
| Rice, Water Seeded | 100 | 100 |
| Sedge, Umbrella | 100 | 100 |
| Sprangletop, Brdd. | 100 | 100 |
| Watergrass, Late | 80 | 70 |
| 125 g ai/ha Flood | | |
| Barnyardgrass | 100 | 35 |
| Bulrush, Hardstem | 65 | 0 |
| Flatsedge, Rice | 100 | 100 |
| Monochoria | 100 | 100 |
| Redstem | 85 | 75 |
| Rice, Transplanted | — | 15 |
| Rice, Water Seeded | 100 | 90 |
| Sedge, Umbrella | 100 | 35 |
| Sprangletop, Brdd. | 100 | 90 |
| Watergrass, Late | 0 | 0 |
| 64 g ai/ha Flood | | |
| Barnyardgrass | 40 | 20 |
| Bulrush, Hardstem | 50 | 0 |
| Flatsedge, Rice | 85 | 75 |
| Monochoria | 95 | 95 |
| Redstem | 60 | 0 |
| Rice, Water Seeded | 90 | 60 |
| Sedge, Umbrella | 60 | 20 |
| Sprangletop, Brdd. | 100 | 80 |
| Watergrass, Late | 0 | 0 |
| 32 g ai/ha Flood | | |
| Barnyardgrass | 0 | 0 |
| Bulrush, Hardstem | 40 | 0 |
| Flatsedge, Rice | 40 | 30 |
| Monochoria | 95 | 95 |
| Redstem | 0 | 0 |
| Rice, Transplanted | 0 | — |
| Rice, Water Seeded | 50 | — |
| Sedge, Umbrella | 0 | 0 |
| Sprangletop, Brdd. | 65 | 70 |
| Watergrass, Late | 0 | 0 |

What is claimed is:

1. A compound selected from a compound of Formula 1, N-oxides and salts thereof

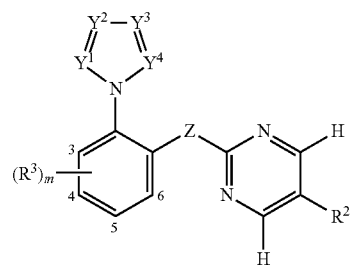

wherein each $Y^1$, $Y^2$, $Y^3$ and $Y^4$ is independently selected from the group consisting of N and $CR^1$, provided no more than 3 of $Y^1$, $Y^2$, $Y^3$ and $Y^4$ are N;

Z is selected from the group consisting of O and S;

each $R^1$ is independently selected from the group consisting of hydrogen, halogen, cyano, nitro, $SF_5$, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_2$-$C_8$ alkylaminocarbonyl, $C_3$-$C_{10}$ dialkylaminocarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $SO_nR^{1A}$, $Si(CH_3)_3$, $B(-OC(R^{1B})_2C(R^{1B})_2O-)$; a phenyl ring optionally substituted with up to 5 substituents independently selected from $R^{1C}$; and a 5- or 6-membered heteroaromatic ring containing ring members selected from carbon atoms and up to 4 heteroatoms independently selected from the group consisting of up to 2 O, up to 2 S and up to 4 N atoms, each ring optionally substituted with up to 3 substituents independently selected from $R^{1C}$ on carbon atom ring members and $R^{1D}$ on nitrogen atom ring members;

$R^2$ is selected from the group consisting of halogen, cyano, nitro, $C_1$-$C_4$ alkoxy, $C_1$-$C_4$ alkyl, $C_2$-$C_6$ alkenyl, $C_2$-$C_6$ alkynyl, $SO_nR^{2A}$, $C_1$-$C_4$ haloalkyl and $C_3$-$C_6$ cycloalkyl;

m is selected from the group consisting of 0, 1, 2 and 3;

each $R^3$ is independently selected from the group consisting of halogen, cyano, hydroxy, nitro, amino, CHO, $C(=O)NH_2$, $C(=S)NH_2$, $SO_2NH_2$, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_4$-$C_8$ cycloalkylalkyl, $C_2$-$C_6$ alkylcarbonyl, $C_2$-$C_6$ haloalkylcarbonyl, $C_2$-$C_6$ alkoxycarbonyl, $C_3$-$C_7$ cycloalkylcarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_4$-$C_8$ cycloalkylalkoxy, $C_2$-$C_6$ alkoxyalkyl, $C_2$-$C_6$ haloalkoxyalkyl, $C_2$-$C_6$ alkoxyhaloalkyl, $C_2$-$C_6$ alkoxyalkoxy, $C_2$-$C_4$ alkylcarbonyloxy, $C_2$-$C_6$ cyanoalkyl, $C_2$-$C_6$ cyanoalkoxy, $C_2$-$C_4$ alkylthioalkyl, $Si(CH_3)_3$, $C≡CSi(CH_3)_3$, $C(=O)N(R^{3A})(R^{3B})$, $C(=NOR^{3C})H$, $C(=NR^{3D})H$, $SO_nR^{3E}$; a phenyl ring optionally substituted with up to 5 substituents independently selected from $R^{3F}$; a 5- or 6-membered heteroaromatic ring containing ring members selected from carbon atoms and up to 4 heteroatoms independently selected from the group consisting of up to 2 O, up to 2 S and up to 4 N atoms, each ring optionally substituted with up to 3 substituents independently selected from $R^{3F}$ on carbon atom ring members and $R^{3G}$ on nitrogen atom ring members; and pyrimidinyloxy;

each n is independently selected from the group consisting of 0, 1 and 2;

each $R^{1A}$, $R^{2A}$ and $R^{3E}$ is independently selected from the group consisting of $C_1$-$C_4$ alkyl, $C_1$-$C_4$ haloalkyl, $C_1$-$C_4$ alkylamino and $C_2$-$C_6$ dialkylamino;

each $R^{1B}$ is independently selected from the group consisting of H and $C_1$-$C_4$ alkyl;

each $R^{1C}$ is independently selected from the group consisting of hydroxy, halogen, cyano, nitro, $C_1$-$C_6$ alkyl, $C_1$-$C_6$ haloalkyl, $C_1$-$C_6$ alkoxy and $C_1$-$C_6$ haloalkoxy;

each $R^{1D}$ is independently selected from the group consisting of cyano, $C_1$-$C_6$ alkyl, $C_1$-$C_6$ haloalkyl, $C_1$-$C_6$ alkoxy and $C_2$-$C_6$ alkylcarbonyl;

each $R^{3A}$ is independently selected from the group consisting of $C_1$-$C_4$ alkyl and $C_1$-$C_4$ haloalkyl;

each $R^{3B}$ is independently selected from the group consisting of H, $C_1$-$C_4$ alkyl and $C_1$-$C_4$ haloalkyl;

each $R^{3C}$ is independently selected from the group consisting of H and $C_1$-$C_4$ alkyl;

each $R^{3D}$ is independently selected from the group consisting of H, amino, $C_1$-$C_4$ alkyl and $C_1$-$C_4$ alkylamino;

each $R^{3F}$ is independently selected from the group consisting of hydroxy, halogen, cyano, nitro, $C_1$-$C_6$ alkyl, $C_1$-$C_6$ haloalkyl, $C_1$-$C_6$ alkoxy and $C_1$-$C_6$ haloalkoxy; and each $R^{3G}$ is independently selected from the group consisting of cyano, $C_1$-$C_6$ alkyl, $C_1$-$C_6$ haloalkyl, $C_1$-$C_6$ alkoxy and $C_2$-$C_6$ alkylcarbonyl;

provided when i) $Y^1$ is N; $Y^2$ is CH; $Y^3$ is CBr; $Y^4$ is CH; and $R^2$ is Cl, then $R^3$ is other than 5-$CF_3$, 5-CN or 5-$NO_2$; ii) $Y^1$ is N; $Y^2$ is CH; $Y^3$ is CBr; $Y^4$ is CH; and $R^2$ is Br, then $R^3$ is other than 5-$CF_3$; and iii) $Y^1$ is N; $Y^2$ is $CCH_3$; $Y^3$ is CCl; $Y^4$ is CCl; and $R^2$ is Cl, then m is other than 0.

2. A compound of claim 1 wherein

—$Y^1$=$Y^2$—$Y^3$=$Y^4$— including the nitrogen to which $Y^1$ and $Y^4$ are both attached is selected from the group consisting of

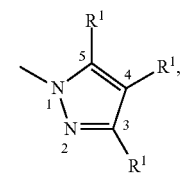

Q-2

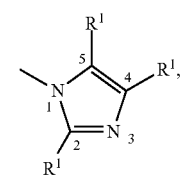

Q-3

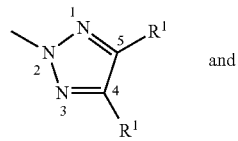

Q-4 and

-continued

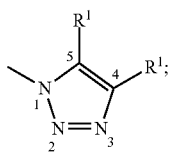

Q-5

Z is O;
each $R^1$ is independently selected from the group consisting of hydrogen, halogen, cyano, $SF_5$, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_6$ cyanoalkyl, $C_2$-$C_4$ alkylthioalkyl, $SO_nR^{14}$, $Si(CH_3)_3$ and B(—OC($R^{1B}$)$_2$C($R^{1B}$)$_2$O—);
$R^2$ is selected from the group consisting of halogen, $C_1$-$C_4$ alkyl and $C_1$-$C_4$ haloalkyl;
each $R^3$ is independently selected from the group consisting of halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_4$-$C_8$ alkylcycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_3$-$C_6$ cycloalkoxy, $C_3$-$C_6$ halocycloalkoxy, $C_2$-$C_6$ alkoxyalkyl, $C_2$-$C_6$ haloalkoxyalkyl, $C_2$-$C_4$ alkylcarbonyloxy, $C_2$-$C_6$ cyanoalkyl, C(=O)N($R^{3A}$)($R^{3B}$), C(=NOR$^{3C}$)H, $SO_nR^{3E}$; a phenyl ring optionally substituted with up to 5 substituents independently selected from $R^{3F}$; and a 5- or 6-membered heteroaromatic ring containing ring members selected from carbon atoms and up to 4 heteroatoms independently selected from up to 2 O, up to 2 S and up to 4 N atoms, each ring optionally substituted with up to 3 substituents independently selected from $R^{3F}$ on carbon atom ring members and $R^{3G}$ on nitrogen atom ring members; and
m is selected from the group consisting of 0, 1 and 2.

3. A compound of claim 2 wherein
—$Y^1$=$Y^2$—$Y^3$=$Y^4$— including the nitrogen to which $Y^1$ and $Y^4$ are both attached is selected from the group consisting of Q-2 and Q-5;
each $R^1$ is independently selected from the group consisting of hydrogen, halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_1$-$C_4$ alkoxy, $C_3$-$C_4$ alkenyloxy, $C_3$-$C_4$ alkynyloxy, $C_1$-$C_4$ haloalkoxy, $C_3$-$C_4$ haloalkenyloxy, $C_3$-$C_4$ haloalkynyloxy, $C_2$-$C_6$ alkoxyalkyl, $C_2$-$C_6$ haloalkoxyalkyl, $C_2$-$C_4$ alkylthioalkyl and $SO_nR^{14}$;
$R^2$ is selected from the group consisting of halogen and $C_1$-$C_4$ alkyl;
each $R^3$ is independently selected from the group consisting of halogen, cyano, CHO, $C_1$-$C_4$ alkyl, $C_2$-$C_4$ alkenyl, $C_2$-$C_4$ alkynyl, $C_1$-$C_4$ haloalkyl, $C_2$-$C_4$ haloalkenyl, $C_2$-$C_4$ haloalkynyl, $C_3$-$C_6$ cycloalkyl, $C_3$-$C_6$ halocycloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl, $C_2$-$C_6$ haloalkoxyalkyl, $C_2$-$C_6$ cyanoalkyl, $SO_nR^{3E}$; and a 5- or 6-membered heteroaromatic ring containing ring members selected from carbon atoms and up to 4 heteroatoms independently selected from the group consisting of up to 2 O, up to 2 S and up to 4 N atoms, each ring optionally substituted with up to 3 substituents independently selected from $R^{3F}$ on carbon atom ring members and $R^{3G}$ on nitrogen atom ring members; and
m is selected from the group consisting of 0 and 1.

4. A compound of claim 3 wherein
each $R^1$ is independently selected from the group consisting of hydrogen, halogen, cyano, $C_1$-$C_4$ alkyl, $C_1$-$C_4$ haloalkyl, $C_1$-$C_4$ alkoxy, $C_1$-$C_4$ haloalkoxy and $SO_nR^{14}$;
$R^2$ is selected from the group consisting of halogen and $CH_3$;
each $R^3$ is independently selected from the group consisting of halogen, cyano, $C_1$-$C_4$ alkyl, $C_2$-$C_4$ alkenyl, $C_2$-$C_4$ alkynyl, $C_1$-$C_4$ haloalkyl, $C_2$-$C_6$ alkylcarbonyl, $C_2$-$C_6$ haloalkylcarbonyl, $C_2$-$C_6$ alkoxycarbonyl, $C_1$-$C_4$ alkoxy, $C_1$-$C_4$ haloalkoxy, $C_2$-$C_6$ alkoxyalkyl and $C_2$-$C_6$ haloalkoxyalkyl; and
each $R^{14}$ is independently selected from the group consisting of $C_1$-$C_4$ alkyl and $C_1$-$C_4$ haloalkyl.

5. A compound of claim 4 wherein
—$Y^1$=$Y^2$—$Y^3$=$Y^4$— including the nitrogen to which $Y^1$ and $Y^4$ are both attached is Q-2;
each $R^1$ is independently selected from the group consisting of hydrogen, halogen, $C_1$-$C_4$ haloalkyl and $C_1$-$C_4$ haloalkoxy; and
each $R^3$ is independently selected from the group consisting of halogen, cyano, $C_1$-$C_4$ alkyl and $C_1$-$C_4$ haloalkyl.

6. A compound of claim 4 wherein
—$Y^1$=$Y^2$—$Y^3$=$Y^4$— including the nitrogen to which $Y^1$ and $Y^4$ are both attached is Q-5;
each $R^1$ is independently selected from the group consisting of hydrogen, halogen, $C_1$-$C_4$ haloalkyl and $C_1$-$C_4$ haloalkoxy; and
each $R^3$ is independently selected from the group consisting of halogen, cyano, $C_1$-$C_4$ alkyl and $C_1$-$C_4$ haloalkyl.

7. A compound of claim 1 selected from the group consisting of
5-chloro-2-[2-[3-(trifluoromethyl)-1H-pyrazol-1-yl]phenoxy]pyrimidine,
5-bromo-2-[2-(4-chloro-1H-pyrazol-1-yl)phenoxy]pyrimidine,
2-[2-(4-bromo-1H-pyrazol-1-yl)phenoxy]-5-chloropyrimidine,
2-[2-(4-bromo-1H-pyrazol-1-yl)phenoxy]-5-fluoropyrimidine,
5-bromo-2-[2-[4-(trifluoromethyl)-1H-pyrazol-1-yl]phenoxy]pyrimidine,
2-(4-bromo-1H-pyrazol-1-yl)-3-[(5-chloro-2-pyrimidinyl)oxy]benzonitrile,
2-[2-(4-bromo-2H-1,2,3-triazol-2-yl)phenoxy]-5-chloropyrimidine,
3[(5-chloro-2-pyrimidinyl)oxy]-2-[4-(trifluoromethyl)-1H-pyrazol-1-yl]benzonitrile,
3-[(5-bromo-2-pyrimidinyl)oxy]-2-[4-(trifluoromethyl)-1H-pyrazol-1-yl]benzonitrile,
5-chloro-2-[2-[4-(difluoromethyl)-1H-1,2,3-triazol-1-yl]-3-fluorophenoxy]pyrimidine,
5-chloro-2-[2-[4-(trifluoromethyl)-1H-1,2,3-triazol-1-yl]phenoxy]pyrimidine,
5-chloro-2-[2-[4-(difluoromethyl)-1H-1,2,3-triazol-1-yl]phenoxy]pyrimidine,
3-[(5-fluoro-2-pyrimidinyl)oxy]-2-[4-(trifluoromethyl)-1H-pyrazol-1-yl]benzonitrile, 2-[2-(4-bromo-1H-pyrazol-1-yl)-3-fluorophenoxy]-5-chloropyrimidine, 3-[(5-chloro-2-pyrimidinyl)oxy]-2-[4-(2,2,2-trifluoroethoxy)-1H-pyrazol-1-yl]benzonitrile, 5-chloro-2-[2-[4-(2,2,2-trifluoroethoxy)-1H-pyrazol-1-yl]phenoxy]pyrimidine, 2-[2-(4-bromo-1H-pyrazol-1-yl)-3-(difluoromethyl)phenoxy]-5-chloropyrimidine, 3-[(5-chloro-2-pyrimidinyl)oxy]-2-[4-(difluoromethyl)-1H-pyrazol-1-yl]benzonitrile, 3-[(5-chloro-2-pyrimidinyl)oxy]-2-[4-(trifluoromethyl)-1H-imidazol-1-yl]benzonitrile, 5-bromo-2-[2-[4-(difluoromethyl)-1H-1,2,3-triazol-1-yl]-3-fluorophenoxy]pyrimidine and 5-chloro-2-[3-fluoro-2-[4-(trifluoromethyl)-1H-pyrazol-1-yl]phenoxy]pyrimidine.

8. A herbicidal composition comprising a compound of claim 1 and at least one component selected from the group consisting of surfactants, solid diluents and liquid diluents.

9. A herbicidal composition comprising a compound of claim 1, at least one additional active ingredient selected from the group consisting of other herbicides and herbicide safeners, and at least one component selected from the group consisting of surfactants, solid diluents and liquid diluents.

10. A herbicidal mixture comprising (a) a compound of claim 1, and (b) at least one additional active ingredient selected from the group consisting of (b1) photosystem II inhibitors, (b2) acetohydroxy acid synthase (AHAS) inhibitors, (b3) acetyl-CoA carboxylase (ACCase) inhibitors, (b4) auxin mimics, (b5) 5-enol-pyruvylshikimate-3-phosphate (EPSP) synthase inhibitors, (b6) photosystem I electron diverters, (b7) protoporphyrinogen oxidase (PPO) inhibitors, (b8) glutamine synthetase (GS) inhibitors, (b9) very long chain fatty acid (VLCFA) elongase inhibitors, (b10) auxin transport inhibitors, (b11) phytoene desaturase (PDS) inhibitors, (b12) 4-hydroxyphenyl-pyruvate dioxygenase (HPPD) inhibitors, (b13) homogentisate solanesyl transferase (HST) inhibitors, (b14) cellulose biosynthesis inhibitors, (b15) other herbicides selected from the group consisting of mitotic disruptors, organic arsenicals, asulam, bromobutide, cinmethylin, cumyluron, dazomet, difenzoquat, dymron, etobenzanid, flurenol, fosamine, fosamine-ammonium, metam, methyldymron, oleic acid, oxaziclomefone, pelargonic acid and pyributicarb, (b16) herbicide safeners and salts of compounds of (b1) through (b16).

11. A method for controlling the growth of undesired vegetation comprising contacting the vegetation or its environment with a herbicidally effective amount of a compound of claim 1.

12. A method for controlling the growth of undesired vegetation in a genetically modified plants that exhibit traits of glyphosate tolerance, glufosinate tolerance, ALS herbicide tolerance, dicamba tolerance, imidazolinone herbicide tolerance, 2,4-D tolerance, HPPD tolerance or mesotrione tolerance, comprising contacting the vegetation or its environment with a herbicidally effective amount of a compound of claim 1.

13. A herbicidal mixture comprising (a) a compound of claim 1, and (b) at least one additional active ingredient selected from the group consisting of (b1) photosystem II inhibitors, (b2) acetohydroxy acid synthase (AHAS) inhibitors, (b4) auxin mimics, (b5) 5-enol-pyruvylshikimate-3-phosphate (EPSP) synthase inhibitors, (b7) protoporphyrinogen oxidase (PPO) inhibitors, (b9) very long chain fatty acid (VLCFA) elongase inhibitors and (b12) 4-hydroxyphenyl-pyruvate dioxygenase (HPPD) inhibitors.

14. A herbicidal mixture comprising (a) a compound of claim 1, and (b) at least one additional active ingredient selected from the group consisting of 2,4-D, acetochlor, alachlor, atrazine, bromoxynil, bentazon, bicyclopyrone, carfentrazone-ethyl, cloransulam-methyl, dicamba, dimethenamid-p, florasulam, flufenacet, flumioxazin, flupyrsulfuron-methyl, fluroxypyr-meptyl, glyphosate, halauxifen-methyl, isoxaflutole, MCPA, mesotrione, metolachlor, metsulfuron-methyl, nicosulfuon, pyrasulfotole, pyroxasulfone, pyroxsulam, rimsulfuron, saflufenacil, tembotrione, thifensulfuron-methyl, topramazone and tribenuron.

* * * * *